(12) United States Patent
Hadari et al.

(10) Patent No.: US 12,391,705 B2
(45) Date of Patent: Aug. 19, 2025

(54) COMPOUNDS THAT INTERACT WITH THE RAS SUPERFAMILY FOR THE TREATMENT OF CANCERS, INFLAMMATORY DISEASES, RASOPATHIES, AND FIBROTIC DISEASE

(71) Applicant: SHY Therapeutics, LLC, Harrison, NY (US)

(72) Inventors: Yaron R. Hadari, Harrison, NY (US); Michael Schmertzler, St. Petersburg, FL (US); Theresa M. Williams, Harleysville, PA (US); Luca Carta, Scarsdale, NY (US); Rebecca Hutcheson, Stamford, CT (US); Charles H. Reynolds, Austin, TX (US)

(73) Assignee: SHY Therapeutics, LLC, Harrison, NY (US)

( * ) Notice: Subject to any disclaimer, the term of this patent is extended or adjusted under 35 U.S.C. 154(b) by 964 days.

(21) Appl. No.: 17/414,565

(22) PCT Filed: Dec. 18, 2019

(86) PCT No.: PCT/US2019/067179
§ 371 (c)(1),
(2) Date: Jun. 16, 2021

(87) PCT Pub. No.: WO2020/132071
PCT Pub. Date: Jun. 25, 2020

(65) Prior Publication Data
US 2023/0078755 A1   Mar. 16, 2023

Related U.S. Application Data

(60) Provisional application No. 62/782,189, filed on Dec. 19, 2018.

(51) Int. Cl.
| | |
|---|---|
| C07D 495/04 | (2006.01) |
| A61P 35/00 | (2006.01) |
| C07D 401/04 | (2006.01) |
| C07D 401/14 | (2006.01) |
| C07D 403/04 | (2006.01) |
| C07D 403/14 | (2006.01) |
| C07D 519/00 | (2006.01) |

(52) U.S. Cl.
CPC ............ *C07D 495/04* (2013.01); *A61P 35/00* (2018.01); *C07D 401/04* (2013.01); *C07D 401/14* (2013.01); *C07D 403/04* (2013.01); *C07D 403/14* (2013.01); *C07D 519/00* (2013.01)

(58) Field of Classification Search
CPC ... C07D 495/04; C07D 401/04; C07D 403/04
See application file for complete search history.

(56) References Cited

U.S. PATENT DOCUMENTS

| | | |
|---|---|---|
| 5,102,877 A | 4/1992 | Murata et al. |
| 5,187,168 A | 2/1993 | Primeau et al. |
| 5,654,307 A | 8/1997 | Bridges et al. |
| 6,133,271 A | 10/2000 | Pamukcu et al. |
| 6,492,383 B1 | 12/2002 | Munchhof et al. |
| 7,173,040 B2 | 2/2007 | Angibaud et al. |
| 8,022,076 B2 | 9/2011 | Ford et al. |
| 8,153,639 B2 | 4/2012 | Chuckowree et al. |
| 8,211,897 B2 | 7/2012 | Holsinger |
| 8,314,112 B2 | 11/2012 | Leblanc et al. |
| 8,691,829 B2 | 4/2014 | Ulrich |
| 9,163,003 B2 | 10/2015 | Chen et al. |
| 9,238,034 B2 | 1/2016 | Tran et al. |
| 9,249,155 B2 | 2/2016 | Ford et al. |
| 9,260,400 B2 | 2/2016 | Leopoldo et al. |
| 9,260,462 B2 | 2/2016 | Leopoldo et al. |
| 9,290,511 B2 | 3/2016 | Madge et al. |
| 9,604,994 B2 | 3/2017 | Dorsey et al. |
| 9,797,882 B2 | 10/2017 | Tran et al. |
| 10,221,191 B2 | 3/2019 | Hadari et al. |
| 10,463,649 B2 | 11/2019 | Srivastava et al. |
| 10,588,894 B2 | 3/2020 | Hadari et al. |
| 10,870,657 B2 | 12/2020 | Hadari et al. |
| 10,933,054 B2 | 3/2021 | Hadari et al. |
| 10,940,139 B2 | 3/2021 | Hadari et al. |
| 11,000,515 B2 | 5/2021 | Hadari et al. |
| 11,026,930 B1 | 6/2021 | Hadari et al. |
| 2005/0176701 A1 | 8/2005 | Borchardt et al. |
| 2006/0167029 A1 | 7/2006 | Matasi et al. |
| 2007/0099877 A1 | 5/2007 | Cai et al. |

(Continued)

FOREIGN PATENT DOCUMENTS

| | | |
|---|---|---|
| CN | 101583616 A | 11/2009 |
| CN | 104230952 A | 12/2014 |

(Continued)

OTHER PUBLICATIONS

Johnson, et al. Current Opinion in Pharmacology 2012, 12:458-463.*
Lala, et al. Cancer and Metastasis Reviews (1998), 17 (1), 91-106.*
Golub, et al. Science 286, 531 (1999).*
Cancer [online], [retrieved on Aug. 11, 2023]. Retrieved from the internet, URLhttps://medlineplus.gov/cancer.html#>.*
Ballell, et al. ChemMedChem 2013, 8, 313-321.*
No new references have been cited.*
No new references cited by the Examiner.*
International Search Report dated Mar. 10, 2020 for PCT/US2019/067179.

(Continued)

*Primary Examiner* — Shawquia Jackson
(74) *Attorney, Agent, or Firm* — Jones Day

(57) ABSTRACT

Provided herein are methods and compositions for treating cancers, inflammatory diseases, rasopathies, and fibrotic disease involving aberrant Ras superfamily signaling through the binding of compounds to the GTP binding domain of Ras superfamily proteins including, in certain cases, K-Ras and mutants thereof, and a method for assaying such compositions.

27 Claims, No Drawings

(56) References Cited

U.S. PATENT DOCUMENTS

| | | |
|---|---|---|
| 2007/0287717 A1 | 12/2007 | Fanning et al. |
| 2008/0161254 A1 | 7/2008 | Green et al. |
| 2008/0161559 A1 | 7/2008 | Penning et al. |
| 2008/0161578 A1 | 7/2008 | Penning et al. |
| 2008/0269228 A1 | 10/2008 | Moore et al. |
| 2009/0030196 A1 | 1/2009 | Wang et al. |
| 2009/0163545 A1 | 6/2009 | Goldfarb et al. |
| 2010/0069383 A1 | 3/2010 | Anderson et al. |
| 2010/0093702 A1 | 4/2010 | Barbay et al. |
| 2011/0144140 A1 | 6/2011 | Eriksen et al. |
| 2012/0046290 A1 | 2/2012 | Dumas et al. |
| 2013/0116267 A1 | 5/2013 | Katsikis et al. |
| 2013/0317045 A1 | 11/2013 | Hadd et al. |
| 2014/0072536 A1 | 3/2014 | Burkin et al. |
| 2014/0228565 A1 | 8/2014 | Choo et al. |
| 2014/0256717 A1 | 9/2014 | Fernandez et al. |
| 2014/0256719 A1 | 9/2014 | Finlay et al. |
| 2015/0175558 A1 | 6/2015 | Stockwell et al. |
| 2015/0239900 A1 | 8/2015 | Li et al. |
| 2015/0291590 A1 | 10/2015 | Kandula |
| 2015/0315207 A1 | 11/2015 | Morales et al. |
| 2016/0146784 A1 | 5/2016 | Tran et al. |
| 2017/0131278 A1 | 5/2017 | Patricelli et al. |
| 2017/0158706 A1 | 6/2017 | Dorsey |
| 2017/0174699 A1 | 6/2017 | Hadari et al. |
| 2018/0118761 A1 | 5/2018 | Sebti et al. |
| 2019/0022074 A1 | 1/2019 | Hadari et al. |
| 2019/0218229 A1 | 7/2019 | Hadari et al. |
| 2020/0054614 A1 | 2/2020 | Hadari et al. |

FOREIGN PATENT DOCUMENTS

| | | |
|---|---|---|
| CN | 107721982 A | 8/2018 |
| DE | 1959402 A1 | 6/1971 |
| DE | 1959403 A1 | 6/1971 |
| DE | 2039662 A1 | 2/1972 |
| DE | 2050814 A1 | 4/1972 |
| DE | 2050815 A1 | 4/1972 |
| DE | 2050816 A1 | 4/1972 |
| DE | 295381 A5 | 10/1991 |
| EP | 0 404 356 A1 | 12/1990 |
| EP | 0 407 899 A2 | 1/1991 |
| EP | 2 014 663 A1 | 5/1991 |
| EP | 0 502 725 A2 | 9/1992 |
| EP | 0 519 307 A2 | 12/1992 |
| EP | 0 579 424 A1 | 1/1994 |
| EP | 0 807 633 A2 | 11/1997 |
| EP | 0 276 057 A2 | 7/1998 |
| EP | 0 884 310 A1 | 12/1998 |
| EP | 0 900 568 A2 | 3/1999 |
| EP | 0 900 799 A1 | 3/1999 |
| EP | 1 254 903 A1 | 11/2002 |
| EP | 0 934 321 B1 | 8/2003 |
| EP | 1 997 812 A1 | 12/2008 |
| EP | 2 508 184 A1 | 10/2012 |
| EP | 3 290 412 A1 | 3/2018 |
| GB | 1057612 | 2/1967 |
| JP | 56059778 A | 5/1981 |
| JP | H04305630 A | 10/1992 |
| JP | 2010-512337 | 4/2010 |
| KR | 10-2018-0066985 A | 6/2018 |
| WO | WO 92/20687 A1 | 11/1992 |
| WO | WO 93/03040 A1 | 2/1993 |
| WO | WO 94/08975 A1 | 4/1994 |
| WO | WO 97/29110 A1 | 8/1997 |
| WO | WO 97/46560 A1 | 12/1997 |
| WO | WO 98/06722 A1 | 2/1998 |
| WO | WO 98/23620 A1 | 6/1998 |
| WO | WO 98/49899 A1 | 11/1998 |
| WO | WO 99/14202 A2 | 3/1999 |
| WO | WO 99/24440 A1 | 5/1999 |
| WO | WO 99/40091 A1 | 8/1999 |
| WO | WO 2000/059912 | 10/2000 |
| WO | WO 2001/002409 A1 | 1/2001 |
| WO | WO 2001/083456 A1 | 11/2001 |
| WO | WO 2002/002549 A1 | 1/2002 |
| WO | WO 2002/026745 A1 | 4/2002 |
| WO | WO 2002/055524 A1 | 7/2002 |
| WO | WO 2003/033476 A1 | 4/2003 |
| WO | WO 2003/035076 A1 | 5/2003 |
| WO | WO 2003/035653 A1 | 5/2003 |
| WO | WO 2003/050064 A2 | 6/2003 |
| WO | WO 2003/059913 A1 | 7/2003 |
| WO | WO 2003/106435 A1 | 12/2003 |
| WO | WO 2004/037176 A2 | 5/2004 |
| WO | WO 2004/065392 A1 | 8/2004 |
| WO | WO 2004/071460 A2 | 8/2004 |
| WO | WO 2004/074270 A2 | 9/2004 |
| WO | WO 2004/111057 A1 | 12/2004 |
| WO | WO 2004/111058 A1 | 12/2004 |
| WO | WO 2005/023782 A1 | 3/2005 |
| WO | WO 2005/026126 A1 | 3/2005 |
| WO | WO 2005/047292 A1 | 5/2005 |
| WO | WO 2005/047293 A1 | 5/2005 |
| WO | WO 2005/082887 A1 | 9/2005 |
| WO | WO 2005/105760 A1 | 11/2005 |
| WO | WO 2005/105780 A2 | 11/2005 |
| WO | WO 2005/121147 A1 | 12/2005 |
| WO | WO 2006/022955 A2 | 3/2006 |
| WO | WO 2006/040966 A1 | 4/2006 |
| WO | WO 2006/043145 A1 | 4/2006 |
| WO | WO 2006/046040 A1 | 5/2006 |
| WO | WO 2006/072831 A1 | 7/2006 |
| WO | WO 2006/122200 A1 | 11/2006 |
| WO | WO 2007/002701 A2 | 1/2007 |
| WO | WO 2007/035010 A2 | 3/2007 |
| WO | WO 2007/056214 A2 | 5/2007 |
| WO | WO 2007/064883 A2 | 6/2007 |
| WO | WO 2007/076085 A2 | 7/2007 |
| WO | WO 2007/093365 A2 | 8/2007 |
| WO | WO 2007/0102679 A1 | 9/2007 |
| WO | WO 2007/127183 A1 | 11/2007 |
| WO | WO 2007/132171 A1 | 11/2007 |
| WO | WO 2007/139951 A1 | 12/2007 |
| WO | WO 2008/012413 A2 | 1/2008 |
| WO | WO 2008/016123 A1 | 2/2008 |
| WO | WO 2008/020622 A1 | 2/2008 |
| WO | WO 2008/024433 A2 | 2/2008 |
| WO | WO 2008/024724 A1 | 2/2008 |
| WO | WO 2008/028935 A2 | 3/2008 |
| WO | WO 2008/063668 A1 | 5/2008 |
| WO | WO 2008/064018 A1 | 5/2008 |
| WO | WO 2008/066664 A1 | 6/2008 |
| WO | WO 2008/092860 A1 | 8/2008 |
| WO | WO 2008/092861 A1 | 8/2008 |
| WO | WO 2008/092862 A1 | 8/2008 |
| WO | WO 2008/094909 A2 | 8/2008 |
| WO | WO 2008/131050 A1 | 10/2008 |
| WO | WO 2008/134397 A1 | 11/2008 |
| WO | WO 2009/026241 A1 | 2/2009 |
| WO | WO 2009/027346 A2 | 3/2009 |
| WO | WO 2009/064388 A2 | 5/2009 |
| WO | WO 2009/065472 A1 | 5/2009 |
| WO | WO 2009/087225 A2 | 7/2009 |
| WO | WO 2009/119880 A1 | 10/2009 |
| WO | WO 2009/121036 A2 | 10/2009 |
| WO | WO 2010/027236 | 3/2010 |
| WO | WO 2010/037765 A2 | 4/2010 |
| WO | WO 2010/045006 | 4/2010 |
| WO | WO 2010/126960 A1 | 11/2010 |
| WO | WO 2010/138828 A2 | 12/2010 |
| WO | WO 2011/011550 A1 | 1/2011 |
| WO | WO 2011/101429 A1 | 2/2011 |
| WO | WO 2011/025774 A1 | 3/2011 |
| WO | WO 2011/082337 A1 | 7/2011 |
| WO | WO 2011/102399 A1 | 8/2011 |
| WO | WO 2011/104183 A1 | 9/2011 |
| WO | WO 2011/130628 A1 | 10/2011 |
| WO | WO 2012/004900 A1 | 1/2012 |
| WO | WO 2012/009452 A1 | 1/2012 |
| WO | WO 2012/030894 A1 | 3/2012 |
| WO | WO 2012/037204 A1 | 3/2012 |
| WO | WO 2012/151567 A1 | 11/2012 |
| WO | WO 2012/153796 A1 | 11/2012 |

(56) References Cited

FOREIGN PATENT DOCUMENTS

| | | |
|---|---|---|
| WO | WO 2012/156756 A2 | 11/2012 |
| WO | WO 2013/008217 A1 | 1/2013 |
| WO | WO 2013/032591 A1 | 3/2013 |
| WO | WO 2013/078126 A1 | 5/2013 |
| WO | WO 2013/087578 A1 | 6/2013 |
| WO | WO 2013/154878 A1 | 10/2013 |
| WO | WO 2014/040077 A1 | 3/2014 |
| WO | WO 2014/045039 A2 | 3/2014 |
| WO | WO 2014/124757 A1 | 8/2014 |
| WO | WO 2014/138562 A1 | 9/2014 |
| WO | WO 2014/143610 A1 | 9/2014 |
| WO | WO 2014/169167 A1 | 10/2014 |
| WO | WO 2015/025026 A1 | 2/2015 |
| WO | WO 2015/042497 A2 | 3/2015 |
| WO | WO 2015/043398 A1 | 4/2015 |
| WO | WO 2015/050798 A1 | 4/2015 |
| WO | WO 2015/054572 A1 | 4/2015 |
| WO | WO 2015/148714 A1 | 10/2015 |
| WO | WO 2015/160192 A1 | 10/2015 |
| WO | WO 2015/169421 A1 | 11/2015 |
| WO | WO 2015/183989 A1 | 12/2015 |
| WO | WO 2016/044772 A1 | 3/2016 |
| WO | WO 2016/049568 A1 | 3/2016 |
| WO | WO 2016/068580 A2 | 5/2016 |
| WO | WO 2016/142312 A1 | 9/2016 |
| WO | WO 2016/161361 A1 | 10/2016 |
| WO | WO 2016/164675 A1 | 10/2016 |
| WO | WO 2016/172692 A1 | 10/2016 |
| WO | WO 2016/183398 A1 | 11/2016 |
| WO | WO 2016/201257 A2 | 12/2016 |
| WO | WO 2017/015425 A1 | 1/2017 |
| WO | WO 2017/015562 A1 | 1/2017 |
| WO | WO 2017/031176 A1 | 2/2017 |
| WO | WO 2017/034377 A1 | 3/2017 |
| WO | WO 2017/040448 A1 | 3/2017 |
| WO | WO 2017/058728 A1 | 4/2017 |
| WO | WO 2017/058768 A1 | 4/2017 |
| WO | WO 2017/058805 A1 | 4/2017 |
| WO | WO 2017/058807 A1 | 4/2017 |
| WO | WO 2017/058902 A1 | 4/2017 |
| WO | WO 2017/059191 A1 | 4/2017 |
| WO | WO 2017/070256 | 4/2017 |
| WO | WO 2017/087528 A1 | 5/2017 |
| WO | WO 2017/112777 A1 | 6/2017 |
| WO | WO 2017/0172565 A1 | 10/2017 |
| WO | WO 2018/237084 | 12/2018 |
| WO | WO 2019/018359 A1 | 1/2019 |
| WO | WO 2019/105734 A1 | 6/2019 |
| WO | WO 2019/129059 A1 | 7/2019 |
| WO | WO 2019/180141 A1 | 9/2019 |

OTHER PUBLICATIONS

Written Opinion dated Mar. 10, 2020 for PCT/US2019/067179.
Al-Zaydi et al., Microwave assisted reaction of condensed thiophenes with electron poor olefins, J. Korean Chem. Soc., 47(6):591-596 (2003).
Anastassiadis et al., A Highly Selective Dual Insulin Receptor (IR)/insulin-like Growth Factor 1 Receptor (IGF-1R) Inhibitor Derived from an Extracellular Signal-Regulated Kinase (ERK) Inhibitor, J. Biol. Chem., 28(29):26068-28077 (2013).
Andrews M. et al., Cellular Mechanisms Underlying Complete Hematological Response of Chronic Myeloid Leukemia to BRAF and MEK1/2 Inhibition in a Patient with Concomitant Metastatic Melanoma, Clin Cancer Res., Dec. 1, 2015;21(23):5222-34.
Arlt A. and Schäfer H., Role of the immediate early response 3 (IER3) gene in cellular stress response, inflammation and tumorigenesis, Eur J Cell Biol., Jun.-Jul. 2011;90(6-7):545-52.
Arnst et al., Discovery and characterization of small molecule Rac1 inhibitors, Oncotarget, 8(21):34586-34600 (2017).
Arthur, J. et al., Mitogen-activated protein kinases in innate immunity, Nat. Rev. Immunol, 13, 679-692 (2013).
Bakir-Gungor, B. et al., Identification of possible pathogenic pathways in Behçet's disease using genome-wide association study data from two different populations, Eur. J. Hum. Genet., 23, 678-687 (2015).
Barili et al., 1985, A facile one pot synthesis of 2,9-disubstiuted 8-azapurin-6-ones (3,5-disubstitued 7-hydroxy-3H-1,2,3-triazolo[4,5-d]pyrimidines), J. Heterocyclic Chem., 22(6): 1607-1609.
Bartold, P. M. and Narayanan, A. S., Molecular and cell biology of healthy and diseased periodontal tissues, Periodontol., 2000 40, 29-49 (2006).
Bhatia, M. and Moochhala, S., Role of inflammatory mediators in the pathophysiology of acute respiratory distress syndrome, J. Pathol., 202, 145-156 (2004).
Bioorganic & Medicinal Chemistry Letters, 2013, vol. 23(9), pp. 2688-2691.
Bivona et al., Analysis of Ras and Rap activation in living cells using fluorescent Ras binding domains, Methods 37:138-145 (2005).
Bogolubsky et al., An old story in the parallel synthesis world: an approach to hydantoin libraries, ACS Comb. Sci., 20(1):35-43 (2018).
Bogolubsky et al., Dry HCl in parallel synthesis of fused pyrimidin-4-ones, J. Comb. Chem., 10(6):858-862 (2008).
Bohm et al., Über thieno-verbindungen 5. Mitteilung: basisch substituierte thieno[2,3-]pyrimidine, Pharmazie, Govi Verlag Pharmazeutischer Verlag GmbH, DE 41(1):23-25 (1986) with an English abstract.
Bonventre, J. V. and Zuk, A., Ischemic acute renal failure: An inflammatory disease?, Kidney Int, 66, 480-485 (2004).
Bourguignon, J. et al., Synthesis of thieno[2,3-d]pyrimidines substituted in positions 2 and 4, Bulletin de la Societe Chimique de France, 1975, 2(11-12):2483-2487.
Bourguignon, J. et al., Synthesis of thieno[2,3-d]pyrimidines substituted in positions 2 and 4, Bulletin de la Societe Chimique de France, 1975, 3-4(2):815-19.
Bouskine A. et al., Estrogens promote human testicular germ cell cancer through a membrane-mediated activation of extracellular regulated kinase and protein kinase A, Endocrinology, Feb. 2008;149(2):565-73. Epub Nov. 26, 2007.
Briel et al., Selective nucleophilic replacement of the benzylsulfanyl group in 2,4-disulfanyl-substituted thieno [2,3-d]pyrimidin-6-carboxylic acid derivatives by secondary amines, J. Heterocylic Chem., 42(5):841-846 (2005).
Briel et al., Synthesis of thieno[3,3-d]- and -[3,4-d]pyrimidines by alternative ring closure reactions, Pharmazie, 47(8):577-579 (1992) with English abstract.
Briel, Synthesis of thieno-heterocycles from substituted 5-(methylthio)thiophene-4-carbonitriles, Pharmazie, 53(4):227-231 (1998).
Buhler et al., 2014, p38 MAPK inhibitors: a patent review (2012-2013), Expert Opinion on Therapeutic Patents, 24(5): 535-554.
Burgess, J. K. et al., Dual ERK and phosphatidylinositol 3-kinase pathways control airway smooth muscle proliferation: Differences in asthma, J. Cell. Physiol., 216, 673-679 (2008).
Burotto et al., 2014, The MAPK Pathway Across Different Malignancies: A New Perspective, Cancer: 3446-3456.
CAS Registry No. 1030794-89-8; STN Entry Date Jun. 26, 2008.
CAS Registry No. 1119273-11-8; STN Entry Date Mar. 11, 2009.
CAS Registry No. 1259076-97-5; STN Entry Date Jan. 12, 2011.
CAS Registry No. 1290302-15-6; STN Entry Date May 5, 2011.
CAS Registry No. 1295857-87-2; STN Entry Date May 17, 2011.
CAS Registry No. 1298619-26-7; STN Entry Date May 22, 2011.
CAS Registry No. 941144-73-6; STN Entry Date Jul. 4, 2007.
CAS Registry No. 1033735-94-2; STN Entry Date Jul. 11, 2008.
CAS Registry No. 1032754-93-0; STN Entry Date Jul. 4, 2008.
CAS Registry No. 957054-30-7; STN Entry Date Dec. 7, 2007.
Caunt C. et al., MEK1 and MEK2 inhibitors and cancer therapy: the long and winding road, Nat Rev Cancer, Oct. 2015; 15(10):577-92.
Chang and Karin, Mammalian MAP kinase signalling cascades, Nature, 410, 37-40 (2001).
Chapman and Miner, Novel mitogen-activated protein kinase kinase inhibitors, Expert Opin Investig Drugs, Feb. 2011;20(2):209-20.

(56) References Cited

OTHER PUBLICATIONS

Choi et al., In silico discovery of quinoxaline derivatives as novel LRP5/6-sclerostin interaction inhibitors, Bioorg. Med. Chem. Lett., 28(6):1116-1121 (2018).
Choi, H. et al., Pathogenesis of Gout, Ann. Intern. Med., 143, 499-516 (2005).
Chu, A. J., Antagonism by bioactive polyphenols against inflammation: a systematic view, Inflamm. Allergy Drug Targets, 13, 34-64 (2014).
Chung, Pentafluorophenylhydrazine, Encyclopedia Reagents Organic Synthesis, e-EROS published online (2001) (5 pages).
Cichero et al., Exhaustive 3D-QSAR analyses as a computational tool to explore the potency and selectivity profiles of thieno[3,2-d]pyrimidin-4(3H)-one derivatives as PDE7 inhibitors, RSC Advances, 6(66):61088-61108 (2016).
Collin et al., Discovery of Rogaratinib (BAY 1163877): A pan-FGFR Inhibitor, Chem. Med. Chem., 13(5):437-445 (2018).
Colvin, R. B. and Smith, R. N., Antibody-mediated organ-allograft rejection. Nat. Rev. Immunol. 5, 807-817 (2005).
Crespo et al., Design, synthesis, and biological activities of new thieno[3,2-d] pyrimidines as selective type 4 phosphodiesterase inhibitors, J. Med. Chem., 41(21):4021-4035 (1998).
Croft M. et al., Clinical targeting of the TNF and TNER superfamilies, Nat. Rev. Drug Discov., 12 (2013) 147-168.
Cuevas, B. et al., Role of mitogen-activated protein kinase kinase kinases in signal integration, Oncogene, 26, 3159-3171 (2007).
Cummins A. et al., Persistent Localization of Activated Extracellular Signal-Regulated Kinases (ERK1/2) Is Epithelial Cell-Specific in an Inhalation Model of Asbestosis, Am. J. Pathol., 162, 713-720 (2003).
De Schutter et al., Targeting Bacillosamine Biosynthesis in Bacterial Pathogens: Development of Inhibitors to a Bacterial Amino-Sugar Acetyltransferase from *Campylobacter jejuni*, J. Med. Chem., 60(5):2099-2118 (2017).
Desai et al., Thieno(3,2-d)pyrimidines. Part-I. Preparation and Antimicrobial Activity of 3-N-Substituted-thioureido-2-methyl-6-phenylthieno(3, 2-d)pyrimidin-4(3H)-ones, J. Indian Chem. Soc., 74(2):160 (1997).
Desai et al., Thieno[3,2-d]pyrimidines. Part II: Preparation and antimicrobial activity of 2-methyl-3-N-arylsulfonamido-6-phenylthieno[3,2-d]pyrimidin-4(3H)-ones, J. Institution of Chemists (India), 67(5):136-137 (1995).
Desroches et al., Discovery of new hit-molecules targeting Plasmodium falciparum through a global SAR study of the 4-substituted-2-trichloromethylquinazoline antiplasmodial scaffold, Eur. J. Med. Chem., 125:68-86 (2017).
Dhillon et al., 2007, MAP kinase signaling pathways in cancer, Oncogene, vol. 26: 3279-3290.
Doddareddy MR. et al., Targeting mitogen-activated protein kinase phosphatase-1 (MKP-1): structure-based design of MKP-1 inhibitors and upregulators, Curr Med Chem., 2012;19(2):163-73. Review.
Dolly et al., 2016, Phase I study of apitolisib (GDC-0980), dual phosphatidylinositol-3-kinase and mammalian target of rapamycin kinase inhibitor, in patients with advanced solid tumors, Clin. Cancer Res., 22(12):2874-2884.
Dumaitre et al., Synthesis and cyclic GMP phosphodiesterase inhibitory activity of a series of 6-phenylpyrazolo[3,4-d]pyrimidones, J. Med. Chem., 39(8):1635-1644 (1996).
Dumitru C.D. et al., TNF-alpha induction by LPS is regulated posttranscriptionally via a Tp12/ERK-dependent pathway, Cell 103 (2000) 1071-1083.
Dupati et al., 2014, Vemurafenib: Background, Patterns of Resistance, and Strategies to Combat Resistance in Melanoma, Med. Student Res. Journal, 3(Winter): 36-43.
Elneairy et al., Bis-(cyanoacetamide)alkanes in heterocyclic synthesis: synthesis of bis-heteryl(carboxymido)alkanes and bis-(heteryl)alkanes of thiophene, pyrrole, thiazole and pyrimidinone series, J. Sulfur Chem., 33(3):373-383 (2012).

Endo et al., 2-(Isopropylamino)thieno[3,2-d]pyrimidin-4(3H)-one derivatives as selective phosphodiesterase 7 inhibitors with potent in vivo efficacy, Bioorg. Med. Chem. Lett., 25(9):1910-1914 (2015).
Englert et al., Fragment-based lead discovery: screening and optimizing fragments for thermolysin inhibition, ChemMedChem., 5(6):930-940 (2010).
Fan W. et al., Marsdenia tenacissima extract induces G0/G1 cell cycle arrest in human esophageal carcinoma cells by inhibiting mitogen-activated protein kinase (MAPK) signaling pathway, Chin J Nat Med., Jun. 2015; 13(6):428-37.
Feuerstein et al., Characterisation of the metal-ion-GDP complex at the active sites of transforming and nontransforming p21 proteins by observation of the $^{17}$O-Mn superhyperfine coupling and by kinetic methods, Eur. J. Biochem., 162:49-55 (1987).
Fortea, 4-Oxo-1,2,3,4-tetrahydrothienopyrimidine, Afinidad, 30(305):225-229 (1973) with English abstract.
Gaestel, M. et al., Targeting innate immunity protein kinase signalling in inflammation, Nat. Rev. Drug Discov., 8, 480-499 (2009).
Gantke T. et al., IKB kinase regulation of the TPL-2/ERK Mapk pathway, Immunol Rev., Mar. 2012;246(1):168-82.
Garg et al., Identification of new insulin growth factor receptor-1 (IGF-1R) inhibitors via exploring ATPas kinase domain of IGF-1R through virtual screening, Med. Chem. Res., 26:205-219 (2017).
Gascoigne et al., Cancer cells display profound intra- and interline variation following prolonged exposure to antimitotic drugs, Cancer Cell, 14(2):111-122 (2008).
Gellibert et al., 2009, Design of novel quinazoline derivatives and related analogues as potent and selective ALK5 inhibitors, Bioorganic & Medicinal Chemistry Letters, 19(8): 2277-2281.
Gillespie et al., Antagonists of the human adenosine A2A receptor, Part 1: Discovery and synthesis of thieno[3,2-d]pyrimidine-4-methanone derivatives, Bioorg. Med. Chem. Lett., 18(9):2916-2919 (2008).
Gillespie et al., Antagonists of the human adenosine A2A receptor. Part 2: Design and synthesis of 4-arylthieno[3,2-d]pyrimidine derivatives, Bioorg. Med. Chem. Lett., 18(9):2920-2923 (2008).
Girolomoni, G. and Pastore, S., The role of keratinocytes in the pathogenesis of atopic dermatitis, J. Am. Acad. Dermatol., 45, S25-S28 (2001).
Gronowitz et al., On thiophene analogues of metaqualone-like compounds, Acta Pharm. Suec., 5(6):563-578 (1968).
Guilding C. et al., Restored plasticity in a mouse model of neurofibromatosis type 1 via inhibition of hyperactive ERK and CREB, Eur J Neurosci., Jan. 2007;25(1):99-105.
Gupta et al., Identification of novel HIV-1 integrase inhibitors using shape-based screening, QSAR, and docking approach, Chem. Biol. Drug Des., 79(5):835-849 (2012).
Haase and Hunzelmann, Activation of Epidermal Growth Factor Receptor/ERK Signaling Correlates with Suppressed Differentiation in Malignant Acanthosis Nigricans, J. Invest. Dermatol., 118, 891-893 (2002).
Hajjem et al., Action Des Amines Et Des Hydrazines Sur Les Imidates Issus Du Methyl 3-Amino-2-Thiophene Carboxylate, Nouvelle Voie D'Acces Aux [3,2-d]4(3H)Thienopyrimidinones, Bulletin des Societes Chimiques Belges, 101(6):445-448 (1992).
Harikrishnan et al., Heterobicyclic Inhibitors of Transforming Growth Factor Beta Receptor I (TGFβRI), Bioorg. Med. Chem., 26(5):1026-1034 (2018).
Haswani et al., 2011, Synthesis and antimicrobial activity of novel 2-(pyridine-2-y1)thieno[2,3-d]pyrimidin-4(3H)-ones, Turk. J. Chem., Jan. 1, 2011, 925-924.
Hayakawa et al., Synthesis and biological evaluation of 4-morpholino-2-phenylquinazolines and related derivatives as novel PI3 kinase p110alpha inhibitors, Bioorg. Med. Chem., 14(20):6847-6858 (2006).
Hilger et al., 2002, The Ras-Raf-MEK-ERK Pathway in the Treatment of Cancer, Onkologie, 25: 511-518.
Holland et al., 1975, Antiallergic activity of 8-azapurin-6-ones with heterocyclic 2-substituents, European Journal of Medicinal Chemistry, 10(5), 447-44.
Howlett M. et al., Cytokine signalling via gp130 in gastric cancer, Biochim Biophys Acta, Nov. 2009;1793(11):1623-33.

(56) References Cited

OTHER PUBLICATIONS

Hrast et al., Synthesis and structure-activity relationship study of novel quinazolinone-based inhibitors of MurA, Bioorg. Med. Chem. Lett., 27(15):3529-3533 (2017).
Huang et al., 2010, MAPK signaling in inflammation-associated cancer development, Protein Cell, 1(3):218-226.
Huang et al., 2013, B-RAf and the inhibitors: from bench to bedside, J. of Hematol. & Oncology, 6: 30.
Hyman et al., 2015, Vemurafenib in Multiple Nonmelanoma Cancers with BRAF V600 Mutations, N Engl J Med., 373(8):726-36.
Iyer et al., Synthesis of 1,3,4-oxadizoles as promising anticoagulant agents, RSC Adv., 6:24797-24807 (2016).
Jeffrey, K. et al., Targeting dual-specificity phosphatases: manipulating MAP kinase signalling and immune responses, Nat. Rev. Drug Discov., 6, 391-403 (2007).
Ji, R. et al., MAP kinase and pain, Brain Res. Rev., 60(1), 135-148 (2009).
Ji, R.-R. and Suter, M. R., p38 MAPK, microglial signaling, and neuropathic pain, Mol. Pain, 3, 33 (2007).
Johansen, C. et al., The mitogen-activated protein kinases p38 and ERK1/2 are increased in lesional psoriatic skin, Br. J. Dermatol., 152, 37-42 (2005).
John et al., Kinetic and structural analysis of the Mg2+-binding site of the guanine nucleotide-binding protein $p21^{H-ras}$, J. Bio. Chem., 268(2):923-929 (1993).
John et al., Kinetics of interaction of nucleotides with nucleotide-free H-ras p21, Biochem., 29:6058-6065 (1990).
Jokinen and Koivunen, Mek and PI3K inhibition in solid tumors: rationale and evidence to date. Ther Adv Med Oncol., May 2015;7(3):170-80.
Juszczak, Bioorg. & Med. Chem. Lett., 22:5466-5469 (2012).
Kabir S., The role of interleukin-17 in the Helicobacter pylori induced infection and immunity. Helicobacter, Feb. 2011;16(1):1-8.
Kadmiel, M. and Cidlowski, J. A., Glucocorticoid receptor signaling in health and disease, Trends Pharmacol. Sci., 34, 518-530 (2013).
Kammoun et al., Action des hydrazines perfluoroalkylees sur les iminoesters synthese des perfluoroalkyl-3-aminothienopyrimidinones et des perfluoroalkyl-1,2,4-triazin-6-ones, J. Fluorine Chem., 105(1):83-86 (2000).
Karnoub et al., Ras oncogenes: split personalities, Nat. Rev. Mol. Cell Biol., 9(7):517-531 (2008).
Kaul, M. et al., Pathways to neuronal injury and apoptosis in HIV-associated dementia, Nature, 410, 988-994 (2001).
Kfoury A. et al., Dual function of MyD88 in inflammation and oncogenesis: implications for therapeutic intervention, Curr Opin Oncol., Jan. 2014;26(1):86-91.
Khan et al., 2013, 2,5-Disubstituted-1,3,4-oxadiazoles: thymidine phosphorylase inhibitors, Medicinal Chemistry Research, 22(12): 6022-6028.
Kim and Choi, Compromised MAPK signaling in human diseases: an update, Arch Toxicol., Jun. 2015;89(6):867-82.
Kim et al., Serendipitous discovery of 2-((phenylsulfonyl)methyl)-thieno[3,2-d]pyrimidine derivatives as novel HIV-1 replication inhibitors, Bioorg. Med. Chem. Lett., 24(23):5473-5477 (2014).
Kim et al., Structural modifications at the 6-position of thieno [2,3-d]pyrimidines and their effects on potency at FLT3 for treatment of acute myeloid leukemia, Eur. J. Med. Chem., 120:74-85 (2016).
Kim, E. K. and Choi, E.-J., Pathological roles of MAPK signaling pathways in human diseases, Biochim. Biophys., Acta BBA-Mol. Basis Dis., 1802, 396-405 (2010).
King et al., 2013, Dabrafenib: Preclinical Characterization, Increased Efficacy when Combined with Trametinib, while BRAF/MEK Tool Combination Reduced Skin Legions, PLOS ONE, 8(7): e67583.
Ko Jk and Auyeung Kk., Target-oriented mechanisms of novel herbal therapeutics in the chemotherapy of gastrointestinal cancer and inflammation, Curr Pharm Des., 2013;19(1):48-66. Review.
Kolata, G., A Faster Way to Try Many Drugs on Many Cancers, The New York Times article dated Feb. 25, 2015 (5 pages); https://www.nytimes.com/2015/02/26/health/fast-track-attacks-on-cancer-accelerate-hopes.html accessed on Apr. 4, 2018.
Kontoyiannis D., et al., Genetic dissection of the cellular pathways and signaling mechanisms in modeled tumor necrosis factor-induced Crohn's-like inflammatory bowel disease, J. Exp. Med., 196 (2002) 1563-1574.
Kopra et al., A homogeneous quenching resonance energy transfer assay for the kinetic analysis of the GTPase nucleotide exchange reaction, Anal. Bioanal. Chem., 406:4147-4156 (2014).
Kucherenko et al., Positional isomers of thienopyrimidinones, Chem. Heterocycl. Comp., 44(6):750-758 (2008).
Kumar et al., 2009, An efficient synthesis and biological study of novel indolyl-1,3,4-oxadiazoles as potent anticancer agents, Bioorganic & Medicinal Chemistry Letters, 19(15): 4492-4494.
Kumar et al., Merging C-H Bond Functionalization with Amide Alcoholysis: En Route to 2-Aminopyridines, ACS Catalysis, 6(6):3531-3536 (2016).
Kumar, S. et al., Intracellular signaling pathways as a target for the treatment of rheumatoid arthritis, Curr. Opin. Pharmacol., 1, 307-313 (2001).
Kurasawa et al., 2-Aminomethylthieno[3,2-d]pyrimidin-4(3H)-ones bearing 3-methylpyrazole hinge binding moiety: Highly potent, selective, and time-dependent inhibitors of Cdc7 kinase, Bioorg. Med. Chem., 25(14):3658-3670 (2017).
Kyriakis and Avruch, Mammalian Mitogen-Activated Protein Kinase Signal Transduction Pathways Activated by Stress and Inflammation, Physiol. Rev., 81, 807-869 (2001).
Kyrmizi, I. et al., Tp12 kinase regulates FcgammaR signaling and immune thrombocytopenia in mice, J. Leukoc. Biol., 94 (2013) 751-757.
Labib et al., Design, synthesis and biological evaluation of novel thiophene and theinopyrimidine derivatives as anticancer agents, Med. Chem. Res., 25(11):2607-2618 (2016).
Lack et al., Correction to Targeting the Binding Function 3 (BF3) Site of the Human Androgen Receptor through Virtual Screening, J. Med. Chem.,55(1):565 (2012).
Lack et al., Targeting the binding function 3 (BF3) site of the human androgen receptor through virtual screening, J. Med. Chem., 54(24):8563-8573 (2011).
Lawrenz, M. et al., Genetic and pharmacological targeting of TPL-2 kinase ameliorates experimental colitis: a potential target for the treatment of Crohn's disease?, Mucosal Immunol., 5 (2012) 129-139,.
Lee et al., A facile synthesis of 3-substituted 2-cyanoquinazolin-4(3H)-ones and 3-alkyl-2-cyanothieno[3,2-d]pyrimidin-4(3H)-ones via 1,2,3-dithiazoles, J. Heterocyc. Chem., 35(3):659-668 (1998).
Lenzen et al., Kinetic analysis by fluorescence of the interaction between Ras and the catalytic domain of the guanine nucleotide exchange factor Cdc25, Biochem., 37:7420-7430 (1998).
Lerner, C. G. et al., Novel approach to mapping of resistance mutations in whole genomes by using restriction enzyme modulation of transformation efficiency, Antimicrobial Agents and Chemotherapy, 2005, vol. 49(7), pp. 2767-2777.
Leung, P. S. and Chan, Y. C., Role of oxidative stress in pancreatic inflammation, Antioxid. Redox Signal, 11, 135-165 (2009).
Li et al., 2011, Induction of Cancer Cell Death by Isoflavone: The Role of Multiple Signaling Pathways, Nutrients, 3: 877-896.
Lindh et al., Toward a benchmarking data set able to evaluate ligand- and structure-based virtual screening using public HTS data, J. Chem. Inf. Model., 55(2):343-353 (2015).
Lingayya et al., Palladium(ii)-catalyzed direct O-alkenylation of 2-arylquinazolinones with N-tosylhydrazones: an efficient route to O-alkenylquinazolines, Chem. Commun. (Camb)., 53(10):1672-1675 (2017).
Liu et al., Design, synthesis and biological evaluation of novel thieno[3,2-d]pyrimidine derivatives containing diaryl urea moiety as potent antitumor agents, Eur. J. Med. Chem., 85:215-227 (2014).
Liu et al., Design, synthesis and biological evaluation of novel thieno[3,2-d]pyrimidine derivatives possessing diaryl semicarbazone scaffolds as potent antitumor agents, Eur. J. Med. Chem., 87:782-793 (2014).
Liu, Y. et al., MAPK phosphatases—regulating the immune response. Nat. Rev. Immunol., 7, 202-212 (2007).

(56) References Cited

OTHER PUBLICATIONS

Lorusso et al., One step at a time—clinical evidence that KRAS is indeed druggable, N. Engl. J. Med., doi: 10.1056/NEJMe202637, Epub Sep. 20, 2020.

Lu et al., Drugging Ras GTPase: A Comprehensive Mechanistic and Signaling Structural View, Chem. Soc. Rev., 45:4929 (2016) DOI: 10.1039/c5cs00911a.

Manzoor et al., 2012, Mitogen-activated protein kinases in inflammation, J. Bacter, Virology, vol. 42(3): 189-195.

Mao, H. et al., Deregulated Signaling Pathways in Glioblastoma Multiforme: Molecular Mechanisms and Therapeutic Target, Cancer Invest., Jan. 2012;30(1):48-56.

McCoull et al., Identification of pyrazolo-pyrimidinones as GHS-R1a antagonists and inverse agonists for the treatment of obesity, Med. Chem. Commun., 4(2):456-462 (2013).

McLendon, R. et al., Comprehensive genomic characterization defines human glioblastoma genes and core pathways, Nature, 2008; 455(7216):1061-1068.

Memorial Sloan Kettering Press Release on Aug. 19, 2015 titled Memorial Sloan Kettering Cancer Center Researchers Publish Landmark 'Basket Study' (3 pages); https://www.mskcc.org/press-releases/memorial-sloan-kettering-center-researchers-publish-landmark-basket-study accessed on Apr. 4, 2018.

Memorial Sloan Kettering Press Release on Nov. 6, 2017 titled FDA Announces First Approval of Targeted Therapy Based on Basket Study (3 pages); https://www.mskcc.org/trending-topics/fda-announces-first-approval-targeted-therapy-based-basket-study accessed on Apr. 4, 2018.

Metz et al., From determinants of RUNX1/ETO tetramerization to small-molecule protein-protein interaction inhibitors targeting acute myeloid leukemia, J. Chem. Inf. Model., 53(9):2197-2202 (2013).

Milligan, E. D. and Watkins, L. R., Pathological and protective roles of glia in chronic pain, Nat. Rev. Neurosci., 10, 23-36 (2009).

Mitra and Cote Molecular pathogenesis and diagnostics of bladder cancer, Annu Rev Pathol., 2009;4:251-85.

Miyamoto, Antitumor activity of 5-substituted 2-acylamino-1,3,4-thiadiazoles against transplantable rodent tumors, Chem. Pharm. Bull., 33(11):5126-5129 (1985).

Mohan et al., A facile synthesis and thio-Claisen rearrangement of 3-aryl-2-phenyl-5-prop-2-ynylsulfanyl-3H-pyrimidin-4-ones: regioselective transformation to thieno [3,2-d]pyrimidin-4-ones, Tetrahedron, 45(31):6075-6077 (2004).

Mohan et al., Facile synthesis and regioselective thio-Claisen rearrangements of 5-prop-2-ynyl/enyl-sulfanyl pyrimidinones: transformation to thienopyrimidinones, Tetrahedron, 61(45):10774-10780 (2005).

Mohanta et al., A short synthesis of quinazolinocarboline alkaloids rutaecarpine, hortiacine, euxylophoricine A and euxylophoricine D from methyl N-(4-chloro-5H-1,2,3-dithiazol-5-ylidene)anthranilates, Tetrahedron Letters, 43(22):3993-3996 (2002).

Mohanta et al., New Synthetic Route to Tetracyclic Quinazolin-4(3H)-one Ring System, Heterocycles, 57(8):1471-1485 (2002).

Morel, J. and Berenbaum, F., Signal transduction pathways: new targets for treating rheumatoid arthritis, Joint Bone Spine, 71, 503-510 (2004).

Mossman, B. et al., Oxidants and Signaling by Mitogen-Activated Protein Kinases in Lung Epithelium, Am. J. Respir, Cell Mol. Biol., 34, 666-669 (2006).

Muranen et al., ERK and p38 MAPK activities determine sensitivity to P13K/mTOR inhibition via regulation of MYC and YAP, Cancer Res., 76(24):7168-7180 (2016).

Muranen et al., ERK and p38 MAPK activities determine sensitivity to P13K/mTOR inhibition via regulation of MYC and YAP, Cancer Res., 76(24):7168-7180 (2016). Abstract Only.

Murdoch et al., 1986, Synthesis of [1,2,4]triazoloquinazolinones and imidazoquinazolinones, J. of Heterocyclic Chem., 23(3): 833-841.

Nara et al., Thieno[2,3-d]pyrimidine-2-carboxamides bearing a carboxybenzene group at 5-position: highly potent, selective, and orally available MMP-13 inhibitors interacting with the S1" binding site, Bioorg. Med. Chem., 22(19):5487-5505 (2014).

National Cancer Institute, Mek: A Single Drug Target Shows Promise in Multiple Cancers [https://www.cancer.gov/about-cancer/treatement/research/mek, accessed Nov. 27, 2017].

Neidlein et al., Synthesis of 1,2,3,4-Tetrahydro-4-oxothieno[3,2-d]pyrimidine and Perhydropyrimidine Derivates from Alkyl Dicyanoacetates, Helvetica Chimica Acta, 74(3):579-584 (1991).

Ni et al., Drugging K-RASG12C through Covalent Inhibitors: Mission Possible?, Pharmacology & Therapeutics, 202:1-17 (2019).

Nolan et al., Identification of a novel selective serotonin reuptake inhibitor by coupling monoamine transporter-based virtual screening and rational molecular hybridization, ACS Chem. Neurosci., 2(9):544-552 (2011).

Obata, K. and Noguchi, K., Mapk activation in nociceptive neurons and pain hypersensitivity, Life Sci., 74, 2643-2653 (2004).

O'Dowd et al., Identification and Structure-Guided Development of Pyrimidinone Based USP7 Inhibitors, ACS Med. Chem. Lett., 9(3):238-243 (2018).

Oh et al., Synthetic strategy for increasing solubility of potential FLT3 inhibitor thieno[2,3-d]pyrimidine derivatives through structural modifications at the C2 and C6 positions, Bioorg. Med. Chem. Lett., 27:496-500 (2017).

Ostrem et al., Direct small-molecule inhibitors of KRAS: from structural insights to mechanism-based design, Nature Reviews Drug Discovery, doi: 10.1038/nrd.2016.139, pp. 1-25 (2016).

Pace et al., Dihydroxypyrimidine-4-carboxamides as Novel Potent and Selective HIV Integrase Inhibitors, J. Med. Chem., 50:2225-2239 (2007).

Pagare et al., 1,2,4-triazole - a versatile azole, proves and popular as an antifungal agent, Int. J. Chem. Concepts, 2(2): 132-144 (2016).

Papke et al., Drugging RAS: know the enemy, Science, 355:1158-1163 (2017).

Park et al., Discovery of thienopyrimidine-based FLT3 inhibitors from the structural modification of known IKKB inhibitors, Bioorg. Med. Chem. Letts., 24:2655-2660 (2014).

Pearson and Regad, Targeting cellular pathways in glioblastoma multiforme, Signal Transduction and Targeted Therapy, 2017; 2:e17040.

Pereda, J. et al., Effect of Simultaneous Inhibition of TNF-a Production and Xanthine Oxidase in Experimental Acute Pancreatitis. Ann. Surg., 240, 108-116 (2004).

Pereira et al., Synthesis of novel 2,3-condensed thieno[2,3-d]pyrimidin-4-ones via Appel's salt chemistry, J. Sulfur Chem., 27(1):49-55 (2005).

Perspicace et al., Design, synthesis and biological evaluation of new classes of thieno [3,2-d]pyrimidinone and thieno[1,2,3]triazine as inhibitor of vascular endothelial growth factor receptor-2 (VEGFR-2), Eur. J. Med. Chem., 63:765-781 (2013).

Perspicace et al., Synthesis and biological evaluation of thieno[3,2-d]- pyrimidinones, thieno[3,2-d]pyrimidines and quinazolinones: conformationally restricted 17b-hydroxysteroid dehydrogenase type 2 (17b-HSD2) inhibitors, Molecules, 18(4):4487-4509 (2013).

Peti, W and Page R., Molecular basis of MAP kinase regulation, Protein Sci., Dec. 2013;22(12):1698-710.

Plaskon et al., A synthesis of 5-hetaryl-3-(2-hydroxybenzoyl)pyrroles, Tetrahedron, 64(25):5933-5943 (2008).

Principi M. et al., Fibrogenesis and fibrosis in inflammatory bowel diseases: Good and bad side of same coin?, World J Gastrointest Pathophysiology: 100-7.

Puneet, P. et al., Chemokines in acute respiratory distress syndrome. Am. J. Physiol.-Lung Cell. Mol. Physiol., 288, L3-L15 (2005).

Qiu et al., Potassium hydroxide-promoted transition-metal-free synthesis of 4(3H)-quinazolinones, Monatsh. Chem., 146:1343-1347 (2015).

Rhee et al., Synthesis and biological studies of catechol ether type derivatives as potential phosphodiesterase (PDE) IV inhibitors, Arch. Pharm. Res., 22(2):202-207 (1999).

Ried et al., New 4-hydroxythienopyrimidines, Angewandte Chemie, International Edition in English, 7(2):136 (1968).

Ried et al., Reactions with imidic acid esters, Justus Liebigs Annalen der Chemie, 713:143-148 (1968) with English abstract.

(56) References Cited

OTHER PUBLICATIONS

Ried et al., Thienopyrimidones, Justus Liebigs Annalen der Chemie, 716:219-221 (1968) with English abstract.
RN 1082254-06-5 Registry, Database Registry [Online], Retrieved from STN, Dec. 9, 2008, retrieved on Sep. 16, 2020.
RN 1082254-09-8 Registry, Database Registry [Online], Retrieved from STN, Dec. 9, 2008, retrieved on Sep. 16, 2020.
RN 1082254-12-3 Registry, Database Registry [Online], Retrieved from STN, Dec. 9, 2008, retrieved on Sep. 16, 2020.
RN 1082254-15-6 Registry, Database Registry [Online], Retrieved from STN, Dec. 9, 2008, retrieved on Sep. 16, 2020.
RN 1082436-68-7 Registry, Database Registry [Online], Retrieved from STN, Dec. 9, 2008, retrieved on Sep. 16, 2020.
RN 1082436-69-8 Registry, Database Registry [Online], Retrieved from STN, Dec. 9, 2008, retrieved on Sep. 16, 2020.
RN 1082436-71-2 Registry, Database Registry [Online], Retrieved from STN, Dec. 9, 2008, retrieved on Sep. 16, 2020.
RN 1082436-72-3 Registry, Database Registry [Online], Retrieved from STN, Dec. 9, 2008, retrieved on Sep. 16, 2020.
RN 1082436-73-4 Registry, Database Registry [Online], Retrieved from STN, Dec. 9, 2008, retrieved on Sep. 16, 2020.
RN 1082466-26-9 Registry, Database Registry [Online], Retrieved from STN, Dec. 9, 2008, retrieved on Sep. 16, 2020.
RN 1082466-31-6 Registry, Database Registry [Online], Retrieved from STN, Dec. 9, 2008, retrieved on Sep. 16, 2020.
RN 1082466-33-8 Registry, Database Registry [Online], Retrieved from STN, Dec. 9, 2008, retrieved on Sep. 16, 2020.
RN 1082466-37-2 Registry, Database Registry [Online], Retrieved from STN, Dec. 9, 2008, retrieved on Sep. 16, 2020.
RN 1082466-38-3 Registry, Database Registry [Online], Retrieved from STN, Dec. 9, 2008, retrieved on Sep. 16, 2020.
RN 1082530-53-7 Registry, Database Registry [Online], Retrieved from STN, Dec. 9, 2008, retrieved on Sep. 16, 2020.
RN 1082530-59-3 Registry, Database Registry [Online], Retrieved from STN, Dec. 9, 2008, retrieved on Sep. 16, 2020.
RN 1082530-61-7 Registry, Database Registry [Online], Retrieved from STN, Dec. 9, 2008, retrieved on Sep. 16, 2020.
RN 1159822-04-4 Registry, Database Registry [Online], Retrieved from STN, Jun. 24, 2009, retrieved on Sep. 16, 2020.
RN 1248137-85-0 Registry, Database Registry [Online], Retrieved from STN, Oct. 28, 2010, retrieved on Sep. 16, 2020.
RN 1248693-25-5 Registry, Database Registry [Online], Retrieved from STN, Oct. 29, 2010, retrieved on Sep. 16, 2020.
RN 1248913-17-8 Registry, Database Registry [Online], Retrieved from STN, Nov. 1, 2010, retrieved on Sep. 16, 2020.
RN 1248997-75-2 Registry, Database Registry [Online], Retrieved from STN, Oct. 31, 2010, retrieved on Sep. 16, 2020.
RN 1285166-39-3 Registry, Database Registry [Online], Retrieved from STN, Apr. 24, 2011, retrieved on Sep. 16, 2020.
RN 1484414-46-1 Registry, Database Registry [Online], Retrieved from STN, Dec. 1, 2013, retrieved on Sep. 16, 2020.
RN 1489808-81-2 Registry, Database Registry [Online], Retrieved from STN, Dec. 8, 2013, retrieved on Sep. 16, 2020.
RN 1517154-38-9 Registry, Database Registry [Online], Retrieved from STN, Jan. 12, 2014, retrieved on Sep. 16, 2020.
Ryabukhin et al., Chlorotrimethylsilane-mediated synthesis of 2-ayl-1-chloro-1-heteroarylalkenes, Synthesis, 20:3163-3170 (2007).
Sampognaro et al., Proline Isosteres in a Series of 2,4-disubstituted pyrrolo[1,2-f][1,2,4]triazine Inhibitors of IGF-IR Kinase and IR Kinase, Bioorg. Med. Chem. Lett., 20(17):5027-5030 (2010).
Sanchez et al., Microwave-assisted synthesis of potent PDE7 inhibitors containing a thienopyrimidin-4-amine scaffold, Org. Biomol. Chem., 12(24):4233-4242 (2014).
Santarpia et al., 2012, Targeting the MAPK-RAS-RAF signaling pathway in cancer therapy, Expert Opin. Ther. Targets, vol. 16(1):103-119.
Sanz-Garcia C. et al., Sterile inflammation in acetaminophen-induced liver injury is mediated by Cot/tp12, J. Biol. Chem., 288 (2013) 15342-15351.
Sarker et al., 2015, First-in-human phase I study of pictilisib (GDC-0941), a potent pan-class I phosphatidylinositol-3-kinase (PI3K) inhibitor, in patients with advanced solid tumors, Clin Cancer Res., 21(1):77-86.
Sasaki, K. et al., The role of MAPK pathway in bone and soft tissue tumors, Anticancer Res., Feb. 2011;31(2):549-554.
Sasikumar et al., A-ring Modifications on the Triazafluorenone Core Structure and Their mGluR1 Antagonist Properties, Bioorg. Med. Chem. Lett., 20(8):2474-2477 (2010).
Savino, B. et al., ERK-dependent downregulation of the atypical chemokine receptor D6 drives tumor aggressiveness in Kaposi sarcoma, Cancer Immunol Res., Jul. 2014;2(7):679-89.
Saxena, A. S. et al., A convenient and expeditious synthesis of annulated N,S-heterocycles, Journal of the Indian Chemical Society, 2003, vol. 80(4), pp. 311-318.
Schuh, K. and Pahl, A., Inhibition of the MAP kinase ERK protects from lipopolysaccharide-induced lung injury. Biochem. Pharmacol., 77, 1827-1834 (2009).
Schultze, S. et al., PI3K/AKT, Mapk and AMPK signalling: protein kinases in glucose homeostasis, Expert Rev. Mol. Med., 14, el (2012).
Shishoo et al., Synthesis of some tituted-6-phenyl-thieno(3,2-d)pyrimidin-4(3H)-ones and 7-phenyl-thieno[3,2-d]pyrimidin-4(3H)-ones, Indian J. Chem. Sect. B: Organic Chemistry, including Medicinal Chemistry, 33B(5):436-440 (1994).
Shook, B. C. et al., Substituted thieno[2,3-d]pyrimidines as adenosine A2A receptor antagonists, Bioorganic & Medicinal Chemistry Letters, 2013, vol. 23(9), pp. 2688-2691.
Shutes et al., Specificity and mechanism of action of EHT 1864, a novel small molecule inhibitor of Rac family small GTPases, J. Biol. Chem., 282(49):35666-35678 (2007).
Smith et al., Activating K-Ras mutations outwith 'hotspot' codons in sporadic colorectal tumours—implications for personalised cancer medicine, Br. J. Cancer, 102:693-703 (2010).
Smith, R. et al., Recent advances in the research and development of RAF kinase inhibitors. Curr Top Med Chem., 2006;6(11):1071-89. Review.
Snegaroff et al., Direct metallation of thienopyrimidines using a mixed lithium-cadmium base and antitumor activity of functionalized derivatives, Org. Biomol. Chem., 7(22):4782-4788 (2009).
Souza, R. F. et al., Acid exposure activates the mitogen-activated protein kinase pathways in Barrett's esophagus, Gastroenterology, 122, 299-307 (2002).
Spangler et al., Kinetic determination of the GTPase activity of Ras proteins by means of a luminescent terbium complex, Anal. Bioanal. Chem., 394:989-996 (2009).
Sriskantharajah, S. et al., Regulation of experimental autoimmune encephalomyelitis by TPL-2 kinase, J. Immunol., 192 (2014) 3518-3529.
Stephen et al., Dragging Ras back in the ring, Cancer Cell, 25:272-281 (2014).
Supuran et al., 2000, Carbonic anhydrase inhibitors- Part 94. 1,3,4-Thiadiazole-2-sulfonamide derivatives as antitumor agents?, European J. of Medicinal Chemistry, Editions Scientifique, 35(9): 867-874.
Supuran et al., 2001, Carbonic Anhydrase Inhibitors: Sulfonamides as Antitumor Agents?, Bioorganic & Medicinal Chemistry, 9(3): 703-714.
Sutherlin et al., 2011, Discovery of a potent, selective, and orally available class I phosphatidylinositol 3-kinase (PI3K)/mammalian target of rapamycin (mTOR) kinase inhibitor (GDC-0980) for the treatment of cancer, J Med Chem., 54(21):7579-87.
Svejda, B. et al., Limitations in small intestinal neuroendocrine tumor therapy by mTor kinase inhibition reflect growth factor-mediated PI3K feedback loop activation via ERK1/2 and AKT, Cancer, Sep. 1, 20115;117(18):4141-54.
Theoclitou et al., Discovery of (+)-N-(3-aminopropyl)-N-[1-(5-benzyl-3-methyl-4-oxo-[1,2]thiazolo[5,4-d]pyrimidin-6-yl)-2-methylpropyl]-4-methylbenzamide (AZD4877), a kinesin spindle protein inhibitor and potential anticancer agent, J. Med. Chem., 54(19):6734-6750 (2011).
Tominaga et al., Synthesis and Reaction of 3, 4-Diaminothiophenes, Yakugaku Zasshi, 99(11):1081-1090 (1979) with English abstract.

(56) References Cited

OTHER PUBLICATIONS

Toney et al., Antibiotic sensitization using biphenyl tetrazoles as potent inhibitors of Bacteroides fragilis metallo-beta-lactamase, Chem. Biol., 5(4): 185-196 (1998).

Trujillo, 2011, MEK inhibitors: a patent review 2008- 2010, Expert Opinion on Therapeutic Patents, 21(7): 1045-1069.

Tsuboi et al., Potent and selective inhibitors of glutathione S-transferase omega 1 that impair cancer drug resistance, J. Am. Chem. Soc., 133(41):16605-16616 (2011).

Turkmen et al., 2005, Carbonic anhydrase inhibitors. Novel sulfanilimide/acetazolamide derivatives obtained by the tail approach and their interaction with the cytosolic isozymes I and II, and the tumor-associated isozyme IX, Bioorganic & Medicinal Chemistry Letters, 15(2): 367-372.

Vairaktaris, E. et al., Diabetes and oral oncogenesis, Anticancer Res., Nov. 2007-Dec. 27(6B):4185-93. Review.

Vasan et al., Inhibitors of the salicylate synthase (MbtI) from Mycobacterium tuberculosis discovered by high-throughput screening, ChemMedChem, 5(12):2079-2087 (2010).

Vigil et al., Ras superfamily GEFs and GAPs: validated and tractable targets for cancer therapy?, Nat. Rev. Cancer, 10(12):842-857 (2010).

Vlaeminck-Guillem, V. et al., SRC: marker or actor in prostate cancer aggressiveness, Front Oncol., Aug. 18, 2014;4:222.

Vougioukalaki, M. et al., Eliopoulos, Tpl2 kinase signal transduction in inflammation and cancer, Cancer Lett., 304 (2011) 80-89.

Vyas et al., Pharmacophore and docking-based hierarchical virtual screening for the designing of aldose reductase inhibitors: synthesis and biological evaluation, Med. Chem. Res., 25(4):609-626 (2016).

Wang et al., Inhibition of tumor cell proliferation by thieno[2,3-d]pyrimidin-4(1H)-one-based analogs, Bioorg. Med. Chem. Lett., 15(16):3763-3766 (2005).

Wang et al., MicroRNA-302b suppresses cell proliferation by targeting EGFR in human hepatocellular carcinoma SMMC-7721 cells, BMC Cancer, 2013; 13:448.

Wei et al., An environment-friendly synthesis of 4(3H)-quinazolinones, Toxicol. Environ. Chem., 97(1):2-10 (2015).

Welsch, M.E. et al., Multivalent Small-Molecule Pan-RAS Inhibitors Cell, Feb. 2, 20173;168(5):878-889.e29.

Westerlund, The synthetic utility of heteroaromatic azido compounds. Part VII. Preparation of some 2- and 4-substituted thieno[3,2-d]pyrimidines, J. Heterocyclic Chem., 17(8):1771-1775 (1980).

Wick, G. et al., Autoimmune and Inflammatory Mechanisms in Atherosclerosis, Annu. Rev. Immunol., 22, 361-403 (2004).

Williams, B. et al., Age-dependent loss of NGF signaling in the rat basal forebrain is due to disrupted MAPK activation, Neurosci. Lett., 413, 110-114 (2007).

Williams, Reverse fingerprinting, similarity searching by group fusion and fingerprint bit importance, Mol. Divers., 10(3):311-332 (2006).

Wong, W. F., Inhibitors of the tyrosine kinase signaling cascade for asthma, Curr. Opin. Pharmacol., 5, 264-271 (2005).

Wu and Park, MEK1/2 Inhibitors: Molecular Activity and Resistance Mechanisms, Semin Oncol., Dec. 2015;42(6):849-62.

Wu et al., Cyclooxygenase-2 in tumorigenesis of gastrointestinal cancers: an update on the molecular mechanisms, Cancer Lett, Sep. 1, 2010;295(1):7-16.

Xia et al., 2010, Synthesis and biological activity test of some new five membered heterocycles, Chinese J. of Chemistry, 28(12): 2433-2440.

Yamamoto, R. et al., B7-H1 expression is regulated by MEK/ERK signaling pathway in anaplastic large cell lymphoma and Hodgkin lymphoma, Cancer Sci., Nov. 2009;100(11):2093-100.

Yang et al., Synthesis and biological evaluation of novel thieno[2,3-d]pyrimidine-based FLT3 inhibitors as anti-leukemic agents, Eur. J. Med. Chem., 85:399-407 (2014).

Yin, D. et al., mi-R-34a functions as a tumor suppressor modulating EGFR in glioblastoma multiforme. Oncogene 2013; 32:1155-63.

Yurchenko and Sidorenko, Hodgkin's lymphoma: the role of cell surface receptors in regulation of tumor cell fate, Exp Oncol., Dec. 2010;32(4):214-23. Review.

Zadorozhny et al., Condensed isoquinolines 32. Synthesis of 4H-thieno-[3',2':5,6]-and-[2',3': 5,6]pyrimido-[1,2-b]isoquinolines and 6,12-dihydro-5H-isoquino-[2,3-a]quinazoline-5,12-dione derivatives, Chem. Heterocycl. Comp., 44(7):845-851 (2008).

Zadorozhny et al., Synthesis of substituted 4-oxo-3,4-dihydro-thieno[3,4-d]pyrimidines and comparison of their properties with those of positionally isomeric thienopyrimidinones and benzo isosteres, Chem. Heterocycl. Comp., 46(8):991-997 (2010).

Zaganjor et al., 2011, Functions and modulation of MAP kinase pathways, Tocris Reviews, No. 35, 12 pages.

Zebisch, A. et al., Signaling through RAS-RAF-MEK-ERK: from basics to bedside. Curr Med Chem. 2007;14(5):601-23. Review.

Zenali, M .et al., Morphoproteomic confirmation of constitutively activated mTOR, ERK, and NF-kappaB pathways in Ewing family of tumors. Ann Clin Lab Sci. 2009 Spring;39(2):160-6. Review.

Zhang, H. Y. et al., Differences in activity and phosphorylation of MAPK enzymes in esophageal squamous cells of GERD patients with and without Barrett's esophagus, Am. J. Physiol.-Gastrointest. Liver Physiol, 295, G470-G478 (2008).

Zhao and Ramaswamy, Mechanisms and therapeutic advances in the management of endocrine-resistant breast cancer, World J Clin Oncol, Aug. 10, 2014;5(3):248-62.

Zhou and Qi, Larynx carcinoma regulates tumor-associated macrophages through PLGF signaling, Sci Rep, May 1, 20151;5:10071.

\* cited by examiner

COMPOUNDS THAT INTERACT WITH THE RAS SUPERFAMILY FOR THE TREATMENT OF CANCERS, INFLAMMATORY DISEASES, RASOPATHIES, AND FIBROTIC DISEASE

CROSS REFERENCE TO RELATED APPLICATIONS

This application is the National Phase application of International Application No. PCT/US2019/067179, filed Dec. 18, 2019, which designates the United States and was published in English, which further claims the benefit under 35 U.S.C. § 119 (e) of U.S. Provisional Application No. 62/782,189 filed on Dec. 19, 2018. The entire contents of the aforesaid application is applications are incorporated by reference herein in its their entirety.

1. FIELD

Provided herein are compositions and methods for treating cancers, inflammatory diseases, rasopathies, and fibrotic disease resulting from aberrant Ras signaling involving Ras, Rac, Rho, and Cdc42 members of the Ras superfamily of proteins through the binding of compounds to the GTP binding domain of these molecules.

2. BACKGROUND

Pathobiology of Cancer

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites. Clinical data and molecular biologic studies indicate that cancer is a multistep process that begins with minor preneoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. (Roitt, I., Brostoff, J. and Kale, D., *Immunology*, 17.1-17.12 (3rd ed., Mosby, St. Louis, Mo., 1993))

Various stages of tumor development can be described generally as follows:

a) Tumor evolution commences when a cell within a normal population sustains a genetic mutation that expands its tendency to proliferate.

b) Such genetically altered cells and their offspring continue to appear normal, but they reproduce excessively and lead to a condition termed hyperplasia. The altered cells may also secrete signaling factors or other molecules that cause changes in their local cellular and extracellular environment, including without limitation, the response of the immune system to them. Such environmental effects may in turn affect the viability, proliferation, and further mutations of the altered cells. After some time (months or years) a very small fraction of these altered cells may sustain additional mutation with subsequent loss of control of cell growth and further potential effects on their environment.

c) The offspring of these cells not only proliferate excessively but also appear abnormal in shape and in orientation. The tissue is now said to exhibit a condition termed dysplasia. After some time, one or more additional mutations may further alter cell behavior and the effect of the cells on their environment.

d) The influenced and genetically altered cells turn still more abnormal in growth and appearance. If the tumor mass does not invade through any boundaries between tissues, it is termed an in situ tumor. This tumor may stay contained indefinitely, however, some cells may acquire still more mutations.

e) A malignant or invasive tumor results if the genetic changes allow the tumor mass to initiate invading underlying tissue and to cast off cells into the blood or lymph. The defector cells may install new tumors loci (metastases) throughout the body.

Metastases represent the end products of a multistep cell-biological process termed the invasion-metastasis cascade, which involves dissemination of cancer cells to anatomically distant organ sites and their subsequent adaptation to foreign tissue microenvironments. Each of these events is driven by the acquisition of genetic and/or epigenetic alterations within tumor cells and the co-option of non-neoplastic stromal cells, which together endow incipient metastatic cells with traits needed to generate macroscopic metastases. (Volastyan, S., et al., *Cell*, 2011, vol. 147, 275-292)

An enormous variety of cancers affect different tissues throughout the body, which are described in detail in the medical literature. Over 85% of human cancers are solid tumors, including carcinomas, sarcomas and lymphomas. Different types of solid tumors are named for the type of cells that form them. Examples include cancer of the lung, colon, rectum, pancreatic, prostate, breast, brain, and intestine. Other human tumors derive from cells involved in the formation of immune cells and other blood cells, including leukemias and myelomas.

The incidence of cancer continues to climb as the general population ages, as new cancers develop, and as susceptible populations grow. A tremendous demand therefore exists for new methods and compositions that can be used to treat subjects with cancer.

Methods of Treating Cancer

Current cancer therapy may involve surgery, chemotherapy, hormonal therapy, biological therapy, targeted therapy, immunotherapy and/or radiation treatment to eradicate neoplastic cells in a patient (see, e.g., Stockdale, 1998, *Medicine*, vol. 3, Rubenstein and Federman, eds., Chapter 12, Section IV; and Baudino T A "Targeted Cancer Therapy: The Next Generation of Cancer Treatment", Curr Drug Discov Technol. 2015; 12(1):3-20).

Such therapies may be used independently or in combinations. Choices of therapy will depend on the history and nature of the cancer, the condition of the patient, and, under the circumstances, the anticipated efficacy and adverse effects of the therapeutic agents and methods considered.

With respect to chemotherapy, there are a variety of chemotherapeutic agents and methods of delivery of such agents available for the treatment of different cancers. Most first generation chemotherapeutic agents were not tumor specific, have broad systemic effects, are toxic, and may cause significant and often dangerous side effects, including severe nausea, bone marrow depression, and immunosuppression.

Additionally, even with administration of combinations of chemotherapeutic agents, many tumor cells are or become resistant to chemotherapeutic agents. In fact, cells resistant to the particular chemotherapeutic agents used in a treatment protocol often prove to be resistant to other drugs, even if those agents act by different mechanism from those of the drugs used in the specific treatment. This phenomenon is referred to as multidrug resistance. Because of drug resistance, many cancers prove refractory to standard chemotherapeutic treatment protocols.

Thus, there exists a significant need for alternative compounds, compositions and methods for treating, preventing and managing cancer.

Further, whereas surgical resection and adjuvant therapy can cure well-confined primary tumors, metastatic disease is largely incurable because of its systemic nature and the resistance of disseminated tumor cells to existing therapeutic agents. This explains why greater than 90% of mortality from cancer is attributable to metastases, not the primary tumors from which these malignant lesions arise.

Pathobiology of Inflammatory Disease

Inflammation is a complex protective biological response of body tissues to harmful stimuli, such as pathogens, damaged cells, or irritants, involving immune cells, blood vessels, and molecular mediators. The function of inflammation is to eliminate the initial cause of cell injury, clear out necrotic cells and tissues damaged from the original insult and the inflammatory process, and to initiate tissue repair. (Ferrero-Miliani L, Nielsen O H, Andersen P S, Girardin S E; Nielsen; Andersen; Girardin (February 2007) *Clin. Exp. Immunol.* 147)

Inflammation is classified as either acute or chronic. Acute inflammation is the initial response of the body to harmful stimuli and is achieved by the increased movement of plasma and leukocytes (especially granulocytes) from the blood into the injured tissues. A series of biochemical events propagates and matures the inflammatory response, involving the local vascular system, the immune system, and various cells within the injured tissue.

Prolonged inflammation, known as chronic inflammation, is characterized by simultaneous destruction and healing of the tissue from the inflammatory process. It leads to a progressive shift in the type of cells present at the site of inflammation, such as mononuclear cells, and increases in systemic concentrations of cytokines such as TNF-α, IL-6, and CRP. (Petersen, A. M.; Pedersen, B. K. (2005). *J Appl Physiol.* 98 (4): 1154-1162)

Many proteins are involved in inflammation. Any of them are susceptible to genetic mutation which may impair or otherwise dysregulate their normal function and expression.

Methods of Treating Inflammatory Disease

Both small molecules and biologics are used to treat inflammatory diseases. Most treatments, however, are largely palliative.

A clear unmet medical need remains to find treatments that can mechanistically reduce chronic inflammatory diseases.

Pathobiology of Fibrotic Disease

Fibrosis, or the accumulation of extracellular matrix molecules that constitute scar tissue, is a common result of tissue injury. Pulmonary fibrosis, renal fibrosis, and hepatic cirrhosis are among the common fibrotic diseases which altogether represent a large unmet medical need. (Friedman S L, Sheppard D, Duffield J S, Violette S. Sci Transl Med 2013 Jan. 9; 5(167): 167srl).

Mechanisms of fibrogenesis include inflammation as well as other pathways and generally involve reorganization of the actin cytoskeleton of affected cells, including epithelial cells, fibroblasts, endothelial cells, and macrophages.

Actin filament assembly and actomyosin contraction are directed by the Rho-associated coiled-coil forming protein kinase (ROCK) family of serine/threonine kinases (ROCK1 and ROCK2) and thus Rho is associated with fibrogenesis.

Tissue fibrosis is a leading cause of morbidity and mortality. 45% of deaths in the United States are attributable to fibrotic disorders. (Wynn T A. "Fibrotic Disease and the TH1/TH2 Paradigm." Nat Rev Immunol 2004 August: 4(8): 583-594.) Treatments are generally palliative.

Idiopathic pulmonary fibrosis (IPF) is characterized by progressive lung scarring, short median survival, and limited therapeutic options, creating great need for new pharmacologic therapies. It is thought to result from repetitive environmental injury to the lung epithelium.

Targeted Therapy of Cancer, Inflammatory, and Fibrotic Diseases

Targeted therapies are a cornerstone of what is also referred to as precision medicine, a form of medicine that uses information about a person's genes and proteins to prevent, diagnose, and treat disease. Such therapeutics are sometimes called "molecularly targeted drugs," "molecularly targeted therapies," or similar names. The process of discovering them is often referred to as "rational drug design." This concept can also be referred to as "personalized medicine."

A series of actions among molecules in a cell that leads to a certain end point or cell function is referred to as a molecular pathway.

Molecularly targeted drugs interact with a particular target molecule, or structurally related set of target molecules, in a pathway; thus modulating the endpoint effect of that pathway, such as a disease-related process; and, thus, yielding a therapeutic benefit.

Molecularly targeted drugs may be small molecules or biologics, usually antibodies. They may be useful alone or in combinations with other therapeutic agents and methods.

Because they target a particular molecule, or related set of molecules, and are usually designed to minimize their interactions with other molecules, targeted therapeutics may have fewer adverse side effects.

Targeted cancer drugs block the growth and spread of cancer by interacting with specific molecules or sets of structurally related molecules (altogether, "molecular targets") that are involved, broadly speaking, in the growth, progression, lack of suppression or elimination, or spread of cancer. Such molecular targets may include proteins or genes involved in one or more cellular functions including, for example and without limitation, signal transduction, gene expression modulation, apoptosis induction or suppression, angiogenesis inhibition, or immune system modulation.

In some cases, the development of targeted cancer therapeutics involves identifying genes or proteins that are present in cancer cells but not normal cells or that are more abundant or more highly stimulated in cancer cells, especially if they are known to be involved in cancer processes, and then discovering agents that will interact with those targets and be associated with a desired therapeutic effect.

Targeted cancer therapies generally differ from standard cancer chemotherapy in several ways:

a. Targeted therapies are deliberately chosen or designed to interact with their target(s), whereas many standard chemotherapies were identified because they were found in general to kill cells.

b. Targeted therapies are intended to act on specific molecular targets that are associated with cancer, whereas most standard chemotherapies act on all rapidly dividing normal and cancerous cells. They may, however, also have known and sometime unknown interactions with other molecules, so-called off-target effects.

c. Most targeted therapies are cytostatic (that is, they block tumor cell proliferation), whereas standard chemotherapy agents are usually cytotoxic (that is, they kill tumor cells). However, some targeted therapies such as Antibody Drug Conjugates are cytotoxic.

Targeted therapy monoclonal antibodies (mAbs) and targeted small molecules are being used as treatments for inflammatory diseases (Kotsovilis S, Andreakos E., *Methods Mol Biol.* 2014; 1060:37-59). They are used either as a monotherapy or in combination with other conventional therapeutic modalities, particularly if the disease under treatment is refractory to therapy using solely conventional techniques.

Some treatments for fibrotic disorders, such as idiopathic pulmonary fibrosis, hepatic fibrosis, and systemic sclerosis, target inflammatory pathways.

The Ras GTPase Family

The Ras superfamily of proteins are small GTPases with substantial amino acid sequence homology that act as signal transducers between cell surface receptors and several intracellular signaling cascades. These molecules are involved in the regulation of such essential cellular functions as cell survival, proliferation, motility, and cytoskeletal organization (see Karnoub et al., *Nat. Rev. Mol. Cell Biol.*, 9: 517-531 (2008)).

Research has defined a number of subfamilies of the Ras superfamily, based largely on amino acid sequence homologies. These subfamilies are often referred to in an abbreviated manner based on the most commonly studied member of the class.

The GTP binding domains of one subfamily of the Ras superfamily having substantial sequence homology is commonly referred to as the Ras family or Ras.

There are four isoforms of Ras proteins, expressed from three different genes: H-Ras (Harvey sarcoma viral oncogene), N-Ras (neuroblastoma oncogene), and the splice variants K-Ras4A and K-Ras4B (Kirsten sarcoma viral oncogene) (see Karnoub et al., supra).

The GTP binding domains of another subfamily of the Ras superfamily having substantial sequence homology is commonly referred to as the Rho family and includes proteins and groups of proteins referred to as Rho, Rac and Cdc42.

Ras Function and Pathways

All Ras isoforms share sequence identity in all of the regions that are responsible for GDP/GTP binding, GTPase activity, and effector interactions, suggesting a functional redundancy. However, studies clearly demonstrate that each Ras isoform can function in a unique, different way from the other Ras proteins in normal physiological processes as well as in pathogenesis (Quinlan et al., *Future Oncol.*, 5: 105-116 (2009)).

Several cell surface receptors activate Ras, such as Receptor Tyrosine Kinases (RTKs), growth factor receptors, cytokine receptors and integrins.

Ras proteins cycle between 'on' and 'off' conformations that are conferred by the binding of GTP and GDP, respectively. Under physiological conditions, the transition between these two states is regulated by guanine nucleotide exchange factors (GEFs), such as Son of sevenless (Sos) (Bar-Sagi D, Trends Endocrin. Metab. 5, 165-169 (1994)), which promote the activation of Ras proteins by stimulating the exchange of GDP for GTP exchange, and by GTPase-activating proteins (GAPs), which accelerate Ras-mediated GTP hydrolysis to GDP.

The region of Sos functional for nucleotide exchange on Ras spans about 500 residues, and contains blocks of sequence that are conserved in Sos and other Ras-specific GEF's such as Cdc25, Sdc25 and Ras guanine-nucleotide-release factor (GRF) (Boguske et al, Nature 366, 643-654 (1993)).

Once activated, Ras initiates signaling of the "MAPK pathway" (also referred to as the Ras-RAF-MEK-MAPK/ERK pathway) that affects cell growth, differentiation, proliferation, apoptosis and migration. The MAPK pathway operates through a sequence of interactions among kinases. Activated by Ras in the "on", GTP bound, state, a MAPK kinase kinase (MAPK3), such as Raf, MLK, or TAK, phosphorylates and activates a MAPK kinase, such as MEK, which then phosphorylates and increases the activity of one or more MAPKs, such as ERK1/2.

Ras activation also initiates signaling of the "Akt pathway" that affects cellular survival, proliferation, migration, anti-apoptotic and cell cycle regulation. Ras in the "on", GTP bound, state, activates phosphoinositide 3-kinase (PI3K) which, in turn, induces the production of phosphatidylinositol (3,4,5) trisphosphates (PIP3). These lipids serve as plasma membrane docking sites for proteins that harbor pleckstrin-homology (PH) domains, including Akt (also known as protein kinase B or PKB) and its upstream activator PDK1. There are three highly related isoforms of Akt (Akt1, Akt2 and Akt3) that phosphorylate shared substrates, but isoform-specific Akt substrates have also been identified. At the membrane, Akt is phosphorylated and activated by PDK1, PDK2 and mTORC2. The Akt pathway can also be activated by receptor tyrosine kinases, integrins, B and T cell receptors, cytokine receptors and G-protein-coupled receptors that directly interact and activate PI3K.

Ras activation is also associated with signaling through other molecular pathways other than phosphoinositide 3-kinases (PI3Ks), such as Rac1 GEF and the Ral-guanine nucleotide dissociation stimulator (GDS). Regarding PI3K, that is part of the PI3K/AKT/mTOR pathway regulating intracellular signaling important for several cellular functions such as survival, anti-apoptotic and cell cycle regulation.

Ras Dysfunction is Causally Associated with Important Diseases and Disease Processes Ras and its downstream pathways, including MAPK and Akt, have been studied extensively. They are causally associated with a range of diseases, including certain cancers, inflammatory disorders, Ras-associated autoimmune leukoproliferative disorder, type II diabetes, and certain Rasopathies.

There is more than one distinct route to aberrant Ras activation including mutational activation of Ras itself, excessive activation of the wild-type protein through upstream signaling, and loss of a GAP function that is required to terminate activity of the protein.

One million deaths per year are attributed in the literature to mutations in K-Ras alone. (Frank McCormick. "K-Ras protein as a drug target." *Journal of Molecular Medicine* (Berlin) 2016: 94: 253-258)

Ras is well documented in the literature as an oncogene. Ras oncogenes can initiate cancer in model organisms. Microinjection studies with antibodies that block Ras activity or block specific mutant alleles of Ras; ablation of K-Ras in mouse models of lung adenocarcinoma or pancreas cancer; and ablation of H-Ras all lead to tumor regression in mouse models.

About 30% (Prior I A, Lewis P D, Mattos C. *Cancer Res.* 2012 May 15; 72(10):2457-67) of human cancers have a mutated Ras protein with the most frequent mutations in residues G12, G13 and Q61. These oncogenic mutations result in impaired GTP hydrolysis and accumulation of Ras in the GTP-bound state leading to increased activation of Ras-dependent downstream effector pathways.

Table 1 summarizes recent data concerning the frequency of K-Ras and N-Ras mutations in an illustrative, but not exhaustive list, of human malignancies.

TABLE 1

| Mutation | Tumor Type | Frequency |
|---|---|---|
| K-Ras | Pancreas | 71% |
| K-Ras | Colon | 35% |
| K-Ras | Small intestine | 35% |
| K-Ras | Biliary tract | 28% |
| K-Ras | Endometrium | 22% |
| K-Ras | Lung | 20% |
| N-Ras | Skin (melanoma) | 20% |
| K-Ras | Cervix | 19% |
| K-Ras | Urinary tract | 16% |

Stephen A G, Esposito D, Bagni R K, McCormick F. *Cancer Cell*. 2014 Mar. 17; 25(3): 272-81.

Ras mutants, and in some cases Ras over-activation, are associated in the literature with a wide range of significant cancer associated processes including: cell proliferation, DNA checkpoint integrity, replicative stress related clonal selection, suppression of apoptosis, metabolic reprogramming, autophagy, microenvironment remodeling, immune response evasion, and metastatic processes. The detailed mechanisms, interdependencies, and frequency of these effects across different tumor types and stages of cancer development remain to be elucidated comprehensively.

Proliferative effects associated in the literature with oncogenic Ras include transcriptional upregulation of growth factors; upregulation of growth factor receptor expression; upregulation of integrins that promote proliferation and downregulation of those associated with cellular quiescence; upregulation of transcription factors required for cell cycle entry; acceleration through cell cycle transitions; downregulation of anti-proliferative TGFβ signaling; and the suppression of cyclin-dependent kinase inhibitors.

MAPK signaling has been shown to enhance programmed death-ligand 1 (PD-L1) expression in KRas mutant lung cancer cells. Thus, Ras mutations are associated with the suppression of immune responses to cancer. (Sumimoto et al., *PLOS One* 2016 Nov. 15; DOI:10.1371/journal.pone.0166626) Anti-PD-1 and anti-PD-L1 monoclonal antibodies have demonstrated clinical activity against tumors including non-small cell lung cancers.

Ras is also implicated through the MAPK and Akt pathways as a cause of a range of pathological inflammatory conditions. In addition to ERK1/2 and Akt1, Akt2 and Akt3, the MAPKs ERK5, c-Jun N-terminal kinases (JNKs) and p38 isoforms have been implicated in inflammatory response. (Huang, et al. 2010, *Protein Cell*, 1(3), 218-226)

Ras is causally associated with inflammatory diseases including the following: rheumatoid arthritis (Abreu J R, de Launay D, Sanders M E, Grabiec A M, Sande van de M G, Tak P P, Reedquist K A: The Ras guanine nucleotide exchange factor RasGRF1 promotes matrix metalloproteinase-3 production in rheumatoid arthritis synovial tissue (Arthritis Res Ther. 2009, 11: R121-10.1186/ar2785), which is the most common cause of disability (Hootman J M, Brault M W, Helmick C G, Theis K A, Armour B S. Prevalence and most common causes of disability among adults—United States 2005, *MMWR*, 2009, 58(16):421-6); atherosclerosis (Fonarow G (2003), *Cleve. Clin. J. Med.* 70: 431-434); inflammatory bowel disease (IBD), such as Crohn's disease (Ignacio C S, Sandvik A K, Bruland T, Andreu-Ballester J C, *J. Crohns Colitis*, 2017 Mar. 16. doi: 10); ulcerative colitis; spondyloarthropathies; idiopathic pulmonary fibrosis; juvenile arthritis; psoriasis; psoriatic arthritis; and others.

Ras has been causally associated with Ras-associated autoimmune leukoproliferative disorder, a nonmalignant clinical syndrome initially identified in a subset of putative autoimmune lymphoproliferative syndrome (ALPS) patients. (Katherin Calvo, et al. "JMML and RALD (Ras-associated autoimmune leukoproliferative disorder): common genetic etiology yet clinically distinct entities" *Blood*, 2015 Apr. 30; 125(18): 2753-2758)

Aberrant Ras signaling is causally implicated in the family of Rasopathies including neurofibromatosis type 1, Noonan's syndrome, and Costello syndrome.

Ras as a Therapeutic Molecular Target

Interference with Ras superfamily member signaling in cell based and animal models of the aforementioned diseases modulates disease processes.

Ras superfamily proteins, and particularly Ras and downstream pathway elements, have thus long been discussed as theoretical molecular targets for the development of targeted therapeutics. In theory, a molecule could serve as a therapeutic agent in diseases associated with aberrant Ras signaling if it could disrupt such Ras signaling.

In theory, it was recognized that a mechanism for downregulating aberrant Ras signaling could be to interfere with one or more steps in the Ras signaling process involving GTP binding in a manner that left Ras in other than an "on" configuration. In theory, a molecule could serve as therapeutic agent in diseases associated with aberrant Ras signaling if it could disrupt such Ras signaling.

However, while this was a theoretical therapeutic strategy based on two widely accepted findings, it has also long been accepted by the scientific community that it would not be possible to achieve.

GTP and GDP had been found to bind to the GTP binding domain of Ras with single to double digit picomolar affinities.

The cellular concentration of GTP had been found to be substantially in excess of this range.

The widely accepted findings concerning the single to double digit picomolar range of affinities of GTP and GDP for the Ras GTP binding domain were determined by kinetic and filter binding measurements between Ras and radiolabeled GDP and GTP (Feuerstein J, Kalbitzer H R, John J, Goody R S, Wittinghofer A. *Eur. J. Biochem.*, 1987 Jan. 2, 162(1):49-55; and John J, Sohmen R, Feuerstein J, Linke R, Wittinghofer A, Goody R S. *Biochemistry*, 1990 Jun. 26, 29(25):6058-65).

Based on these findings, and often citing them, the GTP binding domain of Ras has widely been accepted and reported in preeminent journal editorials, reviews, and research papers to be "undruggable." (Papke B, Der C J., *Science*, 2017 Mar. 17, 355(6330):1158-1163; Stephen A G, Esposito D, Bagni R K, McCormick F, *Cancer Cell*, 2014 Mar. 17, 25(3):272-81; and Ostrem J M, Shokat K M, *Nat. Rev. Drug Discov.*, 2016 Nov. 15(11):771-785)

Accordingly, research concerning targeted Ras therapeutics has focused on domains of the Ras protein other than the GTP binding site. These efforts have included, for example, seeking to develop farnesyltransferase inhibitors (FTIs) that prevent Ras attachment to the inner side of the plasma membrane, and to develop molecules that compete with the interaction of Ras with the exchange factor Sos or downstream effectors.

Thus, it has been thought that a molecule could not be developed to reversibly compete with GTP binding to the GTP binding domain of Ras. Compounds that do so, however, would fill a need in the field.

The Rho Family Function and Pathways

The Rho subfamily of the Ras superfamily currently includes approximately 22 proteins most of which scientists commonly divide into subgroups including those referred to as Cdc42, Rac, and Rho. (Boureux A, Vignal E, Faure S, Fort P (2007). "Evolution of the Rho family of ras-like GTPases in eukaryotes". Mol Biol Evol 24 (1): 203-16).

The three most commonly studied members of the Rho subfamily have been Cdc42, Rac1, and RhoA.

The Cdc42 group includes Cdc42, TC10, TCL, Chip, and Wrch-1.

The Rac group includes Rac1, Rac2, Rac3, and RhoG.

The RhoA group includes RhoA, RhoB, and RhoC.

Other Rho subfamily GTPases not included in the Cdc42, Rac, or Rho groups include RhoE/Rnd3, RhoH/TTF, Rif, RhoBTB1, RhoBTB2, Miro-1, Miro-2, RhoD, Rnd1, and Rnd2.

Like other Ras superfamily proteins, the Rho subfamily GTPases cycle between 'on' and 'off' conformations that are conferred by the binding of GTP and GDP, respectively. Under physiological conditions, the transition between these two states is regulated by guanine nucleotide exchange factors (GEFs), which promote the activation of Rho subfamily proteins by stimulating the release of GDP and the binding of GTP, and by GTPase-activating proteins (GAPs), which accelerate Rho subfamily member-mediated GTP hydrolysis to GDP. Guanine nucleotide dissociation inhibitors (GDIs) proteins form a large complex with the Rho protein, helping to prevent diffusion within the membrane and into the cytosol and thus acting as an anchor and allowing tight spatial control of Rho activation.

The Rho subfamily members are intracellular proteins that affect a large number of downstream pathways broadly involving cytoskeleton organization, cell polarity, migration, transcription and proliferation, and, more particularly, membrane and vesicular trafficking, cell cycling, microtubule stability, actin membrane linkages, actin polymerization, myosin phosphorylation, API dependent gene expression, cell adhesion, cell contractility, cell adhesion, and MTOC orientation. (Martin Schwartz. "Rho Signalling at a Glance." Journal of Cell Science. 2004: (117: pp. 5457-5458) and (Bustelo X R, Sauzeau V, Berenjeno I M (2007). "GTP-binding proteins of the Rho/Rac family: regulation, effectors and functions in vivo" BioEssays. 29 (4): 356-370).

Rho Family Dysfunction is Causally Associated with Important Diseases

Rho subfamily GTPases have been reported to contribute to most steps of cancer initiation and progression including the acquisition of unlimited proliferation potential, survival and evasion from apoptosis, angiogenesis, tissue invasion, motility, and the establishment of metastases. (Matteo Parri and Paolo Chiarugi. "Rac and Rho GTPases in Cancer Cell Motility Control." Cell Communication and Signalling. 2010 (8:23))

High Rho subfamily protein levels are frequently associated with human tumors. High RhoA levels have been associated with human liver, skin, colon, ovarian, bladder, gastric, esophageal squamous cell, testicular, and breast cancer. High Rho B, C, or H levels have been associated with breast, squamous cell, pancreatic, breast, liver, ovarian, head and neck, prostate, non-small cell lung, and gastric cancers and melanoma metastase. High Rac1 levels have been associated with human testicular, gastric, breast, and squamous cell cancers. High Rac2 or Rac3 have been associated with breast colon, head and neck, and squamous cell cancers. (Matteo Parri and Paolo Chiarugi. "Rac and Rho GTPases in Cancer Cell Motility Control." Cell Communication and Signalling. 2010 (8:23). Gain-of-function mutations such as P29S of Rac1 were detected in melanoma, breast, head and neck cancers (Alan J K, Lundquist E A. Mutationally activated Rho GTPases in cancer. Small GTPases. 2013 July-September; 4(3):159-63)

Unlike Ras proteins, which are frequently mutated in cancer (around 30%), Rho subfamily proteins themselves are generally not found to be mutated in cancer. Rather, aberrant activity of Rho subfamily proteins in cancer appears to occur by overexpression of these proteins or by aberrant regulation of molecules that control their activity, such as activation or overexpression of GEFs and inactivation or loss of GAPs or GDIs (Alan J K, Lundquist E A. Mutationally activated Rho GTPases in cancer. Small GTPases. 2013 July-September; 4(3):159-63).

Interactions between Rac and Rho proteins are believed to modulate certain forms of mesenchymal and amoeboid cell movement associated with cancer.

Rho subfamily associated kinases (ROCK1 and ROCK2) are implicated as mediators of multiple profibrotic processes including those associated with idiopathic pulmonary fibrosis. (Knipe R S, Tager E M, and Liao J K. "The Rho kinases: critical mediators of multiple profibrotic processes and rational targets for new therapies for pulmonary fibrosis." Pharmacol Rev. 2015 67(1):103-17.)

Rho Family Members as Therapeutic Molecular Targets

Given their roles in disease processes, Rho subfamily members have been identified as potential Therapeutic Molecular Targets.

Rho subfamily members have been identified as potential Therapeutic Molecular Targets in cancer.

Rho subfamily members have been identified as potential Therapeutic Molecular Targets in fibrotic disease.

3. SUMMARY

As disclosed in International Application No. PCT/US2018/038613 and U.S. patent application Ser. No. 16/013,872, the affinity of GTP for the GTP binding domain of K-Ras utilizing a Scintillation Proximity Assay (SPA) and MicroScale Thermophoresis (MST) has been measured. These methods were not available when Wittinghofer and colleagues (referenced above) undertook their studies. The contents of International Application No. PCT/US2018/038613 and U.S. patent application Ser. No. 16/013,872 are incorporated by reference herein.

In SPA and MST studies, it was found and is disclosed herein that the affinity of GTP for the K-Ras GTP binding domain across wild type and mutant K-Ras is in the range of 100-465 nanomolar. This therefore led to the novel, unanticipated conclusion that compounds such as small molecules could be discovered that would bind to a Ras GTP binding domain and compete with the binding of GTP to Ras.

Provided herein is a cell-free assay for the identification of small molecules that bind to the GTP binding domain and compete with GTP binding to, for example, wild-type KRas, KRas G12D mutant, KRas G12C mutant, KRas Q61H mutant, Rac1 and RhoA proteins.

Provided herein is a cell-free assay for the identification of small molecules that bind to the GTP binding domain and compete with GTP binding to, for example, wild-type KRas, KRas G12D mutant, KRas G12C mutant, KRas Q61H mutant, HRas, Rac1 and RhoA proteins.

Utilizing this assay as a screening and analytical tool, over 80 small molecules are provided that bind competitively with GTP to a Ras GTP binding domain, thereby confirming the significance of the novel and unanticipated binding affinity findings. Provided herein is a method of testing the affinity of a compound for a Ras GTP binding domain comprising the cell-free assay.

Utilizing this assay, it was also demonstrated that over 80 small molecules provided herein also bind competitively with GTP to both Rac and Rho GTPase binding domains. Provided herein is a method of testing the affinity of a compound for Rac and Rho GTP binding domains comprising the cell-free assay.

It is also demonstrated herein in cell-based assays that certain of these molecules inhibit activation of the MAPK pathway and downregulate the proliferation of different human tumor cell lines.

It is also demonstrated herein in cell-based assays that certain of these molecules inhibit activation of the AKT pathway and downregulate the proliferation of different human tumor cell lines.

It is also demonstrated herein in cell-based assays that certain of these molecules inhibit activation of the MAPK pathway and AKT pathway and downregulate the proliferation of different human tumor cell lines.

It is further demonstrated herein in cell-based assays that certain of these molecules downregulate the secretion of inflammatory cytokines.

It has also been discovered and disclosed in International Application No. PCT/US2018/038613 and U.S. patent application Ser. No. 16/013,872 that certain amino acids in the Ras GTP binding domain enable the heretofore unanticipated GTP-competitive binding to that domain for compounds, such as small molecules. They include the following amino acids: Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147, and also Mg202 which is required for GTP binding.

It has also been discovered and disclosed in International Application No. PCT/US2018/038613 and U.S. patent application Ser. No. 16/013,872 that certain amino acids in the Rac1 GTP binding domain enable the heretofore unanticipated GTP-competitive binding to that domain for compounds, such as small molecules. They include the following amino acids: Gly12, Ala13, Gly15, Lys16, Thr17, Cys18, Leu19, Phe28, Ile33, Pro34, Val36, Ala59, Thr115, Lys116, Asp118, Leu119, Cys157, Ala159, and also Mg202 which is required for GTP binding.

It has also been discovered and disclosed in International Application No. PCT/US2018/038613 and U.S. patent application Ser. No. 16/013,872 that certain amino acids in the RhoA GTP binding domain enable the heretofore unanticipated GTP-competitive binding to that domain for compounds, such as small molecules. They include the following amino acids: Gly14, Ala15, Cys16, Gly17, Lys18, Thr19, Cys20, Phe30, Pro31, Glu32, Tyr34, Val35, Pro36, Thr37, Asp59, Lys118, Asp120, Lys162, and also Mg202 which is required for GTP binding.

Therefore, provided herein is a method of inhibiting the function of Ras, comprising administering to a subject a compound which competitively binds to a Ras GTP binding domain. In one embodiment, the compound for use in the method has a binding affinity ($K_d$) to a Ras GTP binding domain of less than 10 μM. In one embodiment, the compound for use in the method has a binding affinity ($K_d$) to a Ras GTP binding domain of less than 1 μM. In one embodiment, the compound for use in the method has a binding affinity ($K_d$) to a Ras GTP binding domain of less than 500 nM. In one embodiment, the compound for use in the method has a binding affinity ($K_d$) to a Ras GTP binding domain of less than 465 nM. In one embodiment, the compound for use in the method has a binding affinity ($K_d$) to a Ras GTP binding domain of less than 270 nM. In one embodiment, the compound for use in the method has a binding affinity ($K_d$) to a Ras GTP binding domain of less than 200 nM. In one embodiment, the compound for use in the method has a binding affinity ($K_d$) to a Ras GTP binding domain of less than 150 nM. In one embodiment, the compound for use in the method has a binding affinity ($K_d$) to a Ras GTP binding domain of less than 100 nM. In one embodiment, the method of inhibiting the function of Ras, comprises administering to a subject a compound which binds to one or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain with a binding affinity ($K_d$) of less than 465 nM. In one embodiment, the method of inhibiting the function of Ras, comprises administering to a subject a compound which binds to one or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain with a binding affinity ($K_d$) of less than 270 nM. In one embodiment, the method of inhibiting the function of Ras, comprises administering to a subject a compound which binds to one or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146 and Lys147 or Mg202 in a highly conserved Ras GTP binding domain with a binding affinity ($K_d$) of less than 10 μM. In some embodiments, the compound for use in the method is a compound as disclosed herein of Formula I, IA, IIA, IIA1, IIB, IC, IID, IIE, IIIA, IIIA1, IIIA2, IIIB, IIIC, IIID, IIIE, or IIIF, or a pharmaceutically acceptable salt thereof. In some embodiments, the compound as disclosed herein for use in the method is a compound of Examples 1-135, or a pharmaceutically acceptable salt thereof.

In an assay described herein, e.g., a cell-free assay, the compound for use in the method inhibits Ras. In one embodiment, the compound for use in the method inhibits Ras and has an $IC_{50}$ value of less than 10 μM. In one embodiment, the compound for use in the method inhibits Ras and has an $IC_{50}$ value of less than 1 μM. In one embodiment, the compound for use in the method inhibits Ras and has an $IC_{50}$ value of less than 500 nM. In one embodiment, the compound for use in the method inhibits Ras and has an $IC_{50}$ value of less than 465 nM. In one embodiment, the compound for use in the method inhibits Ras and has an $IC_{50}$ value of less than 270 nM. In one embodiment, the compound for use in the method inhibits Ras and has an $IC_{50}$ value of less than 200 nM. In one embodiment, the compound for use in the method inhibits Ras and has an $IC_{50}$ value of less than 150 nM. In one embodiment, the compound for use in the method inhibits Ras and has an $IC_{50}$ value of less than 100 nM. In one embodiment, the compound for use in the method inhibits Ras with greater than 15% inhibition at 20 μM. In one embodiment, the compound for use in the method inhibits Ras with greater than 25% inhibition at 20 μM. In one embodiment, the compound for use in the method inhibits Ras with greater than 50% inhibition at 20 µM. In one embodiment, the compound for use in the method inhibits Ras with greater than 75% inhibition at 20 µM. In one embodiment, the compound for use in the method inhibits Ras with greater than 80% inhibition at 20 µM. In one embodiment, the compound for use in the method inhibits Ras with greater than 85% inhibition at 20 µM. In one embodiment, the compound for use in the method inhibits Ras with greater than 90% inhibition at 20 µM. In one embodiment, the compound for use in the method inhibits Ras with greater than 95% inhibition at 20 µM. In one embodiment, the compound for use in the method inhibits Ras with greater than 99% inhibition at 20 µM. In one embodiment, the method of inhibiting the function of Ras, comprises administering to a subject a compound which binds to one or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain and inhibits Ras with a corresponding $IC_{50}$ value of less than 465 nM. In one embodiment, the method of inhibiting the function of Ras, comprises administering to a subject a compound which binds to one or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain and inhibits Ras with a corresponding $IC_{50}$ value of less than 270 nM. In one embodiment, the method of inhibiting the function of Ras, comprises administering to a subject a compound which binds to one or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a highly conserved Ras GTP binding domain and inhibits Ras with a corresponding $IC_{50}$ value of less than 10 µM. In one embodiment, the method of inhibiting the function of Ras, comprises administering to a subject a compound which binds to one or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a highly conserved Ras GTP binding domain and inhibits Ras with greater than 15% inhibition at 20 µM, such as greater than 25% inhibition at 20 µM. In one embodiment, the method of inhibiting the function of Ras, comprises administering to a subject a compound which binds to one or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a highly conserved Ras GTP binding domain and inhibits Ras with greater than 50% inhibition at 20 µM. In some embodiments, the compound for use in the method is a compound as disclosed herein of Formula I, IA, IIA, IIA1, IIB, IIC, IID, IIE, IIIA, IIIA1, IIIA2, IIIB, IIIC, IIID, IIIE, or IIIF, or a pharmaceutically acceptable salt thereof. In some embodiments, the compound as disclosed herein for use in the method is a compound of Examples 1-135, or a pharmaceutically acceptable salt thereof.

In one embodiment, the Ras is DIRAS1; DIRAS2; DIRAS3; ERAS; GEM; HRAS; KRAS; MRAS; NKIRAS1; NKIRAS2; NRAS; RALA; RALB; RAP1A; RAP1B; RAP2A; RAP2B; RAP2C; RASD1; RASD2; RASL10A; RASL10B; RASL11A; RASL11B; RASL12; REM1; REM2; RERG; RERGL; RRAD; RRAS; or RRAS2. In one embodiment, the Ras is HRAS, KRAS or NRAS. In one embodiment, the Ras is HRAS. In one embodiment, the Ras is KRAS. In one embodiment, the Ras is NRAS. In another embodiment, the Ras is a mutant form of a Ras described herein.

Also provided herein is a method of inhibiting the function of Rho, comprising administering to a subject a compound which competitively binds to a Rho GTP binding domain. In one embodiment, the compound for use in the method has a binding affinity ($K_d$) to a Rho GTP binding domain of less than 10 µM. In one embodiment, the compound for use in the method has a binding affinity ($K_d$) to a Rho GTP binding domain of less than 1 µM. In one embodiment, the compound for use in the method has a binding affinity ($K_d$) to a Rho GTP binding domain of less than 500 nM. In one embodiment, the compound for use in the method has a binding affinity ($K_d$) to a Rho GTP binding domain of less than 270 nM. In one embodiment, the compound for use in the method has a binding affinity ($K_d$) to a Rho GTP binding domain of less than 200 nM. In one embodiment, the compound for use in the method has a binding affinity ($K_d$) to a Rho GTP binding domain of less than 150 nM. In one embodiment, the compound for use in the method has a binding affinity ($K_d$) to a Rho GTP binding domain of less than 130 nM. In one embodiment, the compound for use in the method has a binding affinity ($K_d$) to a Rho GTP binding domain of less than 100 nM. In one embodiment, the method of inhibiting the function of Rho, comprises administering to a subject a compound which binds to one or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain with a binding affinity ($K_d$) of less than 270 nM. In one embodiment, the method of inhibiting the function of Rho, comprises administering to a subject a compound which binds to one or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain with a binding affinity ($K_d$) of less than 130 nM. In one embodiment, the method of inhibiting the function of Rho, comprises administering to a subject a compound which binds to one or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a highly conserved Rho GTP binding domain with a binding affinity ($K_d$) of less than 10 µM. In some embodiments, the compound for use in the method is a compound as disclosed herein of Formula I, IA, IIA, IIA1, IIB, IIC, IID, IIE, IIA, IIIA1, IIIA2, IIIB, IIIC, IIID, IIIE, or IIIF, or a pharmaceutically acceptable salt thereof. In some embodiments, the compound as disclosed herein for use in the method is a compound of Examples 1-135, or a pharmaceutically acceptable salt thereof.

In an assay described herein, e.g., a cell-free assay, the compound for use in the method inhibits Rho. In one embodiment, the compound for use in the method inhibits Rho and has an $IC_{50}$ value of less than 10 µM. In one embodiment, the compound for use in the method inhibits Rho and has an $IC_{50}$ value of less than 1 µM. In one embodiment, the compound for use in the method inhibits Rho and has an $IC_{50}$ value of less than 500 nM. In one embodiment, the compound for use in the method inhibits Rho and has an $IC_{50}$ value of less than 270 nM. In one embodiment, the compound for use in the method inhibits Rho and has an $IC_{50}$ value of less than 200 nM. In one embodiment, the compound for use in the method inhibits Rho and has an $IC_{50}$ value of less than 150 nM. In one embodiment, the compound for use in the method inhibits Rho and has an $IC_{50}$ value of less than 130 nM. In one embodiment, the compound for use in the method inhibits Rho and has an $IC_{50}$ value of less than 100 nM. In one embodiment, the compound for use in the method inhibits Rho with greater than 15% inhibition at 20 μM. In one embodiment, the compound for use in the method inhibits Rho with greater than 25% inhibition at 20 μM. In one embodiment, the compound for use in the method inhibits Rho with greater than 50% inhibition at 20 μM. In one embodiment, the compound for use in the method inhibits Rho with greater than 75% inhibition at 20 μM. In one embodiment, the compound for use in the method inhibits Rho with greater than 80% inhibition at 20 μM. In one embodiment, the compound for use in the method inhibits Rho with greater than 85% inhibition at 20 μM. In one embodiment, the compound for use in the method inhibits Rho with greater than 90% inhibition at 20 μM. In one embodiment, the compound for use in the method inhibits Rho with greater than 95% inhibition at 20 μM. In one embodiment, the compound for use in the method inhibits Rho with greater than 99% inhibition at 20 μM. In one embodiment, the method of inhibiting the function of Rho, comprises administering to a subject a compound which binds to one or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain and inhibits Rho with a corresponding $IC_{50}$ value of less than 270 nM. In one embodiment, the method of inhibiting the function of Rho, comprises administering to a subject a compound which binds to one or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain and inhibits Rho with a corresponding $IC_{50}$ value of less than 130 nM. In one embodiment, the method of inhibiting the function of Rho, comprises administering to a subject a compound which binds to one or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a highly conserved Rho GTP binding domain and inhibits Rho with a corresponding $IC_{50}$ value of less than 10 μM. In one embodiment, the method of inhibiting the function of Rho, comprises administering to a subject a compound which binds to one or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a highly conserved Rho GTP binding domain and inhibits Rho with greater than 15% inhibition at 20 μM, such as greater than 25% inhibition at 20 μM. In one embodiment, the method of inhibiting the function of Rho, comprises administering to a subject a compound which binds to one or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a highly conserved Rho GTP binding domain and inhibits Rho with greater than 50% inhibition at 20 μM. In some embodiments, the compound for use in the method is a compound as disclosed herein of Formula I, IA, IIA, IIA1, IIB, IIC, IID, IIE, IIIA, IIIA1, IIA2, IIIB, IIIC, IIID, IIIE, or IIIF, or a pharmaceutically acceptable salt thereof. In some embodiments, the compound as disclosed herein for use in the method is a compound of Examples 1-135, or a pharmaceutically acceptable salt thereof.

In one embodiment, the Rho is RHOA; RHOB; RHOBTB1; RHOBTB2; RHOBTB3; RHOC; RHOD; RHOF; RHOG; RHOH; RHOJ; RHOQ; RHOU; RHOV; RND1, RND2; RND3; RAC1; RAC2; RAC3 or CDC42. In one embodiment, the Rho is RHOA. In another embodiment, the Rho is a mutant form of a Rho described herein.

Also provided herein is a method of inhibiting the function of Rac, comprising administering to a subject a compound which competitively binds to a Rac GTP binding domain. In one embodiment, the compound for use in the method has a binding affinity ($K_d$) to a Rac GTP binding domain of less than 10 μM. In one embodiment, the compound for use in the method has a binding affinity ($K_d$) to a Rac GTP binding domain of less than 1 μM. In one embodiment, the compound for use in the method has a binding affinity ($K_d$) to a Rac GTP binding domain of less than 500 nM. In one embodiment, the compound for use in the method has a binding affinity ($K_d$) to a Rac GTP binding domain of less than 270 nM. In one embodiment, the compound for use in the method has a binding affinity ($K_d$) to a Rac GTP binding domain of less than 200 nM. In one embodiment, the compound for use in the method has a binding affinity ($K_d$) to a Rac GTP binding domain of less than 170 nM. In one embodiment, the compound for use in the method has a binding affinity ($K_d$) to a Rac GTP binding domain of less than 150 nM. In one embodiment, the compound for use in the method has a binding affinity ($K_d$) to a Rac GTP binding domain of less than 100 nM. In one embodiment, the method of inhibiting the function of Rac, comprises administering to a subject a compound which binds to one or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain with a binding affinity ($K_d$) of less than 270 nM. In one embodiment, the method of inhibiting the function of Rac, comprises administering to a subject a compound which binds to one or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain with a binding affinity ($K_d$) of less than 170 nM. In one embodiment, the method of inhibiting the function of Rac, comprises administering to a subject a compound which binds to one or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a highly conserved Rac GTP binding domain with a binding affinity ($K_d$) of less than 10 μM. In some embodiments, the compound for use in the method is a compound as disclosed herein of Formula I, IA, IIA, IIA1, IIB, IC, IID, HE, IIIAA, IIA2, IIIB, IIIC, IIID, IIIE, or IIIF, or a pharmaceutically acceptable salt thereof. In some embodiments, the compound as disclosed herein for use in the method is a compound of Examples 1-135, or a pharmaceutically acceptable salt thereof.

In an assay described herein, e.g., a cell-free assay, the compound for use in the method inhibits Rac. In one embodiment, the compound for use in the method inhibits Rac and has an $IC_{50}$ value of less than 10 μM. In one embodiment, the compound for use in the method inhibits Rac and has an $IC_{50}$ value of less than 1 μM. In one embodiment, the compound for use in the method inhibits Rac and has an $IC_{50}$ value of less than 500 nM. In one embodiment, the compound for use in the method inhibits Rac and has an $IC_{50}$ value of less than 270 nM. In one embodiment, the compound for use in the method inhibits Rac and has an $IC_{50}$ value of less than 200 nM. In one embodiment, the compound for use in the method inhibits Rac and has an $IC_{50}$ value of less than 170 nM. In one embodiment, the compound for use in the method inhibits Rac and has an IC$_{50}$ value of less than 150 nM. In one embodiment, the compound for use in the method inhibits Rac and has an IC$_{50}$ value of less than 100 nM. In one embodiment, the compound for use in the method inhibits Rac with greater than 15% inhibition at 20 µM. In one embodiment, the compound for use in the method inhibits Rac with greater than 25% inhibition at 20 µM. In one embodiment, the compound for use in the method inhibits Rac with greater than 50% inhibition at 20 µM. In one embodiment, the compound for use in the method inhibits Rac with greater than 75% inhibition at 20 µM. In one embodiment, the compound for use in the method inhibits Rac with greater than 80% inhibition at 20 µM. In one embodiment, the compound for use in the method inhibits Rac with greater than 85% inhibition at 20 µM. In one embodiment, the compound for use in the method inhibits Rac with greater than 90% inhibition at 20 µM. In one embodiment, the compound for use in the method inhibits Rac with greater than 95% inhibition at 20 µM. In one embodiment, the compound for use in the method inhibits Rac with greater than 99% inhibition at 20 µM. In one embodiment, the method of inhibiting the function of Rac, comprises administering to a subject a compound which binds to one or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain and inhibits Rac with a corresponding IC$_{50}$ value of less than 270 nM. In one embodiment, the method of inhibiting the function of Rac, comprises administering to a subject a compound which binds to one or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain and inhibits Rac with a corresponding IC$_{50}$ value of less than 270 nM. In one embodiment, the method of inhibiting the function of Rac, comprises administering to a subject a compound which binds to one or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain and inhibits Rac with a corresponding IC$_{50}$ value of less than 170 nM. In one embodiment, the method of inhibiting the function of Rac, comprises administering to a subject a compound which binds to one or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain and inhibits Rac with a corresponding IC$_{50}$ value of less than 170 nM. In one embodiment, the method of inhibiting the function of Rac, comprises administering to a subject a compound which binds to one or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a highly conserved Rac GTP binding domain and inhibits Rac with a corresponding IC$_{50}$ value of less than 10 µM. In one embodiment, the method of inhibiting the function of Rac, comprises administering to a subject a compound which binds to one or more of Gly12, Ala 13, Gly15, Lys16, Thr17, Cys18, Leu19, Phe28, Ile33, Pro34, Val36, Ala59, Thr115, Lys116, Asp118, Leu119, Cys157, Ala159, or Mg202 in a highly conserved Rac GTP binding domain and inhibits Rac with greater than 15% inhibition at 20 µM, such as greater than 25% inhibition at 20 µM. In one embodiment, the method of inhibiting the function of Rac, comprises administering to a subject a compound which binds to one or more of Gly12, Ala 13, Gly15, Lys16, Thr17, Cys18, Leu19, Phe28, Ile33, Pro34, Val36, Ala59, Thr115, Lys116, Asp118, Leu119, Cys157, Ala159, or Mg202 in a highly conserved Rac GTP binding domain and inhibits Rac with greater than 50% inhibition at 20 µM. In one embodiment, the method of inhibiting the function of Rac, comprises administering to a subject a compound which binds to one or more of Gly12, Ala 13, Gly15, Lys16, Thr17, Cys18, Leu19, Phe28, Ile33, Pro34, Val36, Ala59, Thr115, Lys116, Asp118, Leu119, Cys157, Ala159, or Mg202 in a highly conserved Rac GTP binding domain and inhibits Rac with greater than 99% inhibition at 20 µM. In some embodiments, the compound for use in the method is a compound as disclosed herein of Formula I, IA, IIA, IIA1, IIB, IIC, IID, IIE, IIIA, IIIA1, IIIA2, IIIB, IIIC, IIID, IIIE, or IIIF, or a pharmaceutically acceptable salt thereof. In some embodiments, the compound as disclosed herein for use in the method is a compound of Examples 1-135, or a pharmaceutically acceptable salt thereof.

In one embodiment, the Rho is Rac. In one embodiment the Rac is RAC1; RAC2; RAC3 or RHOG. In one embodiment, the Rac is RAC1. In another embodiment, the Rac is a mutant form of a Rac described herein.

In one embodiment, provided herein is a method of treating or preventing cancer by administering a compound that inhibits one or more members of the Ras superfamily. In one embodiment, provided herein is a method of treating or preventing cancer by administering a compound that inhibits the binding of GTP to the GTP binding domain of one or more members of the Ras superfamily. In one embodiment, provided herein is a method of treating or preventing inflammation by administering a compound that inhibits one or more members of the Ras superfamily. In one embodiment, provided herein is a method of treating or preventing inflammation by administering a compound that inhibits the binding of GTP to the GTP binding domain of one or more members of the Ras superfamily. In one embodiment, provided herein is a method of treating or preventing a rasopathy by administering a compound that inhibits one or more members of the Ras superfamily. In one embodiment, provided herein is a method of treating or preventing a rasopathy by administering a compound that inhibits the binding of GTP to the GTP binding domain of one or more members of the Ras superfamily. In one embodiment, provided herein is a method of treating or preventing fibrotic disease by administering a compound that inhibits one or more members of the Ras superfamily. In one embodiment, provided herein is a method of treating or preventing fibrotic disease by administering a compound that inhibits the binding of GTP to the GTP binding domain of one or more members of the Ras superfamily. In one embodiment, provided herein is a method of treating or preventing cancer by administering a compound that inhibits the binding of GTP to a Ras GTP binding domain. In one embodiment, provided herein is a method of treating or preventing inflammation by administering a compound that inhibits the binding of GTP to a Ras GTP binding domain. In one embodiment, provided herein is a method of treating or preventing a rasopathy by administering a compound that inhibits the binding of GTP to a Ras GTP binding domain. In one embodiment, provided herein is a method of treating or preventing Ras-associated autoimmune leukoproliferative disorder by administering a compound that inhibits the binding of GTP to a Ras GTP binding domain. In one embodiment, provided herein is a method of treating or preventing fibrotic disease by administering a compound that inhibits the binding of GTP to a Ras GTP binding domain. In one embodiment, provided herein is a method of treating or preventing cancer by administering a compound that inhibits the binding of GTP to a Rho GTP binding domain. In one embodiment, provided herein is a method of treating or preventing inflammation by administering a compound that inhibits the binding of GTP to a Rho GTP binding domain. In one embodiment, provided herein is a method of treating or preventing a rasopathy by administering a compound that inhibits the binding of GTP to a Rho GTP binding domain. In one embodiment, provided herein is a method of treating or preventing fibrotic disease by administering a compound that inhibits the binding of GTP to a Rho GTP binding domain. In one embodiment, provided herein is a method of treating or preventing cancer by administering a compound that inhibits the binding of GTP to a Rac GTP binding domain. In one embodiment, provided herein is a method of treating or preventing inflammation by administering a compound that inhibits the binding of GTP to a Rac GTP binding domain. In one embodiment, provided herein is a method of treating or preventing a rasopathy by administering a compound that inhibits the binding of GTP to a Rac GTP binding domain. In one embodiment, provided herein is a method of treating or preventing fibrotic disease by administering a compound that inhibits the binding of GTP to a Rac GTP binding domain. In some embodiments, the compound for use in the method is a compound as disclosed herein of Formula I, IA, IIA, IIA1, IIB, IIC, ID, IE, IIIA, IIIA1, IIIA2, IIIB, IIIC, IIID, IIIE, or IIIF, or a pharmaceutically acceptable salt thereof. In some embodiments, the compound as disclosed herein for use in the method is a compound of Examples 1-135, or a pharmaceutically acceptable salt thereof.

Provided herein are compounds which bind to a Ras GTP binding domain and compete with the binding of GTP to Ras. In one embodiment, the compounds also inhibit phosphorylation of MAPK, in particular MAPK1/2, Akt (for example, Akt1, Akt2 and Akt3) cellular proliferation, secretion of IL-6 or TNF-α cytokines. The compounds provided herein are therefore useful in compositions and methods of treating cancer, inflammatory diseases, Ras-associated autoimmune leukoproliferative disorder and rasopathies.

Provided herein are compounds which bind to a Rac GTP binding domain and compete with the binding of GTP to Rac. In one embodiment, the compounds also inhibit the MAPK and Akt signaling pathways. In one embodiment, the compounds also inhibit the ROCK signaling pathway. The compounds provided herein are therefore useful in compositions and methods of treating cancer, inflammatory diseases and fibrotic disease.

Provided herein are compounds which bind to a Rho GTP binding domain and compete with the binding of GTP to Rho. In one embodiment, the compounds also inhibit the MAPK and Akt signaling pathways. In one embodiment, the compounds also inhibit the ROCK signaling pathway. The compounds provided herein are therefore useful in compositions and methods of treating cancer, inflammatory diseases and fibrotic disease.

In one embodiment, the compounds provided herein inhibit GTP binding to one or more members of the Ras superfamily. In one embodiment, the compounds provided herein inhibit GTP binding to Ras. In one embodiment, the compounds provided herein inhibit GTP binding to Rho. In one embodiment, the compounds provided herein inhibit GTP binding to Rac. In one embodiment, the compounds provided herein inhibit GTP binding to Ras and Rho. In one embodiment, the compounds provided herein inhibit GTP binding to Ras and Rac. In one embodiment, the compounds provided herein inhibit GTP binding to Rho and Rac. In one embodiment, the compounds provided herein inhibit GTP binding to Ras, Rho and Rac.

In one embodiment, the compound for use in the methods and compositions provided herein has a molecular weight less than 2000 daltons. In one embodiment, the compound for use in the methods and compositions provided herein has a molecular weight less than 1750 daltons. In one embodiment, the compound for use in the methods and compositions provided herein has a molecular weight less than 1500 daltons. In one embodiment, the compound for use in the methods and compositions provided herein has a molecular weight less than 1250 daltons. In one embodiment, the compound for use in the methods and compositions provided herein has a molecular weight less than 1000 daltons. In one embodiment, the compound for use in the methods and compositions provided herein has a molecular weight less than 750 daltons. In one embodiment, the compound for use in the methods and compositions provided herein has a molecular weight less than 665 daltons. In one embodiment, the compound for use in the methods and compositions provided herein has a molecular weight less than 500 daltons. In another embodiment, the compound for use in the methods and compositions provided herein contains a thienopyrimidine, pyrimidine or pyrrolotriazine moiety. In another embodiment, the compound for use in the methods and compositions provided herein contains a thieno[3,2-d]pyrimidine, thieno[2,3-d]pyrimidine or pyrrolo[2,1-f][1,2,4]triazine moiety. In another embodiment, the compound for use in the methods and compositions provided herein contains a thieno[3,2-d]pyrimidin-4-ol, thieno[2,3-d]pyrimidin-4-amine, pyrrolo[2,1-f][1,2,4]triazin-4-amine, 5,6-dimethoxy-N-(heteroaryl)-2-(pyridin-2-yl)pyrimidin-4-amine, 5,6-dihydroxy-2-(pyridin-2-yl)pyrimidine-4-carboxamide, 5,6-dihydroxy-2-(1-methyl-1H-imidazol-2-yl)pyrimidine-4-carboxamide, 5-methoxy-6-aryloxy-2-(pyridin-2-yl)pyrimidin-4-ol, 5-methoxy-6-heteroaryloxy-2-(pyridin-2-yl)pyrimidin-4-ol, 5-methoxy-6-(arylamino)-2-(pyridin-2-yl)pyrimidin-4-ol, 6-((heteroaryl)amino)-5-methoxy-2-(pyridin-2-yl)pyrimidin-4-ol, 6-amino-5-methyl-2-(1-methyl-1H-imidazol-2-yl)pyrimidine-4-carboxamide, thieno[2,3-d]pyrimidin-4-ol, or 4-alkoxythieno[3,2-d]pyrimidine moiety.

4. DETAILED DESCRIPTION

4.1. Definitions

To facilitate understanding of the disclosure set forth herein, a number of terms are defined below.

Unless defined otherwise, all technical and scientific terms used herein have the same meaning as is commonly understood by one of ordinary skill in the art. All patents, applications, published applications and other publications are incorporated by reference in their entirety. In the event that there is a plurality of definitions for a term herein, those in this section prevail unless stated otherwise.

The singular forms "a," "an," and "the" include plural references, unless the context clearly dictates otherwise.

As used herein "subject" is an animal, such as a mammal, including human, such as a patient.

As used herein, biological activity refers to the in vivo activities of a compound or physiological responses that result upon in vivo administration of a compound, composition or other mixture. Biological activity, thus, encompasses therapeutic effects and pharmacokinetic behavior of such compounds, compositions and mixtures. Biological activities can be observed in in vitro systems designed to test for such activities.

As used herein, pharmaceutically acceptable derivatives of a compound include, but are not limited to, salts, esters, enol ethers, enol esters, acetals, ketals, orthoesters, hemiacetals, hemiketals, acids, bases, clathrates, solvates or hydrates thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-yl-methylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and inorganic salts, such as but not limited to, sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates, mesylates, and fumarates. Pharmaceutically acceptable esters include, but are not limited to, alkyl, alkenyl, alkynyl, aryl, aralkyl, and cycloalkyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is alkyl, alkenyl, alkynyl, aryl, aralkyl and cycloalkyl. Pharmaceutically acceptable enol esters include, but are not limited to, derivatives of formula C=C(OC(O)R) where R is hydrogen, alkyl, alkenyl, alkynyl, aryl, aralkyl and cycloalkyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, treatment means any manner in which one or more of the symptoms of a disease or disorder are ameliorated or otherwise beneficially altered. Treatment also encompasses any pharmaceutical use of the compositions herein, such as use for treating cancer, inflammation or rasopathies.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein, and unless otherwise indicated, the terms "manage," "managing" and "management" encompass preventing the recurrence of the specified disease or disorder in a subject who has already suffered from the disease or disorder, and/or lengthening the time that a subject who has suffered from the disease or disorder remains in remission. The terms encompass modulating the threshold, development and/or duration of the disease or disorder, or changing the way that a subject responds to the disease or disorder.

As used herein, the $IC_{50}$ refers to an amount, concentration or dosage of a particular test compound that achieves a 50% inhibition of a maximal response in an assay that measures such response.

As used herein, the $K_d$ refers to the measured equilibrium dissociation constant between a compound (or ligand) and a protein (or binding domain of a protein).

As used herein, "Ras superfamily" means the protein superfamily of small guanosine triphosphatases (GTPases) which consists of the five main families Ras, Rho, Rab, Ran and Arf, or mutants thereof. Subfamilies of the five main families are also included, e.g., the Rac subfamily of the Rho main family.

As used herein, "Ras" or "Ras family" or "Ras subfamily" or "Ras group" means DIRAS1; DIRAS2; DIRAS3; ERAS, GEM; HRAS, KRAS, MRAS; NKIRAS1; NKIRAS2; NRAS, RALA; RALB; RAP1A; RAP1B; RAP2A; RAP2B; RAP2C; RASD1; RASD2; RASL10A; RASL10B; RASL11A; RASL11B; RASL12; REM1; REM2; RERG; RERGL; RRAD; RRAS; RRAS2, or mutants thereof.

As used herein, "Rho" or "Rho family" or "Rho subfamily" or "Rho group" means RHOA; RHOB; RHOBTB1; RHOBTB2; RHOBTB3, RHOC; RHOD; RHOF; RHOG; RHOH; RHOJ; RHOQ; RHOU; RHOV; RND1; RND2; RND3; RAC1; RAC2; RAC3; CDC42, or mutants thereof.

As used herein, "Rac" or "Rac family" or "Rac subfamily" or "Rac group" means RAC1; RAC2; RAC3; RHOG, or mutants thereof.

As used herein, "GTP binding site" or "GTP binding domain" both mean the region of a protein which binds GTP, and the surrounding region of said protein in which another compound may bind, wherein such binding blocks the ability of GTP to bind to said protein.

As used herein, "GDP binding site" or "GDP binding domain" both mean the region of a protein which binds GDP, and the surrounding region of said protein in which another compound may bind, wherein such binding blocks the ability of GDP to bind to said protein.

As used herein, "guanosine binding region" means a region of a protein which is part of the GDP binding domain or GTP binding domain, that mediates interaction with the guanosine portion of GDP or GTP.

As used herein, "metal region" means a region of a protein which is part of the GDP binding domain or GTP binding domain, that is proximal to a magnesium (Mg202) binding site.

As used herein, "alternative Tyr32 conformation" means the conformation of the GTP or GDP binding domain in the region of Tyr32 in KRas crystal structure PDB code:3gft in comparison to the KRas crystal structure PDB code:4epr.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. As such, one of skill in the art will recognize that administration of a compound in its (R) form is equivalent, for compounds that undergo epimerization in vivo, to administration of the compound in its (S) form.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter enzymatic and biological activities of the substance. Methods for purification of the compounds to produce substantially chemically pure compounds are known to those of skill in the art. A substantially chemically pure compound may, however, be a mixture of stereoisomers. In such instances, further purification might increase the specific activity of the compound. The instant disclosure is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as chiral reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included. For example, Formula A includes, but is not limited to, the three tautomeric structures below.

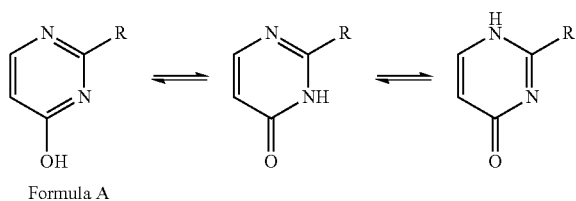

Formula A

As used herein, the nomenclature alkyl, alkoxy, carbonyl, etc. is used as is generally understood by those of skill in this art.

As used herein, alkyl, alkenyl and alkynyl carbon chains, if not specified, contain from 1 to 20 carbons, or 1 to 16 carbons, and are straight or branched. Alkenyl carbon chains of from 2 to 20 carbons, in certain embodiments, contain 1 to 8 double bonds, and the alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-pentyl, isohexyl, ethenyl, propenyl, butenyl, pentenyl, acetylenyl and hexynyl. As used herein, lower alkyl, lower alkenyl, and lower alkynyl refer to carbon chains having from about 1 or about 2 carbons up to about 6 carbons. As used herein, "alk(en)(yn)yl" refers to an alkyl group containing at least one double bond and at least one triple bond.

As used herein, "heteroalkyl" refers to a straight or branched aliphatic hydrocarbon group having, inserted in the hydrocarbon chain one or more oxygen, sulfur, including S(=O) and S(=O)$_2$ groups, or substituted or unsubstituted nitrogen atoms, including —NR— and —N$^+$RR— groups, where the nitrogen substituent(s) is(are) alkyl, aryl, aralkyl, heteroaryl, heteroaralkyl, S(=O)$_2$R' or COR', where R' is alkyl, aryl, aralkyl, heteroaryl, heteroaralkyl, OY or —NYY', where Y and Y' are each independently hydrogen, alkyl, aryl, heteroaryl, cycloalkyl or heterocyclyl, in one embodiment having from 1 to about 20 atoms, in another embodiment having from 1 to 12 atoms in the chain.

As used herein, "cycloalkyl" refers to a saturated mono- or multicyclic ring system, in certain embodiments of 3 to 10 carbon atoms, in other embodiments of 3 to 6 carbon atoms; cycloalkenyl and cycloalkynyl refer to mono- or multicyclic ring systems that respectively include at least one double bond and at least one triple bond. Cycloalkenyl and cycloalkynyl groups may, in certain embodiments, contain 3 to 10 carbon atoms, with cycloalkenyl groups, in further embodiments, containing 4 to 7 carbon atoms and cycloalkynyl groups, in further embodiments, containing 8 to 10 carbon atoms. The ring systems of the cycloalkyl, cycloalkenyl and cycloalkynyl groups may be composed of one ring or two or more rings which may be joined together in a fused, bridged or spiro-connected fashion. "Cycloalk(en)(yn)yl" refers to a cycloalkyl group containing at least one double bond and at least one triple bond. In some embodiments, the cycloalkyl ring is unsaturated or partially saturated.

As used herein, "carbocyclic" refers to a mono- or multicyclic ring system, in which all of the atoms composing the ring are carbon atoms, such as benzene or cyclopropane. In some embodiments, the carbocyclic ring is unsaturated or partially saturated.

As used herein, "substituted alkyl," "substituted alkenyl," "substituted alkynyl," "substituted cycloalkyl," "substituted cycloalkenyl," and "substituted cycloalkynyl" refer to alkyl, alkenyl, alkynyl, cycloalkyl, cycloalkenyl and cycloalkynyl groups, respectively, that are substituted with one or more substituents, in certain embodiments one to three or four substituents, where the substituents are as defined herein, in one embodiment selected from Q.

As used herein, "aryl" refers to aromatic monocyclic or multicyclic groups containing from 6 to 19 carbon atoms. Aryl groups include, but are not limited to groups such as fluorenyl, substituted fluorenyl, phenyl, substituted phenyl, naphthyl and substituted naphthyl.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, N-methylpyrrolyl, quinolinyl and isoquinolinyl.

As used herein, "heterocycloalkyl," "heterocyclyl" or "heterocyclic" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, amidino, sulfonyl or the nitrogen may be quaternized to form an ammonium group where the substituents are selected as above. In some embodiments, the heterocyclyl ring is saturated. In some embodiments, the heterocyclyl ring is unsaturated or partially saturated.

As used herein, "substituted aryl," "substituted heteroaryl" and "substituted heterocyclyl" refer to aryl, heteroaryl and heterocyclyl groups, respectively, that are substituted with one or more substituents, in certain embodiments one to three or four substituents, where the substituents are as defined herein, in one embodiment selected from Q.

As used herein, "aralkyl" or "arylalkyl" refers to an alkyl group in which one of the hydrogen atoms of the alkyl is replaced by an aryl group.

As used herein, "heteroaralkyl" refers to an alkyl group in which one of the hydrogen atoms of the alkyl is replaced by a heteroaryl group.

As used herein, "halo", "halogen" or "halide" refers to F, Cl, Br or I.

As used herein, pseudohalides or pseudohalo groups are groups that behave substantially similar to halides. Such compounds can be used in the same manner and treated in the same manner as halides. Pseudohalides include, but are not limited to, cyano, thiocyanate, selenocyanate, trifluoromethoxy, and azide.

As used herein, "haloalkyl" refers to an alkyl group in which one or more of the hydrogen atoms are replaced by halogen. Such groups include, but are not limited to, chloromethyl, trifluoromethyl and 1-chloro-2-fluoroethyl.

As used herein, "haloalkoxy" refers to RO in which R is a haloalkyl group.

As used herein, "carboxy" refers to a divalent radical, —C(O)O—.

As used herein, "aminocarbonyl" refers to —C(O)NH$_2$.

As used herein, "alkylaminocarbonyl" refers to —C(O)NHR in which R is alkyl, including lower alkyl. As used herein, "dialkylaminocarbonyl" refers to —C(O)NR'R in which R' and R are independently alkyl, including lower alkyl; "carboxamide" refers to groups of formula —NR'COR in which R' and R are independently alkyl, including lower alkyl.

As used herein, "arylalkylaminocarbonyl" refers to —C(O)NRR' in which one of R and R' is aryl, including lower aryl, such as phenyl, and the other of R and R' is alkyl, including lower alkyl.

As used herein, "arylaminocarbonyl" refers to —C(O)NHR in which R is aryl, including lower aryl, such as phenyl.

As used herein, "hydroxycarbonyl" refers to —COOH.

As used herein, "alkoxycarbonyl" refers to —C(O)OR in which R is alkyl, including lower alkyl.

As used herein, "aryloxycarbonyl" refers to —C(O)OR in which R is aryl, including lower aryl, such as phenyl.

As used herein, "alkoxy" and "alkylthio" refer to RO— and RS—, in which R is alkyl, including lower alkyl.

As used herein, "aryloxy" and "arylthio" refer to RO— and RS—, in which R is aryl, including lower aryl, such as phenyl.

Where the number of any given substituent is not specified (e.g., "haloalkyl"), there may be one or more substituents present. For example, "haloalkyl" may include one or more of the same or different halogens.

As used herein, "cyclic structure" may be a cycloalkyl, carbocyclic, heterocyclic, aryl or heteroaryl group.

Where substitution is not specified (e.g., "aryl"), there may be one or more substituents present. For example, "aryl" may include a "substituted aryl" group. In some embodiments, each alkyl, alkenyl, alkynyl, cycloalkyl, cycloalkenyl, cycloalkynyl, aryl, aralkyl, heteroaryl, and heterocyclyl is optionally substituted with one or more substituents, in one embodiment one, two, three or four substituents Q, where each Q is independently selected from (a) deuterium, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen or deuterium; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^a$; or (iii) R$^b$ and R$^c$ together with the N atom to which they are attached form heterocyclyl, optionally substituted with one or more, in one embodiment, one, two, three, or four, substituents $Q^a$;

wherein each $Q^a$ is independently selected from the group consisting of (a) deuterium, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$(O)OR$^f$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen or deuterium; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^f$ and R$^g$ together with the N atom to which they are attached form heterocyclyl. In some embodiments, two Q substituents together with the atoms to which they are attached, may form a fused ring system.

As used herein, the abbreviations for any protective groups, amino acids and other compounds, are, unless indicated otherwise, in accord with their common usage, recognized abbreviations, the IUPAC-IUB Commission on Biochemical Nomenclature (see, (1972) Biochem. 11:942-944), or the IUPAC Nomenclature of Organic Chemistry (see, Favre H A and Powell W H, Nomenclature of Organic Chemistry: IUPAC Recommendations and Preferred Names 2013, Cambridge, UK: The Royal Society of Chemistry, 2013: Print ISBN 978-0-85404-182-4, PDF eISBN 978-1-84973-306-9, DOI 10.1039/9781849733069; Nomenclature of Organic Chemistry, Sections A, B, C, D, E, F, and H, Pergamon Press, Oxford, 1979. Copyright 1979 IUPAC; and A Guide to IUPAC Nomenclature of Organic Compounds (Recommendations 1993), 1993, Blackwell Scientific publications, Copyright 1993 IUPAC).

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician. A therapeutically effective amount of a compound provided herein can be administered in one dose (i.e., a single dose administration) or divided and administered over time (i.e., continuous administration or multiple sub-dose administration). Single dose administration, continuous administration, or multiple sub-dose administration can be repeated, for example, to maintain the level of the compound in a biological molecule (e.g., a protein, enzyme, RNA, or DNA), cell, tissue, system, animal, or human.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy*, 22nd ed.; Loyd et al., Eds.; The Pharmaceutical Press, 2012; *Handbook of Pharmaceutical Excipients*, 7th ed.; Rowe et al., Eds.; The Pharmaceutical Press, 2012; *Handbook of Pharmaceutical Additives*, 3rd ed.; Ash and Ash Eds.; Synapse Information Resources, Inc., 2007; *Pharmaceutical Preformulation and Formulation*, 2nd ed.; Gibson Ed.; CRC Press LLC, 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The term "percent by weight" or "% by weight" refers to the weight of a specified component (e.g., an active compound or excipient) in a composition (e.g., a pharmaceutical composition) as a percentage of the total weight of the composition. Thus, the sum of the weight percentages of all the components in a composition is 100%.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer or an isotopic variant of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of one enantiomer and about 5% or less of the other enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The term "isotopic variant" refers to a compound that contains an unnatural proportion of an isotope at one or more of the atoms that constitute such compounds. In certain embodiments, an "isotopic variant" of a compound contains unnatural proportions of one or more isotopes, including, but not limited to, hydrogen ($^1H$), deuterium ($^2H$), tritium ($^3H$), carbon-11 ($^{11}C$), carbon-12 ($^{12}C$), carbon-13 ($^{13}C$), carbon-14 ($^{14}C$), nitrogen-13 ($^{13}N$), nitrogen-14 ($^{14}N$), nitrogen-15 ($^{15}N$), oxygen-14 ($^{14}O$), oxygen-15 ($^{15}O$), oxygen-16 ($^{16}O$), oxygen-17 ($^{17}O$), oxygen-18 ($^{18}O$), fluorine-17 ($^{17}F$), fluorine-18 ($^{18}F$), phosphorus-31 ($^{31}P$), phosphorus-32 ($^{32}P$), phosphorus-33 ($^{33}P$), sulfur-32 ($^{32}S$), sulfur-33 ($^{33}S$), sulfur-34 ($^{34}S$), sulfur-35 ($^{35}S$), sulfur-36 ($^{36}S$), chlorine-35 ($^{35}Cl$), chlorine-36 ($^{36}Cl$), chlorine-37 ($^{37}Cl$), bromine-79 ($^{79}Br$), bromine-81 ($^{81}Br$), iodine-123 ($^{123}I$), iodine-125 ($^{125}I$), iodine-127 ($^{127}I$), iodine-129 ($^{129}I$), and iodine-131 ($^{131}I$). In certain embodiments, an "isotopic variant" of a compound is in a stable form, that is, non-radioactive. In certain embodiments, an "isotopic variant" of a compound contains unnatural proportions of one or more isotopes, including, but not limited to, hydrogen ($^1H$), deuterium ($^2H$), carbon-12 ($^{12}C$), carbon-13 ($^{13}C$), nitrogen-14 ($^{14}N$), nitrogen-15 ($^{15}N$), oxygen-16 ($^{16}O$), oxygen-17 ($^{17}O$), oxygen-18 ($^{18}O$), fluorine-17 ($^{17}F$), phosphorus-31 ($^{31}P$), sulfur-32 ($^{32}S$), sulfur-33 ($^{33}S$), sulfur-34 ($^{34}S$), sulfur-36 ($^{36}S$), chlorine-35 ($^{35}Cl$), chlorine-37 ($^{37}Cl$), bromine-79 ($^{79}Br$), bromine-81 ($^{81}Br$), and iodine-127 ($^{127}I$). In certain embodiments, an "isotopic variant" of a compound is in an unstable form, that is, radioactive. In certain embodiments, an "isotopic variant" of a compound contains unnatural proportions of one or more isotopes, including, but not limited to, tritium ($^3H$), carbon-11 ($^{11}C$), carbon-14 ($^{14}C$), nitrogen-13 ($^{13}N$), oxygen-14 ($^{14}O$), oxygen-15 ($^{15}O$), fluorine-18 ($^{18}F$), phosphorus-32 ($^{32}P$), phosphorus-33 ($^{33}P$), sulfur-35 ($^{35}S$), chlorine-36 ($^{36}Cl$), iodine-123 ($^{123}I$), iodine-125 ($^{125}I$), iodine-129 ($^{129}I$), and iodine-131 ($^{131}I$). It will be understood that, in a compound as provided herein, any hydrogen can be $^2H$, for example, or any carbon can be $^{13}C$, as example, or any nitrogen can be $^{15}N$, as example, and any oxygen can be $^{18}O$, where feasible according to the judgment of one of skill. In certain embodiments, an "isotopic variant" of a compound contains unnatural proportions of deuterium. In some embodiments, a pharmaceutically acceptable derivative of a compound is an isotopic variant.

The term "solvate" refers to a complex or aggregate formed by one or more molecules of a solute, e.g., a compound provided herein, and one or more molecules of a solvent, which present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The phrase "an isotopic variant thereof; or a pharmaceutically acceptable salt thereof; or a pharmaceutically acceptable solvate thereof" has the same meaning as the phrase "an isotopic variant of the compound referenced therein; or a pharmaceutically acceptable salt of the compound referenced therein; or a pharmaceutically acceptable salt of an isotopic variant of the compound referenced therein; or a pharmaceutically acceptable solvate of the compound referenced therein; or a pharmaceutically acceptable solvate of an isotopic variant of the compound referenced therein; or a pharmaceutically acceptable solvate of a pharmaceutically acceptable salt of the compound referenced therein; or a pharmaceutically acceptable solvate of a pharmaceutically acceptable salt of an isotopic variant of the compound referenced therein or its variant or its variant."

4.2. Ras GTP Binding Domain

Data Concerning the Affinity of GTP to the Ras GTP Binding Domain

As disclosed in International Application No. PCT/US2018/038613 and U.S. patent application Ser. No. 16/013,872, the affinity of GTP for the GTP binding domain of K-Ras utilizing a Scintillation Proximity Assay (SPA) and MicroScale Thermophoresis (MST) has been measured. These methods were not available when Wittinghofer and colleagues undertook their studies.

In SPA and MST studies, it was found and is disclosed in International Application No. PCT/US2018/038613 and U.S. patent application Ser. No. 16/013,872 that the affinity of GTP for the K-Ras GTP binding domain across wild type and mutant K-Ras is in the range of 100-465 nanomolar (see results in Table 2). This therefore led to the novel, unanticipated conclusion that compounds such as small molecules could be discovered that would bind to a Ras GTP binding domain and compete with the binding of GTP to Ras. SPA and MST studies performed on the Rac-1 and Rho-A members of the Rho subfamily show that the affinity of GTP for the binding domain of these Rho subfamily members is in the range of 120-170 nanomolar (see results in Table 2).

TABLE 2

MST and SPA Results for GTP Affinity for K-Ras and Rho Subfamily Binding Domains

| Protein | MST | SPA |
| --- | --- | --- |
| K-Ras (wild type) | 463 ± 2 nM | 243 ± 15 nM |
| K-Ras (G12D) | 244 ± 12 nM | 270 ± 15 nM |

TABLE 2-continued

MST and SPA Results for GTP Affinity for K-Ras and Rho Subfamily Binding Domains

| Protein | MST | SPA |
| --- | --- | --- |
| K-Ras (G12C) | 207 ± 46 nM | 258 ± 18 nM |
| K-Ras (Q61H) | 157 ± 21 nM | 118 ± 11 nM |
| Rac-1 | 166 ± 10 nM | 151 ± 14 nM |
| Rho-A | 130 ± 5 nM | 129 ± 12 nM |

See Khawaja et al., "Scintillation proximity assay in lead discovery", Expert Opin. Drug Discov., 2008 November; 3(11):1267-80 regarding SPA procedures. See the following references regarding MST technology: Wienken et al., Nature Communications (2010), Protein binding assays in biological liquids using MicroScale Thermophoresis; Jerabek-Willemsen et al., ASSAY and Drug Development Technologies (2011), Molecular interaction studies using MicroScale Thermophoresis; Lin et al., Cell (2012), Inhibition of basal FGF receptor signaling by dimeric Grb2; Seidel et al., Angewandte Chemie (2012), Label-Free MicroScale Thermophoresis discriminates sites and affinity of protein-ligand binding; Seidel et al., Methods (2012), MicroScale Thermophoresis quantifies biomolecular interactions under previously challenging conditions; Parker & Newstead, Nature (2014), Molecular basis of nitrate uptake by the plant nitrate transporter NRT1.1; and Jerabek-Willemsen et al., Journal of Molecular Structure (2014), MicroScale Thermophoresis: Interaction analysis and beyond.

The Discovery of Small Molecules that Bind to a Ras GTP Binding Domain in Competition with GTP Provided herein is an assay for the identification of small molecules that bind to a Ras GTP binding domain in competition with GTP.

The useful approach for drug discovery described herein and in International Application No. PCT/US2018/038613 and U.S. patent application Ser. No. 16/013,872 is to identify small molecule inhibitors that will compete and block interactions between GTP and GTP-binding proteins. By interacting with the GDP/GTP-binding site of GTP-binding proteins small molecules so identified may induce a GDP-bound or other inactive conformation of the GTP-binding proteins and thus block signal transduction pathways downstream of the GTP-binding protein.

The assay disclosed herein measures and quantifies the ability of tested small molecules in a cell-free system to compete with GTP or GDP binding. The assay can be used in low volumes or for High Throughput Screening (HTS) to screen a compound library and to support medicinal chemistry Structure Activity Relationship (SAR) studies and optimization efforts.

This is a competitive binding assay. It involves the immobilization of a protein on solid phase, interaction with a small molecule drug candidate, and then competitive binding with a labeled native GTP or GDP ligand.

In one embodiment, provided herein is a method of testing the ability of one or more compounds to bind to the GTP binding domain and to compete for GTP binding of one or more members of the Ras superfamily comprising:

a) expressing a Ras superfamily protein or mutant thereof as a tagged protein;

b) contacting the one or more compounds to the tagged protein, followed by incubating the combination;

c) adding labeled-GTP or labeled-GDP to each protein-compound combination, followed by incubating the resulting mixture; and d) measuring the amount of bound, labeled-GTP or bound, labeled-GDP.

In one embodiment, the method further comprises between step a) and step b): adding the tagged protein to one or more wells of a ligand-coated single or multi-well plate and incubating the tagged protein.

In one embodiment of the method, one or more members of the Ras superfamily is Ras. In one embodiment of the method, the Ras is DIRAS1; DIRAS2; DIRAS3; ERAS; GEM; HRAS; KRAS; MRAS; NKIRAS1; NKIRAS2; NRAS; RALA; RALB; RAP1A; RAP1B; RAP2A; RAP2B; RAP2C; RASD1; RASD2; RASL10A; RASL10B; RASL11A; RASL11B; RASL12; REM1; REM2; RERG; RERGL; RRAD; RRAS; or RRAS2. In one embodiment of the method, the Ras is HRAS, KRAS, NRAS, or a mutant thereof. In one embodiment of the method, the Ras is HRAS or a mutant thereof. In one embodiment of the method, the Ras is KRAS or a mutant thereof. In one embodiment of the method, the Ras is NRAS or a mutant thereof.

In one embodiment of the method, the Ras superfamily protein is KRas G12D mutant protein. In one embodiment of the method, the Ras superfamily protein is KRas G12C mutant protein. In one embodiment of the method, the Ras superfamily protein is KRas wild type protein. In one embodiment of the method, the Ras superfamily protein is KRas Q61H mutant protein.

In one embodiment of the method, one or more members of the Ras superfamily is Rho. In one embodiment of the method, the Rho is RHOA, RHOB; RHOBTB1; RHOBTB2; RHOBTB3; RHOC; RHOD; RHOF; RHOG; RHOH; RHOJ; RHOQ; RHOU; RHOV; RND1; RND2; RND3; RAC1; RAC2; RAC3; CDC42, or a mutant thereof. In one embodiment of the method, the Ras superfamily protein is Rho-A protein.

In one embodiment of the method, one or more members of the Ras superfamily is Rac. In one embodiment of the method, the Rho is Rac or a mutant thereof. In one embodiment of the method, the Rac is RAC1; RAC2; RAC3; RHOG, or a mutant thereof. In one embodiment of the method, the Ras superfamily protein is Rac-1 protein.

In one embodiment of the method, the tagged protein is tagged with His. In one embodiment of the method, the ligand is nickel. In one embodiment of the method, the labeled-GTP is Cy3-GTP or Cy5-GTP. In one embodiment of the method, the buffer is Buffer-I which comprises 25 mM Tris (pH 7.4), 150 mM NaCl, 1 mM MgCl$_2$, and 1 mM DTT. In another embodiment of the method, the buffer is Buffer-II which comprises 50 mM Tris (pH 7.0), 1 mM MgCl$_2$, and 1 mM DTT.

The form of the assay involves the binding of His-tagged protein to nickel coated plates and a native form of GTP covalently labeled with Cy3 or Cy5 fluorescent probes.

In theory, the assay is suitable for use with any GTP or GDP binding protein. The Examples demonstrate that the assay can be utilized for Ras and Ras mutants, Rac-1 and Rho-A human proteins expressed and purified as recombinant proteins.

Different tag/ligand combinations can be used in the assay. The protein may be expressed as a fusion protein with a tag such as His, HA, Flag or GST; or, the protein can be labeled by a tag such as biotin via chemical reaction. The counter molecule (ligand or binder) interacting with the tag will bind or coat the solid phase. The solid phase could be a plate (96, 384 or 1536 wells plate) and column beads such as sepharose, agarose and cellulose. Binders could include metals such as nickel, copper or cobalt, and antibodies, glutathione and streptavidin. Examples of tag:ligand combinations include His (polyhistidine, at least 6 histidines): nickel, GST (Glutathione-S-transferase):glutathione, HA (amino acids 98-106 of human influenza hemagglutinin): anti-HA antibodies, Fc (constant region of human IgG): protein A, FLAG (the peptide DYDDDDK):Antibodies (M1. M2, 4E11), Myc (the peptide EQKLISEED derived the myc protein): Anti-myc antibodies, and biotin: streptavidin (or avidin).

Heretofore, attempts to measure small molecule competitors for GTP protein interactions have relied on the ability of the tested small molecules to prevent binding of labeled GTP to the GTP-binding protein. A component of this assay is the use of the highly sensitive Cy3 or Cy5 probes. Similar probes which might be used include other high sensitivity fluorophores that can be detected at concentrations below 1 micromolar in solution, and radioactive labeling.

The Identification of Amino Acids in the Ras GTP Binding Domain Enabling the Development and Function of Small Molecule Targeted Therapeutics As noted in International Application No. PCT/US2018/038613 and U.S. patent application Ser. No. 16/013,872, it has also been discovered that amino acids in the Ras GTP binding domain, including Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146 and Lys147 and Mg202, enable the competitive binding to that domain between compounds, such as small molecules, and GTP.

As described in International Application No. PCT/US2018/038613 and U.S. patent application Ser. No. 16/013,872, molecular modeling studies incorporating Ras superfamily protein structures from the RCSB PDB (www.rcsb.org) with either GDP, the GTP analog GNP (guanosine 5'-[β,γ-imido]triphosphate trisodium salt hydrate), or small molecules, were used to determine the amino acids in the Ras superfamily domain in close proximity to the GDP, GTP or small molecules when bound to the Ras superfamily protein.

As noted in International Application No. PCT/US2018/038613 and U.S. patent application Ser. No. 16/013,872, it has also been discovered that amino acids in the Rac1 GTP binding domain, including Gly12, Ala13, Gly15, Lys16, Thr17, Cys18, Leu19, Phe28, Ile33, Pro34, Val36, Ala59, Thr115, Lys116, Asp118, Leu119, Cys157, Ala159, and Mg202, enable the competitive binding to that domain between compounds, such as small molecules, and GTP.

As noted in International Application No. PCT/US2018/038613 and U.S. patent application Ser. No. 16/013,872, it has also been discovered that amino acids in the RhoA GTP binding domain, including Gly14, Ala15, Cys16, Gly17, Lys18, Thr19, Cys20, Phe30, Pro31, Glu32, Tyr34, Val35, Pro36, Thr37, Asp59, Lys118, Asp120, Lys162, and Mg202, enable the competitive binding to that domain between compounds, such as small molecules, and GTP.

4.3. Methods of Treatment 4.3.1 Cancer

In one embodiment, provided herein is a method of treating or preventing cancer, which comprises administering to a subject a compound that inhibits the function of one or more members of the Ras superfamily. In one embodiment, provided herein is a method of treating or preventing cancer, which comprises administering to a subject a compound that inhibits the function of one or more members of the Ras superfamily by binding to the GTP binding domain of one or more members of the Ras superfamily. In one embodiment, provided herein is a method of treating or preventing cancer, which comprises administering to a subject a compound that inhibits the function of Ras by binding to a Ras GTP binding domain. In another embodiment, provided herein is a method of treating or preventing cancer, which comprises administering to a subject a compound that binds to a Ras GTP binding domain with an $IC_{50}$ of less than 10 μM and a $K_d$ of less than 10 μM. In another embodiment, provided herein is a method of treating or preventing cancer, which comprises administering to a subject a compound that binds to a Ras GTP binding domain with an $IC_{50}$ of less than 1 μM and a $K_d$ of less than 1 μM. In another embodiment, provided herein is a method of treating or preventing cancer, which comprises administering to a subject a compound that binds to a Ras GTP binding domain with an $IC_{50}$ of less than 500 nM and a $K_d$ of less than 500 nM. In another embodiment, provided herein is a method of treating or preventing cancer, which comprises administering to a subject a compound that binds to a Ras GTP binding domain with an $IC_{50}$ of less than 470 nM and a $K_d$ of less than 470 nM. In another embodiment, provided herein is a method of treating or preventing cancer, which comprises administering to a subject a compound that binds to a Ras GTP binding domain with an $IC_{50}$ of less than 270 nM and a $K_d$ of less than 270 nM. In another embodiment, provided herein is a method of treating or preventing cancer, which comprises administering to a subject a compound that binds to a Ras GTP binding domain with an $IC_{50}$ of less than 200 nM and a $K_d$ of less than 200 nM. In another embodiment, provided herein is a method of treating or preventing cancer, which comprises administering to a subject a compound that binds to a Ras GTP binding domain with an $IC_{50}$ of less than 150 nM and a $K_d$ of less than 150 nM. In another embodiment, provided herein is a method of treating or preventing cancer, which comprises administering to a subject a compound that binds to a Ras GTP binding domain with an $IC_{50}$ of less than 100 nM and a $K_d$ of less than 100 nM. In another embodiment, provided herein is a method of treating or preventing cancer, which comprises administering to a subject a compound that binds to a Ras GTP binding domain with greater than 15% inhibition at 20 μM. In another embodiment, provided herein is a method of treating or preventing cancer, which comprises administering to a subject a compound that binds to a Ras GTP binding domain with greater than 25% inhibition at 20 μM. In another embodiment, provided herein is a method of treating or preventing cancer, which comprises administering to a subject a compound that binds to a Ras GTP binding domain with greater than 50% inhibition at 20 μM. In another embodiment, provided herein is a method of treating or preventing cancer, which comprises administering to a subject a compound that binds to a Ras GTP binding domain with greater than 75% inhibition at 20 μM. In another embodiment, provided herein is a method of treating or preventing cancer, which comprises administering to a subject a compound that binds to a Ras GTP binding domain with greater than 80% inhibition at 20 μM. In another embodiment, provided herein is a method of treating or preventing cancer, which comprises administering to a subject a compound that binds to a Ras GTP binding domain with greater than 85% inhibition at 20 μM. In another embodiment, provided herein is a method of treating or preventing cancer, which comprises administering to a subject a compound that binds to a Ras GTP binding domain with greater than 90% inhibition at 20 μM. In another embodiment, provided herein is a method of treating or preventing cancer, which comprises administering to a subject a compound that binds to a Ras GTP binding domain with greater than 95% inhibition at 20 μM. In another embodiment, provided herein is a method of treating or preventing cancer, which comprises administering to a subject a compound that binds to a Ras GTP binding domain with greater than 99% inhibition at 20 μM. In one embodiment, provided herein is a method of treating or preventing cancer, which comprises administering to a subject a compound that inhibits the function of Rho. In one embodiment, provided herein is a method of treating or preventing cancer, which comprises administering to a subject a compound that inhibits the function of Rho by binding to a Rho GTP binding domain. In another embodiment, provided herein is a method of treating or preventing cancer, which comprises administering to a subject a compound that binds to a Rho GTP binding domain with an $IC_{50}$ of less than 10 μM and a $K_d$ of less than 10 μM. In another embodiment, provided herein is a method of treating or preventing cancer, which comprises administering to a subject a compound that binds to a Rho GTP binding domain with an $IC_{50}$ of less than 1 μM and a $K_d$ of less than 1 μM. In another embodiment, provided herein is a method of treating or preventing cancer, which comprises administering to a subject a compound that binds to a Rho GTP binding domain with an $IC_{50}$ of less than 500 nM and a $K_d$ of less than 500 nM. In another embodiment, provided herein is a method of treating or preventing cancer, which comprises administering to a subject a compound that binds to a Rho GTP binding domain with an $IC_{50}$ of less than 270 nM and a $K_d$ of less than 270 nM. In another embodiment, provided herein is a method of treating or preventing cancer, which comprises administering to a subject a compound that binds to a Rho GTP binding domain with an $IC_{50}$ of less than 200 nM and a $K_d$ of less than 200 nM. In another embodiment, provided herein is a method of treating or preventing cancer, which comprises administering to a subject a compound that binds to a Rho GTP binding domain with an $IC_{50}$ of less than 150 nM and a $K_d$ of less than 150 nM. In another embodiment, provided herein is a method of treating or preventing cancer, which comprises administering to a subject a compound that binds to a Rho GTP binding domain with an $IC_{50}$ of less than 130 nM and a $K_d$ of less than 130 nM. In another embodiment, provided herein is a method of treating or preventing cancer, which comprises administering to a subject a compound that binds to a Rho GTP binding domain with an $IC_{50}$ of less than 100 nM and a $K_d$ of less than 100 nM. In another embodiment, provided herein is a method of treating or preventing cancer, which comprises administering to a subject a compound that binds to a Rho GTP binding domain with greater than 15% inhibition at 20 μM. In another embodiment, provided herein is a method of treating or preventing cancer, which comprises administering to a subject a compound that binds to a Rho GTP binding domain with greater than 25% inhibition at 20 μM. In another embodiment, provided herein is a method of treating or preventing cancer, which comprises administering to a subject a compound that binds to a Rho GTP binding domain with greater than 50% inhibition at 20 μM. In another embodiment, provided herein is a method of treating or preventing cancer, which comprises administering to a subject a compound that binds to a Rho GTP binding domain with greater than 75% inhibition at 20 μM. In another embodiment, provided herein is a method of treating or preventing cancer, which comprises administering to a subject a compound that binds to a Rho GTP binding domain with greater than 80% inhibition at 20 μM. In another embodiment, provided herein is a method of treating or preventing cancer, which comprises administering to a subject a compound that binds to a Rho GTP binding domain with greater than 85% inhibition at 20 μM. In another embodiment, provided herein is a method of treating or preventing cancer, which comprises administering to a subject a compound that binds to a Rho GTP binding domain with greater than 90% inhibition at 20 μM. In another embodiment, provided herein is a method of treating or preventing cancer, which comprises administering to a subject a compound that binds to a Rho GTP binding domain with greater than 95% inhibition at 20 μM. In another embodiment, provided herein is a method of treating or preventing cancer, which comprises administering to a subject a compound that binds to a Rho GTP binding domain with greater than 99% inhibition at 20 μM. In one embodiment, provided herein is a method of treating or preventing cancer, which comprises administering to a subject a compound that inhibits the function of Rac. In one embodiment, provided herein is a method of treating or preventing cancer, which comprises administering to a subject a compound that inhibits the function of Rac by binding to a Rac GTP binding domain. In another embodiment, provided herein is a method of treating or preventing cancer, which comprises administering to a subject a compound that binds to a Rac GTP binding domain with an $IC_{50}$ of less than 10 μM and a $K_d$ of less than 10 μM. In another embodiment, provided herein is a method of treating or preventing cancer, which comprises administering to a subject a compound that binds to a Rac GTP binding domain with an $IC_{50}$ of less than 1 μM and a $K_d$ of less than 1 μM. In another embodiment, provided herein is a method of treating or preventing cancer, which comprises administering to a subject a compound that binds to a Rac GTP binding domain with an $IC_{50}$ of less than 500 nM and a $K_d$ of less than 500 nM. In another embodiment, provided herein is a method of treating or preventing cancer, which comprises administering to a subject a compound that binds to a Rac GTP binding domain with an $IC_{50}$ of less than 270 nM and a $K_d$ of less than 270 nM. In another embodiment, provided herein is a method of treating or preventing cancer, which comprises administering to a subject a compound that binds to a Rac GTP binding domain with an $IC_{50}$ of less than 200 nM and a $K_d$ of less than 200 nM. In another embodiment, provided herein is a method of treating or preventing cancer, which comprises administering to a subject a compound that binds to a Rac GTP binding domain with an $IC_{50}$ of less than 170 nM and a $K_d$ of less than 170 nM. In another embodiment, provided herein is a method of treating or preventing cancer, which comprises administering to a subject a compound that binds to a Rac GTP binding domain with an $IC_{50}$ of less than 150 nM and a $K_d$ of less than 150 nM. In another embodiment, provided herein is a method of treating or preventing cancer, which comprises administering to a subject a compound that binds to a Rac GTP binding domain with an $IC_{50}$ of less than 100 nM and a $K_d$ of less than 100 nM. In another embodiment, provided herein is a method of treating or preventing cancer, which comprises administering to a subject a compound that binds to a Rac GTP binding domain with greater than 15% inhibition at 20 μM. In another embodiment, provided herein is a method of treating or preventing cancer, which comprises administering to a subject a compound that binds to a Rac GTP binding domain with greater than 25% inhibition at 20 μM. In another embodiment, provided herein is a method of treating or preventing cancer, which comprises administering to a subject a compound that binds to a Rac GTP binding domain with greater than 50% inhibition at 20 μM. In another embodiment, provided herein is a method of treating or preventing cancer, which comprises administering to a subject a compound that binds to a Rac GTP binding domain with greater than 75% inhibition at 20 μM. In another embodiment, provided herein is a method of treating or preventing cancer, which comprises administering to a subject a compound that binds to a Rac GTP binding domain with greater than 80% inhibition at 20 μM. In another embodiment, provided herein is a method of treating or preventing cancer, which comprises administering to a subject a compound that binds to a Rac GTP binding domain with greater than 85% inhibition at 20 μM. In another embodiment, provided herein is a method of treating or preventing cancer, which comprises administering to a subject a compound that binds to a Rac GTP binding domain with greater than 90% inhibition at 20 μM. In another embodiment, provided herein is a method of treating or preventing cancer, which comprises administering to a subject a compound that binds to a Rac GTP binding domain with greater than 95% inhibition at 20 μM. In another embodiment, provided herein is a method of treating or preventing cancer, which comprises administering to a subject a compound that binds to a Rac GTP binding domain with greater than 99% inhibition at 20 μM. In some embodiments, the compound for use in the method is a compound as disclosed herein of Formula I, IA, IIA, IIA1, IIB, IIC, IID, IIE, IIIA, IIIA1, IIIA2, IIIB, IIIC, IIID, IIIE, or IIIF, or a pharmaceutically acceptable salt thereof. In some embodiments, the compound as disclosed herein for use in the method is a compound of Examples 1-135, or a pharmaceutically acceptable salt thereof.

In another embodiment, provided herein is a method of treating or preventing cancer, which comprises administering to a subject a compound that binds to one or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to two or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to three or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to four or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to five or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to six or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to seven or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to eight or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to nine or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to ten or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to eleven or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to twelve or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to thirteen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to fourteen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to fifteen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to sixteen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to seventeen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to eighteen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to nineteen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to twenty or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to twenty-one or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to twenty-two or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to twenty-three or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing cancer, which comprises administering to a subject a compound that binds to all of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In some embodiments, the compound for use in the method is a compound as disclosed herein of Formula I, IA, IIA, IIA1, IIB, IC, IIID, IE, IIIA, IIIA1, IIIA2, IIIB, IIIC, IIID, IIIE, or IIIF, or a pharmaceutically acceptable salt thereof. In some embodiments, the compound as disclosed herein for use in the method is a compound of Examples 1-135, or a pharmaceutically acceptable salt thereof.

In one embodiment, the Ras is DIRAS1; DIRAS2; DIRAS3; ERAS; GEM; HRAS; KRAS; MRAS; NKIRAS1; NKIRAS2; NRAS; RALA; RALB; RAP1A; RAP1B; RAP2A; RAP2B; RAP2C; RASD1; RASD2; RASL10A; RASL10B; RASL11A, RAS11B; RASL12; REM1; REM2; RERG; RERGL; RRAD; RRAS; or RRAS2. In another embodiment, the Ras is HRAS, KRAS or NRAS. In one embodiment, the Ras is HRAS. In one embodiment, the Ras is KRAS. In one embodiment, the Ras is NRAS. In another embodiment, the Ras is a mutant form of a Ras described herein.

In another embodiment, provided herein is a method of treating or preventing cancer, which comprises administering to a subject a compound that binds to one or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to two or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to three or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to four or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to five or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to six or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to seven or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to eight or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to nine or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to ten or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to eleven or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to twelve or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to thirteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to fourteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to fifteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to sixteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds to seventeen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing cancer, which comprises administering to a subject a compound that binds all of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In some embodiments, the compound for use in the method is a compound as disclosed herein of Formula I, IA, IIA, IIA1, IIB, IIC, IID, IIE, IIA, IIIA1, IIIA2, IIIB, IIIC, IIID, IIIE, or IIIF, or a pharmaceutically acceptable salt thereof. In some embodiments, the compound as disclosed herein for use in the method is a compound of Examples 1-135, or a pharmaceutically acceptable salt thereof.

In one embodiment, the Rho is RHOA; RHOB; RHOBTB1; RHOBTB2, RHOBTB3; RHOC; RHOD; RHOF; RHOG; RHOH; RHOJ; RHOQ; RHOU; RHOV; RND1; RND2; RND3; RAC1; RAC2; RAC3 or CDC42. In one embodiment, the Rho is RHOA. In another embodiment, the Rho is a mutant form of a Rho described herein.

In one embodiment, provided herein is a method of treating or preventing cancer, which comprises administering to a subject a compound that binds to one or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to two or more of Gly12, Ala13, Gly15, Lys16, Thr17, Cys18, Leu19, Phe28, Ile33, Pro34, Val36, Ala59, Thr115, Lys16, Asp118, Leu119, Cys157, Ala159, or Mg202 in a highly conserved Rho GTP binding domain. In one embodiment, provided herein is a method of treating or preventing cancer, which comprises administering to a subject a compound that binds to three or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to four or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to five or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to six or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to seven or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to eight or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to nine or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to ten or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to eleven or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to twelve or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to thirteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to fourteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to fifteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to sixteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to seventeen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to eighteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing cancer, which comprises administering to a subject a compound that binds to all of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In some embodiments, the compound for use in the method is a compound as disclosed herein of Formula I, IA, IA, IIA1, IIB, IC, IID, IIE, IIIA, IIIA1, IIIA2, IIIB, IIIC, IIID, IIIE, or IIIF, or a pharmaceutically acceptable salt thereof. In some embodiments, the compound as disclosed herein for use in the method is a compound of Examples 1-135, or a pharmaceutically acceptable salt thereof.

In one embodiment, the Rho is Rac. In one embodiment the Rac is RAC1; RAC2; RAC3 or RHOG. In one embodiment, the Rac is RAC1. In another embodiment, the Rac is a mutant form of a Rac described herein.

In one embodiment, the compound for use in the methods and compositions provided herein inhibit GTP binding to one or more members of the Ras superfamily. In one embodiment, the compound for use in the methods and compositions provided herein inhibit GTP binding to Ras. In one embodiment, the compounds provided herein inhibit GTP binding to Rho. In one embodiment, the compound for use in the methods and compositions provided herein inhibit GTP binding to Rac. In one embodiment, the compound for use in the methods and compositions provided herein inhibit GTP binding to Ras and Rho. In one embodiment, the compound for use in the methods and compositions provided herein inhibit GTP binding to Ras and Rac. In one embodiment, the compound for use in the methods and compositions provided herein inhibit GTP binding to Rho and Rac. In one embodiment, the compound for use in the methods and compositions provided herein inhibit GTP binding to Ras, Rho and Rac. In one embodiment, the compound for use in the methods and compositions provided herein has a molecular weight less than 2000 daltons. In one embodiment, the compound for use in the methods and compositions provided herein has a molecular weight less than 1750 daltons. In one embodiment, the compound for use in the methods and compositions provided herein has a molecular weight less than 1500 daltons. In one embodiment, the compound for use in the methods and compositions provided herein has a molecular weight less than 1250 daltons. In one embodiment, the compound for use in the methods and compositions provided herein has a molecular weight less than 1000 daltons. In one embodiment, the compound for use in the methods and compositions provided herein has a molecular weight less than 750 daltons. In one embodiment, the compound for use in the methods and compositions provided herein has a molecular weight less than 665 daltons. In one embodiment, the compound for use in the methods and compositions provided herein has a molecular weight less than 500 daltons. In another embodiment, the compound for use in the methods and compositions provided herein contains a thienopyrimidine, pyrimidine or pyrrolotriazine moiety. In another embodiment, the compound for use in the methods and compositions provided herein contains a thieno[3,2-d]pyrimidine, thieno[2,3-d]pyrimidine or pyrrolo[2,1-f][1,2,4]triazine moiety. In another embodiment, the compound for use in the methods and compositions provided herein contains a thieno[3,2-d]pyrimidin-4-ol, thieno[2,3-d]pyrimidin-4-amine, pyrrolo[2,1-f][1,2,4]triazin-4-amine, 5,6-dimethoxy-N-(heteroaryl)-2-(pyridin-2-yl)pyrimidin-4-amine, 5,6-dihydroxy-2-(pyridin-2-yl)pyrimidine-4-carboxamide, 5,6-dihydroxy-2-(1-methyl-1H-imidazol-2-yl)pyrimidine-4-carboxamide, 5-methoxy-6-aryloxy-2-(pyridin-2-yl)pyrimidin-4-ol, 5-methoxy-6-heteroaryloxy-2-(pyridin-2-yl)pyrimidin-4-ol, 5-methoxy-6-(arylamino)-2-(pyridin-2-yl)pyrimidin-4-ol, 6-((heteroaryl)amino)-5-methoxy-2-(pyridin-2-yl)pyrimidin-4-ol, 6-amino-5-methyl-2-(1-methyl-1H-imidazol-2-yl)pyrimidine-4-carboxamide, thieno[2,3-d]pyrimidin-4-ol, or 4-alkoxythieno[3,2-d]pyrimidine moiety. In some embodiments, the compound for use in the method is a compound as disclosed herein of Formula I, IA, IIA, IIA1, IIB, IIC, IID, IIE, IIIA, IIIA1, IIIA2, IIIB, IIIC, IIID, IIIE, or IIIF, or a pharmaceutically acceptable salt thereof. In some embodiments, the compound as disclosed herein for use in the method is a compound of Examples 1-135, or a pharmaceutically acceptable salt thereof.

In one embodiment, provided herein is a method of treating or preventing cancer, which comprises administering to a subject a compound provided herein, or a derivative thereof. In some embodiments, the compound for use in the method is a compound as disclosed herein of Formula I, IA, IIA, IIA1, IIB, IIC, IID, IIE, IIIA, IIIA1, IIIA2, IIIB, IIIC, IIID, IIIE, or IIIF, or a pharmaceutically acceptable salt thereof. In some embodiments, the compound as disclosed herein for use in the method is a compound of Examples 1-135, or a pharmaceutically acceptable salt thereof.

In another embodiment, provided herein is method of managing cancer, which comprises administering to a subject a compound provided herein, or a derivative thereof. In some embodiments, the compound for use in the method is a compound as disclosed herein of Formula I, IA, IIA, IIA1, IIB, IIC, IID, IIE, IIIA, IIIA1, IIIA2, IIIB, IIIC, IIID, IIIE, or IIIF, or a pharmaceutically acceptable salt thereof. In some embodiments, the compound as disclosed herein for use in the method is a compound of Examples 1-135, or a pharmaceutically acceptable salt thereof.

Also provided herein are methods of treating subjects who have been previously treated for cancer but are non-responsive to standard therapies, as well as those who have not previously been treated. Also provided are methods of treating subjects regardless of subject's age, although some diseases or disorders are more common in certain age groups. Also provided are methods of treating subjects who have undergone surgery in an attempt to treat the disease or condition at issue, as well as those who have not. Because subjects with cancer have heterogeneous clinical manifestations and varying clinical outcomes, the treatment given to a subject may vary, depending on his/her prognosis. The skilled clinician will be able to readily determine without undue experimentation specific secondary agents, types of surgery, and types of non-drug based standard therapy that can be effectively used to treat an individual subject with cancer.

As used herein, the term "cancer" includes, but is not limited to, solid tumors and blood borne tumors. The term "cancer" refers to disease of skin tissues, organs, blood, and vessels, including, but not limited to, cancers of the bladder, bone, blood, brain, breast, cervix, chest, colon, endometrium, esophagus, eye, head, kidney, liver, lymph nodes, lung, mouth, neck, ovaries, pancreas, prostate, rectum, stomach, testis, throat, and uterus. Specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant giolma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma.

In certain embodiments, the cancer is a solid tumor. In certain embodiments, the solid tumor is metastatic. In certain embodiments, the solid tumor is drug-resistant. In certain embodiments, the solid tumor is hepatocellular carcinoma, prostate cancer, pancreatic cancer, lung cancer, ovarian cancer, colon cancer, small intestine cancer, biliary tract cancer, endometrium cancer, skin cancer (melanoma), cervix cancer, urinary tract cancer, or glioblastoma.

In certain embodiments, the cancer is a blood borne tumor. In certain embodiments, the blood borne tumor is metastatic. In certain embodiments, the blood borne tumor is drug resistant. In certain embodiments, the cancer is leukemia.

In one embodiment, methods provided herein encompass treating, preventing or managing various types of leukemias such as chronic lymphocytic leukemia (CLL), chronic myelocytic leukemia (CML), acute lymphoblastic leukemia (ALL), acute myeloid leukemia (AML), and acute myeloblastic leukemia (AML) by administering a therapeutically effective amount of a compound provided herein or a derivative thereof.

In some embodiments, the methods provided herein encompass treating, preventing or managing acute leukemia in a subject. In some embodiments, the acute leukemia is acute myeloid leukemia (AML), which includes, but is not limited to, undifferentiated AML (M0), myeloblastic leukemia (M1), myeloblastic leukemia (M2), promyelocytic leukemia (M3 or M3 variant (M3V)), myelomonocytic leukemia (M4 or M4 variant with eosinophilia (M4E)), monocytic leukemia (M5), erythroleukemia (M6), and megakaryoblastic leukemia (M7). In one embodiment, the acute myeloid leukemia is undifferentiated AML (M0). In one embodiment, the acute myeloid leukemia is myeloblastic leukemia (M1). In one embodiment, the acute myeloid leukemia is myeloblastic leukemia (M2). In one embodiment, the acute myeloid leukemia is promyelocytic leukemia (M3 or M3 variant (M3V)). In one embodiment, the acute myeloid leukemia is myelomonocytic leukemia (M4 or M4 variant with eosinophilia (M4E)). In one embodiment, the acute myeloid leukemia is monocytic leukemia (M5). In one embodiment, the acute myeloid leukemia is erythroleukemia (M6). In one embodiment, the acute myeloid leukemia is megakaryoblastic leukemia (M7). Thus, the methods of treating, preventing or managing acute myeloid leukemia in a subject comprise the step of administering to the subject an amount of a compound provided herein or a derivative thereof effective to treat, prevent or manage acute myeloid leukemia alone or in combination. In some embodiments, the methods comprise the step of administering to the subject a compound provided herein or a derivative thereof in combination with a second active agent in amounts effective to treat, prevent or manage acute myeloid leukemia.

In some embodiments, the methods provided herein encompass treating, preventing or managing acute lymphocytic leukemia (ALL) in a subject. In some embodiments, acute lymphocytic leukemia includes leukemia that originates in the blast cells of the bone marrow (B-cells), thymus (T-cells), and lymph nodes. The acute lymphocytic leukemia can be categorized according to the French-American-British (FAB) Morphological Classification Scheme as L1—Mature-appearing lymphoblasts (T cells or pre-B-cells), L2—Immature and pleomorphic (variously shaped) lymphoblasts (T-cells or pre-B-cells), and L3—Lymphoblasts (B-cells; Burkitt's cells). In one embodiment, the acute lymphocytic leukemia originates in the blast cells of the bone marrow (B-cells). In one embodiment, the acute lymphocytic leukemia originates in the thymus (T-cells). In one embodiment, the acute lymphocytic leukemia originates in the lymph nodes. In one embodiment, the acute lymphocytic leukemia is L1 type characterized by mature-appearing lymphoblasts (T-cells or pre-B-cells). In one embodiment, the acute lymphocytic leukemia is L2 type characterized by immature and pleomorphic (variously shaped) lymphoblasts (T-cells or pre-B-cells). In one embodiment, the acute lymphocytic leukemia is L3 type characterized by lymphoblasts (B-cells; Burkitt's cells). In certain embodiments, the acute lymphocytic leukemia is T cell leukemia. In one embodiment, the T-cell leukemia is peripheral T-cell leukemia. In another embodiment, the T-cell leukemia is T-cell lymphoblastic leukemia. In another embodiment, the T-cell leukemia is cutaneous T-cell leukemia. In another embodiment, the T-cell leukemia is adult T-cell leukemia. Thus, the methods of treating, preventing or managing acute lymphocytic leukemia in a subject comprise the step of administering to the subject an amount of a compound provided herein or a derivative thereof effective to treat, prevent or manage acute lymphocytic leukemia alone or in combination with a second active agent. In some embodiments, the methods comprise the step of administering to the subject a compound provided herein or a derivative thereof in combination with a second active agent in amounts effective to treat, prevent or manage acute lymphocytic leukemia.

In some embodiments, the methods provided herein encompass treating, preventing or managing chronic myelogenous leukemia (CML) in a subject. The methods comprise the step of administering to the subject an amount of a compound provided herein or a derivative thereof effective to treat, prevent or manage chronic myelogenous leukemia. In some embodiments, the methods comprise the step of administering to the subject a compound provided herein or a derivative thereof in combination with a second active agent in amounts effective to treat, prevent or manage chronic myelogenous leukemia.

In some embodiments, the methods provided herein encompass treating, preventing or managing chronic lymphocytic leukemia (CLL) in a subject. The methods comprise the step of administering to the subject an amount of a compound provided herein or a derivative thereof effective to treat, prevent or manage chronic lymphocytic leukemia. In some embodiments, the methods comprise the step of administering to the subject a compound provided herein or a derivative thereof in combination with a second active agent in amounts effective to treat, prevent or manage chronic lymphocytic leukemia.

In certain embodiments, provided herein are methods of treating, preventing, and/or managing disease in subjects with impaired renal function. In certain embodiments, provided herein are method of treating, preventing, and/or managing cancer in subjects with impaired renal function. In certain embodiments, provided herein are methods of providing appropriate dose adjustments for subjects with impaired renal function due to, but not limited to, disease, aging, or other subject factors.

In certain embodiments, provided herein are methods of treating, preventing, and/or managing lymphoma, including non-Hodgkin's lymphoma. In some embodiments, provided herein are methods for the treatment or management of non-Hodgkin's lymphoma (NHL), including but not limited to, diffuse large B-cell lymphoma (DLBCL), using prognostic factors.

In certain embodiments, provided herein are methods of treating, preventing, and/or managing multiple myeloma, including relapsed/refractory multiple myeloma in subjects with impaired renal function or a symptom thereof, comprising administering a therapeutically effective amount of a compound provided herein, or a derivative thereof to a subject having relapsed/refractory multiple myeloma with impaired renal function.

In certain embodiments, a therapeutically or prophylactically effective amount of the compound is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, from about 0.05 to about 10 mg per day, from about 0.05 to about 5 mg per day, from about 0.1 to about 5 mg per day, or from about 0.5 to about 5 mg per day.

In certain embodiments, the therapeutically or prophylactically effective amount is about 0.1, about 0.2, about 0.5, about 1, about 2, about 3, about 4, about 5, about 6, about 7, about 8, about 9, about 10, about 15, about 20, about 25, about 30, about 40, about 45, about 50, about 60, about 70, about 80, about 90, about 100, or about 150 mg per day.

In one embodiment, the recommended daily dose range of the compound provided herein, or a derivative thereof, for the conditions described herein lie within the range of from about 0.5 mg to about 50 mg per day, in one embodiment given as a single once-a-day dose, or in divided doses throughout a day. In some embodiments, the dosage ranges from about 1 mg to about 50 mg per day. In other embodiments, the dosage ranges from about 0.5 to about 5 mg per day. Specific doses per day include 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg per day.

In a specific embodiment, the recommended starting dosage may be 0.5, 1, 2, 3, 4, 5, 10, 15, 20, 25 or 50 mg per day. In another embodiment, the recommended starting dosage may be 0.5, 1, 2, 3, 4, or 5 mg per day. The dose may be escalated to 15, 20, 25, 30, 35, 40, 45 and 50 mg/day. In a specific embodiment, the compound can be administered in an amount of about 25 mg/day. In a particular embodiment, the compound can be administered in an amount of about 10 mg/day. In a particular embodiment, the compound can be administered in an amount of about 5 mg/day. In a particular embodiment, the compound can be administered in an amount of about 4 mg/day. In a particular embodiment, the compound can be administered in an amount of about 3 mg/day.

In certain embodiments, the therapeutically or prophylactically effective amount is from about 0.001 to about 100 mg/kg/day, from about 0.01 to about 50 mg/kg/day, from about 0.01 to about 25 mg/kg/day, from about 0.01 to about 10 mg/kg/day, from about 0.01 to about 9 mg/kg/day, 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, from about 0.01 to about 1 mg/kg/day, or from about 0.01 to about 0.05 mg/kg/day.

The administered dose can also be expressed in units other than mg/kg/day. For example, doses for parenteral administration can be expressed as mg/m$^2$/day. One of ordinary skill in the art would readily know how to convert doses from mg/kg/day to mg/m$^2$/day to given either the height or weight of a subject or both (see, e.g., Nair A B, Jacob S. A simple practice guide for dose conversion between animals and human. J Basic Clin Pharma 2016; 7:27-31). For example, a dose of 1 mg/kg/day for a 60 kg human is approximately equal to 37 mg/m$^2$/day.

In certain embodiments, the amount of the compound administered is sufficient to provide a plasma concentration of the compound at steady state, ranging from about 0.001 to about 500 µM, about 0.002 to about 200 µM, about 0.005 to about 100 µM, about 0.01 to about 50 µM, from about 1 to about 50 µM, about 0.02 to about 25 µM, from about 0.05 to about 20 µM, from about 0.1 to about 20 µM, from about 0.5 to about 20 µM, or from about 1 to about 20 µM.

In other embodiments, the amount of the compound administered is sufficient to provide a plasma concentration of the compound at steady state, ranging from about 5 to about 100 nM, about 5 to about 50 nM, about 10 to about 100 nM, about 10 to about 50 nM or from about 50 to about 100 nM.

As used herein, the term "plasma concentration at steady state" is the concentration reached after a period of administration of a compound provided herein, or a derivative thereof. Once steady state is reached, there are minor peaks and troughs on the time dependent curve of the plasma concentration of the compound.

In certain embodiments, the amount of the compound administered is sufficient to provide a maximum plasma concentration (peak concentration) of the compound, ranging from about 0.001 to about 500 µM, about 0.002 to about 200 µM, about 0.005 to about 100 µM, about 0.01 to about 50 µM, from about 1 to about 50 µM, about 0.02 to about 25 µM, from about 0.05 to about 20 µM, from about 0.1 to about 20 µM, from about 0.5 to about 20 µM, or from about 1 to about 20 µM.

In certain embodiments, the amount of the compound administered is sufficient to provide a minimum plasma concentration (trough concentration) of the compound, ranging from about 0.001 to about 500 µM, about 0.002 to about 200 µM, about 0.005 to about 100 µM, about 0.01 to about 50 µM, from about 1 to about 50 µM, about 0.01 to about 25 µM, from about 0.01 to about 20 µM, from about 0.02 to about 20 µM, from about 0.02 to about 20 µM, or from about 0.01 to about 20 µM.

In certain embodiments, the amount of the compound administered is sufficient to provide an area under the curve (AUC) of the compound, ranging from about 100 to about 100,000 ng*hr/mL, from about 1,000 to about 50,000 ng*hr/mL, from about 5,000 to about 25,000 ng*hr/mL, or from about 5,000 to about 10,000 ng*hr/mL.

In some embodiments, the compound administered is a compound as disclosed herein of Formula I, IA, IIA, IIA1, IIB, IIC, IID, IIE, IIIA, IIIA1, IIIA2, IIIB, IIIC, IIID, IIIE, or IIIF, or a pharmaceutically acceptable salt thereof. In some embodiments, the administered compound is a compound of Examples 1-135, or a pharmaceutically acceptable salt thereof.

In certain embodiments, the subject to be treated with one of the methods provided herein has not been treated with anticancer therapy prior to the administration of the compound provided herein, or a derivative thereof. In certain embodiments, the subject to be treated with one of the methods provided herein has been treated with anticancer therapy prior to the administration of the compound provided herein, or a derivative thereof. In certain embodiments, the subject to be treated with one of the methods provided herein has developed drug resistance to the anticancer therapy.

The methods provided herein encompass treating a patient regardless of subject's age, although some diseases or disorders are more common in certain age groups.

Depending on the disease to be treated and the subject's condition, the compound provided herein, or a derivative thereof, may be administered by oral, parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. The compound provided herein, or a derivative thereof, may be formulated, alone or together, in suitable dosage unit with pharmaceutically acceptable excipients, carriers, adjuvants and vehicles, appropriate for each route of administration.

In one embodiment, the compound provided herein, or a derivative thereof, is administered orally. In another embodiment, the compound provided herein, or a derivative thereof, is administered parenterally. In yet another embodiment, the compound provided herein, or a derivative thereof, is administered intravenously.

The compound provided herein, or a derivative thereof, can be delivered as a single dose such as, e.g., a single bolus injection, or oral tablets or pills; or over time, such as, e.g., continuous infusion over time or divided bolus doses over time. The compound can be administered repeatedly if necessary, for example, until the subject experiences stable disease or regression, or until the subject experiences disease progression or unacceptable toxicity. For example, stable disease for solid tumors generally means that the perpendicular diameter of measurable lesions has not increased by 25% or more from the last measurement. Response Evaluation Criteria in Solid Tumors (RECIST) Guidelines, Journal of the National Cancer Institute 92(3): 205 216 (2000). Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

The compound provided herein, or a derivative thereof, can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound, such as the compound provided herein, or a derivative thereof, is administered once or more than once each day, for example, for a period of time. The term "continuous" is intended to mean that a therapeutic compound, such as the compound provided herein or a derivative thereof, is administered daily for an uninterrupted period of at least 10 days to 52 weeks. The term "intermittent" or "intermittently" as used herein is intended to mean stopping and starting at either regular or irregular intervals. For example, intermittent administration of the compound provided herein or a derivative thereof is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as the compound provided herein or a derivative thereof, is administered daily or continuously but with a rest period. In some such embodiments, administration is once a day for two to six days, then a rest period with no administration for five to seven days.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, the compound provided herein or a derivative thereof, is administered once a day. In another embodiment, the compound provided herein, or a derivative thereof, is administered twice a day. In yet another embodiment, the compound provided herein, or a derivative thereof, is administered three times a day. In still another embodiment, the compound provided herein, or a derivative thereof, is administered four times a day.

In certain embodiments, the compound provided herein, or a derivative thereof, is administered once per day from one day to six months, from one week to three months, from one week to four weeks, from one week to three weeks, or from one week to two weeks. In certain embodiments, the compound provided herein, or a derivative thereof, is administered once per day for one week, two weeks, three weeks, or four weeks. In one embodiment, the compound provided herein, or a derivative thereof, is administered once per day for 4 days. In one embodiment, the compound provided herein, or a derivative thereof, is administered once per day for 5 days. In one embodiment, the compound provided herein, or a derivative thereof, is administered once per day for 6 days. In one embodiment, the compound provided herein, or a derivative thereof, is administered once per day for one week. In another embodiment, the compound provided herein, or a derivative thereof, is administered once per day for two weeks. In yet another embodiment, the compound provided herein, or a derivative thereof, is administered once per day for three weeks. In still another embodiment, the compound provided herein, or a derivative thereof, is administered once per day for four weeks.

Combination Therapy with a Second Active Agent

The compound provided herein, or a derivative thereof, can also be combined or used in combination with other therapeutic agents useful in the treatment and/or prevention of cancer described herein.

In one embodiment, provided herein is a method of treating, preventing, or managing cancer, comprising administering to a subject a compound provided herein, or a derivative thereof; in combination with one or more second active agents, and optionally in combination with radiation therapy, blood transfusions, or surgery. Examples of second active agents are disclosed herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound provided herein, a compound provided herein, e.g., the compound provided herein, or a derivative thereof) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

Administration of the compound provided herein, or a derivative thereof and one or more second active agents to a subject can occur simultaneously or sequentially by the same or different routes of administration. The suitability of a particular route of administration employed for a particular active agent will depend on the active agent itself (e.g., whether it can be administered orally without decomposing prior to entering the blood stream) and the cancer being treated.

The route of administration of the compound provided herein, or a derivative thereof, is independent of the route of administration of a second therapy. In one embodiment, the compound provided herein, or a derivative thereof, is administered orally. In another embodiment, the compound provided herein, or a derivative thereof, is administered intravenously. Thus, in accordance with these embodiments, the compound provided herein, or a derivative thereof, is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, the compound provided herein, or a derivative thereof, and a second therapy are administered by the same mode of administration, orally or by IV. In another embodiment, the compound provided herein, or a derivative thereof, is administered by one mode of administration, e.g., by IV, whereas the second agent (an anticancer agent) is administered by another mode of administration, e.g., orally.

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount of the compound provided herein, or a derivative thereof, and any optional additional active agents concurrently administered to the subject.

One or more second active ingredients or agents can be used together with the compound provided herein, or a derivative thereof, in the methods and compositions provided herein. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies, particularly, therapeutic antibodies to cancer antigens. Typical large molecule active agents are biological molecules, such as naturally occurring or synthetic or recombinant proteins. Proteins that are particularly useful in the methods and compositions provided herein include proteins that stimulate the survival and/or proliferation of hematopoietic precursor cells and immunologically active poietic cells in vitro or in vivo. Other useful proteins stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-Ib; GM-CF and GM-CSF; and EPO.

In certain embodiments, GM-CSF, G-CSF, SCF or EPO is administered subcutaneously during about five days in a four or six week cycle in an amount ranging from about 1 to about 750 mg/m$^2$/day, from about 25 to about 500 mg/m$^2$/day, from about 50 to about 250 mg/m$^2$/day, or from about 50 to about 200 mg/m$^2$/day. In certain embodiments, GM-CSF may be administered in an amount of from about 60 to about 500 mcg/m$^2$ intravenously over 2 hours or from about 5 to about 12 mcg/m$^2$/day subcutaneously. In certain embodiments, G-CSF may be administered subcutaneously in an amount of about 1 mcg/kg/day initially and can be adjusted depending on rise of total granulocyte counts. The maintenance dose of G-CSF may be administered in an amount of about 300 (in smaller subjects) or 480 mcg subcutaneously. In certain embodiments, EPO may be administered subcutaneously in an amount of 10,000 Unit 3 times per week.

Particular proteins that can be used in the methods and compositions include, but are not limited to: filgrastim, which is sold in the United States under the trade name Neupogen® (Amgen, Thousand Oaks, CA); sargramostim, which is sold in the United States under the trade name Leukine® (Immunex, Seattle, WA); and recombinant EPO, which is sold in the United States under the trade name Epogen® (Amgen, Thousand Oaks, CA).

Recombinant and mutated forms of GM-CSF can be prepared as described in U.S. Pat. Nos. 5,391,485; 5,393, 870; and 5,229,496; all of which are incorporated herein by reference. Recombinant and mutated forms of G-CSF can be prepared as described in U.S. Pat. Nos. 4,810,643; 4,999, 291; 5,528,823; and 5,580,755; the entireties of which are incorporated herein by reference.

Also provided for use in combination with a compound provided herein, or a derivative thereof, of are native, naturally occurring, and recombinant proteins. Further encompassed are mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., J. Immunol. Methods 248:91-101 (2001).

Antibodies that can be used in combination with a compound provided herein, or a derivative thereof, include monoclonal and polyclonal antibodies. Examples of antibodies include, but are not limited to, trastuzumab (Herceptin®), rituximab (Rituxan®), bevacizumab (Avastin™), pertuzumab (Omnitarg™), tositumomab (Bexxar®), edrecolomab (Panorex®), and G250. The compounds provided herein or an enantiomer or a mixture of enantiomers thereof, or a pharmaceutically acceptable salt, solvate, hydrate, co-crystal, clathrate, or polymorph thereof can also be combined with, or used in combination with, anti-TNF-α antibodies, and/or anti-EGFR antibodies, such as, for example, Erbitux® or panitumumab.

Large molecule active agents may be administered in the form of anti-cancer vaccines. For example, vaccines that secrete, or cause the secretion of, cytokines such as IL-2, G-CSF, and GM-CSF can be used in the methods and pharmaceutical compositions provided. See, e.g., Emens, L. A., et al., Curr. Opinion Mol. Ther. 3(1):77-84 (2001).

Second active agents that are small molecules can also be used to alleviate adverse effects associated with the administration of a compound provided herein, or a derivative thereof. However, like some large molecules, many are believed to be capable of providing a synergistic effect when administered with (e.g., before, after or simultaneously) a compound provided herein, or a derivative thereof. Examples of small molecule second active agents include, but are not limited to, anti-cancer agents, antibiotics, immunosuppressive agents, and steroids.

In certain embodiments, the second agent is an HSP inhibitor, a proteasome inhibitor, a FLT3 inhibitor or a TOR kinase inhibitor.

Examples of anti-cancer agents to be used within the methods or compositions described herein include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; clofarabine; crisnatol mesylate; cyclophosphamide; Ara-C; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; omacetaxine; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sorafenib; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs to be included within the methods or compositions include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; Ara-C ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., Gleevec); imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); 06 benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents particularly useful in the methods or compositions include, but are not limited to, rituximab, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, Ara-C, doxetaxol, paclitaxel, vinblastine, IL-2, GM CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

In certain embodiments of the methods provided herein, use of a second active agent in combination with a compound provided herein, or a derivative thereof, may be modified or delayed during or shortly following administration of a compound provided herein, or a derivative thereof, as deemed appropriate by the practitioner of skill in the art. In certain embodiments, subjects being administered a compound provided herein, or a derivative thereof, alone or in combination with other therapies may receive supportive care including antiemetics, myeloid growth factors, and transfusions of platelets, when appropriate. In some embodiments, subjects being administered a compound provided herein, or a derivative thereof, may be administered a growth factor as a second active agent according to the judgment of the practitioner of skill in the art. In some embodiments, provided is administration of a compound provided herein, or a derivative thereof, in combination with erythropoietin or darbepoetin (Aranesp).

In certain embodiments, a compound provided herein, or a derivative thereof, is administered with gemcitabine and cisplatinum to subjects with locally advanced or metastatic transitional cell bladder cancer.

In certain embodiments, a compound provided herein, or a derivative thereof, is administered in combination with a second active ingredient as follows: temozolomide to pediatric subjects with relapsed or progressive brain tumors or recurrent neuroblastoma; celecoxib, etoposide and cyclophosphamide for relapsed or progressive CNS cancer; temodar to subjects with recurrent or progressive meningioma, malignant meningioma, hemangiopericytoma, multiple brain metastases, relapsed brain tumors, or newly diagnosed glioblastoma multiforms; irinotecan to subjects with recurrent glioblastoma; carboplatin to pediatric subjects with brain stem glioma; procarbazine to pediatric subjects with progressive malignant gliomas; cyclophosphamide to subjects with poor prognosis malignant brain tumors, newly diagnosed or recurrent glioblastoma multiforms; Gliadel® for high grade recurrent malignant gliomas; temozolomide and tamoxifen for anaplastic astrocytoma; or topotecan for gliomas, glioblastoma, anaplastic astrocytoma or anaplastic oligodendroglioma.

In certain embodiments, a compound provided herein, or a derivative thereof, is administered with methotrexate, cyclophosphamide, taxane, abraxane, lapatinib, herceptin, aromatase inhibitors, selective estrogen modulators, estrogen receptor antagonists, and/or PLX3397 (Plexxikon) to subjects with metastatic breast cancer.

In certain embodiments, a compound provided herein, or a derivative thereof, is administered with temozolomide to subjects with neuroendocrine tumors.

In certain embodiments, a compound provided herein, or a derivative thereof, is administered with gemcitabine to subjects with recurrent or metastatic head or neck cancer.

In certain embodiments, a compound provided herein, or a derivative thereof, is administered with gemcitabine to subjects with pancreatic cancer.

In certain embodiments, a compound provided herein, or a derivative thereof, is administered to subjects with colon cancer in combination with ARISA®, avastin, taxol, and/or taxotere.

In certain embodiments, a compound provided herein, or a derivative thereof, is administered with capecitabine and/or PLX4032 (Plexxikon) to subjects with refractory colorectal cancer or subjects who fail first line therapy or have poor performance in colon or rectal adenocarcinoma.

In certain embodiments, a compound provided herein, or a derivative thereof, is administered in combination with fluorouracil, leucovorin, and irinotecan to subjects with Dukes C & D colorectal cancer or to subjects who have been previously treated for metastatic colorectal cancer.

In certain embodiments, a compound provided herein, or a derivative thereof, is administered to subjects with refractory colorectal cancer in combination with capecitabine, xeloda, and/or CPT-11.

In certain embodiments, a compound provided herein, or a derivative thereof, is administered with capecitabine and irinotecan to subjects with refractory colorectal cancer or to subjects with unresectable or metastatic colorectal carcinoma.

In certain embodiments, a compound provided herein, or a derivative thereof, is administered alone or in combination with interferon alpha or capecitabine to subjects with unresectable or metastatic hepatocellular carcinoma; or with cisplatin and thiotepa to subjects with primary or metastatic liver cancer.

In certain embodiments, a compound provided herein, or a derivative thereof, is administered in combination with pegylated interferon alpha to subjects with Kaposi's sarcoma.

In certain embodiments, a compound provided herein, or a derivative thereof, is administered in combination with fludarabine, carboplatin, and/or topotecan to subjects with refractory or relapsed or high-risk acute myeloid leukemia.

In certain embodiments, a compound provided herein, or a derivative thereof, is administered in combination with liposomal daunorubicin, topotecan and/or cytarabine to subjects with unfavorable karotype acute myeloblastic leukemia.

In certain embodiments, a compound provided herein, or a derivative thereof, is administered in combination with gemcitabine, abraxane, erlotinib, geftinib, and/or irinotecan to subjects with non-small cell lung cancer.

In certain embodiments, a compound provided herein, or a derivative thereof, is administered in combination with carboplatin and irinotecan to subjects with non-small cell lung cancer.

In certain embodiments, a compound provided herein, or a derivative thereof, is administered with doxetaxol to subjects with non-small cell lung cancer who have been previously treated with carbo/VP 16 and radiotherapy.

In certain embodiments, a compound provided herein, or a derivative thereof, is administered in combination with carboplatin and/or taxotere, or in combination with carboplatin, pacilitaxel and/or thoracic radiotherapy to subjects with non-small cell lung cancer.

In certain embodiments, a compound provided herein, or a derivative thereof, is administered in combination with taxotere to subjects with stage IIIB or IV non-small cell lung cancer.

In certain embodiments, a compound provided herein, or a derivative thereof, is administered in combination with oblimersen (Genasense®) to subjects with small cell lung cancer.

In certain embodiments, a compound provided herein, or a derivative thereof, is administered in combination with ABT-737 (Abbott Laboratories) and/or obatoclax (GX15-070) to subjects with lymphoma and other blood cancers.

In certain embodiments, a compound provided herein, or a derivative thereof, is administered alone or in combination with a second active ingredient such as vinblastine or fludarabine to subjects with various types of lymphoma, including, but not limited to, Hodgkin's lymphoma, non-Hodgkin's lymphoma, cutaneous T-Cell lymphoma, cutaneous B-Cell lymphoma, diffuse large B-Cell lymphoma or relapsed or refractory low grade follicular lymphoma.

In certain embodiments, a compound provided herein, or a derivative thereof, is administered in combination with taxotere, IL-2, IFN, GM-CSF, PLX4032 (Plexxikon) and/or dacarbazine to subjects with various types or stages of melanoma.

In certain embodiments, a compound provided herein, or a derivative thereof, is administered alone or in combination with vinorelbine to subjects with malignant mesothelioma, or stage IIIB non-small cell lung cancer with pleural implants or malignant pleural effusion mesothelioma syndrome.

In certain embodiments, a compound provided herein, or a derivative thereof, is administered to subjects with various types or stages of multiple myeloma in combination with dexamethasone, zoledronic acid, palmitronate, GM-CSF, biaxin, vinblastine, melphalan, busulphan, cyclophosphamide, IFN, palmidronate, prednisone, bisphosphonate, celecoxib, arsenic trioxide, PEG INTRON-A, vincristine, or a combination thereof.

In certain embodiments, a compound provided herein, or a derivative thereof, is administered to subjects with relapsed or refractory multiple myeloma in combination with doxorubicin (Doxil), vincristine and/or dexamethasone (Decadron®).

In certain embodiments, a compound provided herein, or a derivative thereof, is administered to subjects with various types or stages of ovarian cancer such as peritoneal carcinoma, papillary serous carcinoma, refractory ovarian cancer or recurrent ovarian cancer, in combination with taxol, carboplatin, doxorubicin, gemcitabine, cisplatin, xeloda, paclitaxel, dexamethasone, or a combination thereof.

In certain embodiments, a compound provided herein, or a derivative thereof, is administered to subjects with various types or stages of prostate cancer, in combination with xeloda, 5 FU/LV, gemcitabine, irinotecan plus gemcitabine, cyclophosphamide, vincristine, dexamethasone, GM-CSF, celecoxib, taxotere, ganciclovir, paclitaxel, adriamycin, docetaxel, estramustine, Emcyt, denderon or a combination thereof.

In certain embodiments, a compound provided herein, or a derivative thereof, is administered to subjects with various types or stages of renal cell cancer, in combination with capecitabine, IFN, tamoxifen, IL-2, GM-CSF, Celebrex®, or a combination thereof.

In certain embodiments, a compound provided herein, or a derivative thereof, is administered to subjects with various types or stages of gynecologic, uterus or soft tissue sarcoma cancer in combination with IFN, a COX-2 inhibitor such as Celebrex®, and/or sulindac.

In certain embodiments, a compound provided herein, or a derivative thereof, is administered to subjects with various types or stages of solid tumors in combination with celebrex, etoposide, cyclophosphamide, docetaxel, apecitabine, IFN, tamoxifen, IL-2, GM-CSF, or a combination thereof.

In certain embodiments, a compound provided herein, or a derivative thereof, is administered to subjects with scleroderma or cutaneous vasculitis in combination with celebrex, etoposide, cyclophosphamide, docetaxel, apecitabine, IFN, tamoxifen, IL-2, GM-CSF, or a combination thereof.

Also encompassed herein is a method of increasing the dosage of an anti-cancer drug or agent that can be safely and effectively administered to a subject, which comprises administering to the subject (e.g., a human) a compound provided herein, or a derivative thereof. Subjects that can benefit by this method are those likely to suffer from an adverse effect associated with anti-cancer drugs for treating a specific cancer of the skin, subcutaneous tissue, lymph nodes, brain, lung, liver, bone, intestine, colon, heart, pancreas, adrenal, kidney, prostate, breast, colorectal, or combinations thereof. The administration of a compound provided herein, or a derivative thereof, alleviates or reduces adverse effects which are of such severity that it would otherwise limit the amount of anti-cancer drug.

In one embodiment, a compound provided herein, or a derivative thereof, is administered orally and daily in an amount ranging from about 0.1 to about 150 mg, from about 1 to about 50 mg, or from about 2 to about 25 mg, prior to, during, or after the occurrence of the adverse effect associated with the administration of an anti-cancer drug to a subject. In certain embodiments, a compound provided herein, or a derivative thereof, is administered in combination with specific agents such as heparin, aspirin, coumadin, or G CSF to avoid adverse effects that are associated with anti-cancer drugs such as but not limited to neutropenia or thrombocytopenia.

In one embodiment, a compound provided herein, or a derivative thereof, is administered to subjects with diseases and disorders associated with or characterized by, undesired angiogenesis in combination with additional active ingredients, including, but not limited to, anti-cancer drugs, anti-inflammatories, antihistamines, antibiotics, and steroids.

In another embodiment, encompassed herein is a method of treating, preventing and/or managing cancer, which comprises administering the compound provided herein, or a derivative thereof, in conjunction with (e.g. before, during, or after) conventional therapy including, but not limited to, surgery, immunotherapy, biological therapy, radiation therapy, or other non-drug based therapy presently used to treat, prevent or manage cancer. The combined use of the compound provided herein, or a derivative thereof, and conventional therapy may provide a unique treatment regimen that is unexpectedly effective in certain subjects. Without being limited by theory, it is believed that the compound provided herein, or a derivative thereof, may provide additive or synergistic effects when given concurrently with conventional therapy.

As discussed elsewhere herein, encompassed herein is a method of reducing, treating and/or preventing adverse or undesired effects associated with conventional therapy including, but not limited to, surgery, chemotherapy, radiation therapy, hormonal therapy, biological therapy and immunotherapy. A compound provided herein, or a derivative thereof, and other active ingredient can be administered to a subject prior to, during, or after the occurrence of the adverse effect associated with conventional therapy.

In one embodiment, the compound provided herein, or a derivative thereof, can be administered in an amount ranging from about 0.1 to about 150 mg, from about 1 to about 25 mg, or from about 2 to about 10 mg orally and daily alone, or in combination with a second active agent disclosed herein, prior to, during, or after the use of conventional therapy.

In certain embodiments, a compound provided herein, or a derivative thereof, and doxetaxol are administered to subjects with non-small cell lung cancer who were previously treated with carbo/VP 16 and radiotherapy.

In certain embodiments, a compound provided herein, or a derivative thereof, is administered to subjects with various types or stages of cancer, in combination with an immune oncology drug or a combination of immune oncology drugs. In one embodiment, a compound provided herein, or a derivative thereof, is administered to subjects with various types or stages of cancer, in combination with Opdivo, Keytruda, Yervoy or a combination thereof.

4.3.2 Inflammation

As discussed herein, activation of MAPKs is a component of the inflammatory response. Thus, the compounds provided herein, which are MAPK inhibitors via inhibition of Ras and/or a Ras superfamily member, are useful in the treatment of inflammatory diseases.

As discussed herein, activation of Akt is a component of the inflammatory response. Thus, the compounds provided herein, which are Akt inhibitors via inhibition of Ras and/or a Ras superfamily member, are useful in the treatment of inflammatory diseases.

In one embodiment, provided herein is a method of treating or preventing inflammatory disease, which comprises administering to a subject a compound that inhibits the function of one or more members of the Ras superfamily. In one embodiment, provided herein is a method of treating or preventing inflammatory disease, which comprises administering to a subject a compound that inhibits the function of one or more members of the Ras superfamily by binding to the GTP binding domain or one or more members of the Ras superfamily. In one embodiment, provided herein is a method of treating or preventing inflammatory disease, which comprises administering to a subject a compound that inhibits the function of Ras by binding to a Ras GTP binding domain. In another embodiment, provided herein is a method of treating or preventing inflammatory disease, which comprises administering to a subject a compound that binds to a Ras GTP binding domain with an $IC_{50}$ of less than 10 μM and a $K_d$ of less than 10 μM. In another embodiment, provided herein is a method of treating or preventing inflammatory disease, which comprises administering to a subject a compound that binds to a Ras GTP binding domain with an $IC_{50}$ of less than 1 μM and a $K_d$ of less than 1 μM. In another embodiment, provided herein is a method of treating or preventing inflammatory disease, which comprises administering to a subject a compound that binds to a Ras GTP binding domain with an $IC_{50}$ of less than 500 nM and a $K_d$ of less than 500 nM. In another embodiment, provided herein is a method of treating or preventing inflammatory disease, which comprises administering to a subject a compound that binds to a Ras GTP binding domain with an $IC_{50}$ of less than 470 nM and a $K_d$ of less than 470 nM. In another embodiment, provided herein is a method of treating or preventing inflammatory disease, which comprises administering to a subject a compound that binds to a Ras GTP binding domain with an $IC_{50}$ of less than 270 nM and a $K_d$ of less than 270 nM. In another embodiment, provided herein is a method of treating or preventing inflammatory disease, which comprises administering to a subject a compound that binds to a Ras GTP binding domain with an $IC_{50}$ of less than 200 nM and a $K_d$ of less than 200 nM. In another embodiment, provided herein is a method of treating or preventing inflammatory disease, which comprises administering to a subject a compound that binds to a Ras GTP binding domain with an $IC_{50}$ of less than 150 nM and a $K_d$ of less than 150 nM. In another embodiment, provided herein is a method of treating or preventing inflammatory disease, which comprises administering to a subject a compound that binds to a Ras GTP binding domain with an $IC_{50}$ of less than 100 nM and a $K_d$ of less than 100 nM. In another embodiment, provided herein is a method of treating or preventing inflammatory disease, which comprises administering to a subject a compound that binds to a Ras GTP binding domain with greater than 15% inhibition at 20 µM. In another embodiment, provided herein is a method of treating or preventing inflammatory disease, which comprises administering to a subject a compound that binds to a Ras GTP binding domain with greater than 25% inhibition at 20 µM. In another embodiment, provided herein is a method of treating or preventing inflammatory disease, which comprises administering to a subject a compound that binds to a Ras GTP binding domain with greater than 50% inhibition at 20 µM. In another embodiment, provided herein is a method of treating or preventing inflammatory disease, which comprises administering to a subject a compound that binds to a Ras GTP binding domain with greater than 75% inhibition at 20 µM. In another embodiment, provided herein is a method of treating or preventing inflammatory disease, which comprises administering to a subject a compound that binds to a Ras GTP binding domain with greater than 80% inhibition at 20 µM. In another embodiment, provided herein is a method of treating or preventing inflammatory disease, which comprises administering to a subject a compound that binds to a Ras GTP binding domain with greater than 85% inhibition at 20 µM. In another embodiment, provided herein is a method of treating or preventing inflammatory disease, which comprises administering to a subject a compound that binds to a Ras GTP binding domain with greater than 90% inhibition at 20 µM. In another embodiment, provided herein is a method of treating or preventing inflammatory disease, which comprises administering to a subject a compound that binds to a Ras GTP binding domain with greater than 95% inhibition at 20 µM. In another embodiment, provided herein is a method of treating or preventing inflammatory disease, which comprises administering to a subject a compound that binds to a Ras GTP binding domain with greater than 99% inhibition at 20 µM. In one embodiment, provided herein is a method of treating or preventing inflammatory disease, which comprises administering to a subject a compound that inhibits the function of Rho. In one embodiment, provided herein is a method of treating or preventing inflammatory disease, which comprises administering to a subject a compound that inhibits the function of Rho by binding to a Rho GTP binding domain. In another embodiment, provided herein is a method of treating or preventing inflammatory disease, which comprises administering to a subject a compound that binds to a Rho GTP binding domain with an $IC_{50}$ of less than 10 µM and a $K_d$ of less than 10 µM. In another embodiment, provided herein is a method of treating or preventing inflammatory disease, which comprises administering to a subject a compound that binds to a Rho GTP binding domain with an $IC_{50}$ of less than 1 µM and a $K_d$ of less than 1 µM. In another embodiment, provided herein is a method of treating or preventing inflammatory disease, which comprises administering to a subject a compound that binds to a Rho GTP binding domain with an $IC_{50}$ of less than 500 nM and a $K_d$ of less than 500 nM. In another embodiment, provided herein is a method of treating or preventing inflammatory disease, which comprises administering to a subject a compound that binds to a Rho GTP binding domain with an $IC_{50}$ of less than 270 nM and a $K_d$ of less than 270 nM. In another embodiment, provided herein is a method of treating or preventing inflammatory disease, which comprises administering to a subject a compound that binds to a Rho GTP binding domain with an $IC_{50}$ of less than 200 nM and a $K_d$ of less than 200 nM. In another embodiment, provided herein is a method of treating or preventing inflammatory disease, which comprises administering to a subject a compound that binds to a Rho GTP binding domain with an $IC_{50}$ of less than 150 nM and a $K_d$ of less than 150 nM. In another embodiment, provided herein is a method of treating or preventing inflammatory disease, which comprises administering to a subject a compound that binds to a Rho GTP binding domain with an $IC_{50}$ of less than 130 nM and a $K_d$ of less than 130 nM. In another embodiment, provided herein is a method of treating or preventing inflammatory disease, which comprises administering to a subject a compound that binds to a Rho GTP binding domain with an $IC_{50}$ of less than 100 nM and a $K_d$ of less than 100 nM. In another embodiment, provided herein is a method of treating or preventing inflammatory disease, which comprises administering to a subject a compound that binds to a Rho GTP binding domain with greater than 15% inhibition at 20 µM. In another embodiment, provided herein is a method of treating or preventing inflammatory disease, which comprises administering to a subject a compound that binds to a Rho GTP binding domain with greater than 25% inhibition at 20 µM. In another embodiment, provided herein is a method of treating or preventing inflammatory disease, which comprises administering to a subject a compound that binds to a Rho GTP binding domain with greater than 50% inhibition at 20 µM. In another embodiment, provided herein is a method of treating or preventing inflammatory disease, which comprises administering to a subject a compound that binds to a Rho GTP binding domain with greater than 75% inhibition at 20 µM. In another embodiment, provided herein is a method of treating or preventing inflammatory disease, which comprises administering to a subject a compound that binds to a Rho GTP binding domain with greater than 80% inhibition at 20 µM. In another embodiment, provided herein is a method of treating or preventing inflammatory disease, which comprises administering to a subject a compound that binds to a Rho GTP binding domain with greater than 85% inhibition at 20 µM. In another embodiment, provided herein is a method of treating or preventing inflammatory disease, which comprises administering to a subject a compound that binds to a Rho GTP binding domain with greater than 90% inhibition at 20 µM. In another embodiment, provided herein is a method of treating or preventing inflammatory disease, which comprises administering to a subject a compound that binds to a Rho GTP binding domain with greater than 95% inhibition at 20 µM. In another embodiment, provided herein is a method of treating or preventing inflammatory disease, which comprises administering to a subject a compound that binds to a Rho GTP binding domain with greater than 99% inhibition at 20 µM. In one embodiment, provided herein is a method of treating or preventing inflammatory disease, which comprises administering to a subject a compound that inhibits the function of Rac. In one embodiment, provided herein is a method of treating or preventing inflammatory disease, which comprises administering to a subject a compound that inhibits the function of Rac by binding to a Rac GTP binding domain. In another embodiment, provided herein is a method of treating or preventing inflammatory disease, which comprises administering to a subject a compound that binds to a Rac GTP binding domain with an $IC_{50}$ of less than 10 µM and a $K_d$ of less than 10 µM. In another embodiment, provided herein is a method of treating or preventing inflammatory disease, which comprises administering to a subject a compound that binds to a Rac GTP binding domain with an $IC_{50}$ of less than 1 µM and a $K_d$ of less than 1 µM. In another embodiment, provided herein is a method of treating or preventing inflammatory disease, which comprises administering to a subject a compound that binds to a Rac GTP binding domain with an $IC_{50}$ of less than 500 nM and a $K_d$ of less than 500 nM. In another embodiment, provided herein is a method of treating or preventing inflammatory disease, which comprises administering to a subject a compound that binds to a Rac GTP binding domain with an $IC_{50}$ of less than 270 nM and a $K_d$ of less than 270 nM. In another embodiment, provided herein is a method of treating or preventing inflammatory disease, which comprises administering to a subject a compound that binds to a Rac GTP binding domain with an $IC_{50}$ of less than 200 nM and a $K_d$ of less than 200 nM. In another embodiment, provided herein is a method of treating or preventing inflammatory disease, which comprises administering to a subject a compound that binds to a Rac GTP binding domain with an $IC_{50}$ of less than 170 nM and a $K_d$ of less than 170 nM. In another embodiment, provided herein is a method of treating or preventing inflammatory disease, which comprises administering to a subject a compound that binds to a Rac GTP binding domain with an $IC_{50}$ of less than 150 nM and a $K_d$ of less than 150 nM. In another embodiment, provided herein is a method of treating or preventing inflammatory disease, which comprises administering to a subject a compound that binds to a Rac GTP binding domain with an $IC_{50}$ of less than 100 nM and a $K_d$ of less than 100 nM. In one embodiment, provided herein is a method of treating or preventing inflammatory disease, which comprises administering to a subject a compound that binds to a Rac GTP binding domain with greater than 15% inhibition at 20 µM. In another embodiment, provided herein is a method of treating or preventing inflammatory disease, which comprises administering to a subject a compound that binds to a Rac GTP binding domain with greater than 25% inhibition at 20 µM. In another embodiment, provided herein is a method of treating or preventing inflammatory disease, which comprises administering to a subject a compound that binds to a Rac GTP binding domain with greater than 50% inhibition at 20 µM. In another embodiment, provided herein is a method of treating or preventing inflammatory disease, which comprises administering to a subject a compound that binds to a Rac GTP binding domain with greater than 75% inhibition at 20 µM. In another embodiment, provided herein is a method of treating or preventing inflammatory disease, which comprises administering to a subject a compound that binds to a Rac GTP binding domain with greater than 80% inhibition at 20 µM. In another embodiment, provided herein is a method of treating or preventing inflammatory disease, which comprises administering to a subject a compound that binds to a Rac GTP binding domain with greater than 85% inhibition at 20 µM. In another embodiment, provided herein is a method of treating or preventing inflammatory disease, which comprises administering to a subject a compound that binds to a Rac GTP binding domain with greater than 90% inhibition at 20 µM. In another embodiment, provided herein is a method of treating or preventing inflammatory disease, which comprises administering to a subject a compound that binds to a Rac GTP binding domain with greater than 95% inhibition at 20 µM. In another embodiment, provided herein is a method of treating or preventing inflammatory disease, which comprises administering to a subject a compound that binds to a Rac GTP binding domain with greater than 99% inhibition at 20 µM. In some embodiments, the compound for use in the method is a compound as disclosed herein of Formula I, IA, IIA, IIA1, IIB, IIC, IID, IIE, IIIA, IIIA1, IIIA2, IIIB, IIIC, IIID, IIIE, or IIIF, or a pharmaceutically acceptable salt thereof. In some embodiments, the compound as disclosed herein for use in the method is a compound of Examples 1-135, or a pharmaceutically acceptable salt thereof.

In another embodiment, provided herein is a method of treating or preventing inflammatory disease, which comprises administering to a subject a compound that binds to one or more of Ala11, Gly12, Val14, Gly15, Lys16, Ser17, Ala 18, Phe28, Val 29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to two or more of Ala11, Gly12, Val14, Gly15, Lys16, Ser17, Ala 18, Phe28, Val 29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to three or more of Ala11, Gly12, Val14, Gly15, Lys16, Ser17, Ala 18, Phe28, Val 29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to four or more of Ala11, Gly12, Val14, Gly15, Lys16, Ser17, Ala 18, Phe28, Val 29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to five or more of Ala11, Gly12, Val14, Gly15, Lys16, Ser17, Ala 18, Phe28, Val 29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to six or more of Ala11, Gly12, Val14, Gly15, Lys16, Ser17, Ala 18, Phe28, Val 29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to seven or more of Ala11, Gly12, Val14, Gly15, Lys16, Ser17, Ala 18, Phe28, Val 29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to eight or more of Ala11, Gly12, Val14, Gly15, Lys16, Ser17, Ala 18, Phe28, Val 29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to nine or more of Ala11, Gly12, Val14, Gly15, Lys16, Ser17, Ala 18, Phe28, Val 29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to ten or more of Ala11, Gly12, Val14, Gly15, Lys16, Ser17, Ala 18, Phe28, Val 29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to eleven or more of Ala11, Gly12, Val14, Gly15, Lys16, Ser17, Ala 18, Phe28, Val 29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing inflammatory disease, which comprises administering to a subject a compound that binds to twelve or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to thirteen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to fourteen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to fifteen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to sixteen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to seventeen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to eighteen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to nineteen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to twenty or more of Ala11, Gly12, Val 14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to twenty-one or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to twenty-two or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to twenty-three or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing inflammatory disease, which comprises administering to a subject a compound that binds to all of Ala11, Gly12, Val14, Gly15, Lys16, Ser17, Ala 18, Phe28, Val 29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In some embodiments, the compound for use in the method is a compound as disclosed herein of Formula I, IA, IIA, IIA1, IIB, IIC, IID, IIE, IIIA, IIIA1, IIIA2, IIIB, IIIC, IIID, IIIE, or IIIF, or a pharmaceutically acceptable salt thereof. In some embodiments, the compound as disclosed herein for use in the method is a compound of Examples 1-135, or a pharmaceutically acceptable salt thereof.

In one embodiment, the Ras is DIRAS1, DIRAS2; DIRAS3; ERAS; GEM; HRAS; KRAS; MRAS; NKIRAS1; NKIRAS2; NRAS; RALA; RALB; RAP1A; RAP1B; RAP2A; RAP2B; RAP2C; RASD1; RASD2; RASL10A; RASL10B; RASL11A, RASL11B; RASL12; REM1; REM2; RERG; RERGL; RRAD; RRAS; or RRAS2. In another embodiment, the Ras is HRAS, KRAS or NRAS. In one embodiment, the Ras is HRAS. In one embodiment, the Ras is KRAS. In one embodiment, the Ras is NRAS. In another embodiment, the Ras is a mutant form of a Ras described herein.

In another embodiment, provided herein is a method of treating or preventing inflammatory disease, which comprises administering to a subject a compound that binds to one or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to two or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to three or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to four or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to five or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to six or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to seven or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to eight or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to nine or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to ten or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to eleven or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to twelve or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to thirteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to fourteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to fifteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to sixteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds to seventeen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing inflammatory disease, which comprises administering to a subject a compound that binds all of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In some embodiments, the compound for use in the method is a compound as disclosed herein of Formula I, IA, IIA, IIA1, IIB, IIC, IID, HE, IIIA, IIIA1, IIIA2, IIIB, IIIC, IID, IIIE, or IIIF, or a pharmaceutically acceptable salt thereof. In some embodiments, the compound as disclosed herein for use in the method is a compound of Examples 1-135, or a pharmaceutically acceptable salt thereof.

In one embodiment, the Rho is RHOA; RHOB; RHOBTB1; RHOBTB2; RHOBTB3; RHOC; RHOD; RHOF; RHOG; RHOH; RHOJ; RHOQ; RHOU; RHOV; RND1; RND2; RND3; RAC1; RAC2; RAC3 or CDC42. In one embodiment, the Rho is RHOA. In another embodiment, the Rho is a mutant form of a Rho described herein.

In one embodiment, provided herein is a method of treating or preventing inflammatory disease, which comprises administering to a subject a compound that binds to one or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to two or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to three or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to four or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to five or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to six or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to seven or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to eight or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to nine or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to ten or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to eleven or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to twelve or more of Gly12, Ala 13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to thirteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to fourteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to fifteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to sixteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to seventeen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to eighteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing inflammatory disease, which comprises administering to a subject a compound that binds to all of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In some embodiments, the compound for use in the method is a compound as disclosed herein of Formula I, IA, IIA, IIA1, IIB, IIC, IID, IIE, IIA, IIIA1, IIIA2, IUB, IIIC, IID, IIE, or IIIF, or a pharmaceutically acceptable salt thereof. In some embodiments, the compound as disclosed herein for use in the method is a compound of Examples 1-135, or a pharmaceutically acceptable salt thereof.

In one embodiment, the Rho is Rac. In one embodiment the Rac is RAC1; RAC2; RAC3 or RHOG. In one embodiment, the Rac is RAC1. In another embodiment, the Rac is a mutant form of a Rac described herein.

In one embodiment, the compound for use in the methods and compositions provided herein inhibit GTP binding to one or more members of the Ras superfamily. In one embodiment, the compound for use in the methods and compositions provided herein inhibit GTP binding to Ras. In one embodiment, the compounds provided herein inhibit GTP binding to Rho. In one embodiment, the compound for use in the methods and compositions provided herein inhibit GTP binding to Rac. In one embodiment, the compound for use in the methods and compositions provided herein inhibit GTP binding to Ras and Rho. In one embodiment, the compound for use in the methods and compositions provided herein inhibit GTP binding to Ras and Rac. In one embodiment, the compound for use in the methods and compositions provided herein inhibit GTP binding to Rho and Rac. In one embodiment, the compound for use in the methods and compositions provided herein inhibit GTP binding to Ras, Rho and Rac.

In one embodiment, the compound for use in the methods and compositions provided herein has a molecular weight less than 2000 daltons. In one embodiment, the compound for use in the methods and compositions provided herein has a molecular weight less than 1750 daltons. In one embodiment, the compound for use in the methods and compositions provided herein has a molecular weight less than 1500 daltons. In one embodiment, the compound for use in the methods and compositions provided herein has a molecular weight less than 1250 daltons. In one embodiment, the compound for use in the methods and compositions provided herein has a molecular weight less than 1000 daltons. In one embodiment, the compound for use in the methods and compositions provided herein has a molecular weight less than 750 daltons. In one embodiment, the compound for use in the methods and compositions provided herein has a molecular weight less than 665 daltons. In one embodiment, the compound for use in the methods and compositions provided herein has a molecular weight less than 500 daltons. In another embodiment, the compound for use in the methods and compositions provided herein contains a thienopyrimidine, pyrimidine or pyrrolotriazine moiety. In another embodiment, the compound for use in the methods and compositions provided herein contains a thieno[3,2-d]pyrimidine, thieno[2,3-d]pyrimidine or pyrrolo[2,1-f][1,2,4]triazine moiety. In another embodiment, the compound for use in the methods and compositions provided herein contains a thieno[3,2-d]pyrimidin-4-ol, thieno[2,3-d]pyrimidin-4-amine, pyrrolo[2,1-f][1,2,4]triazin-4-amine, 5,6-dimethoxy-N-(heteroaryl)-2-(pyridin-2-yl)pyrimidin-4-amine, 5,6-dihydroxy-2-(pyridin-2-yl)pyrimidine-4-carboxamide, 5,6-dihydroxy-2-(1-methyl-1H-imidazol-2-yl)pyrimidine-4-carboxamide, 5-methoxy-6-aryloxy-2-(pyridin-2-yl)pyrimidin-4-ol, 5-methoxy-6-heteroaryloxy-2-(pyridin-2-yl)pyrimidin-4-ol, 5-methoxy-6-(arylamino)-2-(pyridin-2-yl)pyrimidin-4-ol, 6-((heteroaryl)amino)-5-methoxy-2-(pyridin-2-yl)pyrimidin-4-ol, 6-amino-5-methyl-2-(1-methyl-1H-imidazol-2-yl)pyrimidine-4-carboxamide, thieno[2,3-d]pyrimidin-4-ol, or 4-alkoxythieno[3,2-d]pyrimidine moiety. In some embodiments, the compound for use in the method is a compound as disclosed herein of Formula I, IA, IIA, IIA1, IIB, IIC, IID, IIE, IIIA, IIIA1, IIIA2, IIIB, IIIC, IIID, IIIE, or IIIF, or a pharmaceutically acceptable salt thereof. In some embodiments, the compound as disclosed herein for use in the method is a compound of Examples 1-135, or a pharmaceutically acceptable salt thereof.

In one embodiment, the inflammatory disease is inflammation-associated cancer development. As disclosed here, the compounds provided herein are useful in treatment of cancer. It is well recognized that the immune inflammatory state serves as a key mediator of the middle stages of tumor development. It is also well known that chronic inflammation can predispose an individual to cancer. Chronic inflammation is caused by a variety of factors, including bacterial, viral, and parasitic infections. The longer the inflammation persists, the higher the risk of associated carcinogenesis. Anti-inflammatory cancer therapy prevents premalignant cells from turning fully cancerous or impedes existing tumors from spreading to distant sites in the body. Thus, in one embodiment, the compounds provided herein are useful in treating inflammatory cancers. Such cancers, and the chronic inflammatory conditions that predispose susceptible cells to neoplastic transformation, include gastric adenocarcinoma (gastritis), mucosa-associated lymphoid tissue (MALT) lymphoma (gastritis), bladder, liver and rectal carcinomas (schistosomiasis), cholangiocarcinoma and colon carcinoma (cholangitis), gall bladder cancer (chronic cholecystitis), ovarian and cervical carcinoma (pelvic inflammatory disease, chronic cervicitis), skin carcinoma (osteomyelitis), colorectal carcinoma (inflammatory bowel disease), esophageal carcinoma (reflux esophagitis, Barrett's esophagus), bladder cancer (bladder inflammation (cystitis)), mesothelioma and lung carcinoma (asbestosis, silicosis), oral squamous cell carcinoma (gingivitis, lichen planus), pancreatic carcinoma (pancreatitis, protease mutation), vulvar squamous cell carcinoma (lichen sclerosis), salivary gland carcinoma (slaladenitis), lung carcinoma (bronchitis) and MALT lymphoma (Sjogren syndrome, Hashimoto's thyroiditis). Shacter, et al., 2002, *Oncology,* 16(2), 217-26.

In certain embodiments, the compounds provided herein are useful in treating inflammatory diseases in the airways, such as nonspecific bronchial hyper-reactivity, chronic bronchitis, cystic fibrosis, and acute respiratory distress syndrome (ARDS).

In certain embodiments, the compounds provided herein are useful in treating asthma and idiopathic lung fibrosis or idiopathic pulmonary fibrosis (IPF), pulmonary fibrosis, and interstitial lung disease. As known to one of skill in the art, the differentiation of fibroblasts into cell types called myofibroblasts occurs during wound healing, when the cells contribute to the deposition of extracellular matrix (ECM) in the transient process of wound repair. In chronic inflammatory diseases such as asthma, pathological tissue remodeling often occurs, and is mediated by the functions of increased numbers of myofibroblasts in the diseased tissue, see Hinz, B. et al. Am J Pathol. 2007; 170: 1807-1816. In certain embodiments, the compounds provided herein prevent or reduce TGF-β-induced myofibroblast differentiation, as measured by the expression of alpha smooth muscle actin (α-SMA), a hallmark of myofibroblast differentiation (Serini, G. and Gabbiani, G. 1999; Exp. Cell Res. 250: 273-283).

In certain embodiments, the compounds provided herein are useful in treating psoriasis, chronic plaque psoriasis, psoriatic arthritis, acanthosis, atopic dermatitis, various forms of eczema, contact dermatitis (includes allergic dermatitis), systemic sclerosis (scleroderma), wound healing, and drug eruption.

In one embodiment, the disease is inflammation, arthritis, rheumatoid arthritis, spondylarthropathies, gouty arthritis, osteoarthritis, juvenile arthritis, and other arthritic conditions, systemic lupus erthematosus (SLE), skin-related conditions, eczema, Sjögren's syndrome, burns, dermatitis, neuroinflammation, allergy pain, autoimmune myositis, neuropathic pain, fever, pulmonary disorders, lung inflammation, adult respiratory distress syndrome, pulmonary sarcoisosis, asthma, silicosis, chronic pulmonary inflammatory disease, and chronic obstructive pulmonary disease (COPD), cardiovascular disease, arteriosclerosis, myocardial infarction (including post-myocardial infarction indications), thrombosis, congestive heart failure, cardiac reperfusion injury, as well as complications associated with hypertension and/or heart failure such as vascular organ damage, restenosis, cardiomyopathy, stroke including ischemic and hemorrhagic stroke, reperfusion injury, renal reperfusion injury, ischemia including stroke and brain ischemia, and ischemia resulting from cardiac/coronary bypass, neurodegenerative disorders, liver disease and nephritis, gastrointestinal conditions, inflammatory bowel disease, Crohn's disease, gastritis, irritable bowel syndrome, ulcerative colitis, ulcerative diseases, gastric ulcers, viral and bacterial infections, sepsis, septic shock, gram negative sepsis, malaria, meningitis, HIV infection, opportunistic infections, cachexia secondary to infection or malignancy, cachexia secondary to acquired immune deficiency syndrome (AIDS), AIDS, ARC (AIDS related complex), pneumonia, herpes virus, myalgias due to infection, influenza, autoimmune disease, graft vs. host reaction and allograft rejections, treatment of bone resorption diseases, osteoporosis, multiple sclerosis, acute gout, pneumonitis, myocarditis, pericarditis, myositis, eczema, alopecia, vitiligo, bullous skin diseases, atherosclerosis, depression, retinitis, uveitis, scleritis, hepatitis, pancreatitis, primary biliary cirrhosis, sclerosing cholangitis, Addison's disease, hypophysitis, thyroiditis, type I diabetes, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, vasculitis with organ involvement, acute rejection of transplanted organs, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, postsurgical syndromes, sarcoidosis, Herxheimer reactions, encephalitis, myelitis, SIRS associated with viral infections such as influenza, herpes zoster, herpes simplex, coronavirus or dry eye syndrome (or keratoconjunctivitis sicca (KCS)).

In certain embodiments, the compounds provided herein are useful in treating neuropathic and nociceptive pain, chronic or acute, such as, without limitation, allodynia, inflammatory pain, inflammatory hyperalgesia, post herpetic neuralgia, neuropathies, neuralgia, diabetic neuropathy, HIV-related neuropathy, nerve injury, rheumatoid arthritic pain, osteoarthritic pain, burns, back pain, ocular pain, visceral pain, cancer pain, dental pain, headache, migraine, carpal tunnel syndrome, fibromyalgia, neuritis, sciatica, pelvic hypersensitivity, pelvic pain, post operative pain, post stroke pain, and menstrual pain.

In certain embodiments, the compounds provided herein are useful in treating Alzheimer's disease (AD), mild cognitive impairment (MCI), age-associated memory impairment (AAMI), multiple sclerosis, Parkinson's disease, vascular dementia, senile dementia, AIDS dementia, Pick's disease, dementia caused by cerebrovascular disorders, corticobasal degeneration, amyotrophic lateral sclerosis (ALS), Huntington's disease, diminished CNS function associated with traumatic brain injury.

In one embodiment, the compounds provided herein are useful in treating Alzheimer's disease (AD), ankylosing spondylitis, arthritis (osteoarthritis, rheumatoid arthritis (RA), psoriatic arthritis), asthma, atherosclerosis, Crohn's disease, colitis, dermatitis, diverticulitis, fibromyalgia, hepatitis, irritable bowel syndrome (IBS), systemic lupus, erythematous (SLE), nephritis, Parkinson's disease, ulcerative colitis.

When used for the treatment of inflammatory disease, the compounds provided herein may be administered in dosages, routes of administration and/or to achieve pK profiles as described herein for the treatment of cancer.

4.3.3 Rasopathies

As discussed herein, Ras signaling is causally implicated in rasopathies. Thus, the compounds provided herein, which inhibit the function of one or more members of the Ras superfamily, are useful in the treatment of rasopathies including neurofibromatosis type 1, Noonan's syndrome, and Costello syndrome.

In one embodiment, provided herein is a method of treating or preventing a rasopathy, which comprises administering to a subject a compound that inhibits the function of one or more members of the Ras superfamily. In one embodiment, provided herein is a method of treating or preventing a rasopathy, which comprises administering to a subject a compound that inhibits the function of one or more members of the Ras superfamily by binding to the GTP binding domain or one or more members of the Ras superfamily. In one embodiment, provided herein is a method of treating or preventing a rasopathy, which comprises administering to a subject a compound that inhibits the function of Ras by binding to a Ras GTP binding domain. In another embodiment, provided herein is a method of treating or preventing a rasopathy, which comprises administering to a subject a compound that binds to a Ras GTP binding domain with an $IC_{50}$ of less than 10 µM and $K_d$ of less than 10 µM. In another embodiment, provided herein is a method of treating or preventing a rasopathy, which comprises administering to a subject a compound that binds to a Ras GTP binding domain with an $IC_{50}$ of less than 1 µM and a $K_d$ of less than 1 µM. In another embodiment, provided herein is a method of treating or preventing a rasopathy, which comprises administering to a subject a compound that binds to a Ras GTP binding domain with an $IC_{50}$ of less than 500 nM and a $K_d$ of less than 500 nM. In another embodiment, provided herein is a method of treating or preventing a rasopathy, which comprises administering to a subject a compound that binds to a Ras GTP binding domain with an $IC_{50}$ of less than 470 nM and a $K_d$ of less than 470 nM. In another embodiment, provided herein is a method of treating or preventing a rasopathy, which comprises administering to a subject a compound that binds to a Ras GTP binding domain with an $IC_{50}$ of less than 270 nM and a $K_d$ of less than 270 nM. In another embodiment, provided herein is a method of treating or preventing a rasopathy, which comprises administering to a subject a compound that binds to a Ras GTP binding domain with an $IC_{50}$ of less than 200 nM and a $K_d$ of less than 200 nM. In another embodiment, provided herein is a method of treating or preventing a rasopathy, which comprises administering to a subject a compound that binds to a Ras GTP binding domain with an $IC_{50}$ of less than 150 nM and a $K_d$ of less than 150 nM. In another embodiment, provided herein is a method of treating or preventing a rasopathy, which comprises administering to a subject a compound that binds to a Ras GTP binding domain with an $IC_{50}$ of less than 100 nM and a $K_d$ of less than 100 nM. In another embodiment, provided herein is a method of treating or preventing a rasopathy, which comprises administering to a subject a compound that binds to a Ras GTP binding domain with greater than 15% inhibition at 20 µM. In another embodiment, provided herein is a method of treating or preventing a rasopathy, which comprises administering to a subject a compound that binds to a Ras GTP binding domain with greater than 25% inhibition at 20 µM. In another embodiment, provided herein is a method of treating or preventing a rasopathy, which comprises administering to a subject a compound that binds to a Ras GTP binding domain with greater than 50% inhibition at 20 µM. In another embodiment, provided herein is a method of treating or preventing a rasopathy, which comprises administering to a subject a compound that binds to a Ras GTP binding domain with greater than 75% inhibition at 20 µM. In another embodiment, provided herein is a method of treating or preventing a rasopathy, which comprises administering to a subject a compound that binds to a Ras GTP binding domain with greater than 80% inhibition at 20 µM. In another embodiment, provided herein is a method of treating or preventing a rasopathy, which comprises administering to a subject a compound that binds to a Ras GTP binding domain with greater than 85% inhibition at 20 µM. In another embodiment, provided herein is a method of treating or preventing a rasopathy, which comprises administering to a subject a compound that binds to a Ras GTP binding domain with greater than 90% inhibition at 20 µM. In another embodiment, provided herein is a method of treating or preventing a rasopathy, which comprises administering to a subject a compound that binds to a Ras GTP binding domain with greater than 95% inhibition at 20 µM. In another embodiment, provided herein is a method of treating or preventing a rasopathy, which comprises administering to a subject a compound that binds to a Ras GTP binding domain with greater than 99% inhibition at 20 µM. In one embodiment, provided herein is a method of treating or preventing a rasopathy, which comprises administering to a subject a compound that inhibits the function of Rho. In one embodiment, provided herein is a method of treating or preventing a rasopathy, which comprises administering to a subject a compound that inhibits the function of Rho by binding to a Rho GTP binding domain. In another embodiment, provided herein is a method of treating or preventing a rasopathy, which comprises administering to a subject a compound that binds to a Rho GTP binding domain with an $IC_{50}$ of less than 10 µM and a $K_d$ of less than 10 µM. In another embodiment, provided herein is a method of treating or preventing a rasopathy, which comprises administering to a subject a compound that binds to a Rho GTP binding domain with an $IC_{50}$ of less than 1 µM and a $K_d$ of less than 1 µM. In another embodiment, provided herein is a method of treating or preventing a rasopathy, which comprises administering to a subject a compound that binds to a Rho GTP binding domain with an $IC_{50}$ of less than 500 nM and a $K_d$ of less than 500 nM. In another embodiment, provided herein is a method of treating or preventing a rasopathy, which comprises administering to a subject a compound that binds to a Rho GTP binding domain with an $IC_{50}$ of less than 270 nM and a $K_d$ of less than 270 nM. In another embodiment, provided herein is a method of treating or preventing a rasopathy, which comprises administering to a subject a compound that binds to a Rho GTP binding domain with an $IC_{50}$ of less than 200 nM and a $K_d$ of less than 200 nM. In another embodiment, provided herein is a method of treating or preventing a rasopathy, which comprises administering to a subject a compound that binds to a Rho GTP binding domain with an $IC_{50}$ of less than 150 nM and a $K_d$ of less than 150 nM. In another embodiment, provided herein is a method of treating or preventing a rasopathy, which comprises administering to a subject a compound that binds to a Rho GTP binding domain with an $IC_{50}$ of less than 130 nM and a $K_d$ of less than 130 nM. In another embodiment, provided herein is a method of treating or preventing a rasopathy, which comprises administering to a subject a compound that binds to a Rho GTP binding domain with an $IC_{50}$ of less than 100 nM and a $K_d$ of less than 100 nM. In another embodiment, provided herein is a method of treating or preventing a rasopathy, which comprises administering to a subject a compound that binds to a Rho GTP binding domain with greater than 15% inhibition at 20 µM. In another embodiment, provided herein is a method of treating or preventing a rasopathy, which comprises administering to a subject a compound that binds to a Rho GTP binding domain with greater than 25% inhibition at 20 µM. In another embodiment, provided herein is a method of treating or preventing a rasopathy, which comprises administering to a subject a compound that binds to a Rho GTP binding domain with greater than 50% inhibition at 20 µM. In another embodiment, provided herein is a method of treating or preventing a rasopathy, which comprises administering to a subject a compound that binds to a Rho GTP binding domain with greater than 75% inhibition at 20 µM. In another embodiment, provided herein is a method of treating or preventing a rasopathy, which comprises administering to a subject a compound that binds to a Rho GTP binding domain with greater than 80% inhibition at 20 µM. In another embodiment, provided herein is a method of treating or preventing a rasopathy, which comprises administering to a subject a compound that binds to a Rho GTP binding domain with greater than 85% inhibition at 20 µM. In another embodiment, provided herein is a method of treating or preventing a rasopathy, which comprises administering to a subject a compound that binds to a Rho GTP binding domain with greater than 90% inhibition at 20 µM. In another embodiment, provided herein is a method of treating or preventing a rasopathy, which comprises administering to a subject a compound that binds to a Rho GTP binding domain with greater than 95% inhibition at 20 µM. In another embodiment, provided herein is a method of treating or preventing a rasopathy, which comprises administering to a subject a compound that binds to a Rho GTP binding domain with greater than 99% inhibition at 20 µM. In one embodiment, provided herein is a method of treating or preventing a rasopathy, which comprises administering to a subject a compound that inhibits the function of Rac In one embodiment, provided herein is a method of treating or preventing a rasopathy, which comprises administering to a subject a compound that inhibits the function of Rac by binding to a Rac GTP binding domain. In another embodiment, provided herein is a method of treating or preventing a rasopathy, which comprises administering to a subject a compound that binds to a Rac GTP binding domain with an $IC_{50}$ of less than 10 µM and a $K_d$ of less than 10 µM. In another embodiment, provided herein is a method of treating or preventing a rasopathy, which comprises administering to a subject a compound that binds to a Rac GTP binding domain with an $IC_{50}$ of less than 1 µM and a $K_d$ of less than 1 µM. In another embodiment, provided herein is a method of treating or preventing a rasopathy, which comprises administering to a subject a compound that binds to a Rac GTP binding domain with an $IC_{50}$ of less than 500 nM and a $K_d$ of less than 500 nM. In another embodiment, provided herein is a method of treating or preventing a rasopathy, which comprises administering to a subject a compound that binds to a Rac GTP binding domain with an $IC_{50}$ of less than 270 nM and a $K_d$ of less than 270 nM. In another embodiment, provided herein is a method of treating or preventing a rasopathy, which comprises administering to a subject a compound that binds to a Rac GTP binding domain with an $IC_{50}$ of less than 200 nM and a $K_d$ of less than 200 nM. In another embodiment, provided herein is a method of treating or preventing a rasopathy, which comprises administering to a subject a compound that binds to a Rac GTP binding domain with an $IC_{50}$ of less than 170 nM and a $K_d$ of less than 170 nM. In another embodiment, provided herein is a method of treating or preventing a rasopathy, which comprises administering to a subject a compound that binds to a Rac GTP binding domain with an $IC_{50}$ of less than 150 nM and a $K_d$ of less than 150 nM. In another embodiment, provided herein is a method of treating or preventing a rasopathy, which comprises administering to a subject a compound that binds to a Rac GTP binding domain with an $IC_{50}$ of less than 100 nM and a $K_d$ of less than 100 nM. In another embodiment, provided herein is a method of treating or preventing a rasopathy, which comprises administering to a subject a compound that binds to a Rac GTP binding domain with greater than 15% inhibition at 20 µM. In another embodiment, provided herein is a method of treating or preventing a rasopathy, which comprises administering to a subject a compound that binds to a Rac GTP binding domain with greater than 25% inhibition at 20 µM. In another embodiment, provided herein is a method of treating or preventing a rasopathy, which comprises administering to a subject a compound that binds to a Rac GTP binding domain with greater than 50% inhibition at 20 µM. In another embodiment, provided herein is a method of treating or preventing a rasopathy, which comprises administering to a subject a compound that binds to a Rac GTP binding domain with greater than 75% inhibition at 20 µM. In another embodiment, provided herein is a method of treating or preventing a rasopathy, which comprises administering to a subject a compound that binds to a Rac GTP binding domain with greater than 80% inhibition at 20 µM. In another embodiment, provided herein is a method of treating or preventing a rasopathy, which comprises administering to a subject a compound that binds to a Rac GTP binding domain with greater than 85% inhibition at 20 µM. In another embodiment, provided herein is a method of treating or preventing a rasopathy, which comprises administering to a subject a compound that binds to a Rac GTP binding domain with greater than 90% inhibition at 20 µM. In another embodiment, provided herein is a method of treating or preventing a rasopathy, which comprises administering to a subject a compound that binds to a Rac GTP binding domain with greater than 95% inhibition at 20 µM. In another embodiment, provided herein is a method of treating or preventing a rasopathy, which comprises administering to a subject a compound that binds to a Rac GTP binding domain with greater than 99% inhibition at 20 µM. In some embodiments, the compound for use in the method is a compound as disclosed herein of Formula I, IA, IIA, IIA1, IIB, IIC, IID, IIE, IIIA, IIIA1, IIIA2, IIIB, IIIC, IIID, IIIE, or IIIF, or a pharmaceutically acceptable salt thereof. In some embodiments, the compound as disclosed herein for use in the method is a compound of Examples 1-135, or a pharmaceutically acceptable salt thereof.

In another embodiment, provided herein is a method of treating or preventing a rasopathy, which comprises administering to a subject a compound that binds to one or more of Ala11, Gly12, Val14, Gly15, Lys16, Ser17, Ala18, Phe28, Val 29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to two or more of Ala11, Gly12, Val14, Gly15, Lys16, Ser17, Ala18, Phe28, Val 29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to three or more of Ala11, Gly12, Val14, Gly15, Lys16, Ser17, Ala18, Phe28, Val 29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to four or more of Ala11, Gly12, Val14, Gly15, Lys16, Ser17, Ala18, Phe28, Val 29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to five or more of Ala11, Gly12, Val14, Gly15, Lys16, Ser17, Ala18, Phe28, Val 29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to six or more of Ala11, Gly12, Val14, Gly15, Lys16, Ser17, Ala18, Phe28, Val 29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to seven or more of Ala11, Gly12, Val14, Gly15, Lys16, Ser17, Ala18, Phe28, Val 29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to eight or more of Ala11, Gly12, Val14, Gly15, Lys16, Ser17, Ala18, Phe28, Val 29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to nine or more of Ala11, Gly12, Val14, Gly15, Lys16, Ser17, Ala18, Phe28, Val 29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to ten or more of Ala11, Gly12, Val14, Gly15, Lys16, Ser17, Ala18, Phe28, Val 29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to eleven or more of Ala11, Gly12, Val14, Gly15, Lys16, Ser17, Ala18, Phe28, Val 29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing a rasopathy, which comprises administering to a subject a compound that binds to twelve or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to thirteen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to fourteen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to fifteen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to sixteen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to seventeen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to eighteen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to nineteen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to twenty or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to twenty-one or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to twenty-two or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to twenty-three or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing a rasopathy, which comprises administering to a subject a compound that binds to all of Ala11, Gly12, Val14, Gly15, Lys16, Ser17, Ala18, Phe28, Val 29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In some embodiments, the compound for use in the method is a compound as disclosed herein of Formula I, IA, IIA, IIA1, IIB, IIC, IID, IIE, IIA, IIIA1, IIIA2, IIIB, IIIC, IIID, IIIE, or IIIF, or a pharmaceutically acceptable salt thereof. In some embodiments, the compound as disclosed herein for use in the method is a compound of Examples 1-135, or a pharmaceutically acceptable salt thereof.

In one embodiment, the Ras is DIRAS1; DIRAS2; DIRAS3; ERAS; GEM; HRAS; KRAS; MRAS; NKIRAS1; NKIRAS2; NRAS; RALA; RALB; RAP1A; RAP1B; RAP2A; RAP2B; RAP2C; RASD1; RASD2; RASL10A; RASL10B; RASL11A; RASL11B; RASL12; REM1; REM2; RERG; RERGL; RRAD; RRAS; or RRAS2. In another embodiment, the Ras is HRAS, KRAS or NRAS. In one embodiment, the Ras is HRAS. In one embodiment, the Ras is KRAS. In one embodiment, the Ras is NRAS. In another embodiment, the Ras is a mutant form of a Ras described herein.

In another embodiment, provided herein is a method of treating or preventing a rasopathy, which comprises administering to a subject a compound that binds to one or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another III embodiment, provided herein is a method of treating or preventing a rasopathy, which comprises administering to a subject a compound that binds to two or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds to three or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds to four or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds to five or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds to six or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds to seven or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds to eight or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds to nine or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds to ten or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds to eleven or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds to twelve or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds to thirteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds to fourteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds to fifteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds to sixteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds to seventeen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing a rasopathy, which comprises administering to a subject a compound that binds all of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In some embodiments, the compound for use in the method is a compound as disclosed herein of Formula I, IA, IIA, IIA1, IIB, IIC, ID, IE, IIIA, IIIA1, IIIA2, IIIB, IIIC, IIID, IIIE, or IIIF, or a pharmaceutically acceptable salt thereof. In some embodiments, the compound as disclosed herein for use in the method is a compound of Examples 1-135, or a pharmaceutically acceptable salt thereof.

In one embodiment, the Rho is RHOA; RHOB; RHOBTB1; RHOBTB2; RHOBTB3; RHOC; RHOD; RHOF; RHOG; RHOH; RHOJ; RHOQ; RHOU; RHOV; RND1; RND2; RND3; RAC1; RAC2; RAC3 or CDC42. In one embodiment, the Rho is RHOA. In another embodiment, the Rho is a mutant form of a Rho described herein.

In one embodiment, provided herein is a method of treating or preventing a rasopathy, which comprises administering to a subject a compound that binds to one or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to two or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a highly conserved Rho GTP binding domain. In one embodiment, provided herein is a method of treating or preventing a rasopathy, which comprises administering to a subject a compound that binds to three or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to four or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to five or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to six or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to seven or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to eight or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to nine or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to ten or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to eleven or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to twelve or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to thirteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to fourteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to fifteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to sixteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to seventeen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to eighteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing a rasopathy, which comprises administering to a subject a compound that binds to all of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In some embodiments, the compound for use in the method is a compound as disclosed herein of Formula I, IA, IIA, IIA1, IIB, IIC, IID, IIE, IIIA, IIIA1, IIIA2, IIIB, IIIC, IIID, IIIE, or IIIF, or a pharmaceutically acceptable salt thereof. In some embodiments, the compound as disclosed herein for use in the method is a compound of Examples 1-135, or a pharmaceutically acceptable salt thereof.

In one embodiment, the Rho is Rac. In one embodiment the Rac is RAC1; RAC2; RAC3 or RHOG. In one embodiment, the Rac is RAC1. In another embodiment, the Rac is a mutant form of a Rac described herein.

In one embodiment, the compound for use in the methods and compositions provided herein inhibit GTP binding to one or more members of the Ras superfamily. In one embodiment, the compound for use in the methods and compositions provided herein inhibit GTP binding to Ras. In one embodiment, the compounds provided herein inhibit GTP binding to Rho. In one embodiment, the compound for use in the methods and compositions provided herein inhibit GTP binding to Rac. In one embodiment, the compound for use in the methods and compositions provided herein inhibit GTP binding to Ras and Rho. In one embodiment, the compound for use in the methods and compositions provided herein inhibit GTP binding to Ras and Rac. In one embodiment, the compound for use in the methods and compositions provided herein inhibit GTP binding to Rho and Rac. In one embodiment, the compound for use in the methods and compositions provided herein inhibit GTP binding to Ras, Rho and Rac.

In one embodiment, the compound for use in the methods and compositions provided herein has a molecular weight less than 2000 daltons. In one embodiment, the compound for use in the methods and compositions provided herein has a molecular weight less than 1750 daltons. In one embodiment, the compound for use in the methods and compositions provided herein has a molecular weight less than 1500 daltons. In one embodiment, the compound for use in the methods and compositions provided herein has a molecular weight less than 1250 daltons. In one embodiment, the compound for use in the methods and compositions provided herein has a molecular weight less than 1000 daltons. In one embodiment, the compound for use in the methods and compositions provided herein has a molecular weight less than 750 daltons. In one embodiment, the compound for use in the methods and compositions provided herein has a molecular weight less than 665 daltons. In one embodiment, the compound for use in the methods and compositions provided herein has a molecular weight less than 500 daltons. In another embodiment, the compound for use in the methods and compositions provided herein contains a thienopyrimidine, pyrimidine or pyrrolotriazine moiety. In another embodiment, the compound for use in the methods and compositions provided herein contains a thieno[3,2-d]pyrimidine, thieno[2,3-d]pyrimidine or pyrrolo[2,1-f][1,2,4]triazine moiety. In another embodiment, the compound for use in the methods and compositions provided herein contains a thieno[3,2-d]pyrimidin-4-ol, thieno[2,3-d]pyrimidin-4-amine, pyrrolo[2,1-f][1,2,4]triazin-4-amine, 5,6-dimethoxy-N-(heteroaryl)-2-(pyridin-2-yl)pyrimidin-4-amine, 5,6-dihydroxy-2-(pyridin-2-yl)pyrimidine-4-carboxamide, 5,6-dihydroxy-2-(1-methyl-1H-imidazol-2-yl)pyrimidine-4-carboxamide, 5-methoxy-6-aryloxy-2-(pyridin-2-yl)pyrimidin-4-ol, or 5-methoxy-6-heteroaryloxy-2-(pyridin-2-yl)pyrimidin-4-ol moiety. In some embodiments, the compound for use in the method is a compound as disclosed herein of Formula I, IA, IIA, IIA1, IIB, IIC, IID, IIE, IIIA, IIIA1, IIIA2, IIIB, IIIC, IIID, IIIE, or IIIF, or a pharmaceutically acceptable salt thereof. In some embodiments, the compound as disclosed herein for use in the method is a compound of Examples 1-135, or a pharmaceutically acceptable salt thereof.

4.3.4 Ras-Associated Autoimmune Leukoproliferative Disorder

As discussed herein, Ras has been causally associated with Ras-associated autoimmune leukoproliferative disorder. Thus, the compounds provided herein, which inhibit the function of Ras, are useful in the treatment of Ras-associated autoimmune leukoproliferative disorder.

In one embodiment, provided herein is a method of treating or preventing Ras-associated autoimmune leukoproliferative disorder, which comprises administering to a subject a compound that inhibits the function of Ras. In one embodiment, provided herein is a method of treating or preventing Ras-associated autoimmune leukoproliferative disorder, which comprises administering to a subject a compound that inhibits the function of Ras by binding to a Ras GTP binding domain. In another embodiment, provided herein is a method of treating or preventing Ras-associated autoimmune leukoproliferative disorder, which comprises administering to a subject a compound that binds to a Ras GTP binding domain with an $IC_{50}$ of less than 10 μM and $K_d$ of less than 10 μM. In another embodiment, provided herein is a method of treating or preventing Ras-associated autoimmune leukoproliferative disorder, which comprises administering to a subject a compound that binds to a Ras GTP binding domain with an $IC_{50}$ of less than 1 μM and a $K_d$ of less than 1 μM. In another embodiment, provided herein is a method of treating or preventing Ras-associated autoimmune leukoproliferative disorder, which comprises administering to a subject a compound that binds to a Ras GTP binding domain with an $IC_{50}$ of less than 500 nM and a $K_d$ of less than 500 nM. In another embodiment, provided herein is a method of treating or preventing Ras-associated autoimmune leukoproliferative disorder, which comprises administering to a subject a compound that binds to a Ras GTP binding domain with an $IC_{50}$ of less than 470 nM and a $K_d$ of less than 470 nM. In another embodiment, provided herein is a method of treating or preventing Ras-associated autoimmune leukoproliferative disorder, which comprises administering to a subject a compound that binds to a Ras GTP binding domain with an $IC_{50}$ of less than 270 nM and a $K_d$ of less than 270 nM. In another embodiment, provided herein is a method of treating or preventing Ras-associated autoimmune leukoproliferative disorder, which comprises administering to a subject a compound that binds to a Ras GTP binding domain with an $IC_{50}$ of less than 200 nM and a $K_d$ of less than 200 nM. In another embodiment, provided herein is a method of treating or preventing Ras-associated autoimmune leukoproliferative disorder, which comprises administering to a subject a compound that binds to a Ras GTP binding domain with an $IC_{50}$ of less than 150 nM and a $K_d$ of less than 150 nM. In another embodiment, provided herein is a method of treating or preventing Ras-associated autoimmune leukoproliferative disorder, which comprises administering to a subject a compound that binds to a Ras GTP binding domain with an $IC_{50}$ of less than 100 nM and a $K_d$ of less than 100 nM. In another embodiment, provided herein is a method of treating or preventing Ras-associated autoimmune leukoproliferative disorder, which comprises administering to a subject a compound that binds to a Ras GTP binding domain with greater than 15% inhibition at 20 μM. In another embodiment, provided herein is a method of treating or preventing Ras-associated autoimmune leukoproliferative disorder, which comprises administering to a subject a compound that binds to a Ras GTP binding domain with greater than 25% inhibition at 20 μM. In another embodiment, provided herein is a method of treating or preventing Ras-associated autoimmune leukoproliferative disorder, which comprises administering to a subject a compound that binds to a Ras GTP binding domain with greater than 50% inhibition at 20 μM. In another embodiment, provided herein is a method of treating or preventing Ras-associated autoimmune leukoproliferative disorder, which comprises administering to a subject a compound that binds to a Ras GTP binding domain with greater than 75% inhibition at 20 μM. In another embodiment, provided herein is a method of treating or preventing Ras-associated autoimmune leukoproliferative disorder, which comprises administering to a subject a compound that binds to a Ras GTP binding domain with greater than 80% inhibition at 20 μM. In another embodiment, provided herein is a method of treating or preventing Ras-associated autoimmune leukoproliferative disorder, which comprises administering to a subject a compound that binds to a Ras GTP binding domain with greater than 85% inhibition at 20 μM. In another embodiment, provided herein is a method of treating or preventing Ras-associated autoimmune leukoproliferative disorder, which comprises administering to a subject a compound that binds to a Ras GTP binding domain with greater than 90% inhibition at 20 μM. In another embodiment, provided herein is a method of treating or preventing Ras-associated autoimmune leukoproliferative disorder, which comprises administering to a subject a compound that binds to a Ras GTP binding domain with greater than 95% inhibition at 20 μM. In another embodiment, provided herein is a method of treating or preventing Ras-associated autoimmune leukoproliferative disorder, which comprises administering to a subject a compound that binds to a Ras GTP binding domain with greater than 99% inhibition at 20 μM. In some embodiments, the compound for use in the method, or the administered compound, is a compound as disclosed herein of Formula I, IA, IIA, IIA1, IIB, IIC, IID, IIE, IIIA, IIIA1, IIIA2, IIIB, IIIC, IIID, IIIE, or IIIF, or a pharmaceutically acceptable salt thereof. In some embodiments, the compound as disclosed herein for use in the method, or the administered compound, is a compound of Examples 1-135, or a pharmaceutically acceptable salt thereof.

In another embodiment, provided herein is a method of treating or preventing Ras-associated autoimmune leukoproliferative disorder, which comprises administering to a subject a compound that binds to one or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to two or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to three or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to four or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to five or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to six or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to seven or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to eight or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to nine or more of Ala11, Gly12, Val14, Gly15, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to ten or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to eleven or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146 and Lys147 or Mg202 in a Ras GTP binding domain. In another embodiment, provided herein is a method of treating or preventing Ras-associated autoimmune leukoproliferative disorder, which comprises administering to a subject a compound that binds to twelve or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to thirteen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to fourteen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to fifteen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to sixteen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to seventeen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to eighteen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to nineteen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to twenty or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to twenty-one or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to twenty-two or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to twenty-three or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing Ras-associated autoimmune leukoproliferative disorder, which comprises administering to a subject a compound that binds to all of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys17, Asp119, Leu120, Ser145, Ala146 and Lys147 or Mg202 in a Ras GTP binding domain. In some embodiments, the compound for use in the method is a compound as disclosed herein of Formula I, IA, IIA, IIA1, IIB, IIC, ID, IIE, IIIA, IIIA1, IIIA2, IIIB, IIIC, IIID, IIIE, or IIIF, or a pharmaceutically acceptable salt thereof. In some embodiments, the compound as disclosed herein for use in the method is a compound of Examples 1-135, or a pharmaceutically acceptable salt thereof.

In one embodiment, the Ras is DIRAS1; DIRAS2; DIRAS3; ERAS; GEM; HRAS; KRAS; MRAS; NKIRAS1; NKIRAS2; NRAS; RALA; RALB; RAP1A; RAP1B; RAP2A; RAP2B; RAP2C; RASD1; RASD2; RASL10A; RASL10B; RAS11A; RAS11B; RASL12; REM1; REM2; RERG; RERGL; RRAD; RRAS; or RRAS2. In another embodiment, the Ras is HRAS, KRAS or NRAS. In one embodiment, the Ras is HRAS. In one embodiment, the Ras is KRAS. In one embodiment, the Ras is NRAS. In another embodiment, the Ras is a mutant form of a Ras described herein.

In one embodiment, the compound for use in the methods and compositions provided herein has a molecular weight less than 2000 daltons. In one embodiment, the compound for use in the methods and compositions provided herein has a molecular weight less than 1500 daltons. In one embodiment, the compound for use in the methods and compositions provided herein has a molecular weight less than 1250 daltons. In one embodiment, the compound for use in the methods and compositions provided herein has a molecular weight less than 1000 daltons. In one embodiment, the compound for use in the methods and compositions provided herein has a molecular weight less than 750 daltons. In one embodiment, the compound for use in the methods and compositions provided herein has a molecular weight less than 665 daltons. In one embodiment, the compound for use in the methods and compositions provided herein has a molecular weight less than 500 daltons. In another embodiment, the compound for use in the methods and compositions provided herein contains a thienopyrimidine, pyrimidine or pyrrolotriazine moiety. In another embodiment, the compound for use in the methods and compositions provided herein contains a thieno[3,2-d]pyrimidine, thieno[2,3-d]pyrimidine or pyrrolo[2,1-f][1,2,4]triazine moiety. In another embodiment, the compound for use in the methods and compositions provided herein contains a thieno[3,2-d]pyrimidin-4-ol, thieno[2,3-d]pyrimidin-4-amine, pyrrolo[2,1-f][1,2,4]triazin-4-amine, 5,6-dimethoxy-N-(heteroaryl)-2-(pyridin-2-yl)pyrimidin-4-amine, 5,6-dihydroxy-2-(pyridin-2-yl)pyrimidine-4-carboxamide, 5,6-dihydroxy-2-(1-methyl-1H-imidazol-2-yl)pyrimidine-4-carboxamide, 5-methoxy-6-aryloxy-2-(pyridin-2-yl)pyrimidin-4-ol, 5-methoxy-6-heteroaryloxy-2-(pyridin-2-yl)pyrimidin-4-ol, 5-methoxy-6-(arylamino)-2-(pyridin-2-yl)pyrimidin-4-ol, 6-((heteroaryl)amino)-5-methoxy-2-(pyridin-2-yl)pyrimidin-4-ol, 6-amino-5-methyl-2-(1-methyl-1H-imidazol-2-yl)pyrimidine-4-carboxamide, thieno[2,3-d]pyrimidin-4-ol, or 4-alkoxythieno[3,2-d]pyrimidine moiety. In some embodiments, the compound for use in the method is a compound as disclosed herein of Formula I, IA, IIA, IIA1, IIB, IIC, IID, IIE, IIIA, IIIA1, IIIA2, IIIB, IIIC, IIID, IIIE, or IIIF, or a pharmaceutically acceptable salt thereof. In some embodiments, the compound as disclosed herein for use in the method is a compound of Examples 1-135, or a pharmaceutically acceptable salt thereof.

4.3.5 Fibrotic Disease

As discussed herein, Ras superfamily members are potential targets in fibrotic disease treatment. In one embodiment, provided herein is a method of treating or preventing fibrotic disease, which comprises administering to a subject a compound that inhibits the function of one or more members of the Ras superfamily. In one embodiment, provided herein is a method of treating or preventing fibrotic disease, which comprises administering to a subject a compound that inhibits the function of one or more members of the Ras superfamily by binding to the GTP binding domain or one or more members of the Ras superfamily. In one embodiment, provided herein is a method of treating or preventing fibrotic disease, which comprises administering to a subject a compound that inhibits the function of Ras by binding to a Rho GTP binding domain. In another embodiment, provided herein is a method of treating or preventing fibrotic disease, which comprises administering to a subject a compound that binds to a Ras GTP binding domain with an $IC_{50}$ of less than 10 μM and $K_d$ of less than 10 μM. In another embodiment, provided herein is a method of treating or preventing fibrotic disease, which comprises administering to a subject a compound that binds to a Ras GTP binding domain with an $IC_{50}$ of less than 1 μM and a $K_d$ of less than 1 μM. In another embodiment, provided herein is a method of treating or preventing fibrotic disease, which comprises administering to a subject a compound that binds to a Ras GTP binding domain with an $IC_{50}$ of less than 500 nM and a $K_d$ of less than 500 nM. In another embodiment, provided herein is a method of treating or preventing fibrotic disease, which comprises administering to a subject a compound that binds to a Ras GTP binding domain with an $IC_{50}$ of less than 470 nM and a $K_d$ of less than 470 nM. In another embodiment, provided herein is a method of treating or preventing fibrotic disease, which comprises administering to a subject a compound that binds to a Ras GTP binding domain with an $IC_{50}$ of less than 270 nM and a $K_d$ of less than 270 nM. In another embodiment, provided herein is a method of treating or preventing fibrotic disease, which comprises administering to a subject a compound that binds to a Ras GTP binding domain with an $IC_{50}$ of less than 200 nM and a $K_d$ of less than 200 nM. In another embodiment, provided herein is a method of treating or preventing fibrotic disease, which comprises administering to a subject a compound that binds to a Ras GTP binding domain with an $IC_{50}$ of less than 150 nM and a $K_d$ of less than 150 nM. In another embodiment, provided herein is a method of treating or preventing fibrotic disease, which comprises administering to a subject a compound that binds to a Ras GTP binding domain with an $IC_{50}$ of less than 100 nM and a $K_d$ of less than 100 nM. In another embodiment, provided herein is a method of treating or preventing fibrotic disease, which comprises administering to a subject a compound that binds to a Ras GTP binding domain with greater than 15% inhibition at 20 μM. In another embodiment, provided herein is a method of treating or preventing fibrotic disease, which comprises administering to a subject a compound that binds to a Ras GTP binding domain with greater than 25% inhibition at 20 µM. In another embodiment, provided herein is a method of treating or preventing fibrotic disease, which comprises administering to a subject a compound that binds to a Ras GTP binding domain with greater than 50% inhibition at 20 µM. In another embodiment, provided herein is a method of treating or preventing fibrotic disease, which comprises administering to a subject a compound that binds to a Ras GTP binding domain with greater than 75% inhibition at 20 µM. In another embodiment, provided herein is a method of treating or preventing fibrotic disease, which comprises administering to a subject a compound that binds to a Ras GTP binding domain with greater than 80% inhibition at 20 µM. In another embodiment, provided herein is a method of treating or preventing fibrotic disease, which comprises administering to a subject a compound that binds to a Ras GTP binding domain with greater than 85% inhibition at 20 µM. In another embodiment, provided herein is a method of treating or preventing fibrotic disease, which comprises administering to a subject a compound that binds to a Ras GTP binding domain with greater than 90% inhibition at 20 µM. In another embodiment, provided herein is a method of treating or preventing fibrotic disease, which comprises administering to a subject a compound that binds to a Ras GTP binding domain with greater than 95% inhibition at 20 µM. In another embodiment, provided herein is a method of treating or preventing fibrotic disease, which comprises administering to a subject a compound that binds to a Ras GTP binding domain with greater than 99% inhibition at 20 µM. In one embodiment, provided herein is a method of treating or preventing fibrotic disease, which comprises administering to a subject a compound that inhibits the function of Rho. In one embodiment, provided herein is a method of treating or preventing fibrotic disease, which comprises administering to a subject a compound that inhibits the function of Rho by binding to a Rho GTP binding domain. In another embodiment, provided herein is a method of treating or preventing fibrotic disease, which comprises administering to a subject a compound that binds to a Rho GTP binding domain with an $IC_{50}$ of less than 10 µM and $K_d$ of less than 10 µM. In another embodiment, provided herein is a method of treating or preventing fibrotic disease, which comprises administering to a subject a compound that binds to a Rho GTP binding domain with an $IC_{50}$ of less than 1 µM and a $K_d$ of less than 1 µM. In another embodiment, provided herein is a method of treating or preventing fibrotic disease, which comprises administering to a subject a compound that binds to a Rho GTP binding domain with an $IC_{50}$ of less than 500 nM and a $K_d$ of less than 500 nM. In another embodiment, provided herein is a method of treating or preventing fibrotic disease, which comprises administering to a subject a compound that binds to a Rho GTP binding domain with an $IC_{50}$ of less than 270 nM and a $K_d$ of less than 270 nM. In another embodiment, provided herein is a method of treating or preventing fibrotic disease, which comprises administering to a subject a compound that binds to a Rho GTP binding domain with an $IC_{50}$ of less than 200 nM and a $K_d$ of less than 200 nM. In another embodiment, provided herein is a method of treating or preventing fibrotic disease, which comprises administering to a subject a compound that binds to a Rho GTP binding domain with an $IC_{50}$ of less than 150 nM and a $K_d$ of less than 150 nM. In another embodiment, provided herein is a method of treating or preventing fibrotic disease, which comprises administering to a subject a compound that binds to a Rho GTP binding domain with an $IC_{50}$ of less than 130 nM and a $K_d$ of less than 130 nM. In another embodiment, provided herein is a method of treating or preventing fibrotic disease, which comprises administering to a subject a compound that binds to a Rho GTP binding domain with an $IC_{50}$ of less than 100 nM and a $K_d$ of less than 100 nM. In another embodiment, provided herein is a method of treating or preventing fibrotic disease, which comprises administering to a subject a compound that binds to a Rho GTP binding domain with greater than 15% inhibition at 20 µM. In another embodiment, provided herein is a method of treating or preventing fibrotic disease, which comprises administering to a subject a compound that binds to a Rho GTP binding domain with greater than 25% inhibition at 20 µM. In another embodiment, provided herein is a method of treating or preventing fibrotic disease, which comprises administering to a subject a compound that binds to a Rho GTP binding domain with greater than 50% inhibition at 20 µM. In another embodiment, provided herein is a method of treating or preventing fibrotic disease, which comprises administering to a subject a compound that binds to a Rho GTP binding domain with greater than 75% inhibition at 20 µM. In another embodiment, provided herein is a method of treating or preventing fibrotic disease, which comprises administering to a subject a compound that binds to a Rho GTP binding domain with greater than 80% inhibition at 20 µM. In another embodiment, provided herein is a method of treating or preventing fibrotic disease, which comprises administering to a subject a compound that binds to a Rho GTP binding domain with greater than 85% inhibition at 20 µM. In another embodiment, provided herein is a method of treating or preventing fibrotic disease, which comprises administering to a subject a compound that binds to a Rho GTP binding domain with greater than 90% inhibition at 20 µM. In another embodiment, provided herein is a method of treating or preventing fibrotic disease, which comprises administering to a subject a compound that binds to a Rho GTP binding domain with greater than 95% inhibition at 20 µM. In another embodiment, provided herein is a method of treating or preventing fibrotic disease, which comprises administering to a subject a compound that binds to a Rho GTP binding domain with greater than 99% inhibition at 20 µM. In one embodiment, provided herein is a method of treating or preventing fibrotic disease, which comprises administering to a subject a compound that inhibits the function of Rac. In one embodiment, provided herein is a method of treating or preventing fibrotic disease, which comprises administering to a subject a compound that inhibits the function of Rac by binding to a Rac GTP binding domain. In another embodiment, provided herein is a method of treating or preventing fibrotic disease, which comprises administering to a subject a compound that binds to a Rac GTP binding domain with an $IC_{50}$ of less than 10 µM and $K_d$ of less than 10 µM. In another embodiment, provided herein is a method of treating or preventing fibrotic disease, which comprises administering to a subject a compound that binds to a Rac GTP binding domain with an $IC_{50}$ of less than 1 µM and a $K_d$ of less than 1 µM. In another embodiment, provided herein is a method of treating or preventing fibrotic disease, which comprises administering to a subject a compound that binds to a Rac GTP binding domain with an $IC_{50}$ of less than 500 nM and a $K_d$ of less than 500 nM. In another embodiment, provided herein is a method of treating or preventing fibrotic disease, which comprises administering to a subject a compound that binds to a Rac GTP binding domain with an $IC_{50}$ of less than 270 nM and a $K_d$ of less than 270 nM. In another embodiment, provided herein is a method of treating or preventing fibrotic disease, which comprises administering to a subject a compound that binds to a Rac GTP binding domain with an $IC_{50}$ of less than 200 nM and a $K_d$ of less than 200 nM. In another embodiment, provided herein is a method of treating or preventing fibrotic disease, which comprises administering to a subject a compound that binds to a Rac GTP binding domain with an $IC_{50}$ of less than 170 nM and a $K_d$ of less than 170 nM. In another embodiment, provided herein is a method of treating or preventing fibrotic disease, which comprises administering to a subject a compound that binds to a Rac GTP binding domain with an $IC_{50}$ of less than 150 nM and a $K_d$ of less than 150 nM. In another embodiment, provided herein is a method of treating or preventing fibrotic disease, which comprises administering to a subject a compound that binds to a Rac GTP binding domain with an $IC_{50}$ of less than 100 nM and a $K_d$ of less than 100 nM. In another embodiment, provided herein is a method of treating or preventing fibrotic disease, which comprises administering to a subject a compound that binds to a Rac GTP binding domain with greater than 15% inhibition at 20 μM. In another embodiment, provided herein is a method of treating or preventing fibrotic disease, which comprises administering to a subject a compound that binds to a Rac GTP binding domain with greater than 25% inhibition at 20 μM. In another embodiment, provided herein is a method of treating or preventing fibrotic disease, which comprises administering to a subject a compound that binds to a Rac GTP binding domain with greater than 50% inhibition at 20 μM. In another embodiment, provided herein is a method of treating or preventing fibrotic disease, which comprises administering to a subject a compound that binds to a Rac GTP binding domain with greater than 75% inhibition at 20 μM. In another embodiment, provided herein is a method of treating or preventing fibrotic disease, which comprises administering to a subject a compound that binds to a Rac GTP binding domain with greater than 80% inhibition at 20 μM. In another embodiment, provided herein is a method of treating or preventing fibrotic disease, which comprises administering to a subject a compound that binds to a Rac GTP binding domain with greater than 85% inhibition at 20 μM. In another embodiment, provided herein is a method of treating or preventing fibrotic disease, which comprises administering to a subject a compound that binds to a Rac GTP binding domain with greater than 90% inhibition at 20 μM. In another embodiment, provided herein is a method of treating or preventing fibrotic disease, which comprises administering to a subject a compound that binds to a Rac GTP binding domain with greater than 95% inhibition at 20 μM. In another embodiment, provided herein is a method of treating or preventing fibrotic disease, which comprises administering to a subject a compound that binds to a Rac GTP binding domain with greater than 99% inhibition at 20 μM. In some embodiments, the compound for use in the method is a compound as disclosed herein of Formula I, IA, IIA, IIA1, IIB, IC, IID, IIE, IIIA, IIIA1, IIIA2, IIIB, IIIC, IIID, IIIE, or IIIF, or a pharmaceutically acceptable salt thereof. In some embodiments, the compound as disclosed herein for use in the method is a compound of Examples 1-135, or a pharmaceutically acceptable salt thereof.

In another embodiment, provided herein is a method of treating or preventing fibrotic disease, which comprises administering to a subject a compound that binds to one or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to two or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to three or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to four or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to five or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to six or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys17, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to seven or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to eight or more of Ala 11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to nine or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to ten or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to eleven or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to twelve or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to thirteen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to fourteen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to fifteen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to sixteen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to seventeen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to eighteen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to nineteen or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to twenty or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to twenty-one or more of Ala11, Gly12, Val14. Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to twenty-two or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to twenty-three or more of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In another embodiment, provided herein is a method of treating or preventing fibrotic disease, which comprises administering to a subject a compound that binds to all of Ala11, Gly12, Val14, Gly15, Lys16, Ser17, Ala18, Phe28, Val29, Asp30, Glu31, Tyr32, Asp33, Pro34, Thr35, Ile36, Gly60, Gln61, Lys117, Asp119, Leu120, Ser145, Ala146, Lys147 or Mg202 in a Ras GTP binding domain. In some embodiments, the compound for use in the method is a compound as disclosed herein of Formula I, IA, IIA, IIA1, IIB, IC, IID, IE, IIA, IIIA1, IIIA2, IIIB, IIIC, IIID, IIIE, or IIIF, or a pharmaceutically acceptable salt thereof. In some embodiments, the compound as disclosed herein for use in the method is a compound of Examples 1-135, or a pharmaceutically acceptable salt thereof.

In one embodiment, the Ras is DIRAS1; DIRAS2; DIRAS3; ERAS; GEM; HRAS; KRAS; MRAS; NKIRAS1; NKIRAS2; NRAS; RALA; RALB; RAP1A; RAP1B; RAP2A; RAP2B; RAP2C; RASD1; RASD2; RASL10A; RASL10B, RASL11A, RAS11B; RASL12; REM1; REM2; RERG; RERGL; RRAD; RRAS; or RRAS2. In another embodiment, the Ras is HRAS, KRAS or NRAS. In one embodiment, the Ras is HRAS. In one embodiment, the Ras is KRAS. In one embodiment, the Ras is NRAS. In another embodiment, the Ras is a mutant form of a Ras described herein.

In another embodiment, provided herein is a method of treating or preventing fibrotic disease, which comprises administering to a subject a compound that binds to one or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to two or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to three or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to four or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to five or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to six or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to seven or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to eight or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to nine or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to ten or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to eleven or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to twelve or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to thirteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to fourteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to fifteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to sixteen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds to seventeen or more of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In another embodiment, provided herein is a method of treating or preventing fibrotic disease, which comprises administering to a subject a compound that binds all of Gly14, Ala15, Cys16, Gly17, Lys18, Thr19, Cys20, Phe30, Pro31, Glu32, Tyr34, Val35, Pro36, Thr37, Asp59, Lys118, Asp120, Lys162 or Mg202 in a Rho GTP binding domain. In some embodiments, the compound for use in the method is a compound as disclosed herein of Formula I, IA, IA, IIA1, IIB, IIC, IID, IIE, IIIA, IIIA1, IIIA2, IIIB, IIIC, IIID, IIIE, or IIIF, or a pharmaceutically acceptable salt thereof. In some embodiments, the compound as disclosed herein for use in the method is a compound of Examples 1-135, or a pharmaceutically acceptable salt thereof.

In one embodiment, the Rho is RHOA; RHOB; RHOBTB1; RHOBTB2; RHOBTB3; RHOC; RHOD; RHOF; RHOG; RHOH; RHOJ; RHOQ; RHOU; RHOV; RND1; RND2; RND3; RAC1; RAC2; RAC3 or CDC42. In one embodiment, the Rho is RHOA. In another embodiment, the Rho is a mutant form of a Rho described herein.

In one embodiment, provided herein is a method of treating or preventing fibrotic disease, which comprises administering to a subject a compound that binds to one or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to two or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a highly conserved Rho GTP binding domain. In one embodiment, provided herein is a method of treating or preventing fibrotic disease, which comprises administering to a subject a compound that binds to three or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to four or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to five or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to six or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to seven or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to eight or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to nine or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to ten or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to eleven or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to twelve or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to thirteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to fourteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to fifteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to sixteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to seventeen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to eighteen or more of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In one embodiment, provided herein is a method of treating or preventing fibrotic disease, which comprises administering to a subject a compound that binds to all of Gly12, Ala13, Gly15, Lys16, Thr17, Cys18, Leu19, Phe28, Ile33, Pro34, Val36, Ala59, Thr115, Lys116, Asp118, Leu119, Cys157, Ala159, or Mg202 in a Rac GTP binding domain. In some embodiments, the compound for use in the method is a compound as disclosed herein of Formula I, IA, IIA, IIA1, IIB, IIC, IID, IE, IIIA, IIIA1, IIIA2, IIIB, ITC, IIID, IIE, or IIIF, or a pharmaceutically acceptable salt thereof. In some embodiments, the compound as disclosed herein for use in the method is a compound of Examples 1-135, or a pharmaceutically acceptable salt thereof.

In one embodiment, the Rho is Rac. In one embodiment the Rac is RAC1; RAC2; RAC3 or RHOG. In one embodiment, the Rac is RAC1. In another embodiment, the Rac is a mutant form of a Rac described herein.

In one embodiment, the compound for use in the methods and compositions provided herein inhibit GTP binding to one or more members of the Ras superfamily. In one embodiment, the compound for use in the methods and compositions provided herein inhibit GTP binding to Ras. In one embodiment, the compounds provided herein inhibit GTP binding to Rho. In one embodiment, the compound for use in the methods and compositions provided herein inhibit GTP binding to Rac. In one embodiment, the compound for use in the methods and compositions provided herein inhibit GTP binding to Ras and Rho. In one embodiment, the compound for use in the methods and compositions provided herein inhibit GTP binding to Ras and Rac. In one embodiment, the compound for use in the methods and compositions provided herein inhibit GTP binding to Rho and Rac. In one embodiment, the compound for use in the methods and compositions provided herein inhibit GTP binding to Ras, Rho and Rac.

In one embodiment, the compound for use in the methods and compositions provided herein has a molecular weight less than 2000 daltons. In one embodiment, the compound for use in the methods and compositions provided herein has a molecular weight less than 1750 daltons. In one embodiment, the compound for use in the methods and compositions provided herein has a molecular weight less than 1500 daltons. In one embodiment, the compound for use in the methods and compositions provided herein has a molecular weight less than 1250 daltons. In one embodiment, the compound for use in the methods and compositions provided herein has a molecular weight less than 1000 daltons. In one embodiment, the compound for use in the methods and compositions provided herein has a molecular weight less than 750 daltons. In one embodiment, the compound for use in the methods and compositions provided herein has a molecular weight less than 665 daltons. In one embodiment, the compound for use in the methods and compositions provided herein has a molecular weight less than 500 daltons. In another embodiment, the compound for use in the methods and compositions provided herein contains a thienopyrimidine, pyrimidine or pyrrolotriazine moiety. In another embodiment, the compound for use in the methods and compositions provided herein contains a thieno[3,2-d] pyrimidine, thieno[2,3-d]pyrimidine or pyrrolo[2,1-f][1,2,4] triazine moiety. In another embodiment, the compound for use in the methods and compositions provided herein contains a thieno[3,2-d]pyrimidin-4-ol, thieno[2,3-d]pyrimidin-4-amine, pyrrolo[2,1-f][1,2,4]triazin-4-amine, 5,6-dimethoxy-N-(heteroaryl)-2-(pyridin-2-yl)pyrimidin-4-amine, 5,6-dihydroxy-2-(pyridin-2-yl)pyrimidine-4-carboxamide, 5,6-dihydroxy-2-(1-methyl-1H-imidazol-2-yl)pyrimidine-4-carboxamide, 5-methoxy-6-aryloxy-2-(pyridin-2-yl)pyrimidin-4-ol, or 5-methoxy-6-heteroaryloxy-2-(pyridin-2-yl)pyrimidin-4-ol moiety. In some embodiments, the compound for use in the method is a compound as disclosed herein of Formula I, IA, IIA, IIA1, IIB, IIC, IID, IIE, IIA, IIIA1, IIIA2, IIIB, IIIC, IIID, IIIE, or IIIF, or a pharmaceutically acceptable salt thereof. In some embodiments, the compound as disclosed herein for use in the method is a compound of Examples 1-135, or a pharmaceutically acceptable salt thereof.

4.4. Compounds for Use in Compositions and Methods

Provided herein are compounds which bind to the GTP binding domain of one or more Ras superfamily members and compete with the binding of GTP to one or more Ras superfamily members.

Provided herein are compounds which bind to a Ras GTP binding domain and compete with the binding of GTP to Ras. In one embodiment, the compounds also inhibit phosphorylation of MAPK, in particular MAPK1/2, Akt (for example, Akt1, Akt2 and Akt3) cellular proliferation, secretion of IL-6 or TNF-α cytokines. The compounds provided herein are therefore useful in compositions and methods of treating cancer, inflammatory diseases, Ras-associated autoimmune leukoproliferative disorder and rasopathies.

Provided herein are compounds which bind to a Rac GTP binding domain and compete with the binding of GTP to Rac. In one embodiment, the compounds also inhibit the MAPK and Akt signaling pathways. In one embodiment, the compounds also inhibit the ROCK signaling pathway. The compounds provided herein are therefore useful in compositions and methods of treating cancer, inflammatory diseases and fibrotic disease.

Provided herein are compounds which bind to a Rho GTP binding domain and compete with the binding of GTP to Rho. In one embodiment, the compounds also inhibit the MAPK and Akt signaling pathways. In one embodiment, the compounds also inhibit the ROCK signaling pathway. The compounds provided herein are therefore useful in compositions and methods of treating cancer, inflammatory diseases and fibrotic disease.

In one embodiment, the compounds provided herein inhibit GTP binding to one or more members of the Ras superfamily. In one embodiment, the compounds provided herein inhibit GTP binding to Ras. In one embodiment, the compounds provided herein inhibit GTP binding to Rho. In one embodiment, the compounds provided herein inhibit GTP binding to Rac. In one embodiment, the compounds provided herein inhibit GTP binding to Ras and Rho. In one embodiment, the compounds provided herein inhibit GTP binding to Ras and Rac. In one embodiment, the compounds provided herein inhibit GTP binding to Rho and Rac. In one embodiment, the compounds provided herein inhibit GTP binding to Ras, Rho and Rac.

In one embodiment, the compounds provided herein inhibit activation of the MAPK pathway and downregulate the proliferation of different human tumor cell lines. In one embodiment, the compounds provided herein inhibit activation of the AKT pathway and downregulate the proliferation of different human tumor cell lines. In one embodiment, the compounds provided herein inhibit activation of the MAPK pathway and AKT pathway and downregulate the proliferation of different human tumor cell lines.

In certain embodiments, the compounds for use in the compositions and methods provided herein are of Formula I:

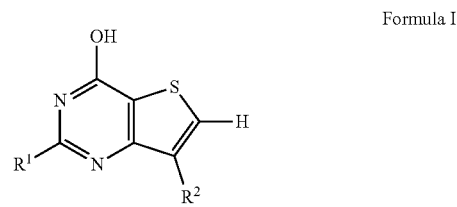

Formula I or pharmaceutically acceptable derivatives thereof, wherein $R^1$ is independently selected from the group consisting of

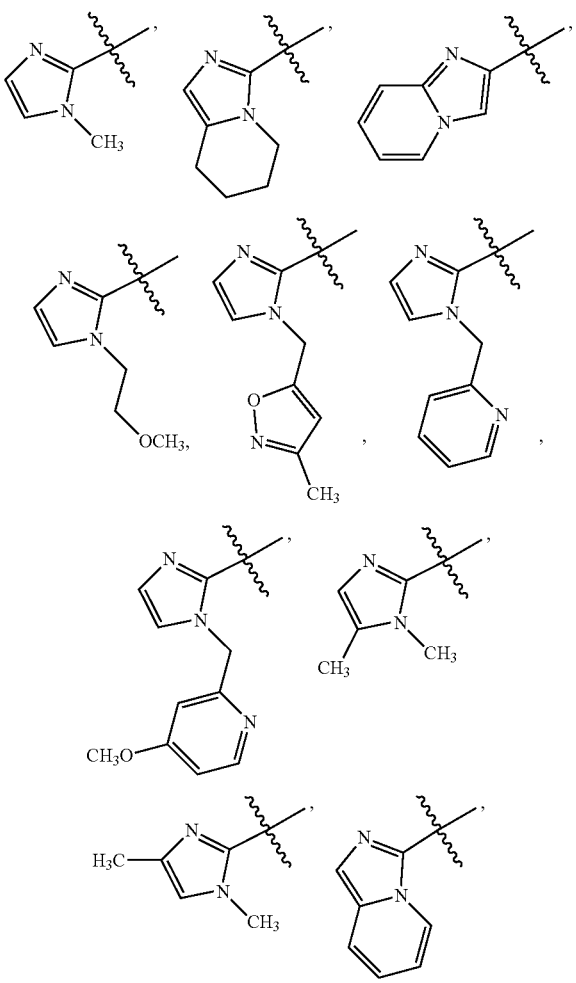

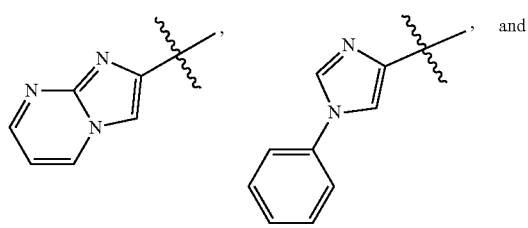
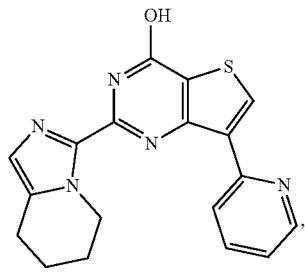
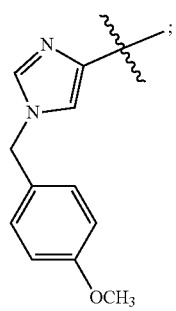
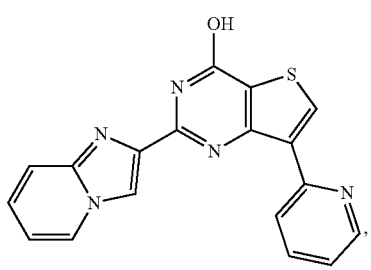
and
R² is
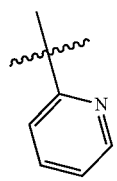 or 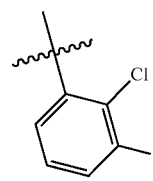
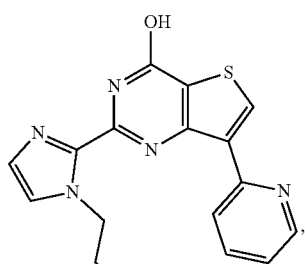
In one embodiment, the compound of Formula I is:
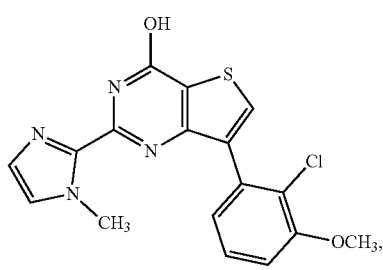
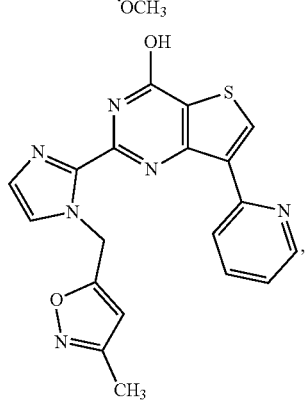
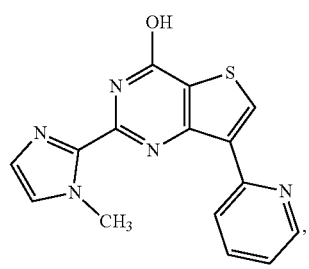
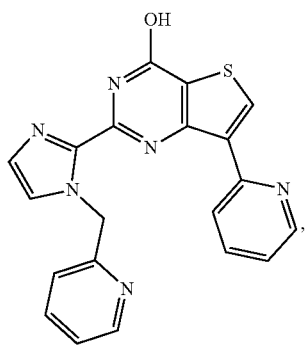

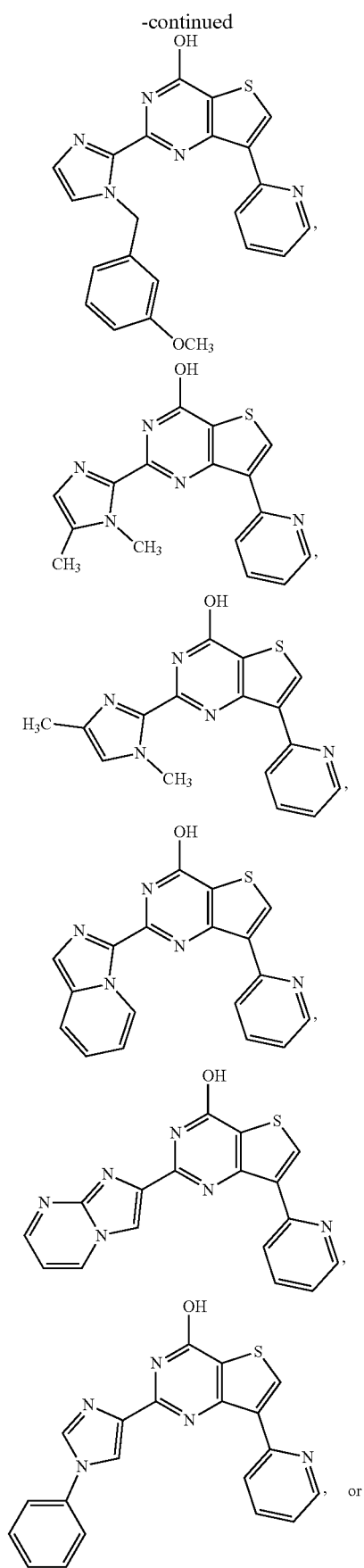

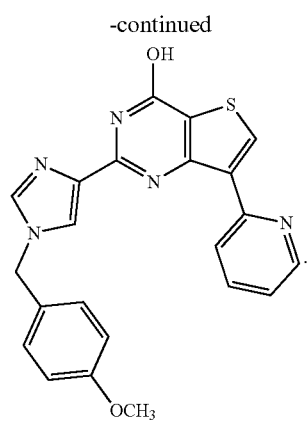

In certain embodiments, the pharmaceutically acceptable derivative of the compound of Formula I is a pharmaceutically acceptable salt of the compound of Formula I.

In certain embodiments, the compounds for use in the compositions and methods provided herein are of Formula IA:

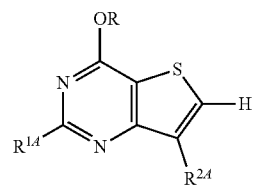

Formula IA or pharmaceutically acceptable derivatives thereof, wherein R is independently selected from the group consisting of hydrogen or methyl;

wherein $R^{1A}$ is independently selected from the group consisting of

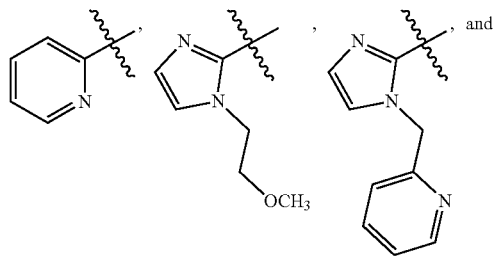

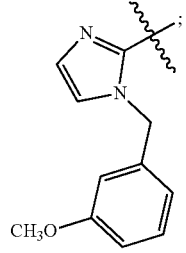

and R²ᴬ is

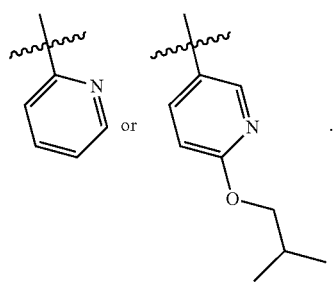 [SMILES: *c1ccccn1 ; *c1ccc(OCC(C)C)nc1]

In one embodiment, the compound of Formula IA is:

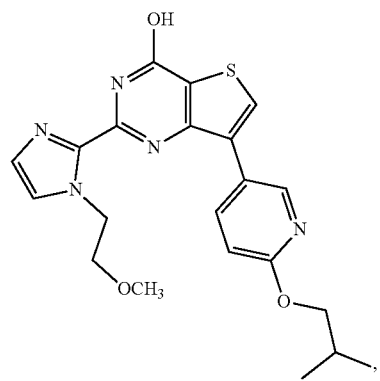

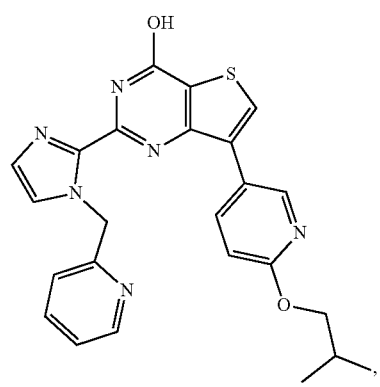

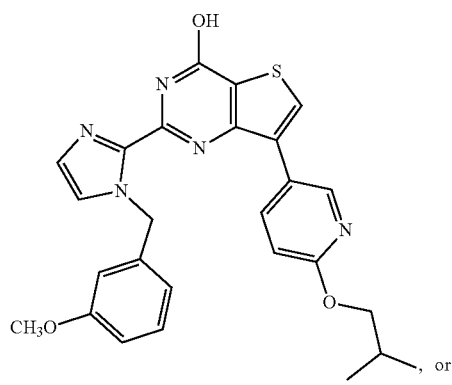

or

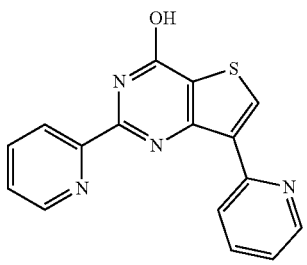

In certain embodiments, the pharmaceutically acceptable derivative of the compound of Formula IA is a pharmaceutically acceptable salt of the compound of Formula IA.

In certain embodiments, the compounds for use in the compositions and methods provided herein are of Formula IIA:

Formula IIA

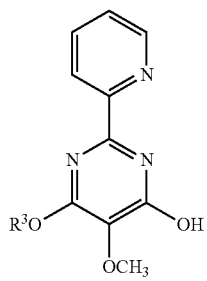

or pharmaceutically acceptable derivatives thereof, wherein $R^3$ is

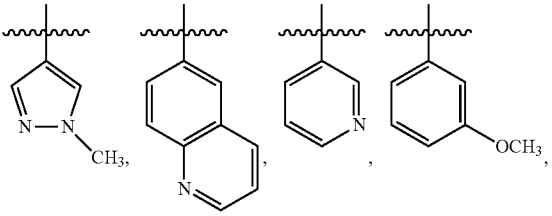

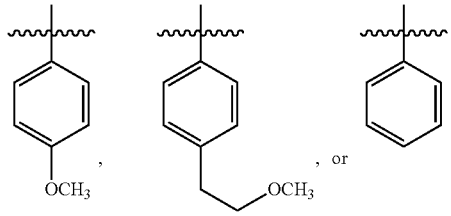

In one embodiment, the compound of Formula IIA is:

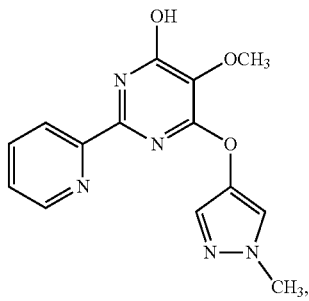

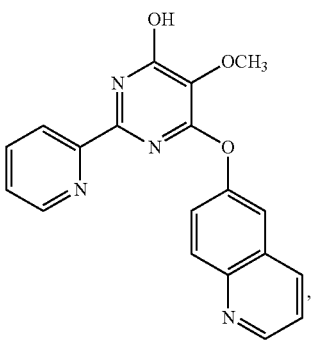

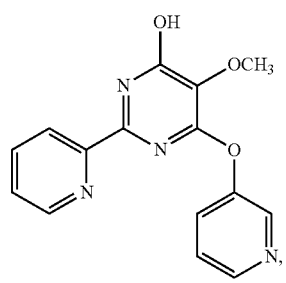

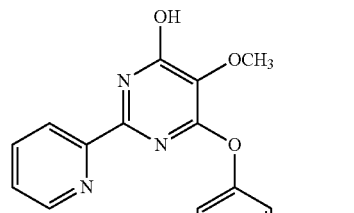

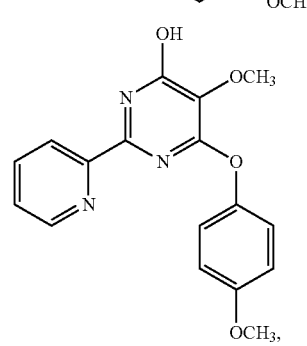

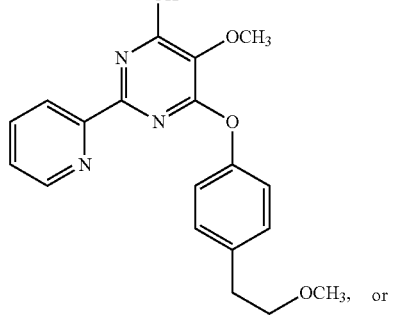

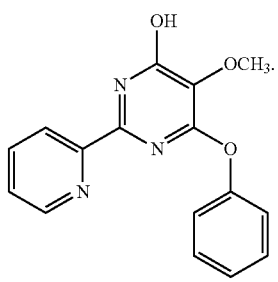

In certain embodiments, the pharmaceutically acceptable derivative of the compound of Formula IIA is a pharmaceutically acceptable salt of the compound of Formula IIA.

In certain embodiments, the compounds for use in the compositions and methods provided herein are of Formula IIA1:

Formula IIA1

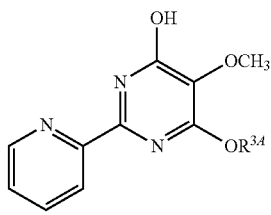

or pharmaceutically acceptable derivatives thereof, wherein $R^{3A}$ is

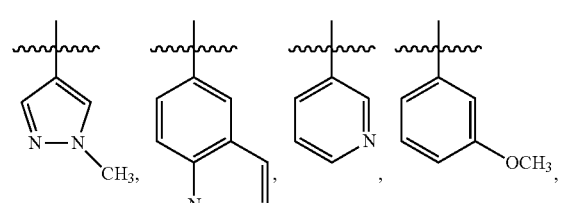

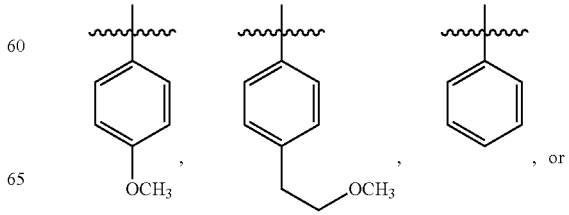

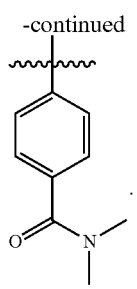
In one embodiment, the compound of Formula IIA1 is:
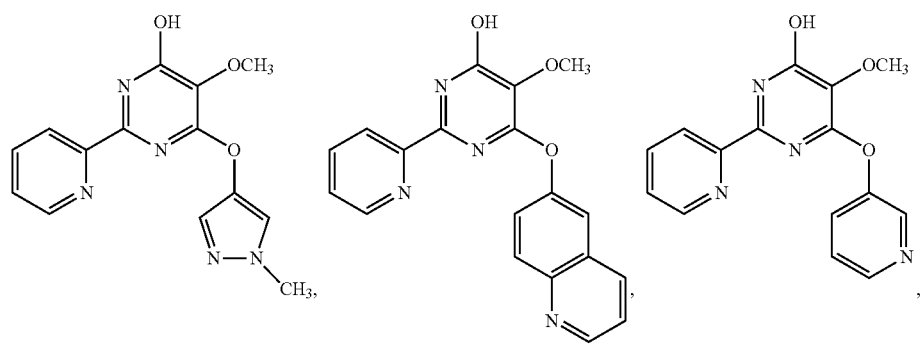
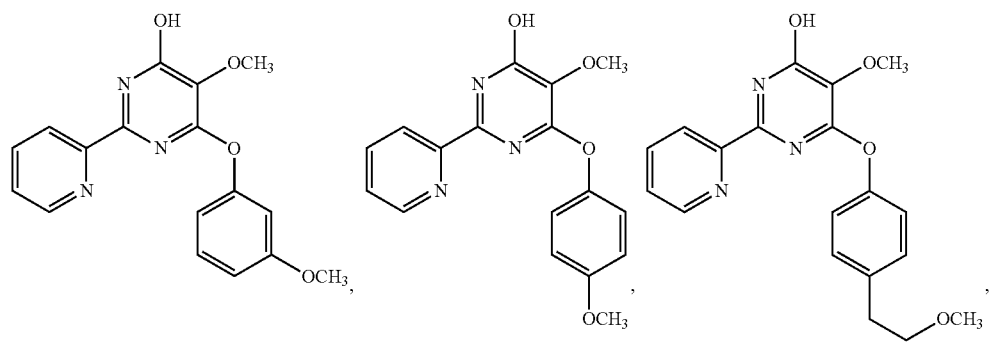
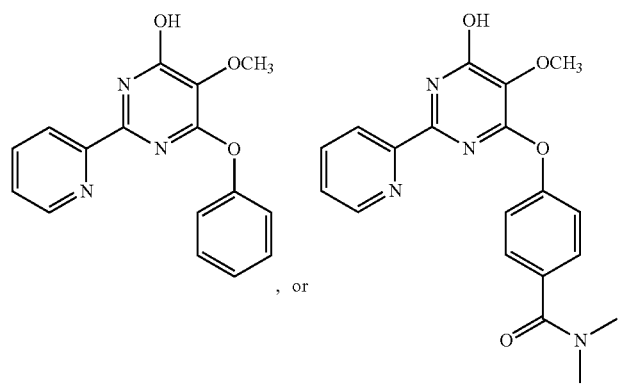

In another embodiment, the compound of Formula IIA1 is:

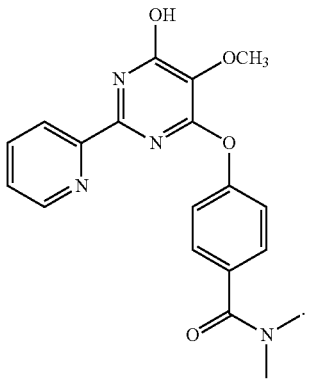

In certain embodiments, the pharmaceutically acceptable derivative of the compound of Formula IIA1 is a pharmaceutically acceptable salt of the compound of Formula IIA1.

In certain embodiments, the compounds for use in the compositions and methods provided herein are of Formula IIB:

Formula IIB

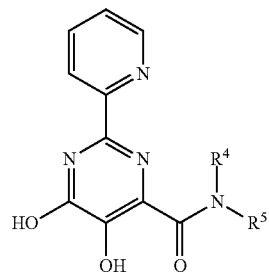

or pharmaceutically acceptable derivatives thereof, wherein —NR⁴R⁵ is

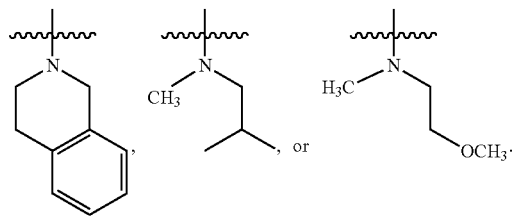

In one embodiment, the compound of Formula IIB is:

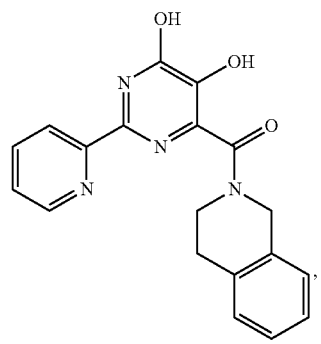

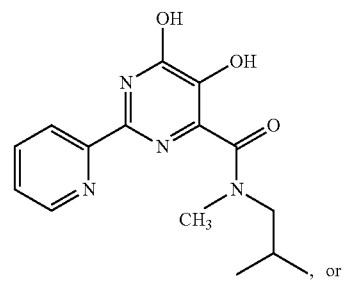

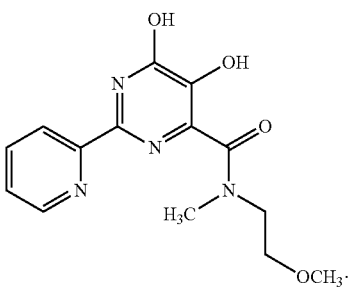

In another embodiment of Formula IIB, a compound of Formula IIB is a compound wherein
—NR⁴R⁵ is

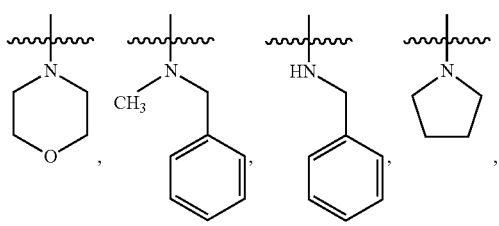

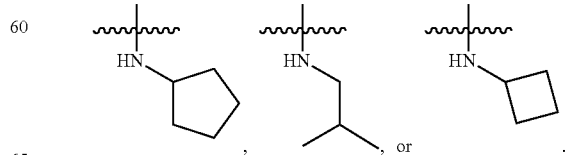

In one embodiment, the compound of Formula IIB is:

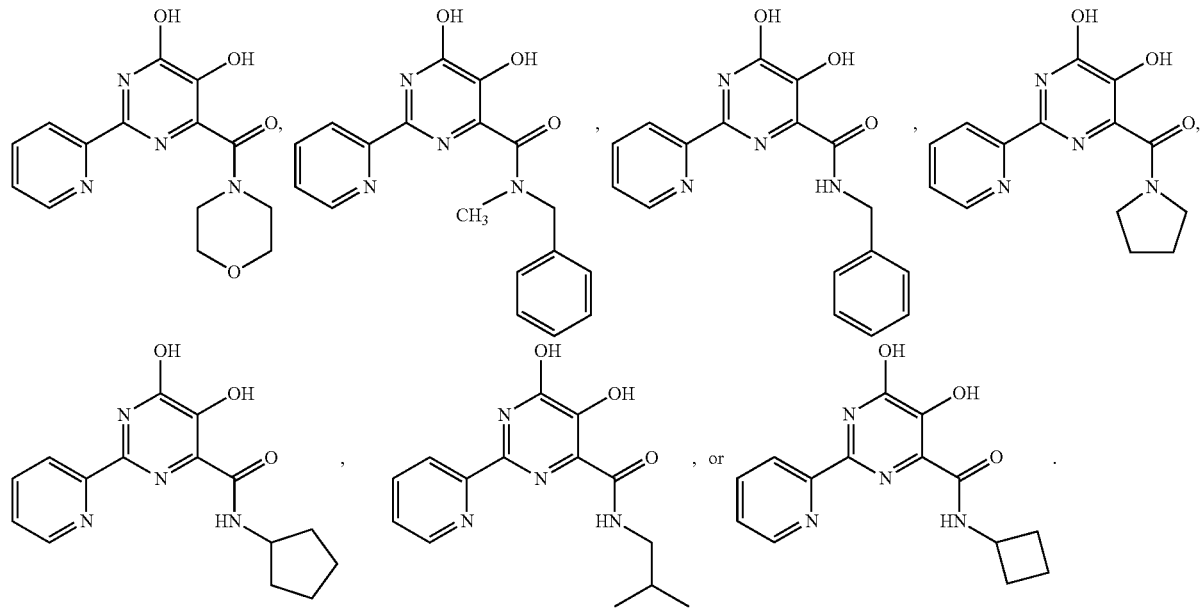

In certain embodiments, the pharmaceutically acceptable derivative of the compound of Formula IIB is a pharmaceutically acceptable salt of the compound of Formula IIB.

In certain embodiments, the compounds for use in the compositions and methods provided herein are of Formula IIC:

Formula IIC

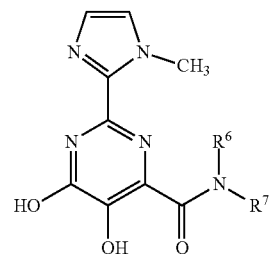

or pharmaceutically acceptable derivatives thereof, wherein —NR⁶R⁷ is

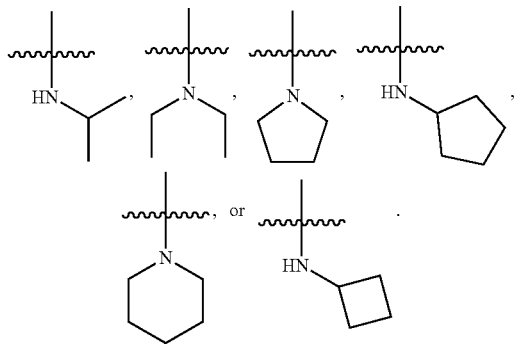

In one embodiment, the compound of Formula IIC is:

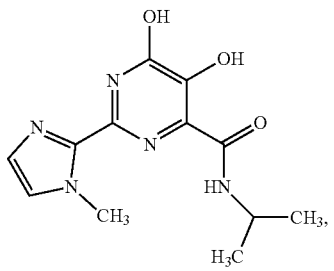

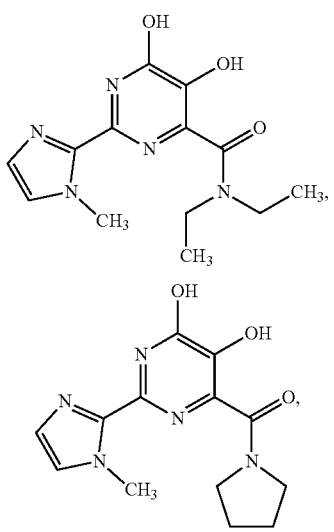

-continued

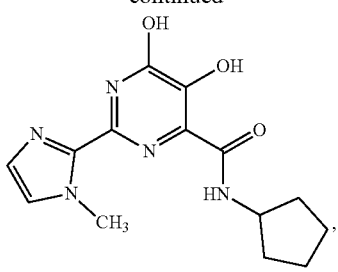

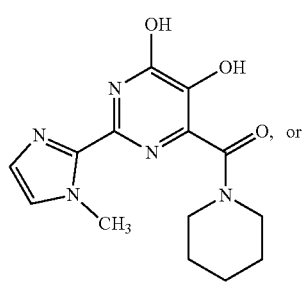, or

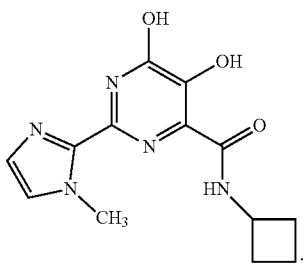

In certain embodiments, the pharmaceutically acceptable derivative of the compound of Formula IIC is a pharmaceutically acceptable salt of the compound of Formula IIC.

In certain embodiments, the compounds for use in the compositions and methods provided herein are of Formula IID:

Formula IID

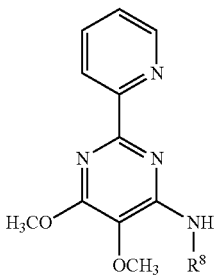

or pharmaceutically acceptable derivatives thereof, wherein $R^8$ is

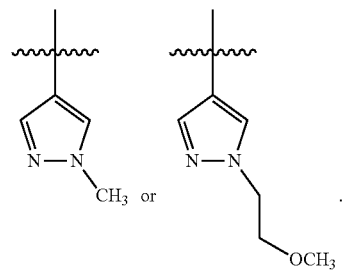

In one embodiment, the compound of Formula IID is:

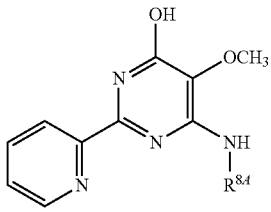

In certain embodiments, the pharmaceutically acceptable derivative of the compound of Formula IID is a pharmaceutically acceptable salt of the compound of Formula IID.

In certain embodiments, the compounds for use in the compositions and methods provided herein are of Formula IIE:

Formula IIE or pharmaceutically acceptable derivatives thereof, wherein $R^{8A}$ is

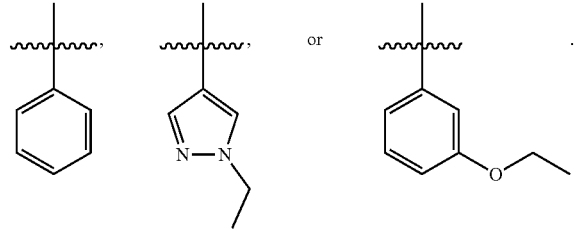

In one embodiment, the compound of Formula IIE is:

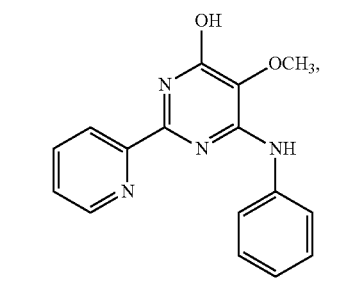

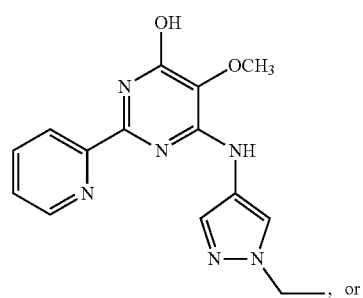, or

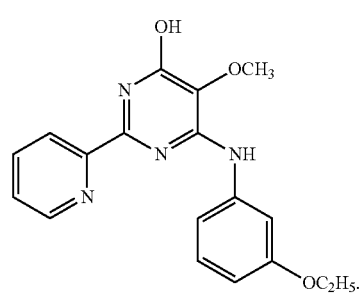

In certain embodiments, the pharmaceutically acceptable derivative of the compound of Formula IIE is a pharmaceutically acceptable salt of the compound of Formula IIE.

In certain embodiments, the compounds for use in the compositions and methods provided herein are of Formula IIA:

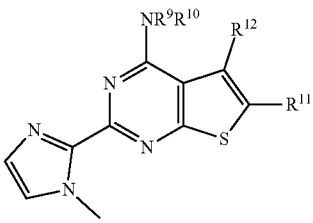

Formula IIIA or pharmaceutically acceptable derivatives thereof, wherein $-NR^9R^{10}$ is

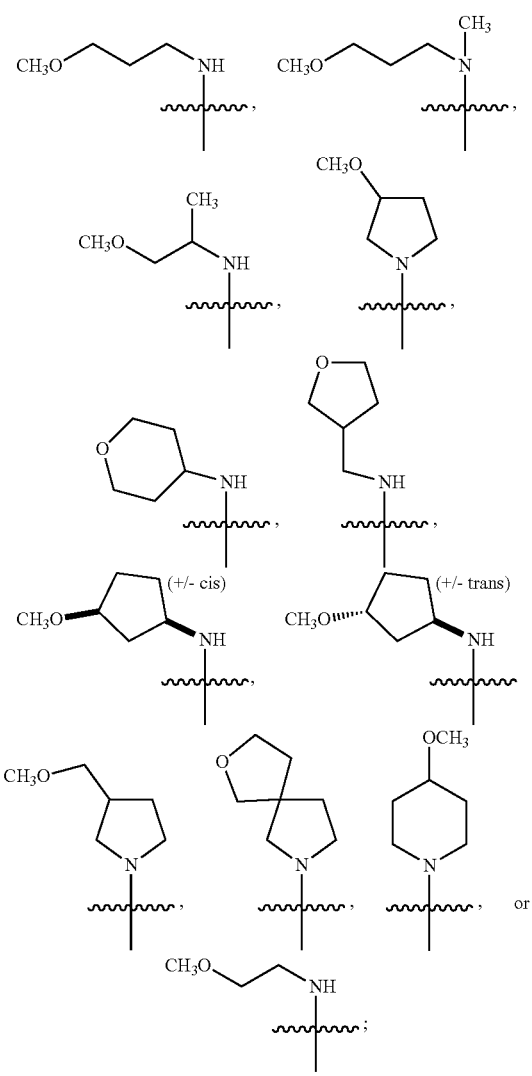

$R^{11}$ is

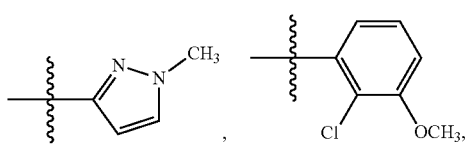

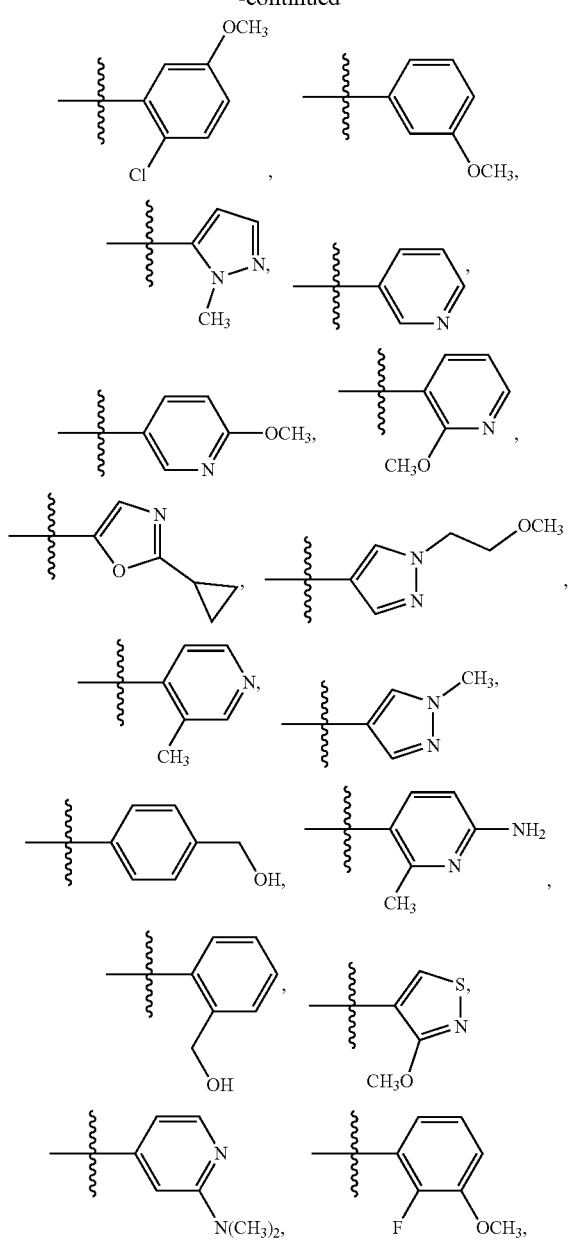
or Br; and
R[12] is Ph.
In one embodiment the compound of Formula IIIA is:
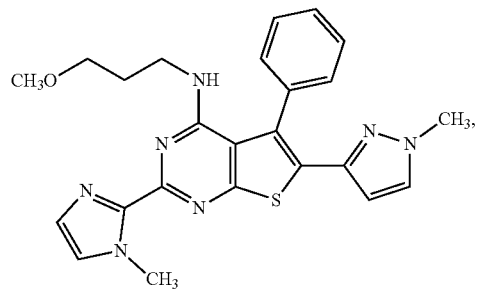
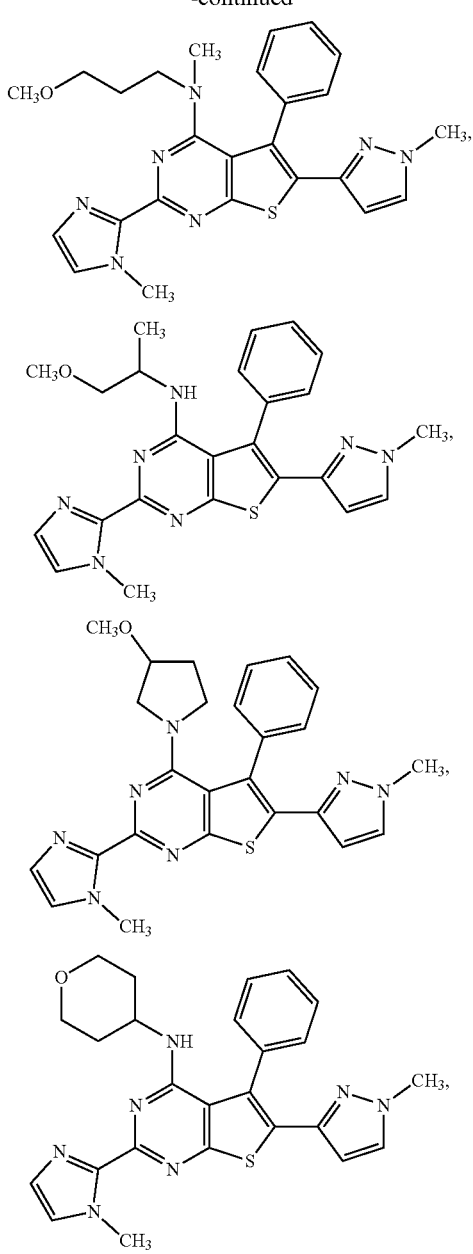
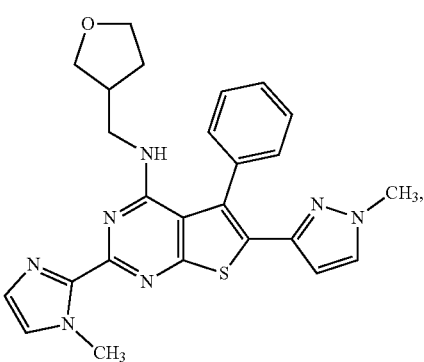

123
-continued
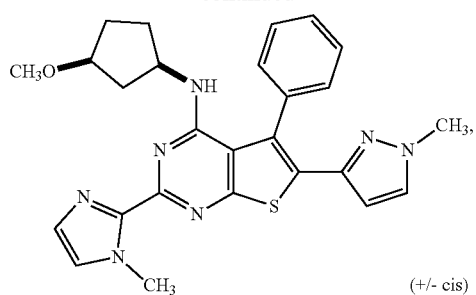
(+/- cis)
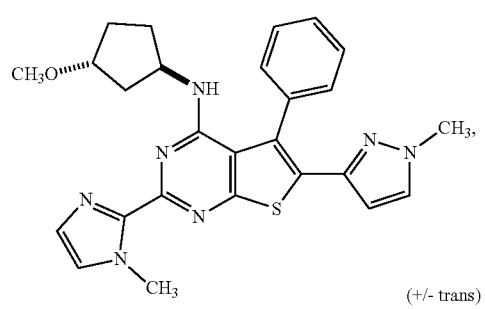
(+/- trans)
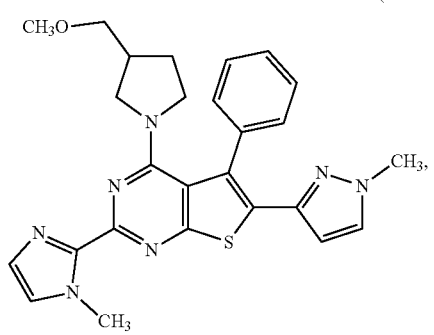
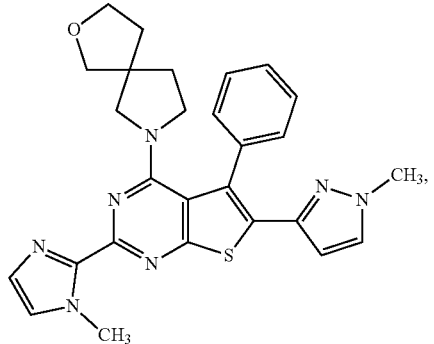
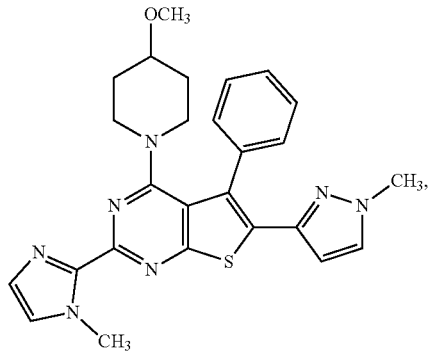
124
-continued
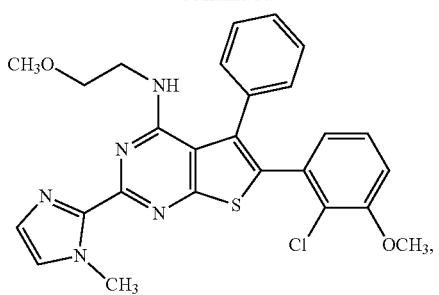
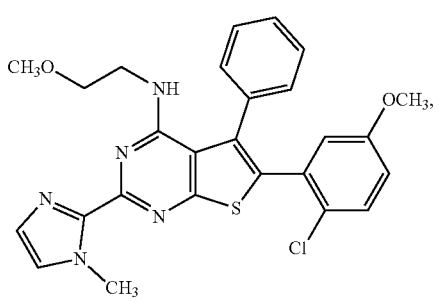
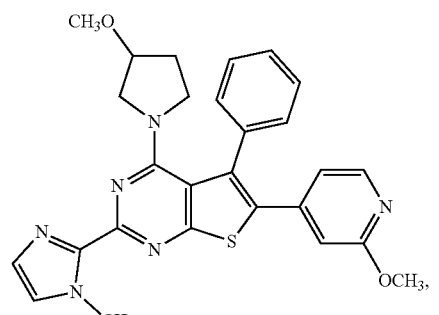
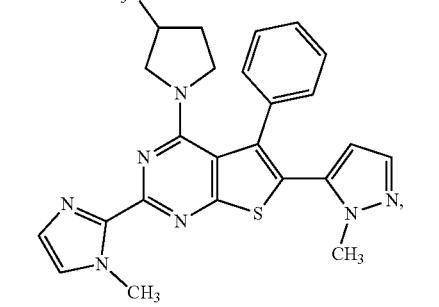
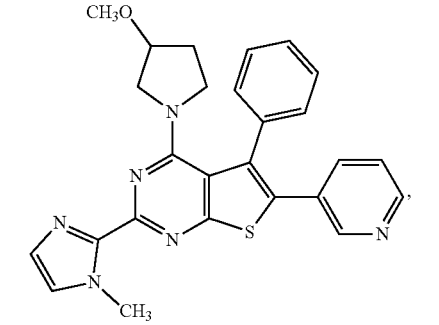

125
-continued
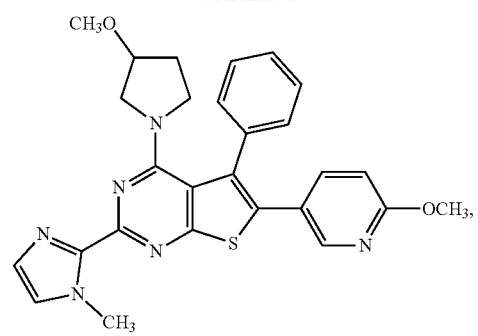
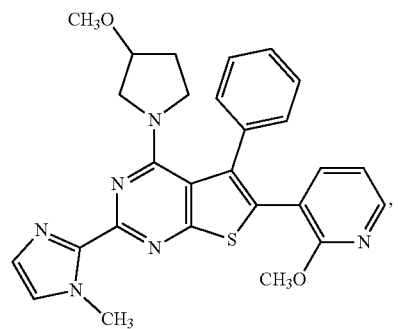
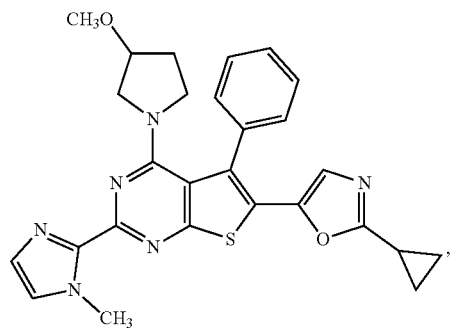
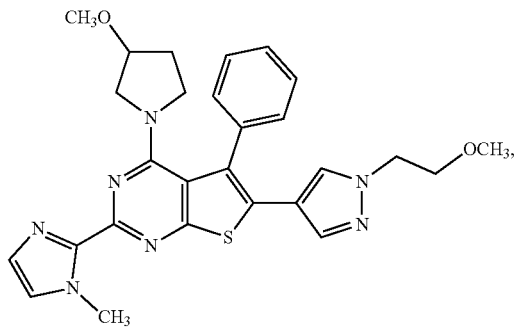
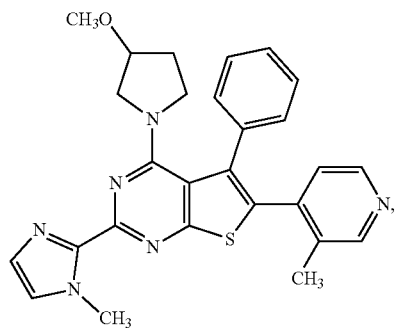
126
-continued
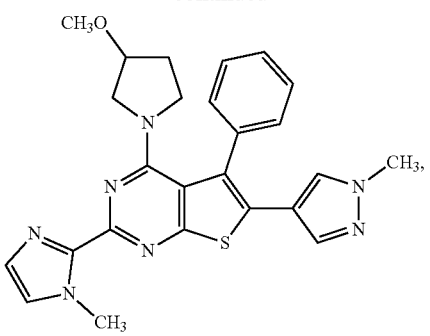
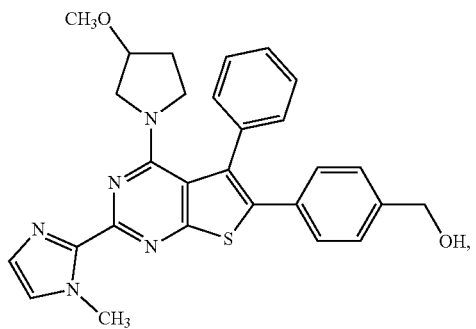
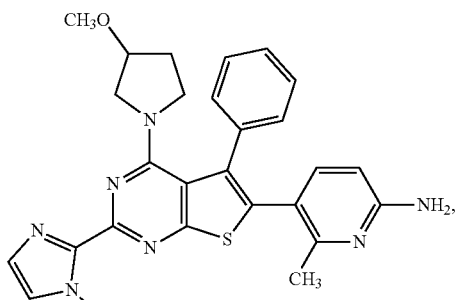
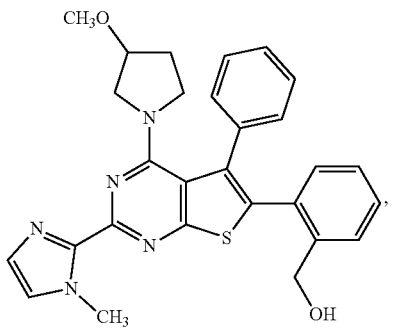
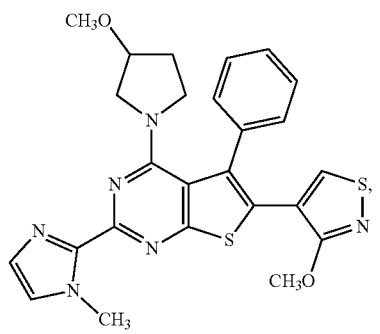

127
-continued

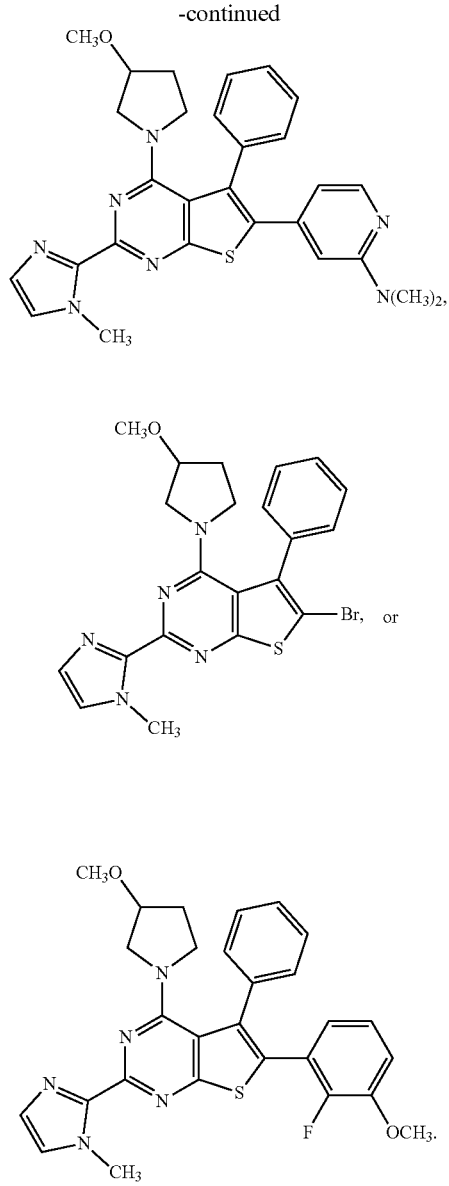

In certain embodiments, the pharmaceutically acceptable derivative of the compound of Formula IIIA is a pharmaceutically acceptable salt of the compound of Formula IIA.

In certain embodiments, the compounds for use in the compositions and methods provided herein are of Formula IIA1:

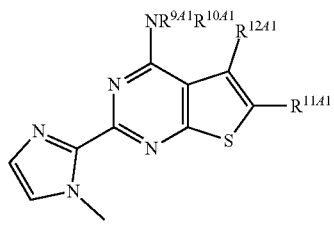

Formula IIIA1 or pharmaceutically acceptable derivatives thereof,

128 wherein $-NR^{9.A1}R^{10.A1}$ is

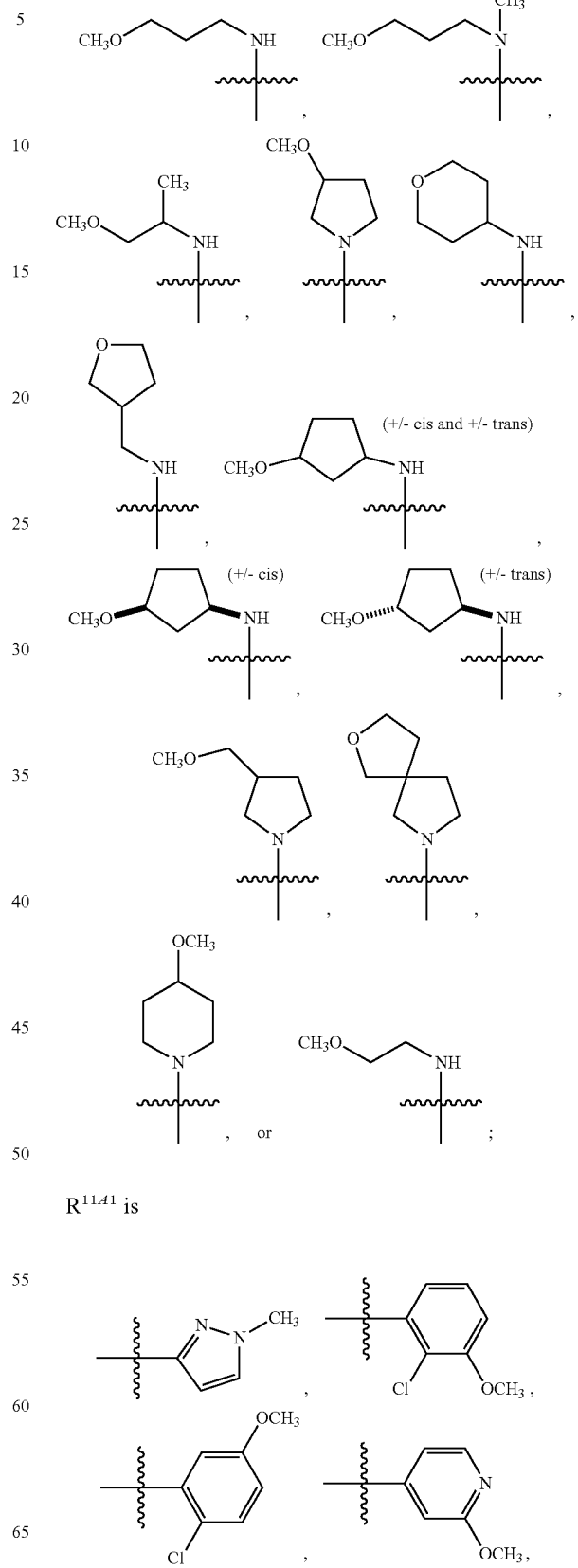

$R^{11.A1}$ is

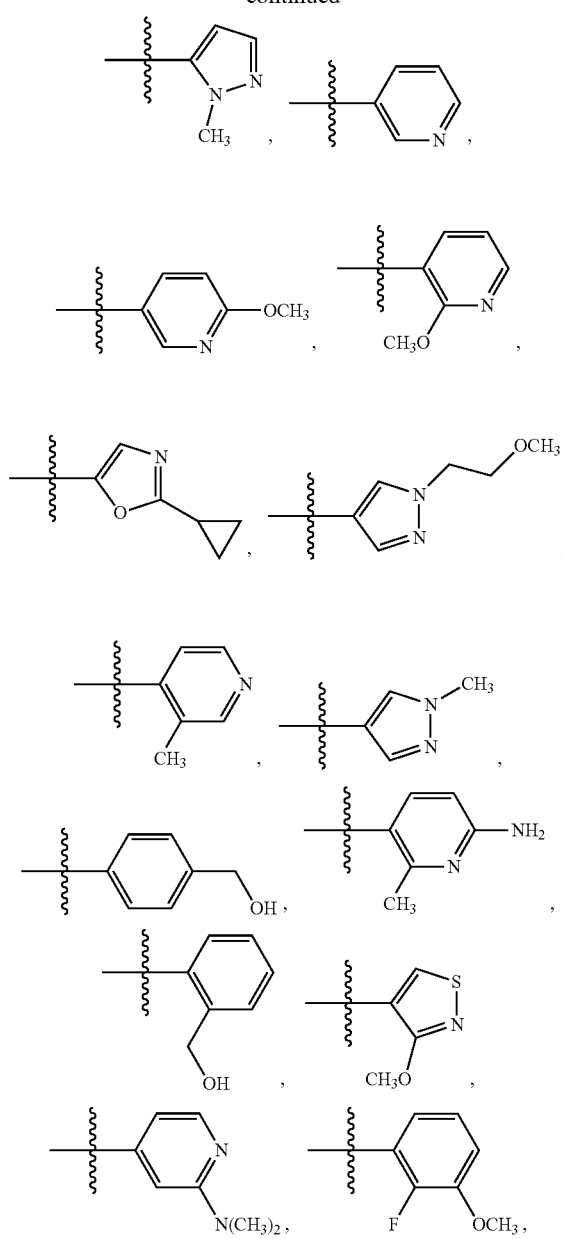
or Br, and
$R^{12A1}$ is Ph.
In one embodiment, the compound of Formula IIIA1 is:
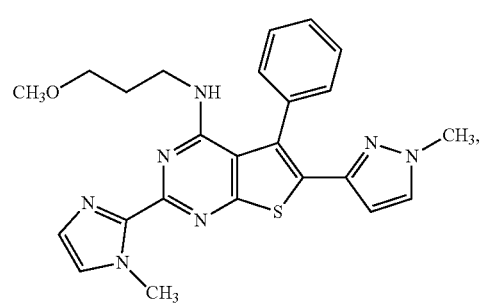
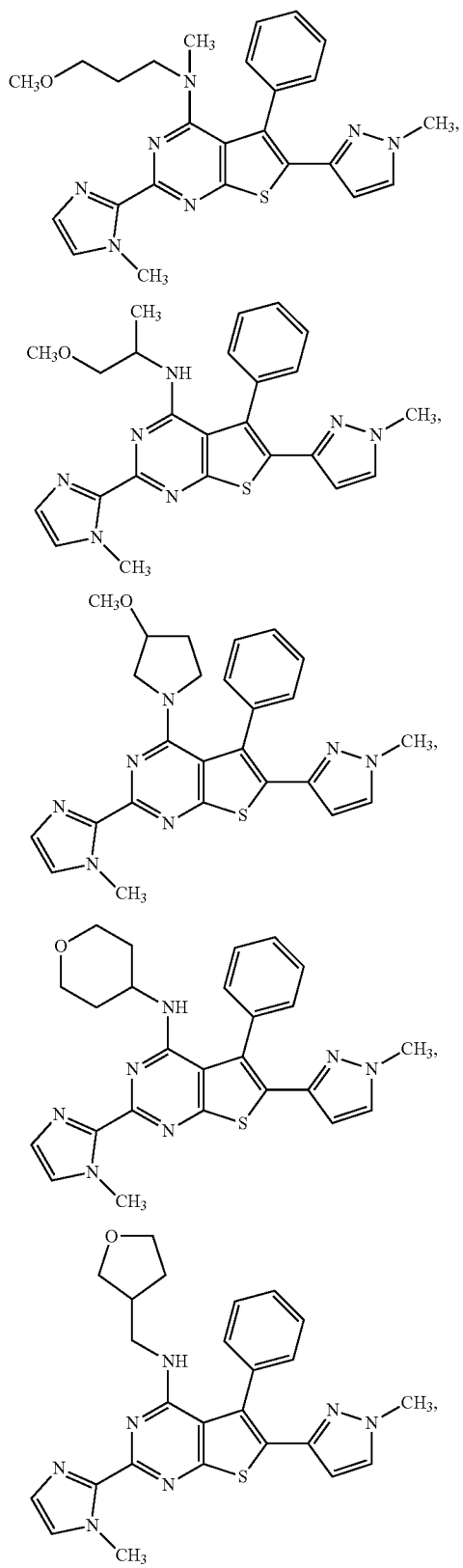

-continued
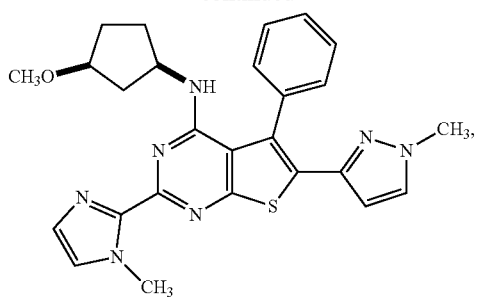
(+/- cis)
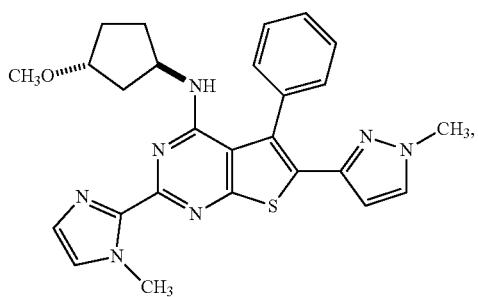
(+/- trans)
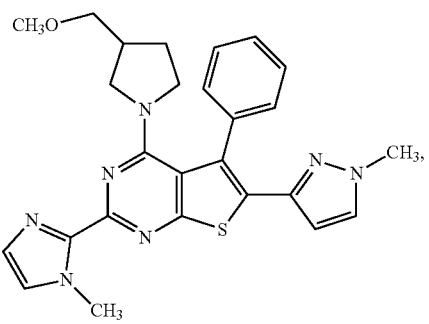
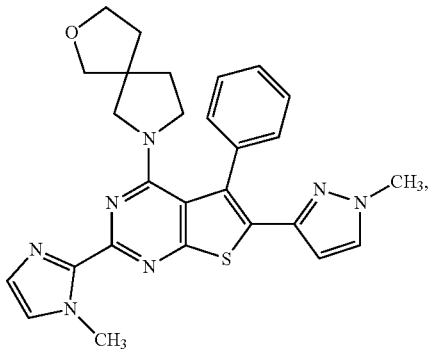
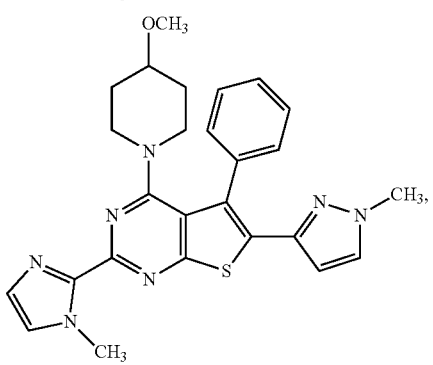
-continued
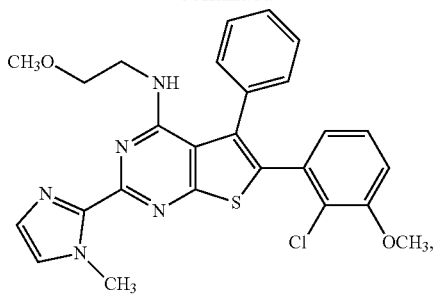
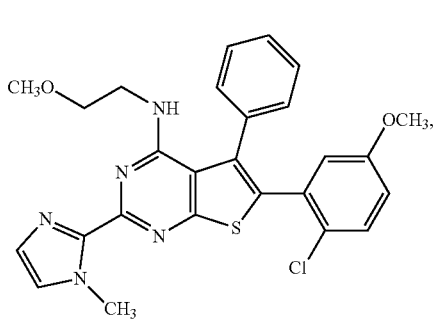
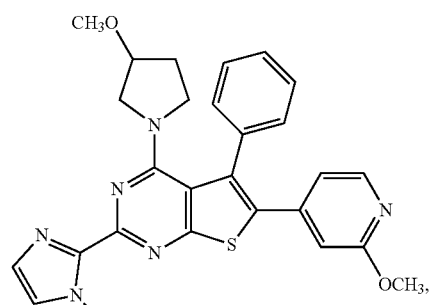
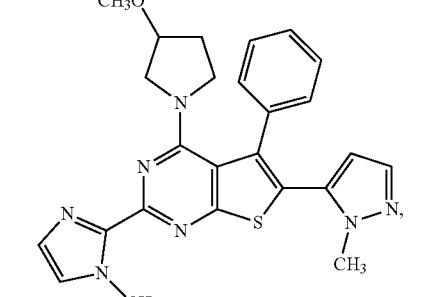
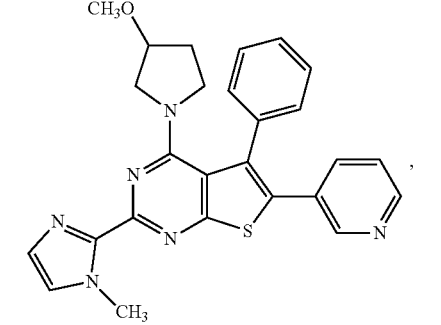

-continued
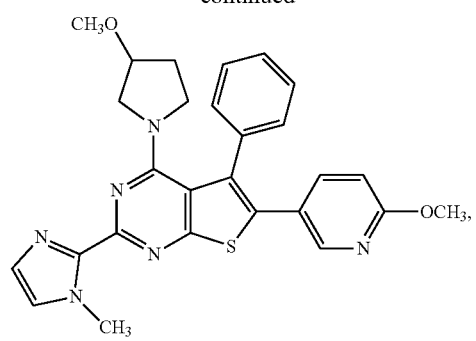
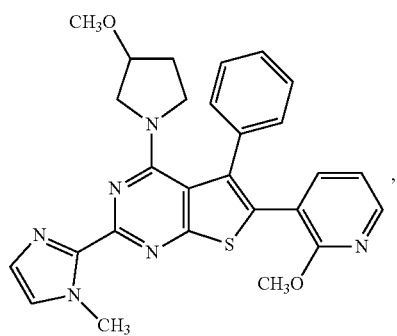
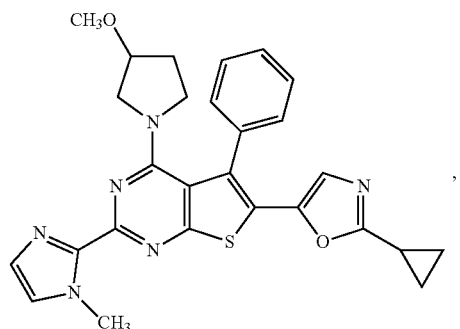
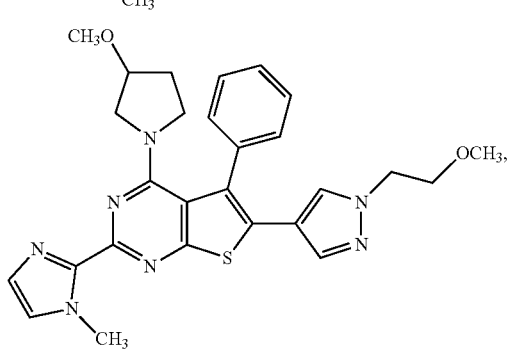
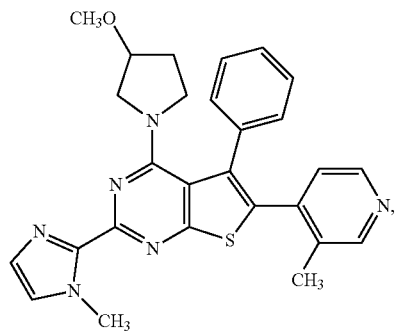
-continued
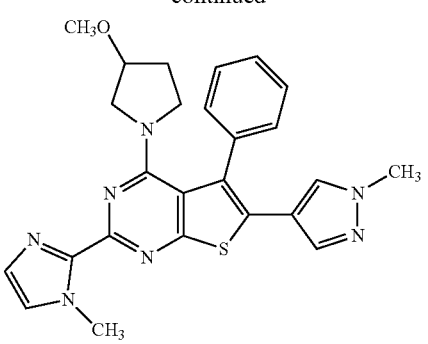
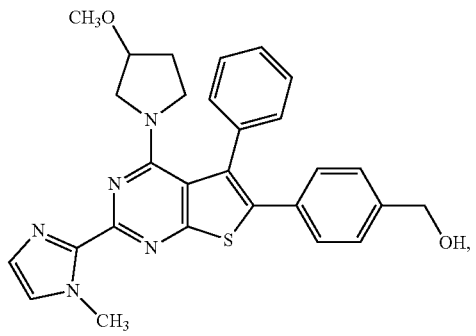
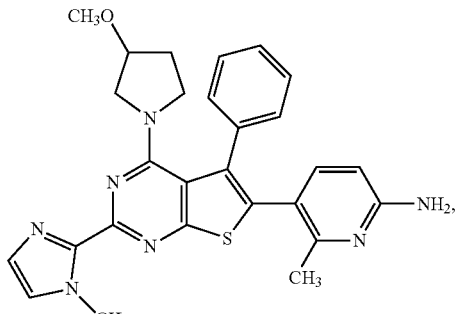
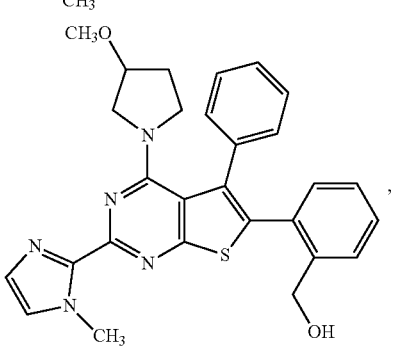
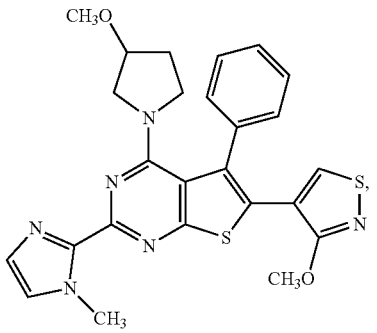

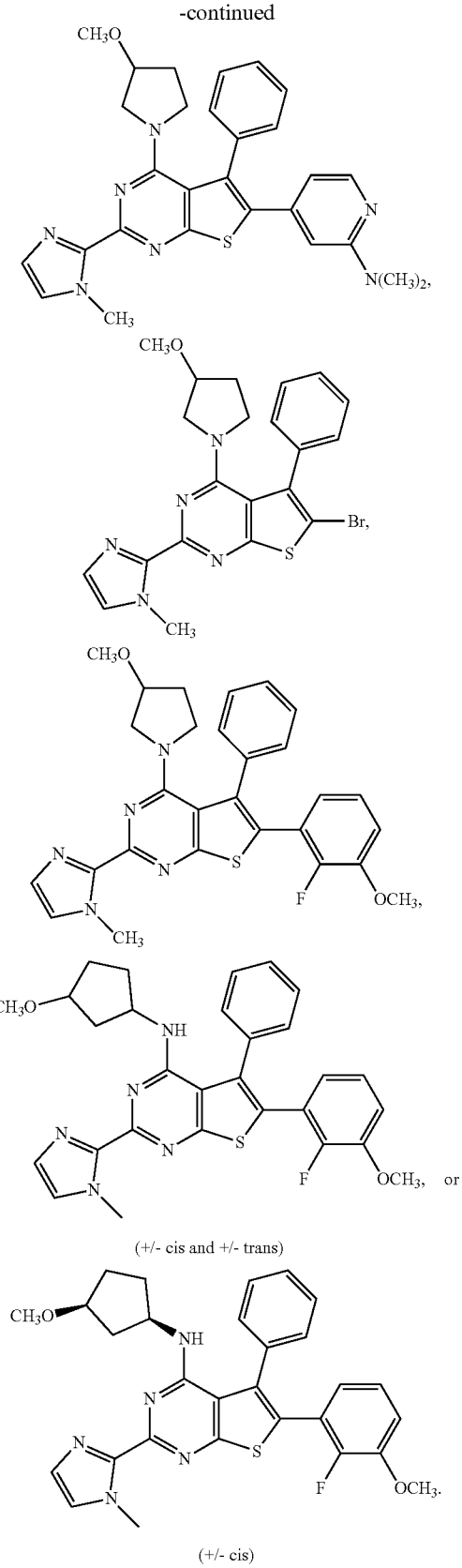

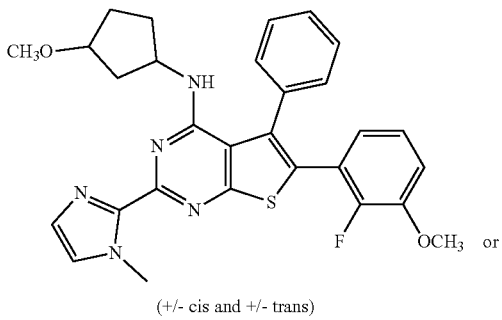

(+/- cis and +/- trans)

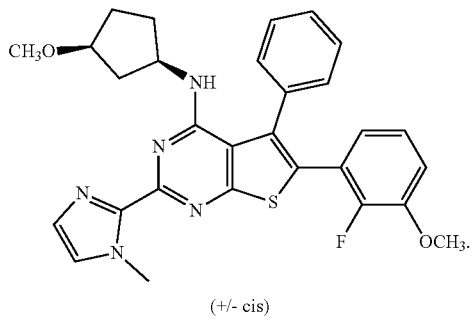

(+/- cis)

In certain embodiments, the pharmaceutically acceptable derivative of the compound of Formula IIIA1 is a pharmaceutically acceptable salt of the compound of Formula IIIA1.

In certain embodiments, the compounds for use in the compositions and methods provided herein are of Formula IIIA2:

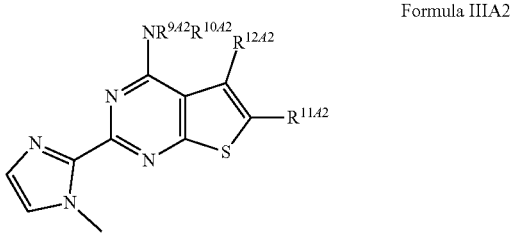

Formula IIIA2 or pharmaceutically acceptable derivatives thereof, wherein —NR$^{9A2}$R$^{10A2}$ is

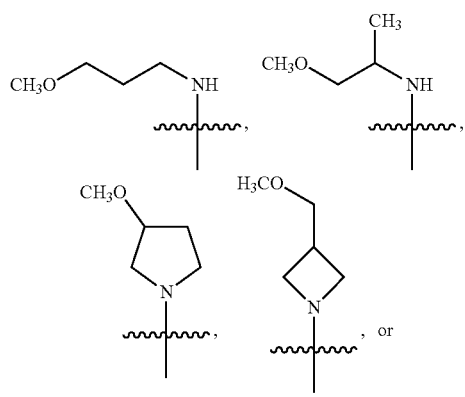

In another embodiment, the compound of Formula IIIA1 is:

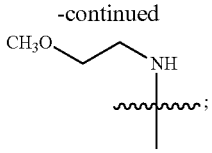
$R^{11A2}$ is
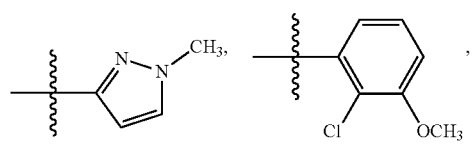
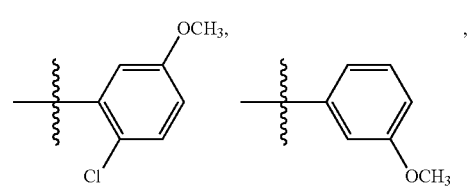
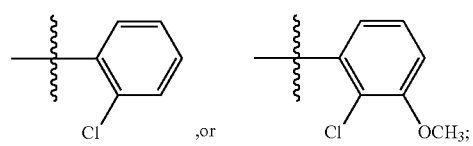
and
$R^{12A2}$ is
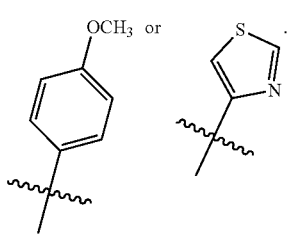 [SMILES: *c1ccc(OC)cc1 ; *c1cscn1]
In one embodiment, the compound of Formula IIIA2 is:
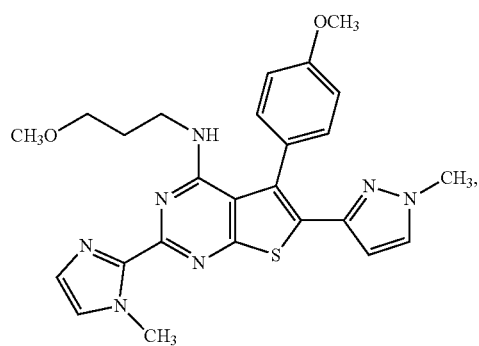
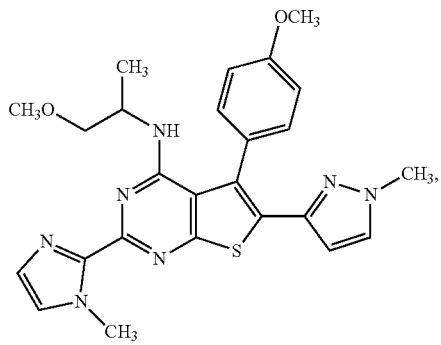
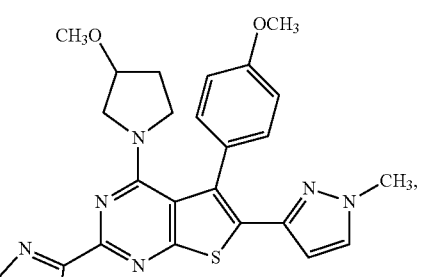
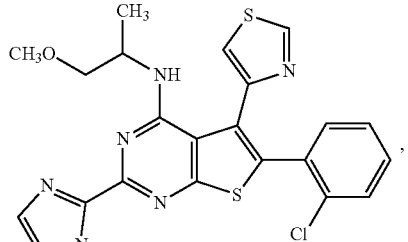
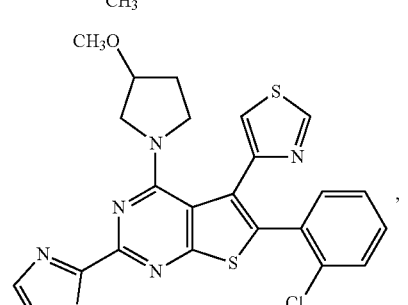
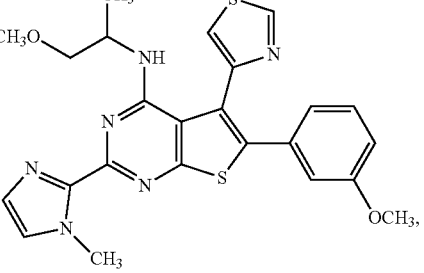

-continued

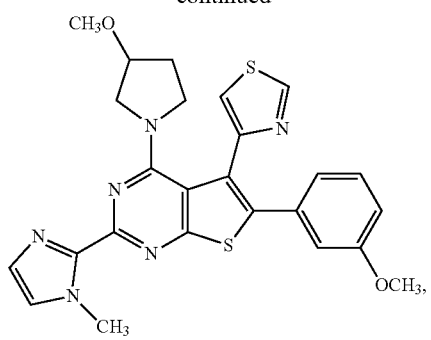

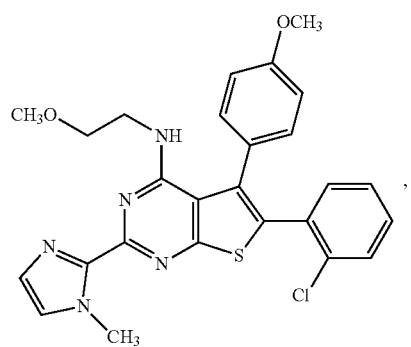

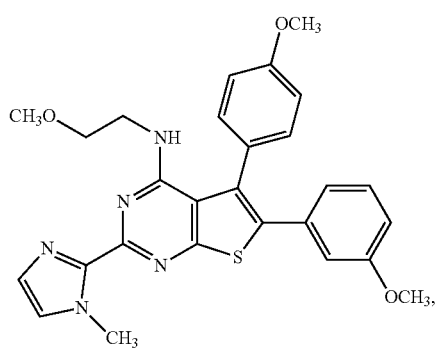

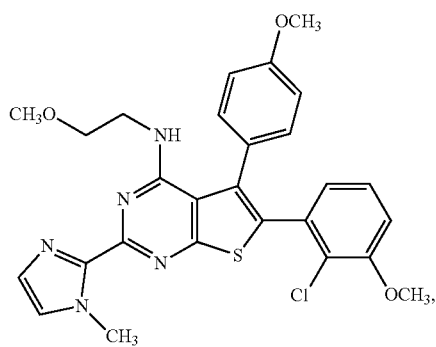

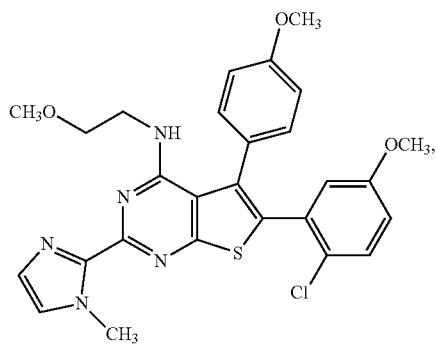

-continued

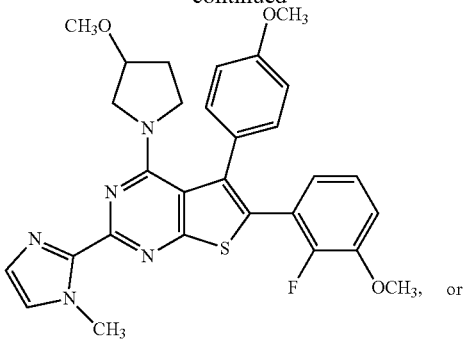, or

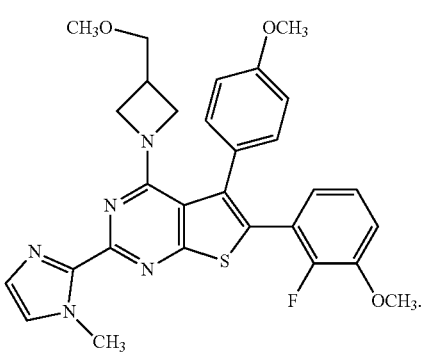.

In certain embodiments, the pharmaceutically acceptable derivative of the compound of Formula IIIA2 is a pharmaceutically acceptable salt of the compound of Formula IIIA2.

In certain embodiments, the compounds for use in the compositions and methods provided herein are of Formula IIIB:

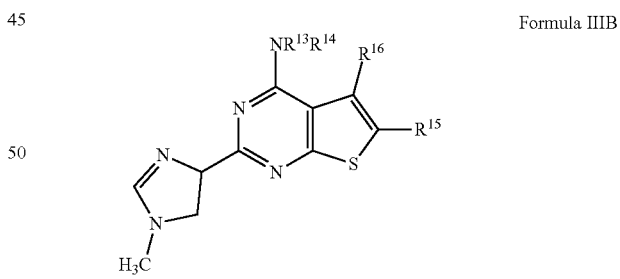

Formula IIIB or pharmaceutically acceptable derivatives thereof, wherein —NR$^{13}$R$^{14}$ is

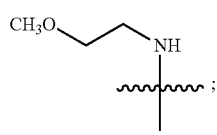;

$R^{15}$ is

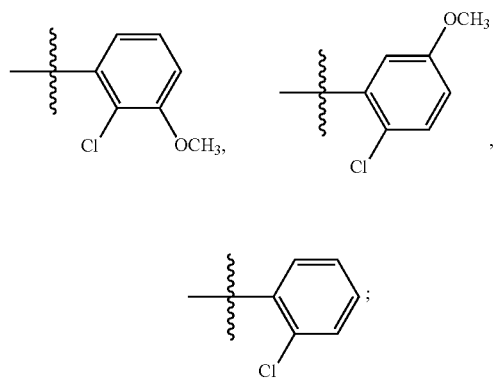

and
$R^{16}$ is

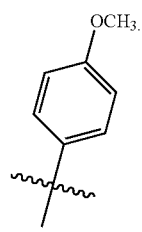

In one embodiment, the compound of Formula IIIB is:

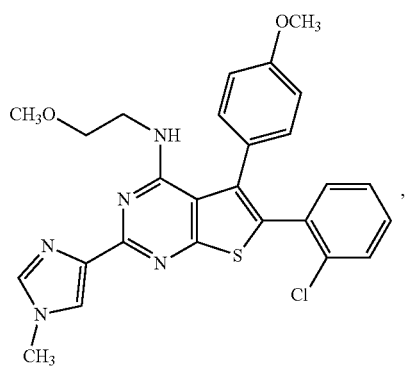

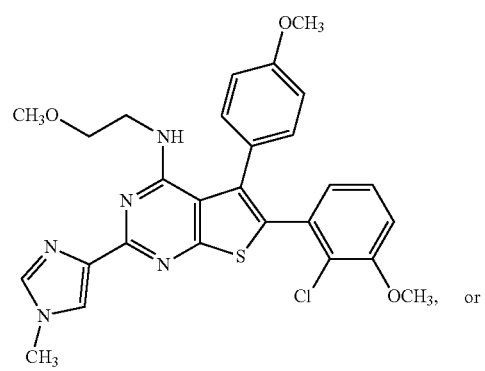

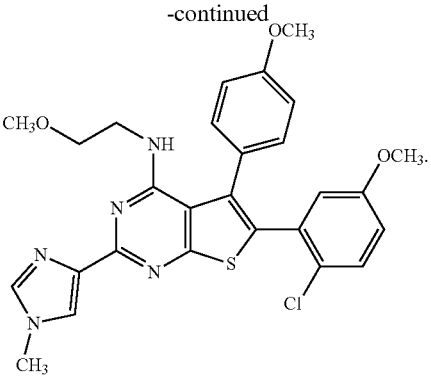

In certain embodiments, the pharmaceutically acceptable derivative of the compound of Formula IIIB is a pharmaceutically acceptable salt of the compound of Formula IIB.

In certain embodiments, the compounds for use in the compositions and methods provided herein are of Formula IIIC:

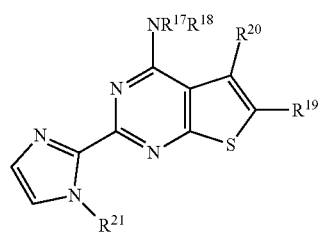

Formula IIIC or pharmaceutically acceptable derivatives thereof, wherein —$NR^{17}R^{18}$ is

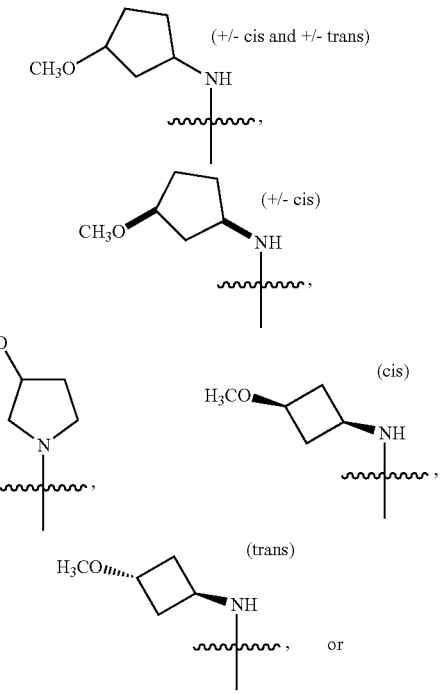

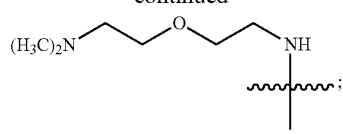
R[19] is
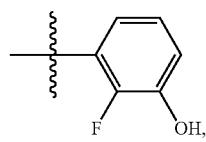 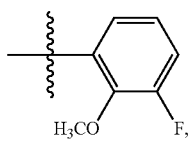
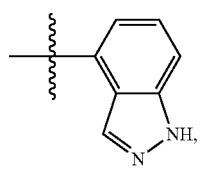 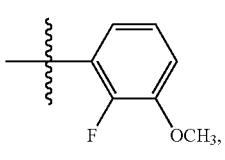
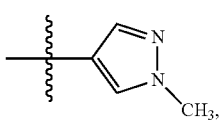 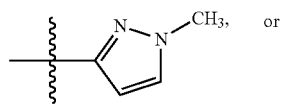 or
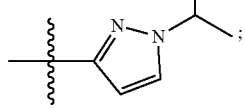;
R[20] is Ph; and
R[21] is hydrogen or methyl.
In one embodiment, the compound of Formula IIIC wherein R[21] is hydrogen.
In one embodiment, the compound of Formula IIIC wherein R[21] is methyl.
In one embodiment, the compound of Formula IIIC is:
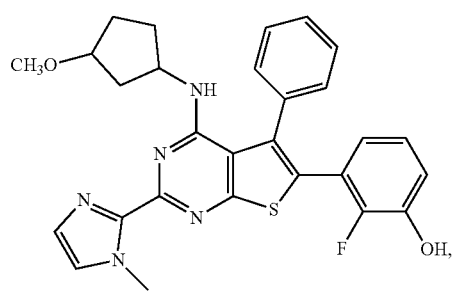
(+/− cis and +/− trans)
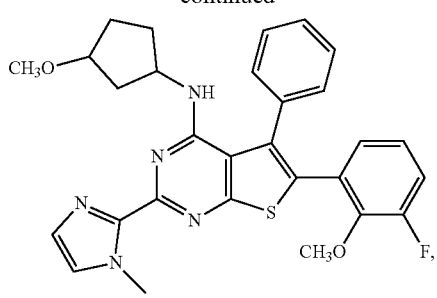
(+/− cis and +/− trans)
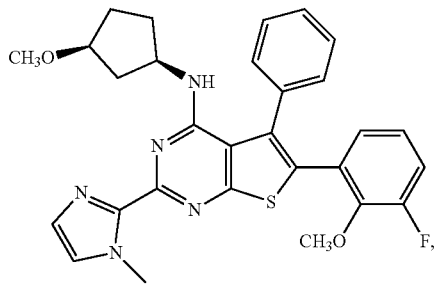
(+/− cis)
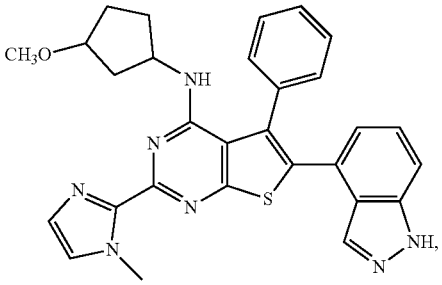
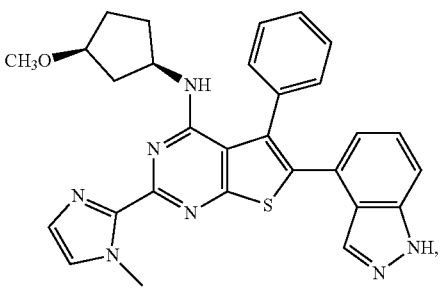
(+/− cis and +/− trans)
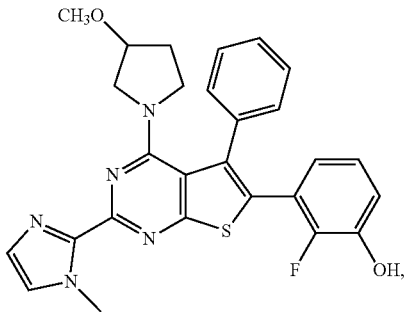
(+/− cis)

-continued

In another embodiment, the compound of Formula IIIC is:

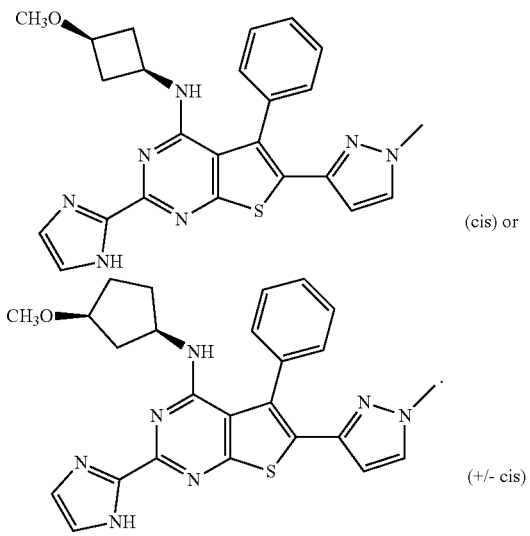

In certain embodiments, the pharmaceutically acceptable derivative of the compound of Formula IIIC is a pharmaceutically acceptable salt of the compound of Formula IIIC.

In certain embodiments, the compounds for use in the compositions and methods provided herein are of Formula IIID:

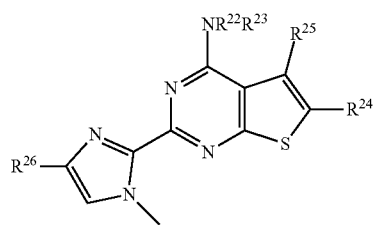

Formula IIID or pharmaceutically acceptable derivatives thereof, wherein —$NR^{22}R^{23}$ is

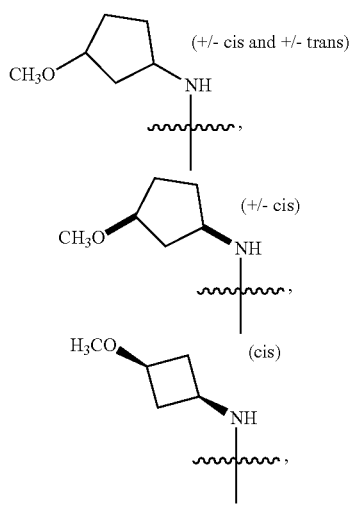

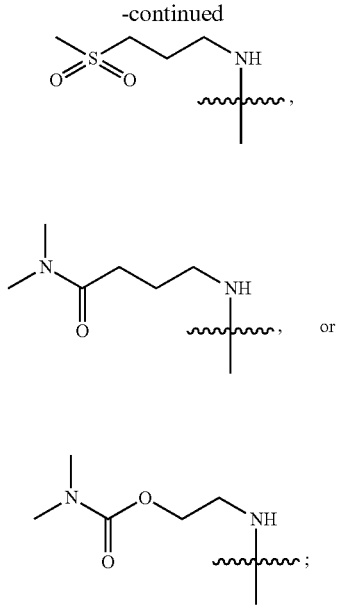

$R^{24}$ is

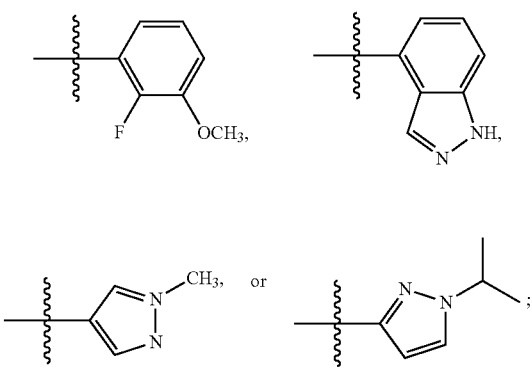

$R^{25}$ is methyl; and
$R^{26}$ is hydrogen or methyl.

In one embodiment, the compound of Formula IIID wherein $R^{26}$ is hydrogen.

In one embodiment, the compound of Formula IIID wherein $R^{26}$ is methyl.

In one embodiment, the compound of Formula IIID is:

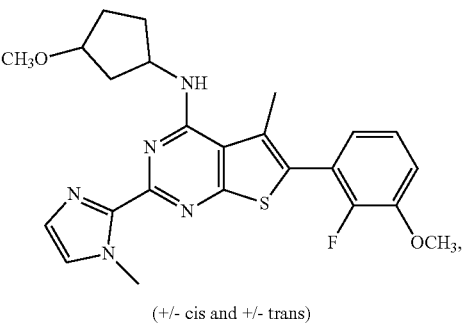

149
-continued
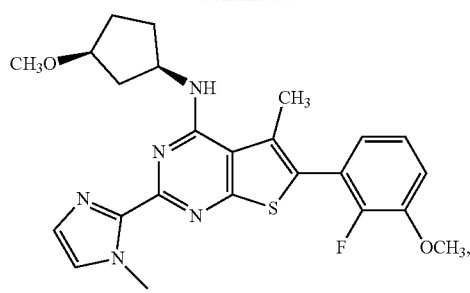
(+/- cis)
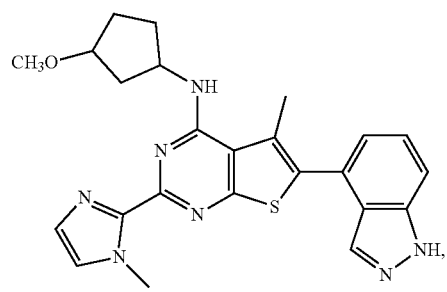
(+/- cis and +/- trans)
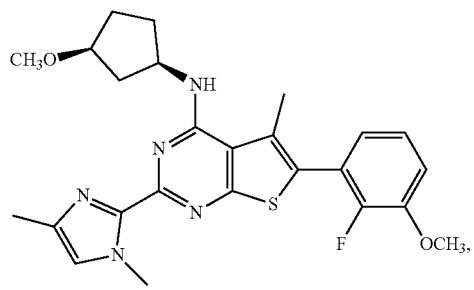
(+/- cis)
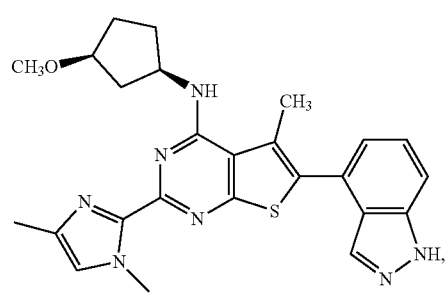
(+/- cis)
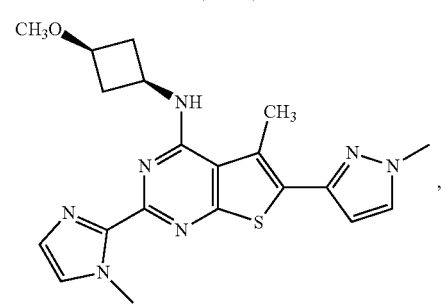
(cis)
150
-continued
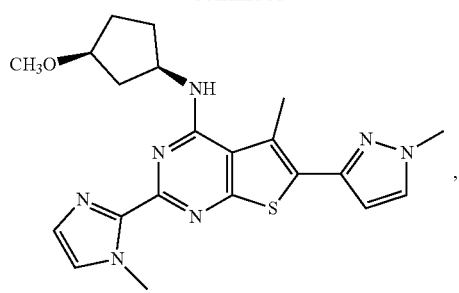
(+/- cis)
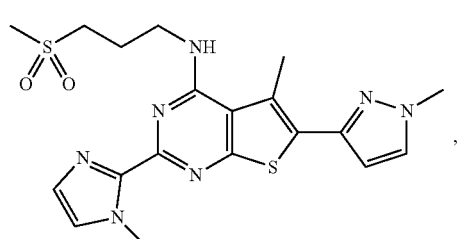
,
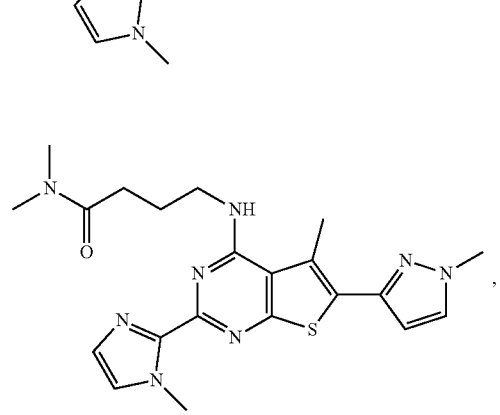
,
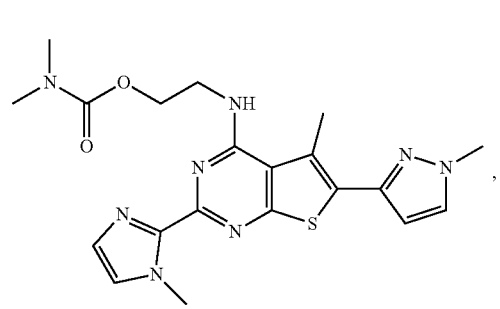
,
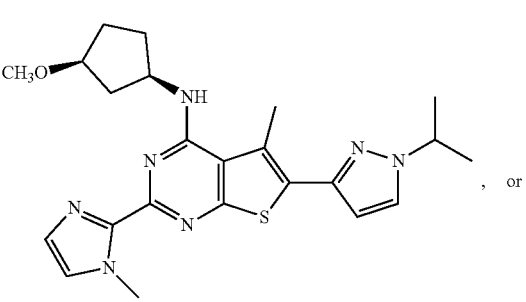
, or
(+/- cis)

-continued

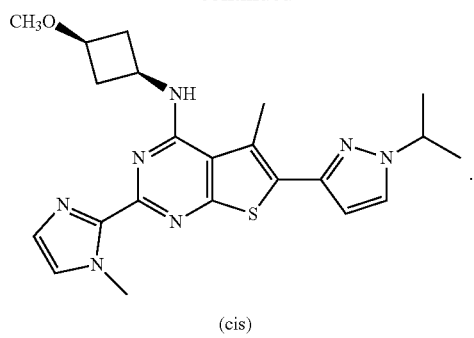

(cis)

In one embodiment, the compound of Formula IIID is exclusive of the compound:

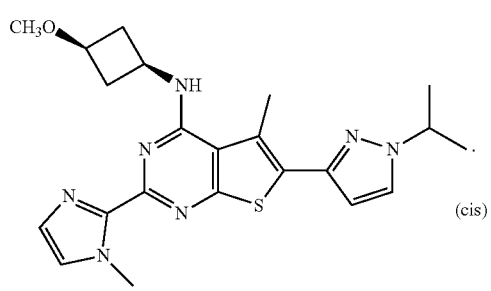

(cis)

In certain embodiments, the pharmaceutically acceptable derivative of the compound of Formula IIID is a pharmaceutically acceptable salt of the compound of Formula IIID.

In certain embodiments, the compounds for use in the compositions and methods provided herein are of Formula IIIE:

Formula IIIE

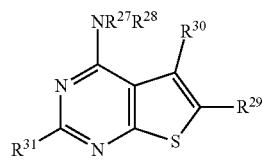

or pharmaceutically acceptable derivatives thereof, wherein —NR²⁷R²⁸ is

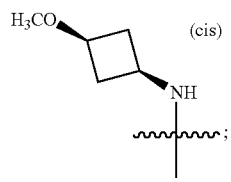 [SMILES: *N[C@H]1C[C@@H](OC)C1]
(cis)

$R^{29}$ is hydrogen;
$R^{30}$ is hydrogen: and $R^{31}$ is

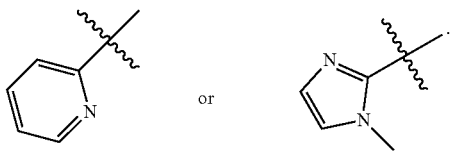

or

In one embodiment, the compound of Formula IIIE is:

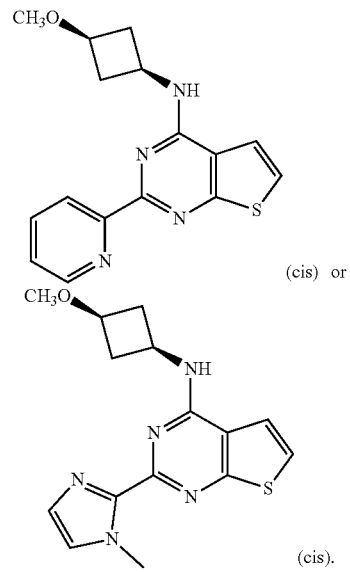

(cis) or (cis).

In certain embodiments, the pharmaceutically acceptable derivative of the compound of Formula IIIE is a pharmaceutically acceptable salt of the compound of Formula IIIE.

In certain embodiments, the compounds for use in the compositions and methods provided herein are of Formula IIIF:

Formula IIIF

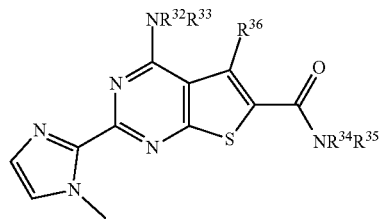

or pharmaceutically acceptable derivatives thereof, wherein —NR³²R³³ is

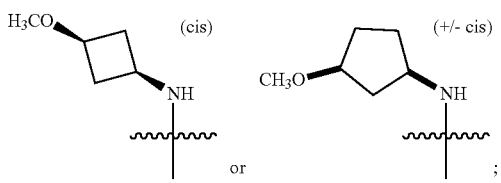

or ;

—NR³⁴R³⁵ is

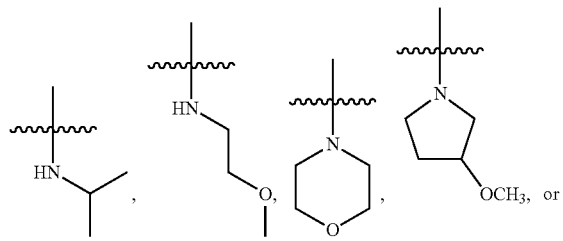

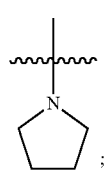

and
R³⁶ is Phenyl.
In one embodiment, the compound of Formula IIIF is:

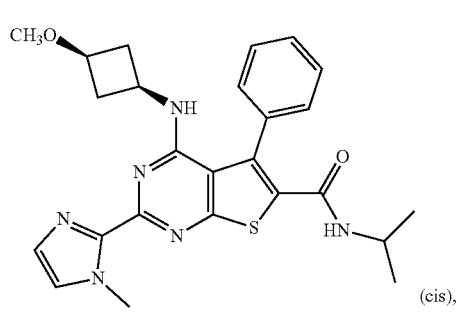
(cis),

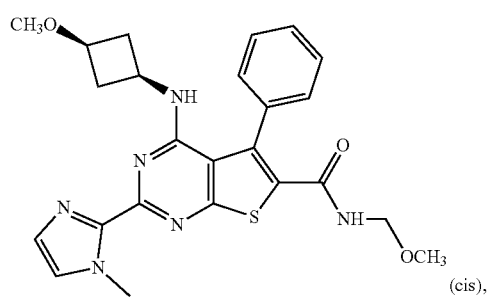
(cis),

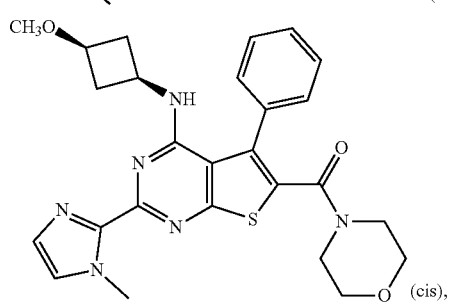
(cis),

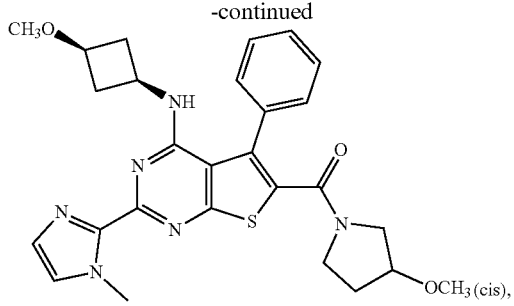
(cis),

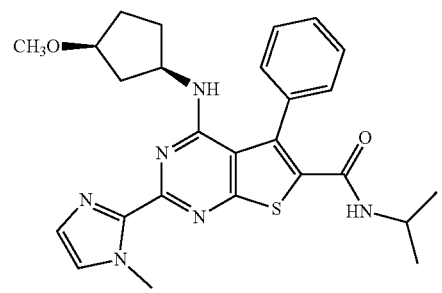
(+/− cis),

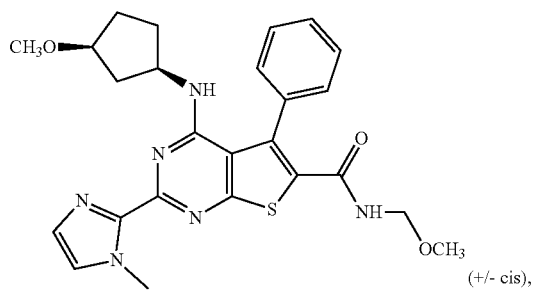
(+/− cis),

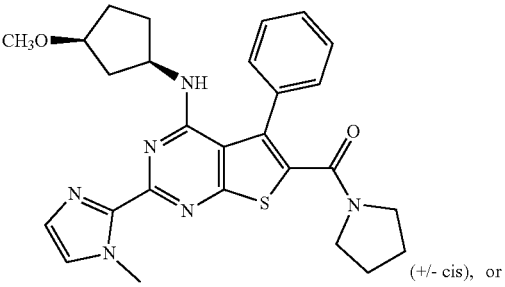
(+/− cis), or

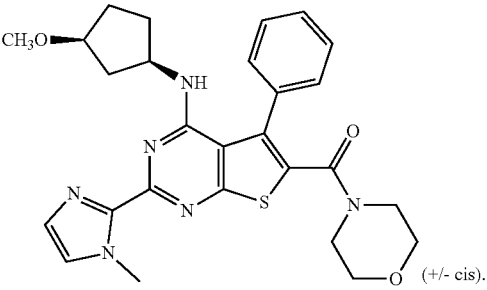
(+/− cis).

In certain embodiments, the pharmaceutically acceptable derivative of the compound of Formula IIIF is a pharmaceutically acceptable salt of the compound of Formula IIIF.

In one embodiment, the compound for use in the compositions and methods provided herein is

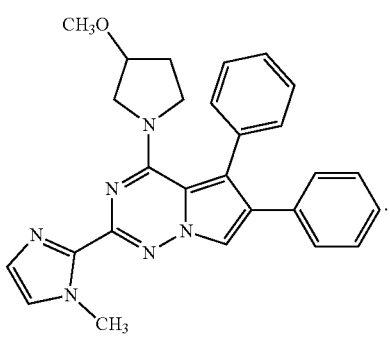

In one embodiment, the compound for use in the compositions and methods provided herein is

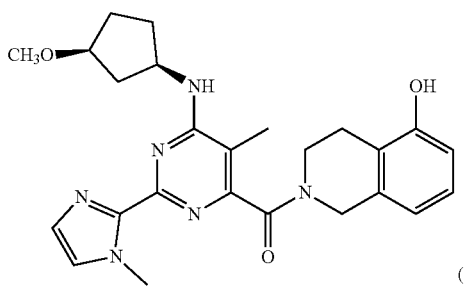

(+/- cis).

In one embodiment, the compound for use in the compositions and methods provided herein is

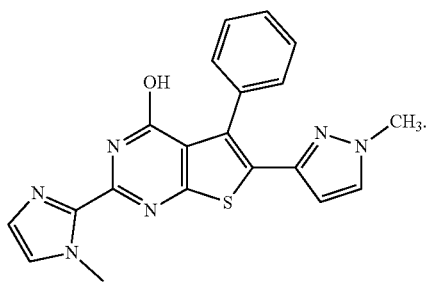 [SMILES: Cn1ccc(-c2sc3nc(-c4nccn4C)nc(O)c3c2-c2ccccc2)n1]

4.5. Synthesis of the Compounds

The compounds provided herein may be obtained from commercial sources or readily synthesized by methods well known to those of skill in the art.

4.5.1 Synthetic Procedures

Scheme 1

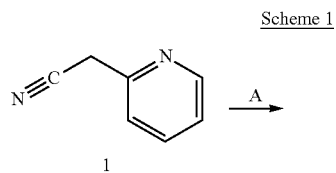

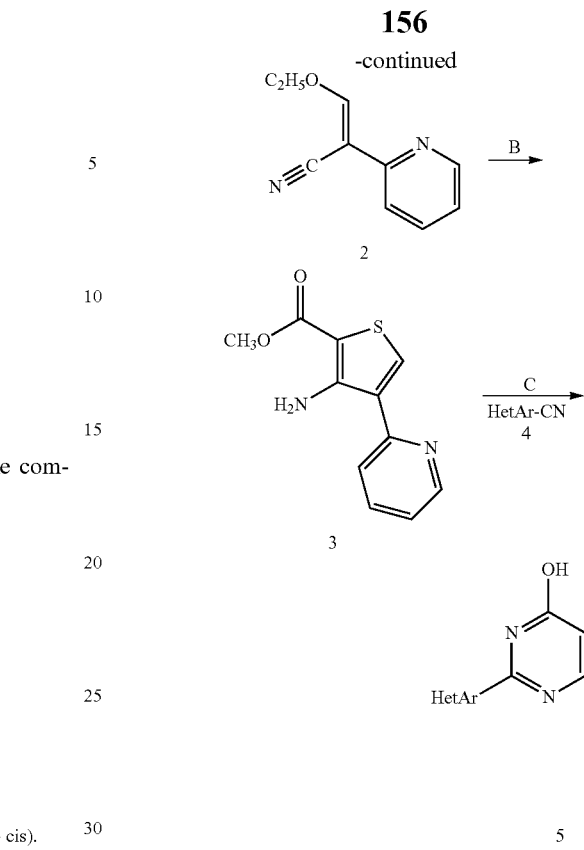

Step A: 2-Pyridyl acetonitrile 1 (32.00 g, 1 equiv) and triethyl orthoformate (40 g, 1 equiv) were added to acetic anhydride (55.3 g, 2 equiv) at room temperature. The resulting reaction mixture was heated at 100° C. for 3 h, cooled to room temperature, diluted with water (500 mL), and extracted with ethyl acetate (100 mL×3). The combined organic layers were washed with brine, dried over anhydrous $Na_2SO_4$, and chromatographed on silica gel yielding target compound 2 as a brown solid (16.4 g, 35%)

Step B: Methyl mercaptoacetate (7.2 g, 1.1 equiv) was dissolved in dry THF (200 mL) and cooled to 0° C. DBU (14.1 g, 1.5 equiv) was added thereto portion wise followed by slow addition of enol 2 (10.7 g, 1 equiv). The mixture was stirred at r.t. overnight, the solvent was evaporated and the residue was chromatographed on silica gel yielding the target compound 3 as a brownish solid (6.2 g, 43/).

Step C: General procedure. Starting ester 3 (0.3 g, 1 equiv) was dissolved in dry dioxane (10 mL) followed by addition of the appropriate nitrile (HetAr-CN 4) (1 equiv) and sodium hydride (2 equiv, 0.1 g). The mixture was heated at reflux under Ar atmosphere for 12 h, cooled to r.t. and acidified with AcOH. The solvent was evaporated, the residue diluted with water and filtered. The crude material was purified using HPLC to give compound 5.

-continued

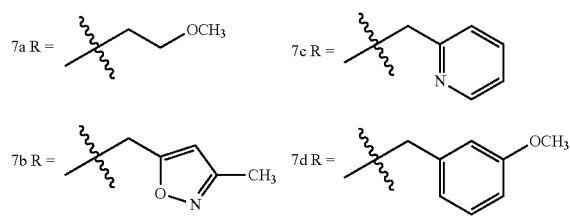

Typical procedure. Starting nitrile 6 (300 mg, 1 equiv) was dissolved in dry DMF followed by addition of $K_2CO_3$ (1.33 g, 3 equiv) and the appropriate chloride (RCl) or bromide (RBr) (1.1. equiv). The mixture was heated at 50° C. overnight, the solvent was evaporated, the residue was diluted with water (50 mL) and extracted with EtOAc (2×30 mL). The combined extracts were dried, evaporated and the residue was flash-chromatographed on silica gel yielding the target compounds 7a-d in the following amounts and yields:

7a (410 mg, 84% yield);
7b (350 mg, 58% yield);
7c (320 mg, 54% yield);
7d (560 mg, 81% yield).

Scheme 3

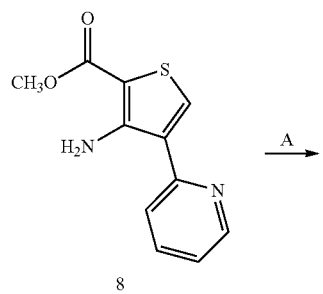

8

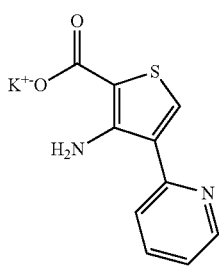

9

-continued

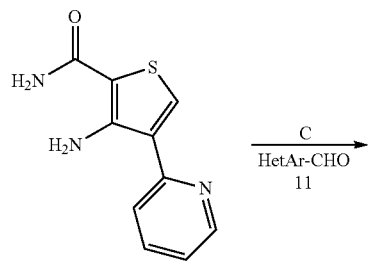

10

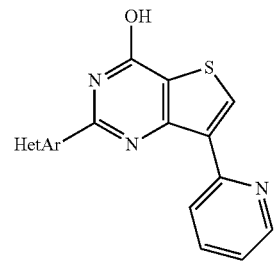

5

Step A: Starting ester 8 (5 g, 1 equiv) was dissolved in dry MeOH (50 mL) and potassium hydroxide (2.4 g, 2 equiv) was added thereto. The mixture was refluxed overnight, cooled to r.t. and the formed precipitate was filtered, washed with MeOH (5 mL) and dried to give target compound 9 as a yellow solid (3.4 g, 62%).

Step B: Starting potassium salt 9 (2.9 g, 1 equiv) was dissolved in dry DMF (50 mL) followed by addition of ammonium hydrochloride (1.2 g, 2 equiv), DIPEA (4.3 g, 3 equiv) and HBTU (4.23 g, 1 equiv). The mixture was heated at 60° C. overnight, the solvent was evaporated and the residue was diluted with water (30 mL) and EtOAc (30 mL). The formed solid was filtered, washed with EtOAc (5 mL) and dried to give target compound 10 as a yellow solid (1.8 g, 74%)

Step C: General procedure. Starting amide 10 (300 mg, 1 equiv) was dissolved in dry DMSO (5 mL) and CuI (26 mg, 10 mol %) was added thereto followed by the appropriate aldehyde (HetAr-CHO 11) (1 equiv). The mixture was heated at 100° C. in air for 12 h. The resulting material was purified using HPLC to give compound 5.

Scheme 4

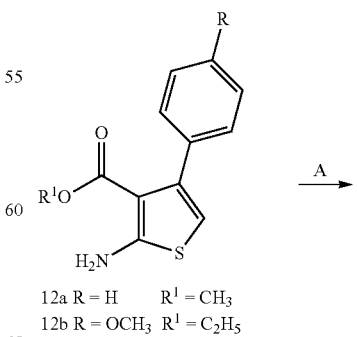

12a R = H     $R^1$ = $CH_3$
12b R = $OCH_3$  $R^1$ = $C_2H_5$

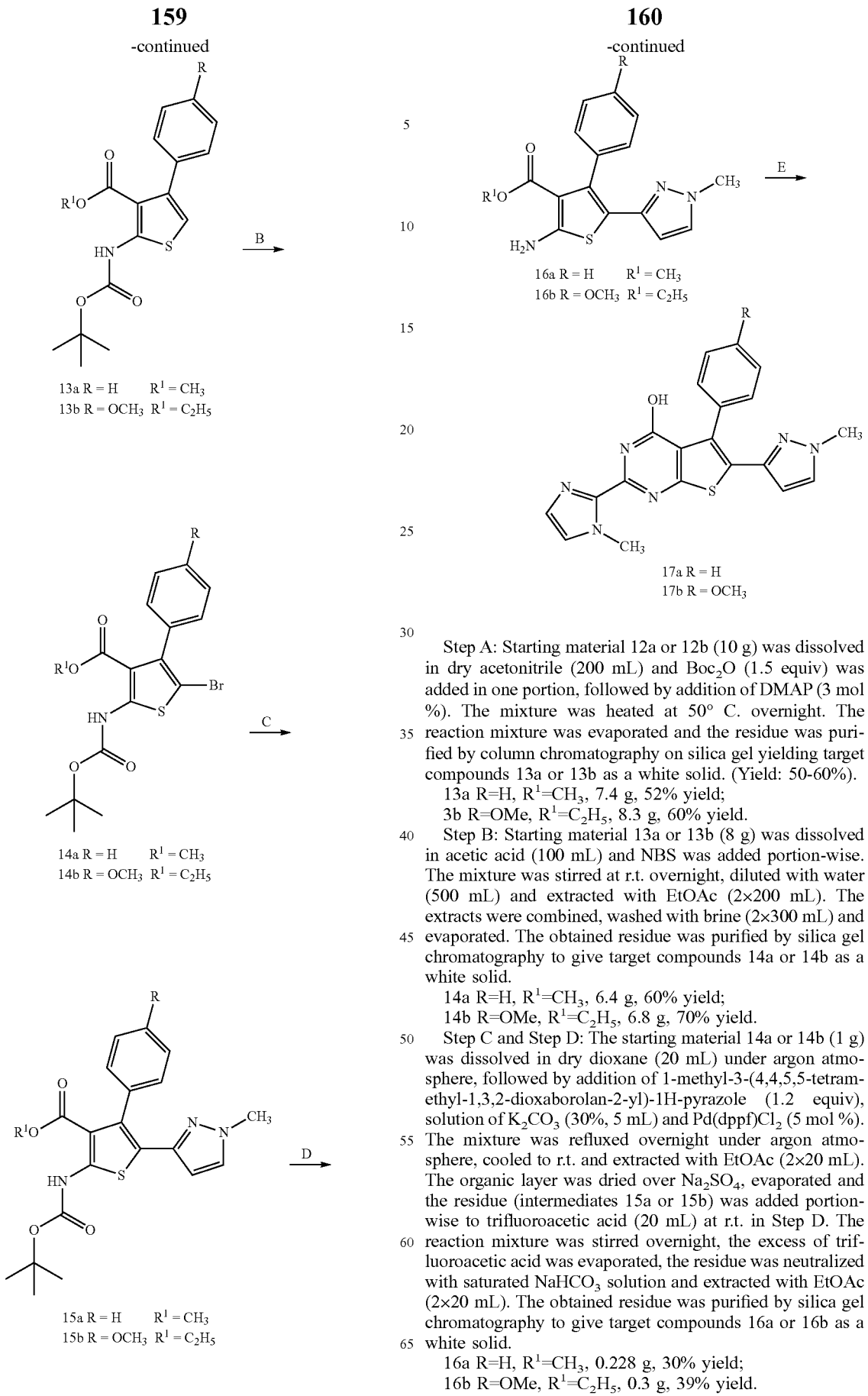

Step A: Starting material 12a or 12b (10 g) was dissolved in dry acetonitrile (200 mL) and Boc₂O (1.5 equiv) was added in one portion, followed by addition of DMAP (3 mol %). The mixture was heated at 50° C. overnight. The reaction mixture was evaporated and the residue was purified by column chromatography on silica gel yielding target compounds 13a or 13b as a white solid. (Yield: 50-60%).

13a R=H, R¹=CH₃, 7.4 g, 52% yield;
3b R=OMe, R¹=C₂H₅, 8.3 g, 60% yield.

Step B: Starting material 13a or 13b (8 g) was dissolved in acetic acid (100 mL) and NBS was added portion-wise. The mixture was stirred at r.t. overnight, diluted with water (500 mL) and extracted with EtOAc (2×200 mL). The extracts were combined, washed with brine (2×300 mL) and evaporated. The obtained residue was purified by silica gel chromatography to give target compounds 14a or 14b as a white solid.

14a R=H, R¹=CH₃, 6.4 g, 60% yield;
14b R=OMe, R¹=C₂H₅, 6.8 g, 70% yield.

Step C and Step D: The starting material 14a or 14b (1 g) was dissolved in dry dioxane (20 mL) under argon atmosphere, followed by addition of 1-methyl-3-(4,4,5,5-tetramethyl-1,3,2-dioxaborolan-2-yl)-1H-pyrazole (1.2 equiv), solution of K₂CO₃ (30%, 5 mL) and Pd(dppf)Cl₂ (5 mol %). The mixture was refluxed overnight under argon atmosphere, cooled to r.t. and extracted with EtOAc (2×20 mL). The organic layer was dried over Na₂SO₄, evaporated and the residue (intermediates 15a or 15b) was added portion-wise to trifluoroacetic acid (20 mL) at r.t. in Step D. The reaction mixture was stirred overnight, the excess of trifluoroacetic acid was evaporated, the residue was neutralized with saturated NaHCO₃ solution and extracted with EtOAc (2×20 mL). The obtained residue was purified by silica gel chromatography to give target compounds 16a or 16b as a white solid.

16a R=H, R¹=CH₃, 0.228 g, 30% yield;
16b R=OMe, R¹=C₂H₅, 0.3 g, 39% yield.

Step E: To a stirred solution of aminothiophene 16a or 16b (from previous step) in dry MeOH (10 mL) was added 1-methyl-2-cyanoimidazole (1 equiv) at r.t. followed by portion-wise addition of potassium tert-butylate (2 equiv). The reaction mixture was refluxed for 16 h, cooled to r.t. and evaporated to dryness. The residue was dissolved in water (100 mL), acidified with acetic acid to pH 5-6, the formed precipitate was filtered, washed with water and dried to give the crude target compound 17a or 17b, which was used in the next step without further purification (yield: 70-80%, purity 40-60%).

17a R=H, R$^1$=CH$_3$, 0.24 g, 85% yield;

17b R=OMe, R$^1$=C$_2$H$_5$, 0.30 g, 83% yield.

Scheme 5

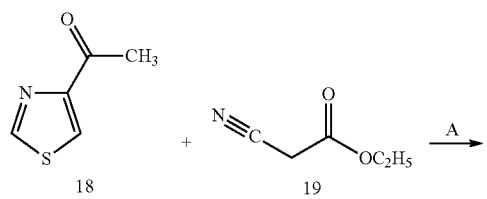

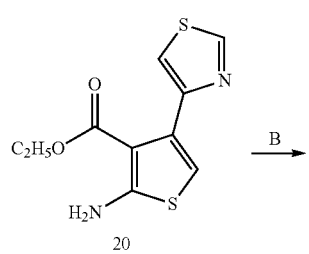

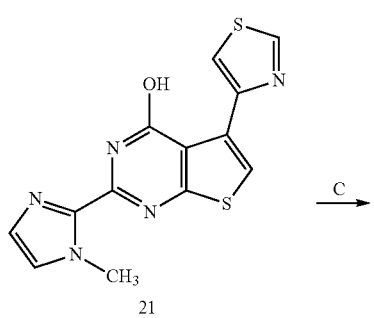

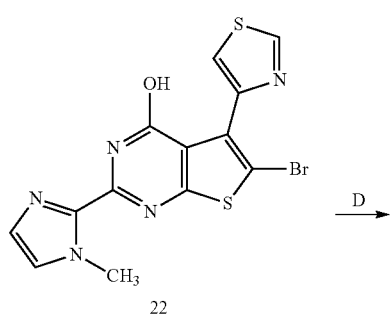

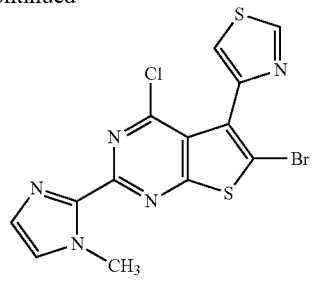

Step A: To a stirred solution of 4-acetylthiazole 18 (10 g, 78.6 mmol) in dry ethanol (100 mL) was added ethyl 2-cyanoacetate 19 (13.32 g, 118 mmol), sulfur (3.77 g, 118 mmol) and morpholine (10.3 g, 118 mmol) at r.t. Then reaction mixture was refluxed for 48 h, evaporated under reduced pressure and purified by column chromatography on silica gel (eluent—EtOAc:Hex—1:2) to give compound 20 as yellow crystalline solid (11.2 g, 56.6% yield).

Step B: To a stirred solution of aminothiophene 20 from previous step (10 g, 39.4 mmol) in dry methanol (100 mL) was added 1-methyl-2-cyanoimidazole (5.48 g, 51.2 mmol) at r.t. and then potassium tert-butylate (13.23 g, 118.2 mmol) was added portion-wise. Then reaction mixture was refluxed for 16 h, cooled to r.t. and precipitate (potassium salt of compound 21) was filtered. After this precipitate was dissolved in water (100 mL), acidified by acetic acid (10 mL) and stirred at r.t for 15 min. Then precipitate was filtered, washed with water and air dried to give compound 21 as a white solid (7.8 g, 62.9% yield).

Step C: To a stirred suspension of thienopyrimidinone 21 from previous step (6 g, 19 mmol) in dry DMF (120 mL) was added N-bromosuccinimide (4.07 g, 22.9 mmol) at r.t. and then reaction mixture was stirred at 80° C. for 16 h. After this, precipitate was filtered and air dried to give the compound 22 as light yellow solid (5.2 g, 69% yield).

Step D: To a stirred suspension of bromide 22 from previous step (4.5 g, 11.4 mmol) in POCl$_3$ (20 mL) was added diisopropylethylamine (6 mL) at r.t. and reaction mixture was refluxed for 16 h. Then solution was cooled to r.t., evaporated under reduced pressure, diluted with water (100 mL) and neutralized by ice cooled water solution of ammonia (50 mL, 20-25% of ammonia), product was extracted by chloroform (2*50 mL). Combined extract was evaporated under reduced pressure and purified by flash chromatography (eluent—CHCl$_3$:MeCN-20:1) to give compound 23 as yellow solid (3.8 g, 80.8% yield).

Scheme 6

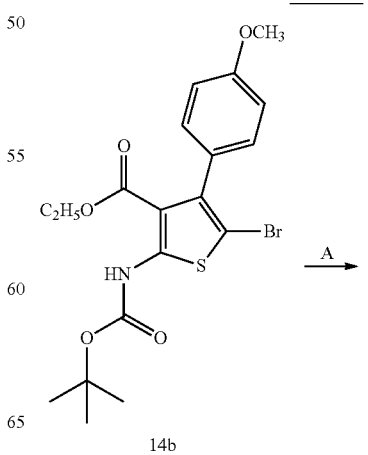

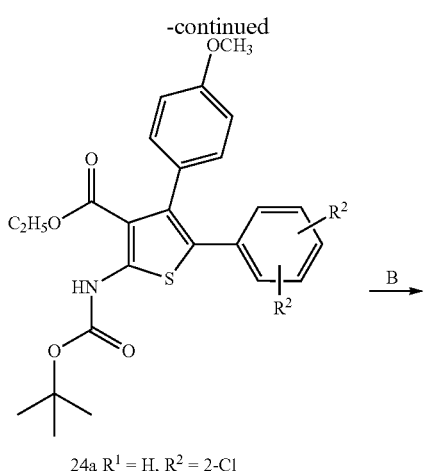

24a R¹ = H, R² = 2-Cl
24b R¹ = H, R² = 3-OCH₃
24c R¹ = 2-Cl, R² = 3-OCH₃
24d R¹ = 2-Cl, R² = 5-OCH₃

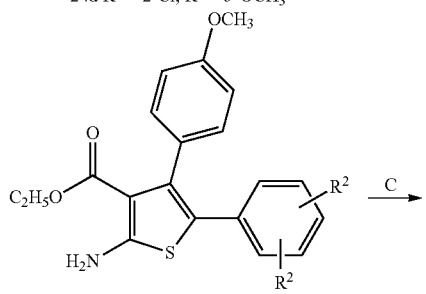

25a R¹ = H, R² = 2-Cl
25b R¹ = H, R² = 3-OCH₃
25c R¹ = 2-Cl, R² = 3-OCH₃
25d R¹ = 2-Cl, R² = 5-OCH₃

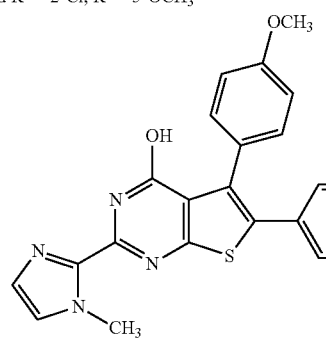

26a R¹ = H, R² = 2-Cl
26b R¹ = H, R² = 3-OCH₃
26c R¹ = 2-Cl, R² = 3-OCH₃
26d R¹ = 2-Cl, R² = 5-OCH₃

Step A and Step B: Using the procedure described in Scheme 4, Step C and Step D, starting with compound 14b, and the appropriate boronic acid in place of 1-methyl-3-(4,4,5,5-tetramethyl-1,3,2-dioxaborolan-2-yl)-1H-pyrazole, the intermediates 24a-d were synthesized (in Step A) and converted to the corresponding compounds 25a-d (in Step B) in the following amounts and combined (Step A-Step B) yields:

25a R¹=H, R²=2-Cl, 0.47 g, 20% yield;
25b R¹=H, R²=3-OCH₃, 0.45 g, 32% yield;
25c R¹=2-Cl, R²=3-OCH₃, 0.46 g, 34% yield; used in the next step;
25c R¹=2-Cl, R²=3-OCH₃, 0.56 g, 35% yield; used in the synthesis of Example 38;
25d R¹=2-Cl, R²=5-OCH₃, 0.49 g, 29% yield; used in the next step;
25d R¹=2-Cl, R²=5-OCH₃, 0.5 g, 32% yield; used in the synthesis of Example 39.

Step C: Using the procedure described in Scheme 4, Step E, except using the starting aminothiophene 25a, 25b, 25c, or 25d (instead of 16a or 16b), the corresponding target compounds 26a-d were respectively obtained in the following amounts and yields:

26a R¹=H, R²=2-Cl, 0.38 g, 70% yield;
26b R¹=H, R²=3-OCH₃, 0.39 g, 75% yield;
26c R¹=2-Cl, R²=3-OCH₃, 0.38 g, 72% yield;
26d R¹=2-Cl, R²=5-OCH₃, 0.38 g, 68% yield.

Scheme 7

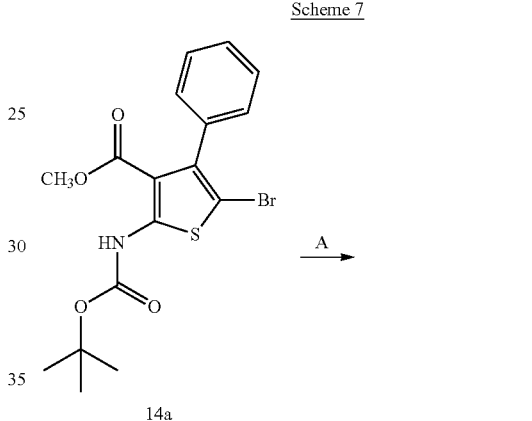

14a

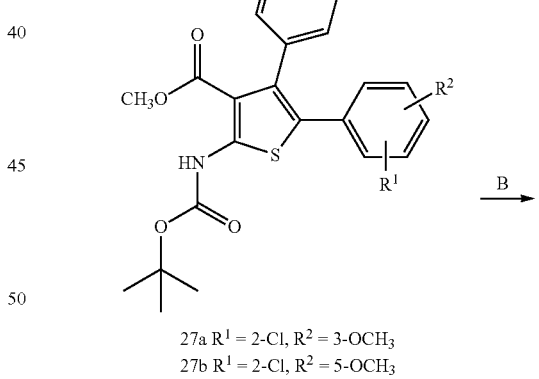

27a R¹ = 2-Cl, R² = 3-OCH₃
27b R¹ = 2-Cl, R² = 5-OCH₃

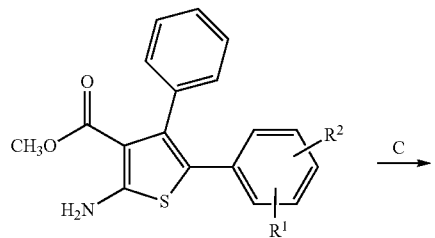

28a R¹ = 2-Cl, R² = 3-OCH₃
28b R¹ = 2-Cl, R² = 5-OCH₃

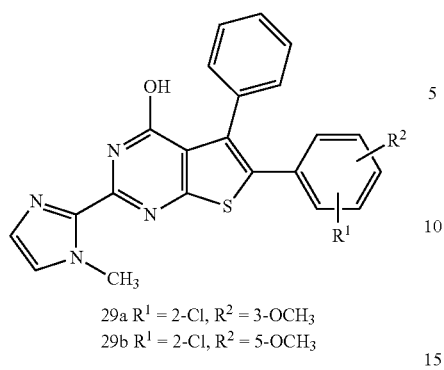

29a R¹ = 2-Cl, R² = 3-OCH₃
29b R¹ = 2-Cl, R² = 5-OCH₃

Step A and Step B: Using the procedure described in Scheme 4, Step C and Step D, starting with compound 14a, and the appropriate boronic acid in place of 1-methyl-3-(4,4,5,5-tetramethyl-1,3,2-dioxaborolan-2-yl)-1H-pyrazole, the intermediates 27a or 27b were synthesized (in Step A) and converted to the corresponding target compounds 28a or 28b (in Step B) in the following amounts and combined (Step A-Step B) yields:

28a R¹=2-Cl, R²=3-OCH₃, 0.45 g, 38% yield;
28b R¹=2-Cl, R²=5-OCH₃, 0.51 g, 30% yield.

Step C: Using the procedure described in Scheme 4, Step E, except using the starting aminothiophene 28a or 28b (instead of 16a or 16b), the corresponding target compounds 29a or 29b were respectively obtained in the following amounts and yields:

29a R¹=2-Cl, R²=3-OCH₃, 0.38 g, 73% yield;
29b R¹=2-Cl, R²=5-OCH₃, 0.38 g, 65% yield.

Scheme 8

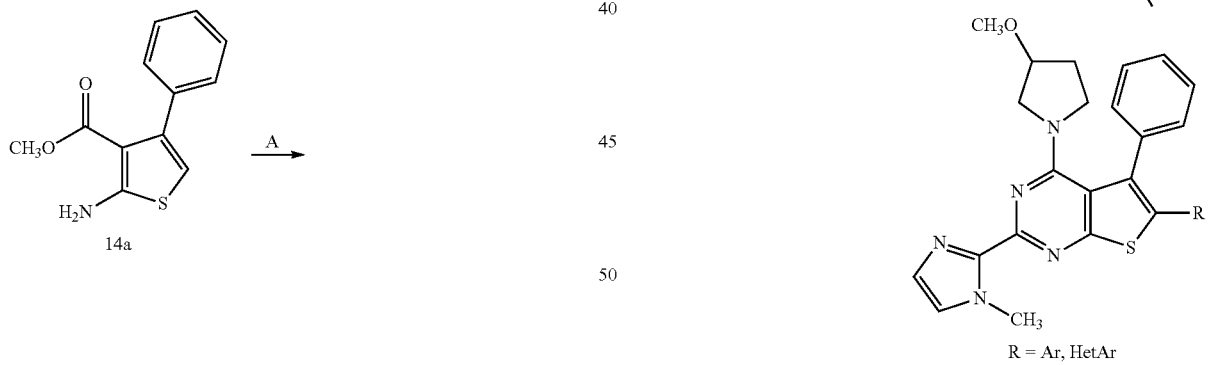

R = Ar, HetAr

Step A: To a stirred solution of 2-amino-3-carbethoxy-4-phenylthiophene 14a (20 g, 81 mmol) in dry methanol (200 mL) was added 1-methyl-2-cyanoimidazole (11.3 g, 105 mmol) at r.t. and then potassium tert-butylate (27.2 g, 243 mmol) was added portion-wise. Then reaction mixture was refluxed for 16 h, cooled to r.t. and precipitate (potassium salt of target compound 30) was filtered. After this precipitate was dissolved in water (200 mL), acidified by acetic acid (20 mL) and stirred at r.t for 15 min. Then precipitate was filtered, washed with water and air dried to give the target compound 30 as white solid (14.7 g, 59% yield).

Step B: To a stirred suspension of thienopyrimidinone 30 from previous step (10 g, 32.5 mmol) in dry DMF (300 mL)

was added N-bromosuccinimide (6.94 g, 39.0 mmol) at r.t. and then reaction mixture was stirred at 80° C. for 16 h. After this, precipitate was filtered and air dried to give the target compound 31 as light yellow solid (8.9 g, 70.8% yield).

Step C: To a stirred suspension of bromide 31 from previous step (7.5 g, 19.4 mmol) in POCl₃ (30 mL) was added diisopropylethylamine (9 mL) at r.t. and reaction mixture was refluxed for 16 h. Then solution was cooled to r.t., evaporated under reduced pressure, diluted with water (300 mL) and neutralized by ice cooled water solution of ammonia (100 mL, 20-25% of ammonia), product was extracted by chloroform (2*100 mL). Combined extract was evaporated under reduced pressure and purified by flash chromatography (eluent—CHCl₃:MeCN—20:1) to give the target compound 32 as yellow solid (4.5 g, 57.3% yield).

Step D: To a stirred solution of chloride 32 from previous step (3.0 g, 7.40 mmol) in chloroform (45 mL) was added triethylamine (2.6 mL, 18.7 mmol) and 3-methoxy-pyrrolidine hydrochloride (1.31 g, 9.62 mmol). Then reaction mixture was refluxed for 1 h, cooled to r.t, diluted with water (100 mL) and extracted twice with chloroform (2*30 mL). Combined organic layer was dried with Na₂SO₄, evaporated under reduced pressure and purified by flash chromatography (eluent—EtOAc:Et₃N—20:1) to give target compound 33 as light yellow solid (3.1 g, 89% yield).

Step E: General procedure: Compound 33 (0.64 mmol) was mixed with the appropriate boronic acid 34 (R=Ar, HetAr) or boronic ester 35 (R=Ar, HetAr) (0.96 mmol), K₂CO₃ (3.84 mmol), Pd(dppf)Cl₂ (0.064 mmol) 1,4-dioxane (15 mL) under argon atmosphere. The reaction was then stirred at 100° C. for 16 h under argon atmosphere. Then reaction mixture was cooled to r.t., diluted with water (50 mL) and extracted twice with chloroform (2*25 mL). Combined organic layer was dried with Na₂SO₄, evaporated under reduced pressure and purified from resins by flash chromatography (eluent—EtOAc:Et₃N—20:1). Finally, crude products was purified by HPLC (eluent—H₂O:MeOH) to give target compound 36.

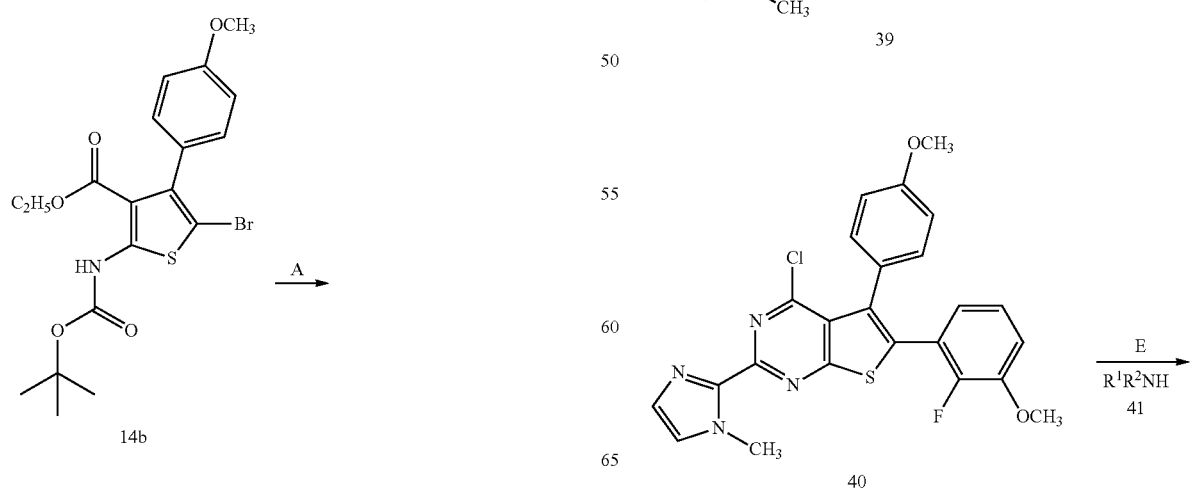

-continued

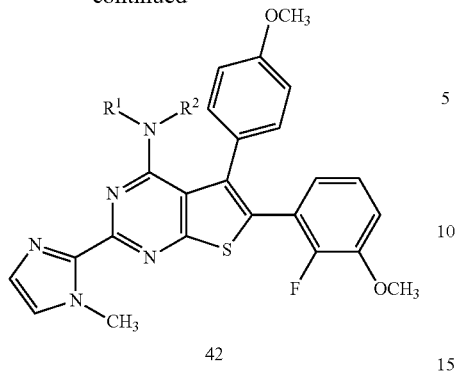

42

Step A and Step B: The starting material 14b (1 g) (prepared as described in Scheme 4) was dissolved in dry dioxane (20 mL) under argon atmosphere, followed by addition of the appropriate boronic acid (1.2 equiv), solution of K₂CO₃ (30%, 5 mL) and Pd(dppf)Cl₂ (5 mol %). The mixture was refluxed overnight under argon atmosphere, cooled to r.t. and extracted with EtOAc (2×20 mL). The organic layer was dried over Na₂SO₄, evaporated and the residue (compound 37) was added portion-wise to trifluoroacetic acid (20 mL) at r.t. The reaction mixture was stirred overnight, the excess of trifluoroacetic acid was evaporated, the residue was neutralized with saturated NaHCO₃ solution and extracted with EtOAc (2×20 mL). The obtained residue was purified by silica gel chromatography to give target compound 38 as a white solid (0.3 g, 39% yield).

Step C: To a stirred solution of aminothiophene 38 from previous step in dry MeOH (10 mL) was added the corresponding nitrile (1 equiv) at r.t. followed by portion wise addition of potassium tert-butylate (2 equiv). The reaction mixture was refluxed for 16 h, cooled to r.t. and evaporated to dryness. The residue was dissolved in water (100 mL), acidified with acetic acid to pH 5-6, the formed precipitate was filtered, washed with water and dried to give the crude title compound which was used in the next step without further purification (for the general procedure: 70-80% yield, purity 40-60%). Using the corresponding nitrile 1-methyl-2-cyanoimidazole in the above procedure, the target compound 39 was obtained (0.30 g, 83% yield).

Step D and Step E: The crude material compound 39 from the previous step was suspended in POCl₃ (2 mL) and diisopropylethylamine (0.6 mL) was added at r.t. The reaction mixture was refluxed for 16 h, the solution was cooled to r.t., evaporated under reduced pressure, diluted with ice-cold ammonia (20 mL, 20-25% of ammonia), the product 40 was extracted with chloroform (2*30 mL) and evaporated. The residue (40) was dissolved in DMSO and the appropriate amine R¹R²NH 41 (5 equiv) was added. The mixture was heated at 100° C. overnight, cooled and purified by HPLC to give final general product 42 (15-25% yield).

Scheme 10

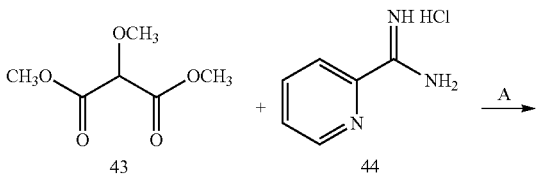

-continued

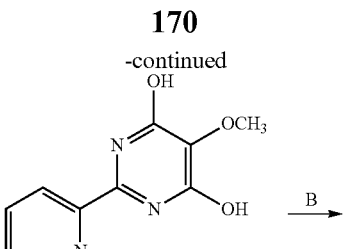

45

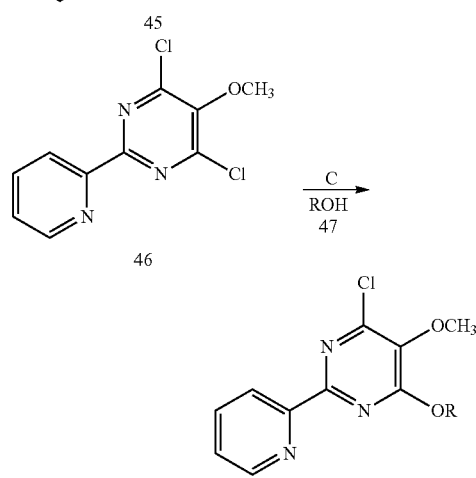

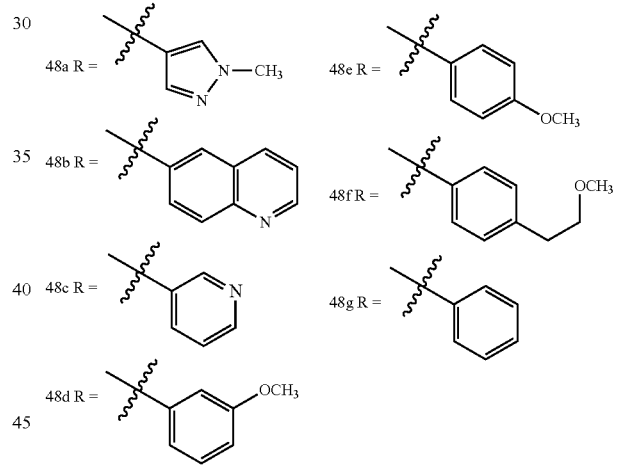

Step A: Sodium (2.27 g, 4 eq) was dissolved in MeOH (80 mL). To this solution, compound 43 (4 g, 1 eq) and amidine hydrochloride 44 (3.88 g, 1 eq) was added. The resulting mixture was heated at 65° C. for 12 hours and evaporated in vacuo. The residue was taken up with cold water (10 mL), acidified with HCl conc. to pH=4 and allowed to stand in fridge for 2 hours. The precipitate was filtered, washed with water 10 mL and dried to obtain compound 45 (4.3 g, yield 79%)

Step B: To a suspension of compound 45 (4.3 g) in POCl₃ (35 mL), DMF (0.5 mL) was added. The reaction mixture was heated at 90° C. for 12 h and evaporated. The residue was quenched with ice-cold water (50 mL) and extracted with MTBE (3*50 mL). The organic extracts was washed with brine (2*50 mL), dried over Na₂SO₄ and evaporated in vacuo to obtain compound 46 (2.3 g).

Step C: To a solution of compound 46 (0.3 g, 1 eq) in DMF (3 mL) was added the appropriate ROH 47 (R=Ar, HetAr) (1 eq) and K₂CO₃ (0.49 g, 3 eq). The resulting mixture was heated at 70° C. for 24 h, cooled, taken up with water (50 mL) and extracted with MTBE (3*30 mL). The organic extracts were washed with brine (2*30 mL), dried over Na₂SO₄ and evaporated in vacuo to obtain compounds 48a-g in the following amounts and yields (80-90% purity). These compounds were used for the next step without purification.

48a 180 mg, 47% yield;
48b 160 mg, 42% yield;
48c 170 mg, 33% yield;
48d 120 mg, 30% yield;
48e 170 mg, 40% yield;
48f 130 mg, 35% yield;
48g 190 mg; 45% yield.

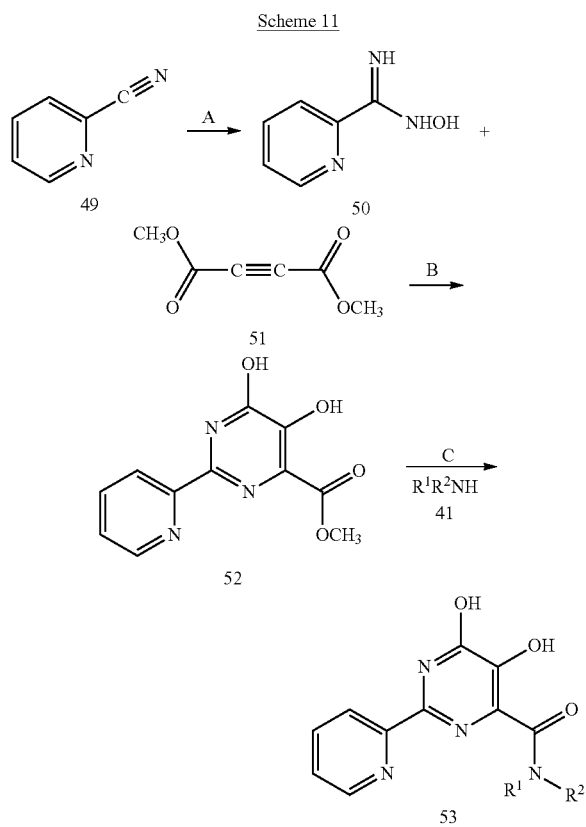

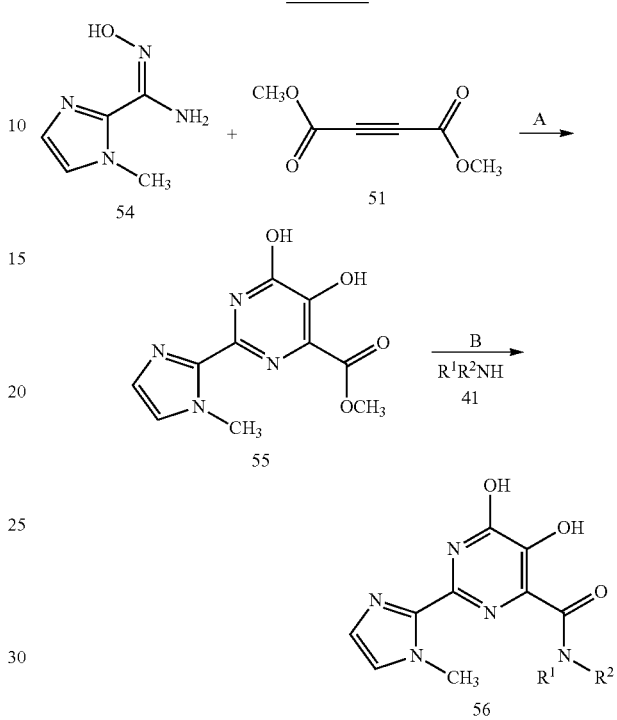

Step A: To a solution of compound 49 (4.50 g, 1 eq) in MeOH (50 mL), NH₂OH*HCl (3.46 g, 1.15 eq) and NaHCO₃ (4.54 g, 1.25 eq) was added. The resulting mixture was heated at 50° C. for 12 h. The precipitate was filtered off and the solvent was evaporated in vacuo to obtain crude amidoxime 50 (5.0 g, 90+% purity). It was used for the next step without purification.

Step B: To a suspension of compound 50 (5.0 g, 1 eq) in CHCl₃ (100 mL), compound 51 (5.2 g, 1 eq) was added. The resulting mixture was heated at 65° C. for 1 h and filtered. The solvent was evaporated in vacuo and the residue was taken up with xylene (50 mL). The resulting mixture was heated at 140° C. with a Dean-Stark trap for 3 h. The reaction mixture was cooled to 25° C., the precipitate was filtered and washed with MTBE (2*20 mL) and dried to obtain compound 52 (4.1 g, 90+% purity).

Step C: A solution of compound 52 (0.3 g, 1 eq) and the appropriate amine R¹R²NH 41 (3 eq) in DMF (2 mL) was heated at 75° C. for 24 h. The resulting mixture was purified by reverse phase HPLC to obtain target compound 53.

Step A: Dimethyl but-2-ynedioate 51 (11.94 g, 3 eq) was added to the solution of compound 54 (3 g) in methanol (60 mL) and the reaction mixture was stirred at 60° C. for 3 hours. The completion of the reaction was controlled by TLC. Then the reaction mixture was evaporated and m-xylene (90 mL) was added. Obtained solution was heated for 8 hours. After that it was filtered off (while it was still hot), filtrate was allowed to cool down to room temperature. The obtained precipitate was filtered, washed with xylene and hexane and was dried to give 55. (2.4 g, 34.3% yield) (purity 65.23%).

Step B: To the solution of compound 55 (0.32 g) in DMF (3 mL) 5 eq of the appropriate amine R¹R²NH 41 was added. The obtained solution was heated to 80° C. for 15 hours. After that the mixture was purified by HPLC to give 56. (mobile phase-methanol).

Purification and Analytical Procedures:

Purification was performed using HPLC (H₂O-MeOH; Agilent 1260 Infinity systems equipped with DAD and mass-detectors. Waters Sunfire C18 OBD Prep Column, 100 Å, 5 μm, 19 mm×100 mm with SunFire C18 Prep Guard Cartridge, 100 Å, 10 μm, 19 mm×10 mm) The material was dissolved in 0.7 mL DMSO. Flow: 30 mL/min. Purity of the obtained fractions was checked via the analytical LCMS. Spectra were recorded for each fraction as it was obtained straight after chromatography in the solution form. The solvent was evaporated under the N₂ flow upon heating to 80° C. On the basis of post-chromatography LCMS analysis fractions were united. Solid fractions were dissolved in 0.5 mL MeOH and transferred into a pre-weighted marked vials. Obtained solutions were again evaporated under the N₂ flow upon heating to 80° C. After drying, products were finally characterized by LCMS and ¹H NMR.

NMR Instrument specifications: Bruker AVANCE DRX 500, Varian UNITYplus 400.

LC/MS Instrument specifications: Agilent 1100 Series LC/MSD system with DAD\LSD and Agilent LC\MSD VL (G1956A), SL (G1956B) mass-spectrometer. Agilent 1200 Series LC/MSD system with DAD\LSD and Agilent LC\MSD SL (G6130A), SL (G6140A) mass-spectrometer. All the LC/MS data were obtained using positive/negative mode switching. Column Zorbax SB-C18 1.8 μm 4.6×15 mm Rapid Resolution cartridge (PN 821975-932) Mobile phase A—acetonitrile, 0.1% formic acid, B—water (0.1% formic acid) Flow rate 3 ml/min Gradient 0 min-100% B, 0.01 min-100% B, 1.5 min-0% B, 1.8 min-0% B, 1.81 min-100% B. Injection volume 1 μl. Ionization mode atmospheric pressure chemical ionization (APCI). Scan range m/z 80-1000.

TABLE 3

Mass Spectral Data

| Compound | MW | M + H (calculated) | M + H (observed) |
|---|---|---|---|
| (structure) | 373 | 373.1 | 373.0 |
| (structure) | 309 | 310.1 | 310.2 |
| (structure) | 349 | 350.1 | 350.2 |
| (structure) | 345 | 346.1 | 346.0 |

TABLE 3-continued
Mass Spectral Data
| Compound | MW | M + H (calculated) | M + H (observed) |
|---|---|---|---|
| 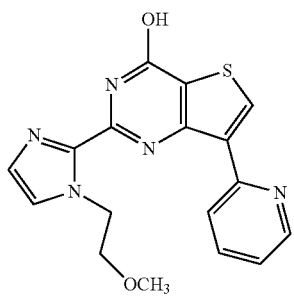 [SMILES: COCCn1ccnc1-c1nc(O)c2scc(-c3ccccn3)c2n1] | 353 | 354.1 | 354.0 |
| 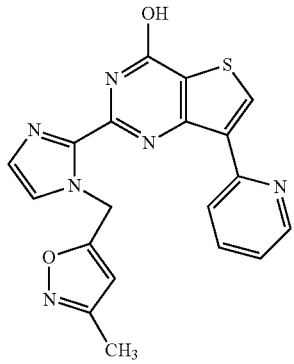 [SMILES: Cc1cc(Cn2ccnc2-c2nc(O)c3scc(-c4ccccn4)c3n2)on1] | 390 | 391.1 | 391.2 |
| 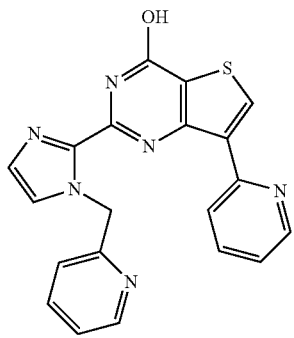 [SMILES: Oc1nc(-c2nccn2Cc2ccccn2)nc2c(-c3ccccn3)csc12] | 386 | 387.1 | 387.0 |
| 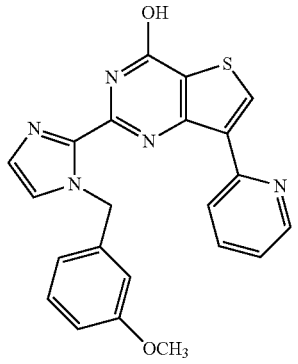 [SMILES: COc1cccc(Cn2ccnc2-c2nc(O)c3scc(-c4ccccn4)c3n2)c1] | 415 | 416.1 | 416.2 |

TABLE 3-continued

Mass Spectral Data

| Compound | MW | M + H (calculated) | M + H (observed) |
|---|---|---|---|
| (structure) | 323 | 324.1 | 324.0 |
| (structure) | 323 | 324.1 | 324.0 |
| (structure) | 345 | 346.1 | 346.0 |
| (structure) | 346 | 347.1 | 347.0 |
| (structure) | 371 | 372.1 | 372.2 |

TABLE 3-continued
| | Mass Spectral Data | | |
|---|---|---|---|
| Compound | MW | M + H (calculated) | M + H (observed) |
| 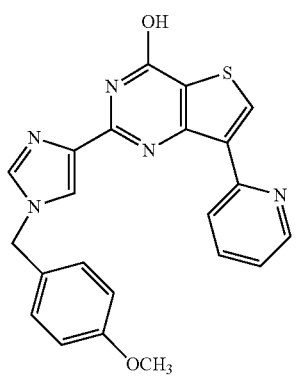 [SMILES: COc1ccc(Cn2cnc(-c3nc(O)c4scc(-c5ccccn5)c4n3)c2)cc1] | 415 | 416.1 | 416.0 |
| 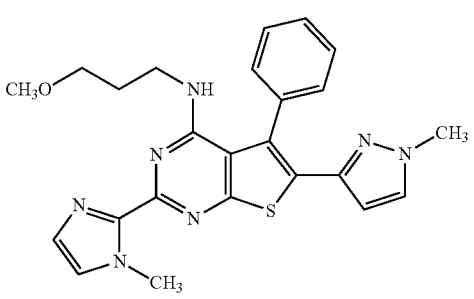 | 460 | 460.2 | 460.2 |
| 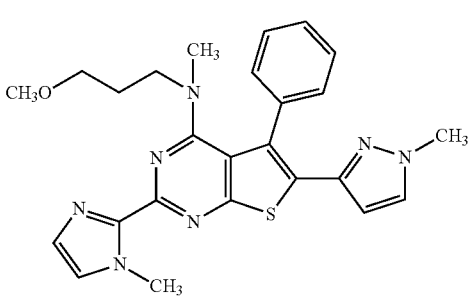 | 474 | 474.2 | 474.2 |
| 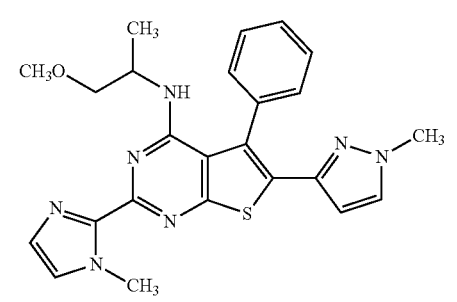 | 460 | 460.2 | 460.2 |

TABLE 3-continued

Mass Spectral Data

| Compound | MW | M + H (calculated) | M + H (observed) |
|---|---|---|---|
| (structure) | 472 | 472.2 | 472.2 |
| (structure) | 472 | 472.2 | 472.2 |
| (structure) | 472 | 472.2 | 472.2 |
| (structure) | 486 | 486.2 | 486.2 |

TABLE 3-continued

Mass Spectral Data

| Compound | MW | M + H (calculated) | M + H (observed) |
|---|---|---|---|
| (structure) (+/−) | 486 | 486.2 | 486.2 |
| (structure) | 486 | 486.2 | 486.2 |
| (structure) | 498 | 498.2 | 498.2 |
| (structure) | 486 | 486.2 | 486.2 |

TABLE 3-continued
Mass Spectral Data
| Compound | MW | M + H (calculated) | M + H (observed) |
|---|---|---|---|
| 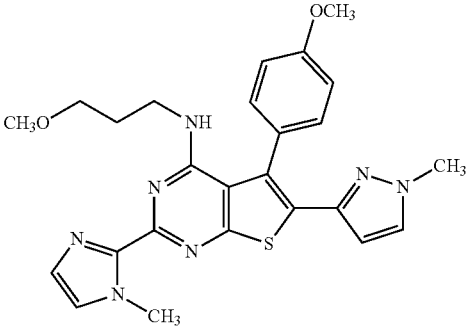 | 490 | 490.2 | 490.2 |
| 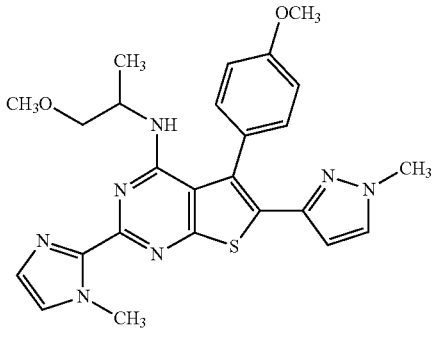 | 490 | 490.2 | 490.2 |
| 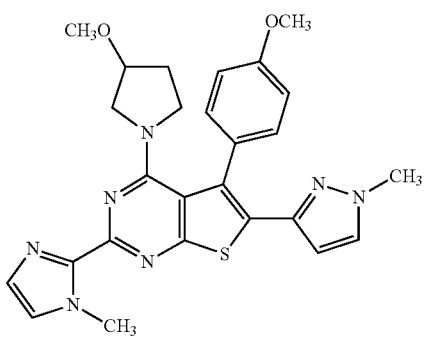 | 502 | 502.2 | 502.2 |
| 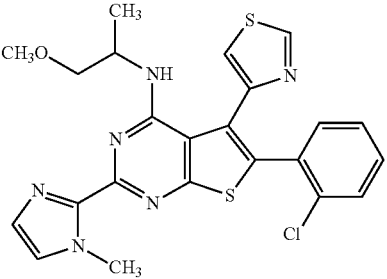 | 497 | 497.1 | 497.0 |

TABLE 3-continued
| Mass Spectral Data | | | |
|---|---|---|---|
| Compound | MW | M + H (calculated) | M + H (observed) |
| 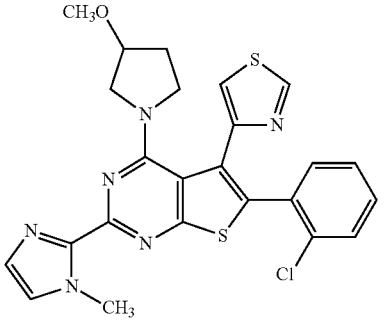 | 509 | 509.1 | 509.0 |
| 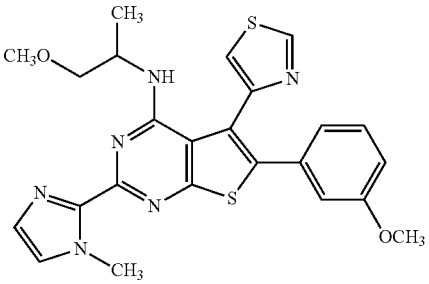 | 493 | 493.2 | 493.2 |
| 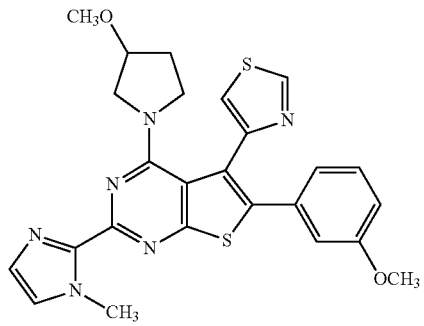 | 541 | 505.2 | 505.2 |
| 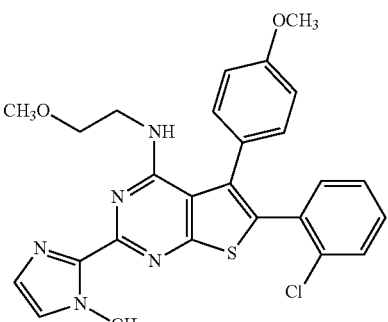 | 506 | 506.2 | 506.2 |

TABLE 3-continued

| Compound | MW | M + H (calculated) | M + H (observed) |
|---|---|---|---|
| (structure) | 502 | 502.2 | 502.2 |
| (structure) | 536 | 536.2 | 536.0 |
| (structure) | 536 | 536.2 | 536.2 |
| (structure) | 506 | 506.2 | 506.2 |

TABLE 3-continued

| Mass Spectral Data | | | |
|---|---|---|---|
| Compound | MW | M + H (calculated) | M + H (observed) |
| | 536 | 536.2 | 536.2 |
| | 536 | 536.2 | 536.2 |
| | 506 | 506.2 | 506.0 |
| | 506 | 506.2 | 506.2 |

TABLE 3-continued

Mass Spectral Data

| Compound | MW | M + H (calculated) | M + H (observed) |
|---|---|---|---|
| [structure] HCl | 535 | 499.2 | 499.2 |
| [structure] HCl | 508 | 472.2 | 472.2 |
| [structure] HCl | 505 | 469.2 | 469.2 |
| [structure] HCl | 535 | 499.2 | 499.2 |

TABLE 3-continued

| | Mass Spectral Data | | |
|---|---|---|---|
| Compound | MW | M + H (calculated) | M + H (observed) |
| [structure with CH₃O-pyrrolidine, phenyl, methoxypyridine, N-methylimidazole, thienopyrimidine] · HCl | 535 | 499.2 | 499.2 |
| [structure with CH₃O-pyrrolidine, phenyl, cyclopropyl-oxazole, N-methylimidazole, thienopyrimidine] · HCl | 535 | 499.2 | 499.2 |
| [structure with CH₃O-pyrrolidine, phenyl, methoxyethyl-pyrazole, N-methylimidazole, thienopyrimidine] · HCl | 552 | 516.2 | 516.2 |
| [structure with CH₃O-pyrrolidine, phenyl, methylpyridine, N-methylimidazole, thienopyrimidine] · HCl | 519 | 483.2 | 483.2 |

TABLE 3-continued
Mass Spectral Data
| Compound | MW | M + H (calculated) | M + H (observed) |
|---|---|---|---|
| 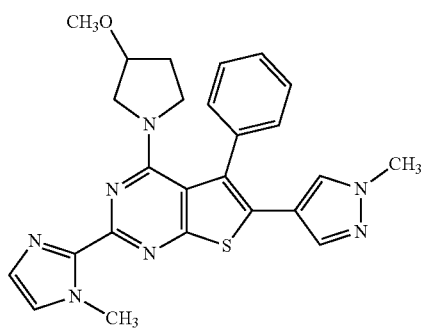 HCl | 508 | 472.2 | 472.2 |
| 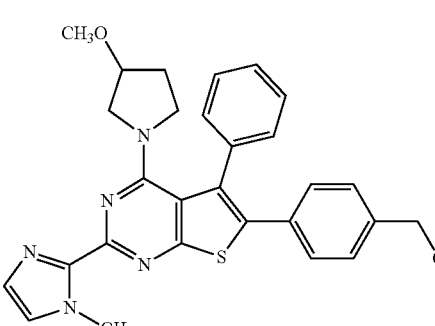 HCl | 534 | 498.2 | 498.2 |
| 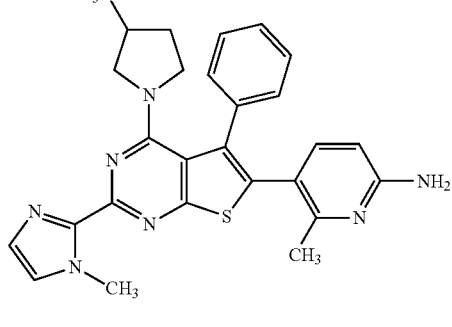 HCl | 534 | 249.6 [M + 2H]/2 | 249.8 [M + 2H]/2 |
| 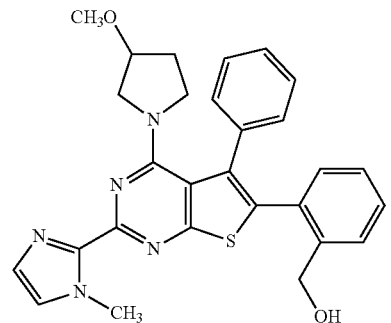 HCl | 534 | 498.2 | 498.2 |

TABLE 3-continued

| | | Mass Spectral Data | |
|---|---|---|---|
| Compound | MW | M + H (calculated) | M + H (observed) |
| (structure) | 541 | 505.2 | 505.2 |
| (structure) | 548 | 256.6 [M + 2H]/2 | 256.6 [M + 2H]/2 |
| (structure) | 470 | 470.0 | 470.0 |
| (structure) | 546 | 546.2 | 546.2 |

TABLE 3-continued

| | Mass Spectral Data | | |
|---|---|---|---|
| Compound | MW | M + H (calculated) | M + H (observed) |
| [structure] | 546 | 546.2 | 546.2 |
| [structure] HCl | 552 | 516.2 | 516.2 |
| [structure] | 299 | 300.1 | 300.0 |
| [structure] | 346 | 347.1 | 347.0 |

TABLE 3-continued

| Mass Spectral Data | | | |
|---|---|---|---|
| Compound | MW | M + H (calculated) | M + H (observed) |
| [structure: 4-OH-5-OCH3-2-(pyridin-2-yl)-6-(pyridin-3-yloxy)pyrimidine] | 296 | 297.1 | 297.2 |
| [structure: 4-OH-5-OCH3-2-(pyridin-2-yl)-6-(3-methoxyphenoxy)pyrimidine] | 325 | 326.1 | 326.0 |
| [structure: 4-OH-5-OCH3-2-(pyridin-2-yl)-6-(4-methoxyphenoxy)pyrimidine] | 325 | 326.1 | 326.0 |
| [structure: 4-OH-5-OCH3-2-(pyridin-2-yl)-6-(4-(2-methoxyethyl)phenoxy)pyrimidine] | 353 | 354.2 | 354.2 |
| [structure: 4-OH-5-OCH3-2-(pyridin-2-yl)-6-phenoxypyrimidine] | 295 | 296.1 | 296.0 |

TABLE 3-continued

| Mass Spectral Data | | | |
|---|---|---|---|
| Compound | MW | M + H (calculated) | M + H (observed) |
| (structure) | 348 | 349.1 | 349.2 |
| (structure) | 302 | 303.1 | 303.2 |
| (structure) | 336 | 337.1 | 337.2 |
| (structure) | 322 | 323.1 | 323.2 |

TABLE 3-continued

| Mass Spectral Data | | | |
|---|---|---|---|
| Compound | MW | M + H (calculated) | M + H (observed) |
| (2-pyridyl pyrimidine with OH, OH, and C(O)-pyrrolidine substituents) | 286 | 287.1 | 287.2 |
| (2-pyridyl pyrimidine with OH, OH, and C(O)NH-cyclopentyl) | 300 | 301.1 | 301.0 |
| (2-pyridyl pyrimidine with OH, OH, and C(O)N(CH₃)-isobutyl) | 302 | 303.1 | 303.2 |
| (2-pyridyl pyrimidine with OH, OH, and C(O)NH-isobutyl) | 288 | 289.1 | 289.0 |
| (2-pyridyl pyrimidine with OH, OH, and C(O)N(CH₃)CH₂CH₂OCH₃) | 304 | 305.1 | 305.0 |

TABLE 3-continued

Mass Spectral Data

| Compound | MW | M + H (calculated) | M + H (observed) |
|---|---|---|---|
| [pyridin-2-yl pyrimidine diol cyclobutyl carboxamide] | 286 | 287.1 | 287.0 |
| [1-methylimidazol-2-yl pyrimidine diol isopropyl carboxamide] | 277 | 278.1 | 278.2 |
| [1-methylimidazol-2-yl pyrimidine diol N,N-diethyl carboxamide] | 291 | 292.1 | 292.2 |
| [1-methylimidazol-2-yl pyrimidine diol pyrrolidinyl carboxamide] | 289 | 290.1 | 290.2 |
| [1-methylimidazol-2-yl pyrimidine diol cyclopentyl carboxamide] | 303 | 304.1 | 304.2 |

TABLE 3-continued
| Mass Spectral Data | | | |
|---|---|---|---|
| Compound | MW | M + H (calculated) | M + H (observed) |
| 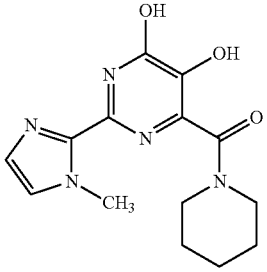 | 303 | 304.1 | 304.2 |
| 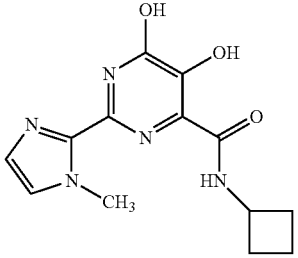 [SMILES: Cn1ccnc1-c1nc(O)c(O)c(C(=O)NC2CCC2)n1] | 289 | 290.1 | 290.2 |
| 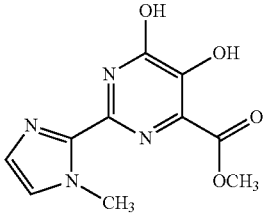 | 250 | 251.1 | 251.2 |
| 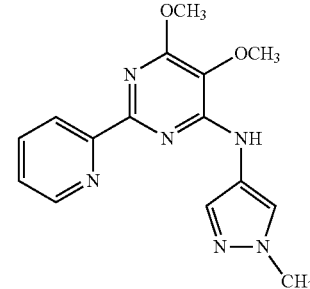 | 312 | 313.1 | 313.2 |
| 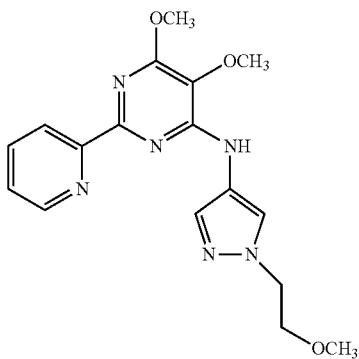 [SMILES: COCCn1cc(Nc2nc(-c3ccccn3)nc(OC)c2OC)cn1] | 356 | 357.2 | 357.2 |

TABLE 3-continued

| Mass Spectral Data | | | |
|---|---|---|---|
| Compound | MW | M + H (calculated) | M + H (observed) |
| [structure: 4-(3-methoxypyrrolidin-1-yl)-5,6-diphenyl-2-(1-methylimidazol-2-yl)pyrrolo[2,1-f][1,2,4]triazine] | 451 | 451.3 | 451.2 |
| [structure: 4-[[6-hydroxy-5-methoxy-2-(pyridin-2-yl)pyrimidin-4-yl]oxy]-N,N-dimethylbenzamide] | 366 | 367.1 | 367.2 |
| [structure: 6-hydroxy-5-methoxy-N-phenyl-2-(pyridin-2-yl)pyrimidin-4-amine] | 294 | 295.1 | 295 |
| [structure: N-(1-ethylpyrazol-4-yl)-6-hydroxy-5-methoxy-2-(pyridin-2-yl)pyrimidin-4-amine] | 312 | 313.1 | 313 |

TABLE 3-continued
| Mass Spectral Data | | | |
|---|---|---|---|
| Compound | MW | M + H (calculated) | M + H (observed) |
| 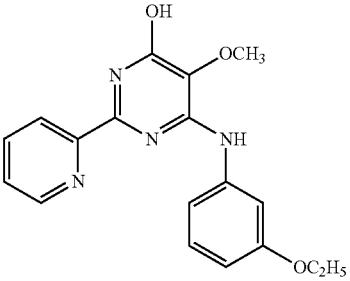 [SMILES: CCOc1cccc(Nc2nc(-c3ccccn3)nc(O)c2OC)c1] | 338 | 339.2 | 339 |
| 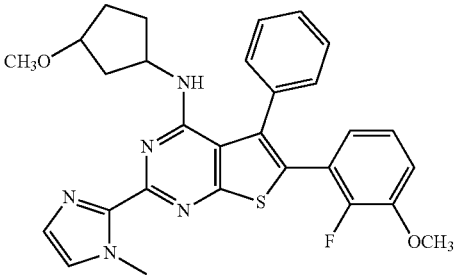 | 530 | 530.2 | 530.2 |
| 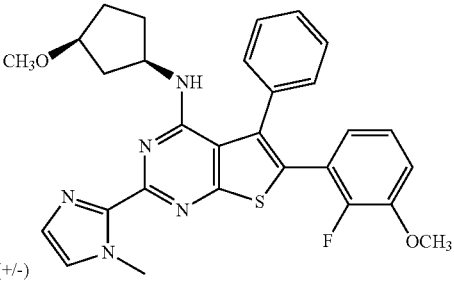 (+/-) | 530 | 530.2 | 529.8 |
| 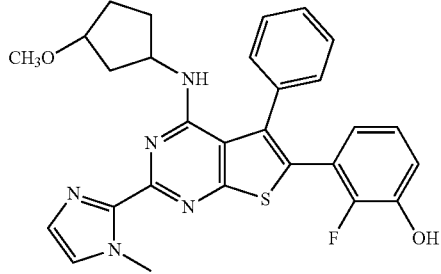 | 516 | 516.2 | 516.2 |
| 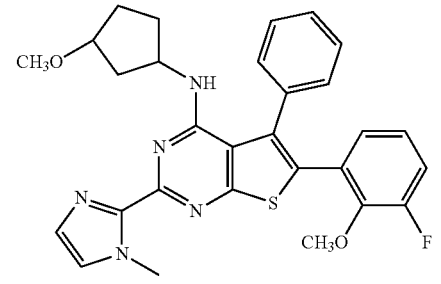 | 530 | 530.2 | 530.2 |

TABLE 3-continued

Mass Spectral Data

| Compound | MW | M + H (calculated) | M + H (observed) |
|---|---|---|---|
| (structure) (+/-) | 530 | 530.2 | 529.8 |
| (structure) | 522 | 522.2 | 522.2 |
| (structure) (+/-) | 522 | 522.2 | 521.9 |
| (structure) | 502 | 502.2 | 502.2 |
| (structure) | 516 | 516.2 | 516.2 |

TABLE 3-continued
Mass Spectral Data
| Compound | MW | M + H (calculated) | M + H (observed) |
|---|---|---|---|
| 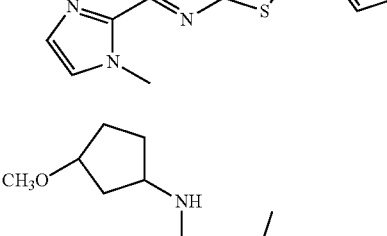 | 472 | 472.2 | 472.2 |
| 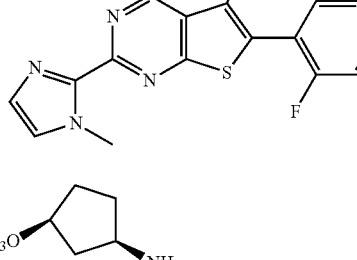 | 468 | 468.2 | 468 |
| 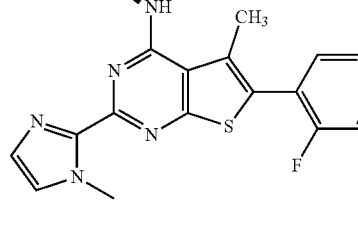 (+/−) | 468 | 468.2 | 468.2 |
| 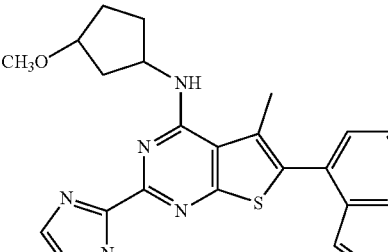 | 460 | 460.2 | 460.2 |
| 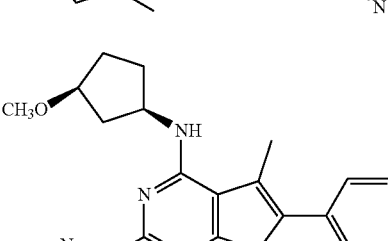 (+/−) | 482 | 482.2 | 482.2 |

TABLE 3-continued
Mass Spectral Data
| Compound | MW | M + H (calculated) | M + H (observed) |
|---|---|---|---|
| 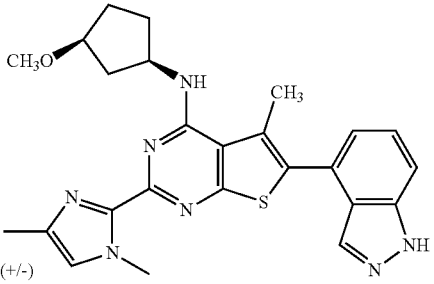 (+/−) | 474 | 474.2 | 474.2 |
| 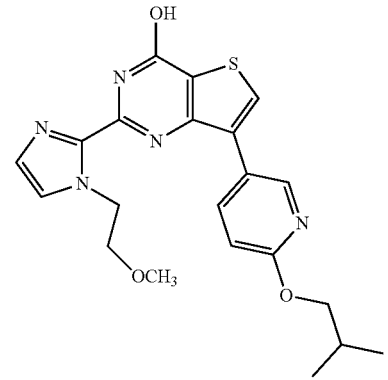 [SMILES: COCCn1ccnc1-c1nc(O)c2scc(-c3ccc(OCC(C)C)nc3)c2n1] | 426 | 426.2 | 426.2 |
| 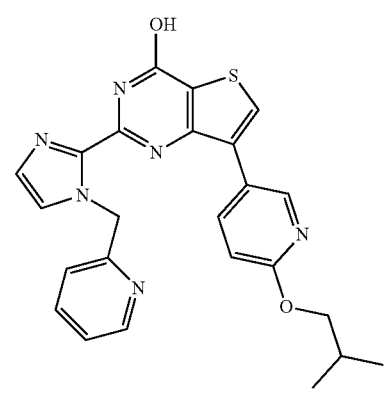 [SMILES: CC(C)COc1ccc(-c2csc3c(O)nc(-c4nccn4Cc4ccccn4)nc23)cn1] | 459 | 459.2 | 459.2 |
| 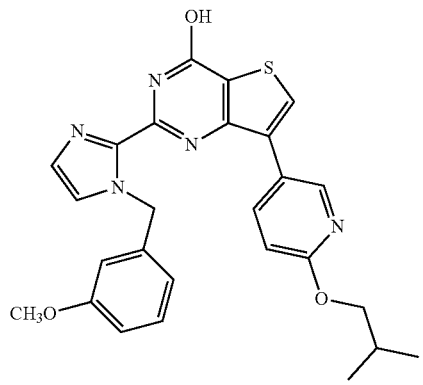 | 488 | 488.2 | 488.2 |

TABLE 3-continued
| Mass Spectral Data | | | |
|---|---|---|---|
| Compound | MW | M + H (calculated) | M + H (observed) |
| 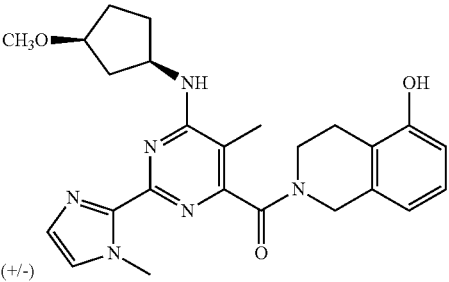 (+/-) | 463 | 463.3 | 463.2 |
| 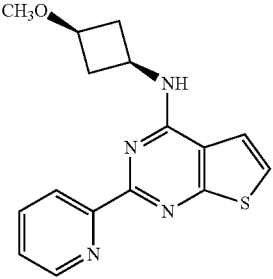 | 312 | 313.1 | 313.2 |
| 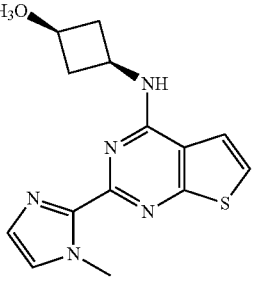 | 315 | 316.1 | 316 |
| 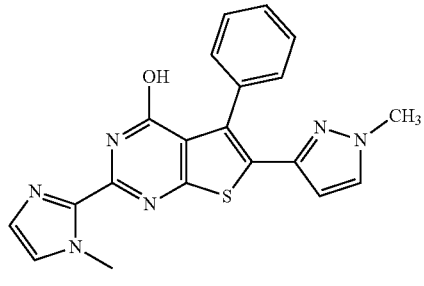 [SMILES: Cn1ccc(-c2sc3nc(-c4nccn4C)nc(O)c3c2-c2ccccc2)n1] | 388 | 389.1 | 389.2 |
| 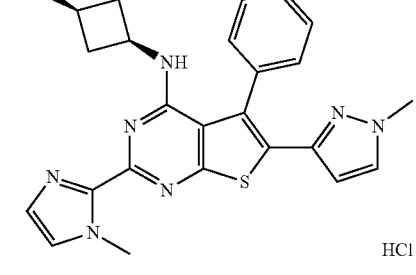 HCl | 508 | 472.2 | 472.2 |

TABLE 3-continued
| | | Mass Spectral Data | | |
| --- | --- | --- | --- | --- |
| Compound | | MW | M + H (calculated) | M + H (observed) |
| 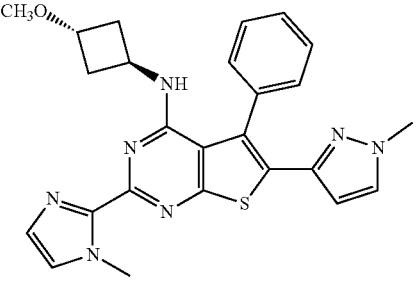 | | 472 | 472.2 | 472.2 |
| 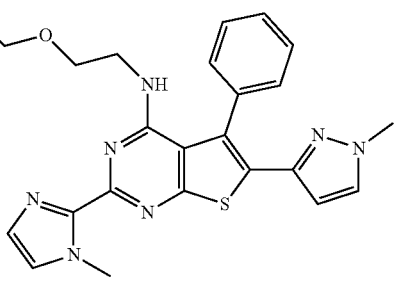 | | 503 | [M + 2H]/2 252.1 | [M + 2H]/2 252.2 |
| 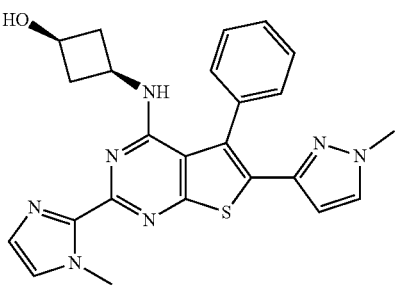 [SMILES: Cn1ccc(-c2sc3nc(-c4nccn4C)nc(N[C@H]4C[C@@H](O)C4)c3c2-c2ccccc2)n1] | | 458 | 458.2 | 458.2 |
| 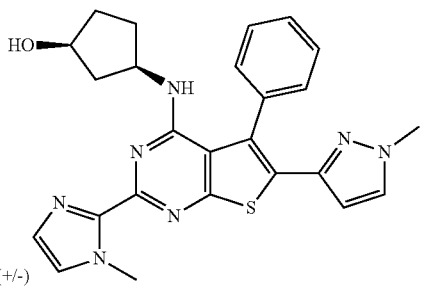 | | 472 | 472.2 | 472.2 |
| 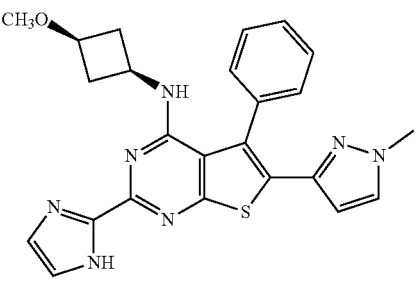 | | 458 | 458.2 | 458.2 |

TABLE 3-continued
Mass Spectral Data
| Compound | MW | M + H (calculated) | M + H (observed) |
|---|---|---|---|
| 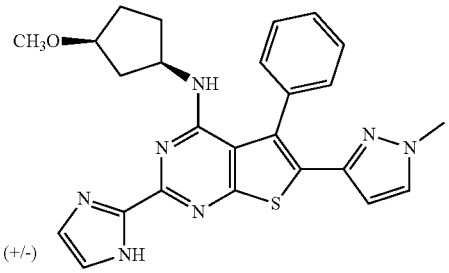 (+/−) | 472 | 472.2 | 472.2 |
| 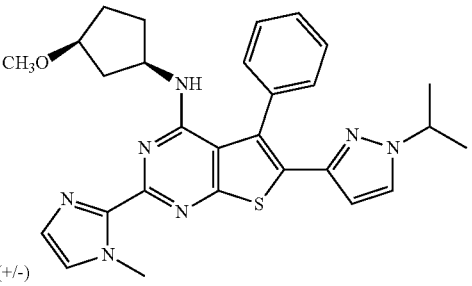 (+/−) | 514 | 514.3 | 514.2 |
| 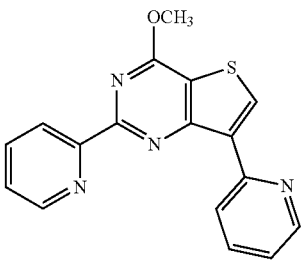 [SMILES: COc1nc(-c2ccccn2)nc2c(-c3ccccn3)csc12] | 320 | 321.1 | 321 |
| 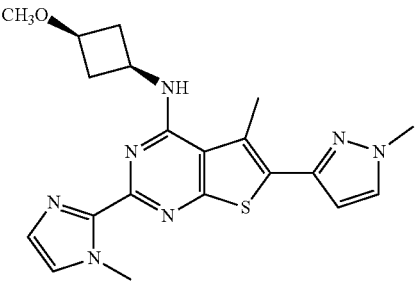 | 410 | 410.2 | 410.2 |
| 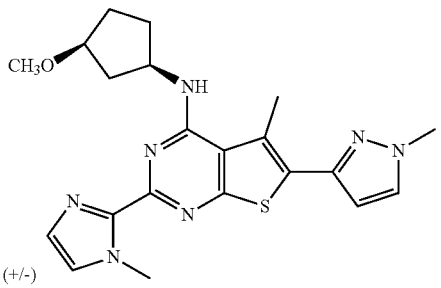 (+/−) | 424 | 424.2 | 424.2 |

TABLE 3-continued

| Mass Spectral Data | | | |
|---|---|---|---|
| Compound | MW | M + H (calculated) | M + H (observed) |
| | 446 | 446.2 | 446.1 |
| | 439 | 439.2 | 439.2 |
| | 441 | 441.2 | 441.1 |
| | 452 | 452.3 | 452.2 |
| | 477 | 477.2 | 477.2 |

TABLE 3-continued
| Compound | MW | M + H (calculated) | M + H (observed) |
|---|---|---|---|
| 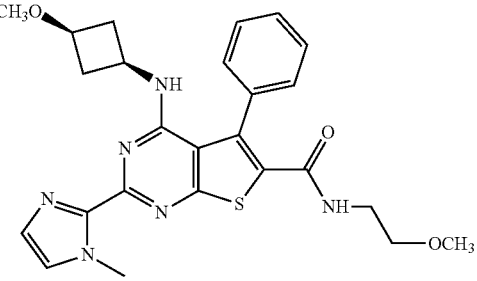 | 493 | 493.2 | 493.2 |
| 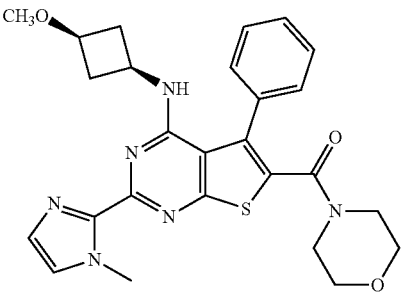 | 505 | 505.2 | 505.2 |
| 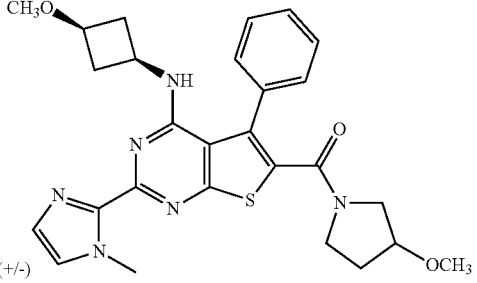 (+/-) | 519 | 519.2 | 519.2 |
| 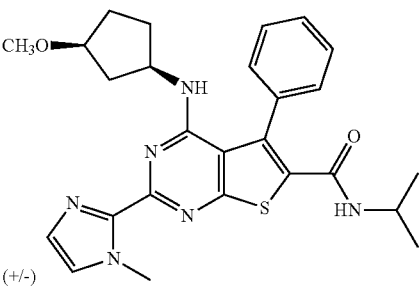 (+/-) | 491 | 491.2 | 491.2 |
| 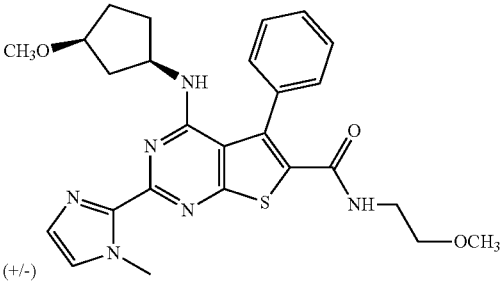 (+/-) | 507 | 507.2 | 507.2 |

TABLE 3-continued

Mass Spectral Data

| Compound | MW | M + H (calculated) | M + H (observed) |
|---|---|---|---|
| 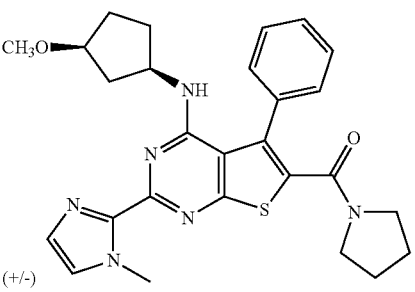 (+/-) | 503 | 503.2 | 503.2 |
| 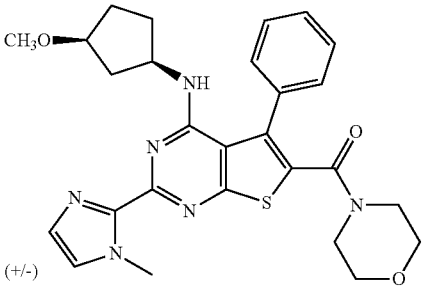 (+/-) | 519 | 519.2 | 519.2 |

Note:
The calclutated MW of the HCl salts include HCl in the calculation. The measured mass of the salts indicate the mass of the free base.

4.6. Pharmaceutical Compositions

The pharmaceutical compositions provided herein contain therapeutically effective amounts of one or more of compounds provided herein and a pharmaceutically acceptable carrier, diluent or excipient.

The compounds can be formulated into suitable pharmaceutical preparations such as solutions, suspensions, tablets, dispersible tablets, pills, capsules, powders, sustained release formulations or elixirs, for oral administration or in sterile solutions or suspensions for ophthalmic or parenteral administration, as well as transdermal patch preparation and dry powder inhalers. Typically the compounds described above are formulated into pharmaceutical compositions using techniques and procedures well known in the art (see, e.g., Ansel Introduction to Pharmaceutical Dosage Forms, Seventh Edition 1999).

In the compositions, effective concentrations of one or more compounds or pharmaceutically acceptable salts is (are) mixed with a suitable pharmaceutical carrier or vehicle. In certain embodiments, the concentrations of the compounds in the compositions are effective for delivery of an amount, upon administration, that treats, prevents, or ameliorates one or more of the symptoms and/or progression of a disease or disorder disclosed herein.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLVs) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the subject treated. The therapeutically effective concentration may be determined empirically by testing the compounds in in vitro and in vivo systems described herein and then extrapolated therefrom for dosages for humans. In some embodiments, the active compound is administered in a method to achieve a therapeutically effective concentration of the drug. In some embodiments, a companion diagnostic (see, e.g., Olsen D and Jorgensen J T, *Front. Oncol.*, 2014 May 16, 4:105, doi: 10.3389/fonc.2014.00105) is used to determine the therapeutic concentration and safety profile of the active compound in specific subjects or subject populations.

The concentration of active compound in the pharmaceutical composition will depend on absorption, tissue distribution, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of a disease or disorder disclosed herein.

In certain embodiments, a therapeutically effective dosage should produce a serum concentration of active ingredient of from about 0.1 ng/mL to about 50-100 µg/mL. In one embodiment, the pharmaceutical compositions provide a dosage of from about 0.001 mg to about 2000 mg of compound per kilogram of body weight per day. Pharmaceutical dosage unit forms are prepared to provide from about 1 mg to about 1000 mg and in certain embodiments, from about 10 to about 500 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Thus, effective concentrations or amounts of one or more of the compounds described herein or pharmaceutically acceptable salts thereof are mixed with a suitable pharmaceutical carrier or vehicle for systemic, topical or local administration to form pharmaceutical compositions. Compounds are included in an amount effective for ameliorating one or more symptoms of, or for treating, retarding progression, or preventing. The concentration of active compound in the composition will depend on absorption, tissue distribution, inactivation, excretion rates of the active compound, the dosage schedule, amount administered, particular formulation as well as other factors known to those of skill in the art.

The compositions are intended to be administered by a suitable route, including but not limited to oral, parenteral, subcutaneous, intravenous, intramuscular, intraperitoneal, intrathecal, mucosal, dermal, transdermal, buccal, rectal, topical, local, nasal or inhalation. For oral administration, capsules and tablets can be formulated. The compositions are in liquid, semi-liquid or solid form and are formulated in a manner suitable for each route of administration.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, pens, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil water emulsions containing suitable quantities of the compounds or pharmaceutically acceptable salts thereof. The pharmaceutically therapeutically active compounds and salts thereof are formulated and administered in unit dosage forms or multiple dosage forms. Unit dose forms as used herein refer to physically discrete units suitable for human and animal subjects and packaged individually as is known in the art. Each unit dose contains a predetermined quantity of the therapeutically active compound sufficient to produce the desired therapeutic effect, in association with the required pharmaceutical carrier, vehicle or diluent. Examples of unit dose forms include ampules and syringes and individually packaged tablets or capsules. Unit dose forms may be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses which are not segregated in packaging.

Sustained-release preparations can also be prepared. Suitable examples of sustained-release preparations include semipermeable matrices of solid hydrophobic polymers containing the compound provided herein, which matrices are in the form of shaped articles, e.g., films, or microcapsule. Examples of sustained-release matrices include iontophoresis patches, polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated compound remain in the body for a long time, they may denature or aggregate as a result of exposure to moisture at 37° C., resulting in a loss of biological activity and possible changes in their structure. Rational strategies can be devised for stabilization depending on the mechanism of action involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Dosage forms or compositions containing active ingredient in the range of 0.005% to 100% with the balance made up from non toxic carrier may be prepared. For oral administration, a pharmaceutically acceptable non toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain about 0.001% to 100% active ingredient, in certain embodiments, about 0.1 85% or about 75-95%.

The active compounds or pharmaceutically acceptable salts may be prepared with carriers that protect the compound against rapid elimination from the body, such as time release formulations or coatings.

The compositions may include other active compounds to obtain desired combinations of properties. The compounds provided herein, or pharmaceutically acceptable salts thereof as described herein, may also be advantageously administered for therapeutic or prophylactic purposes together with another pharmacological agent known in the general art to be of value in treating one or more of the diseases or medical conditions referred to hereinabove, such as diseases related to oxidative stress. It is to be understood that such combination therapy constitutes a further aspect of the compositions and methods of treatment provided herein.

Lactose-free compositions provided herein can contain excipients that are well known in the art and are listed, for example, in the U.S. Pharmocopia (USP) SP (XXI)/NF (XVI). In general, lactose-free compositions contain an active ingredient, a binder/filler, and a lubricant in pharmaceutically compatible and pharmaceutically acceptable amounts. Exemplary lactose-free dosage forms contain an active ingredient, microcrystalline cellulose, pre-gelatinized starch and magnesium stearate.

Further encompassed are anhydrous pharmaceutical compositions and dosage forms containing a compound provided herein. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, NY, 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine are anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs and strip packs.

Oral Dosage Forms

Oral pharmaceutical dosage forms are either solid, gel or liquid. The solid dosage forms are tablets, capsules, granules, and bulk powders. Types of oral tablets include compressed, chewable lozenges and tablets which may be enteric coated, sugar coated or film coated. Capsules may be hard or soft gelatin capsules, while granules and powders may be provided in non-effervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable salt thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric coated tablets, because of the enteric coating, resist the action of stomach acid and dissolve or disintegrate in the neutral or alkaline intestines. Sugar coated tablets are compressed tablets to which different layers of pharmaceutically acceptable substances are applied. Film coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil in-water or water in oil. In some embodiments, the suspension is a suspension of microparticles or nanoparticles. In some embodiments, the emulsion is an emulsion of microparticles or nanoparticles.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. In some embodiments, the suspension is a suspension of microparticles or nanoparticles. In some embodiments, the emulsion is an emulsion of microparticles or nanoparticles. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow release or sustained release system, such that a constant level of dosage is maintained is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple dose containers which include phenols or cresols, mercurials, benzyl alcohol, chlorobutanol, methyl and propyl p hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the subject or animal as is known in the art.

The unit dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, such as more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable salt thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (including but not limited to 10-1000 mg or 100-500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, about 5-35 mg, or about 9-30 mg of lyophilized powder, is added per mL of sterile water or other suitable carrier. The precise amount depends upon the selected compound. Such amount can be empirically determined.

Topical Administration

Topical mixtures are prepared as described for the local and systemic administration. The resulting mixture may be a solution, suspension, emulsion or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable salts thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will have diameters of less than 50 microns or less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

Compositions for Other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin gelatin, carbowax (polyoxyethylene glycol) and appropriate mixtures of mono, di and triglycerides of fatty acids. Combinations of the various bases may be used. Agents to raise the melting point of suppositories include spermaceti and wax. Rectal suppositories may be prepared either by the compressed method or by molding. An exemplary weight of a rectal suppository is about 2 to 3 grams.

Tablets and capsules for rectal administration are manufactured using the same pharmaceutically acceptable substance and by the same methods as for formulations for oral administration.

Sustained Release Compositions

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461, 6,419,961, 6,589,548, 6,613,358, 6,699,500 and 6,740,634, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over that achieved by their non-controlled counterparts. In one embodiment, the use of an optimally designed controlled-release preparation in medical treatment is characterized by a minimum of drug substance being employed to cure or control the condition in a minimum amount of time. In certain embodiments, advantages of controlled-release formulations include extended activity of the drug, reduced dosage frequency, and increased subject compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In one embodiment, a pump may be used (see, Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity of the therapeutic target, i.e., thus requiring only a fraction of the systemic dose (see, e.g., Goodson, Medical Applications of Controlled Release, vol. 2, pp. 115-138 (1984).

In some embodiments, a controlled release device is introduced into a subject in proximity of the site of inappropriate immune activation or a tumor. Other controlled release systems are discussed in the review by Langer (Science 249:1527-1533 (1990). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

Targeted Formulations

The compounds provided herein, or pharmaceutically acceptable salts thereof, may also be formulated to be targeted to a particular tissue, receptor, or other area of the body of the subject to be treated, including liposome-, resealed erythrocyte-, and antibody-based delivery systems. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, the antibody-based delivery system is an antibody-drug conjugate ("ADC"), e.g., as described in Hamilton G S, *Biologicals,* 2015 September, 43(5):318-32; Kim E G and Kim K M, *Biomol. Ther. (Seoul),* 2015 Nov. 23 (6):493-509; and Peters C and Brown S, Biosci. Rep., 2015 Jun. 12, 35(4) pii: e00225, each of which is incorporated herein by reference.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Articles of Manufacture

The compounds or pharmaceutically acceptable salts can be packaged as articles of manufacture containing packaging material, a compound or pharmaceutically acceptable salt thereof provided herein, which is used for treatment, prevention or amelioration of one or more symptoms or progression of a disease or disorder disclosed herein, and a label that indicates that the compound or pharmaceutically acceptable salt thereof is used for treatment, prevention or amelioration of one or more symptoms or progression of a disease or disorder disclosed herein.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, pens, bottles, and any packaging material suitable for a selected formulation and intended mode of administration and treatment. A wide array of formulations of the compounds and compositions provided herein are contemplated.

In certain embodiments, provided herein also are kits which, when used by the medical practitioner, can simplify the administration of appropriate amounts of active ingredients to a subject. In certain embodiments, the kit provided herein includes a container and a dosage form of a compound provided herein, including a single enantiomer or a mixture of diastereomers thereof; or a pharmaceutically acceptable salt, solvate, or prodrug thereof.

In certain embodiments, the kit includes a container comprising a dosage form of the compound provided herein, including a single enantiomer or a mixture of diastereomers thereof; or a pharmaceutically acceptable salt, solvate, or prodrug thereof, in a container comprising one or more other therapeutic agent(s) described herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

4.7. Dosing

The compounds and pharmaceutical compositions provided herein may be dosed in certain therapeutically or prophylactically effective amounts, certain time intervals, certain dosage forms, and certain dosage administration methods as described below.

In certain embodiments, a therapeutically or prophylactically effective amount of the compound is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, from about 0.05 to about 10 mg per day, from about 0.05 to about 5 mg per day, from about 0.1 to about 5 mg per day, or from about 0.5 to about 5 mg per day.

In certain embodiments, the therapeutically or prophylactically effective amount is about 0.1, about 0.2, about 0.5, about 1, about 2, about 3, about 4, about 5, about 6, about 7, about 8, about 9, about 10, about 15, about 20, about 25, about 30, about 40, about 45, about 50, about 60, about 70, about 80, about 90, about 100, or about 150 mg per day.

In one embodiment, the recommended daily dose range of the compound provided herein, or a derivative thereof, for the conditions described herein lie within the range of from about 0.5 mg to about 50 mg per day, in one embodiment given as a single once-a-day dose, or in divided doses throughout a day. In some embodiments, the dosage ranges from about 1 mg to about 50 mg per day. In other embodiments, the dosage ranges from about 0.5 to about 5 mg per day. Specific doses per day include 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg per day.

In a specific embodiment, the recommended starting dosage may be 0.5, 1, 2, 3, 4, 5, 10, 15, 20, 25 or 50 mg per day. In another embodiment, the recommended starting dosage may be 0.5, 1, 2, 3, 4, or 5 mg per day. The dose may be escalated to 15, 20, 25, 30, 35, 40, 45 and 50 mg/day. In a specific embodiment, the compound can be administered in an amount of about 25 mg/day. In a particular embodiment, the compound can be administered in an amount of about 10 mg/day. In a particular embodiment, the compound can be administered in an amount of about 5 mg/day. In a particular embodiment, the compound can be administered in an amount of about 4 mg/day. In a particular embodiment, the compound can be administered in an amount of about 3 mg/day.

In certain embodiments, the therapeutically or prophylactically effective amount is from about 0.001 to about 100 mg/kg/day, from about 0.01 to about 50 mg/kg/day, from about 0.01 to about 25 mg/kg/day, from about 0.01 to about 10 mg/kg/day, from about 0.01 to about 9 mg/kg/day, 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, from about 0.01 to about 1 mg/kg/day, or from about 0.01 to about 0.05 mg/kg/day.

The administered dose can also be expressed in units other than mg/kg/day. For example, doses for parenteral administration can be expressed as mg/m$^2$/day. One of ordinary skill in the art would readily know how to convert doses from mg/kg/day to mg/m$^2$/day to given either the height or weight of a subject or both (see, e.g., Nair A B, Jacob S. A simple practice guide for dose conversion between animals and human. J Basic Clin Pharma 2016; 7:27-31). For example, a dose of 1 mg/kg/day for a 60 kg human is approximately equal to 37 mg/m$^2$/day.

In certain embodiments, the amount of the compound administered is sufficient to provide a plasma concentration of the compound at steady state, ranging from about 0.001 to about 500 µM, about 0.002 to about 200 µM, about 0.005 to about 100 µM, about 0.01 to about 50 µM, from about 1 to about 50 µM, about 0.02 to about 25 µM, from about 0.05 to about 20 µM, from about 0.1 to about 20 µM, from about 0.5 to about 20 µM, or from about 1 to about 20 µM.

In other embodiments, the amount of the compound administered is sufficient to provide a plasma concentration of the compound at steady state, ranging from about 5 to about 100 nM, about 5 to about 50 nM, about 10 to about 100 nM, about 10 to about 50 nM or from about 50 to about 100 nM.

As used herein, the term "plasma concentration at steady state" is the concentration reached after a period of administration of a compound provided herein, or a derivative thereof. Once steady state is reached, there are minor peaks and troughs on the time dependent curve of the plasma concentration of the compound.

In certain embodiments, the amount of the compound administered is sufficient to provide a maximum plasma concentration (peak concentration) of the compound, ranging from about 0.001 to about 500 µM, about 0.002 to about 200 µM, about 0.005 to about 100 µM, about 0.01 to about 50 µM, from about 1 to about 50 µM, about 0.02 to about 25 µM, from about 0.05 to about 20 µM, from about 0.1 to about 20 µM, from about 0.5 to about 20 µM, or from about 1 to about 20 µM.

In certain embodiments, the amount of the compound administered is sufficient to provide a minimum plasma concentration (trough concentration) of the compound, ranging from about 0.001 to about 500 µM, about 0.002 to about 200 µM, about 0.005 to about 100 µM, about 0.01 to about 50 µM, from about 1 to about 50 µM, about 0.01 to about 25 µM, from about 0.01 to about 20 µM, from about 0.02 to about 20 µM, from about 0.02 to about 20 µM, or from about 0.01 to about 20 µM.

In certain embodiments, the amount of the compound administered is sufficient to provide an area under the curve (AUC) of the compound, ranging from about 100 to about 100,000 ng*hr/mL, from about 1,000 to about 50,000 ng*hr/mL, from about 5,000 to about 25,000 ng*hr/mL, or from about 5,000 to about 10,000 ng*hr/mL.

The methods provided herein encompass treating a patient regardless of subject's age, although some diseases or disorders are more common in certain age groups.

Depending on the disease to be treated and the subject's condition, the compound provided herein, or a derivative thereof, may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. The compound provided herein, or a derivative thereof, may be formulated, alone or together, in suitable dosage unit with pharmaceutically acceptable excipients, carriers, adjuvants and vehicles, appropriate for each route of administration.

In one embodiment, the compound provided herein, or a derivative thereof, is administered orally. In another embodiment, the compound provided herein, or a derivative thereof, is administered parenterally. In yet another embodiment, the compound provided herein, or a derivative thereof, is administered intravenously.

The compound provided herein, or a derivative thereof, can be delivered as a single dose such as, e.g., a single bolus injection, or oral tablets or pills; or over time, such as, e.g., continuous infusion over time or divided bolus doses over time. The compound can be administered repeatedly if necessary, for example, until the subject experiences stable disease or regression, or until the subject experiences disease progression or unacceptable toxicity. For example, stable disease for solid tumors generally means that the perpendicular diameter of measurable lesions has not increased by 25% or more from the last measurement. Response Evaluation Criteria in Solid Tumors (RECIST) Guidelines, Journal of the National Cancer Institute 92(3): 205 216 (2000). Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

The compound provided herein, or a derivative thereof, can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound, such as the compound provided herein, or a derivative thereof, is administered once or more than once each day, for example, for a period of time. The term "continuous" is intended to mean that a therapeutic compound, such as the compound provided herein or a derivative thereof, is administered daily for an uninterrupted period of at least 10 days to 52 weeks. The term "intermittent" or "intermittently" as used herein is intended to mean stopping and starting at either regular or irregular intervals. For example, intermittent administration of the compound provided herein or a derivative thereof is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as the compound provided herein or a derivative thereof, is administered daily or continuously but with a rest period. In some such embodiments, administration is once a day for two to six days, then a rest period with no administration for five to seven days.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, the compound provided herein, or a derivative thereof, is administered once a day. In another embodiment, the compound provided herein, or a derivative thereof, is administered twice a day. In yet another embodiment, the compound provided herein, or a derivative thereof, is administered three times a day. In still another embodiment, the compound provided herein, or a derivative thereof, is administered four times a day.

In certain embodiments, the compound provided herein, or a derivative thereof, is administered once per day from one day to six months, from one week to three months, from one week to four weeks, from one week to three weeks, or from one week to two weeks. In certain embodiments, the compound provided herein, or a derivative thereof, is administered once per day for one week, two weeks, three weeks, or four weeks. In one embodiment, the compound provided herein, or a derivative thereof, is administered once per day for 4 days. In one embodiment, the compound provided herein, or a derivative thereof, is administered once per day for 5 days. In one embodiment, the compound provided herein, or a derivative thereof, is administered once per day for 6 days. In one embodiment, the compound provided herein, or a derivative thereof, is administered once per day for one week. In another embodiment, the compound provided herein, or a derivative thereof, is administered once per day for two weeks. In yet another embodiment, the compound provided herein, or a derivative thereof, is administered once per day for three weeks. In still another embodiment, the compound provided herein, or a derivative thereof, is administered once per day for four weeks.

Combination Therapy with a Second Active Agent

The compound provided herein, or a derivative thereof, can also be combined or used in combination with other therapeutic agents useful in the treatment and/or prevention of cancers, inflammatory diseases, rasopathies, or fibrotic disease.

In one embodiment, provided herein is a method of treating, preventing, or managing cancers, inflammatory diseases, rasopathies, and fibrotic disease, comprising administering to a subject a compound provided herein, or a derivative thereof; in combination with one or more second active agents.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound provided herein, a compound provided herein, e.g., the compound provided herein, or a derivative thereof) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

Administration of the compound provided herein, or a derivative thereof and one or more second active agents to a subject can occur simultaneously or sequentially by the same or different routes of administration. The suitability of a particular route of administration employed for a particular active agent will depend on the active agent itself (e.g., whether it can be administered orally without decomposing prior to entering the blood stream) and the disease or disorder being treated.

The route of administration of the compound provided herein, or a derivative thereof, is independent of the route of administration of a second therapy. In one embodiment, the compound provided herein, or a derivative thereof, is administered orally. In another embodiment, the compound provided herein, or a derivative thereof, is administered intravenously. Thus, in accordance with these embodiments, the compound provided herein, or a derivative thereof, is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, the compound provided herein, or a derivative thereof, and a second therapy are administered by the same mode of administration, orally or by IV. In another embodiment, the compound provided herein, or a derivative thereof, is administered by one mode of administration, e.g., by IV, whereas the second agent is administered by another mode of administration, e.g., orally.

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount of the compound provided herein, or a derivative thereof, and any optional additional active agents concurrently administered to the subject.

One or more second active ingredients or agents can be used together with the compound provided herein, or a derivative thereof, in the methods and compositions provided herein. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies, particularly, therapeutic antibodies to cancer antigens. Typical large molecule active agents are biological molecules, such as naturally occurring or synthetic or recombinant proteins.

In one embodiment, the compound provided herein, or a derivative thereof, can be administered in an amount ranging from about 0.1 to about 150 mg, from about 1 to about 25 mg, or from about 2 to about 10 mg orally and daily alone, or in combination with a second active agent, prior to, during, or after the use of conventional therapy.

5. EXAMPLES

The following examples are offered to illustrate but not to limit the disclosure.

Example 1

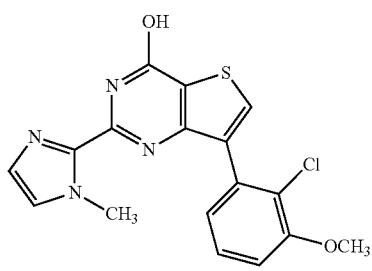

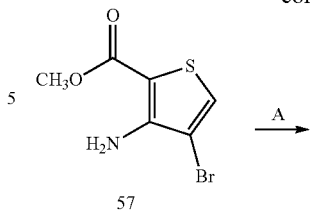

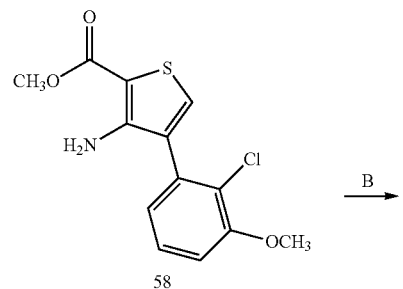

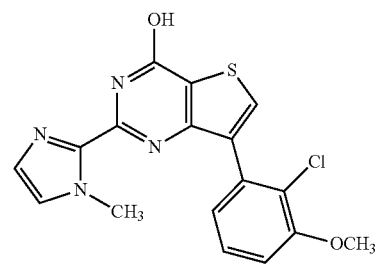

Step A: Starting material 57 (1 g) was dissolved in dry dioxane (20 mL) under argon atmosphere, followed by addition of (2-chloro-3-methoxyphenyl)boronic acid (1.2 equiv), solution of K$_2$CO$_3$ (30%, 5 mL) and Pd(dppf)Cl$_2$ (5 mol %). The mixture was refluxed overnight under argon atmosphere, cooled to room temperature and extracted with EtOAc (2×40 mL). The organic layer was dried over Na$_2$SO$_4$, evaporated and the residue was purified by silica gel chromatography to give target compound 58 as a white solid (0.55 g, 43% yield).

Step B: Starting ester 58 (0.3 g, 1 equiv) was dissolved in dry dioxane (10 mL) followed by addition of 1-methyl-2-cyanoimidazole (1 equiv) and sodium hydride (2 equiv, 0.1 g). The mixture was heated at reflux under Ar atmosphere for 12 h, cooled to r.t. and acidified with AcOH. The solvent was evaporated, the residue diluted with water and filtered. The crude material was purified using HPLC to give the target Example compound (0.0325 g, 8.6% yield).

Example 2-Example 8

Examples 2-8 (shown in Table A) were prepared according to the procedure described in Scheme 1, Steps A-C, using the appropriate nitrile (HetAr-CN 4) in Step C. Nitriles 7a-d used in Examples 5-8, respectively, were prepared as described in Scheme 2.

TABLE A

| Example | Structure | Amount | Yield (Scheme 1, Step C) |
|---|---|---|---|
| 2 | (2-(1-methyl-1H-imidazol-2-yl)-7-(pyridin-2-yl)thieno[3,2-d]pyrimidin-4-ol) | 15.1 mg | 3.95% |
| 3 | (2-(5,6,7,8-tetrahydroimidazo[1,2-a]pyridin-3-yl)-7-(pyridin-2-yl)thieno[3,2-d]pyrimidin-4-ol) | 13.1 mg | 3.04% |
| 4 | (2-(imidazo[1,2-a]pyridin-2-yl)-7-(pyridin-2-yl)thieno[3,2-d]pyrimidin-4-ol) | 8.9 mg | 2.1% |
| 5 | (2-(1-(2-methoxyethyl)-1H-imidazol-2-yl)-7-(pyridin-2-yl)thieno[3,2-d]pyrimidin-4-ol) | 207.8 mg | 47.6% |
| 6 | (2-(1-((3-methylisoxazol-5-yl)methyl)-1H-imidazol-2-yl)-7-(pyridin-2-yl)thieno[3,2-d]pyrimidin-4-ol) | 5 mg | 1.04% |
| 7 | (2-(1-(pyridin-2-ylmethyl)-1H-imidazol-2-yl)-7-(pyridin-2-yl)thieno[3,2-d]pyrimidin-4-ol) | 31.5 mg | 6.6% |
| 8 | (2-(1-(3-methoxybenzyl)-1H-imidazol-2-yl)-7-(pyridin-2-yl)thieno[3,2-d]pyrimidin-4-ol) | 73.5 mg | 14.3% |

Example 9 and Example 10

(two structures: 2-(1,5-dimethyl-1H-imidazol-2-yl)-7-(pyridin-2-yl)thieno[3,2-d]pyrimidin-4-ol and 2-(1,4-dimethyl-1H-imidazol-2-yl)-7-(pyridin-2-yl)thieno[3,2-d]pyrimidin-4-ol)

4-methyl-1H-imidazole-2-carbonitrile 59 $\xrightarrow{A}$ 1,5-dimethyl-1H-imidazole-2-carbonitrile + (isomer) 60

255
-continued

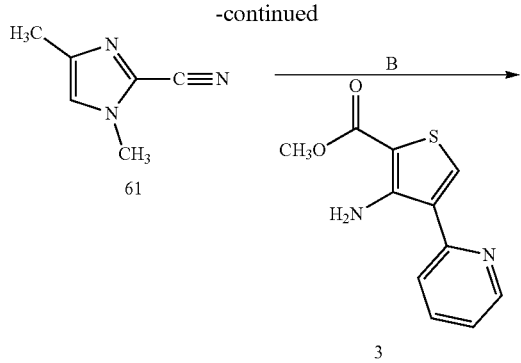

256
Example 11

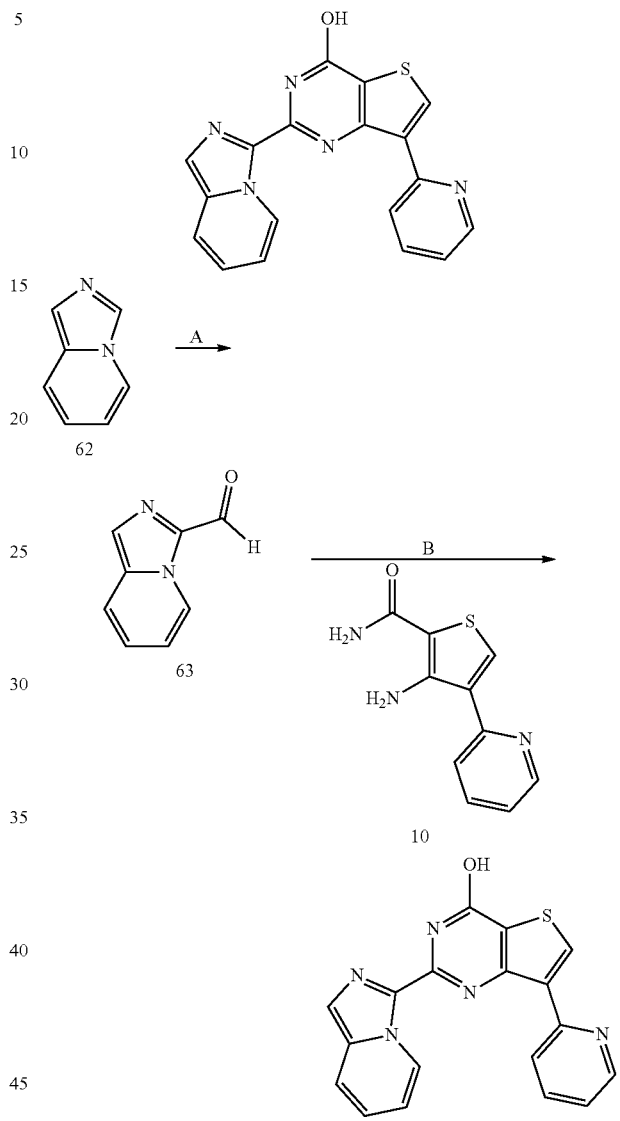

Step A: Iodomethane (1.1 eq, 30.8 mmol) was added to a solution of 4-methyl-1H-imidazole-2-carbonitrile 59 (3 g, 28.0 mmol) in anhydrous DMF (40 mL). The resulting mixture was stirred at room temperature for 24 h. Residual iodomethane was quenched by the slow addition of H₂O (40 mL), followed by stirring for 10 min. The solution was then extracted with EtOAc (3×30 mL). The combined organic layer was washed with brine, dried over Na₂SO₄, filtered, and concentrated in vacuo. The obtained mixture of regioisomers 60 and 61 was used without any additional purification. (2.95 g, 85% yield).

Step B: Nitrile mixture 60 and 61 from Step A was converted to final products using the general procedure described in Scheme 1, Step C, for reaction with compound 3 (synthesis described in Scheme 1), where 60 and 61 correspond to general compound HetAr-CN (4). The obtained mixture of final products was separated by HPLC (10-25% water-(acetonitrile) eluent, flow rate 30 mL/min) to give Example 9 (retention time 8.1-8.6 min) (3.9 mg, 1% yield) and Example 10 (retention time 7.5-8 min) (4.6 mg, 1.15% yield).

Step A: Imidazo[1,5-a]pyridine 62 (2.337 g, 19.78 mmol) in tetrahydrofuran (40 mL) was added n-butyl lithium (2.5 M in hexane, 15.76 mL, 39.4 mmol) at −40° C. The mixture was stirred at −40° C. for 3.5 hours, followed by the addition of dimethylformamide (3.1 mL, 40 mmol). The reaction mixture was stirred at 25° C. overnight and quenched with water. The mixture was then partitioned between dichloromethane (80 mL) and water (15 mL). The organic phase layer was dried with anhydrous sodium sulfate, filtered and concentrated in vacuo. The crude material was purified by chromatography eluting with 0-50% ethyl acetate/dichloromethane to give the target compound 63 (1.78 g, 62% yield).

Step B: Compound 63 from Step A was reacted with compound 10 (synthesized as described in Scheme 3) using the general procedure described in Scheme 3, Step C, where compound 63 corresponds to HetAr-CHO (11). The target compound Example 11 was obtained (4.2 mg, 1% yield).

Examples 12 and Example 13

Examples 12-13 (shown in Table B) were prepared according to the procedure described in Scheme 3, Steps A-C, using the appropriate aldehyde (HetAr-CHO 11) in Step C.

TABLE B

| Example | Structure | Amount | Yield (Scheme 3, Step C) |
|---|---|---|---|
| 12 | 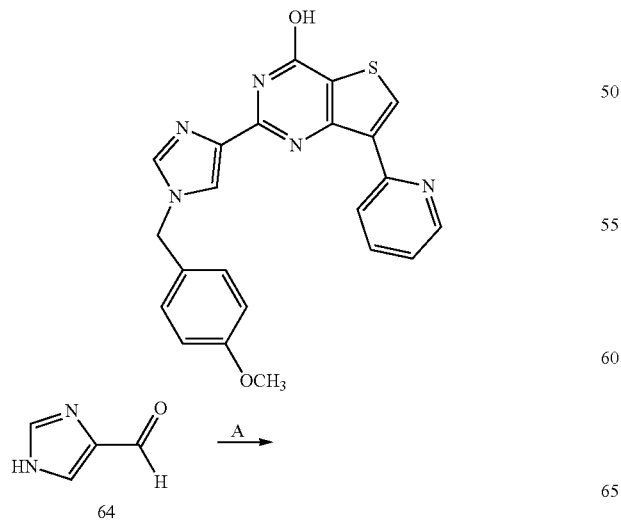 | 87.9 mg | 20.6% |
| 13 | 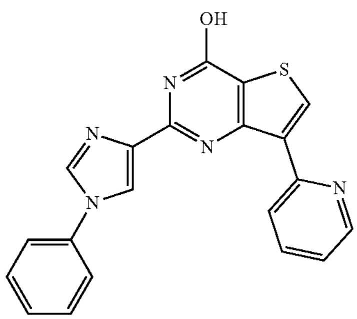 [SMILES: Oc1nc(-c2cn(-c3ccccc3)cn2)nc2c(-c3ccccn3)csc12] | 127.8 mg | 27.9% |

Example 14

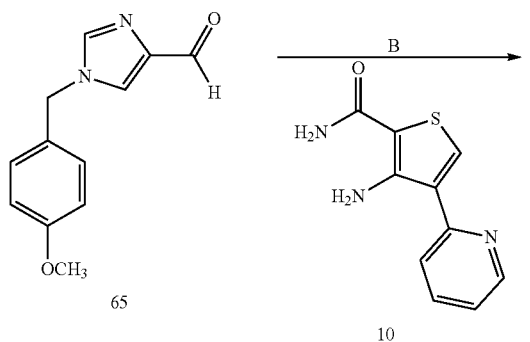

Step A: Using the typical procedure described in Scheme 2, except using imidazole 4-carboxaldehyde 64 in place of nitrile 6, the target aldehyde 65 was prepared (220 mg, 33%).

Step B: Compound 65 from Step A was reacted with compound 10 (synthesized as described in Scheme 3) using the general procedure described in Scheme 3, Step C, where compound 65 corresponds to HetAr-CHO (11). The target compound Example 14 was obtained (42.2 mg, 8.22% yield).

Example 15

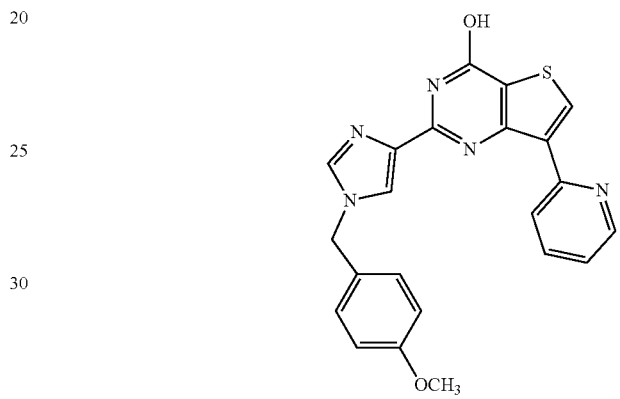

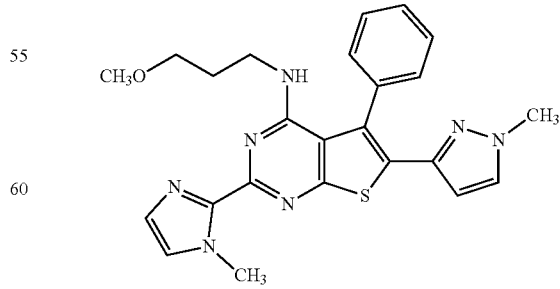

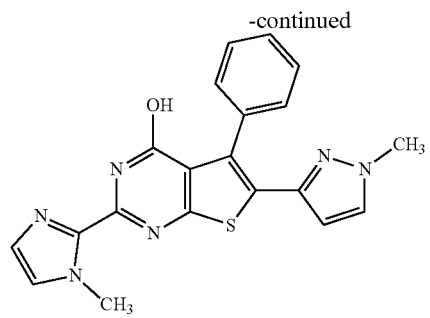

17a

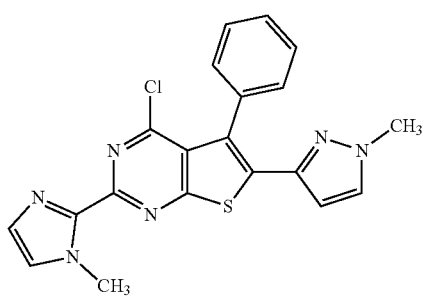

66

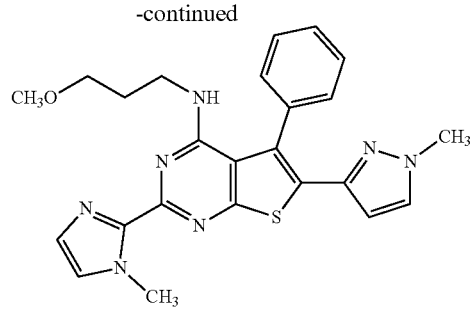

Step A and Step B: In Step A, the crude material 17a (synthesis described in Scheme 4), was suspended in POC$_3$ (2 mL) and diisopropylethylamine (0.6 mL) was added at r.t. The reaction mixture was refluxed for 16 h, the solution was cooled to r.t., evaporated under reduced pressure, diluted with ice-cold ammonia (20 mL, 20-25% of ammonia), the product was extracted with chloroform (2*30 mL) and the solvent evaporated to give compound 66. In Step B, the residue from Step A (66) was dissolved in DMSO and 3-methoxypropan-1-amine (5 equiv) was added. The mixture was heated at 100° C. overnight, cooled and purified by HPLC to obtain the target Example compound (14.4 mg, 4.1% yield).

Example 16-Example 25

Examples 16-25 (shown in Table C) were prepared from 17a (synthesis described in Scheme 4), according to the procedure described in Example 15, Step A and Step B, using the appropriate amine in place of 3-methoxypropan-1-amine in Step B.

TABLE C

| Example | Structure | Amount | Yield (Step A + B) |
|---------|-----------|--------|---------------------|
| 16 | 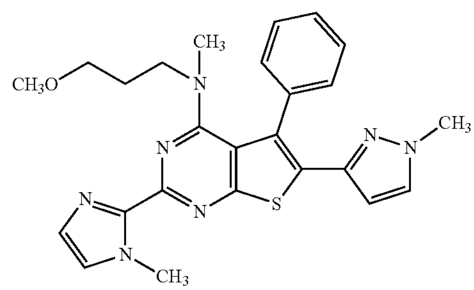 | 15.6 mg | 4.2% |
| 17 | 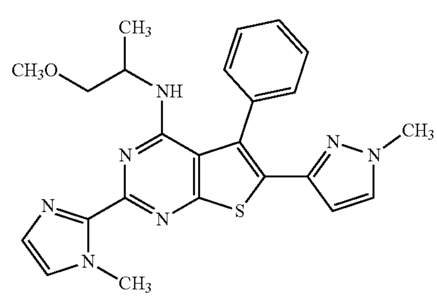 | 6.6 mg | 1.8% |

TABLE C-continued

| Example | Structure | Amount | Yield (Step A + B) |
|---|---|---|---|
| 18 | 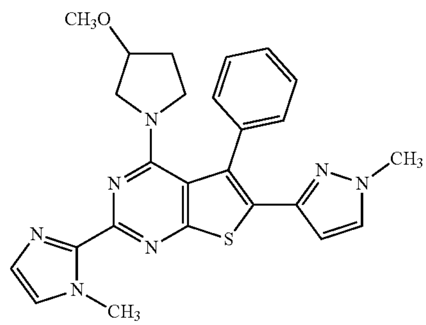 | 11.5 mg | 3.2% |
| 19 | 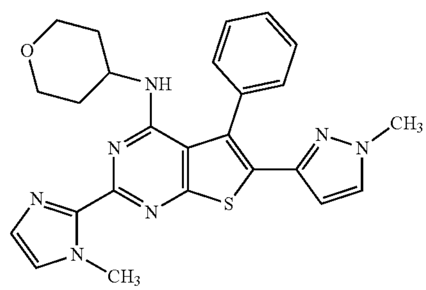 [SMILES: Cn1ccc(-c2sc3nc(-c4nccn4C)nc(NC4CCOCC4)c3c2-c2ccccc2)n1] | 11 mg | 3% |
| 20 | 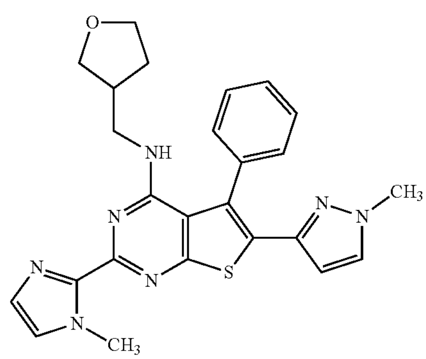 [SMILES: Cn1ccc(-c2sc3nc(-c4nccn4C)nc(NCC4CCOC4)c3c2-c2ccccc2)n1] | 11.7 mg | 3.2% |
| 21 | (+/- cis) | 6 mg | 2.7% |

TABLE C-continued

| Example | Structure | Amount | Yield (Step A + B) |
|---|---|---|---|
| 22 | (+/− trans) | 14 mg | 3% |
| 23 | 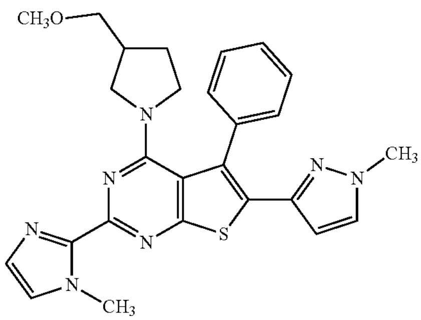 | 17.4 mg | 4.6% |
| 24 | 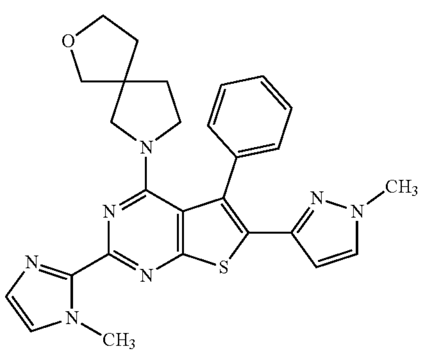 [SMILES: Cn1ccc(-c2sc3nc(-c4nccn4C)nc(N4CCC5(CCOC5)C4)c3c2-c2ccccc2)n1] | 11 mg | 4.3% |
| 25 | 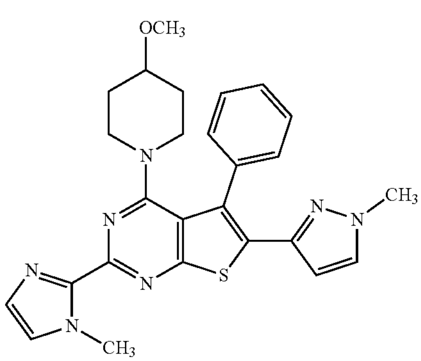 [SMILES: COC1CCN(c2nc(-c3nccn3C)nc3sc(-c4ccn(C)n4)c(-c4ccccc4)c23)CC1] | 14.6 mg | 3.9% |

Example 26

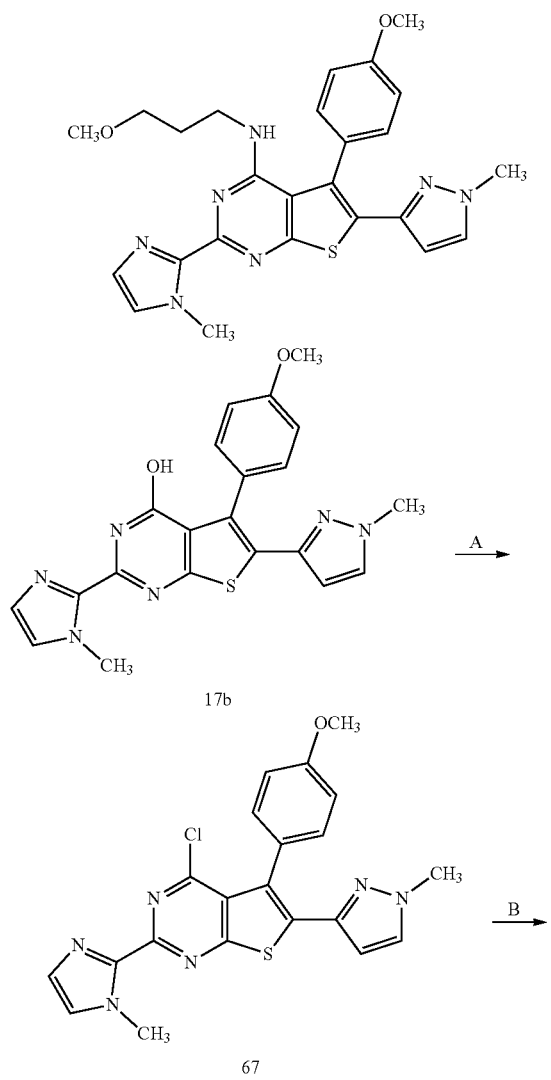

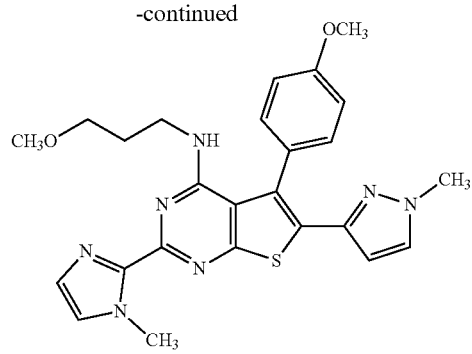

Step A and Step B: In Step A, the crude material 17b (synthesis described in Scheme 4), was suspended in POCl$_3$ (2 mL) and diisopropylethylamine (0.6 mL) was added at r.t. The reaction mixture was refluxed for 16 h, the solution was cooled to r.t., evaporated under reduced pressure, diluted with ice-cold ammonia (20 mL, 20-25% of ammonia), the product 67 was extracted with chloroform (2*30 mL) and the solvent evaporated. In Step B, the residue (compound 67) was dissolved in DMSO and 3-methoxypropan-1-amine (5 equiv) was added. The mixture was heated at 100° C. overnight, cooled and purified by HPLC to obtain the target Example compound (12.2 mg, 3.5% yield).

Example 27-Example 28

Examples 27-28 (shown in Table D) were prepared from 17b (synthesis described in Scheme 4), according to the procedure described for Example 26, Step A and Step B, using the appropriate amine in place of 3-methoxypropan-1-amine in Step B.

TABLE D

| Example | Structure | Amount | Yield (Step A + B) |
|---|---|---|---|
| 27 | ![structure] | 9.6 mg | 2.7% |

TABLE D-continued

| Example | Structure | Amount | Yield (Step A + B) |
|---|---|---|---|
| 28 | 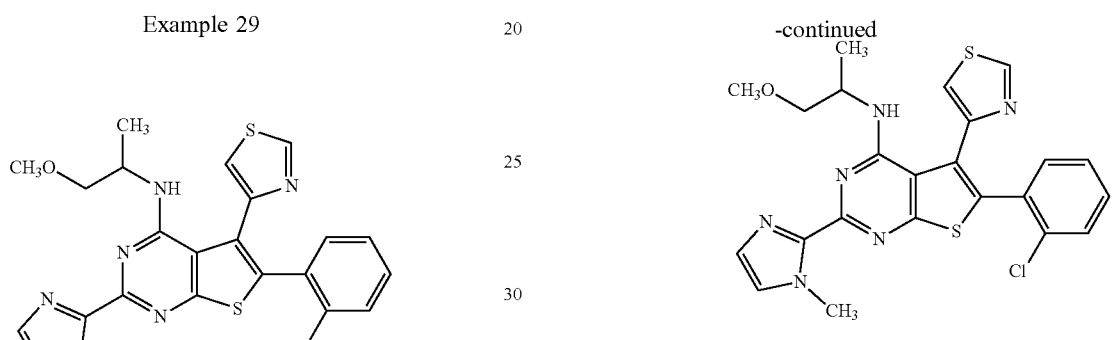 | 17.3 mg | 4.8% |

Example 29

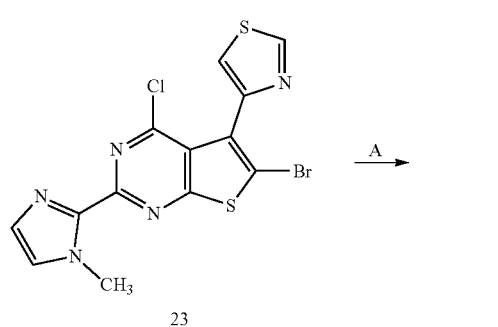

23

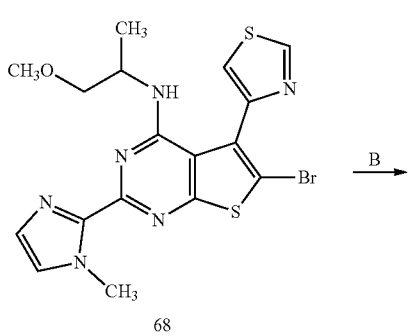

68

-continued

[structure of target Example compound]

Step A: To a stirred solution of chloride 23 (prepared as described in Scheme 5) (1.5 g, 3.64 mmol) in chloroform (30 mL) was added triethylamine (1.5 mL, 10.9 mmol) and hydrochloride of corresponding amine 1-methoxypropan-2-amine (5.45 mmol). Then reaction mixture was refluxed for 1 h, cooled to r.t, diluted with water (75 mL) and extracted twice with chloroform (2*25 mL). Combined organic layer was dried over $Na_2SO_4$, evaporated under reduced pressure and purified by flash chromatography (eluent—EtOAc:$Et_3N$—20:1) to give the target compound 68 as light yellow solid (1.4 g, 83% yield).

Step B: General procedure: Compound 68 from previous step (0.64 mmol) was mixed with corresponding boronic acid (2-chlorophenyl)boronic acid (0.96 mmol), $K_2CO_3$ (3.84 mmol), Pd(dppf)$Cl_2$ (0.064 mmol) 1,4-dioxane (15 mL) under argon atmosphere. The reaction was then stirred at 100° C. for 16 h under argon atmosphere. Then reaction mixture was cooled to r.t., diluted with water (50 mL) and extracted twice with chloroform (2*25 mL). Combined organic layer was dried with $Na_2SO_4$, evaporated under reduced pressure and purified from resins by flash chromatography (eluent—EtOAc:$Et_3N$—20:1). Finally, the crude product was purified by HPLC (eluent—$H_2O$:MeOH) to give the target Example compound (5.2 mg, 4% yield).

Example 30

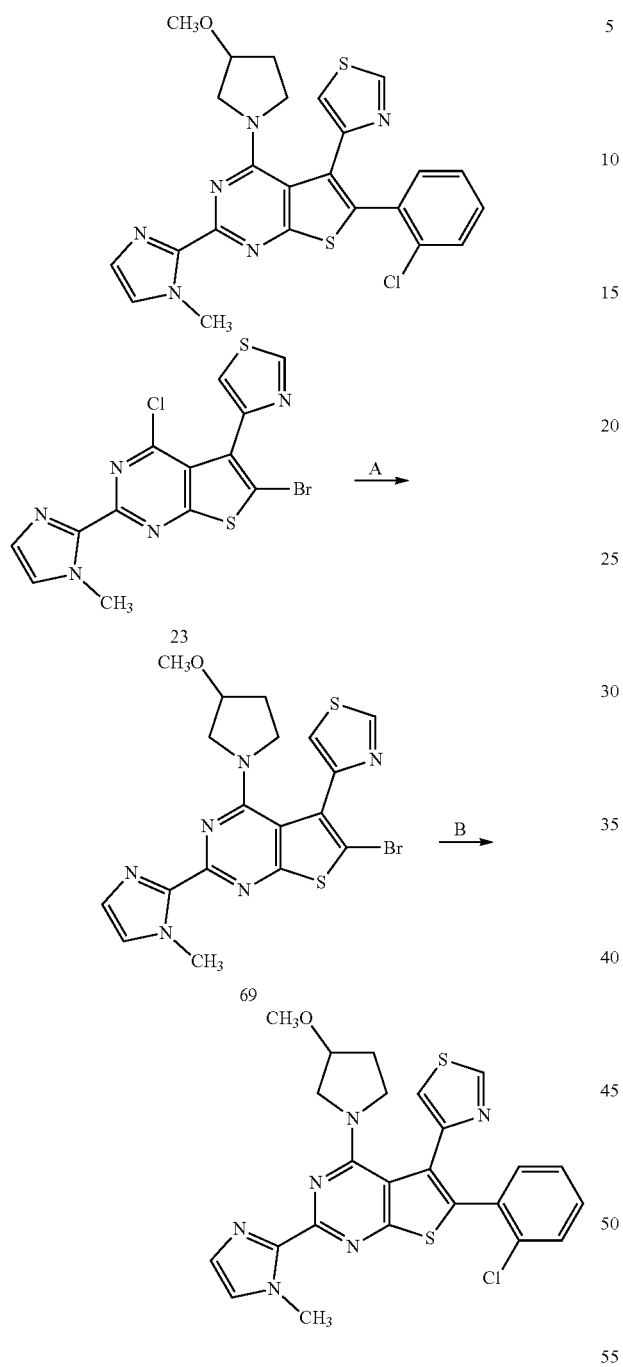

Step A: To a stirred solution of chloride 23 (prepared as described in Scheme 5) (1.5 g, 3.64 mmol) in chloroform (30 mL) was added triethylamine (1.5 mL, 10.9 mmol) and hydrochloride of corresponding amine 3-methoxypyrrolidine (5.45 mmol). Then reaction mixture was refluxed for 1 h, cooled to r.t, diluted with water (75 mL) and extracted twice with chloroform (2*25 mL). Combined organic layer was dried over $Na_2SO_4$, evaporated under reduced pressure and purified by flash chromatography (eluent—EtOAc: $Et_3N$—20:1) to give the target compound 69 as light yellow solid (1.5 g, 87% yield).

Step B: Following the procedure described in Example 29, Step B, except starting with compound 69 in place of compound 68, the target Example compound was obtained (30.3 mg, 6.2% yield).

Example 31

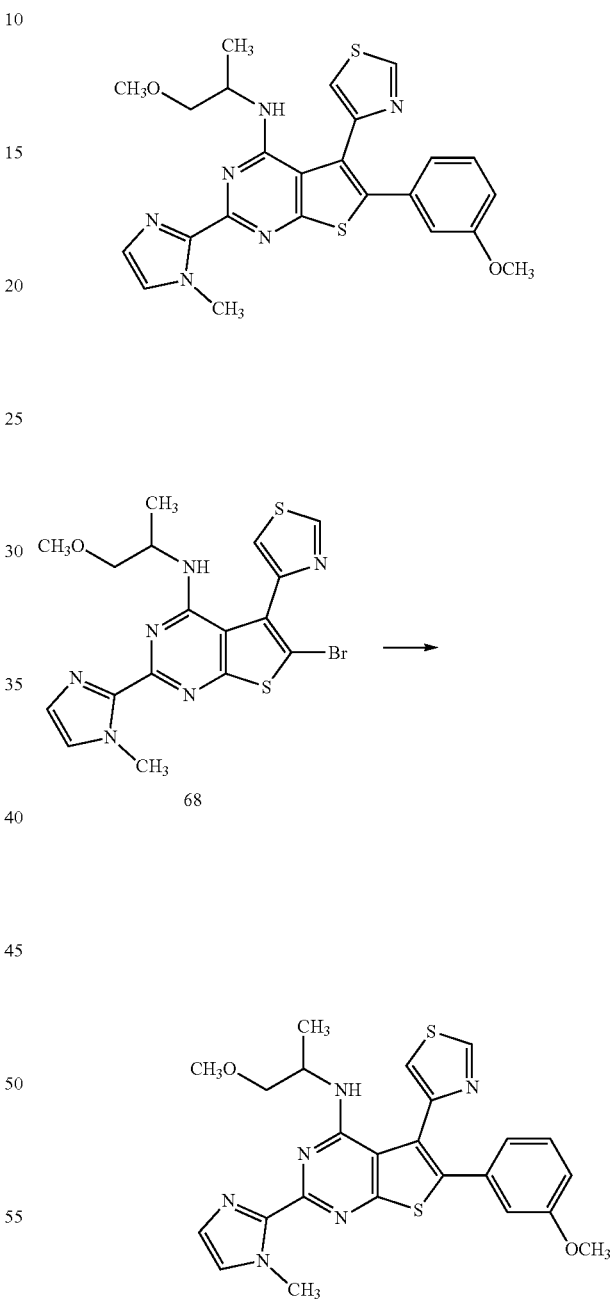

The target compound was prepared from compound 68 (prepared as described in Example 29) following the procedure described in Example 29, Step B, except using (3-methoxyphenyl)boronic acid (0.96 mmol) in place of (2-chlorophenyl)boronic acid. The target Example compound was obtained in the following amount and yield after purification (9.5 mg, 9.47%).

Example 32

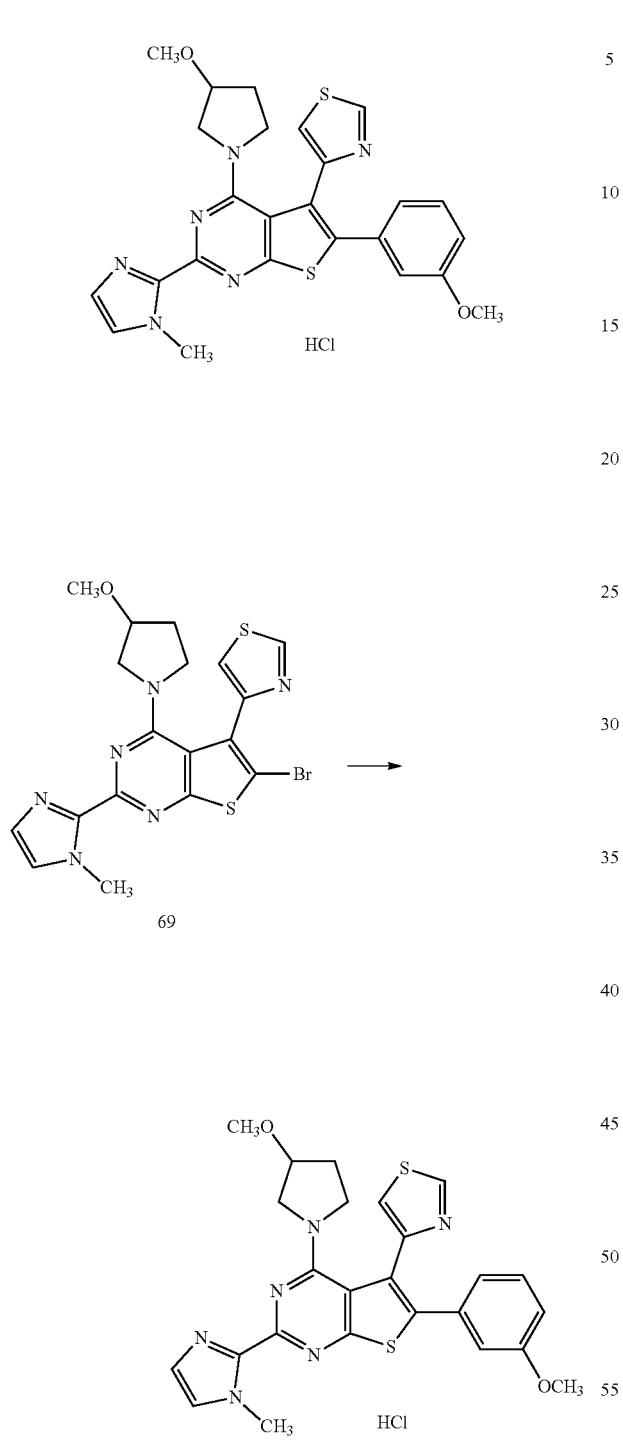

Using the procedure described in Example 29, Step B, except starting with compound 69 (synthesized as described in Example 30, Step A) instead of compound 68, and using (3-methoxyphenyl)boronic acid (0.96 mmol) in place of (2-chlorophenyl)boronic acid. For HPLC purification (10-40% water-(acetonitrile) eluent), 0.1% HCl was added to the sample. The target Example compound was obtained as the HCl salt in the following amount and yield after HPLC purification (44.4 mg, 13.9% yield).

Example 33

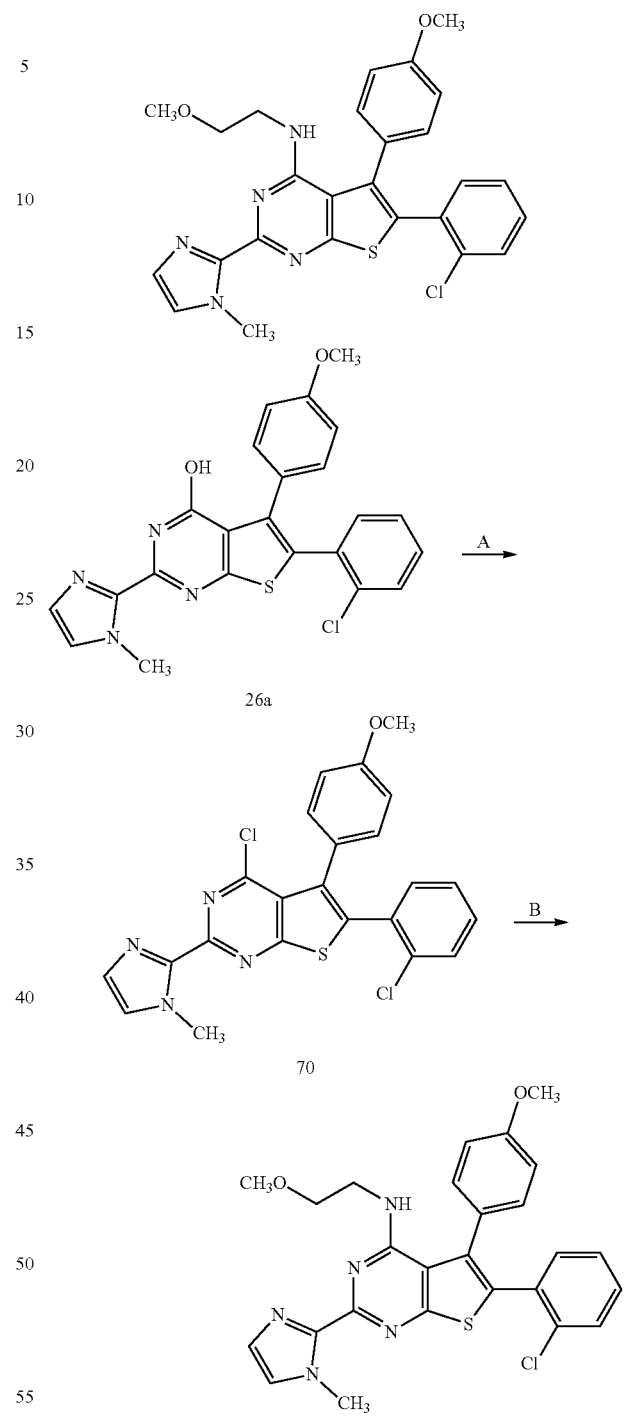

Step A and Step B: In Step A, the crude material 26a (synthesis described in Scheme 6), was suspended in POC$_3$ (2 mL) and diisopropylethylamine (0.6 mL) was added at r.t. The reaction mixture was refluxed for 16 h, the solution was cooled to r.t., evaporated under reduced pressure, diluted with ice-cold ammonia (20 mL, 20-25% of ammonia), the product 70 was extracted with chloroform (2*30 mL) and the solvent evaporated. In Step B, the obtained residue (compound 70) was dissolved in DMSO and 2-methoxyethylamine (5 equiv) was added. The mixture was heated at 100° C. overnight, cooled and purified by HPLC to obtain the target Example compound (15.3 mg, 4.5% yield).

Example 34-Example 36

Examples 34-36 (shown in Table E) were prepared according to the procedure described Example 33, Step A and Step B, except using 26b, 26c or 26d, respectively, in place of 26a in Step A, and the corresponding product of Step A in place of 70 in Example 33, Step B.

TABLE E

| Example | Structure | Amount | Yield (Step A + B) |
|---|---|---|---|
| 34 | 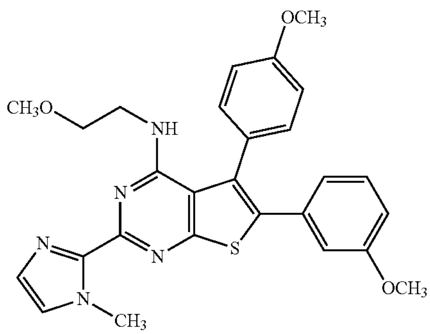 | 7.9 mg | 2.3% |
| 35 | 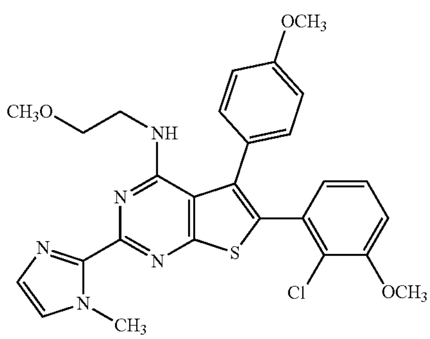 | 23.6 mg | 7% |
| 36 | 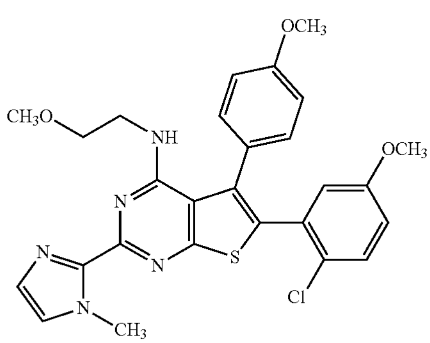 | 5.8 mg | 1.7% |

Example 37

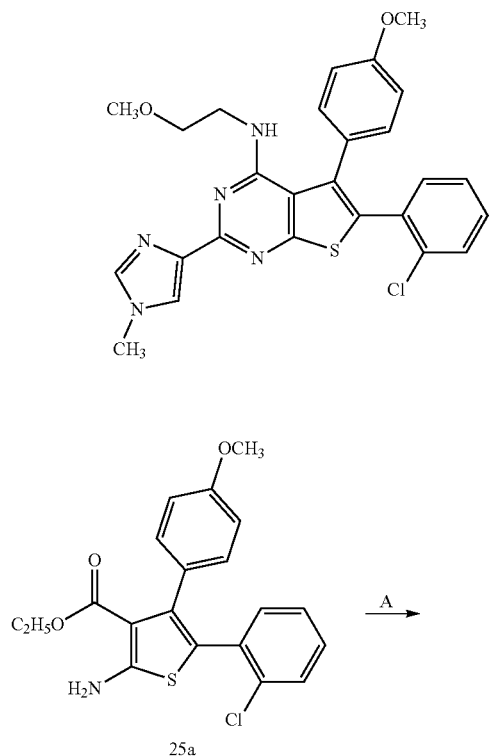

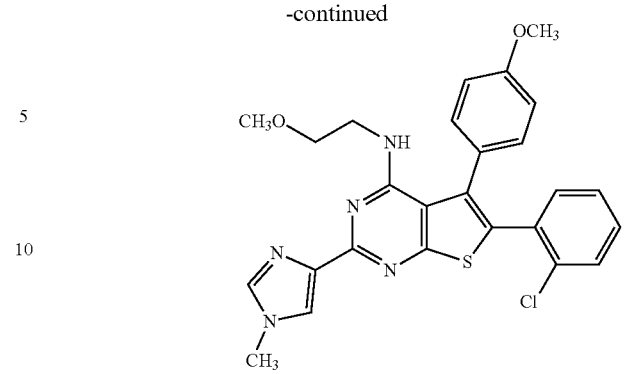

Step A: Using the procedure described in Scheme 4, Step E, except using aminothiophene 25a (prepared as described in Scheme 6) instead of 16a or 16b, and using 1-methyl-4-cyanoimidazole instead of 1-methyl-2-cyanoimidazole, the corresponding target compound 71 was obtained (380 mg, 80% yield).

Step B and Step C: In Step B, the crude material 71 was suspended in POCl$_3$ (2 mL) and diisopropylethylamine (0.6 mL) was added at r.t. The reaction mixture was refluxed for 16 h, the solution was cooled to r.t., evaporated under reduced pressure, diluted with ice-cold ammonia (20 mL, 20-25% of ammonia), the product 72 was extracted with chloroform (2*30 mL) and the solvent evaporated. In Step C, the residue (compound 72) was dissolved in DMSO and 3-methoxypropan-1-amine (5 equiv) was added. The mixture was heated at 100° C. overnight, cooled and purified by HPLC to obtain the target Example compound (9.2 mg, 2.7% yield).

Example 38

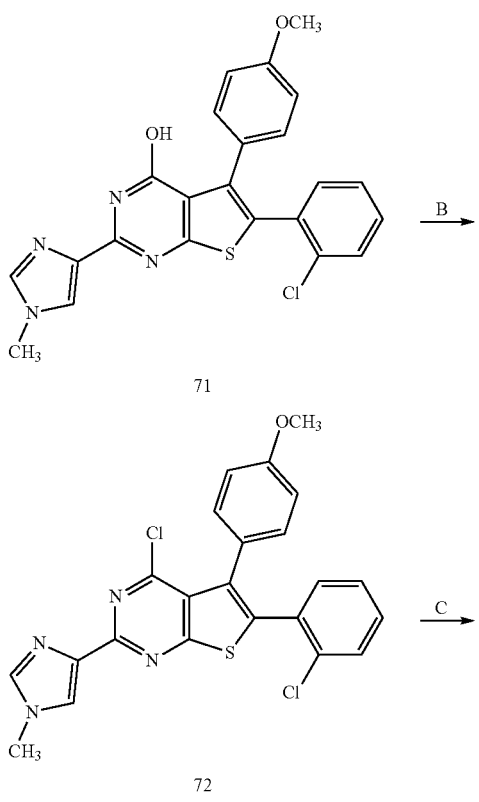

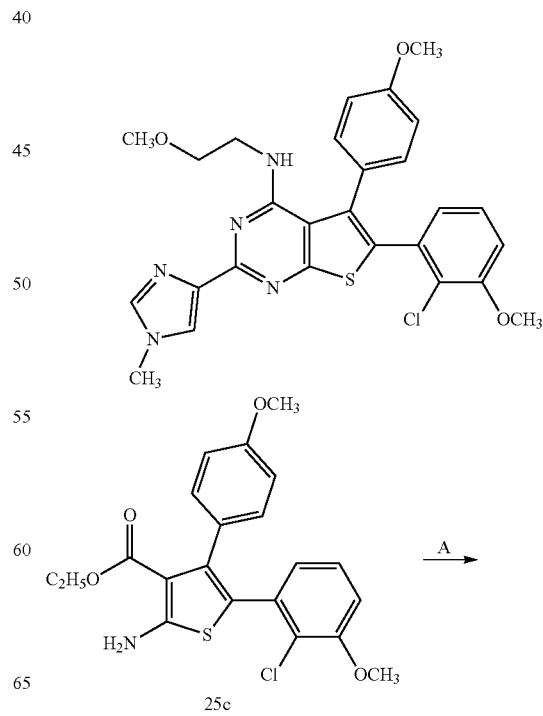

277

-continued

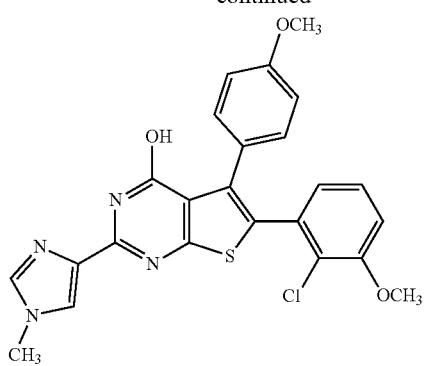

73

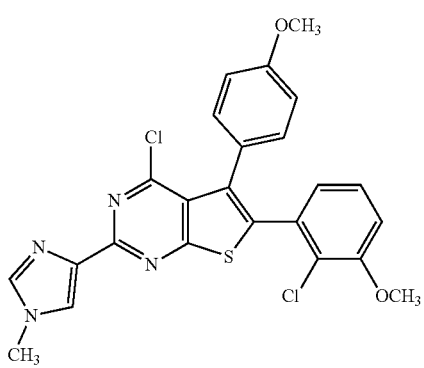

74

CH₃O NH
[structure]
(compound between 74 and text)

The target compound of Example 38 was prepared according to the procedure described in Example 37, Steps A-C, except starting with aminothiophene 25c (prepared as described in Scheme 6 for Example 38) instead of 25a in Example 37, Step A. The product of Step A (compound 73) was obtained in 60% yield (0.348 g). Following Step B (to give compound 74) and Step C produced the target Example compound in a combined 8% yield (34.4 mg).

278

Example 39

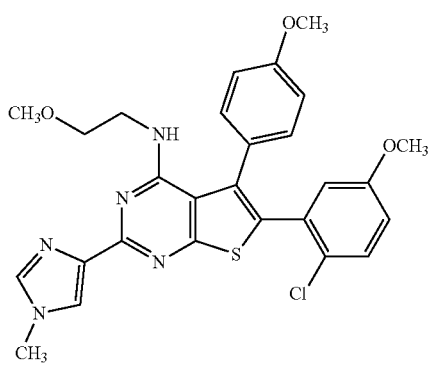

25d

75

76

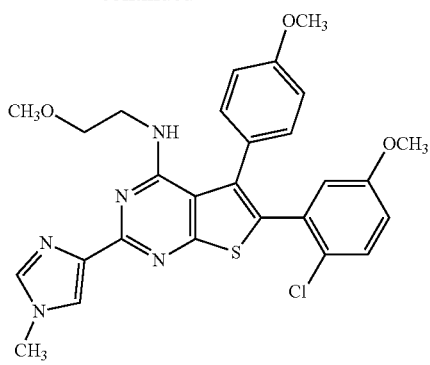

The target compound of Example 39 was prepared according to the procedure described in Example 37, Steps A-C, except starting with aminothiophene 25d (prepared as described in Scheme 6 for Example 39) instead of 25a in Example 37, Step A. The product of Step A (compound 75) was obtained in 62% yield (0.357 g). Following Step B (to give compound 76) and Step C produced the target Example compound in a combined 21% yield (84 mg).

Example 40

Step A and Step B: In Step A, the crude material 29a (synthesis described in Scheme 7), was suspended in $POC_3$ (2 mL) and diisopropylethylamine (0.6 mL) was added at r.t. The reaction mixture was refluxed for 16 h, the solution was cooled to r.t., evaporated under reduced pressure, diluted with ice-cold ammonia (20 mL, 20-25% of ammonia), the product 77 was extracted with chloroform (2*30 mL) and the solvent evaporated. In Step B, the obtained residue (compound 77) was dissolved in DMSO and 2-methoxyethylamine (5 equiv) was added. The mixture was heated at 100° C. overnight, cooled and purified by HPLC to obtain the target Example compound (41.4 mg, 12.3% yield).

Example 41

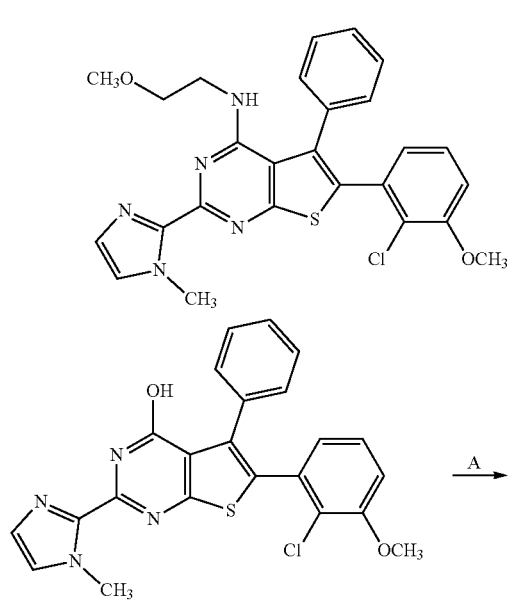

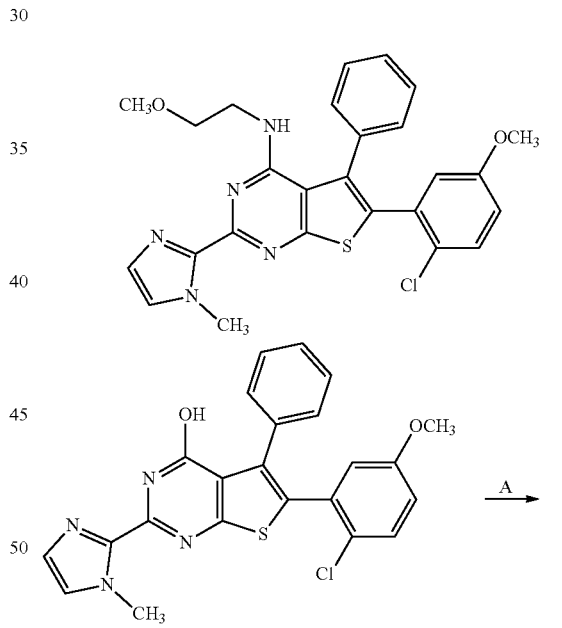

-continued

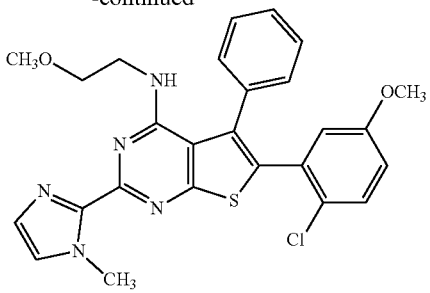

Step A and Step B: In Step A, the crude material 29b (synthesis described in Scheme 7), was suspended in POCl$_3$ (2 mL) and diisopropylethylamine (0.6 mL) was added at r.t. The reaction mixture was refluxed for 16 h, the solution was cooled to r.t., evaporated under reduced pressure, diluted with ice-cold ammonia (20 mL, 20-25% of ammonia), the product 78 was extracted with chloroform (2*30 mL) and the solvent evaporated. In Step B, the obtained residue (compound 78) was dissolved in DMSO and 2-methoxyethylamine (5 equiv) was added. The mixture was heated at 100° C. overnight, cooled and purified by HPLC to obtain the target Example compound (22.0 mg, 6.5% yield).

Example 42-Example 56

Examples 42-55 (shown in Table F) were prepared from compound 33 (prepared as described in Scheme 8) according to the procedure described in Scheme 8, Step E, using the appropriate boronic acid 34 (R=Ar, HetAr) (Examples 42, 44, 45, 46, 51, and 53), or boronic ester 35 (R=Ar, HetAr) (Examples 43, 47, 48, 49, 50, 52, 54, and 55) in Step E. For HPLC purification of the target Example compounds 42-55 (10-40% water-(acetonitrile) eluent), 0.1% HCl was added to the sample to produce the HCl salt. Example 56 is compound 33 in Scheme 8.

TABLE F

| Example | Structure | Amount | Yield (Scheme 8, Step E) |
|---|---|---|---|
| 42 | 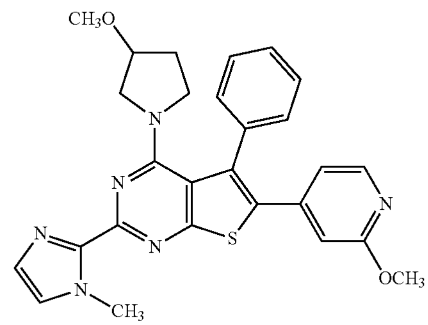 | 47 mg | 15% |
| 43 | 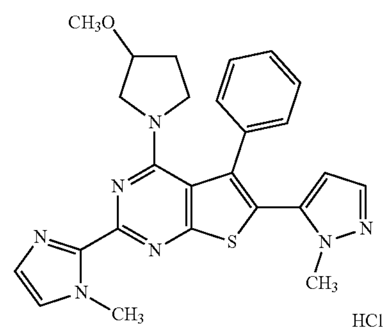 | 27.5 mg | 9% |
| 44 | 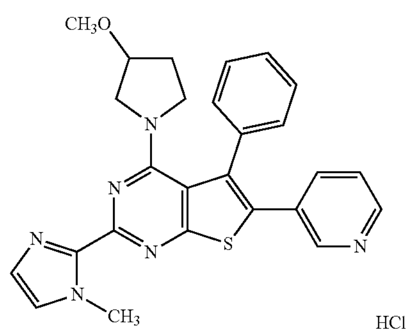 | 56.6 mg | 19% |

TABLE F-continued
| Example | Structure | Amount | Yield (Scheme 8, Step E) |
|---|---|---|---|
| 45 | 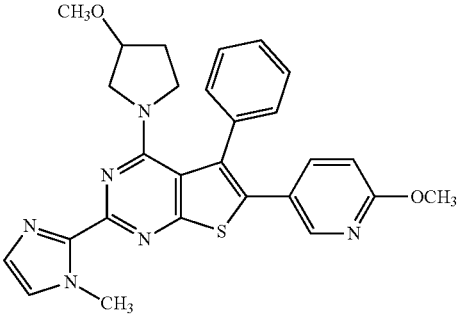 HCl | 54.5 mg | 17% |
| 46 | 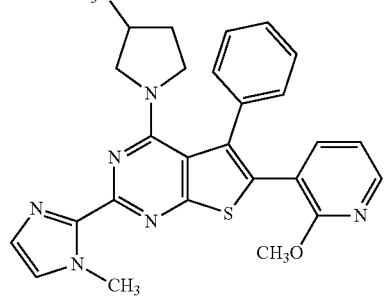 HCl | 19.8 mg | 6.2% |
| 47 | 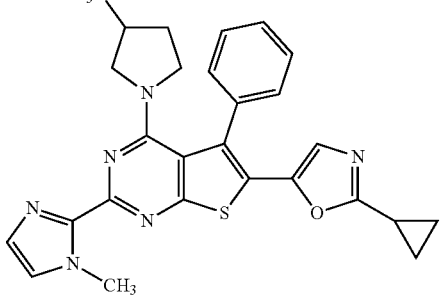 HCl | 21.4 mg | 6.7% |
| 48 | 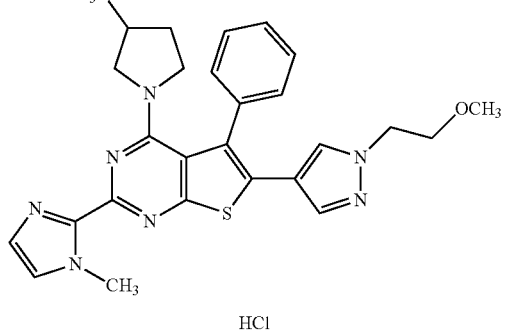 HCl | 152 mg | 48% |

TABLE F-continued

| Example | Structure | Amount | Yield (Scheme 8, Step E) |
|---|---|---|---|
| 49 | (structure) HCl | 35.4 mg | 10.6% |
| 50 | (structure) HCl | 167.2 mg | 55% |
| 51 | (structure) HCl | 69.5 mg | 20% |
| 52 | (structure) HCl | 14.2 mg | 4% |

TABLE F-continued

| Example | Structure | Amount | Yield (Scheme 8, Step E) |
|---|---|---|---|
| 53 | 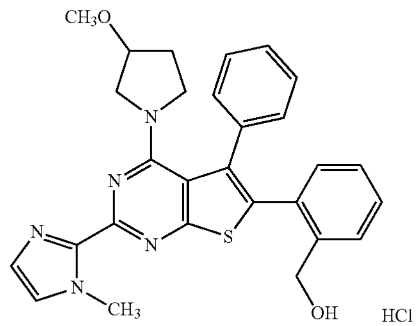 | 58.4 mg | 4% |
| 54 | 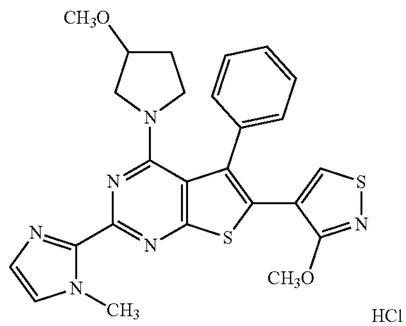 | 94.8 mg | 28% |
| 55 | 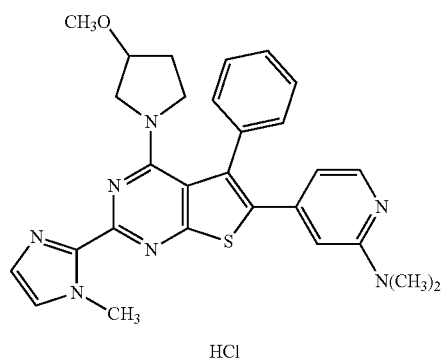 | 25.5 mg | 8% |
| 56 | 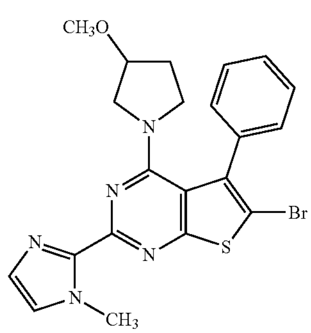 | — | — |

Example 57-Example 59

Examples 57-59 (shown in Table G) were prepared from compound 39 (synthesized as described in Scheme 9), according to the procedure described in Scheme 9, Step D and Step E, using the appropriate amine 41 ($R^1R^2NH$) in Step E. For HPLC purification of the target Example compound 59 (30-45% water-(acetonitrile) eluent), 0.1% HCl was added to the sample to produce the HCl salt.

TABLE G
| Example | Structure | Amount | Yield (Scheme 9 Step D + E) |
|---|---|---|---|
| 57 | 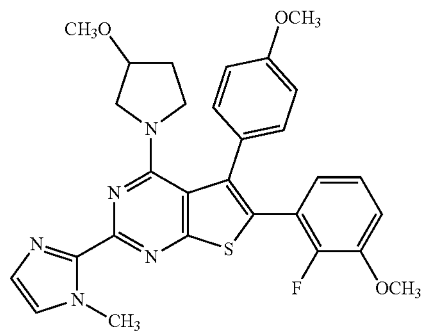 | 120 mg | 28% |
| 58 | 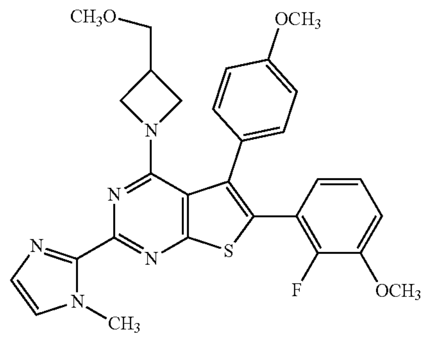 | 93 mg | 25% |
| 59 | 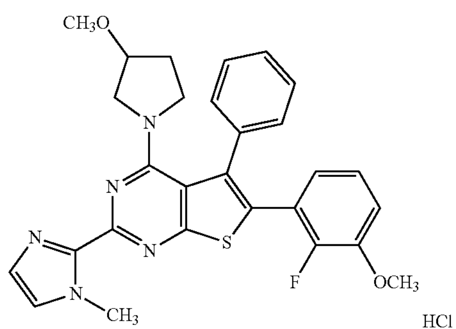 | 70 mg | 20% |
Example 60
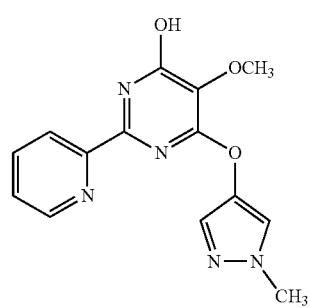
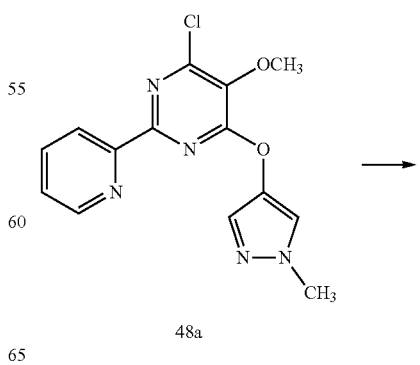
48a -continued

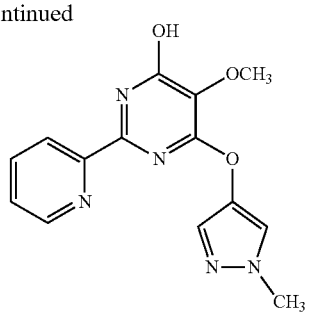

To a solution of compound 48a (1 eq) (synthesis described in Scheme 10) in dioxane (30 mL), a solution of KOH (~1 g, 15 eq) in water (10 mL) was added. The resulting mixture was stirred at 100° C. for 12 h, acidified with HCl and evaporated. The residue was taken up with methanol (30 mL), the precipitate was filtered, washed with MeOH (2*20 mL) and filter cake was discarded. The solvent was evaporated in vacuo and the residue was purified by reverse phase HPLC to obtain 14 mg of the target Example compound.

Example 61-Example 83

Examples 61-66 were prepared according to the procedure described for the synthesis of Example 60, except starting with 48b-g, respectively (synthesis described in Scheme 10) instead of 48a. The amount and yield of the target Example compounds are reported in the Table H below.

Examples 67-76 were prepared according to the procedure described for the synthesis of general compound 53 in Scheme 11, using the appropriate amine $R^1R^2NH$ 41 in Scheme 11, Step C. The amount and yield of the target Example compounds obtained in Scheme 11, Step C are reported in the Table H below.

Examples 77-82 were prepared according to the procedure described for the synthesis of general compound 56, as shown in Scheme 12, using the appropriate amine $R^1R^2NH$ 41 in Scheme 12, Step B. The amount and yield of the target Example compounds obtained in Scheme 12, Step B are reported in the Table H below. A portion of compound 55 (prepared as described in Scheme 12) was purified to give Example 83.

TABLE H

| Example | Structure | Amount | Yield |
|---|---|---|---|
| 61 | (structure) | 48 mg | 25% |
| 62 | (structure) | 19 mg | 28% |
| 63 | (structure) | 19.7 mg | 27% |
| 64 | (structure) | 18 mg | 20% |
| 65 | (structure) | 14 mg | 30% |
| 66 | (structure) | 16 mg | 22% |

TABLE H-continued

| Example | Structure | Amount | Yield |
|---|---|---|---|
| 67 | (pyridin-2-yl pyrimidine with 5,6-diOH, 4-carboxamide linked to 1,2,3,4-tetrahydroisoquinolin-2-yl) | 105 mg | 24.8% |
| 68 | (pyridin-2-yl pyrimidine with 5,6-diOH, 4-carboxamide linked to morpholino) | 80.1 mg | 22.8% |
| 69 | (pyridin-2-yl pyrimidine with 5,6-diOH, 4-carboxamide N-methyl-N-benzyl) | 122.6 mg | 30% |
| 70 | (pyridin-2-yl pyrimidine with 5,6-diOH, 4-carboxamide NH-benzyl) | 69 mg | 17% |
| 71 | (pyridin-2-yl pyrimidine with 5,6-diOH, 4-carboxamide linked to pyrrolidin-1-yl) | 90 mg | 25.9% |
| 72 | (pyridin-2-yl pyrimidine with 5,6-diOH, 4-carboxamide NH-cyclopentyl) | 17 mg | 4.9% |
| 73 | (pyridin-2-yl pyrimidine with 5,6-diOH, 4-carboxamide N-methyl-N-isobutyl) | 198.2 mg | 53.9% |
| 74 | (pyridin-2-yl pyrimidine with 5,6-diOH, 4-carboxamide NH-isobutyl) | 43 mg | 12% |
| 75 | (pyridin-2-yl pyrimidine with 5,6-diOH, 4-carboxamide N-methyl-N-(2-methoxyethyl)) | 15 mg | 4% |
| 76 | (pyridin-2-yl pyrimidine with 5,6-diOH, 4-carboxamide NH-cyclobutyl) | 16 mg | 4.6% |

TABLE H-continued
| Example | Structure | Amount | Yield |
|---|---|---|---|
| 77 | 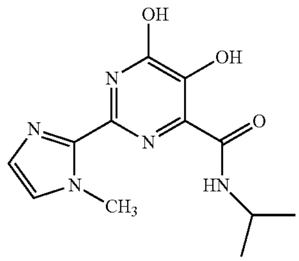 [SMILES: CC(C)NC(=O)c1nc(-c2nccn2C)nc(O)c1O] | 13.3 mg | 3.7% |
| 78 | 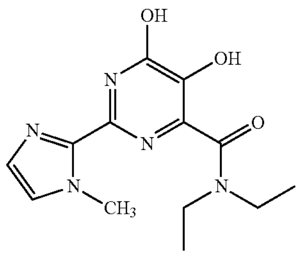 [SMILES: CCN(CC)C(=O)c1nc(-c2nccn2C)nc(O)c1O] | 6.3 mg | 1.7% |
| 79 | 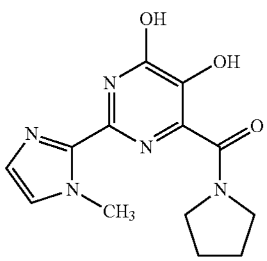 [SMILES: Cn1ccnc1-c1nc(O)c(O)c(C(=O)N2CCCC2)n1] | 16.4 mg | 4.4% |
| 80 | 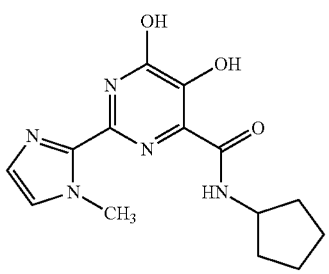 [SMILES: Cn1ccnc1-c1nc(O)c(O)c(C(=O)NC2CCCC2)n1] | 31.5 mg | 8.1% |
| 81 | 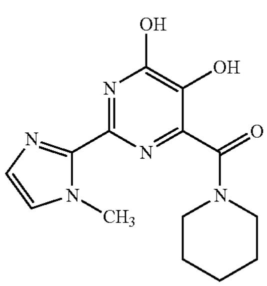 [SMILES: Cn1ccnc1-c1nc(O)c(O)c(C(=O)N2CCCCC2)n1] | 13 mg | 3.3% |
TABLE H-continued
| Example | Structure | Amount | Yield |
|---|---|---|---|
| 82 | | 7.5 mg | 2.0% |
| 83 | | — | — |
Example 84
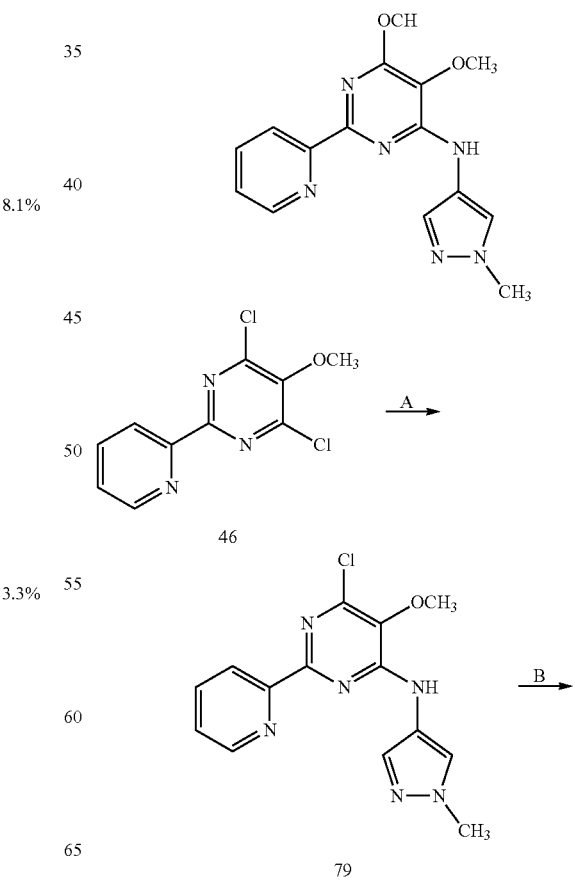

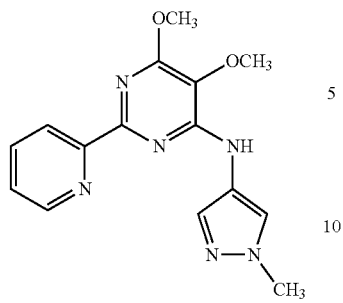

Step A: A mixture of starting compound 46 (1 eq) (prepared as described in Scheme 10), corresponding amine 1-methyl-1H-pyrazol-4-amine (1 eq) and potassium carbonate (2 eq) in acetonitrile was refluxed for 24 hours. The reaction mixture was cooled to room temperature, diluted with water and extracted with CHCl₃. The organic layer was dried over anhydrous MgSO₄, filtered and concentrated under reduced pressure to give compound 79 (0.076 g, 30.4% yield). The product 79 was used without any additional purification.

Step B: Sodium methylate (1.3 eq) was added at room temperature to a solution of corresponding compound 79 in methanol (2 M) and the solution was heated at reflux for 24 hours. The methanol was removed on a rotary evaporator, the residue was taken up in methylene chloride. Product was purified by reverse phase HPLC to give the target Example compound (15.2 mg, 20% yield).

Example 85

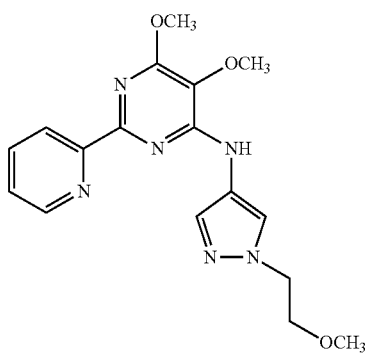

Step A: A mixture of starting compound 46 (1 eq) (prepared as described in Scheme 10), corresponding amine 1-(2-methoxyethyl)-1H-pyrazol-4-amine (1 eq), and potassium carbonate (2 eq) in acetonitrile was refluxed for 24 hours. The reaction mixture was cooled to room temperature, diluted with water and extracted with CHCl₃. The organic layer was dried over anhydrous MgSO₄, filtered and concentrated under reduced pressure to give compound 80 (0.23 g, 70% yield). The product 80 was used without any additional purification.

Step B: Sodium methylate (1.3 eq) was added at room temperature to a solution of corresponding compound 80 in methanol (2 M) and the solution was heated at reflux for 24 hours. The methanol was removed on a rotary evaporator, the residue was taken up in methylene chloride. Product was purified by reverse phase HPLC to give the target Example compound (68.4 mg, 30% yield).

Example 86

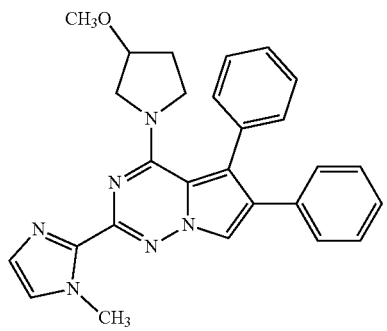

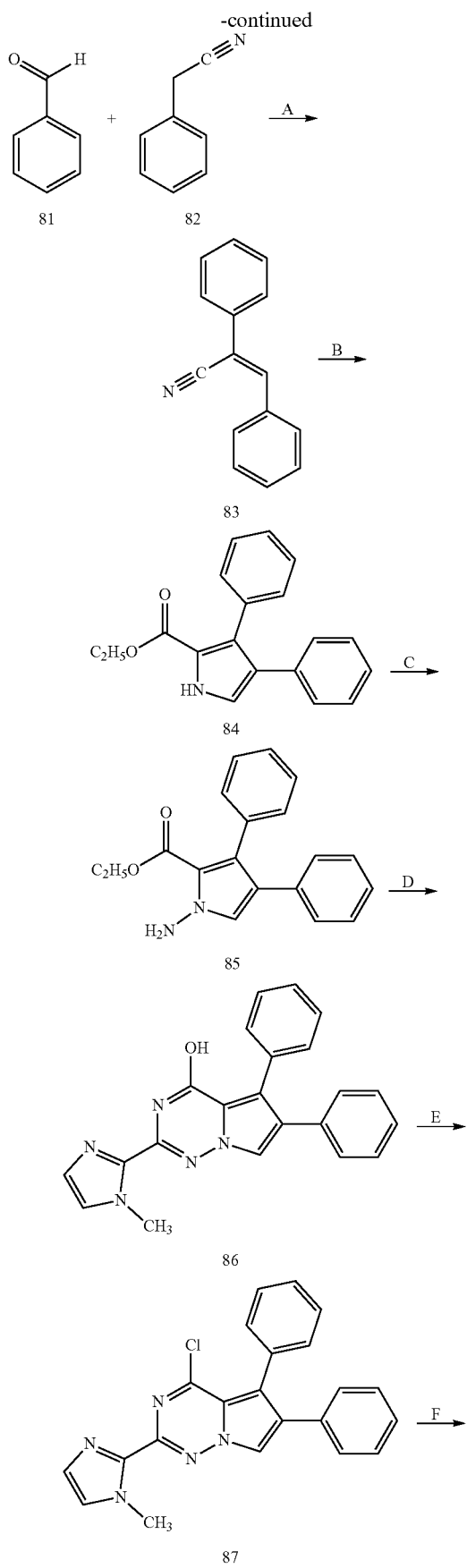

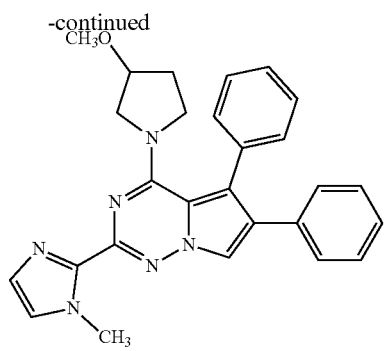

Step A: Benzaldehyde 81 (10.0 g, 94.2 mmol) and phenylacetonitrile 82 (11.0 g, 94.2 mmol) were placed in a round-bottomed flask equipped with a magnetic stirring bar. Absolute ethyl alcohol (300 mL, 3 mL/mmol of benzaldehyde) was added followed by an ethanolic solution of sodium ethoxide (95 mL, 1 M, ca. 1 mL/mmol of benzaldehyde). The mixture was refluxed for 2 h, changing color to yellow. Towards the end of the reaction a yellow precipitate was formed. After cooling the reaction mixture to room temperature, the precipitate was filtered, washed with ethanol and dried to give compound 83 (10 g, 52% yield).

Step B: In a dry flask equipped with magnetic stirring, cyanostilbene 83 (10.0 g, 48.7 mmol) and ethyl isocyanoacetate (5.51 g, 48.7 mmol) were dissolved in dry tetrahydrofuran (100 mL). The mixture was cooled to 0° C. and a solution of potassium tert-butoxide (1 M in tetrahydrofuran) was added. The mixture was stirred under argon until thin-layer chromatography showed complete consumption of the starting material. The mixture was diluted with water and extracted with dichloromethane. Combined organic extracts were dried over anhydrous sodium sulfate, filtered, and the solvents were removed on a rotary evaporator. The product was purified by column chromatography (silica gel, dichloromethane) to yield the product 84 (9.9 g, 70% yield).

Step C: To a solution of pyrrole 84 (4.0 g, 13.73 mmol) in DMF (50 mL) was added NaH (0.66 g, 16.5 mmol, 60% dispersion in mineral oil), and the reaction was stirred for 45 min at room temperature. $NH_2Cl$ (230 mL, ca. 0.12 M in MTBE) was added via syringe while maintaining under Ar. The reaction was monitored by TLC (ethyl acetate:hexane=1:2) until completion. The reaction was then quenched with saturated aqueous $Na_2S_2O_3$, diluted with water, and extracted with MTBE. The ether layer was dried ($Na_2SO_4$), filtered, and concentrated in vacuo to give product 85 (3.4 g, 81% yield).

Step D: To a solution of compound 85 (0.3 g, 0.98 mmol) and 1-methyl-1H-imidazole-2-carbonitrile (0.16 g, 1.47 mmol) in abs. 1,4-dioxane, NaH (78 mg, 1.96 mmol, 60% dispersion in mineral oil) was added. The mixture was stirred at reflux for 2 h. The reaction was monitored by TLC (ethyl acetate:hexane=1:2) until completion. After cooling to room temperature, the mixture was diluted, acidified with acetic acid and formed precipitate was filtered, washed with water, hexane and dried to give product 86 (0.34 g, 94% yield).

Step E: To a suspension of compound 86 (0.34 g, 0.92 mmol) in $POCl_3$ (10 ml) DIPEA (2 mL) was added. The mixture was stirred at 85° C. for 5 h. After cooling to room temperature, the mixture was quenched with 25% ammonia in water with ice. After stirring for 15 min, formed precipitate was filtered, washed with water and dried to give crude product 87 (0.4 g, 78% yield), which was used in the next step without further purification.

Step F: To a solution of compound 87 (0.27 g, 0.7 mmol) in chloroform (5 mL) DIPEA (0.36 mL, 2.1 mmol) and 3-methoxypyrrolidine hydrochloride (0.14 g, 1.0 mmol) were added. The mixture was stirred at 60° C. for 2 h. The reaction was monitored by TLC (ethyl acetate) until completion. After completion of the reaction, the reaction mixture was cooled down to r.t. and diluted with water. Organic phase was separated, washed with water, brine, dried (Na$_2$SO$_4$) and evaporated in vacuo. The residue was purified by preparative HPLC to give the Example compound (70 mg, 22% yield).

Example 87

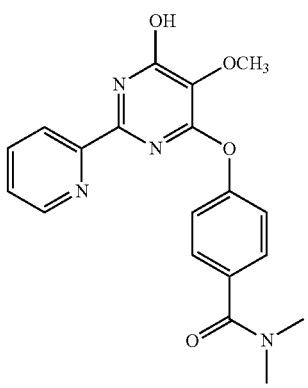

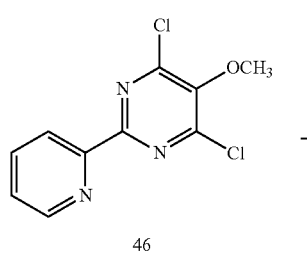

46

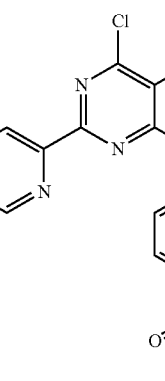

88

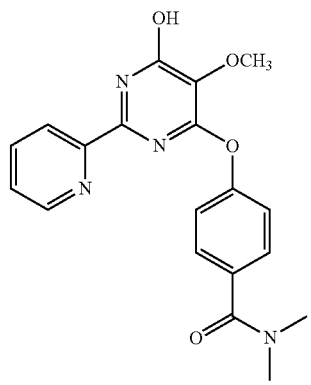

Step A: Compound 88 was prepared from compound 46 (from Scheme 10, Step B) according to the procedure described in Scheme 10, Step C, using 4-hydroxy-N,N-dimethylbenzamide (1 eq.) as ROH 47 and K$_2$CO$_3$ (0.49 g, 3 eq). The resulting mixture was heated at 70° C. for 24 h, cooled, taken up with water (50 mL) and extracted with MTBE (3*30 m L). The organic extracts were washed with brine (2*30 mL), dried over Na$_2$SO$_4$ and evaporated in vacuo to obtain compound 88 (80-90% purity) (0.16 g, 34% yield). This compound was used for the next step without purification.

Step B: To a solution of compound 88 (1 eq) in dioxane (30 mL), a solution of KOH (~1 g, 15 eq) in water (10 mL) was added. The resulting mixture was stirred at 100° C. for 12 h, acidified with HCl and evaporated. The residue was taken up with methanol (30 mL), the precipitate was filtered, washed with MeOH (2*20 mL) and the filtercake was discarded. The solvent was evaporated in vacuo and the residue was purified by reverse phase HPLC to obtain the target compound (9.5 mg, 6.2% yield).

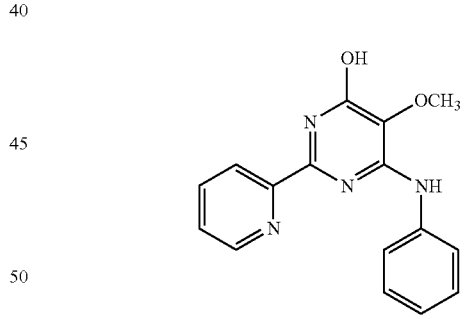

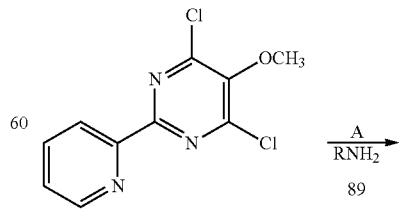

46

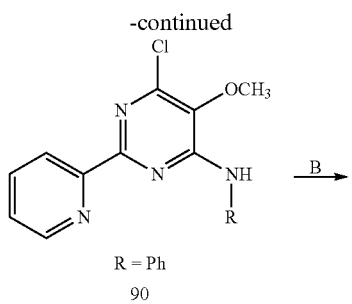

R = Ph
90

B →

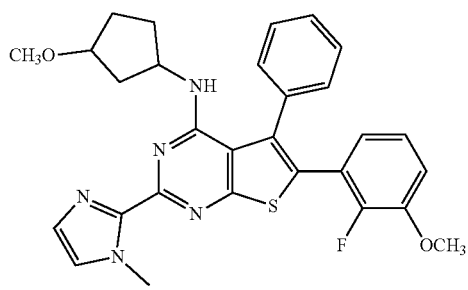

Example 88

Step A: General procedure: To a solution of compound 46 0.3 g (1 eq) (prepared according to the procedure described in Scheme 10, Step B), and the appropriate corresponding amine 89 (1 eq) in DMF (1.5 mL) was added K₂CO₃ (3 eq, 0.5 g). The resulting mixture was stirred at 90° C. for 12 h, taken up with water (20 mL), extracted with EtOAc (3*15 mL). The combined organic extract was washed with brine (2*20 mL), dried over Na₂SO₄ and evaporated in vacuo to obtain the crude product. Using aniline as the amine produced compound 90 which was used for the next step without purification (0.13 g, 35% yield).

Step B: Compound 90 obtained from Step A was dissolved in DMSO (2 mL). To this solution was added KOH (0.8 g) and water 1 mL. The resulting mixture was stirred in sealed tube at 160° C. for 48 h, cooled to ambient temperature, taken up with water (20 mL), extracted with EtOAc (3*15 mL). The combined organic extract was washed with brine (2*20 mL), dried over Na₂SO₄ and evaporated in vacuo to obtain the crude product, which was purified by HPLC to obtain the Example compound (76.8 mg, 63% yield).

Example 89 and Example 90

Example 89 and Example 90 (shown in Table I) were prepared from compound 46 (prepared according to the procedure described in Scheme 10, Step B) according to the general procedure described for Example 88, Steps A and B, except using the appropriate corresponding RNH₂ amine 89 in Step A.

TABLE I

| Example | Structure | Amount and Yield, Step A | Amount and Yield, Step B |
| --- | --- | --- | --- |
| 89 | (structure with OH, OCH₃, pyridyl-pyrimidine-NH linked to 1-ethyl pyrazole) | 0.12 g, 30% | 11.2 mg, 9.9% |
| 90 | (structure with OH, OCH₃, pyridyl-pyrimidine-NH linked to 3-ethoxyphenyl) | 0.13 g, 32% | 31.2 mg, 25.3% |

Example 91

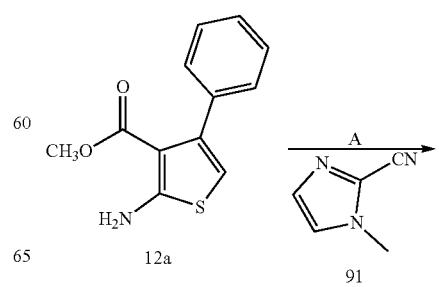

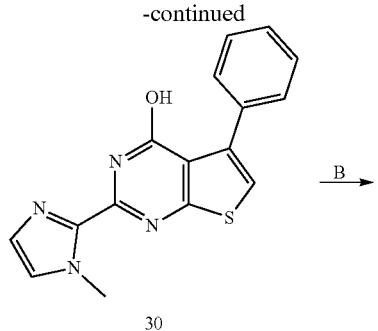

30

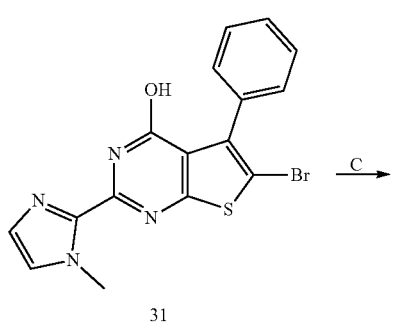

31

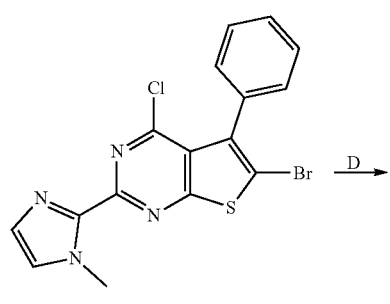

32

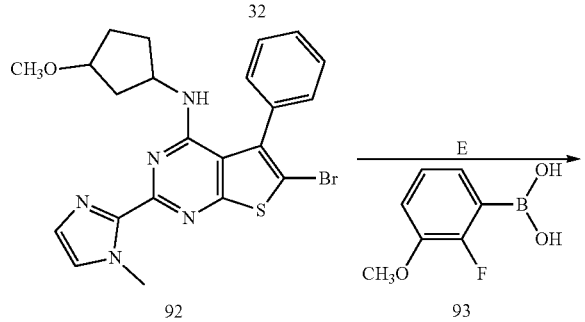

92                                       93

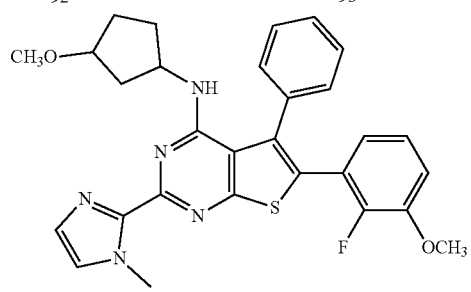

Step A: Compound 30 was prepared as described in Scheme 8, Step A. Thus to a stirred solution of 12a (18 g, 73 mmol) in dry methanol (180 mL) was added 1-methyl-1H-imidazole-2-carbonitrile 91 (10.2 g, 94.5 mmol) at room temperature and then potassium tert-butylate (24.5 g, 219 mmol) was added portion-wise. Then reaction mixture was refluxed for 16 h, cooled to room temperature and precipitate (potassium salt of target compound 30) was filtered. After this precipitate was dissolved in water (180 mL), acidified by acetic acid (18 mL) and stirred at room temperature for 15 min. Then precipitate was filtered, washed with water and air dried to give the target compound 30 as white solid (15.2 g, 64% yield).

Step B: Compound 31 was prepared as described in Scheme 8, Step B. To a stirred suspension of compound 30 from the previous step (13 g, 42.3 mmol) in dry DMF (390 mL) was added N-bromosuccinimide (9.02 g, 50.7 mmol) at room temperature and then the reaction mixture was stirred at 80° C. for 16 h. After this, precipitate was filtered and air dried to give the target compound 31 as light yellow solid (9.8 g, 60% yield).

Step C: Compound 32 was prepared as described in Scheme 8, Step C. To a stirred suspension of bromide 31 from the previous step (8.5 g, 21.3 mmol) in POCl₃ (30 mL) was added diisopropylethylamine (10 mL) at room temperature and reaction mixture was refluxed for 16 h. Then solution was cooled to room temperature, evaporated under reduced pressure, diluted with water (350 mL) and neutralized by ice cooled water solution of ammonia (120 mL, 20-25% of ammonia), product was extracted by chloroform (2*100 mL). Combined extract was evaporated under reduced pressure and purified by flash chromatography (eluent—CHCl₃:MeCN—20:1) to give the target compound 32 as yellow solid (4.7 g, 53% yield).

Step D: To a stirred solution of chloride 32 from the previous step (3.5 g, 8.58 mmol) in chloroform (50 mL) was added triethylamine (3.0 mL, 21.7 mmol) and a mixture of racemic cis-1-amino-3-methoxycyclopentane and racemic trans-1-amino-3-methoxycyclopentane (1.51 g, 11.1 mmol). The reaction mixture was refluxed for 1 h, cooled to r.t, diluted with water (100 mL) and extracted twice with chloroform (2*30 mL). Combined organic layer was dried with Na₂SO₄, evaporated under reduced pressure and purified by flash chromatography (eluent—EtOAc:Et₃N—20:1) to give target compound 92 (a mixture of racemic cis and racemic trans isomers) as a light yellow solid (3.2 g, 80% yield).

Step E: General procedure: Compound 92 from Step D (0.6 mmol) was mixed with the appropriate boronic acid/pinacol boronic ester (0.9 mmol), K₂CO₃ (3.6 mmol), Pd(dppf)Cl₂ (0.06 mmol), in 1,4-dioxane (15 mL) under argon atmosphere. The reaction was then stirred at 100° C. for 16 h under argon atmosphere. Then reaction mixture was cooled to room temperature, diluted with water (50 mL) and extracted twice with chloroform (2*25 mL). Combined organic layer was dried with Na₂SO₄, evaporated under reduced pressure and purified from resins by flash chromatography (eluent—EtOAc:Et₃N—20:1). Finally, crude products were purified by HPLC (eluent—H₂O:MeOH) to give target compounds. Thus, from compound 33 and (2-fluoro-3-methoxyphenyl)boronic acid 93 the target Example compound was obtained as a mixture of racemic cis and racemic trans isomers (0.133 g, 41% yield).

Example 92

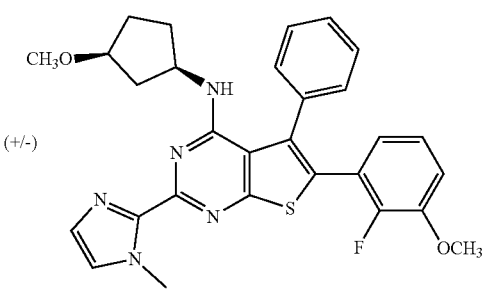

The cis isomer of Example 91 was separated from the cis/trans isomer mixture (obtained in Example 91, Step E) by HPLC utilizing the following conditions: Chiralpak IB column (250×20 mm, particle size 5 um, mobile phase: hexane-isopropyl alcohol-methyl alcohol-diethylamine, 95%-05%-5%-0.1%, flow rate 15 mL/min. The target Example compound was obtained as the racemate (0.0584 g).

Example 93

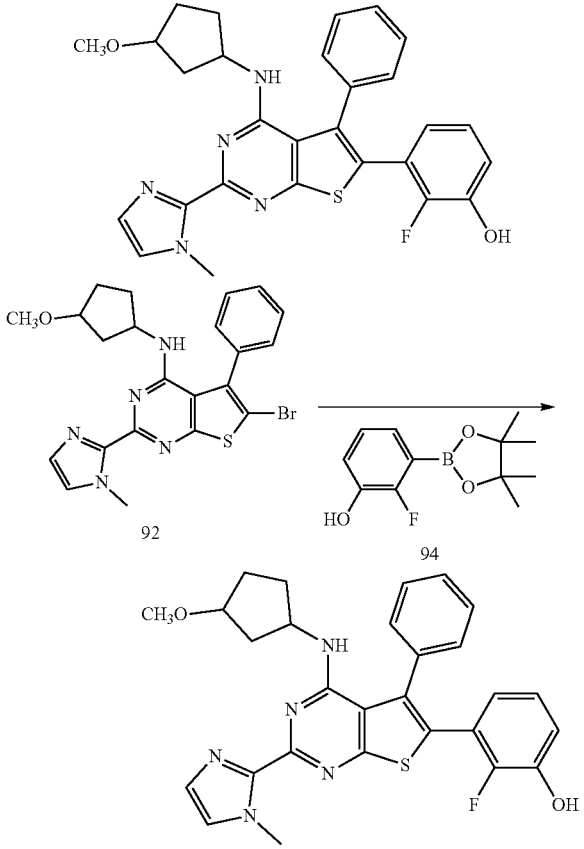

Following the procedure described in Example 91, Step E, compound 92 (prepared as described in Example 91, Step D) and 2-fluoro-3-(4,4,5,5-tetramethyl-1,3,2-dioxaborolan-2-yl)phenol 94 produced the Example compound as a mixture of racemic cis and racemic trans isomers (0.0542 g, 17.5% yield).

Example 94

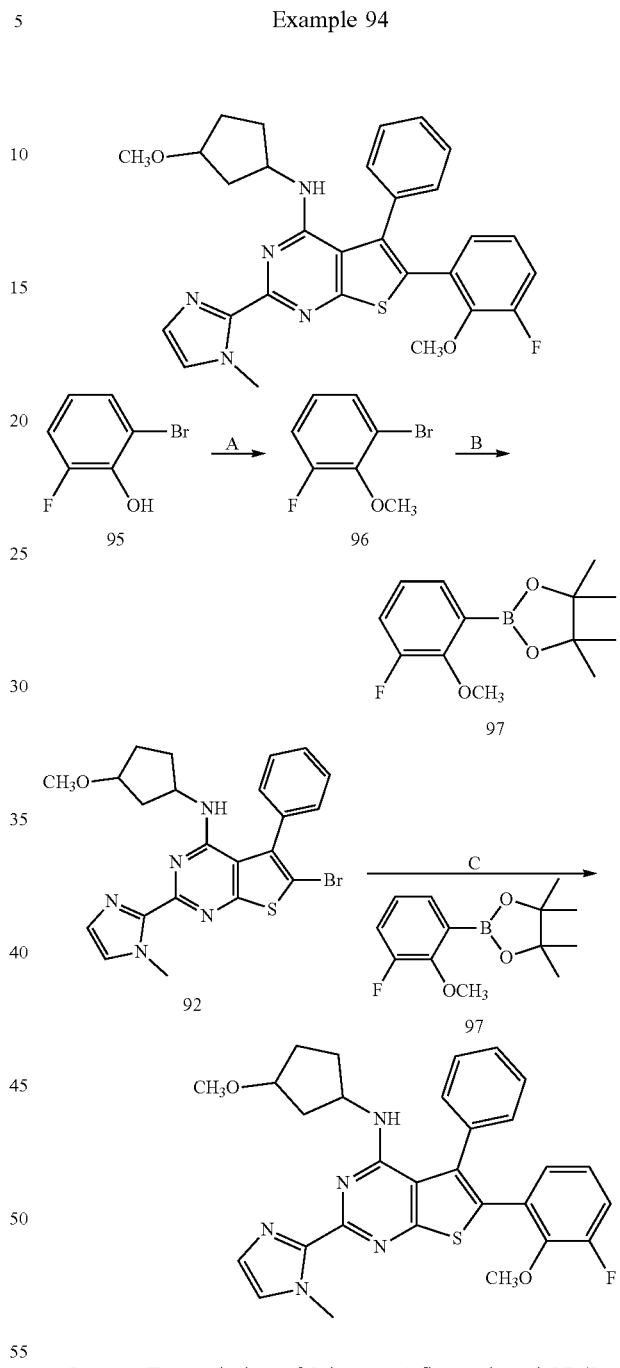

Step A: To a solution of 2-bromo-4-fluorophenol 95 (0.1 mol) in DMF (100 mL) was added $K_2CO_3$ (0.1 mol) and methyl iodide (0.1 mol), and then stirred 24 h at room temperature. Water (400 mL) was added and the mixture was extracted with hexane. The organic phase was washed with water, dried, filtered over a plug of silica gel and evaporated to yield the target compound 96 (3.4 g, yield—88%).

Step B: To a stirred solution of starting material 96 (3.3 g, 16.04 mmol) in 1,4-dioxane (30 mL) was added bis(pinacolato)diboron (4.06 g, 16.04 mmol), $PdCl_2(PPh_3)_2$ (0.56 g, 0.802 mmol) and potassium acetate (3.14 g, 32.08 mmol) at room temperature, and the resulting mixture was stirred at 90° C. under nitrogen for 5 h. The reaction mixture was diluted with ethyl acetate (50 mL) and filtered through celite. The filtrate was concentrated under vacuum and the residue was purified by column chromatography on silica gel (hexane) to give target compound 97 (3.2 g, 80% yield) as a white solid.

Step C: Following the procedure described in Example 91, Step E, compound 92 (prepared as described in Example 91, Step D) and 2-(3-fluoro-2-methoxyphenyl)-4,4,5,5-tetramethyl-1,3,2-dioxaborolane 97 produced the target compound as a mixture of racemic cis and racemic trans isomers (0.1497 g, 47% yield).

Example 95

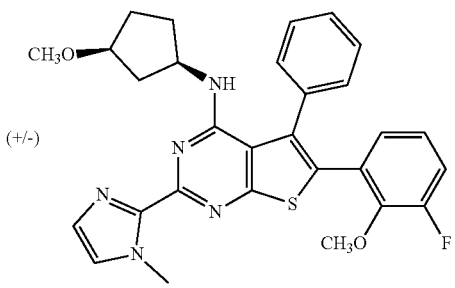

The cis isomer of Example 94 was separated from the cis/trans isomer mixture (obtained in Example 94, Step C) by HPLC utilizing the following conditions: Chiralpak IB column (250×20 mm, particle size 5 um, mobile phase: hexane-isopropyl alcohol-methyl alcohol-diethylamine, 95%-5%-5%-0.1%, flow rate 15 mL/min. The target Example compound was obtained as the racemate (0.0539 g).

Example 96

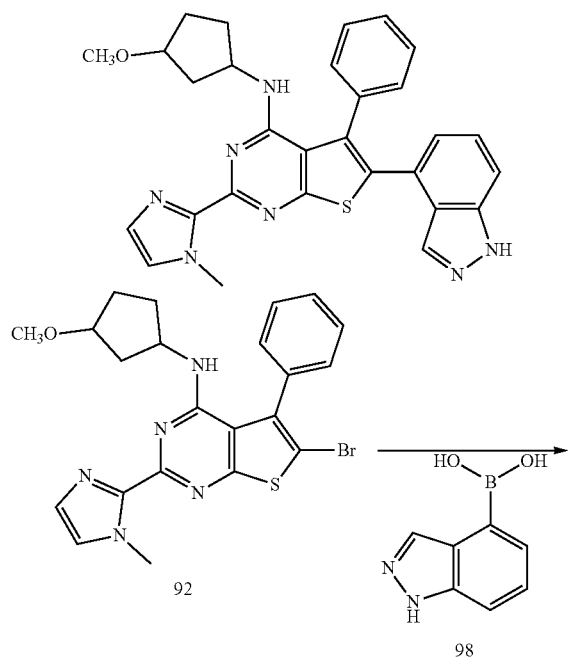

-continued

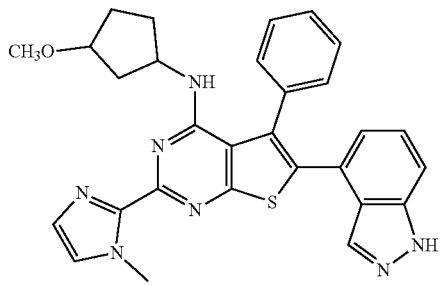

Following the procedure described in Example 91, Step E, compound 92 (prepared as described in Example 91, Step D) and 1H-indazol-4-yl)boronic acid 98 produced the target Example compound as a mixture of racemic cis and racemic trans isomers (0.0798 g, 25.2% yield).

Example 97

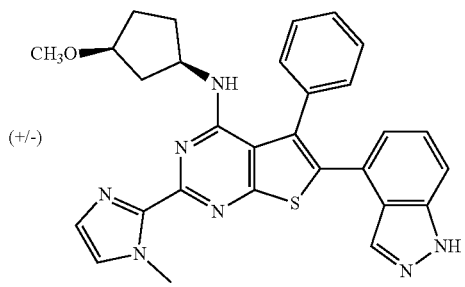

The cis isomer was separated from the cis/trans isomer mixture obtained in Example 96 by HPLC, utilizing the following conditions: column: Chiralpak IB column (250× 20 mm, particle size 5 um, mobile phase: hexane-isopropyl alcohol-methyl alcohol-diethylamine, 95%-5%-5%-0.1%, flow rate 15 mL/min. The target Example compound was obtained as a racemate (0.03594 g).

Example 98

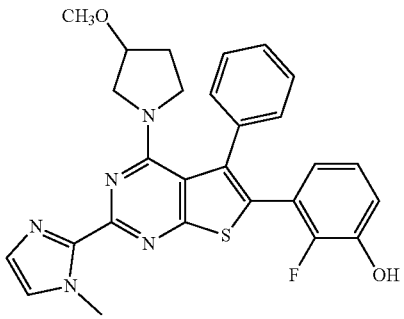

-continued

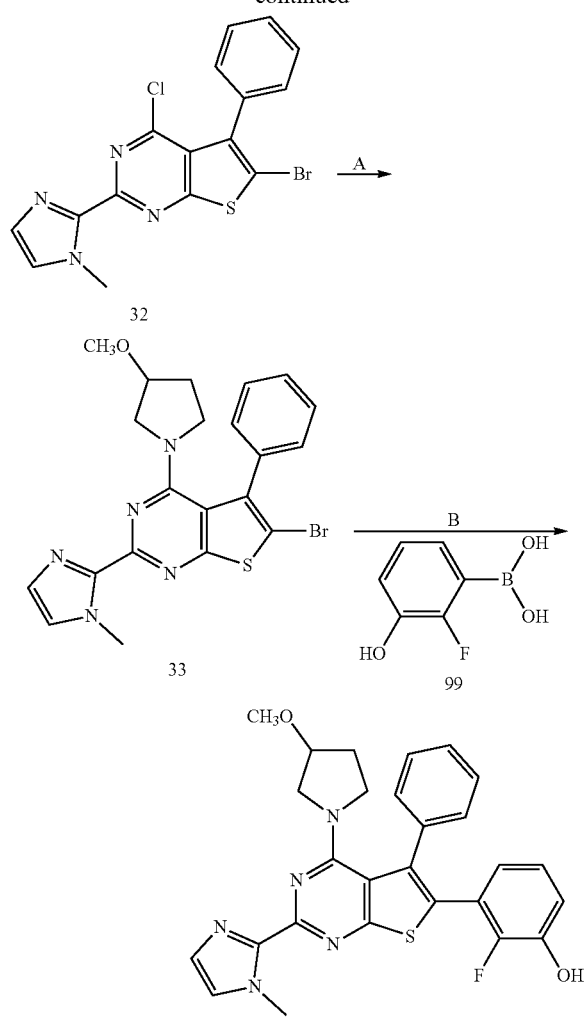

Step A: Starting compound 32 (prepared as described in Scheme 8, Step D) was used in quantity of 0.5 g. Using the procedure described in Scheme 8, Step D, the desired product 33 was obtained with the yield of 51% (0.3 g).

Step B: Starting compound 33 was used in quantity of 0.25 g (0.53 mmol). Using the general procedure described in Example 91, Step E, and boronic acid 99, the Example compound was obtained (0.0445 g, 16.7% yield).

Example 99

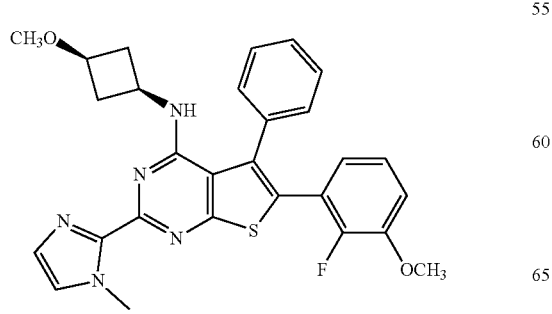

-continued

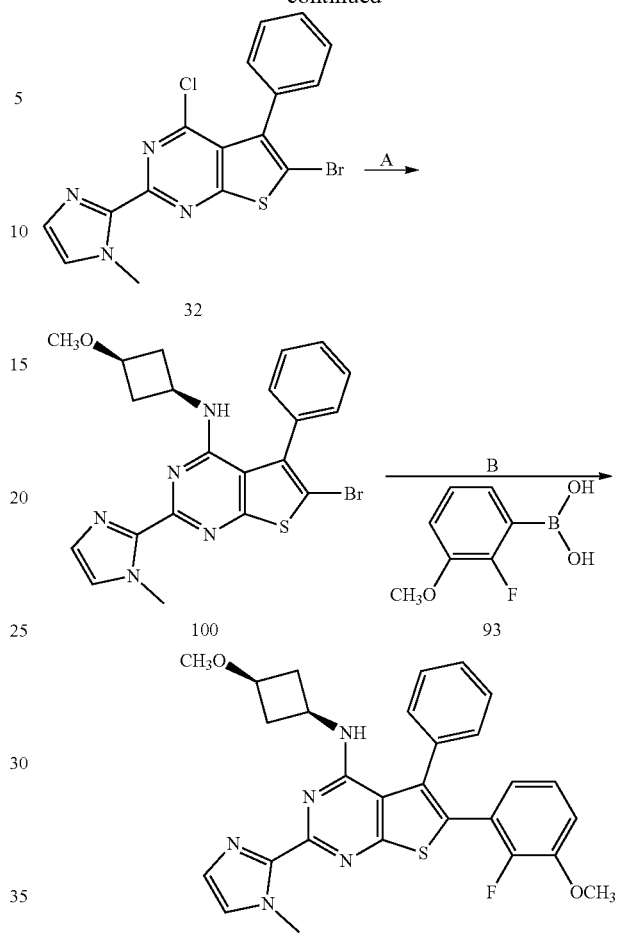

Step A: Starting compound 32 (prepared as described in Scheme 8, Step D) was used in quantity of 0.6 g. Using the procedure described in Example 91, Step D, except using cis-1-amino-2-methoxycyclobutane (in place of the mixture of racemic cis-1-amino-3-methoxycyclopentane and racemic trans-1-amino-3-methoxycyclopentane), produced compound 100 (0.58 g, 84% yield).

Step B: Starting compound 100 was used in quantity of 0.28 g (0.6 mmol). Following the general procedure described in Example 91, Step E, and boronic acid 93, produced the Example compound (0.0235 g, 7.6% yield).

Example 100

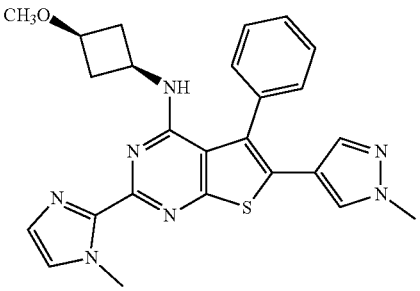

313
-continued

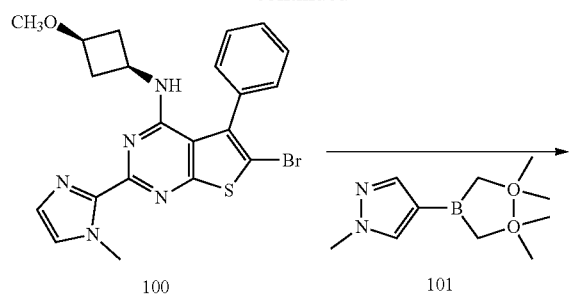
100

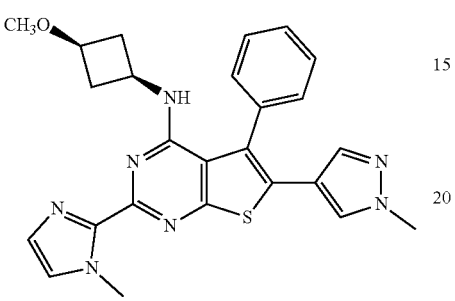

Starting compound cis-6-bromo-N-(3-methoxycyclobutyl)-2-(1-methyl-1H-imidazol-2-yl)-5-phenylthieno[2,3-d]pyrimidin-4-amine 100 (prepared as described in Example 99, Step A) was used in quantity of 0.28 g (0.6 mmol). Using the general procedure described in Example 91, Step E, and boronic acid 101, the target compound was obtained (0.0172 g, 6% yield).

Example 101

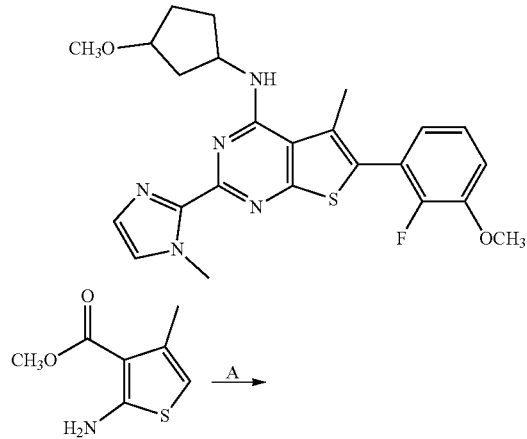

103

314
-continued

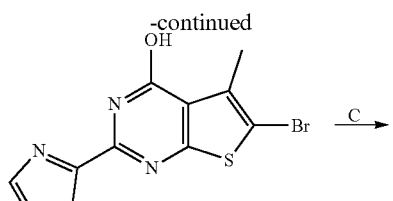
104

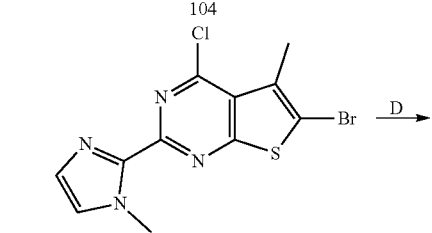
105

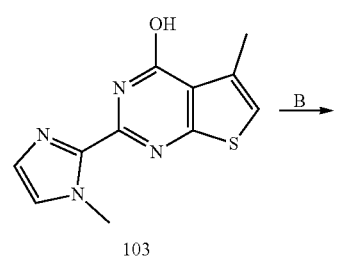
106                    93

[structure with CH₃O, NH, N, N, N, S, F, OCH₃]

Step A: General procedure: To a stirred solution of methyl 2-amino-4-methylthiophene-3-carboxylate 102 (1 eq.) in dry methanol (20 mL) was added the appropriate corresponding cyanoimidazole (1.5 eq.) at room temperature and then potassium tert-butylate (3 eq.) was added portion-wise. The reaction mixture was refluxed for 16 h, cooled to room temperature and the precipitate (potassium salt of the product) was filtered. The precipitate was dissolved in water (50 mL), acidified by acetic acid (10 mL) and stirred at room temperature for 15 min. The precipitate was filtered, washed with water and air dried. Starting with cyanoimidazole 1-methyl-1H-imidazole-2-carbonitrile 91 gave compound 103 as white solid (1.2 g, 69% yield).

Step B: General procedure: To a stirred suspension of compound 103 (1 eq.) in dry DMF (15 mL) was added N-bromosuccinimide (1.2 eq.) at room temperature and then the reaction mixture was stirred at 80° C. for 16 h. After this, the precipitate was filtered and air dried to give 104 as a light yellow solid (1.24 g, 82% yield).

Step C: General procedure: To a stirred suspension of bromide 104 from the previous step in POCl₃ (15 eq.) was added diisopropylethylamine (2 eq.) at room temperature and reaction mixture was refluxed for 16 h. Then solution was cooled to room temperature, evaporated under reduced pressure, diluted with water (300 mL) and neutralized by ice cooled water solution of ammonia (20-25%), and the product was extracted twice with chloroform. The combined extract was evaporated under reduced pressure and purified by flash chromatography (eluent—CHCl₃:MeCN—20:1) to give compound 105 as yellow solid (0.7 g, 57% yield).

Step D: General procedure: To a stirred solution of compound 105 (1 eq.) in chloroform was added triethylamine (1.5 eq.) and a mixture of racemic cis-1-amino-3-methoxycyclopentane and racemic trans-1-amino-3-methoxycyclopentane (1.2 eq.). The reaction mixture was refluxed for 1 h, cooled to room temperature, diluted with water and extracted twice with chloroform. The combined organic layer was dried over Na₂SO₄, evaporated under reduced pressure and purified by flash chromatography (eluent—EtOAc) to give 106 as light yellow solid (0.71 g, 85% yield).

Step E: General procedure: Compound 106 from Step D (0.7 mmol) (1 eq.) was mixed with the corresponding boronic acid (2 eq.), K₂CO₃ (4 eq.), Pd(dppf)Cl₂ (0.05 eq.) 1,4-dioxane:H₂O (1:1) under argon atmosphere. The reaction was then stirred at 100° C. for 16 h under argon atmosphere. Then reaction mixture was cooled to room temperature, diluted with water and extracted twice with chloroform. The combined organic layer was dried over Na₂SO₄, evaporated under reduced pressure and purified from resins by flash chromatography (eluent—EtOAc: Et₃N—20:1). Finally, the crude product was purified by HPLC (eluent—H₂O:MeOH) to give the Example compound as a mixture of racemic cis and racemic trans isomers (0.0294 g, 9% yield).

Example 102

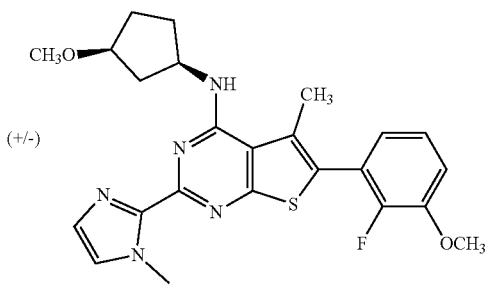

The cis isomer of Example 101 was separated from the cis/trans isomer mixture obtained in Example 101, Step E by HPLC utilizing the following conditions: Chiralpak IB column (250×20 mm, particle size 5 um, mobile phase: hexane-isopropyl alcohol-methyl alcohol-diethylamine, 95%-55%-5%-0.1%, flow rate 15 mL/min. The target Example compound was obtained as a racemate (0.005 g, 1.5% overall yield).

Example 103

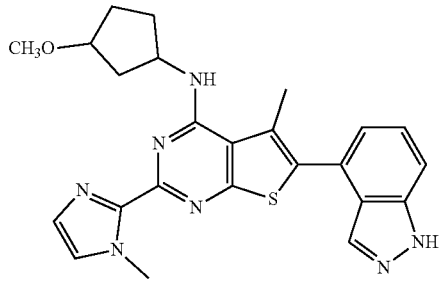

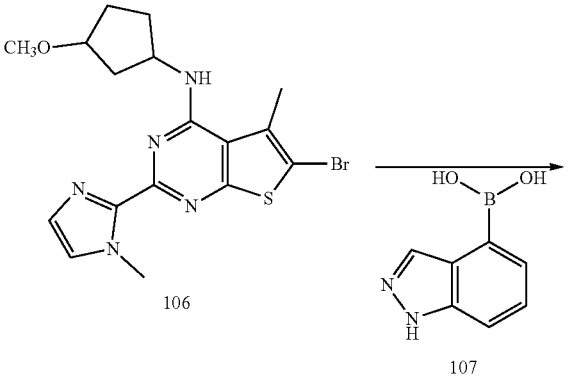

Using the general procedure described in Example 101 Step E, compound 106 (0.7 mmol) and boronic acid 107 (prepared as described in Example 101, Step D) produced the target Example compound as a mixture of racemic cis and racemic trans isomers (0.0263 g, 8.1% yield).

Example 104

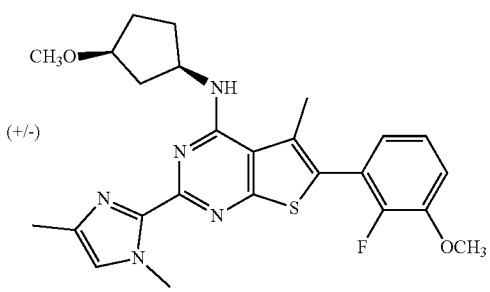

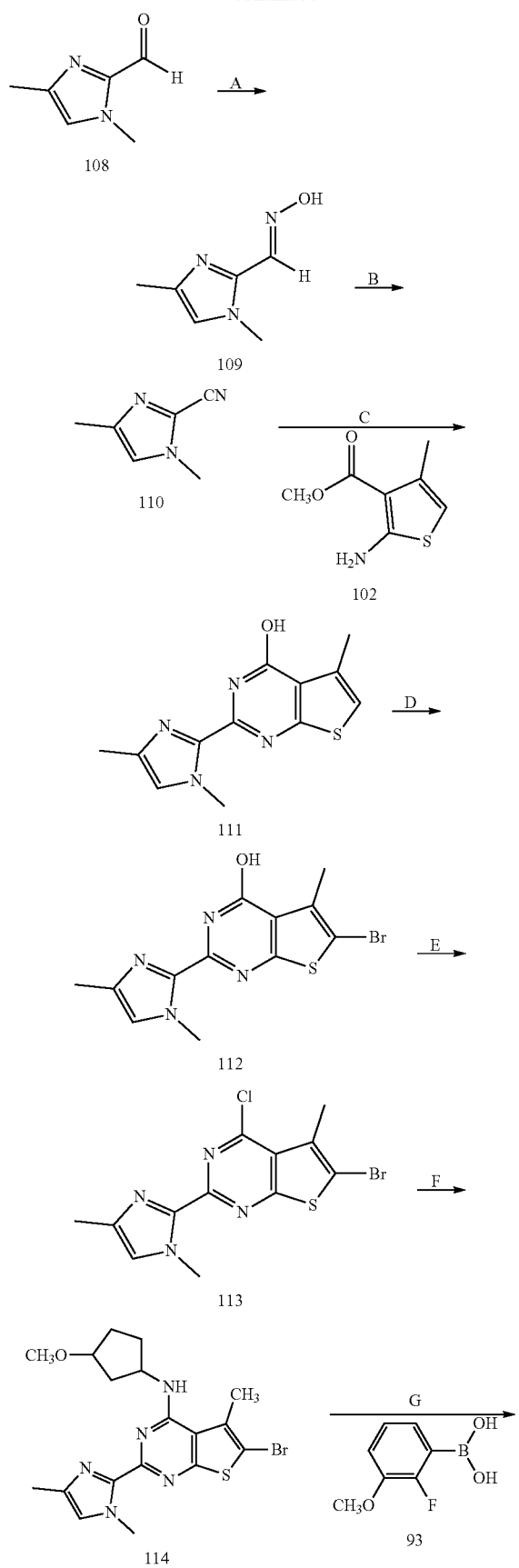

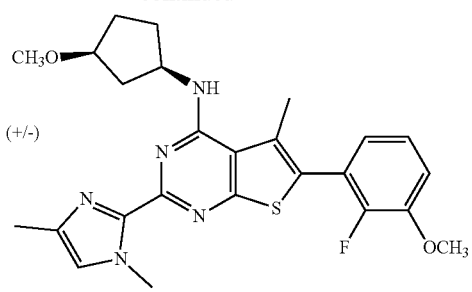

Step A: To a solution of 1,4-dimethyl-1H-imidazole-2-carbaldehyde 108 (1 eq.) in methanol was added hydroxylamine hydrochloride (1.05 eq.) and NaHCO₃ (3 eq.). The resultant mixture was heated at reflux for 5 h before being concentrated to obtain product 109 (2.7 g, 98% yield)

Step B: Trifluoroacetic anhydride (3 eq.) and pyridine (4 eq.) were added to a mixture of oxime 109 (1 eq.) in dichloromethane. After stirring for 4 hours at 40° C., the reaction mixture was quenched by the addition of water and extracted twice with dichloromethane. The combined organic layers were washed with brine, dried over anhydrous sodium sulfate, filtered and concentrated under vacuum to obtain product 110 (1.88 g, yield 80% yield).

Steps C-F: Starting with cyanoimidazole 110 and following the general procedures described in Example 101, Steps A-D, the following products were obtained:

Step C: 111 1.4 g, 62% yield.

Step D: 112 1.36 g, 78% yield.

Step E: 113 0.68 g, 50% yield.

Step F: 114 0.67 g, 82% yield.

Step G: Using the general procedure described in Example 101 Step E, compound 114 (0.7 mmol) and boronic acid 93 produced the target compound as a mixture of racemic cis and racemic trans isomers (0.0633 g, 18.8% yield). The cis isomer was separated from the cis/trans isomer mixture by HPLC utilizing the following conditions: Chiralpak IB column (250×20 mm, particle size 5 um, mobile phase: hexane-isopropyl alcohol-methyl alcohol-diethylamine, 95%-5%-5%-0.1%, flow rate 15 mL/min. The target Example compound was obtained as a racemate (0.0212 g, 6.3% overall yield).

Example 105

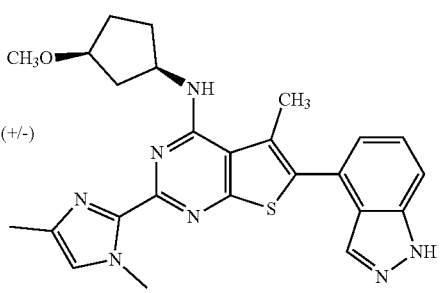

-continued

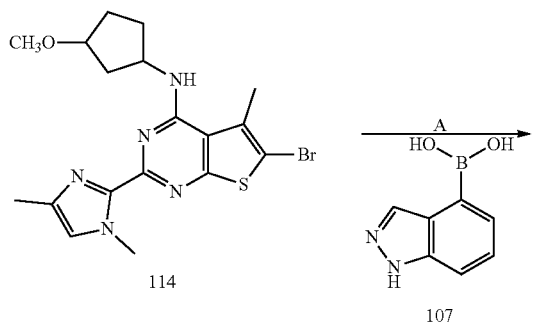

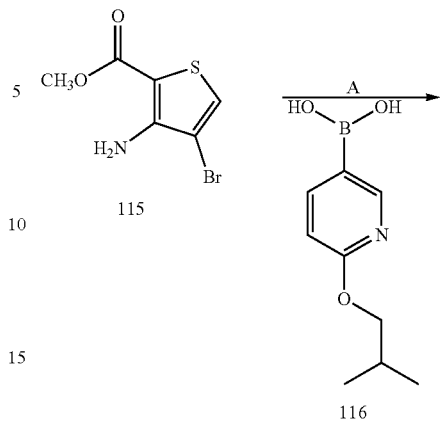

Using the general procedure described in Example 104, Step E, compound 114 (0.7 mmol) (prepared as described in Example 104, Step F) and boronic acid 107 produced the target compound as a mixture of racemic cis and racemic trans isomers (0.0731 g, 22% yield). The cis isomer was separated from the cis/trans isomer mixture by HPLC utilizing the following conditions: Chiralpak IB column (250× 20 mm, particle size 5 um, mobile phase: hexane-isopropyl alcohol-methyl alcohol-diethylamine, 95%6-5%-5%-0.1%, flow rate 15 mL/min. The target Example compound was obtained as a racemate (0.0254 g, 7.7% overall yield).

Example 106

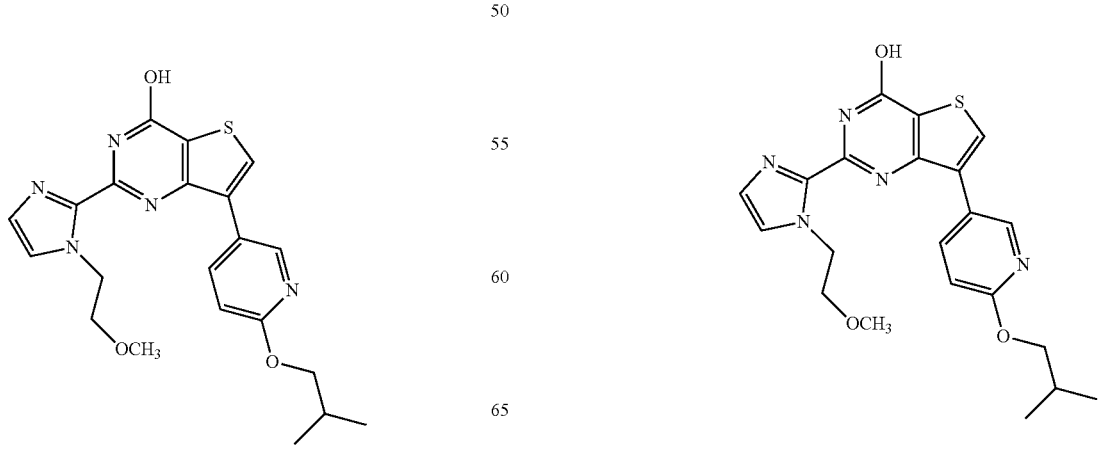

Step A: A solution of methyl 3-amino-4-bromothiophene-2-carboxylate 115 (1 g, 4.3 mmol), diacetoxypalladium (0.048 g, 0.215 mmol), triphenylphosphine (0.23 g, 0.86 mmol), $Cs_2CO_3$ (2 eq) and the corresponding boronic acid (6-isobutoxypyridin-3-yl)boronic acid 116 (1.7 g, 8.6 mmol) in $DMF/H_2O$ (20 mL/2 mL) was stirred at 80° C. until completion of the reaction. Then the reaction mixture was cooled down to the room temperature. Water was added and the mixture was extracted with MTBE. The combined organic layer was dried over $Na_2SO_4$. The solvent was evaporated and the crude product was purified by flash chromatography to give 117 (1.1 g, 60% yield).

Step B: General procedure: Starting ester 117 (0.36 g, 1 equiv) was dissolved in dry dioxane (10 mL) followed by addition of the appropriate corresponding nitrile (prepared as described in Scheme 2) (1 equiv) and sodium hydride (2 equiv, 0.1 g). The mixture was heated at reflux under argon atmosphere for 12 h, cooled to room temperature and acidified with AcOH. The solvent was evaporated, the residue diluted with water and filtered. The crude material was purified using HPLC. Thus the nitrile 7a (from Scheme 2) and ester 117 produced the Example compound (0.1167 g, 23.3% yield).

Example 107 and Example 108

Following the general procedure described in Example 106, Step B, Example 107 and Example 108 (shown in Table J) were prepared from compound 117 (synthesized as described in Example 106, Step A) and the appropriate corresponding nitrile (7c or 7d) from Scheme 2.

TABLE J

| Example | Structure | Amount | Yield |
| --- | --- | --- | --- |
| 107 | ![structure] | 0.0957 g | 17.8% |
| 108 | ![structure] | 0.18 g | 31.4% |

Example 109

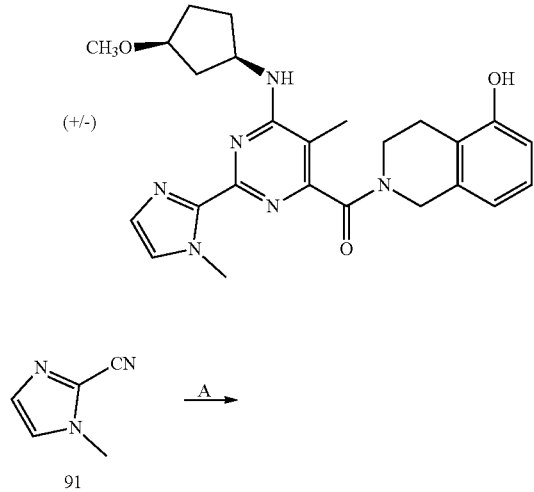

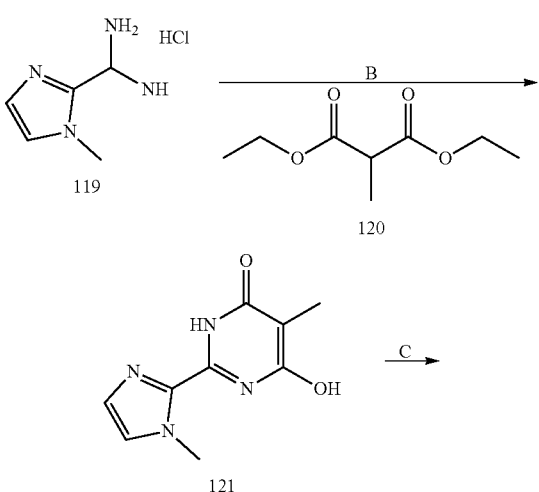

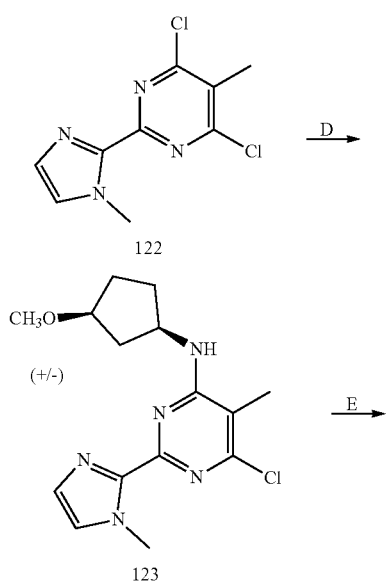

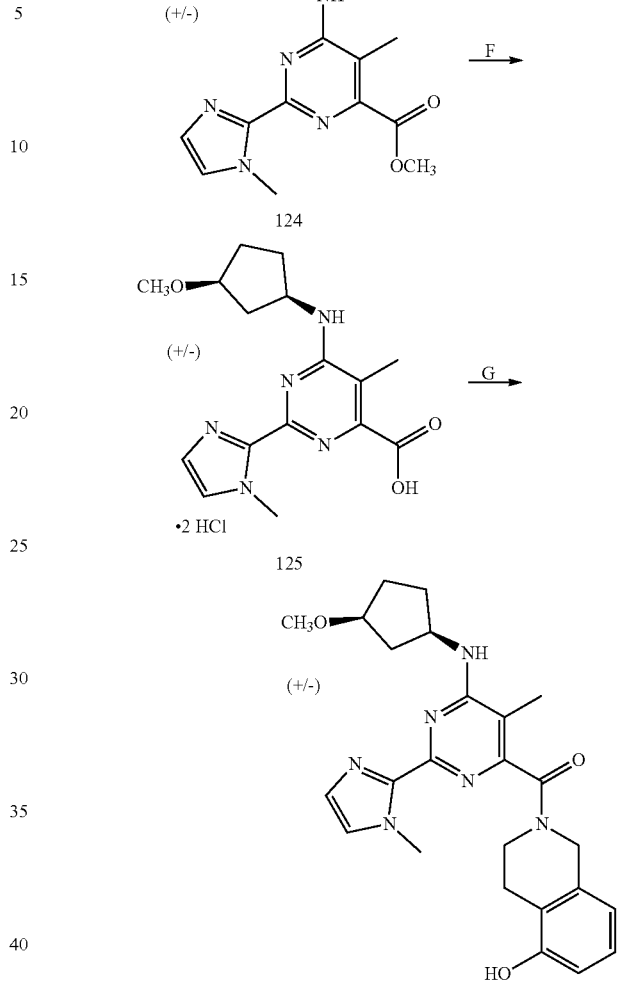

Step A: To 40 mL of dry methyl alcohol was added sodium methoxide (2.52 g, 11 46.7 mmol) with stirring. Then 1-methyl-1H-imidazole-2-carbonitrile 91 (5.0 g, 46.7 mmol) was added. The mixture was stirred at room temperature for 20 h, and ammonium chloride (2.48 g, 46.7 mmol) was added. Then the reaction mixture was stirred at 80° C. for 8 h and cooled to room temperature. The mixture was filtered, and the filtrate is concentrated under reduced pressure. Then residue was diluted with ethyl acetate, and the precipitate was collected by filtration and air dried to give carboxamidine hydrochloride 119 (6.9 g, 92%) as a white solid.

Step B: To a stirred solution of NaOMe (10.04 g, 186 mmol) in dry MeOH (80 mL) was added carboxamidine 119 (6.0 g, 37.2 mmol). The reaction mixture was stirred at room temperature for 30 min and 1,3-diethyl 2-methylpropane-dioate 120 (7.76 g, 44.64 mmol) was then added. The suspension was refluxed for 24 h. Then reaction mixture was diluted with H$_2$O (300 mL) and acidified by excess of acetic acid (20 mL). The resulting solid was filtered, washed with water, and dried under reduced pressure to yield target compound 121 as light yellow solid (6.5 g, 84.7%).

Step C: A suspension of 121 from the previous step (6.0 g, 29.1 mmol) in POCl$_3$ (30 mL) was stirred at 120° C. for 4 h. The solution was concentrated, the residue was taken up in ice cold water with ammonia, then chloroform was added, and the layers were separated. The aqueous phase was extracted with CHCl₃ (2*50 mL) and the combined organic layers were concentrated under reduced pressure. The residue was purified via silica gel chromatography (10-50% EtOAc in hexanes) to give the product 122 (5.2 g, 73.8%) as a yellow solid.

Step D: To a stirred solution of chloride 122 from previous step (3.0 g, 12.34 mmol) in chloroform (30 mL) was added triethylamine (2.56 mL, 18.51 mmol) and racemic cis-3-methoxycyclopentan-1-amine (1.84 g, 16.0 mmol). Then the reaction mixture was refluxed for 1 h, cooled to r.t, diluted with water (100 mL) and extracted twice with chloroform (2*30 mL). The combined organic layer was dried with Na₂SO₄, evaporated under reduced pressure and purified by flash chromatography (eluent—EtOAc:Et₃N—20:1) to give the target compound 123 as light yellow solid (3.1 g, 78%).

Step E: The product 123 from the previous step (2.0 g, 6.23 mmol), 1,1'-bis (diphenylphosphino)ferrocene]dichloropalladium (II), (100 mg, 0.12 mmol), triethylamine (1.3 mL, 9.35 mmol) in 30 mL of dry methanol was stirred under a carbon monoxide atmosphere (30 bar) overnight at 140° C. The mixture was concentrated under vacuum. The residue was purified by silica gel column chromatography (5% Et₃N in EtOAc) to give the target product 124 (1.3 g, 60.4%) as a yellow oil.

Step F: The ester 124 from Step E (1.0 g, 2.89 mmol) was refluxed in 10% water solution of hydrochloric acid (20 mL) for 24 h and then evaporated to dryness under reduced pressure to give the desired carboxylic acid (dihydrochloride) 125 as light brown solid (1.16 g, 99%).

Step G: The product 125 from Step F (250 mg, 0.62 mmol), 1,2,3,4-tetrahydroisoquinolin-5-ol hydrobromide, (0.142 g, 0.62 mmol) DIPEA (0.43 mL, 2.48 mmol) and PyBOP (322 mg, 0.62 mmol) were stirred in 5 mL of dry DMF overnight at RT. The reaction mixture was evaporated under reduced pressure. The residue was purified by HPLC to give the Example compound as a racemate (66 mg, 23%).

Example 110

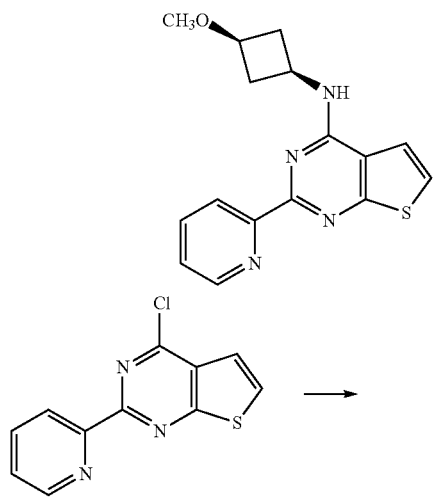

126

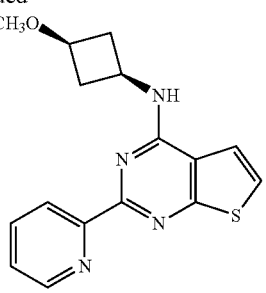

The commercially available starting material 4-chloro-2-(pyridin-2-yl)thieno[2,3-d]pyrimidine 126 (500.0 mg, 2.02 mmol) was dissolved in DMSO and N,N-diisopropylethylamine (1.35 g, 10.42 mmol, 5 equiv) with cis-3-methoxy-cyclobutan-1-amine hydrochloride (1.35 g, 9.78 mmol) (4.4 equiv) was added. The mixture was heated at 100° C. overnight, cooled and the residue was purified by HPLC. The target Example compound was obtained as a yellow gum (57.4 mg, 183.97 μmol, 9.1% yield).

Example 111

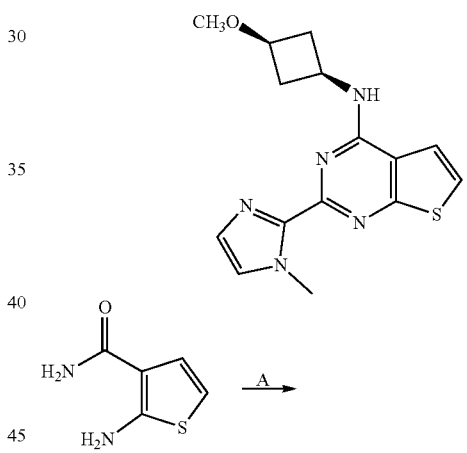

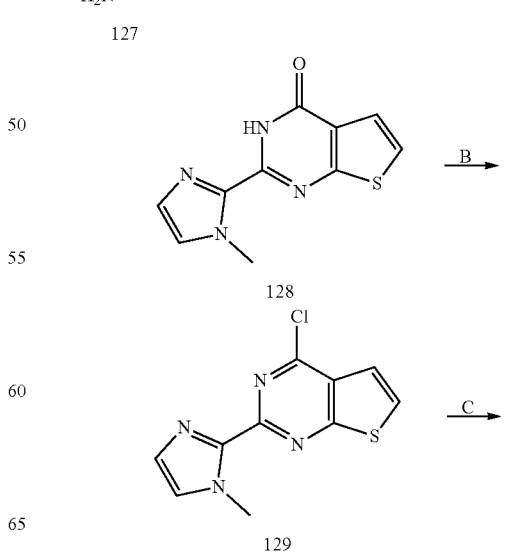

127

128

129

327

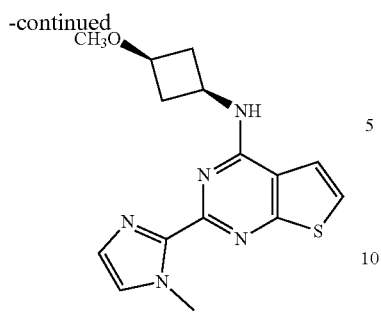

Step A: To a stirred solution of 2-aminothiophene-3-carboxamide 127 (500.0 mg, 3.52 mmol) in dry MeOH (10 mL) was added 1-methyl-1H-imidazole-2-carbonitrile 91 (452.14 mg, 4.22 mmol) (1.2 equiv) at room temperature followed by portion-wise addition of potassium tert-butylate 1.42 g (12.7 mmol, 3.6 equiv). After 16 hours of stirring the reaction mixture was evaporated to dryness. The residue was dissolved in water (10 mL), acidified with acetic acid to pH 5-6, the formed precipitate was filtered, washed with water and dried to give crude compound 128 which was used in the next step without further purification.

Step B: The crude material 128 from Step A (440.0 mg, 1.89 mmol) was suspended in POCl$_3$ (2 mL) and diisopropylethylamine (0.6 mL) was added at room temperature The reaction mixture was refluxed for 16 h, then the solution was cooled to room temperature, evaporated under reduced pressure, poured into ice and basified with liquid ammonia (20 mL, 20-25% of ammonia), and the product was filtered. The product 129 was obtained as brown liquid (150.0 mg, 0.6 mmol, 34.1% yield).

Step C: Compound 129 (150.0 mg, 0.6 mmol) was dissolved in DMSO. Then N,N-diisopropylethylamine (194.0 mg, 1.5 mmol) and cis-3-methoxycyclobutan-1-amine hydrochloride (206.0 mg, 1.5 mmol) were added. The mixture was heated at 100° C. overnight, cooled and purified by HPLC. The target compound was obtained as a yellow gum (8.0 mg, 25.37 µmol, 4.2% yield).

Example 112

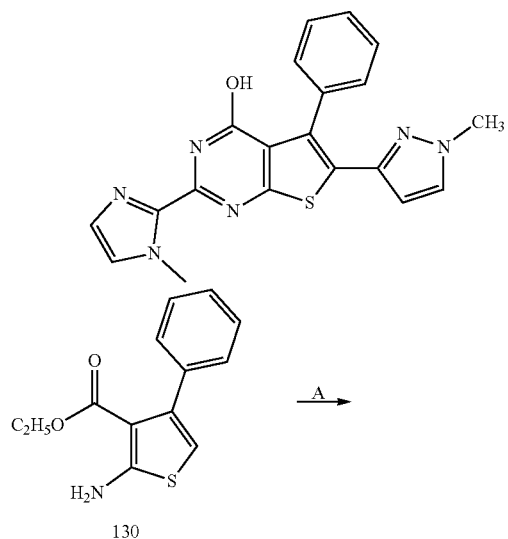

328

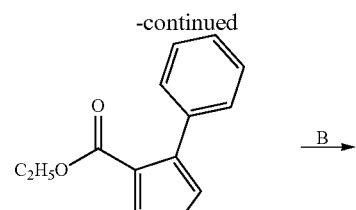

131

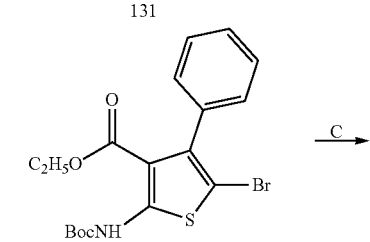

132

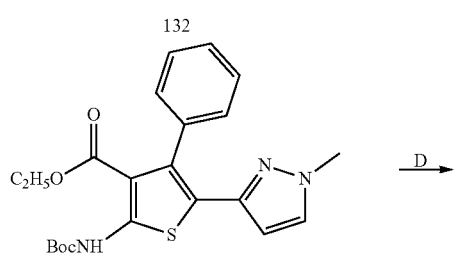

133

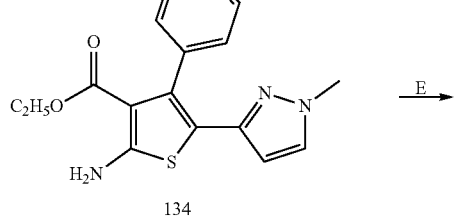

134

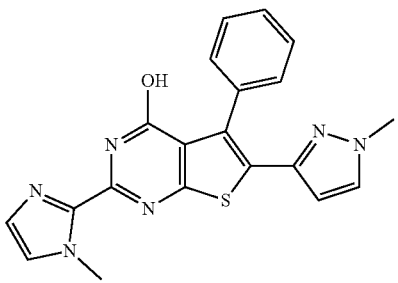

17a

Step A: To a solution of starting material 130 (16.0 g, 64.7 mmol) and di-tert-butyl dicarbonate (16.94 g, 77.63 mmol) in dioxane (210 mL) was added N,N-dimethylpyridin-4-amine (790.37 mg, 6.47 mmol). The mixture was stirred 80° C. overnight. Then it was cooled, concentrated and purified by column chromatography using Hexane/EtOAc-10:1 as eluant. The product 131 was obtained as white powder (15.0 g, 95.0% purity, 41.02 mmol, 63.4% yield).

Step B: To a stirred solution of compound 131 (15.0 g, 43.17 mmol) in 30 mL DMF N-bromosuccinimide (9.22 g, 51.81 mmol) was added in one portion. Mixture was stirred at RT overnight. Then it was poured in ice water and diluted withe EtOAc. The organic phase was washed 5 times with water, dried under Na$_2$SO$_4$ and concentrated and purified by column chromatography using Hex/EtOAc-7:1 as eluant. The product 132 was obtained as light-yellow powder (10.5 g, 95.0% purity, 23.4 mmol, 54.2% yield).

Step C: A portion of Pd(dppf)Cl₂ (634.98 mg, 867.8 µmol) was added to a suspension of compound 132 (3.7 g, 8.68 mmol), 1-methyl-3-(tetramethyl-1,3,2-dioxaborolan-2-yl)-1H-pyrazole (2.17 g, 10.41 mmol) and Cs₂CO₃ (5.65 g, 17.36 mmol) in 74 mL of dioxane and 3.7 mL of H₂O under Ar. The mixture was stirred at 60° C. overnight. After cooling, the solid was collected by filtration and washed with EtOAc. The filtrate was concentrated and purified by column chromatography. Eluent Hex/EtOac—100:1 to 10:1. The product 133 was obtained as yellow powder (1.9 g, 95.0% purity, 4.22 mmol, 48.7% yield).

Step D: To a solution of compound 133 (1.9 g, 4.44 mmol) in 20 mL CH₂Cl₂ was added 7 mL 8M Dioxane*HCl. The mixture was stirred overnight at room temperature. The product 134 was obtained as black oil (1.1 g, 3.36 mmol, 75.6% yield).

Step E: Compound 134 (400.35 mg, 1.22 mmol), potassium tert-butylate (411.65 mg, 3.67 mmol) and 1-methyl-1H-imidazole-2-carbonitrile (157.18 mg, 1.47 mmol) was dissolved in dry MeOH (10 mL) and stirred overnight at room temperature. Then the reaction mixture was evaporated and AcOH aq (50%) was added to resulted residue dropwise to pH~5, after that organics was extracted by EtOAc (20 mL), dried over Na₂SO₄ and evaporated to give crude product. It was purified by HPLC to give 17a as a yellow solid (43 mg, 97% by LCMS, 11% yield).

Example 113

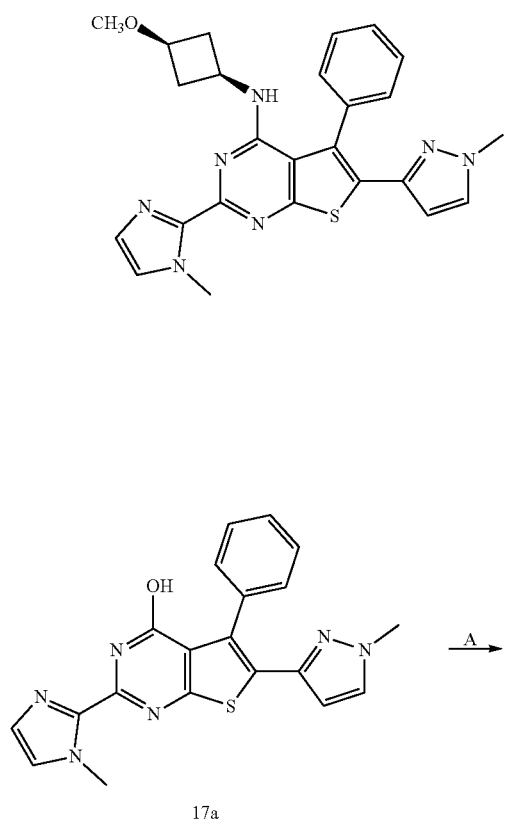

17a

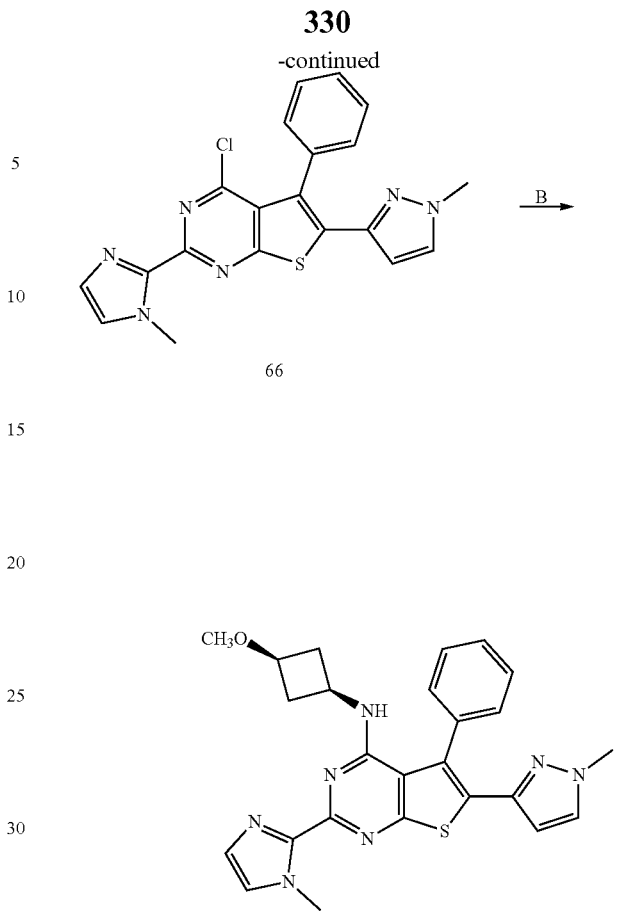

66

-continued

Step A: The starting compound 17a (20.0 mg, 51.49 µmol) (prepared as described in Example 112, Step E) was suspended in POCl₃ (78.76 mg, 513.65 µmol, 50.0 µL) and N,N-diisopropylethylamine (26.55 mg, 205.46 µmol, 40.0 µL) was added at room temperature The reaction mixture was refluxed for 16 h, the solution was cooled to room temperature, evaporated under reduced pressure, poured in ice (5 mL) and diluted with ice-cold ammonia (10 mL, 20-25% of ammonia); the product was extracted with chloroform (2*5 mL) and combined organic layer was evaporated. The product 66 (19.0 mg, 46.7 µmol, 90.9% yield) was obtained as brown solid and was used on the next step as crude material.

Step B: (General procedure) To the stirred solution of compound 66 (23.99 mg, 58.95 µmol) in DMSO (2 mL) was added N,N-diisopropylethylamine (22.86 mg, 176.85 µmol) and the appropriate corresponding amine (2.5 eq). The mixture was heated at 100° C. overnight, cooled and purified by HPLC with yields 5-15%. Thus using cis-3-methoxycyclobutan-1-amine hydrochloride as the amine produced the Example compound, which was converted to the HCl salt (0.0029 g, 10.4% yield).

Example 114-Example 117

Following the general procedure described in Example 113, Step B, compound 66 (prepared as described in Example 113, Step A) and the appropriate corresponding amine produced Examples 114-117 below (shown in Table K).

TABLE K

| Example | Structure | Amount | Yield |
|---|---|---|---|
| 114 | 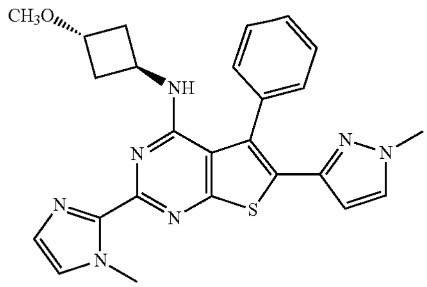 | 0.0125 g | 10.3% |
| 115 | 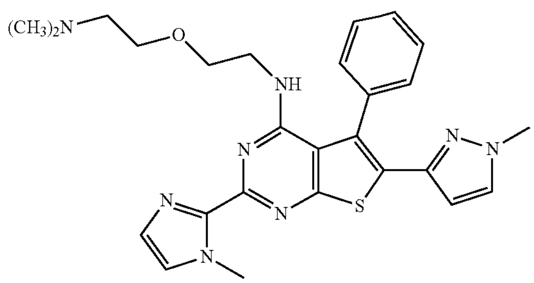 | 0.0078 g | 5.4% |
| 116 | 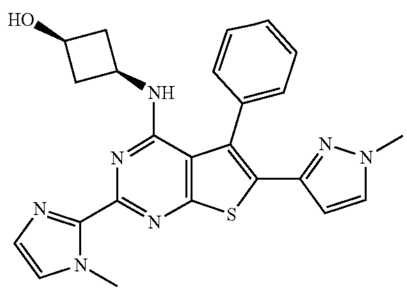 [SMILES: Cn1ccc(-c2sc3nc(-c4nccn4C)nc(N[C@H]4C[C@@H](O)C4)c3c2C2=CC=CCC=C2)n1] | 0.0061 g | 5.1% |
| 117 | (+/-) | 0.0046 g | 15.5% |

Example 118

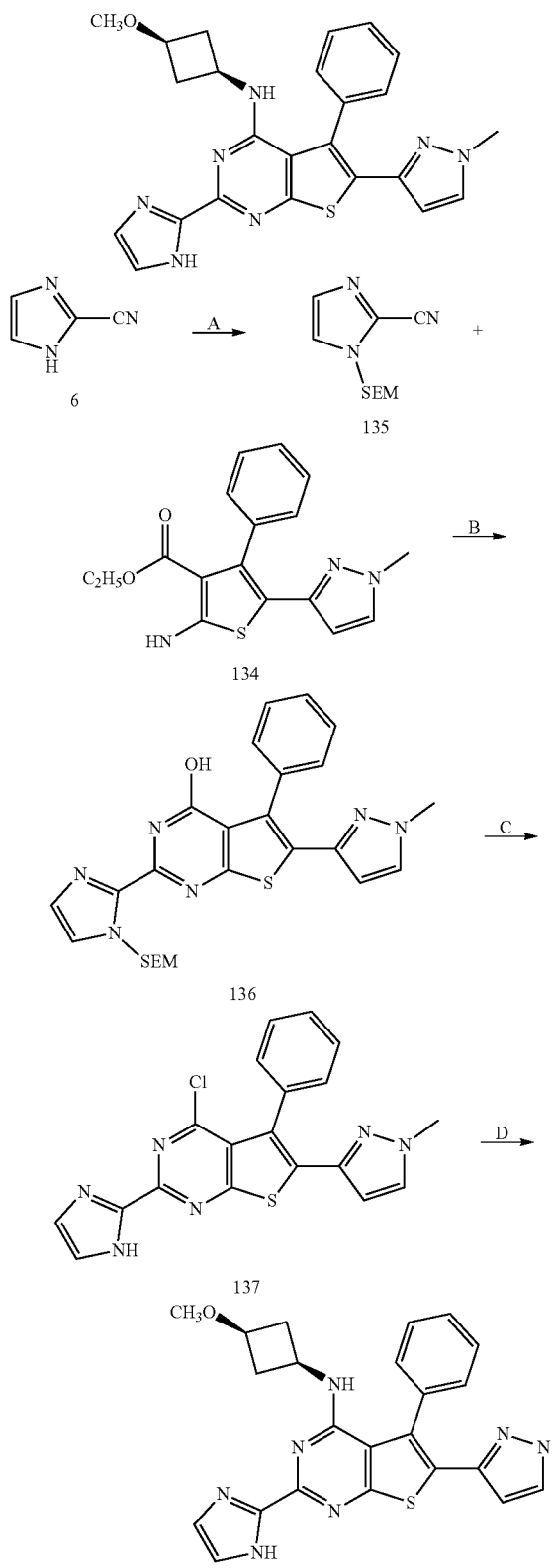

Step A: To a solution of 1H-imidazole-2-carbonitrile 6 (200.0 mg, 2.15 mmol) and potassium carbonate (891.06 mg, 6.45 mmol, 450.0 µL) in 5 mL THF, [2-(chloromethoxy)ethyl]trimethylsilane (394.13 mg, 2.36 mmol, 420.0 µL) was added dropwise at 0° C. Solution was stirred overnight at rt. The mixture was filtered, concentrated, and diluted with EtOAc. The organic phase was washed by water twice. The solvent was dried with sodium sulfate and concentrated. The product 135 was obtained as light-yellow oil (300.0 mg, 95.0% purity, 1.28 mmol, 59.4% yield).

Step B: Compound 134 (99.9 mg, 305.14 µmol) (prepared as described in Example 112, Step D), compound 135 (68.15 mg, 305.14 µmol), and potassium tert-butylate (136.96 mg, 1.22 mmol) was dissolved in dry MeOH and stirred overnight at room temperature. The residue was evaporated and acetic acid (conc) was added to pH=5. After that EtOAc (25 mL) was added and extracted, and the organic phase dried over $Na_2SO_4$, evaporated to give product 136 (100.0 mg, 51.0% purity, 101.05 µmol, 33.1% yield).

Step C: Compound 136 (100.0 mg, 198.15 µmol) was suspended in $P(O)Cl_3$ (303.65 mg, 1.98 mmol, 180.0 µL) and N,N-diisopropylethylamine (76.78 mg, 594.1 µmol, 100.0 µL) was added at room temperature in one portion. The reaction mixture was refluxed for 16 h, the solution was cooled to room temperature, evaporated under reduced pressure, poured in ice (10 mL) and diluted with ice-cold ammonia (20 mL, 20-25% of ammonia), the product was extracted with chloroform (2*20 mL) and evaporated. The product 137 was obtained as brown solid (70.0 mg, 46.0% purity, 81.96 µmol, 41.4% yield).

Step D: Compound 137 (69.89 mg, 177.9 µmol) was dissolved in DMSO and N,N-diisopropylethylamine (69.01 mg, 533.92 µmol, 90.0 µL) with corresponding amine 3-methoxycyclobutan-1-amine hydrochloride (48.96 mg, 355.81 µmol) was added. The mixture was heated at 100° C. overnight, cooled and purified by HPLC. The Example compound was obtained after HPLC (6.9 mg, 95.0% purity, 14.33 µmol, 8.1% yield).

Example 119

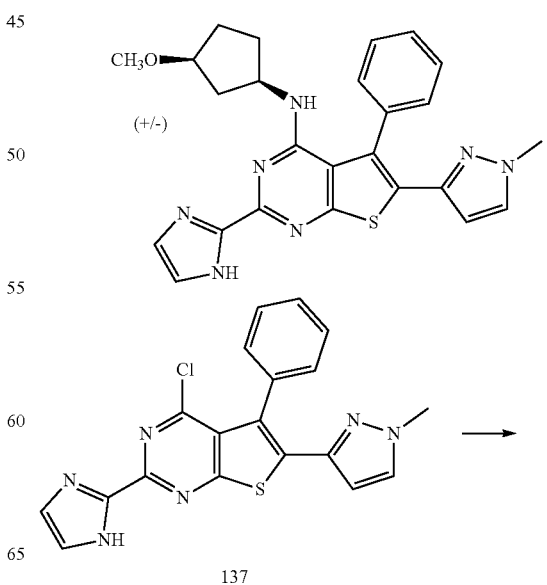

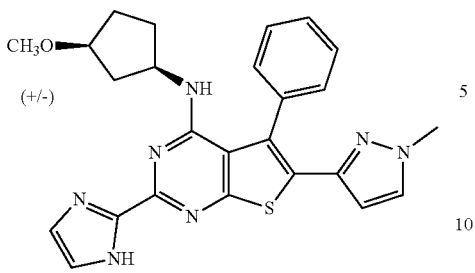

The compound 137 (36.87 mg, 93.84 μmol) and N,N-diisopropylethylamine (36.36 mg, 281.31 μmol, 50.0 μL) was dissolved in DMSO (5 mL) and corresponding racemic amine cis-3-methoxycyclopentan-1-amine (29.69 mg, 257.81 μmol) was added. The mixture was heated at 100° C. overnight, cooled and purified by HPLC to give the Example compound as a racemate (4.6 mg, 94.0% purity, 9.17 μmol, 10.3% yield).

Example 120

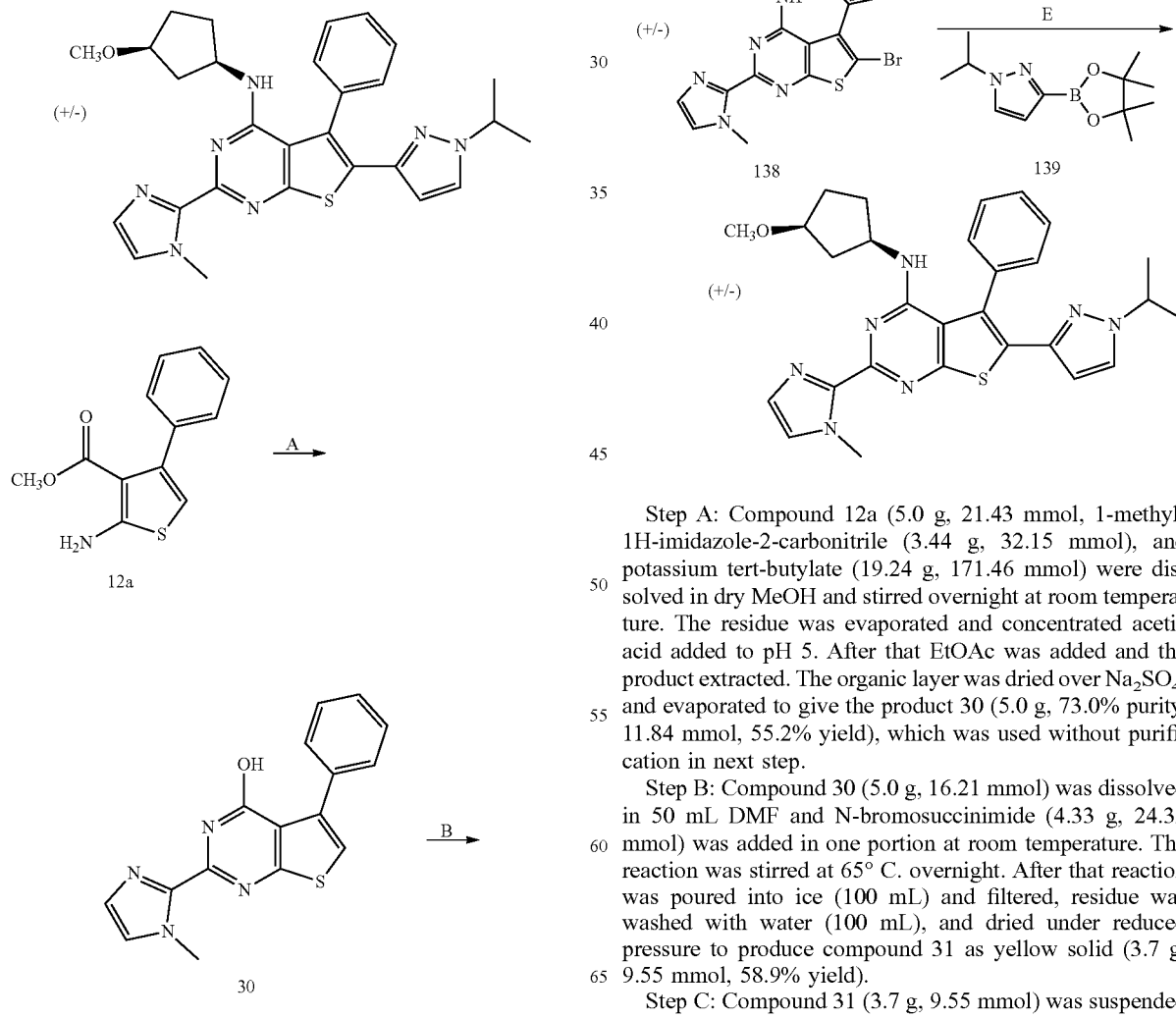

Step A: Compound 12a (5.0 g, 21.43 mmol, 1-methyl-1H-imidazole-2-carbonitrile (3.44 g, 32.15 mmol), and potassium tert-butylate (19.24 g, 171.46 mmol) were dissolved in dry MeOH and stirred overnight at room temperature. The residue was evaporated and concentrated acetic acid added to pH 5. After that EtOAc was added and the product extracted. The organic layer was dried over $Na_2SO_4$, and evaporated to give the product 30 (5.0 g, 73.0% purity, 11.84 mmol, 55.2% yield), which was used without purification in next step.

Step B: Compound 30 (5.0 g, 16.21 mmol) was dissolved in 50 mL DMF and N-bromosuccinimide (4.33 g, 24.32 mmol) was added in one portion at room temperature. The reaction was stirred at 65° C. overnight. After that reaction was poured into ice (100 mL) and filtered, residue was washed with water (100 mL), and dried under reduced pressure to produce compound 31 as yellow solid (3.7 g, 9.55 mmol, 58.9% yield).

Step C: Compound 31 (3.7 g, 9.55 mmol) was suspended in $POC_3$ (14.65 g, 95.54 mmol, 8.91 mL) and N,N-diisopropylethylamine (3.7 g, 28.66 mmol, 4.99 mL) was added at room temperature The reaction mixture was refluxed for 16 h, the solution was cooled to room temperature, evaporated under reduced pressure, poured in ice (50 mL) and diluted with ice-cold ammonia (20 mL, 20-25% of ammonia), the product was extracted with chloroform (2*50 mL) and evaporated. The product 32 was obtained as yellow solid (3.4 g, 91.0% purity, 7.63 mmol, 79.8% yield).

Step D: Compound 32 (1.17 g, 2.89 mmol) was dissolved in DMSO and N,N-diisopropylethylamine (934.92 mg, 7.23 mmol, 1.26 mL) along with racemic cis-3-methoxycyclopentan-1-amine (500.01 mg, 4.34 mmol) was added. The mixture was heated at 100° C. overnight, cooled and purified by HPLC. The product, racemic compound 138, was obtained as yellow gum (340.0 mg, 93.0% purity, 652.75 μmol, 22.6% yield).

Step E: Racemic compound 138 (100.0 mg, 206.44 μmol), 1-(propan-2-yl)-3-(tetramethyl-1,3,2-dioxaborolan-2-yl)-1H-pyrazole 139 (58.45 mg, 247.53 μmol) cesium carbonate (134.42 mg, 412.55 μmol) and PdXphos G3 (17.46 mg, 20.63 μmol) were dissolved in degassed dioxane:H₂O (2 mL:0.1 mL). The mixture was refluxed overnight. The mixture was cooled, filtered, concentrated and purified by HPLC. The Example compound was obtained as the racemate (10.4 mg, 95.0% purity, 19.23 μmol, 9.8% yield).

Example 121

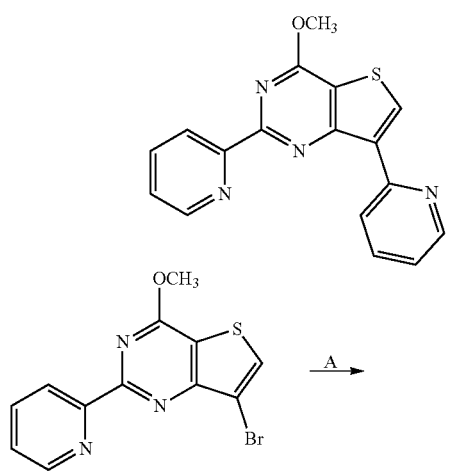

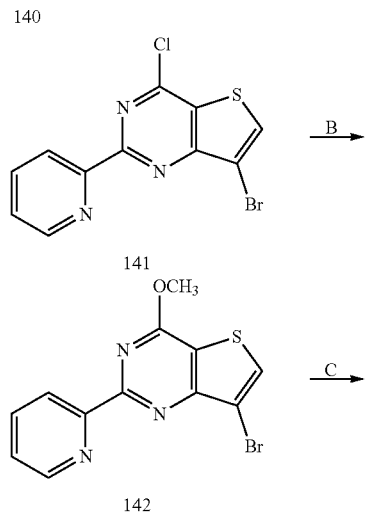

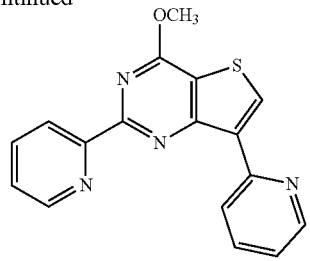

Step A: The starting material 7-bromo-2-(pyridin-2-yl)thieno[3,2-d]pyrimidin-4-ol 140 (1.5 g, 4.86 mmol) (synthesis previously described in US 2019/0022074 A1) was suspended in POCl₃ (7.46 g, 48.62 mmol, 4.53 mL) and N,N-diisopropylethylamine (1.89 g, 14.59 mmol, 2.54 mL) was added at room temperature The reaction mixture was refluxed for 16 h, the solution was cooled to room temperature, evaporated under reduced pressure, poured in ice (25 mL) and diluted with ice-cold ammonia (20 mL, 20-25% of ammonia). The product was extracted with chloroform (2*50 mL) and evaporated. The product 141 was obtained as yellow solid (1.1 g, 3.37 mmol, 69.3% yield).

Step B: Sodium methoxide (202.77 mg, 3.75 mmol) was added in portions to methanol (4 mL), compound 141 (700.0 mg, 2.14 mmol) and the mixture was stirred at reflux overnight. The mixture was diluted with water (2.5 mL) and extracted with diethyl ether (7.5 mL). The organic layer was washed with water (2 mL), brine (2 mL), dried (Na₂SO₄), filtered and the solvent was removed under reduced pressure to give solid 142, which was used in next step without purification. Compound 142 was obtained as brown solid (550.0 mg, 1.71 mmol, 79.6% yield).

Step C: Compound 142 (500.0 mg, 1.55 mmol), 2-(tributylstannyl)pyridine (571.12 mg, 1.55 mmol), tetrakis(triphenylphosphine)palladium(0) (179.89 mg, 155.13 μmol) were suspended in degassed toluene (5 mL). The mixture was heated under argon at 112° C. overnight. After cooling to room temperature, the mixture was diluted with ethyl acetate (20 mL), the organic layer was washed with water (20 mL) and saturated brine (20 mL), dried over magnesium sulfate, filtered, and concentrated in vacuo. The residue was purified by HPLC to afford the Example compound (19.0 mg, 59.31 μmol, 3.8% yield).

Example 122

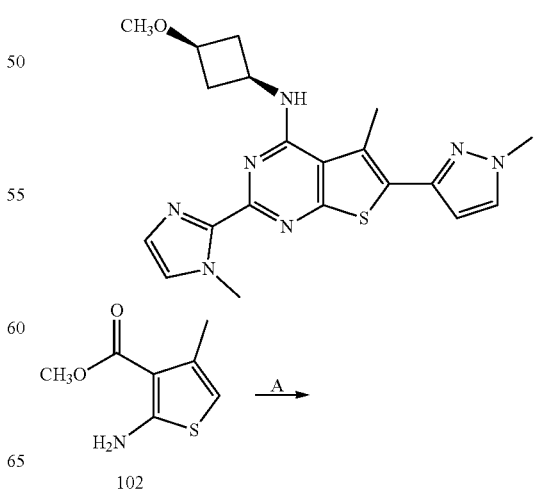

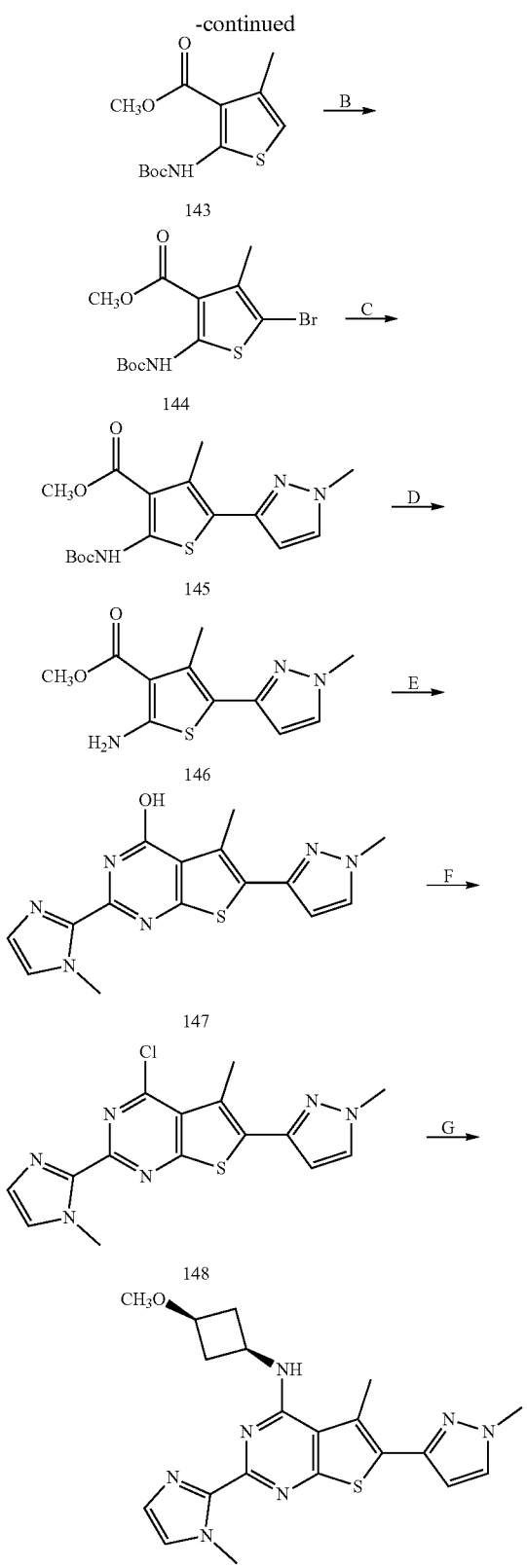

by column chromatography (eluted by Hex:EtOAc 10:1). The product 143 was obtained as white solid (8.1 g, 29.85 mmol, 56.8% yield).

Step B: To a solution of compound 143 (8.1 g, 29.85 mmol) in 160 mL DMF, N-bromosuccinimide (6.38 g, 35.82 mmol) was added in one portion. The mixture was stirred at room temperature overnight. The mixture was cooled and poured in ice water (350 mL). The precipitate was filtered, washed 3 times with water and dried on air. The product 144 was obtained as light-yellow powder (9.2 g, 26.27 mmol, 88% yield).

Step C: Compound 144 (1.5 g, 4.28 mmol), 1-methyl-3-(tetramethyl-1,3,2-dioxaborolan-2-yl)-1H-pyrazole (1.07 g, 5.14 mmol), cesium carbonate (2.79 g, 8.57 mmol), and PdXphos G3 (362.5 mg, 428.26 µmol) were suspended in 30 mL degassed dioxane:water 20:1. The mixture was heated under argon at 100° C. overnight. After cooling to room temperature, the mixture was diluted with ethyl acetate, the organic layer was washed with water and saturated brine, dried over magnesium sulfate, filtered, and concentrated in vacuo. The residue was purified by column chromatography (eluted by Hex:Etoac 20:1 to 1:1). The product 145 was obtained as gray powder (1.1 g, 95.0% purity, 2.97 mmol, 69.4% yield).

Step D: Compound 145 (1.1 g, 3.13 mmol) was dissolved in 5 mL dioxane and 5 mL 6M Dioxane*HCl was added dropwise at 0° C. The solution was stirred overnight at room temperature Solvent was evaporated and the residue was purified by flash chromatography eluted by EtOAc. The product 146 was obtained as dark gray powder (550.0 mg, 95.0% purity, 2.08 mmol, 66.4% yield).

Step E: Compound 146 (50.0 mg, 198.96 µmol), potassium tert-butylate (89.25 mg, 795.4 µmol), 1-methyl-1H-imidazole-2-carbonitrile (25.56 mg, 238.62 µmol) was dissolved in dry MeOH (1 mL) and stirred overnight at room temperature. The residue was evaporated and concentrated acetic acid added to pH 5. After that EtOAc (5 mL) and water (2 mL) was added, and the organic extracts dried over $Na_2SO_4$ and evaporated to give product 147 (200.0 mg, 37.0% purity, 226.73 µmol, 28.5% yield).

Step F: The starting material 147 (599.14 mg, 1.84 mmol) was suspended in $POCl_3$ (2.81 g, 18.36 mmol, 1.71 mL) and N,N-diisopropylethylamine (712.32 mg, 5.51 mmol, 960.0 µL) was added in one portion at room temperature The reaction mixture was refluxed for 16 h, the solution was cooled to room temperature, evaporated under reduced pressure, poured in ice (20 mL) and diluted with ice-cold ammonia (20 mL, 20-25% of ammonia). The product was extracted with chloroform (2*50 mL) and evaporated. The product 148 was obtained as yellow solid (670.0 mg, 63.0% purity, 1.22 mmol, 66.7% yield).

Step G: General procedure: Compound 148 (118.73 mg, 344.32 µmol) was dissolved in DMSO (2 mL) and N,N-diisopropylethylamine (133.56 mg, 1.03 mmol, 180.0 µL) along with the appropriate corresponding amine (2.5 eq) was added. The mixture was heated at 100° C. overnight, cooled and purified by HPLC. Using cis-3-methoxycyclobutan-1-amine as the amine, the Example compound was obtained after HPLC purification (0.0031 g, 21% yield).

Example 123-Example 126

Following the procedure described in Example 122, Step G, Example 123-Example 126 (shown in Table L) were prepared from starting compound 148 and the appropriate corresponding amine.

Step A: DMAP (642.19 mg, 5.26 mmol) was added to a stirred solution of compound 102 (9.0 g, 52.56 mmol) and $Boc_2O$ (13.77 g, 63.08 mmol) in 108 mL of dioxane, and refluxed overnight. After 16 h reaction was complete (monitored by NMR). The mixture was concentrated and purified TABLE L
| Example | Structure | Amount | Yield |
|---|---|---|---|
| 123 | (+/-) | 0.0304 g | 18.8% |
| 124 | 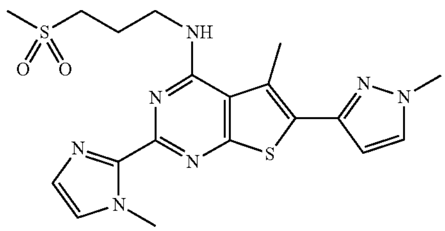 | 0.0347 g | 12.9% |
| 125 | 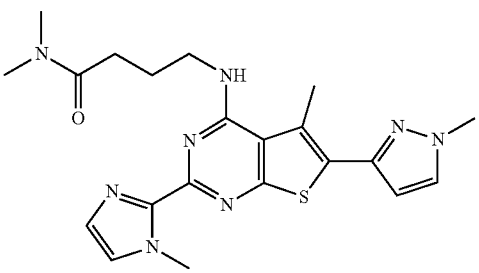 | 0.0191 g | 7.2% |
| 126 | 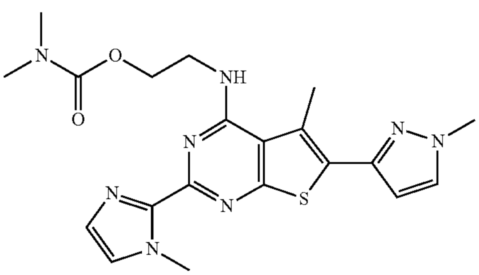 | 0.0245 g | 9.7% |
Example 127
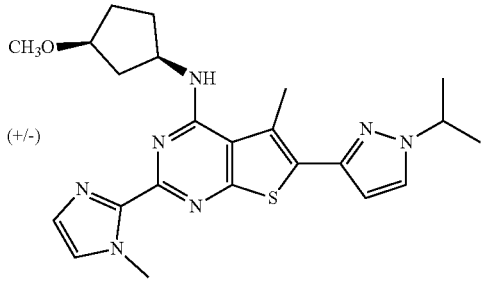
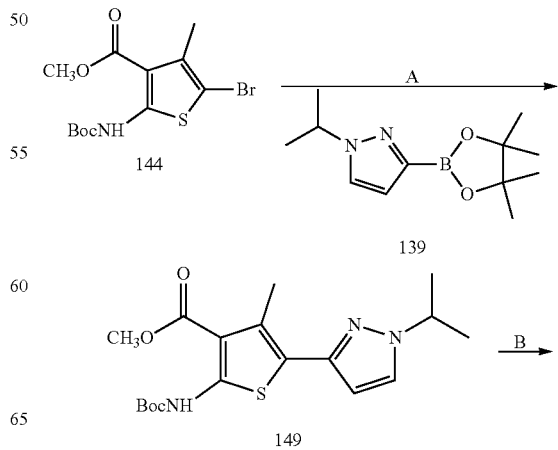

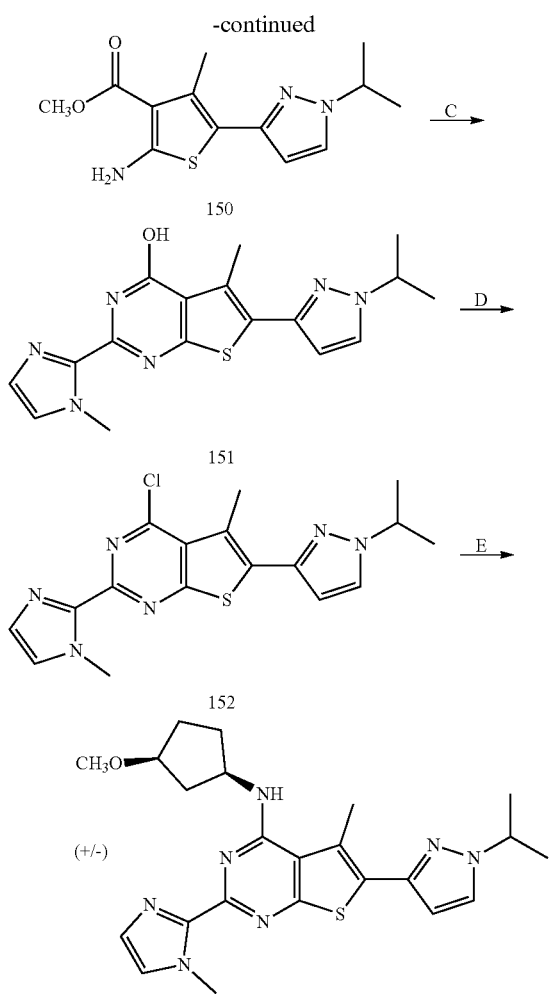

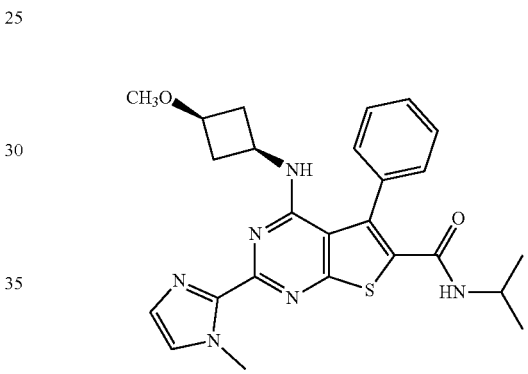

Step D: The crude material from the previous step, compound 151 (100.0 mg, 282.14 µmol) was suspended in POCl₃ (2 mL) and diisopropylethylamine (0.6 mL) was added at room temperature The reaction mixture was refluxed for 16 h, the solution was cooled to room temperature, evaporated under reduced pressure, poured into ice and basified with liquid ammonia (20 mL, 20-25% of ammonia), the product was filtered. The product 152 was obtained as brown liquid (100.0 mg, 55.0% purity, 147.5 µmol, 52.4% yield).

Step E: Compound 152 (142.31 mg, 381.66 µmol) (prepared as described in Example 127, Step D) was dissolved in DMSO (3 mL) and N,N-diisopropylethylamine (148.4 mg, 1.15 mmol, 200.0 µL) with the corresponding amine, racemic cis-3-methoxycyclopentan-1-amine (105.04 mg, 763.32 µmol), was added at room temperature. The mixture was heated at 100° C. overnight, cooled and purified by HPLC. The racemic Example compound was obtained as yellow gum after HPLC (12.1 mg, 95.0% purity, 26.27 µmol, 6.9% yield).

Example 128

Step A: Compound 144 (2.0 g, 5.71 mmol) (prepared as described in Example 22), 1-(propan-2-yl)-3-(tetramethyl-1,3,2-dioxaborolan-2-yl)-1H-pyrazole 139 (1.62 g, 6.85 mmol), cesium carbonate (3.72 g, 11.42 mmol) (2-dicyclohexylphosphino-2',4',6'-triisopropyl-1,1'-biphenyl)[2-(2'-amino-1,1'-biphenyl)]palladium(II) methanesulfonate (966.74 mg, 1.14 mmol) was dissolved in degassed dioxane:H₂O (40 mL:2 mL) and refluxed overnight. The mixture was cooled, filtered and concentrated. The residue was purified by column chromatography (eluted by Hexane:EtOAc 10:1 to 1:10). The product 149 was obtained as orange powder (1.2 g, 90.0% purity, 2.85 mmol, 49.8% yield).

Step B: Compound 149 (1.2 g, 3.16 mmol) was dissolved in 5 mL dioxane. At 0° C. 6M dioxane*HCl was added dropwise. The mixture was stirred overnight at room temperature. The solvent was evaporated and the residue was purified by flash chromatography (eluted by EtOAc). Compound 150 was obtained as dark-grey gum (530.0 mg, 90.0% purity, 1.71 mmol, 57.3% yield).

Step C: Compound 150 (430.35 mg, 1.54 mmol), 1-methyl-1H-imidazole-2-carbonitrile (247.51 mg, 2.31 mmol), and potassium tert-butylate (691.45 mg, 6.16 mmol) were dissolved in dry MeOH (5 mL) and stirred overnight at room temperature. The residue was evaporated and concentrated acetic acid added to pH=5. After that, EtOAc (15 mL) was added and the organic phase dried over Na₂SO₄, evaporated to give product 151 (400.0 mg, 80.0% purity, 902.86 µmol, 58.6% yield).

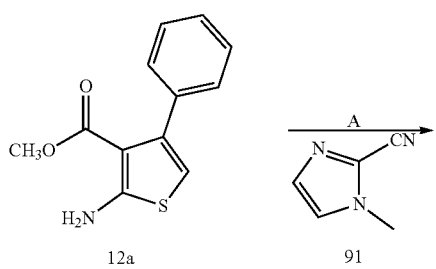

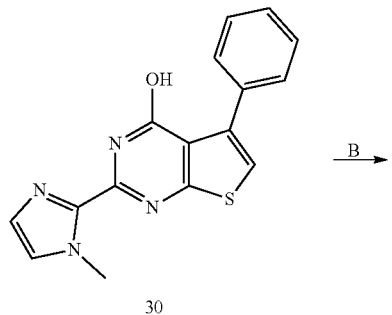

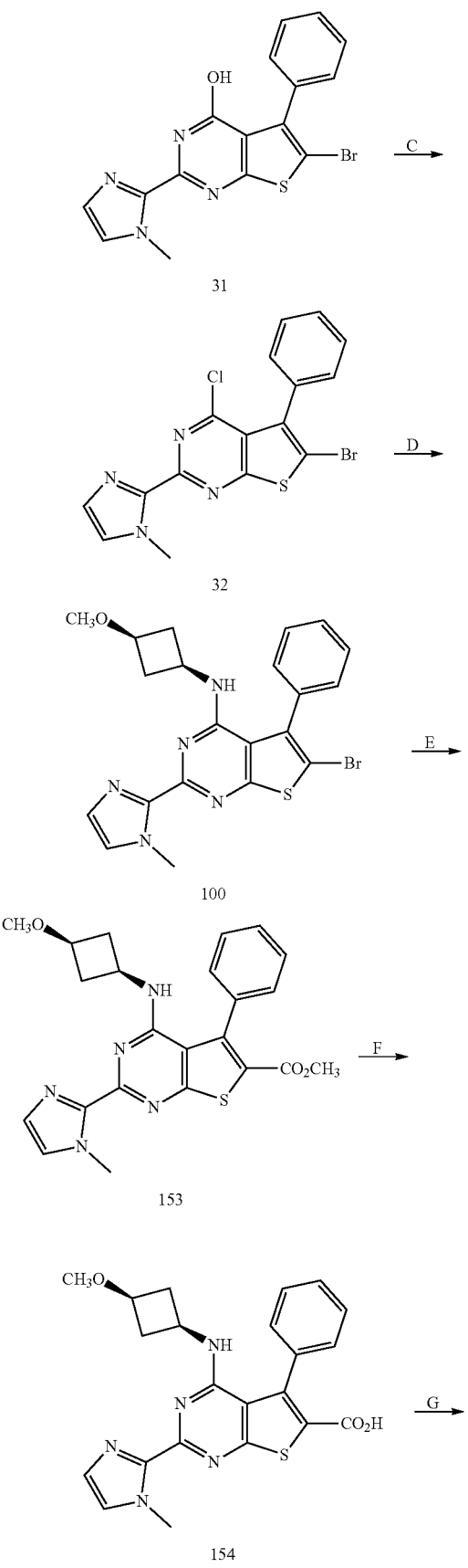

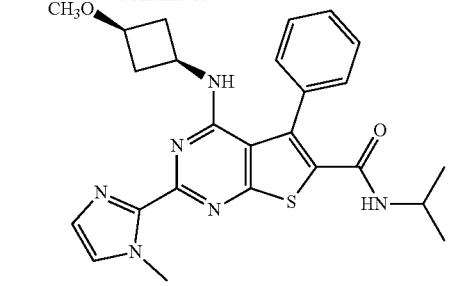

Step A: Methyl 2-amino-4-phenylthiophene-3-carboxylate 12a (5.0 g, 21.43 mmol), 1-methyl-1H-imidazole-2-carbonitrile 91 (3.44 g, 32.15 mmol), potassium tert-butylate (19.24 g, 171.46 mmol) was dissolved in dry MeOH (75 mL) and stirred overnight at RT. The resulting residue was evaporated and acetic acid was added up to pH 5, then EtOAc (150 mL) was added and extracted, then the organic layer was dried over $Na_2SO_4$, and evaporated to give compound 30 (5.0 g, 73.0% purity, 11.84 mmol, 55.2% yield), which was used without additional purification in the next step.

Step B: Compound 30 (5.0 g, 16.21 mmol) was dissolved in DMF (50 mL) and N-bromosuccinimide (4.33 g, 24.32 mmol) was added in one portion at room temperature. The reaction mixture was stirred at 65° C. overnight; then it was poured into ice (100 mL) and filtered. The resulting solid was washed with water (100 mL), dried at reduced pressure to give compound 31 (3.7 g, 9.55 mmol, 58.9% yield) as yellow solid.

Step C: Compound 31 (3.7 g, 9.55 mmol) was suspended in phosphoroyl trichloride (14.65 g, 95.54 mmol, 8.91 mL) and N,N-diisopropylethylamine (3.7 g, 28.66 mmol, 4.99 mL) was added at room temperature. The reaction mixture was refluxed for 16 h, then the solution was cooled to room temperature, evaporated under reduced pressure, poured in ice-water (50 mL) and diluted with ice-cold ammonia (20 mL, 20-25% of ammonia). The desired product was extracted with chloroform (2×50 mL) and the solvent was evaporated to give compound 32 (3.4 g, 91.0% purity, 7.63 mmol, 79.8% yield) as yellow solid.

Step D: Compound 32 (13.76 g, 33.92 mmol) was dissolved in DMSO (140 mL) and diisopropyl ethyl amine (10.96 g, 84.8 mmol, 14.77 mL) with cis-3-methoxycyclobutan-1-amine hydrochloride (7.0 g, 50.88 mmol) was then added. The mixture was heated overnight at 100° C., cooled and purified by HPLC to give compound 100 (2.64 g, 91.0% purity, 5.11 mmol, 15.1% yield).

Step E: Compound 100 (731.44 mg, 1.55 mmol), triethylamine (188.76 mg, 1.87 mmol, 260.0 μL) and Pddppf (38.1 mg, 46.65 μmol) was dissolved in MeOH (30 mL). The solution was stirred 16 h at 120° C. under 30 atm CO in an autoclave. The solution was cooled to room temperature and solvent was evaporated. The residue was diluted with EtOAc (10 mL) and 10 mL water. The organic phase was separated, dried over anhydrous sodium sulfate and concentrated. Compound 153 was obtained as white powder (500.0 mg, 95.0% purity, 1.06 mmol, 68% yield).

Step F: To a solution of compound 153 (400.0 mg, 889.83 μmol) in $THF:H_2O$ (5 mL:5 mL) $LiOH\ H_2O$ (74.77 mg, 1.78 mmol) was added in one portion. This mixture was stirred overnight at room temperature, then it was acidified by addition of 2M HCl and stirred 15 min. The precipitate was filtered and washed with $H_2O$ (5 mL), THF (3 mL) and MTBE (5 mL). Compound 154 was obtained as white powder (300.0 mg, 97.0% purity, 668.2 μmol, 75% yield).

Step G: General Procedure: DIPEA (88.68 mg, 686.12 μmol) was added dropwise at room temperature to a solution of compound 154 (100.0 mg, 229.62 μmol) and HATU (104.35 mg, 274.45 μmol) in DMF (2 mL). The resulting mixture was stirred 30 min at room temperature and the appropriate corresponding amine (2 eq) was added in one portion. Then the mixture was stirred at room temperature overnight and purified by HPLC. Products were obtained as light-brown powder. Using the general procedure with isopropyl amine hydrochloride as the amine produced the Example compound (0.0132 mg, 11.5% yield).

Examples 129-131

Following the general procedure described in Example 128, Step G, Examples 129-131 (shown in Table M) were prepared from compound 154 using the appropriate corresponding amine.

TABLE M

| Example | Structure | Amount | Yield |
|---|---|---|---|
| 129 | (structure) | 0.0421 g | 35.4% |
| 130 | (structure) | 0.0487 g | 38.9% |
| 131 | (structure) | 0.0202 g | 16.5% |

Example 132

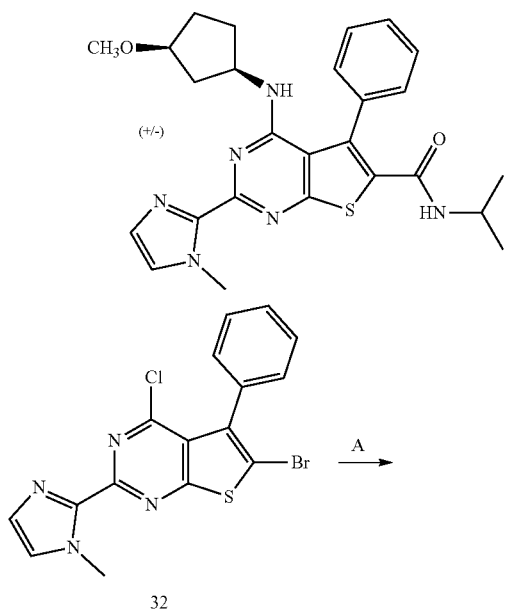

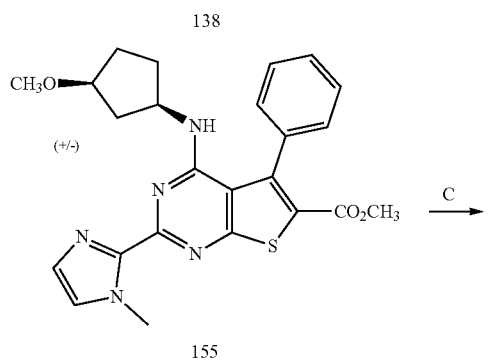

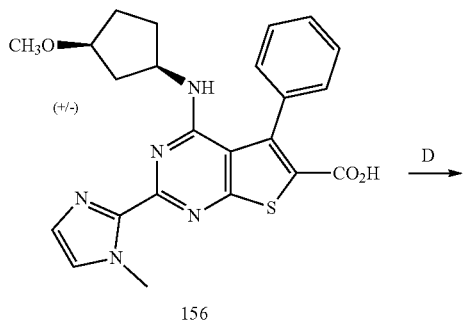

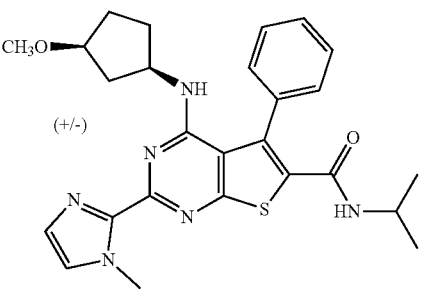

Step A: Compound 32 (prepared as described in Example 128, Step C) was dissolved in DMSO (15 mL) and diisoproplyl ethyl amine (934.92 mg, 7.23 mmol, 1.26 mL) with racemic cis-3-methoxycyclopentan-1-amine (500.01 mg, 4.34 mmol) was added in one portion. The mixture was heated at 100° C. overnight, cooled and purified by HPLC to give compound 138 (340.0 mg, 93.0% purity, 652.75 μmol, 22.6% yield).

Step B: Compound 138 (1.01 g, 2.09 mmol), triethylamine (254.1 mg, 2.51 mmol, 350.0 μL) and Pddppf (51.27 mg, 62.78 μmol) was dissolved in MeOH (30 mL). The resulting solution was stirred 16 h at 120° C. under 30 atm CO in an autoclave. Solution was cooled to room temperature and solvents were evaporated. The resulted residue was treated with EtOAc (10 mL) and water (10 mL), the organic layer was separated, dried over anhydrous $Na_2SO_4$, concentrated and treated with MTBE (5 mL). Precipitate formed was filtered and dried in air. Compound 155 was obtained as white powder (900.0 mg, 92.0% purity, 1.79 mmol, 85.4% yield).

Step C: To a solution of compound 155 (900.0 mg, 1.94 mmol) in THF:$H_2O$ 5 mL:5 mL, lithium hydroxide monohydrate (244.49 mg, 5.83 mmol) was added in one portion. The mixture was stirred overnight at room temperature. Then it was neutralized by addition of 2M HCl and stirred 15 min. Precipitate formed was filtered and washed with $H_2O$ (5 mL), THF (3 mL) and MTBE (5 mL). Compound 156 was obtained as white powder (700.0 mg, 92.0% purity, 1.43 mmol, 73.8% yield).

Step D: General Procedure of amidation: DIPEA (85.97 mg, 665.21 μmol, 120.0 μL) was added dropwise at room temperature to a solution of compound 156 (100.0 mg, 222.46 μmol) and HATU (101.17 mg, 266.09 μmol) in 2 mL DMF. The mixture was stirred 30 min at room temperature. Then the appropriate corresponding amine (2 eq) was added in one portion. The mixture was stirred at room temperature overnight and purified by HPLC. Products were obtained as light-brown powder. Using the general procedure with isopropyl amine hydrochloride as the amine produced the Example compound (0.0367 mg, 30.9% yield).

Examples 133-135

Following the general procedure described in Example 132, Step D, Examples 133-135 (shown in Table N) were prepared from compound 156 using the appropriate corresponding amine.

TABLE N

| Example | Structure | Amount | Yield |
|---|---|---|---|
| 133 | (+/-), CH3O-cyclopentyl-NH-[4-amino-5-phenyl-2-(1-methylimidazol-2-yl)thieno[2,3-d]pyrimidine-6-carboxamide]-NH-CH2CH2-OCH3 | 0.0268 g | 21.9% |
| 134 | (+/-), CH3O-cyclopentyl-NH-[4-amino-5-phenyl-2-(1-methylimidazol-2-yl)thieno[2,3-d]pyrimidin-6-yl]-C(O)-pyrrolidine | 0.0223 g | 18.9% |
| 135 | (+/-), CH3O-cyclopentyl-NH-[4-amino-5-phenyl-2-(1-methylimidazol-2-yl)thieno[2,3-d]pyrimidin-6-yl]-C(O)-morpholine | 0.0368 g | 30.4% |

Example 136

Protocols for MAPK Cell-Based Phosphorylation Assays

Protocol for ELISA MAPK Cell-Based Phosphorylation Assay

Cell lines: Tumor-derived pancreatic cancer cell line PANC-1 was purchased from ATCC and were and grown in DMEM-High Glucose supplemented with penicillin (100 U/mL), streptomycin (100 μg/mL), and 10% heat-inactivated FBS at 37° C. in a humidified incubator with 5% $CO_2$.

Method: Cells were plated at 7500 cells/well density in a 96-well plate, allowed 3 hours to adhere to the plate, then starved in DMEM plus 0.5% FBS overnight. The small molecules to be tested were added to the cells in the final concentration of 10 μM in the presence of 0.3% DMSO for 6 hours incubation at 37° C. For $IC_{50}$ value determination, serial dilutions of compounds were added to cells under the same conditions. Next, cells were stimulated with 1.5 ng/mL EGF for 15 minutes followed by cell fixation with 4% formaldehyde in PBS at room temperature for 20 minutes. Cell-direct ELISA determined phosphorylation level of MAPK.

Cell-direct ELISA: For each well, cells were permeabilized with 0.1% PBS-Triton X-100, quenched with 0.06% $H_2O_2$ in 0.1% PBS-Triton X-100, and probed with anti-phospho-MAPK antibodies (R&D Systems) followed by HRP-conjugated secondary antibody (Jackson Immunoresearch, West Grove, PA). Next, a 50 µM solution of the fluorescent substrate AmpliFlu Red (Sigma) was added and incubated at RT for 20 minutes. At the end of the incubation time, phosphorylation level of MAPK was determined by measuring fluorescence at 595 nm using SpectraMax M3 plate reader (Molecular Devices).

Protocol for Western MAPK Cell-Based Phosphorylation Assay

Cell lines: Human NSCLC cells NCI-H1975 and NCI-H1299, and tumor-derived pancreatic cancer cell lines Panc-1, MIA-PaCa-2, and BxPC3, were all purchased from American Type Culture Collection and grown in complete RPMI medium (BxPC3, NCI-H1975 and NCI-H1299) or DMEM-High Glucose (Panc1 and MIA-PaCa-2), supplemented with penicillin (100 U/mL), streptomycin (100 µg/mL), and 10% heat-inactivated FBS at 37° C. in a humidified incubator with 5% $CO_2$.

Method: Cells were plated at 350000 cells/well density in a 12-well plate, allowed 3 hours to adhere to the plate, then starved in the appropriate medium in the presence of 0.5% FBS overnight. The small molecules to be tested were added to the cells in the final concentration of 10 µM in the presence of 0.3% DMSO for 6 hours incubation at 37° C. For $IC_{50}$ value determination, serial dilutions of compounds were added to cells under the same conditions. Next, cells were stimulated with 1.5 ng/ml EGF for 15 minutes then cells were lysed with lysis buffer containing 1% Triton X-100, EDTA, and Halt™ Protease & Phosphatase Inhibitor Cocktail (Thermo Scientific). Protein concentration was assessed by BCA protein assay (Thermo Scientific). Phosphorylation level of MAPK was determined by western blot.

Western blot protocol: Equal amounts of protein (15-50 µg) were separated by SDS-PAGE and transferred to nitrocellulose membranes (Invitrogen by Thermo Fisher Scientific). The membrane was stained with Ponceau S Stain (Boston BioProducts) to verify uniform protein loading. Membranes were blocked with 10% milk and phosphorylation levels of MAPK were assessed by incubating overnight at 4° C. with anti-phospho-p44/42 (Thr202/Tyr204) antibody (Cell Signaling) followed by HRP-conjugated secondary antibody (Jackson Immunoresearch, West Grove, PA). Bands were incubated in Amersham ECL Prime Western Blotting Detection Reagent (GE Healthcare) and visualized using the ChemiDoc MP imaging system (Bio-Rad).

Protocol for Western AKT Cell-Based Phosphorylation Assay

Human tumor-derived pancreatic cancer cell line Panc-1 was purchased from American Type Culture Collection and grown in complete DMEM-High Glucose supplemented with penicillin (100 U/mL), streptomycin (100 µg/mL), and 10% heat-inactivated FBS at 37° C. in a humidified incubator with 5% $CO_2$.

Method: Cells were plated at 350000 cells/well density in a 12-well plate, allowed 3 hours to adhere to the plate, then starved in the appropriate medium in the presence of 0.5% FBS overnight. The small molecules to be tested were added to the cells in the final concentration of 10 µM in the presence of 0.3% DMSO for 6 hours incubation at 37° C. Next, cells were stimulated with 1.5 ng/ml EGF for 15 minutes then cells were lysed with lysis buffer containing 1% Triton X-100, EDTA, and Halt™ Protease & Phosphatase Inhibitor Cocktail (Thermo Scientific). Protein concentration was assessed by BCA protein assay (Thermo Scientific). Phosphorylation level of Akt was determined by western blot.

Western blot protocol: Equal amounts of protein (15-50 µg) were separated by SDS-PAGE and transferred to nitrocellulose membranes (Invitrogen by Thermo Fisher Scientific). The membrane was stained with Ponceau S Stain (Boston BioProducts) to verify uniform protein loading. Membranes were blocked with 10% milk and phosphorylation levels of Akt were assessed by incubating overnight at 4° C. with anti-phospho-Akt (Ser473) antibody (Cell Signaling) followed by HRP-conjugated secondary antibody (Jackson Immunoresearch, West Grove, PA). Bands were incubated in Amersham ECL Prime Western Blotting Detection Reagent (GE Healthcare) and visualized using the ChemiDoc MP imaging system (Bio-Rad).

Protocol for Western MEK Cell-Based Phosphorylation Assay

Cell lines: Human NSCLC cells NCI-H1975 and tumor-derived pancreatic cancer cell lines Panc-1 and MIA-PaCa-2 were all purchased from American Type Culture Collection and grown in complete RPMI medium (NCI-H1975) or DMEM-High Glucose (Panc1 and MIA-PaCa-2), supplemented with penicillin (100 U/mL), streptomycin (100 µg/mL), and 10% heat-inactivated FBS at 37° C. in a humidified incubator with 5% $CO_2$.

Method: Cells were plated at 350000 cells/well density in a 12-well plate, allowed 3 hours to adhere to the plate, then starved in the appropriate medium in the presence of 0.5% FBS overnight. The small molecules to be tested were added to the cells in the final concentration of 10 µM in the presence of 0.3% DMSO for 6 hours incubation at 37° C. For $IC_{50}$ value determination, serial dilutions of compounds were added to cells under the same conditions. Next, cells were stimulated with 1.5 ng/ml EGF for 15 minutes then cells were lysed with lysis buffer containing 1% Triton X-100, EDTA, and Halt™ Protease & Phosphatase Inhibitor Cocktail (Thermo Scientific). Protein concentration was assessed by BCA protein assay (Thermo Scientific). Phosphorylation level of MEK was determined by western blot.

Western blot protocol: Equal amounts of protein (15-50 µg) were separated by SDS-PAGE and transferred to nitrocellulose membranes (Invitrogen by Thermo Fisher Scientific). The membrane was stained with Ponceau S Stain (Boston BioProducts) to verify uniform protein loading. Membranes were blocked with 10% milk and phosphorylation levels of MEK were assessed by incubating overnight at 4° C. with anti-phospho-MEK 1/2 (Ser217/Ser221) antibody (Cell Signaling) followed by HRP-conjugated secondary antibody (Jackson Immunoresearch, West Grove, PA). Bands were incubated in Amersham ECL Prime Western Blotting Detection Reagent (GE Healthcare) and visualized using the ChemiDoc MP imaging system (Bio-Rad).

Tables 4, 4A, 4B, and 4C show inhibition data for selected compounds tested in one or more of the cellular assays described above.

TABLE 4

% Inhibition of MAPK phosphorylation at 10 μM in the PANC-1, BxPC3,
MIA PaCa-2 pancreatic cancer cell lines, and NCI H1975, NCI H1299 non-small-cell
lung cancer cell lines; and
% Inhibition of AKT phosphorylation at 10 μM in PANC-1 pancreatic cancer cell lines

| Compound | MAPK | | | | | AKT |
| --- | --- | --- | --- | --- | --- | --- |
| | PANC-1 | BxPC3 | MIA PaCa-2 | H1975 | H1299 | PANC-1 |
| *structure* | B | | | | | 0 |
| *structure* | 0 | | | | | 0 |
| *structure* | 0 | | | | | 0 |
| *structure* | B | | | | | 0 |
| *structure* | C | | | | | 0 |

TABLE 4-continued
% Inhibition of MAPK phosphorylation at 10 μM in the PANC-1, BxPC3, MIA PaCa-2 pancreatic cancer cell lines, and NCI H1975, NCI H1299 non-small-cell lung cancer cell lines; and
% Inhibition of AKT phosphorylation at 10 μM in PANC-1 pancreatic cancer cell lines
| | | MAPK | | | | AKT |
|---|---|---|---|---|---|---|
| Compound | PANC-1 | BxPC3 | MIA PaCa-2 | H1975 | H1299 | PANC-1 |
| 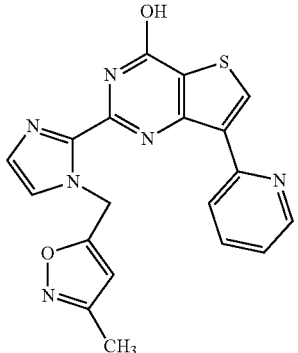 [SMILES: Cc1cc(Cn2ccnc2-c2nc(O)c3scc(-c4ccccn4)c3n2)on1] | 0 | | | | | 0 |
| 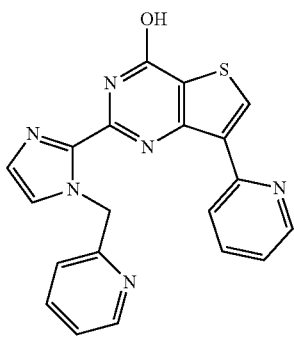 [SMILES: Oc1nc(-c2nccn2Cc2ccccn2)nc2c(-c3ccccn3)csc12] | C | | | | | 0 |
| 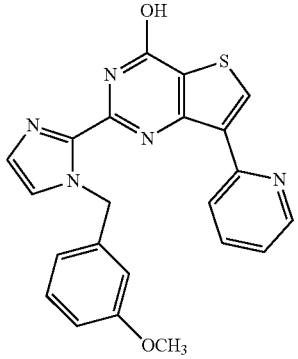 [SMILES: COc1cccc(Cn2ccnc2-c2nc(O)c3scc(-c4ccccn4)c3n2)c1] | C | | | | | 0 |
| 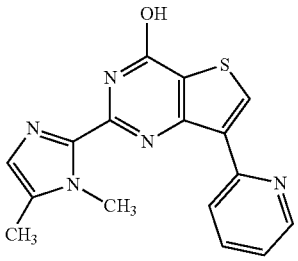 [SMILES: Cc1cnc(-c2nc(O)c3scc(-c4ccccn4)c3n2)n1C] | 0 | | | | | 0 |

TABLE 4-continued
% Inhibition of MAPK phosphorylation at 10 μM in the PANC-1, BxPC3,
MIA PaCa-2 pancreatic cancer cell lines, and NCI H1975, NCI H1299 non-small-cell
lung cancer cell lines; and
% Inhibition of AKT phosphorylation at 10 μM in PANC-1 pancreatic cancer cell lines
| Compound | MAPK | | | | | AKT |
|---|---|---|---|---|---|---|
| | PANC-1 | BxPC3 | MIA PaCa-2 | H1975 | H1299 | PANC-1 |
| 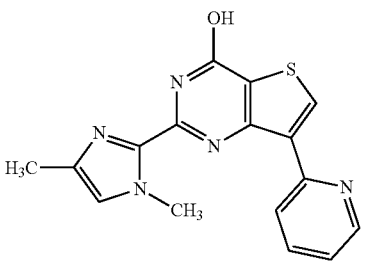 [SMILES: Cc1cn(C)c(-c2nc(O)c3scc(-c4ccccn4)c3n2)n1] | 0 | | | | | 0 |
| 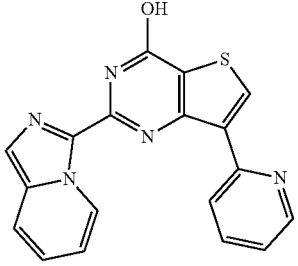 [SMILES: Oc1nc(-c2ncc3ccccn23)nc2c(-c3ccccn3)csc12] | 0 | | | | | 0 |
| 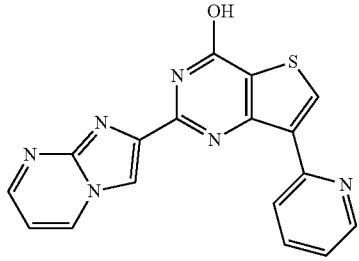 [SMILES: Oc1nc(-c2cn3cccnc3n2)nc2c(-c3ccccn3)csc12] | 0 | | | | | 0 |
| 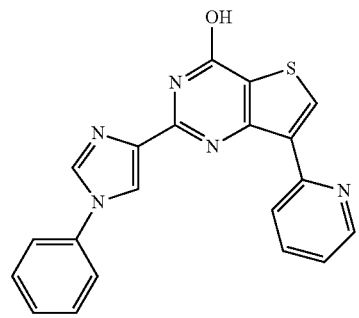 [SMILES: Oc1nc(-c2cn(-c3ccccc3)cn2)nc2c(-c3ccccn3)csc12] | 0 | | | | | 0 |

TABLE 4-continued
% Inhibition of MAPK phosphorylation at 10 µM in the PANC-1, BxPC3,
MIA PaCa-2 pancreatic cancer cell lines, and NCI H1975, NCI H1299 non-small-cell
lung cancer cell lines; and
% Inhibition of AKT phosphorylation at 10 µM in PANC-1 pancreatic cancer cell lines
| Compound | MAPK | | | | | AKT |
| --- | --- | --- | --- | --- | --- | --- |
| | PANC-1 | BxPC3 | MIA PaCa-2 | H1975 | H1299 | PANC-1 |
| 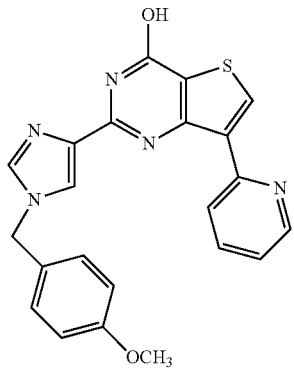 [SMILES: COc1ccc(Cn2cnc(-c3nc(O)c4scc(-c5ccccn5)c4n3)c2)cc1] | | | C | | | 0 |
| 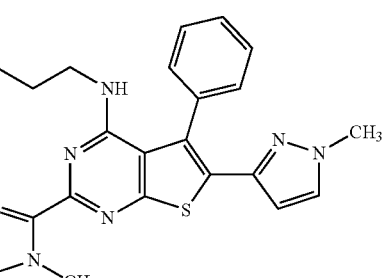 | | | B | | | 0 |
| 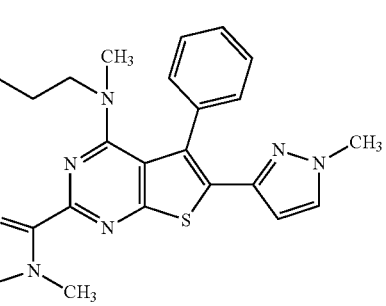 | | | C | | | 0 |
| 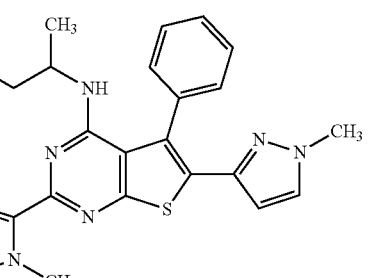 | | | C | | | 0 |

TABLE 4-continued
% Inhibition of MAPK phosphorylation at 10 μM in the PANC-1, BxPC3,
MIA PaCa-2 pancreatic cancer cell lines, and NCI H1975, NCI H1299 non-small-cell
lung cancer cell lines; and
% Inhibition of AKT phosphorylation at 10 μM in PANC-1 pancreatic cancer cell lines
| Compound | MAPK | | | | | AKT |
| --- | --- | --- | --- | --- | --- | --- |
| | PANC-1 | BxPC3 | MIA PaCa-2 | H1975 | H1299 | PANC-1 |
| 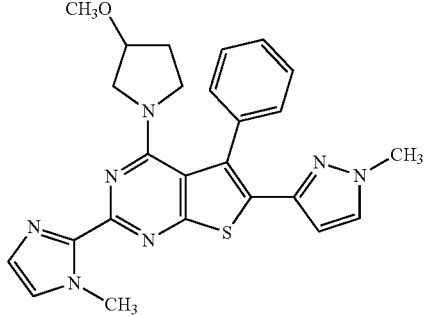 | A | | | | | 0 |
| 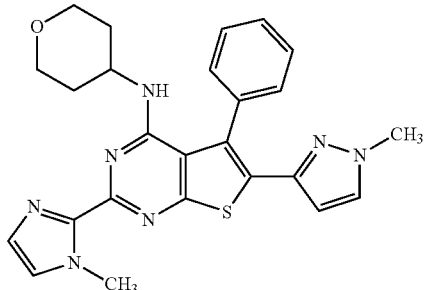 | A | | | | | A |
| 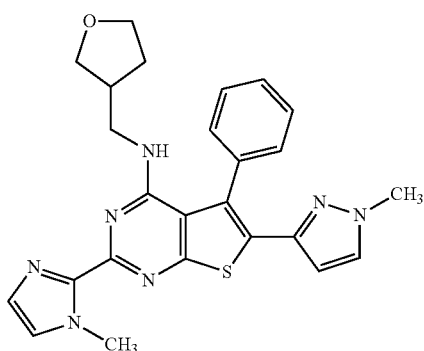 | A | | | | | 0 |
| (+/- cis) 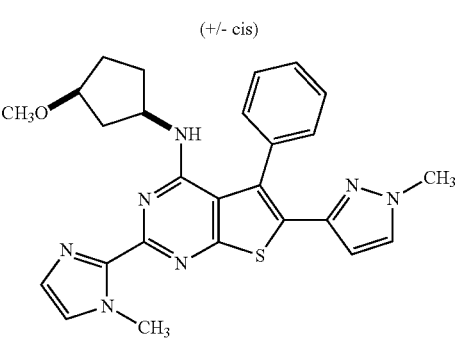 | D | D | D | D | D | D |

TABLE 4-continued

% Inhibition of MAPK phosphorylation at 10 μM in the PANC-1, BxPC3,
MIA PaCa-2 pancreatic cancer cell lines, and NCI H1975, NCI H1299 non-small-cell
lung cancer cell lines; and
% Inhibition of AKT phosphorylation at 10 μM in PANC-1 pancreatic cancer cell lines

| Compound | MAPK | | | | | AKT |
| --- | --- | --- | --- | --- | --- | --- |
| | PANC-1 | BxPC3 | MIA PaCa-2 | H1975 | H1299 | PANC-1 |
| (+/- trans) | D | 0 | 0 | B | B | 0 |
|  | D |  |  | B |  | 0 |
|  | 0 |  |  |  |  | 0 |
|  | D |  |  | B |  | 0 |

TABLE 4-continued

% Inhibition of MAPK phosphorylation at 10 μM in the PANC-1, BxPC3,
MIA PaCa-2 pancreatic cancer cell lines, and NCI H1975, NCI H1299 non-small-cell
lung cancer cell lines; and
% Inhibition of AKT phosphorylation at 10 μM in PANC-1 pancreatic cancer cell lines

| Compound | MAPK | | | | | AKT |
|---|---|---|---|---|---|---|
| | PANC-1 | BxPC3 | MIA PaCa-2 | H1975 | H1299 | PANC-1 |
| (structure) | 0 | | | | | 0 |
| (structure) | A | | | | | 0 |
| (structure) | A | | | | | 0 |
| (structure) | D | B | D | | | 0 |

TABLE 4-continued

% Inhibition of MAPK phosphorylation at 10 μM in the PANC-1, BxPC3,
MIA PaCa-2 pancreatic cancer cell lines, and NCI H1975, NCI H1299 non-small-cell
lung cancer cell lines; and
% Inhibition of AKT phosphorylation at 10 μM in PANC-1 pancreatic cancer cell lines

| Compound | MAPK | | | | | AKT |
|---|---|---|---|---|---|---|
| | PANC-1 | BxPC3 | MIA PaCa-2 | H1975 | H1299 | PANC-1 |
| [structure] | 0 | | | | | 0 |
| [structure] | D | D | B | | | 0 |
| [structure] | 0 | | | | | 0 |
| [structure] | D | 0 | D | 0 | 0 | 0 |

TABLE 4-continued

% Inhibition of MAPK phosphorylation at 10 μM in the PANC-1, BxPC3, MIA PaCa-2 pancreatic cancer cell lines, and NCI H1975, NCI H1299 non-small-cell lung cancer cell lines; and
% Inhibition of AKT phosphorylation at 10 μM in PANC-1 pancreatic cancer cell lines

| Compound | MAPK | | | | | AKT |
| --- | --- | --- | --- | --- | --- | --- |
| | PANC-1 | BxPC3 | MIA PaCa-2 | H1975 | H1299 | PANC-1 |
| *structure 1* | D | 0 | D | D | 0 | 0 |
| *structure 2* | D | A | D | D | 0 | B |
| *structure 3* | C | 0 | 0 | | | 0 |
| *structure 4* | D | B | D | D | 0 | 0 |

TABLE 4-continued

% Inhibition of MAPK phosphorylation at 10 μM in the PANC-1, BxPC3, MIA PaCa-2 pancreatic cancer cell lines, and NCI H1975, NCI H1299 non-small-cell lung cancer cell lines; and
% Inhibition of AKT phosphorylation at 10 μM in PANC-1 pancreatic cancer cell lines

| Compound | MAPK | | | | | AKT |
| --- | --- | --- | --- | --- | --- | --- |
| | PANC-1 | BxPC3 | MIA PaCa-2 | H1975 | H1299 | PANC-1 |
| (structure 1) | D | | | | | 0 |
| (structure 2) | D | | | | | D |
| (structure 3) | D | D | D | D | D | D |
| (structure 4) | C | B | D | | | |

TABLE 4-continued
% Inhibition of MAPK phosphorylation at 10 μM in the PANC-1, BxPC3,
MIA PaCa-2 pancreatic cancer cell lines, and NCI H1975, NCI H1299 non-small-cell
lung cancer cell lines; and
% Inhibition of AKT phosphorylation at 10 μM in PANC-1 pancreatic cancer cell lines
| Compound | MAPK | | | | | AKT |
|---|---|---|---|---|---|---|
| | PANC-1 | BxPC3 | MIA PaCa-2 | H1975 | H1299 | PANC-1 |
| 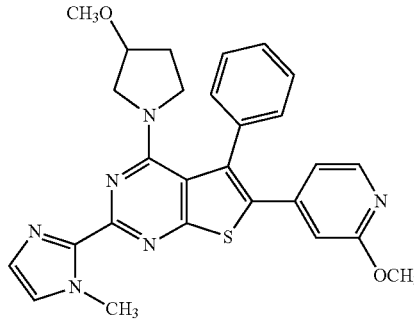 HCl | | | C | | | 0 |
| 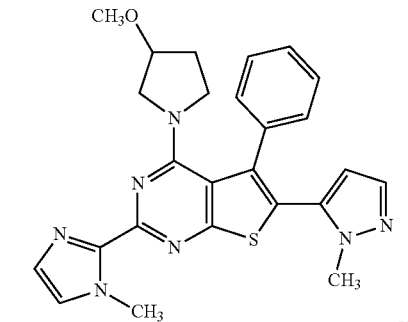 HCl | | | 0 | | | 0 |
| 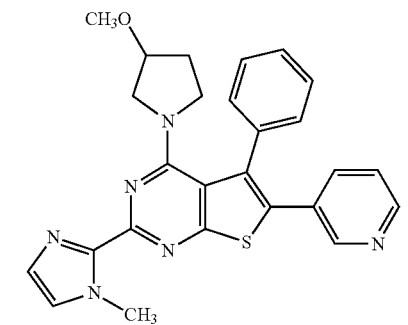 HCl | | | C | | | 0 |
| 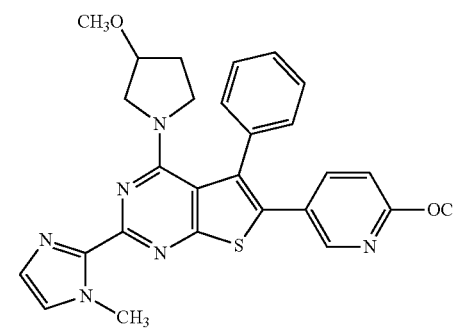 HCl | | | A | | | 0 |

TABLE 4-continued

% Inhibition of MAPK phosphorylation at 10 μM in the PANC-1, BxPC3,
MIA PaCa-2 pancreatic cancer cell lines, and NCI H1975, NCI H1299 non-small-cell
lung cancer cell lines; and
% Inhibition of AKT phosphorylation at 10 μM in PANC-1 pancreatic cancer cell lines

| Compound | MAPK | | | | | AKT |
|---|---|---|---|---|---|---|
| | PANC-1 | BxPC3 | MIA PaCa-2 | H1975 | H1299 | PANC-1 |
| (structure 1) HCl | D | | | | | 0 |
| (structure 2) HCl | C | | | | | 0 |
| (structure 3) HCl | C | | | | | 0 |
| (structure 4) HCl | 0 | | | | | 0 |

TABLE 4-continued
% Inhibition of MAPK phosphorylation at 10 μM in the PANC-1, BxPC3,
MIA PaCa-2 pancreatic cancer cell lines, and NCI H1975, NCI H1299 non-small-cell
lung cancer cell lines; and
% Inhibition of AKT phosphorylation at 10 μM in PANC-1 pancreatic cancer cell lines
| Compound | MAPK | | | | | AKT |
| --- | --- | --- | --- | --- | --- | --- |
| | PANC-1 | BxPC3 | MIA PaCa-2 | H1975 | H1299 | PANC-1 |
| 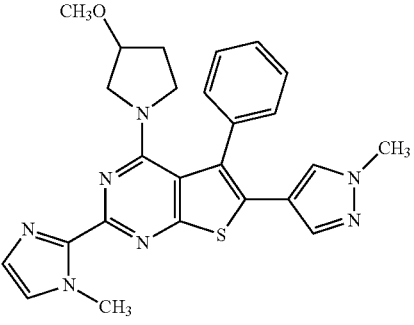 HCl | | | A | | | 0 |
| 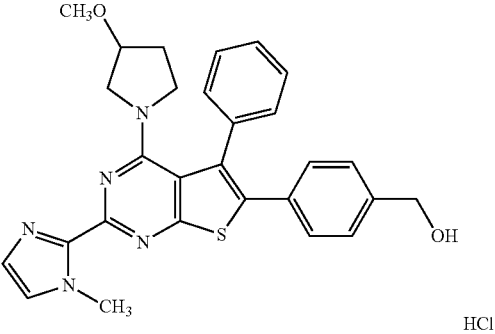 HCl | | | C | | | 0 |
| 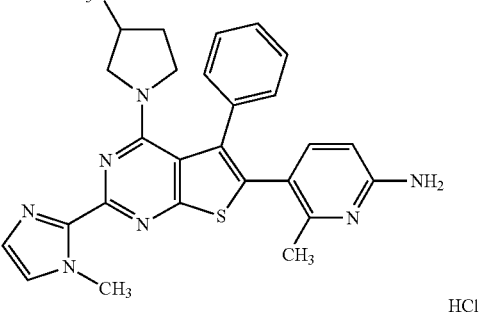 HCl | | | B | | | 0 |
| 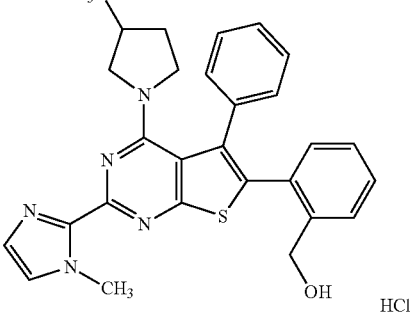 HCl | | | 0 | | | 0 |

TABLE 4-continued
% Inhibition of MAPK phosphorylation at 10 μM in the PANC-1, BxPC3,
MIA PaCa-2 pancreatic cancer cell lines, and NCI H1975, NCI H1299 non-small-cell
lung cancer cell lines; and
% Inhibition of AKT phosphorylation at 10 μM in PANC-1 pancreatic cancer cell lines
| Compound | MAPK | | | | | AKT |
| | PANC-1 | BxPC3 | MIA PaCa-2 | H1975 | H1299 | PANC-1 |
|---|---|---|---|---|---|---|
| 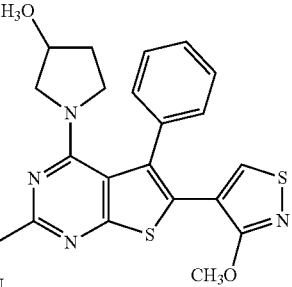 | C | | | | | 0 |
| 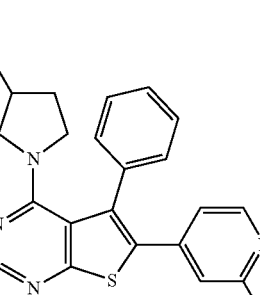 | D | | | | | 0 |
| 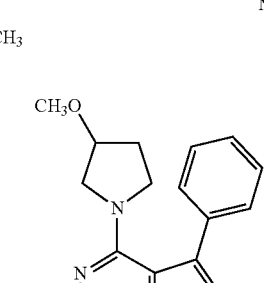 | B | | | | | 0 |
| 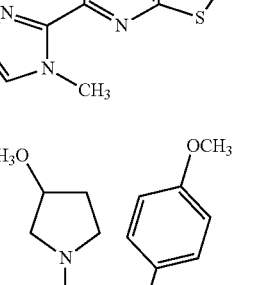 | 0 | | | | | 0 |

TABLE 4-continued
% Inhibition of MAPK phosphorylation at 10 µM in the PANC-1, BxPC3,
MIA PaCa-2 pancreatic cancer cell lines, and NCI H1975, NCI H1299 non-small-cell
lung cancer cell lines; and
% Inhibition of AKT phosphorylation at 10 µM in PANC-1 pancreatic cancer cell lines
| | MAPK | | | | | AKT |
|---|---|---|---|---|---|---|
| Compound | PANC-1 | BxPC3 | MIA PaCa-2 | H1975 | H1299 | PANC-1 |
| 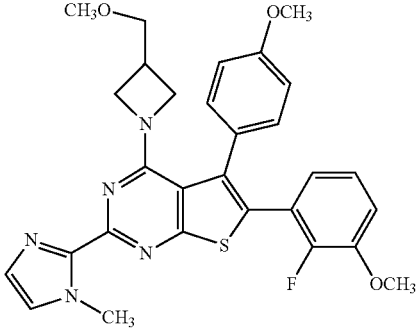 | | | D | | | 0 |
| 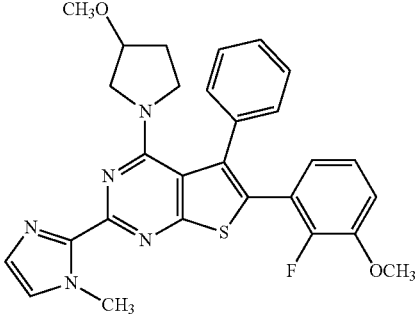 HCl | | | D | | | D |
| 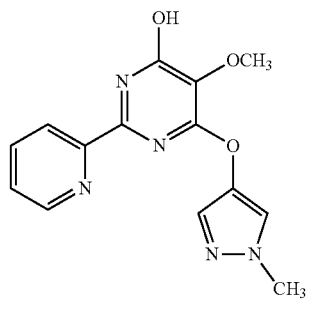 [SMILES: COc1c(O)nc(-c2ccccn2)nc1Oc1cnn(C)c1] | | | A | | | 0 |
| 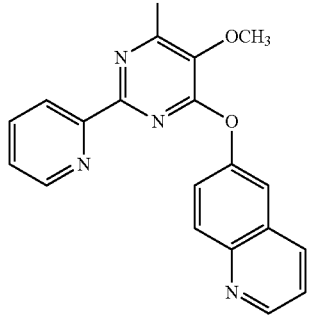 | | | 0 | | | 0 |

TABLE 4-continued

% Inhibition of MAPK phosphorylation at 10 μM in the PANC-1, BxPC3,
MIA PaCa-2 pancreatic cancer cell lines, and NCI H1975, NCI H1299 non-small-cell
lung cancer cell lines; and
% Inhibition of AKT phosphorylation at 10 μM in PANC-1 pancreatic cancer cell lines

| Compound | MAPK | | | | | AKT |
| --- | --- | --- | --- | --- | --- | --- |
| | PANC-1 | BxPC3 | MIA PaCa-2 | H1975 | H1299 | PANC-1 |
| (structure) | 0 | | | | | 0 |
| (structure) | 0 | | | | | 0 |
| (structure) | 0 | | | | | 0 |
| (structure) | 0 | | | | | 0 |

TABLE 4-continued

% Inhibition of MAPK phosphorylation at 10 μM in the PANC-1, BxPC3,
MIA PaCa-2 pancreatic cancer cell lines, and NCI H1975, NCI H1299 non-small-cell
lung cancer cell lines; and
% Inhibition of AKT phosphorylation at 10 μM in PANC-1 pancreatic cancer cell lines

| Compound | MAPK | | | | | AKT |
|---|---|---|---|---|---|---|
| | PANC-1 | BxPC3 | MIA PaCa-2 | H1975 | H1299 | PANC-1 |
| (structure) | 0 | | | | | 0 |
| (structure) | 0 | | | | | 0 |
| (structure) | 0 | | | | | 0 |
| (structure) | 0 | | | | | 0 |

TABLE 4-continued
% Inhibition of MAPK phosphorylation at 10 μM in the PANC-1, BxPC3,
MIA PaCa-2 pancreatic cancer cell lines, and NCI H1975, NCI H1299 non-small-cell
lung cancer cell lines; and
% Inhibition of AKT phosphorylation at 10 μM in PANC-1 pancreatic cancer cell lines
| Compound | MAPK | | | | | AKT |
|---|---|---|---|---|---|---|
| | PANC-1 | BxPC3 | MIA PaCa-2 | H1975 | H1299 | PANC-1 |
| 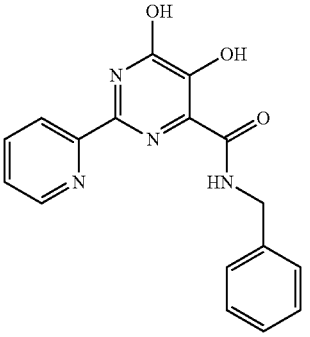 [SMILES: O=C(NCc1ccccc1)c1nc(-c2ccccn2)nc(O)c1O] | A | | | | | 0 |
| 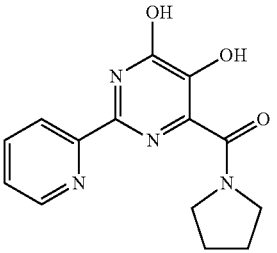 [SMILES: O=C(c1nc(-c2ccccn2)nc(O)c1O)N1CCCC1] | 0 | | | | | 0 |
| 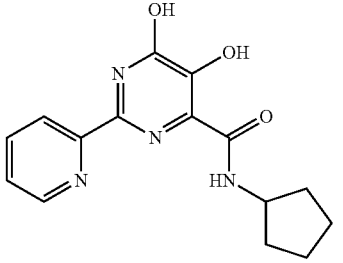 [SMILES: O=C(NC1CCCC1)c1nc(-c2ccccn2)nc(O)c1O] | 0 | | | | | 0 |
| 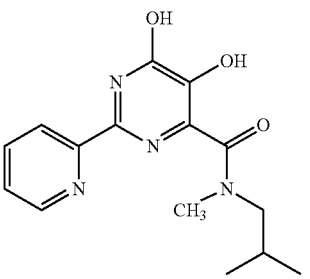 [SMILES: CC(C)CN(C)C(=O)c1nc(-c2ccccn2)nc(O)c1O] | 0 | | | | | 0 |
| 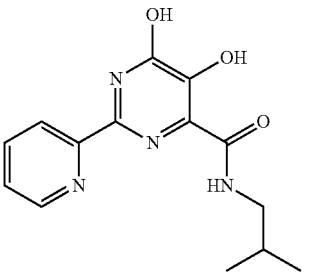 [SMILES: CC(C)CNC(=O)c1nc(-c2ccccn2)nc(O)c1O] | 0 | | | | | 0 |

TABLE 4-continued

% Inhibition of MAPK phosphorylation at 10 μM in the PANC-1, BxPC3,
MIA PaCa-2 pancreatic cancer cell lines, and NCI H1975, NCI H1299 non-small-cell
lung cancer cell lines; and
% Inhibition of AKT phosphorylation at 10 μM in PANC-1 pancreatic cancer cell lines

| | MAPK | | | | | AKT |
|---|---|---|---|---|---|---|
| Compound | PANC-1 | BxPC3 | MIA PaCa-2 | H1975 | H1299 | PANC-1 |
| *structure* | 0 | | | | | 0 |
| *structure* | 0 | | | | | 0 |
| *structure* | 0 | | | | | 0 |
| *structure* | 0 | | | | | 0 |
| *structure* | 0 | | | | | 0 |

TABLE 4-continued

% Inhibition of MAPK phosphorylation at 10 µM in the PANC-1, BxPC3,
MIA PaCa-2 pancreatic cancer cell lines, and NCI H1975, NCI H1299 non-small-cell
lung cancer cell lines; and
% Inhibition of AKT phosphorylation at 10 µM in PANC-1 pancreatic cancer cell lines

| Compound | MAPK | | | | | AKT |
|---|---|---|---|---|---|---|
| | PANC-1 | BxPC3 | MIA PaCa-2 | H1975 | H1299 | PANC-1 |
| [structure] | 0 | | | | | 0 |
| [structure] | 0 | | | | | 0 |
| [structure] | 0 | | | | | 0 |
| [structure] | 0 | | | | | 0 |
| [structure] | 0 | | | | | 0 |

TABLE 4-continued

% Inhibition of MAPK phosphorylation at 10 μM in the PANC-1, BxPC3,
MIA PaCa-2 pancreatic cancer cell lines, and NCI H1975, NCI H1299 non-small-cell
lung cancer cell lines; and
% Inhibition of AKT phosphorylation at 10 μM in PANC-1 pancreatic cancer cell lines

| Compound | MAPK | | | | | AKT |
|---|---|---|---|---|---|---|
| | PANC-1 | BxPC3 | MIA PaCa-2 | H1975 | H1299 | PANC-1 |
| [structure: pyrimidine with OCH3, OCH3, pyridine, NH-pyrazole-CH2CH2OCH3] | 0 | | | | | 0 |
| [structure: pyrrolo[2,1-f][1,2,4]triazine with methoxypyrrolidine, two phenyls, N-methylimidazole] | | | C | | | 0 |

0 = 0% inhibition, A = 1-25% inhibition, B = 26-50% inhibition, C = 51-75% inhibition, D = 76-100% inhibition.

TABLE 4A

MAPK IC$_{50}$ (nM) values in the PANC1, BxPC3, MIA PaCa-2 pancreatic cell lines, and NCI H1975, NCI H1299 non-small-cell lung cancer cell lines

| Compound | PANC-1 | BxPC3 | MIA PaCa-2 | H1975 | H1299 |
|---|---|---|---|---|---|
| [structure: thieno[2,3-d]pyrimidine with CH3OCH2CH2-NH, phenyl, chloro-methoxyphenyl, N-methylimidazole] | F | E | F | E | E |

TABLE 4A-continued
MAPK IC$_{50}$ (nM) values in the PANC1, BxPC3, MIA PaCa-2 pancreatic cell lines, and NCI H1975, NCI H1299 non-small-cell lung cancer cell lines
| Compound | PANC-1 | BxPC3 | MIA PaCa-2 | H1975 | H1299 |
|---|---|---|---|---|---|
| 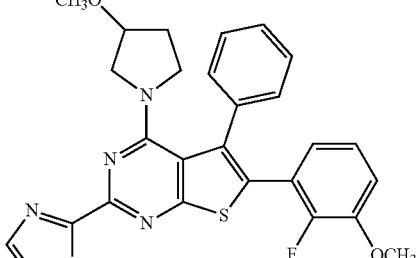 HCl | | | E | | |
| (+/- cis) 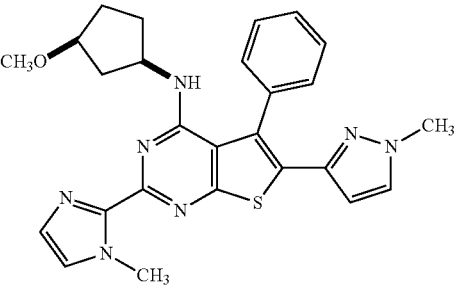 | | | F | E | E |
| 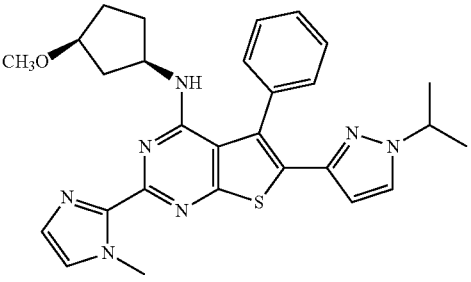 | | | E | | |
E = >1000 nM IC$_{50}$, F = 750-1000 nM IC$_{50}$, G = 500-749 nM IC$_{50}$, H = <500 nM IC$_{50}$.
TABLE 4B
MEK IC50 (nM) values in the PANC-1, MIA PaCa-2 pancreatic cell lines. and NCI H1975 non-small-cell lung cancer cell
| Compound | PANC-1 | MIA PaCa-2 | H1975 |
|---|---|---|---|
| 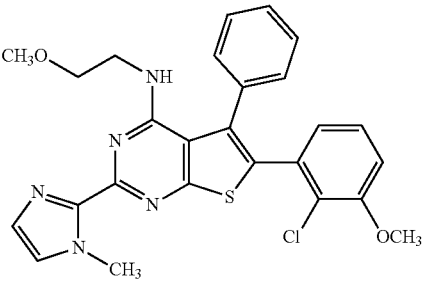 | F | F | E |

TABLE 4B-continued
MEK IC50 (nM) values in the PANC-1, MIA PaCa-2 pancreatic cell lines.
and NCI H1975 non-small-cell lung cancer cell
| Compound | PANC-1 | MIA PaCa-2 | H1975 |
|---|---|---|---|
| 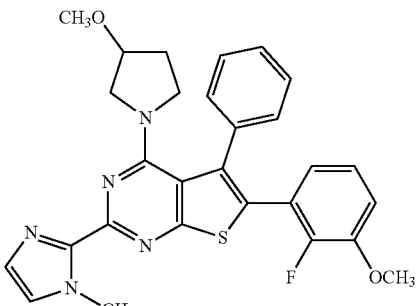 HCl | | E | |
| 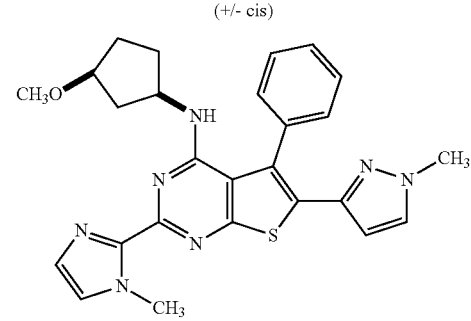 (+/- cis) | F | E | E |
$E = >1000$ nM $IC_{50}$, $F = 750$-$1000$ nM $IC_{50}$, $G = 500$-$749$ nM $IC_{50}$, $H = <500$ nM $IC_{50}$.
TABLE 4C
% Inhibition of MAPK phosphorylation and AKT phosphorylation at 10 μM in
the PANC-1 pancreatic cancer cell lines
| Compound | MAPK | AKT |
|---|---|---|
| 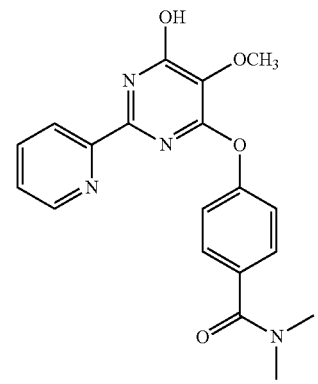 | 0 | 0 |

TABLE 4C-continued

% Inhibition of MAPK phosphorylation and AKT phosphorylation at 10 μM in the PANC-1 pancreatic cancer cell lines

| Compound | MAPK | AKT |
|---|---|---|
| [structure: 2-(pyridin-2-yl)-5-methoxy-6-(phenylamino)pyrimidin-4-ol] | 0 | 0 |
| [structure: 2-(pyridin-2-yl)-5-methoxy-6-((1-ethyl-1H-pyrazol-4-yl)amino)pyrimidin-4-ol] | 0 | 0 |
| [structure: 2-(pyridin-2-yl)-5-methoxy-6-((3-ethoxyphenyl)amino)pyrimidin-4-ol] | 0 | 0 |
| [structure: N-(3-methoxycyclopentyl)-2-(1-methyl-1H-imidazol-2-yl)-6-(2-fluoro-3-methoxyphenyl)-5-phenylthieno[2,3-d]pyrimidin-4-amine] | D | D |
| [structure: N-((1S,3R)-3-methoxycyclopentyl)-2-(1-methyl-1H-imidazol-2-yl)-6-(2-fluoro-3-methoxyphenyl)-5-phenylthieno[2,3-d]pyrimidin-4-amine] (+/−) | D | D |

TABLE 4C-continued

% Inhibition of MAPK phosphorylation and AKT phosphorylation at 10 μM in the PANC-1 pancreatic cancer cell lines

| Compound | MAPK | AKT |
|---|---|---|
| (structure) | D | 0 |
| (structure) | D | D |
| (structure) (+/−) | D | D |
| (structure) | D | D |
| (structure) (+/−) | D | 0 |

TABLE 4C-continued

% Inhibition of MAPK phosphorylation and AKT phosphorylation at 10 μM in the PANC-1 pancreatic cancer cell lines

| Compound | MAPK | AKT |
|---|---|---|
| (methoxypyrrolidinyl-phenyl-(2-fluoro-3-methoxyphenyl)-(1-methylimidazol-2-yl)thienopyrimidine) | D | D |
| (methoxycyclobutyl-NH-phenyl-(2-fluoro-3-methoxyphenyl)-(1-methylimidazol-2-yl)thienopyrimidine) | D | D |
| (methoxycyclobutyl-NH-phenyl-(1-methylpyrazol-4-yl)-(1-methylimidazol-2-yl)thienopyrimidine) | D | B |
| (methoxycyclopentyl-NH-methyl-(2-fluoro-3-methoxyphenyl)-(1-methylimidazol-2-yl)thienopyrimidine) | D | 0 |
| (methoxycyclopentyl-NH-methyl-(2-fluoro-3-methoxyphenyl)-(1-methylimidazol-2-yl)thienopyrimidine) (+/-) | D | 0 |

TABLE 4C-continued
% Inhibition of MAPK phosphorylation and AKT phosphorylation at 10 μM in the PANC-1 pancreatic cancer cell lines
| Compound | MAPK | AKT |
|---|---|---|
| 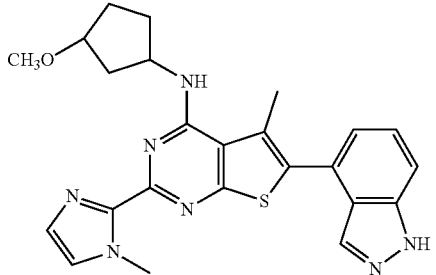 | D | D |
| 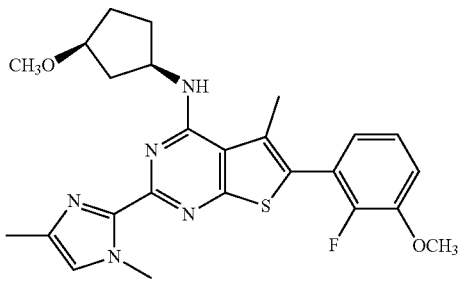 (+/−) | D | 0 |
| 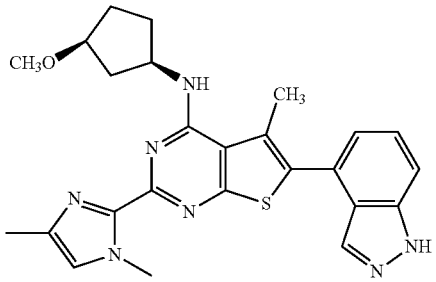 (+/−) | D | 0 |
| 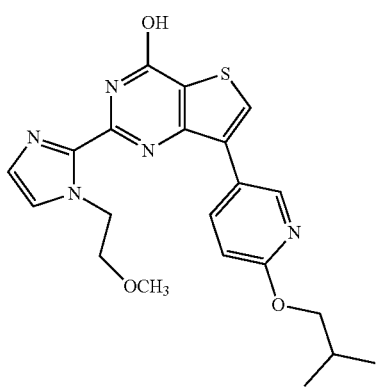 [SMILES: COCCn1ccnc1-c1nc(O)c2scc(-c3ccc(OCC(C)C)nc3)c2n1] | D | 0 |

TABLE 4C-continued
% Inhibition of MAPK phosphorylation and AKT phosphorylation at 10 μM in the PANC-1 pancreatic cancer cell lines
| Compound | MAPK | AKT |
|---|---|---|
| 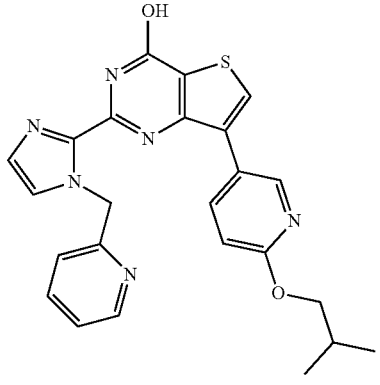 [SMILES: CC(C)COc1ccc(-c2csc3c(O)nc(-c4nccn4Cc4ccccn4)nc23)cn1] | D | 0 |
| 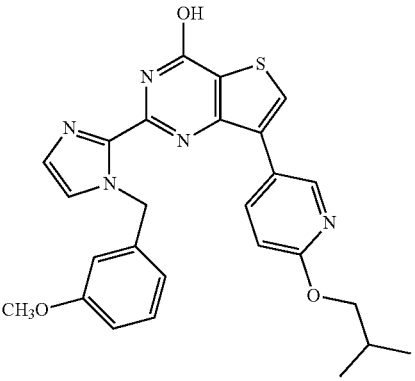 | D | 0 |
| 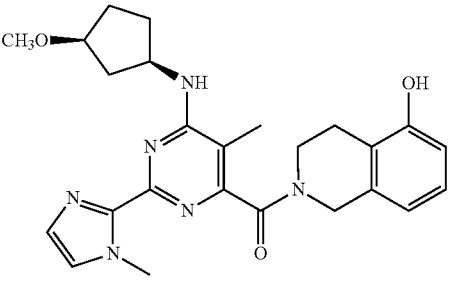<br>(+/-) | B | A |
| 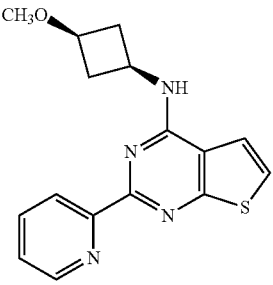 | A | 0 |

TABLE 4C-continued

% Inhibition of MAPK phosphorylation and AKT phosphorylation at 10 μM in the PANC-1 pancreatic cancer cell lines

| Compound | MAPK | AKT |
|---|---|---|
| [structure] | A | 0 |
| [structure] | 0 | 0 |
| [structure] HCl | D | D |
| [structure] | D | D |
| [structure] | 0 | 0 |

TABLE 4C-continued

% Inhibition of MAPK phosphorylation and AKT phosphorylation at 10 μM in the PANC-1 pancreatic cancer cell lines

| Compound | MAPK | AKT |
|---|---|---|
| (structure) | A | 0 |
| (structure) (+/-) | B | 0 |
| (structure) | 0 | 0 |
| (structure) (+/-) | D | D |
| (structure) (+/-) | D | D |

TABLE 4C-continued
% Inhibition of MAPK phosphorylation and AKT phosphorylation at 10 μM in the PANC-1 pancreatic cancer cell lines
| Compound | MAPK | AKT |
|---|---|---|
| 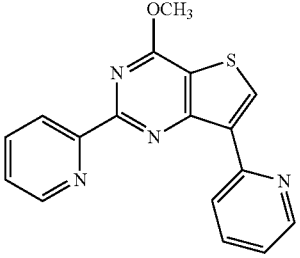 [SMILES: COc1nc(-c2ccccn2)nc2c(-c3ccccn3)csc12] | 0 | 0 |
| 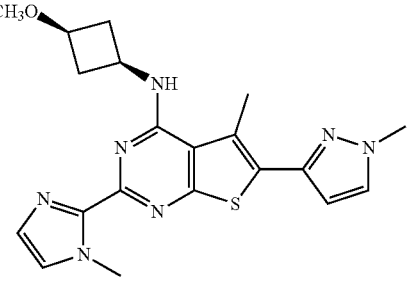 | D | 0 |
| 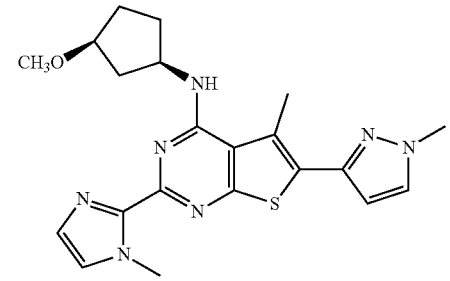 (+/−) | 0 | 0 |
| 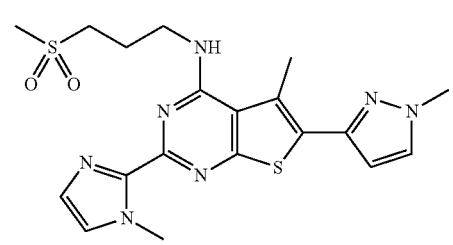 | 0 | 0 |
| 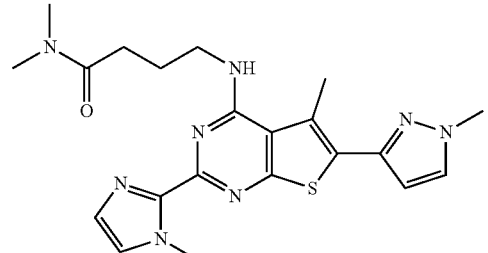 | 0 | 0 |

TABLE 4C-continued

% Inhibition of MAPK phosphorylation and AKT phosphorylation at 10 μM in the PANC-1 pancreatic cancer cell lines

| Compound | MAPK | AKT |
|---|---|---|
| (structure) | 0 | 0 |
| (structure) (+/−) | D | 0 |
| (structure) | 0 | 0 |
| (structure) | 0 | 0 |
| (structure) | 0 | 0 |

TABLE 4C-continued

% Inhibition of MAPK phosphorylation and AKT phosphorylation at 10 μM in the PANC-1 pancreatic cancer cell lines

| Compound | MAPK | AKT |
|---|---|---|
| (+/−) | 0 | 0 |
| (+/−) | 0 | 0 |
| (+/−) | 0 | 0 |
| (+/−) | 0 | 0 |

TABLE 4C-continued

% Inhibition of MAPK phosphorylation and AKT phosphorylation at 10 μM in the PANC-1 pancreatic cancer cell lines

| Compound | MAPK | AKT |
|---|---|---|
| [Structure: 4-((3-methoxycyclopentyl)amino)-2-(1-methylimidazol-2-yl)-5-phenyl-6-(morpholine-4-carbonyl)thieno[2,3-d]pyrimidine] (+/−) | 0 | 0 |

0 = 0% inhibition, A = 1-25% inhibition, B = 26-50% inhibition, C = 5175% inhibition, D = 76-100% inhibition.

Example 137

Protocol for Cell Proliferation Assay

Cell lines: Human NSCLC cells NCI-H1975 and NCI-H1299, and tumor-derived pancreatic cancer cell lines Panc-1, MIA-PACA2, and BxPC3, were all purchased from American Type Culture Collection and grown in complete RPMI medium (BxPC3, NCI-H1975 and NCI-H1299) or DMEM-High Glucose (Panc1 and MIA-PaCa-2), supplemented with penicillin (100 U/mL), streptomycin (100 μg/mL), and 10% heat-inactivated FBS at 37° C. in a humidified incubator with 5% $CO_2$.

Method: Cells were plated at 2000 to 5000 cells/well density in 96-wells plate and cultured ON. Small molecules to be tested were added to the cells in the final concentration of 10 μM in the presence of 0.3% DMSO and 10% FBS, and incubated for 2-4 days at 37° C. in a humidified incubator with 5% $CO_2$. For $IC_{50}$ value determination, serial dilutions of compounds were added to cells under the same conditions.

Assay: At the end of the incubation period, cell cultures were fixed with a 50-50 mixture (v/v) acetone-methanol for 10 minutes at −20° C., followed by rehydration in PBS for 10 minutes at room temperature. DNA total content was determined by staining cells with DAPI (1 ug/ml) in PBS for 10 minutes at room temperature, followed by 3 washes with PBS. After staining, DAPI fluorescence was recorded (358 nm excitation/461 nm emission) with the 96-well plate reader Molecular Devices Spectramax M3; degree of small molecule-dependent proliferation inhibition was calculated from raw data.

Tables 5 and 5A show inhibition data for selected compounds tested in one or more of the cellular assay conditions described above.

TABLE 5

% Inhibition of cell proliferation at 10 μM in MIA-PaCa-2 pancreatic cancer cell lines, with select $IC_{50}$ (nM) values in the PANC-1, BxPC3, MIA PaCa-2 pancreatic cancer cell lines, and NCI H1975, NCI H1299 non-small-cell lung cancer cell lines

| Compound | MIA PaCa-.2 % inh | PANC-1 $IC_{50}$ | BxPC3 $IC_{50}$ | MIA PaCa-2 $IC_{50}$ | H1975 $IC_{50}$ | H1299 $IC_{50}$ |
|---|---|---|---|---|---|---|
| [Structure: 7-(2-chloro-3-methoxyphenyl)-2-(1-methylimidazol-2-yl)thieno[3,2-d]pyrimidin-4-ol] | D | | | E | | |

TABLE 5-continued

% Inhibition of cell proliferation at 10 μM in MIA-PaCa-2 pancreatic cancer cell lines, with select IC$_{50}$ (nM) values in the PANC-1, BxPC3, MIA PaCa-2 pancreatic cancer cell lines, and NCI H1975, NCI H1299 non-small-cell lung cancer cell lines

| Compound | MIA PaCa-2 % inh | PANC-1 IC$_{50}$ | BxPC3 IC$_{50}$ | MIA PaCa-2 IC$_{50}$ | H1975 IC$_{50}$ | H1299 IC$_{50}$ |
|---|---|---|---|---|---|---|
| [structure] | D | | | | | |
| [structure] | D | | | | | |
| [structure] | D | | | | | |
| [structure] | D | | | | | |
| [structure] | D | | | | | |

TABLE 5-continued

% Inhibition of cell proliferation at 10 μM in MIA-PaCa-2 pancreatic cancer cell lines, with select $IC_{50}$ (nM) values in the PANC-1, BxPC3, MIA PaCa-2 pancreatic cancer cell lines, and NCI H1975, NCI H1299 non-small-cell lung cancer cell lines

| Compound | MIA PaCa-.2 % inh | PANC-1 $IC_{50}$ | BxPC3 $IC_{50}$ | MIA PaCa-2 $IC_{50}$ | H1975 $IC_{50}$ | H1299 $IC_{50}$ |
|---|---|---|---|---|---|---|
| [structure] | D | | | | | |
| [structure] | D | | | | | |
| [structure] | D | | | | | |
| [structure] | D | | | | | |

TABLE 5-continued

% Inhibition of cell proliferation at 10 μM in MIA-PaCa-2 pancreatic cancer cell lines, with select IC$_{50}$ (nM) values in the PANC-1, BxPC3, MIA PaCa-2 pancreatic cancer cell lines, and NCI H1975, NCI H1299 non-small-cell lung cancer cell lines

| Compound | MIA PaCa-.2 % inh | PANC-1 IC$_{50}$ | BxPC3 IC$_{50}$ | MIA PaCa-2 IC$_{50}$ | H1975 IC$_{50}$ | H1299 IC$_{50}$ |
|---|---|---|---|---|---|---|
| (structure) | D | | | | | |
| (structure) | 0 | | | | | |
| (structure) | D | | | | | |
| (structure) | D | | | | | |

TABLE 5-continued

% Inhibition of cell proliferation at 10 μM in MIA-PaCa-2 pancreatic cancer cell lines, with select IC$_{50}$ (nM) values in the PANC-1, BxPC3, MIA PaCa-2 pancreatic cancer cell lines, and NCI H1975, NCI H1299 non-small-cell lung cancer cell lines

| Compound | MIA PaCa-.2 % inh | PANC-1 IC$_{50}$ | BxPC3 IC$_{50}$ | MIA PaCa-2 IC$_{50}$ | H1975 IC$_{50}$ | H1299 IC$_{50}$ |
|---|---|---|---|---|---|---|
| | D | F | F | E | | |
| | D | | | E | | |
| | D | F | F | E | | |
| | D | F | E | E | | |
| | A | | | E | | |

TABLE 5-continued

% Inhibition of cell proliferation at 10 μM in MIA-PaCa-2 pancreatic cancer cell lines, with select IC$_{50}$ (nM) values in the PANC-1, BxPC3, MIA PaCa-2 pancreatic cancer cell lines, and NCI H1975, NCI H1299 non-small-cell lung cancer cell lines

| Compound | MIA PaCa-.2 % inh | PANC-1 IC$_{50}$ | BxPC3 IC$_{50}$ | MIA PaCa-2 IC$_{50}$ | H1975 IC$_{50}$ | H1299 IC$_{50}$ |
|---|---|---|---|---|---|---|
| (structure) | D | E | E | E | | |
| (+/- cis) (structure) | D | G | G | G | G | F |
| (+/- trans) (structure) | D | F | F | F | F | F |
| (structure) | D | G | F | F | E | E |

TABLE 5-continued

% Inhibition of cell proliferation at 10 μM in MIA-PaCa-2 pancreatic cancer cell lines, with select IC$_{50}$ (nM) values in the PANC-1, BxPC3, MIA PaCa-2 pancreatic cancer cell lines, and NCI H1975, NCI H1299 non-small-cell lung cancer cell lines

| Compound | MIA PaCa-.2 % inh | PANC-1 IC$_{50}$ | BxPC3 IC$_{50}$ | MIA PaCa-2 IC$_{50}$ | H1975 IC$_{50}$ | H1299 IC$_{50}$ |
|---|---|---|---|---|---|---|
| (structure) | B | | | E | | |
| (structure) | D | | | E | | |
| (structure) | D | | | E | | |
| (structure) | D | | | E | | |

TABLE 5-continued

% Inhibition of cell proliferation at 10 μM in MIA-PaCa-2 pancreatic cancer cell lines, with select IC$_{50}$ (nM) values in the PANC-1, BxPC3, MIA PaCa-2 pancreatic cancer cell lines, and NCI H1975, NCI H1299 non-small-cell lung cancer cell lines

| Compound | MIA PaCa-.2 % inh | PANC-1 IC$_{50}$ | BxPC3 IC$_{50}$ | MIA PaCa-2 IC$_{50}$ | H1975 IC$_{50}$ | H1299 IC$_{50}$ |
|---|---|---|---|---|---|---|
| [structure] | D | | | E | | |
| [structure] | D | | | | E | E |
| [structure] | D | | | | | |
| [structure] | D | F | | | E | E |

TABLE 5-continued

% Inhibition of cell proliferation at 10 μM in MIA-PaCa-2 pancreatic cancer cell lines, with select IC$_{50}$ (nM) values in the PANC-1, BxPC3, MIA PaCa-2 pancreatic cancer cell lines, and NCI H1975, NCI H1299 non-small-cell lung cancer cell lines

| Compound | MIA PaCa-2 % inh | PANC-1 IC$_{50}$ | BxPC3 IC$_{50}$ | MIA PaCa-2 IC$_{50}$ | H1975 IC$_{50}$ | H1299 IC$_{50}$ |
|---|---|---|---|---|---|---|
| (structure) | D | | | E | | |
| (structure) | D | | | E | F | |
| (structure) | D | | | E | E | |
| (structure) | D | G | F | F | F | F |

TABLE 5-continued

% Inhibition of cell proliferation at 10 μM in MIA-PaCa-2 pancreatic cancer cell lines, with select IC$_{50}$ (nM) values in the PANC-1, BxPC3, MIA PaCa-2 pancreatic cancer cell lines, and NCI H1975, NCI H1299 non-small-cell lung cancer cell lines

| Compound | MIA PaCa-.2 % inh | PANC-1 IC$_{50}$ | BxPC3 IC$_{50}$ | MIA PaCa-2 IC$_{50}$ | H1975 IC$_{50}$ | H1299 IC$_{50}$ |
|---|---|---|---|---|---|---|
| (structure) | D | | | E | | |
| (structure) | D | | | E | E | |
| (structure) | D | | | | | |
| (structure) | D | | | | | |

TABLE 5-continued

% Inhibition of cell proliferation at 10 μM in MIA-PaCa-2 pancreatic cancer cell lines, with select IC$_{50}$ (nM) values in the PANC-1, BxPC3, MIA PaCa-2 pancreatic cancer cell lines, and NCI H1975, NCI H1299 non-small-cell lung cancer cell lines

| Compound | MIA PaCa-.2 % inh | PANC-1 IC$_{50}$ | BxPC3 IC$_{50}$ | MIA PaCa-2 IC$_{50}$ | H1975 IC$_{50}$ | H1299 IC$_{50}$ |
|---|---|---|---|---|---|---|
| (structure) | D | F | | F | F | |
| (structure) | D | | | E | | |
| (structure) HCl | D | | | | | |
| (structure) HCl | B | | | | | |

TABLE 5-continued

% Inhibition of cell proliferation at 10 μM in MIA-PaCa-2 pancreatic cancer cell lines, with select IC$_{50}$ (nM) values in the PANC-1, BxPC3, MIA PaCa-2 pancreatic cancer cell lines, and NCI H1975, NCI H1299 non-small-cell lung cancer cell lines

| Compound | MIA PaCa-.2 % inh | PANC-1 IC$_{50}$ | BxPC3 IC$_{50}$ | MIA PaCa-2 IC$_{50}$ | H1975 IC$_{50}$ | H1299 IC$_{50}$ |
|---|---|---|---|---|---|---|
| (structure) HCl | D | | | | | |
| (structure) HCl | D | | | | | |
| (structure) HCl | D | | | | | |
| (structure) HCl | D | | | | | |

TABLE 5-continued
% Inhibition of cell proliferation at 10 μM in MIA-PaCa-2 pancreatic cancer cell lines, with select IC$_{50}$ (nM) values in the PANC-1, BxPC3, MIA PaCa-2 pancreatic cancer cell lines, and NCI H1975, NCI H1299 non-small-cell lung cancer cell lines
| Compound | MIA PaCa-.2 % inh | PANC-1 IC$_{50}$ | BxPC3 IC$_{50}$ | MIA PaCa-2 IC$_{50}$ | H1975 IC$_{50}$ | H1299 IC$_{50}$ |
|---|---|---|---|---|---|---|
| 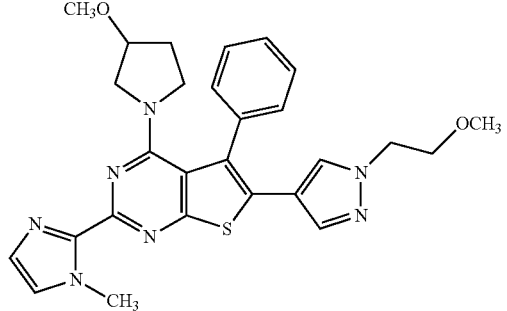 HCl | D | | | | | |
| 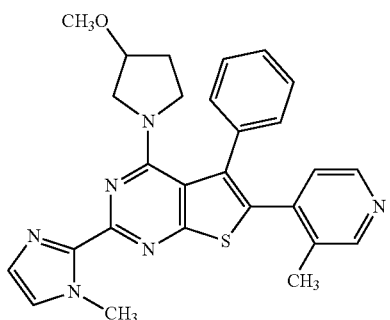 HCl | D | | | | | |
| 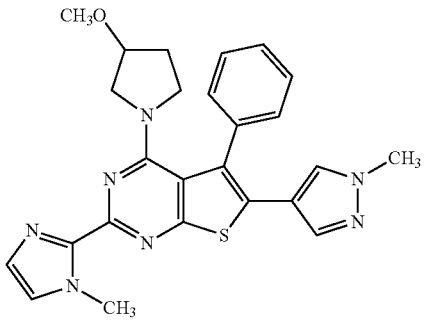 HCl | D | | | | | |
| 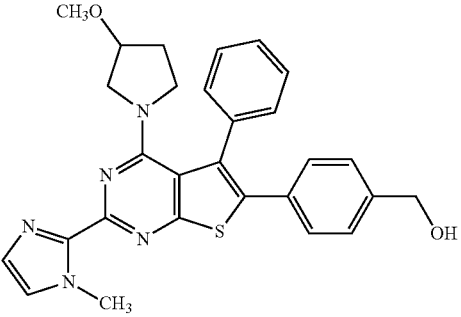 HCl | D | | | | | |

TABLE 5-continued

% Inhibition of cell proliferation at 10 μM in MIA-PaCa-2 pancreatic cancer cell lines, with select IC$_{50}$ (nM) values in the PANC-1, BxPC3, MIA PaCa-2 pancreatic cancer cell lines, and NCI H1975, NCI H1299 non-small-cell lung cancer cell lines

| Compound | MIA PaCa-.2 % inh | PANC-1 IC$_{50}$ | BxPC3 IC$_{50}$ | MIA PaCa-2 IC$_{50}$ | H1975 IC$_{50}$ | H1299 IC$_{50}$ |
|---|---|---|---|---|---|---|
| (structure) HCl | D | | | | | |
| (structure) HCl | D | | | | | |
| (structure) HCl | D | | | | | |
| (structure) HCl | D | | | | | |

TABLE 5-continued

% Inhibition of cell proliferation at 10 μM in MIA-PaCa-2 pancreatic cancer cell lines, with select IC$_{50}$ (nM) values in the PANC-1, BxPC3, MIA PaCa-2 pancreatic cancer cell lines, and NCI H1975, NCI H1299 non-small-cell lung cancer cell lines

| Compound | MIA PaCa-2 % inh | PANC-1 IC$_{50}$ | BxPC3 IC$_{50}$ | MIA PaCa-2 IC$_{50}$ | H1975 IC$_{50}$ | H1299 IC$_{50}$ |
|---|---|---|---|---|---|---|
| [structure] | D | | | | | |
| [structure] | D | | | | | |
| [structure] | D | | | | | |
| [structure] HCl | D | | | | | |

TABLE 5-continued

% Inhibition of cell proliferation at 10 μM in MIA-PaCa-2 pancreatic cancer cell lines, with select IC$_{50}$ (nM) values in the PANC-1, BxPC3, MIA PaCa-2 pancreatic cancer cell lines, and NCI H1975, NCI H1299 non-small-cell lung cancer cell lines

| Compound | MIA PaCa-2 % inh | PANC-1 IC$_{50}$ | BxPC3 IC$_{50}$ | MIA PaCa-2 IC$_{50}$ | H1975 IC$_{50}$ | H1299 IC$_{50}$ |
|---|---|---|---|---|---|---|
| (structure) | 0 | | | | | |
| (structure) | A | | | | | |
| (structure) | 0 | | | | | |
| (structure) | 0 | | | | | |

TABLE 5-continued
% Inhibition of cell proliferation at 10 µM in MIA-PaCa-2 pancreatic cancer cell lines, with select $IC_{50}$ (nM) values in the PANC-1, BxPC3, MIA PaCa-2 pancreatic cancer cell lines, and NCI H1975, NCI H1299 non-small-cell lung cancer cell lines
| Compound | MIA PaCa-2 % inh | PANC-1 $IC_{50}$ | BxPC3 $IC_{50}$ | MIA PaCa-2 $IC_{50}$ | H1975 $IC_{50}$ | H1299 $IC_{50}$ |
|---|---|---|---|---|---|---|
| 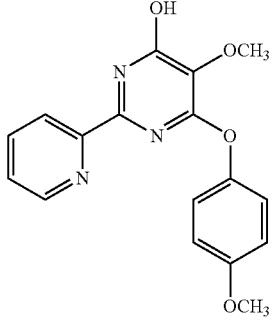 [SMILES: COc1ccc(Oc2nc(-c3ccccn3)nc(O)c2OC)cc1] | B | | | | | |
| 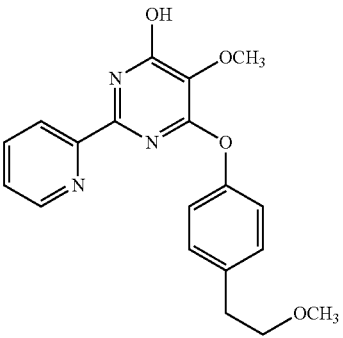 [SMILES: COCCc1ccc(Oc2nc(-c3ccccn3)nc(O)c2OC)cc1] | D | | | | | |
| 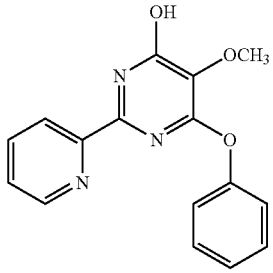 [SMILES: COc1c(O)nc(-c2ccccn2)nc1Oc1ccccc1] | D | | | | | |
| 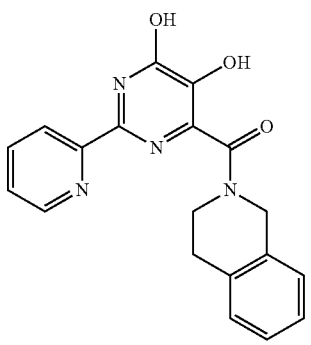 [SMILES: O=C(c1nc(-c2ccccn2)nc(O)c1O)N1CCc2ccccc2C1] | A | | | | | |

TABLE 5-continued

% Inhibition of cell proliferation at 10 μM in MIA-PaCa-2 pancreatic cancer cell lines, with select IC$_{50}$ (nM) values in the PANC-1, BxPC3, MIA PaCa-2 pancreatic cancer cell lines, and NCI H1975, NCI H1299 non-small-cell lung cancer cell lines

| Compound | MIA PaCa-.2 % inh | PANC-1 IC$_{50}$ | BxPC3 IC$_{50}$ | MIA PaCa-2 IC$_{50}$ | H1975 IC$_{50}$ | H1299 IC$_{50}$ |
|---|---|---|---|---|---|---|
| (structure) | 0 | | | | | |
| (structure) | 0 | | | | | |
| (structure) | B | | | | | |
| (structure) | A | | | | | |

TABLE 5-continued

% Inhibition of cell proliferation at 10 μM in MIA-PaCa-2 pancreatic cancer cell lines, with select IC$_{50}$ (nM) values in the PANC-1, BxPC3, MIA PaCa-2 pancreatic cancer cell lines, and NCI H1975, NCI H1299 non-small-cell lung cancer cell lines

| Compound | MIA PaCa-.2 % inh | PANC-1 IC$_{50}$ | BxPC3 IC$_{50}$ | MIA PaCa-2 IC$_{50}$ | H1975 IC$_{50}$ | H1299 IC$_{50}$ |
|---|---|---|---|---|---|---|
| (structure: 2-(pyridin-2-yl)-5,6-dihydroxy-N-cyclopentylpyrimidine-4-carboxamide) | B | | | | | |
| (structure: 2-(pyridin-2-yl)-5,6-dihydroxy-N-methyl-N-isobutylpyrimidine-4-carboxamide) | 0 | | | | | |
| (structure: 2-(pyridin-2-yl)-5,6-dihydroxy-N-isobutylpyrimidine-4-carboxamide) | 0 | | | | | |
| (structure: 2-(pyridin-2-yl)-5,6-dihydroxy-N-methyl-N-(2-methoxyethyl)pyrimidine-4-carboxamide) | 0 | | | | | |
| (structure: 2-(pyridin-2-yl)-5,6-dihydroxy-N-cyclobutylpyrimidine-4-carboxamide) | 0 | | | | | |

TABLE 5-continued
% Inhibition of cell proliferation at 10 μM in MIA-PaCa-2 pancreatic cancer cell lines, with select $IC_{50}$ (nM) values in the PANC-1, BxPC3, MIA PaCa-2 pancreatic cancer cell lines, and NCI H1975, NCI H1299 non-small-cell lung cancer cell lines
| Compound | MIA PaCa-.2 % inh | PANC-1 $IC_{50}$ | BxPC3 $IC_{50}$ | MIA PaCa-2 $IC_{50}$ | H1975 $IC_{50}$ | H1299 $IC_{50}$ |
|---|---|---|---|---|---|---|
| 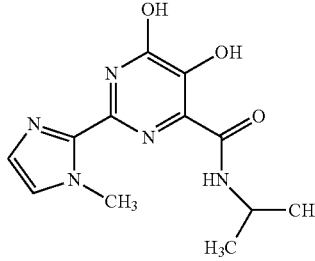 | B | | | | | |
| 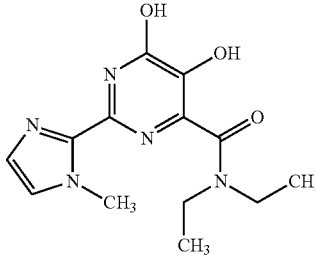 | A | | | | | |
| 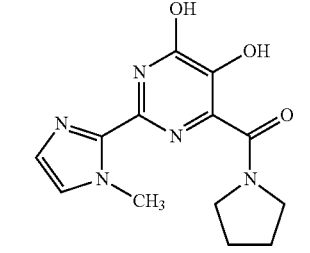 [SMILES: Cn1ccnc1-c1nc(O)c(O)c(C(=O)N2CCCC2)n1] | 0 | | | | | |
| 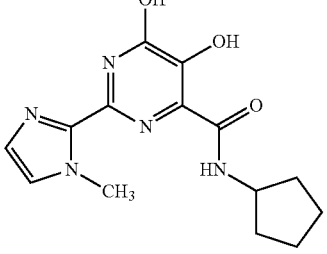 | 0 | | | | | |
| 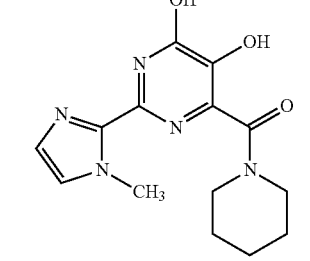 | A | | | | | |

TABLE 5-continued

% Inhibition of cell proliferation at 10 μM in MIA-PaCa-2 pancreatic cancer cell lines, with select IC$_{50}$ (nM) values in the PANC-1, BxPC3, MIA PaCa-2 pancreatic cancer cell lines, and NCI H1975, NCI H1299 non-small-cell lung cancer cell lines

| Compound | MIA PaCa-.2 % inh | PANC-1 IC$_{50}$ | BxPC3 IC$_{50}$ | MIA PaCa-2 IC$_{50}$ | H1975 IC$_{50}$ | H1299 IC$_{50}$ |
|---|---|---|---|---|---|---|
| (structure) | 1 | | | | | |
| (structure) | 0 | | | | | |
| (structure) | A | | | | | |
| (structure) | B | | | | | |

TABLE 5-continued

% Inhibition of cell proliferation at 10 μM in MIA-PaCa-2 pancreatic cancer cell lines, with select IC$_{50}$ (nM) values in the PANC-1, BxPC3, MIA PaCa-2 pancreatic cancer cell lines, and NCI H1975, NCI H1299 non-small-cell lung cancer cell lines

| Compound | MIA PaCa-2 % inh | PANC-1 IC$_{50}$ | BxPC3 IC$_{50}$ | MIA PaCa-2 IC$_{50}$ | H1975 IC$_{50}$ | H1299 IC$_{50}$ |
|---|---|---|---|---|---|---|
| *structure* | D | | | | | |

0 = 0% inhibition, A = 1-25% inhibition, B = 26-50% inhibition, C = 51-75% inhibition, D = 76-100% inhibition, E = >1000 nM IC$_{50}$, F = 750-1000 nM IC$_{50}$, G = 500-749 nM IC$_{50}$, H = <500 nM IC$_{50}$.

TABLE 5A

% Inhibition of cell proliferation at 10 μM in MIA-PaCa-2 pancreatic cancer cell lines with select IC$_{50}$ (nM) values in the MIA PaCa-2 pancreatic cancer cell lines

| Compound | MIA PaCa-2 % inh | MIA PaCa-2 IC$_{50}$ |
|---|---|---|
| *structure* | A | |
| *structure* | D | E |

TABLE 5A-continued

% Inhibition of cell proliferation at 10 μM in MIA-PaCa-2 pancreatic cancer cell lines with select IC$_{50}$ (nM) values in the MIA PaCa-2 pancreatic cancer cell lines

| Compound | MIA PaCa-2 % inh | MIA PaCa-2 IC$_{50}$ |
|---|---|---|
| (structure: 2-(pyridin-2-yl)-5-methoxy-6-((1-ethyl-1H-pyrazol-4-yl)amino)pyrimidin-4-ol) | 0 | E |
| (structure: 2-(pyridin-2-yl)-5-methoxy-6-((3-ethoxyphenyl)amino)pyrimidin-4-ol) | D | E |
| (structure: N-(3-methoxycyclopentyl)-2-(1-methyl-1H-imidazol-2-yl)-6-(2-fluoro-3-methoxyphenyl)-5-phenylthieno[2,3-d]pyrimidin-4-amine) | D | F |
| (structure: N-((1S,3R)-3-methoxycyclopentyl)-2-(1-methyl-1H-imidazol-2-yl)-6-(2-fluoro-3-methoxyphenyl)-5-phenylthieno[2,3-d]pyrimidin-4-amine) (+/−) | D | F |
| (structure: N-(3-methoxycyclopentyl)-2-(1-methyl-1H-imidazol-2-yl)-6-(2-fluoro-3-hydroxyphenyl)-5-phenylthieno[2,3-d]pyrimidin-4-amine) | D | E |

TABLE 5A-continued

% Inhibition of cell proliferation at 10 μM in MIA-PaCa-2 pancreatic cancer cell lines with select IC$_{50}$ (nM) values in the MIA PaCa-2 pancreatic cancer cell lines

| Compound | MIA PaCa-2 % inh | MIA PaCa-2 IC$_{50}$ |
|---|---|---|
| [structure] | D | F |
| [structure] (+/−) | D | F |
| [structure] | D | F |
| [structure] (+/−) | D | F |
| [structure] | D | E |

TABLE 5A-continued

% Inhibition of cell proliferation at 10 μM in MIA-PaCa-2 pancreatic cancer cell lines with select IC$_{50}$ (nM) values in the MIA PaCa-2 pancreatic cancer cell lines

| Compound | MIA PaCa-2 % inh | MIA PaCa-2 IC$_{50}$ |
|---|---|---|
| | D | G |
| | D | F |
| | D | F |
| (+/-) | D | F |
| | D | E |

TABLE 5A-continued

% Inhibition of cell proliferation at 10 μM in MIA-PaCa-2 pancreatic cancer cell lines with select IC$_{50}$ (nM) values in the MIA PaCa-2 pancreatic cancer cell lines

| Compound | MIA PaCa-2 % inh | MIA PaCa-2 IC$_{50}$ |
|---|---|---|
| (structure, +/−) | D | F |
| (structure, +/−) | D | E |
| (structure) | D | H |
| (structure) | D | G |

TABLE 5A-continued

% Inhibition of cell proliferation at 10 μM in MIA-PaCa-2 pancreatic cancer cell lines with select IC$_{50}$ (nM) values in the MIA PaCa-2 pancreatic cancer cell lines

| Compound | MIA PaCa-2 % inh | MIA PaCa-2 IC$_{50}$ |
|---|---|---|
| (structure: thieno[3,2-d]pyrimidin-4-ol with imidazole-N-(3-methoxybenzyl) substituent and 6-isobutoxy-pyridin-4-yl group) | D | H |
| (structure: pyrimidine with (3-methoxycyclopentyl)amino, 5-methyl, 2-(1-methylimidazol-2-yl), and 5-hydroxy-1,2,3,4-tetrahydroisoquinolin-2-yl carbonyl) (+/−) | A | E |
| (structure: 4-((3-methoxycyclobutyl)amino)-2-(pyridin-2-yl)thieno[2,3-d]pyrimidine) | A | E |
| (structure: 4-((3-methoxycyclobutyl)amino)-2-(1-methylimidazol-2-yl)thieno[2,3-d]pyrimidine) | B | E |

TABLE 5A-continued

% Inhibition of cell proliferation at 10 μM in MIA-PaCa-2 pancreatic cancer cell lines with select IC$_{50}$ (nM) values in the MIA PaCa-2 pancreatic cancer cell lines

| Compound | MIA PaCa-2 % inh | MIA PaCa-2 IC$_{50}$ |
|---|---|---|
| (structure) | D | E |
| (structure) HCl | D | E |
| (structure) | D | E |
| (structure) | D | E |
| (structure) | 0 | E |

TABLE 5A-continued

% Inhibition of cell proliferation at 10 μM in MIA-PaCa-2 pancreatic cancer cell lines with select IC$_{50}$ (nM) values in the MIA PaCa-2 pancreatic cancer cell lines

| Compound | MIA PaCa-2 % inh | MIA PaCa-2 IC$_{50}$ |
|---|---|---|
| (+/−) | B | E |
| | D | F |
| (+/−) | D | F |
| (+/−) | D | G |
| | C | E |

TABLE 5A-continued

% Inhibition of cell proliferation at 10 μM in MIA-PaCa-2 pancreatic cancer
cell lines with select IC$_{50}$ (nM) values in the MIA PaCa-2 pancreatic cancer cell lines

| Compound | MIA PaCa-2 % inh | MIA PaCa-2 IC$_{50}$ |
|---|---|---|
| [structure: methoxycyclobutyl-NH thienopyrimidine with methylimidazole and methylpyrazole] | D | E |
| [structure: methoxycyclopentyl-NH thienopyrimidine with methylimidazole and methylpyrazole] (+/-) | D | F |
| [structure: methylsulfonylpropyl-NH thienopyrimidine with methylimidazole and methylpyrazole] | 0 | E |
| [structure: dimethylaminocarbonylpropyl-NH thienopyrimidine with methylimidazole and methylpyrazole] | 0 | E |
| [structure: dimethylcarbamoyloxyethyl-NH thienopyrimidine with methylimidazole and methylpyrazole] | B | E |

TABLE 5A-continued
% Inhibition of cell proliferation at 10 μM in MIA-PaCa-2 pancreatic cancer cell lines with select IC$_{50}$ (nM) values in the MIA PaCa-2 pancreatic cancer cell lines
| Compound | MIA PaCa-2 % inh | MIA PaCa-2 IC$_{50}$ |
|---|---|---|
| 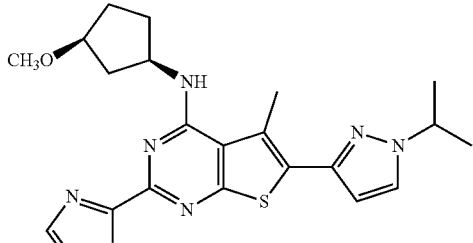 (+/−) | D | G |
| 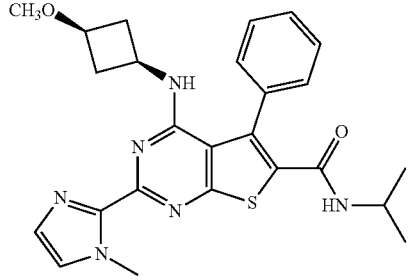 | C | E |
| 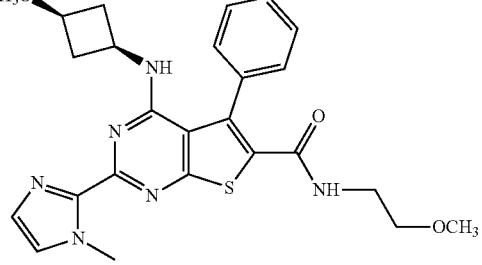 | B | E |
| 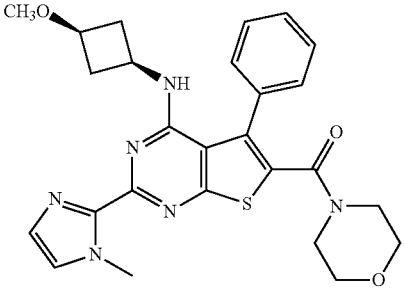 | B | E |
| 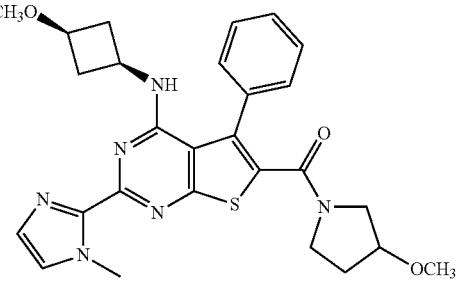 (+/−) | B | E |

TABLE 5A-continued
% Inhibition of cell proliferation at 10 μM in MIA-PaCa-2 pancreatic cancer cell lines with select IC$_{50}$ (nM) values in the MIA PaCa-2 pancreatic cancer cell lines
| Compound | MIA PaCa-2 % inh | MIA PaCa-2 IC$_{50}$ |
|---|---|---|
| 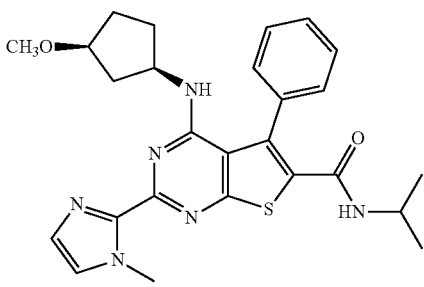 (+/-) | D | E |
| 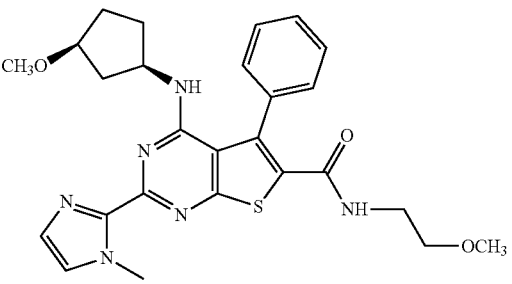 (+/-) | D | E |
| 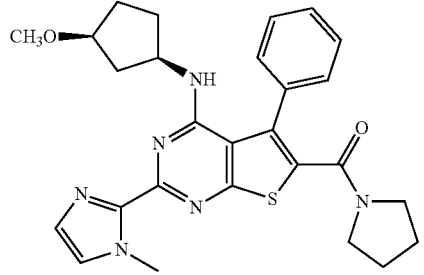 (+/-) | D | E |
| 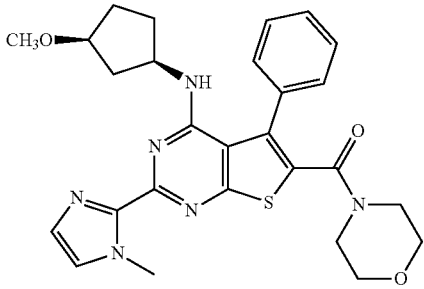 (+/-) | C | E |
0 = 0% inhibition, A = 1-25% inhibition, B = 26-50% inhibition, C = 51-75% inhibition, D = 76-100% inhibition, E = >1000 nM IC$_{50}$, F = 750-1000 nM IC$_{50}$, G = 500-749 nM IC$_{50}$, H = <500 nM IC$_{50}$.

Example 138

Protocol for Mouse TNF Alpha and IL6 Quantification Assay

Cell lines: Abelson murine leukemia virus transformed macrophage cell line RAW 264.7 was purchased from ATCC and grown in complete DMEM-High Glucose medium supplemented with penicillin (100 U/mL), streptomycin (100 µg/mL), and 10% heat-inactivated FBS at 37° C. in a humidified incubator with 5% $CO_2$.

Method: Cells were plated at 25000-40000 cells/well density in a 96-well plate. After a 3-hour incubation, macrophages were starved with DMEM plus 0.5% FBS overnight. The next day the small molecules to be tested were added to the cells in the final concentration of 30 µM (with 0.3% DMSO) 3 hours prior to LPS stimulation (100 ng/ml). After LPS stimulation cells were incubated at 37° C. for 16 h. Alternatively, compounds were also tested at 10 µM and LPS (100 ng/ml) was added concurrently and incubated 5 hours at 37° C. At the end of the incubation periods, culture medium was collected and production of LPS-induced TNF-α and IL-6 cytokine was measured using ELISA detection kits.

Sandwich ELISA: The ELISA Immunoassays Quantikine Mouse TNF-alpha (catalog number MTA00B) and IL6 (catalog number M6000B) were purchased from R&D Systems Inc., Minneapolis, MN. These 4.5 hours solid phase ELISAs were used to measure mouse TNF-α or IL-6 levels in macrophages culture supernatants. Assays were executed according to the manufacturer specifications.

Tables 6 and 6A show inhibition data for selected compounds tested in the cellular assay described above.

TABLE 6

IL-6 and TNFα % Inhibition at 30 µM in RAW 264.7 murine leukemia virus transformed macrophage cell lines

| Compound | IL-6 | TNF-α |
|---|---|---|
| 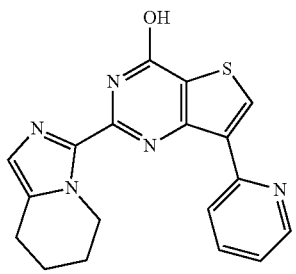 [SMILES: Oc1nc(-c2ncc3n2CCCC3)nc2c(-c3ccccn3)csc12] | D | B |
| 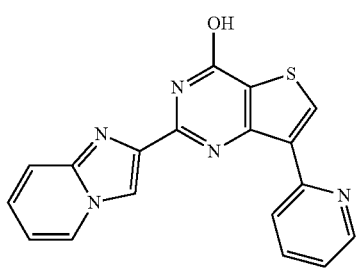 | D | D |

TABLE 6-continued

IL-6 and TNFα % Inhibition at 30 µM in RAW 264.7 murine leukemia virus transformed macrophage cell lines

| Compound | IL-6 | TNF-α |
|---|---|---|
| 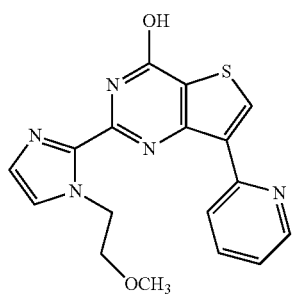 [SMILES: COCCn1ccnc1-c1nc(O)c2scc(-c3ccccn3)c2n1] | D | C |
| (second structure) | D | D |
| (third structure) | D | D |
| 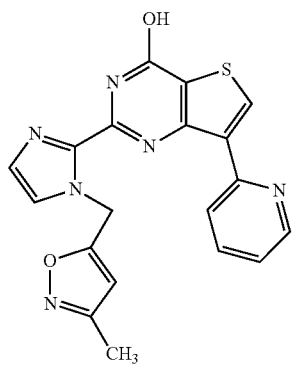 [SMILES: Cc1cc(Cn2ccnc2-c2nc(O)c3scc(-c4ccccn4)c3n2)on1] | D | C |

TABLE 6-continued

IL-6 and TNFα % Inhibition at 30 μM in RAW 264.7 murine leukemia virus transformed macrophage cell lines

| Compound | IL-6 | TNF-α |
|---|---|---|
| (thieno[3,2-d]pyrimidin-4-ol with 2-(1-(pyridin-2-ylmethyl)-1H-imidazol-2-yl) and 7-(pyridin-2-yl)) | D | C |
| (thieno[3,2-d]pyrimidin-4-ol with 2-(1-(3-methoxybenzyl)-1H-imidazol-2-yl) and 7-(pyridin-2-yl)) | D | D |
| (thieno[3,2-d]pyrimidin-4-ol with 2-(1,5-dimethyl-1H-imidazol-2-yl) and 7-(pyridin-2-yl)) | D | D |
| (thieno[3,2-d]pyrimidin-4-ol with 2-(1,4-dimethyl-1H-imidazol-2-yl) and 7-(pyridin-2-yl)) | D | D |
| (thieno[3,2-d]pyrimidin-4-ol with 2-(indolizin-3-yl) and 7-(pyridin-2-yl)) | D | D |
| (thieno[3,2-d]pyrimidin-4-ol with 2-(imidazo[1,2-a]pyrimidin-2-yl) and 7-(pyridin-2-yl)) | 0 | 0 |
| (thieno[3,2-d]pyrimidin-4-ol with 2-(1-phenyl-1H-imidazol-4-yl) and 7-(pyridin-2-yl)) | D | 0 |
| (thieno[3,2-d]pyrimidin-4-ol with 2-(1-(4-methoxybenzyl)-1H-imidazol-4-yl) and 7-(pyridin-2-yl)) | D | A |
| (thieno[3,2-d]pyrimidine with 4-((3-methoxypropyl)amino), 5-phenyl, 6-(1-methyl-1H-pyrazol-3-yl), 2-(1-methyl-1H-imidazol-2-yl)) | D | D |

TABLE 6-continued

IL-6 and TNFα % Inhibition at 30 μM in RAW 264.7 murine leukemia virus transformed macrophage cell lines

| Compound | IL-6 | TNF-α |
|---|---|---|
| (structure: 4-[(3-methoxypropyl)(methyl)amino] thienopyrimidine with 1-methylimidazole and 1-methylpyrazole, phenyl) | A | C |
| (structure: 4-[(1-methoxypropan-2-yl)amino] analog) | D | D |
| (structure: 4-(3-methoxypyrrolidin-1-yl) analog) | B | A |
| (structure: 4-[(tetrahydro-2H-pyran-4-yl)amino] analog) | B | A |
| (structure: 4-[(tetrahydrofuran-3-yl)methylamino] analog) | D | D |
| (structure: 4-[(3-methoxycyclopentyl)amino] analog) (+/− cis) | D | D |
| (+/− trans) | D | D |
| (structure: 4-[(3-(methoxymethyl)pyrrolidin-1-yl] analog) | D | D |

TABLE 6-continued

IL-6 and TNFα % Inhibition at 30 μM in RAW 264.7 murine leukemia virus transformed macrophage cell lines

| Compound | IL-6 | TNF-α |
|---|---|---|
| (2-oxa-7-azaspiro[3.4]octan-7-yl thienopyrimidine with phenyl and N-methylpyrazole, 2-(1-methylimidazol-2-yl)) | C | 0 |
| (4-methoxypiperidinyl thienopyrimidine with phenyl and N-methylpyrazole, 2-(1-methylimidazol-2-yl)) | B | B |
| (3-methoxypropylamino thienopyrimidine with 4-methoxyphenyl and N-methylpyrazole, 2-(1-methylimidazol-2-yl)) | D | 0 |
| (1-methoxypropan-2-ylamino thienopyrimidine with 4-methoxyphenyl and N-methylpyrazole, 2-(1-methylimidazol-2-yl)) | D | 0 |
| (3-methoxypyrrolidinyl thienopyrimidine with 4-methoxyphenyl and N-methylpyrazole, 2-(1-methylimidazol-2-yl)) | A | 0 |
| (1-methoxypropan-2-ylamino thienopyrimidine with 2-chlorophenyl and thiazole, 2-(1-methylimidazol-2-yl)) | D | D |
| (3-methoxypyrrolidinyl thienopyrimidine with 2-chlorophenyl and thiazole, 2-(1-methylimidazol-2-yl)) | C | 0 |
| (1-methoxypropan-2-ylamino thienopyrimidine with 3-methoxyphenyl and thiazole, 2-(1-methylimidazol-2-yl)) | B | B |

TABLE 6-continued
IL-6 and TNFα % Inhibition at 30 μM in RAW 264.7 murine leukemia virus transformed macrophage cell lines
| Compound | IL-6 | TNF-α |
|---|---|---|
| 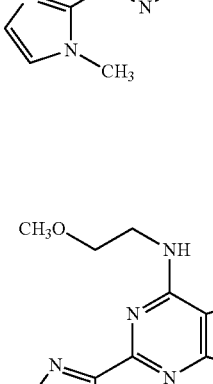 | A | A |
| 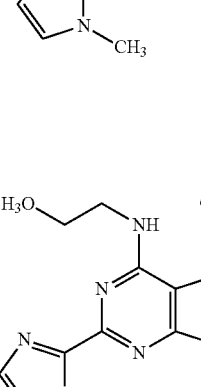 | B | 0 |
| 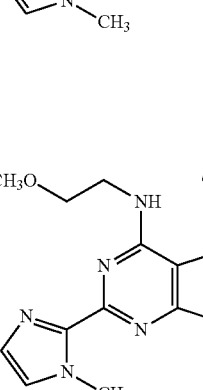 | D | D |
| 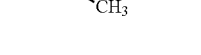 | B | 0 |
TABLE 6-continued
IL-6 and TNFα % Inhibition at 30 μM in RAW 264.7 murine leukemia virus transformed macrophage cell lines
| Compound | IL-6 | TNF-α |
|---|---|---|
| | C | B |
| | D | D |
| | D | D |
| | C | A |

TABLE 6-continued
IL-6 and TNFα % Inhibition at 30 μM in RAW 264.7 murine leukemia virus transformed macrophage cell lines
| Compound | IL-6 | TNF-α |
|---|---|---|
| 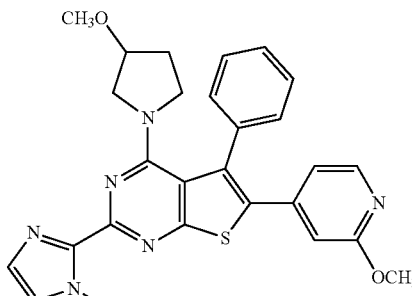 HCl | D | D |
| 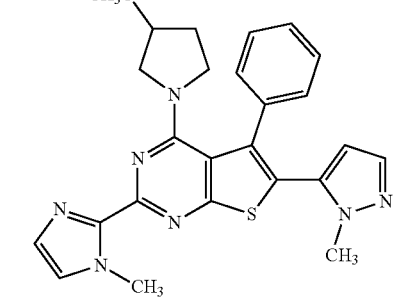 HCl | B | 0 |
| 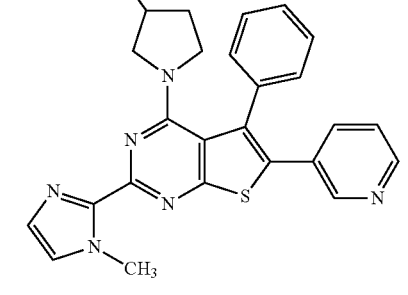 HCl | D | D |
| 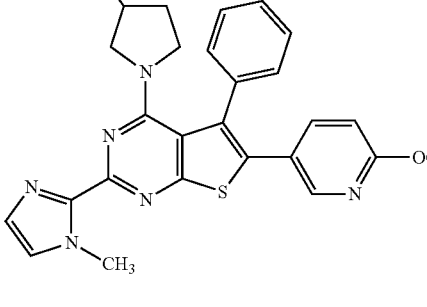 HCl | D | D |
| 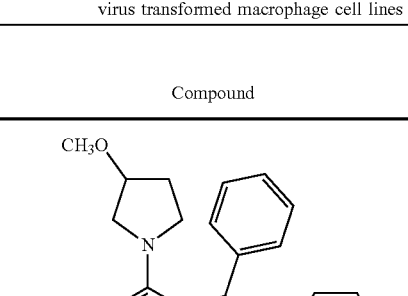 HCl | D | D |
| 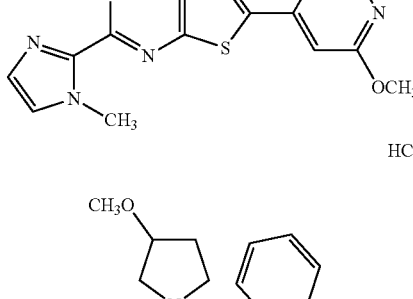 HCl | D | B |
| 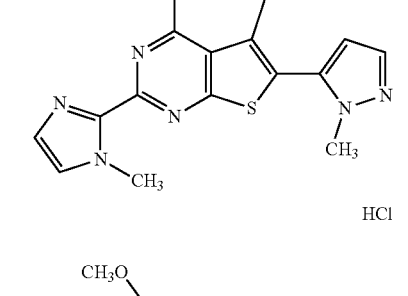 HCl | D | D |
| 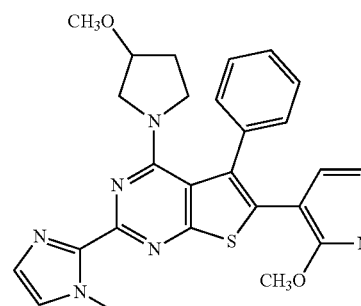 HCl | D | B |

TABLE 6-continued
IL-6 and TNFα % Inhibition at 30 µM in RAW 264.7 murine leukemia virus transformed macrophage cell lines
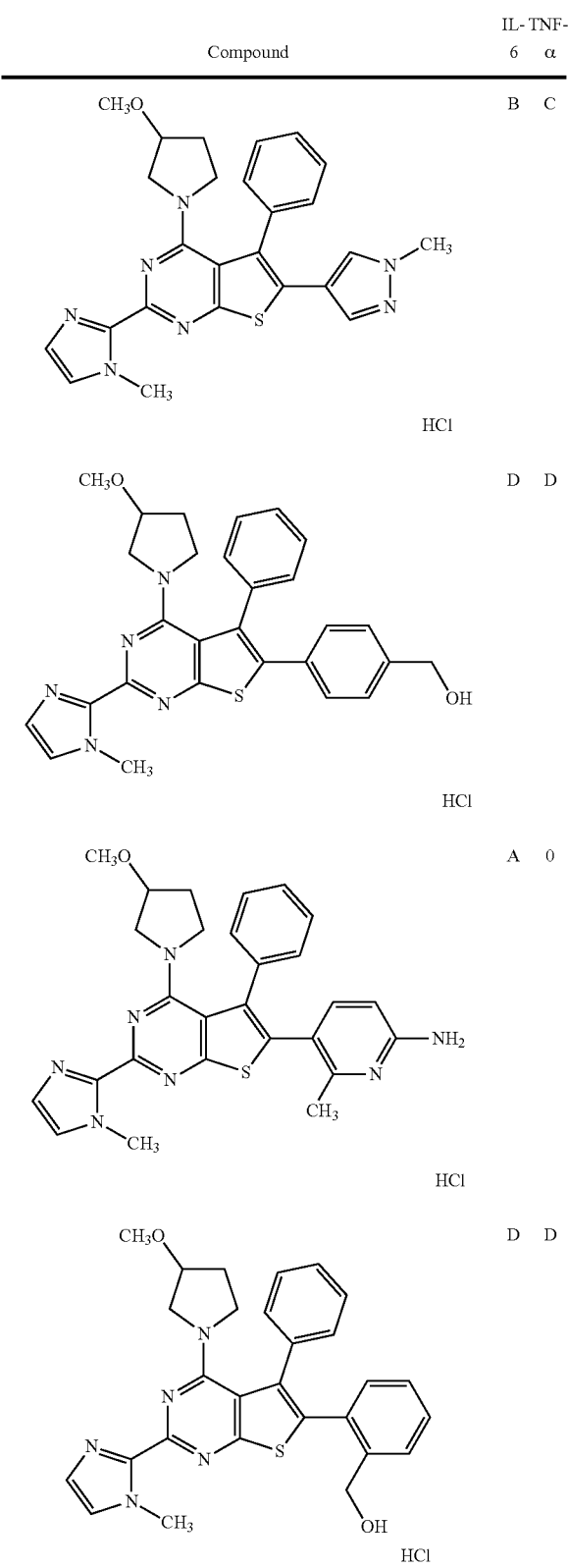
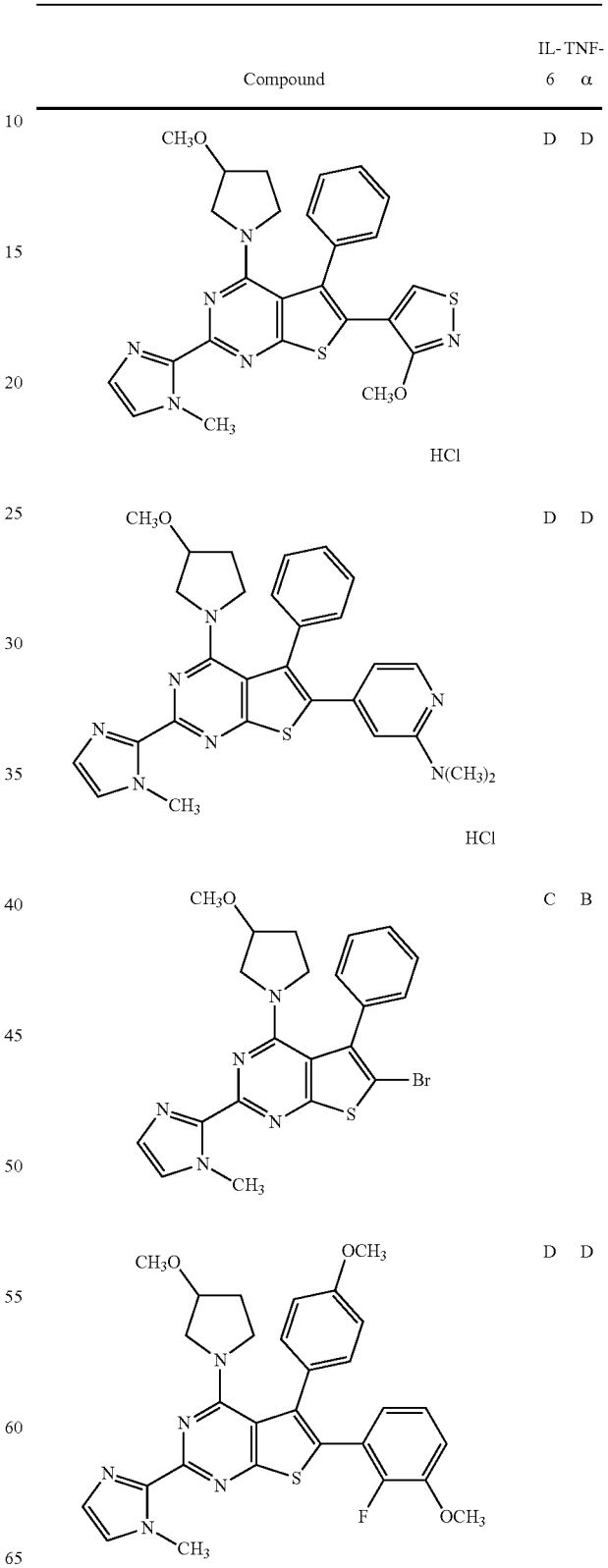

TABLE 6-continued

IL-6 and TNFα % Inhibition at 30 μM in RAW 264.7 murine leukemia virus transformed macrophage cell lines

| Compound | IL-6 | TNF-α |
|---|---|---|
| (structure: 4-(3-(methoxymethyl)azetidin-1-yl)-5-(4-methoxyphenyl)-6-(2-fluoro-3-methoxyphenyl)-2-(1-methyl-1H-imidazol-2-yl)thieno[2,3-d]pyrimidine) | D | D |
| (structure: 4-(3-methoxypyrrolidin-1-yl)-5-phenyl-6-(2-fluoro-3-methoxyphenyl)-2-(1-methyl-1H-imidazol-2-yl)thieno[2,3-d]pyrimidine) HCl | D | D |
| (structure: 5-methoxy-6-((1-methyl-1H-pyrazol-4-yl)oxy)-2-(pyridin-2-yl)pyrimidin-4-ol) | B | 0 |
| (structure: 5-methoxy-6-(quinolin-6-yloxy)-2-(pyridin-2-yl)pyrimidin-4-ol) | D | A |
| (structure: 5-methoxy-6-(pyridin-3-yloxy)-2-(pyridin-2-yl)pyrimidin-4-ol) | C | 0 |
| (structure: 5-methoxy-6-(3-methoxyphenoxy)-2-(pyridin-2-yl)pyrimidin-4-ol) | D | B |
| (structure: 5-methoxy-6-(4-methoxyphenoxy)-2-(pyridin-2-yl)pyrimidin-4-ol) | D | A |
| (structure: 5-methoxy-6-(4-(2-methoxyethyl)phenoxy)-2-(pyridin-2-yl)pyrimidin-4-ol) | D | A |
| (structure: 5-methoxy-6-phenoxy-2-(pyridin-2-yl)pyrimidin-4-ol) | D | A |

TABLE 6-continued

IL-6 and TNFα % Inhibition at 30 μM in RAW 264.7 murine leukemia virus transformed macrophage cell lines

| Compound | IL-6 | TNF-α |
|---|---|---|
| (pyridin-2-yl pyrimidine-4,5-diol with CH2-tetrahydroisoquinoline) | 0 | 0 |
| (pyridin-2-yl pyrimidine-4,5-diol-6-carbonyl morpholine) | 0 | A |
| (pyridin-2-yl pyrimidine-4,5-diol-6-carboxamide N-methyl-N-benzyl) | A | 0 |
| (pyridin-2-yl pyrimidine-4,5-diol-6-carboxamide N-benzyl) | D | D |
| (pyridin-2-yl pyrimidine-4,5-diol-6-carbonyl pyrrolidine) | 0 | A |
| (pyridin-2-yl pyrimidine-4,5-diol-6-carboxamide N-cyclopentyl) | D | B |
| (pyridin-2-yl pyrimidine-4,5-diol-6-carboxamide N-methyl-N-isobutyl) | 0 | 0 |
| (pyridin-2-yl pyrimidine-4,5-diol-6-carboxamide N-isobutyl) | D | B |
| (pyridin-2-yl pyrimidine-4,5-diol-6-carboxamide N-methyl-N-(2-methoxyethyl)) | 0 | A |

TABLE 6-continued
IL-6 and TNFα % Inhibition at 30 μM in RAW 264.7 murine leukemia virus transformed macrophage cell lines
| Compound | IL-6 | TNF-α |
|---|---|---|
| 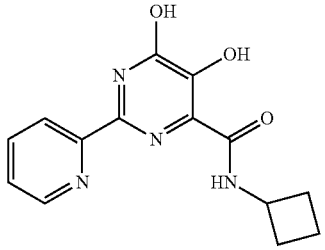 [SMILES: O=C(NC1CCC1)c1nc(-c2ccccn2)nc(O)c1O] | D | A |
| 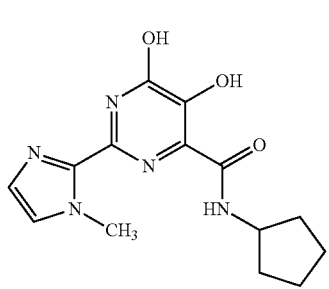 | 0 | A |
| 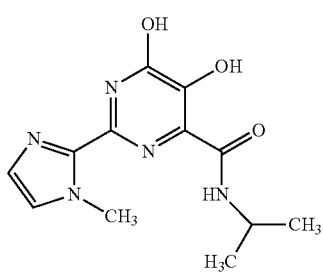 [SMILES: CC(C)NC(=O)c1nc(-c2nccn2C)nc(O)c1O] | 0 | A |
| 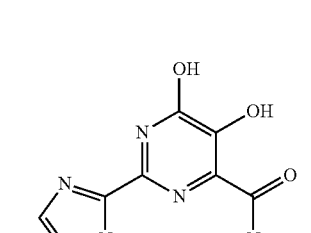 | 0 | A |
TABLE 6-continued
IL-6 and TNFα % Inhibition at 30 μM in RAW 264.7 murine leukemia virus transformed macrophage cell lines
| Compound | IL-6 | TNF-α |
|---|---|---|
| 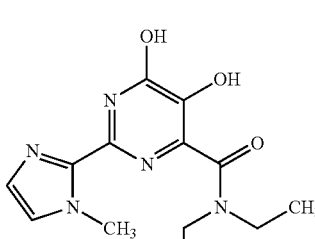 | 0 | A |
| 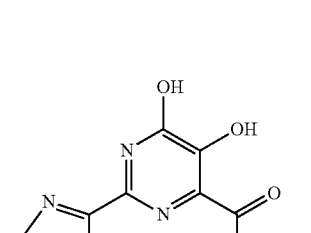 | 0 | A |
| 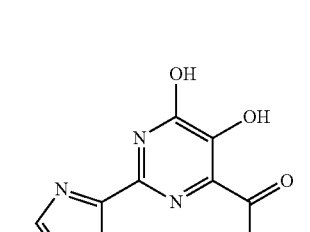 | 0 | A |
| 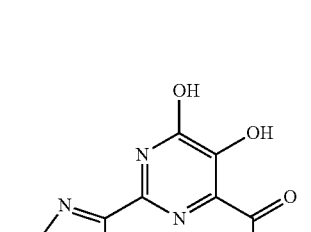 | 0 | 0 |
0 = 0% inhibition, A = 1-25% inhibition, B = 26-50% inhibition, C = 51-75% inhibition, D = 76-100% inhibition.

TABLE 6A

IL-6 and TNFα % Inhibition at 10 μM in RAW 264.7 murine leukemia virus transformed macrophage cell lines

| Compound | IL-6 | TNF-α |
|---|---|---|
| (structure) | A | A |
| (structure) | D | A |
| (structure) | D | A |
| (structure) | C | A |
| (structure) | D | D |

TABLE 6A-continued

IL-6 and TNFα % Inhibition at 10 μM in RAW 264.7 murine leukemia virus transformed macrophage cell lines

| Compound | IL-6 | TNF-α |
|---|---|---|
| (+/-) structure | B | A |
| structure | 0 | 0 |
| structure | A | 0 |
| (+/-) structure | 0 | 0 |
| structure | D | C |

TABLE 6A-continued

IL-6 and TNFα % Inhibition at 10 μM in RAW 264.7 murine leukemia virus transformed macrophage cell lines

| Compound | IL-6 | TNF-α |
|---|---|---|
| (structure) (+/-) | D | D |
| (structure) | B | A |
| (structure) | D | C |
| (structure) | C | A |
| (structure) | A | 0 |

TABLE 6A-continued

IL-6 and TNFα % Inhibition at 10 μM in RAW 264.7 murine leukemia virus transformed macrophage cell lines

| Compound | IL-6 | TNF-α |
|---|---|---|
| (structure) (+/-) | A | A |
| (structure) | C | A |
| (structure) (+/-) | A | 0 |
| (structure) (+/-) | D | B |

TABLE 6A-continued

IL-6 and TNFα % Inhibition at 10 μM in RAW 264.7 murine leukemia virus transformed macrophage cell lines

| Compound | IL-6 | TNF-α |
|---|---|---|
| (structure) | B | A |
| (structure) | D | A |
| (structure) | D | A |
| (structure) (+/−) | 0 | A |

TABLE 6A-continued

IL-6 and TNFα % Inhibition at 10 μM in RAW 264.7 murine leukemia virus transformed macrophage cell lines

| Compound | IL-6 | TNF-α |
|---|---|---|
| (structure) | A | A |
| (structure) | B | A |
| (structure) | C | A |
| (structure) HCl | D | D |
| (structure) | D | D |

TABLE 6A-continued

IL-6 and TNFα % Inhibition at 10 μM in RAW 264.7 murine leukemia virus transformed macrophage cell lines

| Compound | IL-6 | TNF-α |
|---|---|---|
| (structure) | D | B |
| (structure) | B | 0 |
| (structure) (+/-) | B | A |
| (structure) | D | A |
| (structure) (+/-) | D | B |

TABLE 6A-continued

IL-6 and TNFα % Inhibition at 10 μM in RAW 264.7 murine leukemia virus transformed macrophage cell lines

| Compound | IL-6 | TNF-α |
|---|---|---|
| (structure) (+/−) | D | D |
| (structure) | C | A |
| (structure) | D | A |
| (structure) (+/−) | D | A |
| (structure) | A | A |

TABLE 6A-continued

IL-6 and TNFα % Inhibition at 10 μM in RAW 264.7 murine leukemia virus transformed macrophage cell lines

| Compound | IL-6 | TNF-α |
|---|---|---|
| [structure] | A | A |
| [structure] | C | B |
| [structure] (+/−) | C | B |
| [structure] | A | 0 |
| [structure] | B | 0 |

TABLE 6A-continued

IL-6 and TNFα % Inhibition at 10 μM in RAW 264.7 murine leukemia virus transformed macrophage cell lines

| Compound | IL-6 | TNF-α |
|---|---|---|
| (structure) | A | A |
| (structure) (+/-) | 0 | 0 |
| (structure) (+/-) | C | A |
| (structure) (+/-) | C | A |

TABLE 6A-continued

IL-6 and TNFα % Inhibition at 10 µM in RAW 264.7 murine leukemia virus transformed macrophage cell lines

| Compound | IL-6 | TNF-α |
|---|---|---|
| 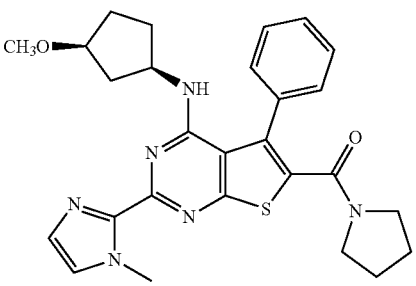 (+/−) | A | A |
| 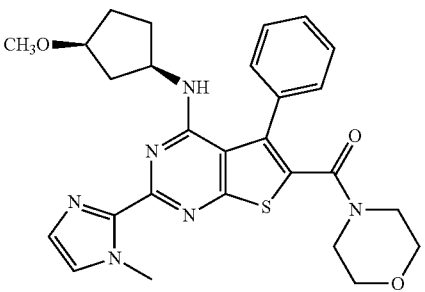 (+/−) | B | A |

0 = 0% inhibition, A = 1-25% inhibition, B = 26-50% inhibition, C = 51-75% inhibition, D = 76-100% inhibition.

Example 139

Ras GTP Binding Domain Inhibition Assay

The following method was developed as specific assay for the following proteins: KRas wild type, KRas Q61H mutant, KRas G12C mutant, KRas G12D mutant, HRas wild type, Rac-1, and Rho-A.

Buffer-I:
 25 mM Tris-HCl, pH 7.4
 27 mM KCl
 137 mM NaCl
 1 mM $MgCl_2$
 1 mM DTT Buffer-II:
 50 mM Tris-HCl, pH 7.0
 1 mM $MgCl_2$
 1 mM DTT The small GTPases proteins: KRas wild type. KRas Q61H mutant, KRas G12C mutant, KRas G12D mutants, HRas wild type, Rac-1, and Rho-A were expressed as His-tagged proteins. In addition, the Guanosine nucleotide Exchange Factor (GEF) Sos protein (residues 556-1049) was expressed as a His-tagged protein. In cells, the guanine nucleotide exchange factor Sos protein promotes activation of Ras proteins by stimulating an exchange of GDP for GTP. The inclusion of Sos to the Ras GTP binding domain inhibition assay may be considered as an alternative representation of physiological cellular conditions for evaluating the inhibitory activity of some of the tested small molecules.

For the assay, all purified small GTPases proteins were diluted in Buffer-I or Buffer-II to a final concentration of 10-30 µg/mL. 200 µL of each diluted protein was added to a nickel-coated 96-well plate and incubated overnight at 4° C. Then the protein solution was discarded and 200 µL of Buffer-I or Buffer-II was added to each well in the presence of 1% DMSO. Compounds to be tested were added to the protein-coated wells at final concentration of 20 µM, and incubated for 3 hours at room temperature with and without 10-30 µg/mL of Sos added to the final hour of the incubation. When performing $IC_{50}$ measurements a serial dilution of all tested concentrations was added. Then Cy3-GTP or Cy5-GTP was added to each well to a final concentration of 100 nM. The labeled GTP was incubated for 45 minutes at room temperature. Following GTP incubation, wells were washed 3× in Buffer-I or Buffer-II and 200 µL of Buffer-I or Buffer-II was added to each well. Following washes, the amount of bound labeled-GTP was measured using a SpectraMax M3 (Molecular Devices).

Tables 7, 7A, 8, 8A, and 9 show inhibition data for selected compounds tested in the screening assays described above.

TABLE 7

| | KRas wild type: % inh. | KRas wild type + SOS: % inh. | KRas G12D mutant: % inh. | KRas G-12D mutant + SOS: % inh. | KRas G12C mutant: % inh. | KRas G12C mutant + SOS: % inh. | KRas Q61H mutant: % inh. | KRas Q61H mutant + SOS: % inh. |
|---|---|---|---|---|---|---|---|---|
| Structure 1 | 0 | A | A | A | A | A | 0 | A |
| Structure 2 | A | 0 | 0 | 0 | 0 | A | 0 | A |
| Structure 3 | B | D | B | B | B | D | B | D |
| Structure 4 | B | A | B | A | A | B | B | B |

TABLE 7-continued
| | % Inhibition at 20 μM of K-Ras mutant and wild-type protein | | | | | | | |
|---|---|---|---|---|---|---|---|---|
| Structure | KRas wild type: % inh. | KRas wild type + SOS: % inh. | KRas G12D mutant: % inh. | KRas G-12D mutant + SOS: % inh. | KRas G12C mutant: % inh. | KRas G12C mutant + SOS: % inh. | KRas Q61H mutant: % inh. | KRas Q61H mutant + SOS: % inh. |
| 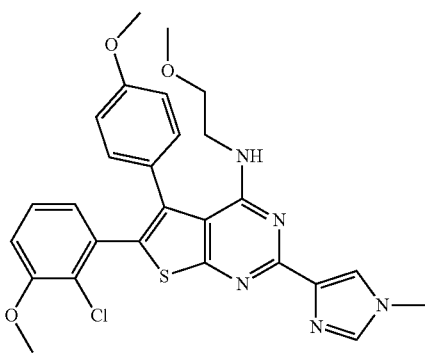 [SMILES: COCCNc1nc(-c2cn(C)cn2)nc2sc(-c3cccc(OC)c3Cl)c(-c3ccc(OC)cc3)c12] | C | D | B | B | B | D | C | D |
| 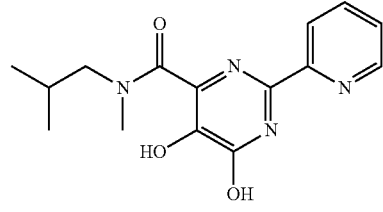 [SMILES: CC(C)CN(C)C(=O)c1nc(-c2ccccn2)nc(O)c1O] | B | A | B | B | C | B | B | B |
| 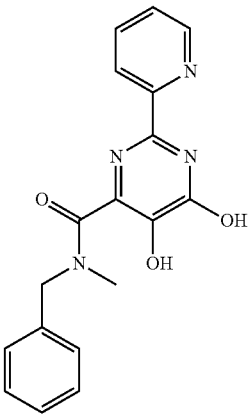 [SMILES: CN(Cc1ccccc1)C(=O)c1nc(-c2ccccn2)nc(O)c1O] | C | B | B | B | C | B | C | B |
| 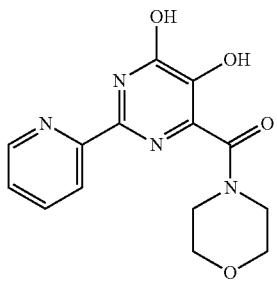 | C | A | B | B | B | A | B | A |

TABLE 7-continued

% Inhibition at 20 μM of K-Ras mutant and wild-type protein

| Structure | KRas wild type: % inh. | KRas wild type + SOS: % inh. | KRas G12D mutant: % inh. | KRas G-12D mutant + SOS: % inh. | KRas G12C mutant: % inh. | KRas G12C mutant + SOS: % inh. | KRas Q61H mutant: % inh. | KRas Q61H mutant + SOS: % inh. |
|---|---|---|---|---|---|---|---|---|
| *structure* | D | C | D | C | C | C | D | C |
| *structure* | D | B | C | C | C | C | D | C |
| *structure* | D | B | C | C | C | C | D | C |
| *structure* | C | B | C | B | C | C | C | C |

TABLE 7-continued
% Inhibition at 20 μM of K-Ras mutant and wild-type protein
| Structure | KRas wild type: % inh. | KRas wild type + SOS: % inh. | KRas G12D mutant: % inh. | KRas G-12D mutant + SOS: % inh. | KRas G12C mutant: % inh. | KRas G12C mutant + SOS: % inh. | KRas Q61H mutant: % inh. | KRas Q61H mutant + SOS: % inh. |
|---|---|---|---|---|---|---|---|---|
| 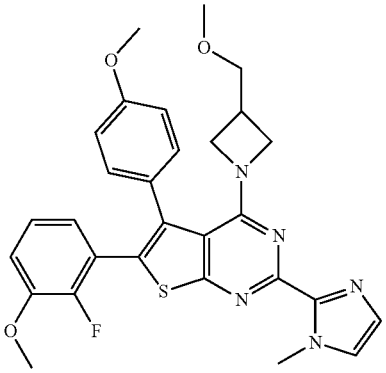 [SMILES: COCC1CN(c2nc(-c3nccn3C)nc3sc(-c4cccc(OC)c4F)c(-c4ccc(OC)cc4)c23)C1] | C | D | C | C | B | D | D | D |
| 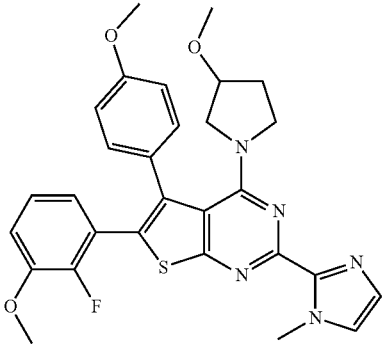 [SMILES: COc1ccc(-c2c(-c3cccc(OC)c3F)sc3nc(-c4nccn4C)nc(N4CCC(OC)C4)c23)cc1] | C | D | C | C | A | D | C | D |
| 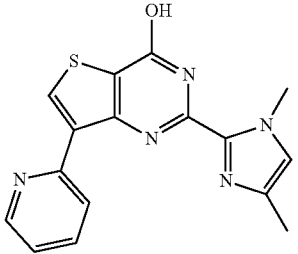 [SMILES: Cc1cn(C)c(-c2nc(O)c3scc(-c4ccccn4)c3n2)n1] | D | B | D | B | C | C | A | C |
| 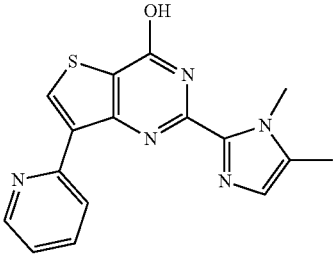 [SMILES: Cc1cnc(-c2nc(O)c3scc(-c4ccccn4)c3n2)n1C] | C | A | C | A | C | B | A | B |

TABLE 7-continued
% Inhibition at 20 µM of K-Ras mutant and wild-type protein
| Structure | KRas wild type: % inh. | KRas wild type + SOS: % inh. | KRas G12D mutant: % inh. | KRas G-12D mutant + SOS: % inh. | KRas G12C mutant: % inh. | KRas G12C mutant + SOS: % inh. | KRas Q61H mutant: % inh. | KRas Q61H mutant + SOS: % inh. |
|---|---|---|---|---|---|---|---|---|
| 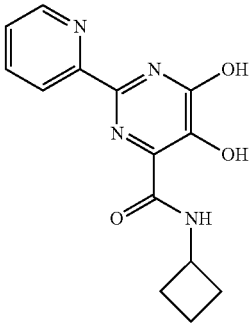 [SMILES: O=C(NC1CCC1)c1nc(-c2ccccn2)nc(O)c1O] | D | A | C | B | C | B | D | B |
| 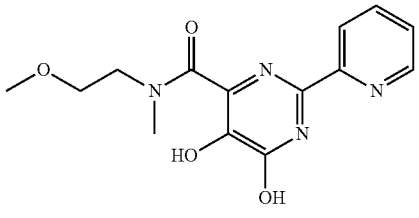 [SMILES: COCCN(C)C(=O)c1nc(-c2ccccn2)nc(O)c1O] | B | A | A | A | C | A | A | A |
| 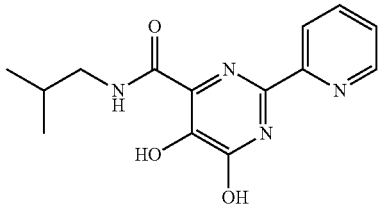 [SMILES: CC(C)CNC(=O)c1nc(-c2ccccn2)nc(O)c1O] | D | A | C | A | D | B | C | B |
| 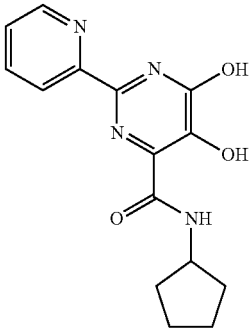 [SMILES: O=C(NC1CCCC1)c1nc(-c2ccccn2)nc(O)c1O] | D | A | C | A | D | B | C | B |
| 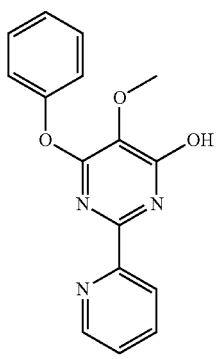 [SMILES: COc1c(O)nc(-c2ccccn2)nc1Oc1ccccc1] | D | B | B | B | C | C | D | C |

TABLE 7-continued

% Inhibition at 20 μM of K-Ras mutant and wild-type protein

| Structure | KRas wild type: % inh. | KRas wild type + SOS: % inh. | KRas G12D mutant: % inh. | KRas G-12D mutant + SOS: % inh. | KRas G12C mutant: % inh. | KRas G12C mutant + SOS: % inh. | KRas Q61H mutant: % inh. | KRas Q61H mutant + SOS: % inh. |
|---|---|---|---|---|---|---|---|---|
| (structure) | D | B | C | B | A | B | B | C |
| (structure) | D | B | D | B | D | C | D | C |
| (structure) | C | A | B | A | B | B | B | B |
| (structure) | B | D | C | C | A | D | B | D |

TABLE 7-continued

% Inhibition at 20 µM of K-Ras mutant and wild-type protein

| Structure | KRas wild type: % inh. | KRas wild type + SOS: % inh. | KRas G12D mutant: % inh. | KRas G-12D mutant + SOS: % inh. | KRas G12C mutant: % inh. | KRas G12C mutant + SOS: % inh. | KRas Q61H mutant: % inh. | KRas Q61H mutant + SOS: % inh. |
|---|---|---|---|---|---|---|---|---|
| [structure] HCl | A | A | A | A | A | A | A | A |
| [structure] HCl | 0 | D | A | C | 0 | D | 0 | D |
| [structure] HCl | B | A | B | B | B | B | A | B |
| [structure] | D | B | C | C | B | C | D | C |

TABLE 7-continued
| | % Inhibition at 20 μM of K-Ras mutant and wild-type protein | | | | | | | |
|---|---|---|---|---|---|---|---|---|
| Structure | KRas wild type: % inh. | KRas wild type + SOS: % inh. | KRas G12D mutant: % inh. | KRas G-12D mutant + SOS: % inh. | KRas G12C mutant: % inh. | KRas G12C mutant + SOS: % inh. | KRas Q61H mutant: % inh. | KRas Q61H mutant + SOS: % inh. |
| 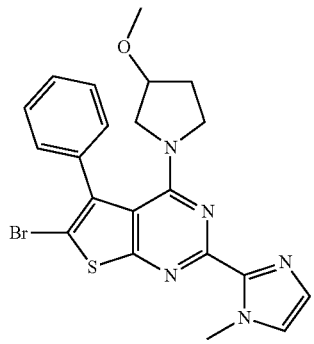 [SMILES: COC1CCN(c2nc(-c3nccn3C)nc3sc(Br)c(-c4ccccc4)c23)C1] | C | D | B | C | B | D | B | C |
| 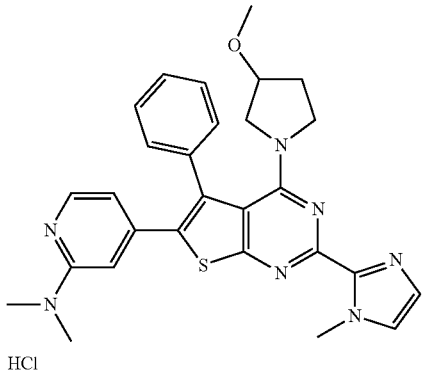 [SMILES: COC1CCN(c2nc(-c3nccn3C)nc3sc(-c4ccnc(N(C)C)c4)c(-c4ccccc4)c23)C1 ; Cl] | C | D | C | C | A | D | D | D |
| 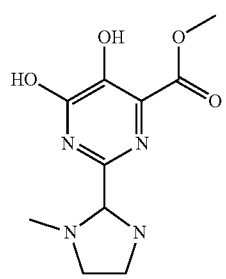 | C | B | C | B | D | C | C | C |
| 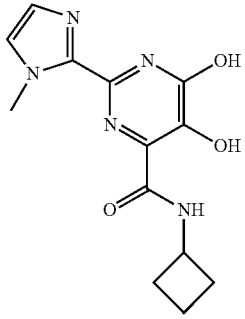 [SMILES: Cn1ccnc1-c1nc(O)c(O)c(C(=O)NC2CCC2)n1] | C | B | C | B | C | B | C | C |

TABLE 7-continued

% Inhibition at 20 μM of K-Ras mutant and wild-type protein

| Structure | KRas wild type: % inh. | KRas wild type + SOS: % inh. | KRas G12D mutant: % inh. | KRas G-12D mutant + SOS: % inh. | KRas G12C mutant: % inh. | KRas G12C mutant + SOS: % inh. | KRas Q61H mutant: % inh. | KRas Q61H mutant + SOS: % inh. |
|---|---|---|---|---|---|---|---|---|
| (structure) | C | A | B | A | B | A | B | B |
| (structure) | C | B | C | B | C | B | C | C |
| (structure) | B | A | B | A | B | A | C | B |
| (structure) | B | A | C | A | A | A | B | B |
| (structure) | C | B | C | B | C | B | C | C |

TABLE 7-continued
% Inhibition at 20 μM of K-Ras mutant and wild-type protein
| Structure | KRas wild type: % inh. | KRas wild type + SOS: % inh. | KRas G12D mutant: % inh. | KRas G-12D mutant + SOS: % inh. | KRas G12C mutant: % inh. | KRas G12C mutant + SOS: % inh. | KRas Q61H mutant: % inh. | KRas Q61H mutant + SOS: % inh. |
|---|---|---|---|---|---|---|---|---|
| 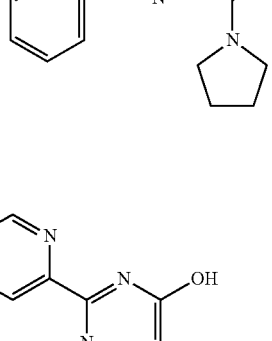 | C | A | C | A | B | A | B | B |
| 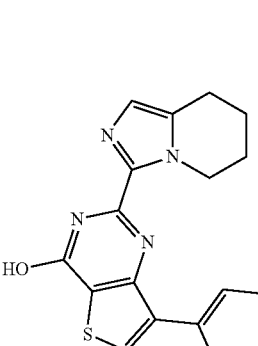 | C | B | C | B | C | B | C | B |
| 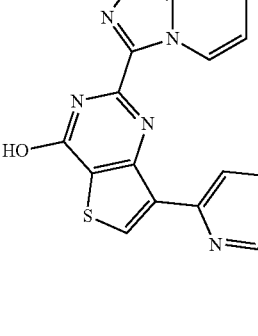 | C | B | C | C | D | C | C | C |
|  | C | C | D | C | C | C | C | C |

TABLE 7-continued

% Inhibition at 20 µM of K-Ras mutant and wild-type protein

| Structure | KRas wild type: % inh. | KRas wild type + SOS: % inh. | KRas G12D mutant: % inh. | KRas G-12D mutant + SOS: % inh. | KRas G12C mutant: % inh. | KRas G12C mutant + SOS: % inh. | KRas Q61H mutant: % inh. | KRas Q61H mutant + SOS: % inh. |
|---|---|---|---|---|---|---|---|---|
| (structure) HCl | B | D | B | D | C | D | B | D |
| (structure) HCl | A | D | B | C | 0 | D | B | D |
| (structure) HCl | B | C | C | C | C | C | B | C |
| (structure) HCl | C | D | C | C | B | D | B | D |

TABLE 7-continued

| | % Inhibition at 20 μM of K-Ras mutant and wild-type protein | | | | | | | |
|---|---|---|---|---|---|---|---|---|
| Structure | KRas wild type: % inh. | KRas wild type + SOS: % inh. | KRas G12D mutant: % inh. | KRas G-12D mutant + SOS: % inh. | KRas G12C mutant: % inh. | KRas G12C mutant + SOS: % inh. | KRas Q61H mutant: % inh. | KRas Q61H mutant + SOS: % inh. |
| [structure] | A | A | A | 0 | B | A | B | A |
| [structure] HCl | B | D | B | C | B | D | C | D |
| [structure] HCl | D | C | C | C | D | D | B | C |
| [structure] HCl | C | C | C | C | C | C | B | C |

TABLE 7-continued
| | % Inhibition at 20 μM of K-Ras mutant and wild-type protein | | | | | | | |
|---|---|---|---|---|---|---|---|---|
| Structure | KRas wild type: % inh. | KRas wild type + SOS: % inh. | KRas G12D mutant: % inh. | KRas G-12D mutant + SOS: % inh. | KRas G12C mutant: % inh. | KRas G12C mutant + SOS: % inh. | KRas Q61H mutant: % inh. | KRas Q61H mutant + SOS: % inh. |
| 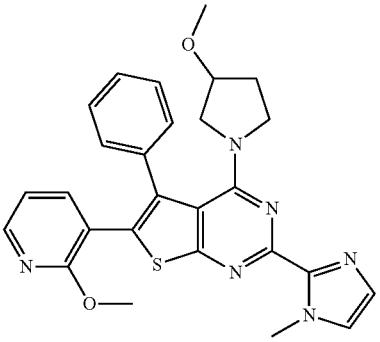 HCl | C | C | C | C | C | C | C | C |
| 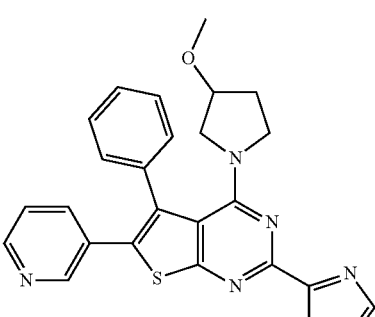 HCl | C | C | C | C | D | D | B | C |
| 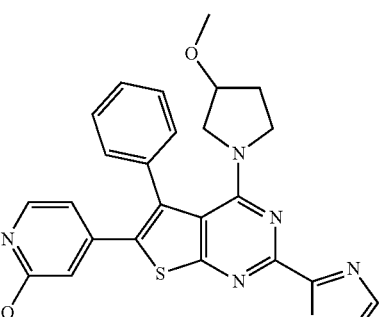 HCl | C | C | C | C | C | D | C | C |
| 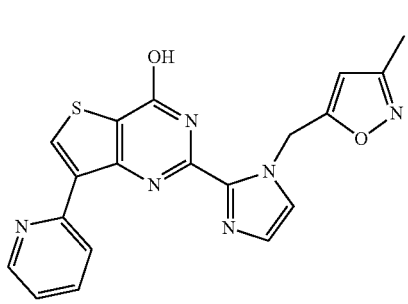 [SMILES: Cc1cc(Cn2ccnc2-c2nc(O)c3scc(-c4ccccn4)c3n2)on1] | C | B | C | B | B | C | B | C |

TABLE 7-continued
| | % Inhibition at 20 μM of K-Ras mutant and wild-type protein | | | | | | | |
|---|---|---|---|---|---|---|---|---|
| Structure | KRas wild type: % inh. | KRas wild type + SOS: % inh. | KRas G12D mutant: % inh. | KRas G-12D mutant + SOS: % inh. | KRas G12C mutant: % inh. | KRas G12C mutant + SOS: % inh. | KRas Q61H mutant: % inh. | KRas Q61H mutant + SOS: % inh. |
| 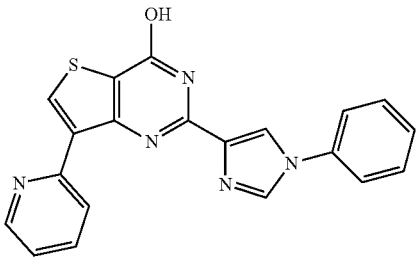 [SMILES: Oc1nc(-c2cn(-c3ccccc3)cn2)nc2c(-c3ccccn3)csc12] | A | A | A | A | 0 | A | B | A |
| 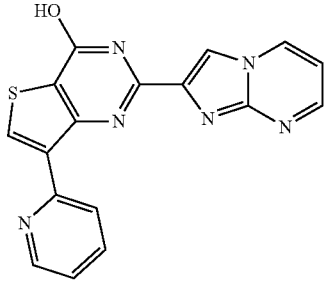 | A | A | A | A | 0 | A | A | A |
| 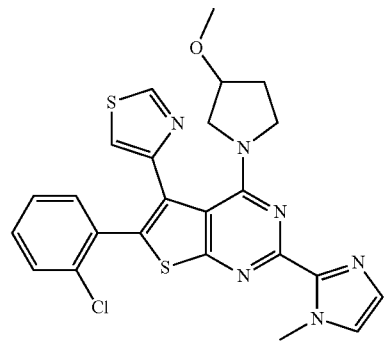 [SMILES: COC1CCN(c2nc(-c3nccn3C)nc3sc(-c4ccccc4Cl)c(-c4cscn4)c23)C1] | C | C | C | C | B | C | B | C |
| 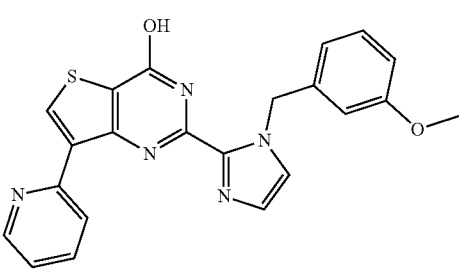 [SMILES: COc1cccc(Cn2ccnc2-c2nc(O)c3scc(-c4ccccn4)c3n2)c1] | C | C | D | C | C | D | C | D |

TABLE 7-continued

| | % Inhibition at 20 μM of K-Ras mutant and wild-type protein | | | | | | | |
|---|---|---|---|---|---|---|---|---|
| Structure | KRas wild type: % inh. | KRas wild type + SOS: % inh. | KRas G12D mutant: % inh. | KRas G-12D mutant + SOS: % inh. | KRas G12C mutant: % inh. | KRas G12C mutant + SOS: % inh. | KRas Q61H mutant: % inh. | KRas Q61H mutant + SOS: % inh. |
| (structure) | D | C | D | C | D | D | C | D |
| (structure) | D | C | D | C | C | D | C | C |
| (structure) | D | C | D | C | D | C | D | C |
| (structure) | B | D | C | C | C | D | C | D |

TABLE 7-continued
% Inhibition at 20 μM of K-Ras mutant and wild-type protein
| Structure | KRas wild type: % inh. | KRas wild type + SOS: % inh. | KRas G12D mutant: % inh. | KRas G-12D mutant + SOS: % inh. | KRas G12C mutant: % inh. | KRas G12C mutant + SOS: % inh. | KRas Q61H mutant: % inh. | KRas Q61H mutant + SOS: % inh. |
|---|---|---|---|---|---|---|---|---|
| 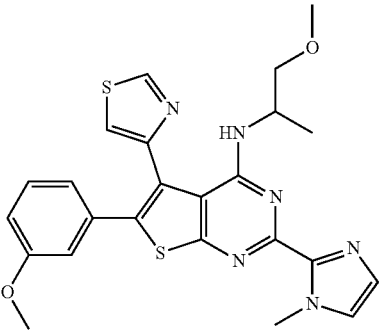 [SMILES: COCC(C)Nc1nc(-c2nccn2C)nc2sc(-c3cccc(OC)c3)c(-c3cscn3)c12] | B | D | C | C | B | D | C | D |
| 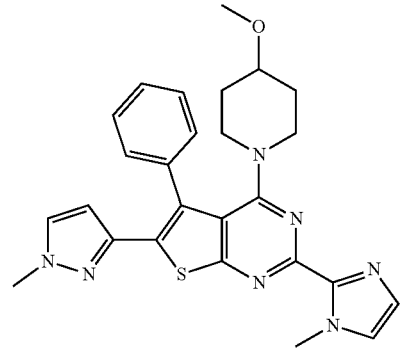 [SMILES: COC1CCN(c2nc(-c3nccn3C)nc3sc(-c4ccn(C)n4)c(-c4ccccc4)c23)CC1] | 0 | B | B | B | B | C | B | C |
| 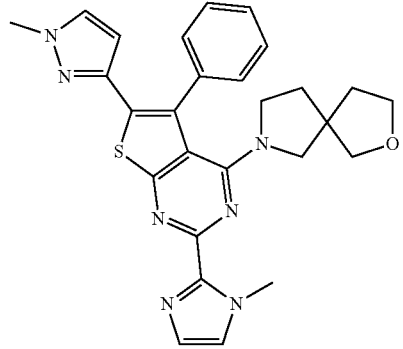 [SMILES: Cn1ccc(-c2sc3nc(-c4nccn4C)nc(N4CCC5(CCOC5)C4)c3c2-c2ccccc2)n1] | A | A | B | A | A | B | B | B |
| 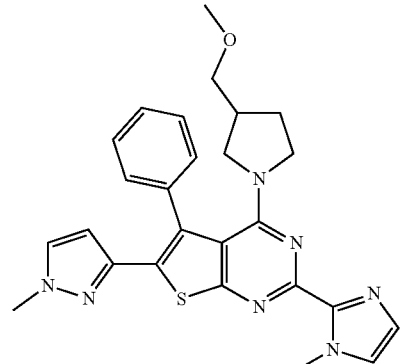 | 0 | C | B | B | B | C | C | D |

TABLE 7-continued

% Inhibition at 20 µM of K-Ras mutant and wild-type protein

| Structure | KRas wild type: % inh. | KRas wild type + SOS: % inh. | KRas G12D mutant: % inh. | KRas G-12D mutant + SOS: % inh. | KRas G12C mutant: % inh. | KRas G12C mutant + SOS: % inh. | KRas Q61H mutant: % inh. | KRas Q61H mutant + SOS: % inh. |
|---|---|---|---|---|---|---|---|---|
| (+/- trans) | A | C | B | B | A | C | B | C |
| (+/- cis) | B | D | B | C | B | D | B | D |
| 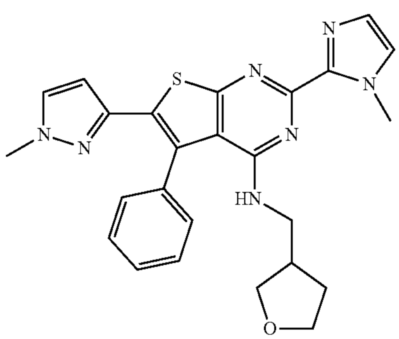 [SMILES: Cn1ccc(-c2sc3nc(-c4nccn4C)nc(NCC4CCOC4)c3c2-c2ccccc2)n1] | 0 | B | B | A | 0 | C | B | C |
|  | B | B | A | A | 0 | A | B | B |

TABLE 7-continued

% Inhibition at 20 μM of K-Ras mutant and wild-type protein

| Structure | KRas wild type: % inh. | KRas wild type + SOS: % inh. | KRas G12D mutant: % inh. | KRas G-12D mutant + SOS: % inh. | KRas G12C mutant: % inh. | KRas G12C mutant + SOS: % inh. | KRas Q61H mutant: % inh. | KRas Q61H mutant + SOS: % inh. |
|---|---|---|---|---|---|---|---|---|
| *(structure)* | A | B | A | A | A | B | B | C |
| *(structure)* | 0 | C | A | B | 0 | C | 0 | C |
| *(structure)* | A | B | C | B | A | B | A | B |
| *(structure)* | C | C | A | B | A | B | B | B |

TABLE 7-continued
% Inhibition at 20 μM of K-Ras mutant and wild-type protein
| Structure | KRas wild type: % inh. | KRas wild type + SOS: % inh. | KRas G12D mutant: % inh. | KRas G-12D mutant + SOS: % inh. | KRas G12C mutant: % inh. | KRas G12C mutant + SOS: % inh. | KRas Q61H mutant: % inh. | KRas Q61H mutant + SOS: % inh. |
|---|---|---|---|---|---|---|---|---|
| 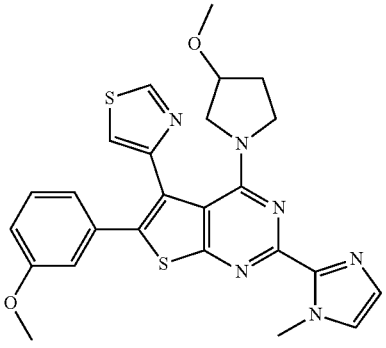 [SMILES: COc1cccc(-c2sc3nc(-c4nccn4C)nc(N4CCC(OC)C4)c3c2-c2cscn2)c1] | A | D | A | C | 0 | D | A | D |
| 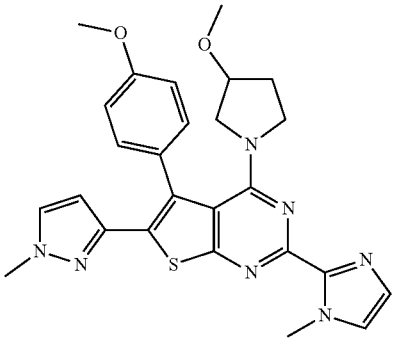 [SMILES: COc1ccc(-c2c(-c3ccn(C)n3)sc3nc(-c4nccn4C)nc(N4CCC(OC)C4)c23)cc1] | 0 | A | 0 | A | 0 | A | A | B |
| 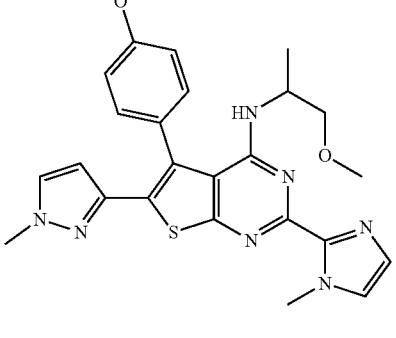 | A | A | 0 | A | 0 | A | A | A |
| 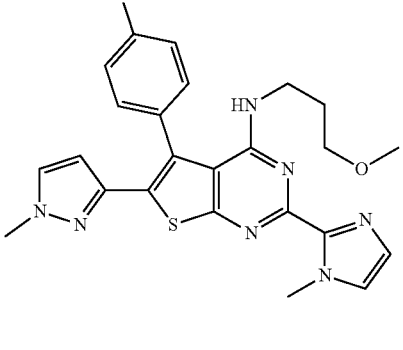 | A | 0 | 0 | A | 0 | A | A | A |

TABLE 7-continued
% Inhibition at 20 μM of K-Ras mutant and wild-type protein
| Structure | KRas wild type: % inh. | KRas wild type + SOS: % inh. | KRas G12D mutant: % inh. | KRas G-12D mutant + SOS: % inh. | KRas G12C mutant: % inh. | KRas G12C mutant + SOS: % inh. | KRas Q61H mutant: % inh. | KRas Q61H mutant + SOS: % inh. |
|---|---|---|---|---|---|---|---|---|
| 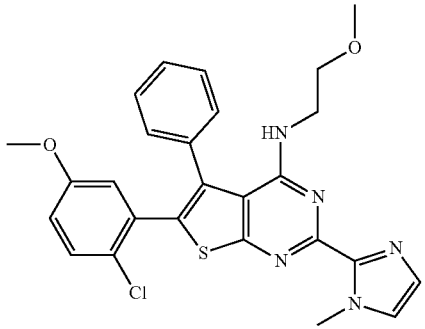 [SMILES: COCCNc1nc(-c2nccn2C)nc2sc(-c3cc(OC)ccc3Cl)c(-c3ccccc3)c12] | B | A | B | A | 0 | A | C | A |
| 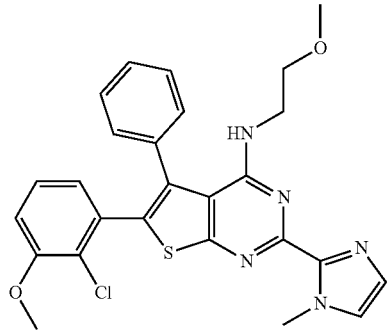 [SMILES: COCCNc1nc(-c2nccn2C)nc2sc(-c3cccc(OC)c3Cl)c(-c3ccccc3)c12] | B | D | A | D | C | D | B | D |
| 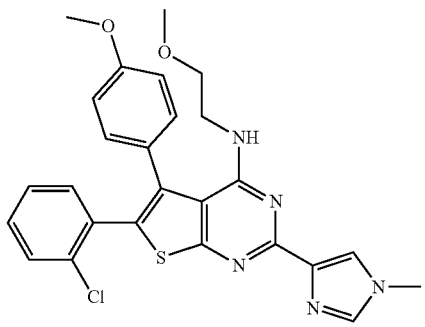 [SMILES: COCCNc1nc(-c2cn(C)cn2)nc2sc(-c3ccccc3Cl)c(-c3ccc(OC)cc3)c12] | A | D | B | D | C | D | B | D |
| 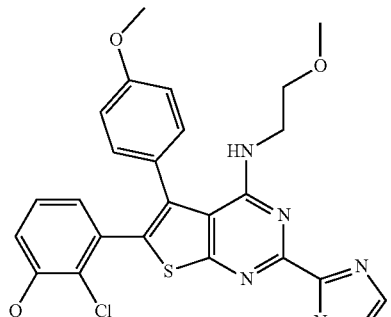 | B | D | A | C | B | D | A | D |

TABLE 7-continued

% Inhibition at 20 μM of K-Ras mutant and wild-type protein

| Structure | KRas wild type: % inh. | KRas wild type + SOS: % inh. | KRas G12D mutant: % inh. | KRas G-12D mutant + SOS: % inh. | KRas G12C mutant: % inh. | KRas G12C mutant + SOS: % inh. | KRas Q61H mutant: % inh. | KRas Q61H mutant + SOS: % inh. |
|---|---|---|---|---|---|---|---|---|
| (structure) | B | D | C | D | C | D | B | D |
| (structure) | B | D | B | D | B | D | B | D |
| (structure) | A | D | A | B | A | C | A | D |
| (structure) | A | A | A | A | A | A | A | A |

0 = 0% inhibition, A = 1-25% inhibition, B = 26-50% inhibition, C = 51-75% inhibition, D = 76-100% inhibition.

TABLE 7A
| | % Inhibition at 20 μM of K-Ras mutant and wild-type protein | | | | | | | |
|---|---|---|---|---|---|---|---|---|
| Compound | KRas wild type % inh. | KRas wild type + SOS: % inh. | KRas G12D mutant: % inh. | KRas G12D mutant + SOS: % inh. | KRas G12C mutant: % inh. | KRas G12C mutant + SOS: % inh. | KRas Q61H mutant: % inh. | KRas Q61H mutant + SOS: % inh. |
| 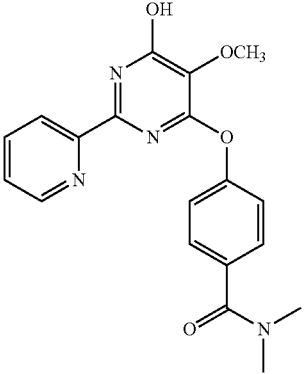 [SMILES: COc1c(O)nc(-c2ccccn2)nc1Oc1ccc(C(=O)N(C)C)cc1] | B | A | C | B | B | A | B | B |
| 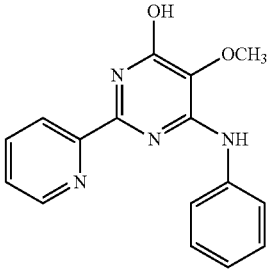 [SMILES: COc1c(O)nc(-c2ccccn2)nc1Nc1ccccc1] | C | B | B | B | C | B | C | C |
| 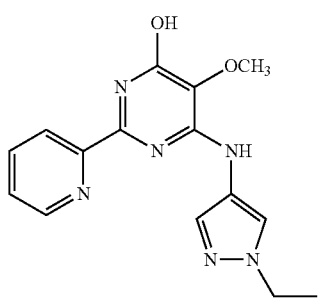 [SMILES: CCn1cc(Nc2nc(-c3ccccn3)nc(O)c2OC)cn1] | C | B | B | B | C | B | A | B |
| 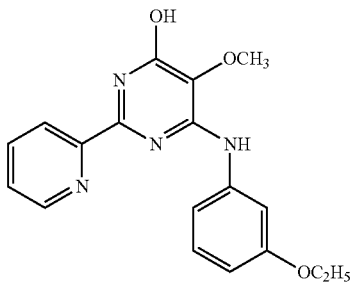 [SMILES: CCOc1cccc(Nc2nc(-c3ccccn3)nc(O)c2OC)c1] | C | B | C | B | C | C | C | C |

TABLE 7A-continued

% Inhibition at 20 μM of K-Ras mutant and wild-type protein

| Compound | KRas wild type % inh. | KRas wild type + SOS: % inh. | KRas G12D mutant: % inh. | KRas G12D mutant + SOS: % inh. | KRas G12C mutant: % inh. | KRas G12C mutant + SOS: % inh. | KRas Q61H mutant: % inh. | KRas Q61H mutant + SOS: % inh. |
|---|---|---|---|---|---|---|---|---|
| (structure) | C | D | B | C | B | D | C | D |
| (+/−) (structure) | C | D | C | C | | | C | D |
| (structure) | B | C | B | C | B | C | B | C |
| (structure) | B | A | A | A | B | A | A | B |

TABLE 7A-continued

% Inhibition at 20 μM of K-Ras mutant and wild-type protein

| Compound | KRas wild type % inh. | KRas wild type + SOS: % inh. | KRas G12D mutant: % inh. | KRas G12D mutant + SOS: % inh. | KRas G12C mutant: % inh. | KRas G12C mutant + SOS: % inh. | KRas Q61H mutant: % inh. | KRas Q61H mutant + SOS: % inh. |
|---|---|---|---|---|---|---|---|---|
| (+/−) [structure] | D | D | D | D | | | D | D |
| [structure] | B | D | B | B | B | D | C | D |
| (+/−) [structure] | C | D | C | C | | | C | D |
| [structure] | B | C | A | C | A | C | B | C |

TABLE 7A-continued

% Inhibition at 20 μM of K-Ras mutant and wild-type protein

| Compound | KRas wild type % inh. | KRas wild type + SOS: % inh. | KRas G12D mutant: % inh. | KRas G12D mutant + SOS: % inh. | KRas G12C mutant: % inh. | KRas G12C mutant + SOS: % inh. | KRas Q61H mutant: % inh. | KRas Q61H mutant + SOS: % inh. |
|---|---|---|---|---|---|---|---|---|
| [structure] | C | D | B | C | C | D | D | D |
| [structure] | D | D | C | D | D | D | D | D |
| [structure] | C | C | D | C | D | C | C | C |
| (+/−) [structure] | C | D | C | C | | | C | D |
| [structure] | B | D | B | C | B | D | B | D |

TABLE 7A-continued

% Inhibition at 20 μM of K-Ras mutant and wild-type protein

| Compound | KRas wild type % inh. | KRas wild type + SOS: % inh. | KRas G12D mutant: % inh. | KRas G12D mutant + SOS: % inh. | KRas G12C mutant: % inh. | KRas G12C mutant + SOS: % inh. | KRas Q61H mutant: % inh. | KRas Q61H mutant + SOS: % inh. |
|---|---|---|---|---|---|---|---|---|
| (+/-) [structure] | A | B | A | B | | | A | B |
| (+/-) [structure] | B | B | B | B | | | B | B |
| [structure] | C | C | C | C | C | C | D | C |
| [structure] | D | C | D | C | C | C | C | D |

TABLE 7A-continued
% Inhibition at 20 μM of K-Ras mutant and wild-type protein
| Compound | KRas wild type % inh. | KRas wild type + SOS: % inh. | KRas G12D mutant: % inh. | KRas G12D mutant + SOS: % inh. | KRas G12C mutant: % inh. | KRas G12C mutant + SOS: % inh. | KRas Q61H mutant: % inh. | KRas Q61H mutant + SOS: % inh. |
|---|---|---|---|---|---|---|---|---|
| 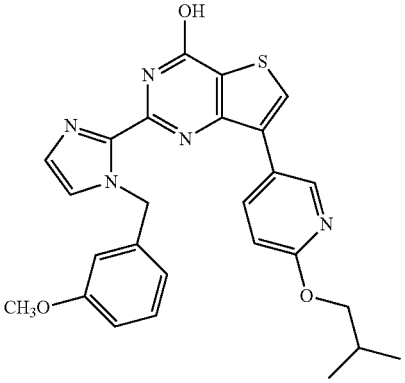 | C | B | C | C | C | B | C | C |
| (+/-) 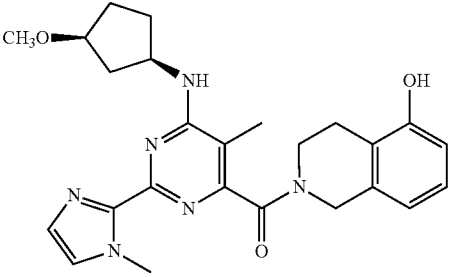 | B | A | B | B | B | A | B | B |
| 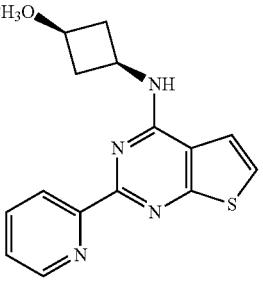 | C | C | C | C | C | C | D | C |
| 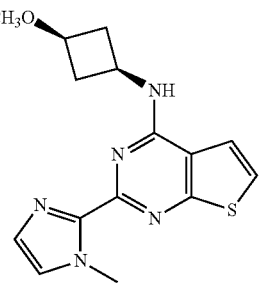 | C | D | D | D | D | D | D | D |

TABLE 7A-continued

% Inhibition at 20 µM of K-Ras mutant and wild-type protein

| Compound | KRas wild type % inh. | KRas wild type + SOS: % inh. | KRas G12D mutant: % inh. | KRas G12D mutant + SOS: % inh. | KRas G12C mutant: % inh. | KRas G12C mutant + SOS: % inh. | KRas Q61H mutant: % inh. | KRas Q61H mutant + SOS: % inh. |
|---|---|---|---|---|---|---|---|---|
| [structure] | A | A | B | B | B | B | C | B |
| [structure] HCl | C | D | B | C | C | D | C | D |
| [structure] | C | D | B | C | C | D | C | D |
| [structure] | C | C | B | C | C | C | C | D |
| [structure] | A | 0 | 0 | 0 | A | A | A | 0 |

TABLE 7A-continued

% Inhibition at 20 μM of K-Ras mutant and wild-type protein

| Compound | KRas wild type % inh. | KRas wild type + SOS: % inh. | KRas G12D mutant: % inh. | KRas G12D mutant + SOS: % inh. | KRas G12C mutant: % inh. | KRas G12C mutant + SOS: % inh. | KRas Q61H mutant: % inh. | KRas Q61H mutant + SOS: % inh. |
|---|---|---|---|---|---|---|---|---|
| (structure 1, +/−) | A | A | 0 | 0 | A | A | A | 0 |
| (structure 2, +/−) | B | A | B | B | B | B | C | B |
| (structure 3, +/−) | C | C | B | C | C | C | B | C |
| (structure 4, +/−) | D | D | C | C | C | D | D | D |

TABLE 7A-continued
| | % Inhibition at 20 μM of K-Ras mutant and wild-type protein | | | | | | |
|---|---|---|---|---|---|---|---|
| Compound | KRas wild type % inh. | KRas wild type + SOS: % inh. | KRas G12D mutant: % inh. | KRas G12D mutant + SOS: % inh. | KRas G12C mutant: % inh. | KRas G12C mutant + SOS: % inh. | KRas Q61H mutant: % inh. | KRas Q61H mutant + SOS: % inh. |
| B | A | B | A | A | A | B | A |
| C | C | C | C | C | C | C | C |
(+/−)
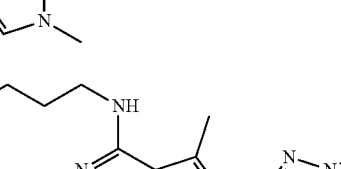
| C | D | B | C | C | D | C | D |
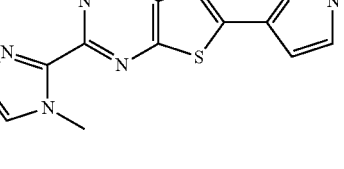
| C | C | D | D | C | C | D | C |
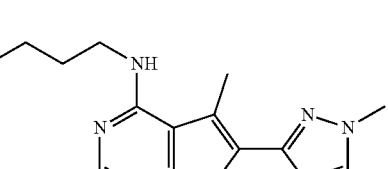
| D | C | C | D | C | C | D | C |

TABLE 7A-continued
% Inhibition at 20 μM of K-Ras mutant and wild-type protein
| Compound | KRas wild type % inh. | KRas wild type + SOS: % inh. | KRas G12D mutant: % inh. | KRas G12D mutant + SOS: % inh. | KRas G12C mutant: % inh. | KRas G12C mutant + SOS: % inh. | KRas Q61H mutant: % inh. | KRas Q61H mutant + SOS: % inh. |
|---|---|---|---|---|---|---|---|---|
| 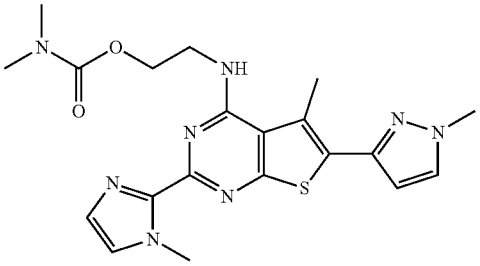 | D | D | D | D | D | C | C | D |
| 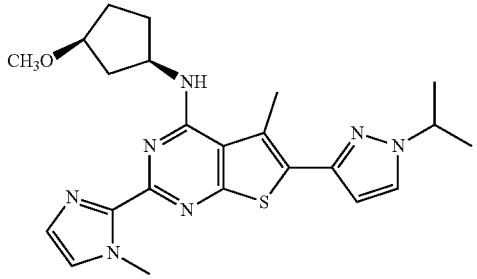 (+/−) | D | D | C | C | C | D | D | D |
| 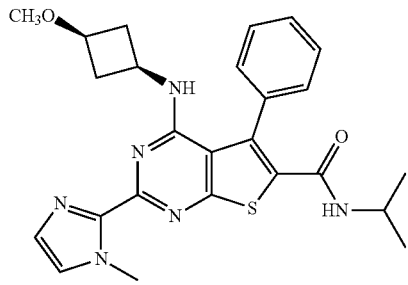 | C | D | C | C | D | D | D | D |
| 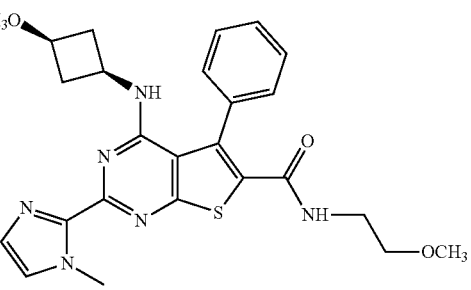 | D | C | C | C | D | D | D | D |
|  | C | C | C | C | D | C | D | C |

TABLE 7A-continued

% Inhibition at 20 μM of K-Ras mutant and wild-type protein

| Compound | KRas wild type % inh. | KRas wild type + SOS: % inh. | KRas G12D mutant: % inh. | KRas G12D mutant + SOS: % inh. | KRas G12C mutant: % inh. | KRas G12C mutant + SOS: % inh. | KRas Q61H mutant: % inh. | KRas Q61H mutant + SOS: % inh. |
|---|---|---|---|---|---|---|---|---|
| (structure 1) | C | C | C | C | C | C | C | C |
| (structure 2) | D | D | D | D | C | D | D | D |
| (structure 3) | D | D | D | D | D | D | D | D |
| (structure 4) | C | C | C | C | D | D | D | D |

TABLE 7A-continued

% Inhibition at 20 μM of K-Ras mutant and wild-type protein

| Compound | KRas wild type: % inh. | KRas wild type + SOS: % inh. | KRas G12D mutant: % inh. | KRas G12D mutant + SOS: % inh. | KRas G12C mutant: % inh. | KRas G12C mutant + SOS: % inh. | KRas Q61H mutant: % inh. | KRas Q61H mutant + SOS: % inh. |
|---|---|---|---|---|---|---|---|---|
| [Structure: methoxycyclopentyl-NH-thienopyrimidine with phenyl, methylimidazole, morpholine carbonyl] (+/−) | D | C | D | C | C | C | D | D |

0 = 0% inhibition, A = 1-25% inhibition, B = 26-50% inhibition, C = 51-75% inhibition, D = 76-100% inhibition.

TABLE 8

% Inhibition at 20 μM of KRas G12D mutant, Rac-1 and Rho-A protein

| Structure | KRas G12D mutant: % inh. | KRas G12D mutant + SOS: % inh. | Rac-1: % inh. | Rac-1 + SOS: % inh. | Rho-A: % inh. | Rho-A + SOS: % inh. |
|---|---|---|---|---|---|---|
| [Structure: methoxyethyl-pyrazole-NH-dimethoxypyrimidine-pyridine] | A | A | A | A | 0 | 0 |
| [Structure: pyridine-dimethoxypyrimidine-NH-methylpyrazole] | 0 | 0 | A | 0 | 0 | A |

TABLE 8-continued
% Inhibition at 20 μM of KRas G12D mutant, Rac-1 and Rho-A protein
| Structure | KRas G12D mutant: % inh. | KRas G12D mutant + SOS: % inh. | Rac-1: % inh. | Rac-1 + SOS: % inh. | Rho-A: % inh. | Rho-A + SOS: % inh. |
|---|---|---|---|---|---|---|
| 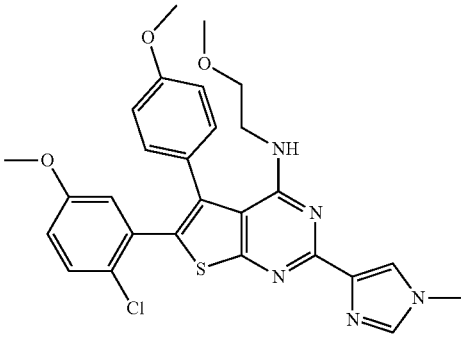 | B | B | C | C | C | B |
| 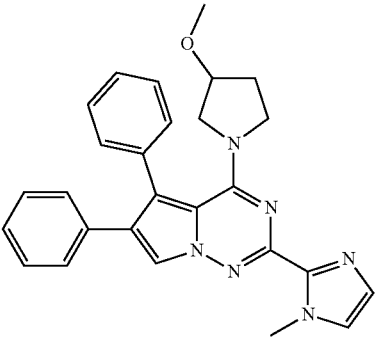 [SMILES: COC1CCN(c2nc(-c3nccn3C)nn3cc(-c4ccccc4)c(-c4ccccc4)c23)C1] | B | A | B | C | C | B |
| 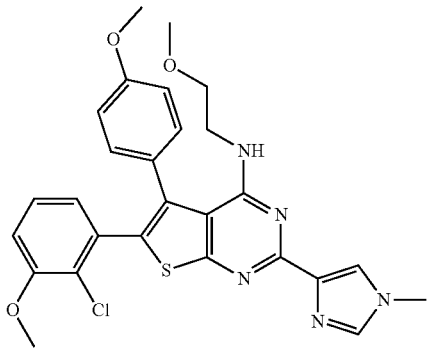 [SMILES: COCCNc1nc(-c2cn(C)cn2)nc2sc(-c3cccc(OC)c3Cl)c(-c3ccc(OC)cc3)c12] | B | B | C | C | C | C |
| 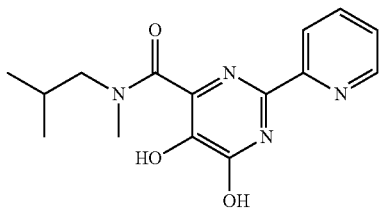 [SMILES: CC(C)CN(C)C(=O)c1nc(-c2ccccn2)nc(O)c1O] | B | B | C | B | B | C |

TABLE 8-continued
% Inhibition at 20 μM of KRas G12D mutant, Rac-1 and Rho-A protein
| Structure | KRas G12D mutant: % inh. | KRas G12D mutant + SOS: % inh. | Rac-1: % inh. | Rac-1 + SOS: % inh. | Rho-A: % inh. | Rho-A + SOS: % inh. |
|---|---|---|---|---|---|---|
| 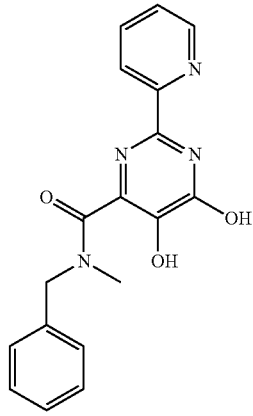 [SMILES: CN(Cc1ccccc1)C(=O)c1nc(-c2ccccn2)nc(O)c1O] | B | B | C | B | C | C |
| 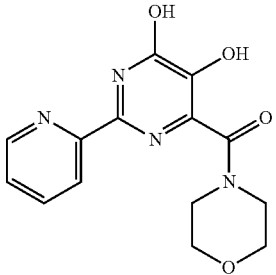 [SMILES: O=C(c1nc(-c2ccccn2)nc(O)c1O)N1CCOCC1] | B | B | C | B | B | B |
| 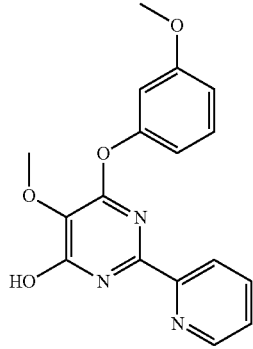 [SMILES: COc1cccc(Oc2nc(-c3ccccn3)nc(O)c2OC)c1] | D | C | D | D | C | C |
| 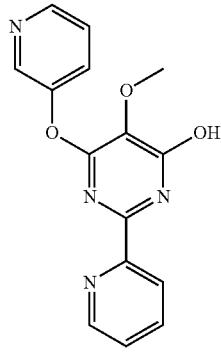 [SMILES: COc1c(O)nc(-c2ccccn2)nc1Oc1cccnc1] | C | C | D | D | D | D |

TABLE 8-continued

% Inhibition at 20 μM of KRas G12D mutant, Rac-1 and Rho-A protein

| Structure | KRas G12D mutant: % inh. | KRas G12D mutant + SOS: % inh. | Rac-1: % inh. | Rac-1 + SOS: % inh. | Rho-A: % inh. | Rho-A + SOS: % inh. |
|---|---|---|---|---|---|---|
| (structure) | C | C | D | D | C | C |
| (structure) | C | B | C | C | D | D |
| (structure) | C | C | 0 | 0 | C | C |
| (structure) | C | C | 0 | 0 | C | C |

TABLE 8-continued

% Inhibition at 20 μM of KRas G12D mutant, Rac-1 and Rho-A protein

| Structure | KRas G12D mutant: % inh. | KRas G12D mutant + SOS: % inh. | Rac-1: % inh. | Rac-1 + SOS: % inh. | Rho-A: % inh. | Rho-A + SOS: % inh. |
|---|---|---|---|---|---|---|
| *(thieno-pyrimidine with pyridine and 1,4-dimethylimidazole)* | D | B | C | C | D | D |
| *(thieno-pyrimidine with pyridine and 1,5-dimethylimidazole)* | C | A | A | C | C | C |
| *(pyrimidine-carboxamide with pyridyl and cyclobutyl)* | C | B | D | D | C | D |
| *(pyrimidine-carboxamide with pyridyl and N-methyl-N-(2-methoxyethyl))* | A | A | C | C | B | B |
| *(pyrimidine-carboxamide with pyridyl and isobutyl)* | C | A | C | D | C | C |

TABLE 8-continued

% Inhibition at 20 μM of KRas G12D mutant, Rac-1 and Rho-A protein

| Structure | KRas G12D mutant: % inh. | KRas G12D mutant + SOS: % inh. | Rac-1: % inh. | Rac-1 + SOS: % inh. | Rho-A: % inh. | Rho-A + SOS: % inh. |
|---|---|---|---|---|---|---|
| *structure* | C | A | C | C | C | C |
| *structure* | B | B | D | D | C | D |
| *structure* | C | B | C | D | D | D |
| *structure* | D | B | D | C | C | C |

TABLE 8-continued
% Inhibition at 20 μM of KRas G12D mutant, Rac-1 and Rho-A protein
| Structure | KRas G12D mutant: % inh. | KRas G12D mutant + SOS: % inh. | Rac-1: % inh. | Rac-1 + SOS: % inh. | Rho-A: % inh. | Rho-A + SOS: % inh. |
|---|---|---|---|---|---|---|
| 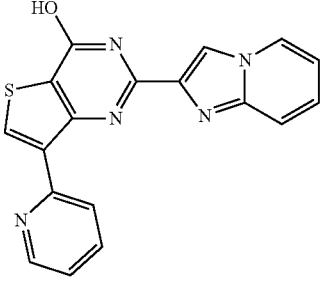 [SMILES: Oc1nc(-c2cn3ccccc3n2)nc2c(-c3ccccn3)csc12] | B | A | A | B | A | A |
| 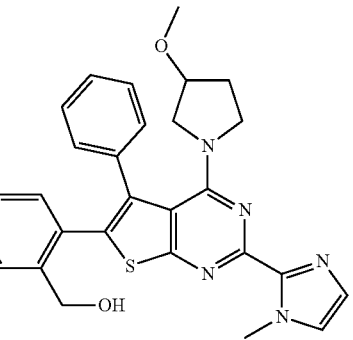 HCl | C | C | 0 | 0 | 0 | B |
| 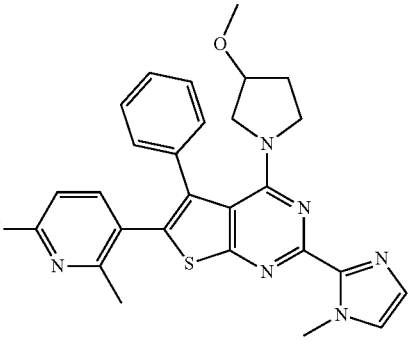 HCl | A | A | 0 | 0 | 0 | B |
| 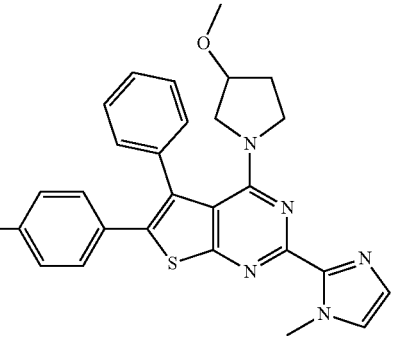 HCl | A | C | 0 | 0 | 0 | 0 |

TABLE 8-continued
% Inhibition at 20 µM of KRas G12D mutant, Rac-1 and Rho-A protein
| Structure | KRas G12D mutant: % inh. | KRas G12D mutant + SOS: % inh. | Rac-1: % inh. | Rac-1 + SOS: % inh. | Rho-A: % inh. | Rho-A + SOS: % inh. |
|---|---|---|---|---|---|---|
| 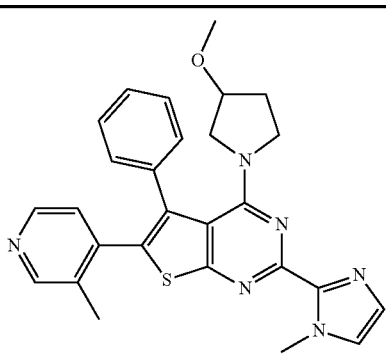 HCl | B | B | A | 0 | C | 0 |
| 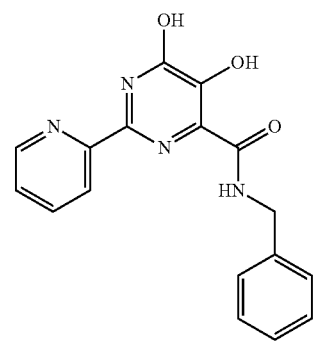 [SMILES: O=C(NCc1ccccc1)c1nc(-c2ccccn2)nc(O)c1O] | C | C | C | C | 0 | B |
| 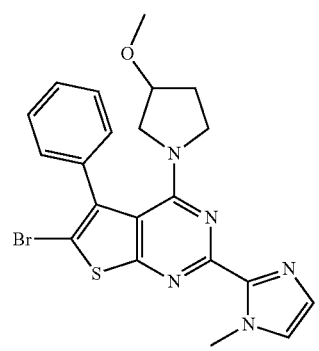 [SMILES: COC1CCN(c2nc(-c3nccn3C)nc3sc(Br)c(-c4ccccc4)c23)C1] | B | C | A | A | A | B |
| 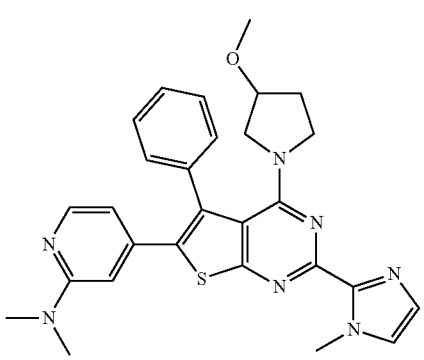 HCl | C | C | B | C | B | B |

TABLE 8-continued
% Inhibition at 20 μM of KRas G12D mutant, Rac-1 and Rho-A protein
| Structure | KRas G12D mutant: % inh. | KRas G12D mutant + SOS: % inh. | Rac-1: % inh. | Rac-1 + SOS: % inh. | Rho-A: % inh. | Rho-A + SOS: % inh. |
| --- | --- | --- | --- | --- | --- | --- |
| 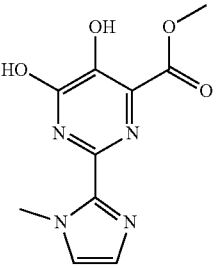 | C | B | D | C | A | C |
| 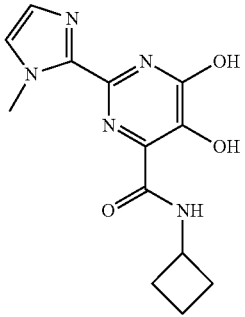 [SMILES: Cn1ccnc1-c1nc(O)c(O)c(C(=O)NC2CCC2)n1] | C | B | D | C | B | C |
| 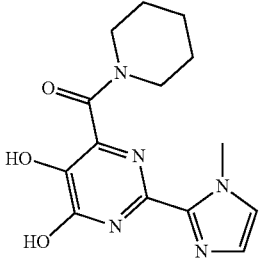 [SMILES: Cn1ccnc1-c1nc(O)c(O)c(C(=O)N2CCCCC2)n1] | B | A | C | A | B | C |
| 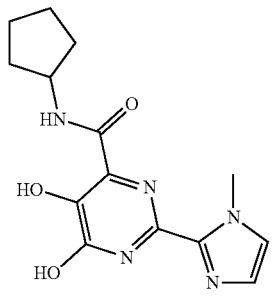 [SMILES: Cn1ccnc1-c1nc(O)c(O)c(C(=O)NC2CCCC2)n1] | C | B | C | C | B | D |
| 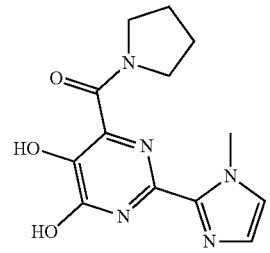 [SMILES: Cn1ccnc1-c1nc(O)c(O)c(C(=O)N2CCCC2)n1] | B | A | C | B | A | C |

TABLE 8-continued

% Inhibition at 20 μM of KRas G12D mutant, Rac-1 and Rho-A protein

| Structure | KRas G12D mutant: % inh. | KRas G12D mutant + SOS: % inh. | Rac-1: % inh. | Rac-1 + SOS: % inh. | Rho-A: % inh. | Rho-A + SOS: % inh. |
|---|---|---|---|---|---|---|
|  | C | A | B | A | B | C |
|  | C | B | C | C | C | D |
|  | C | A | B | B | D | C |
|  | C | B | D | C | D | D |
|  | C | C | C | D | B | D |

TABLE 8-continued
% Inhibition at 20 μM of KRas G12D mutant, Rac-1 and Rho-A protein
| Structure | KRas G12D mutant: % inh. | KRas G12D mutant + SOS: % inh. | Rac-1: % inh. | Rac-1 + SOS: % inh. | Rho-A: % inh. | Rho-A + SOS: % inh. |
|---|---|---|---|---|---|---|
| 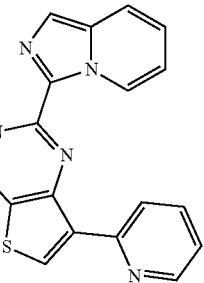 | D | C | D | D | D | D |
| 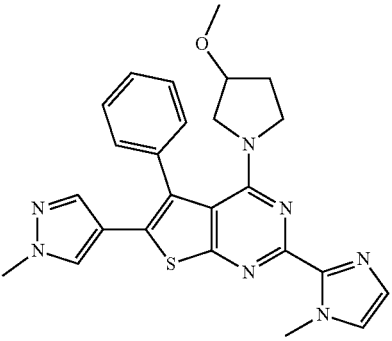 HCl | B | D | 0 | 0 | B | D |
| 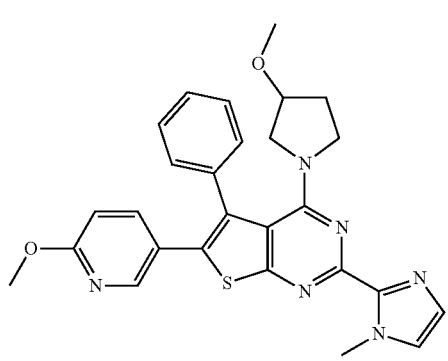 HCl | B | C | 0 | 0 | C | B |
| 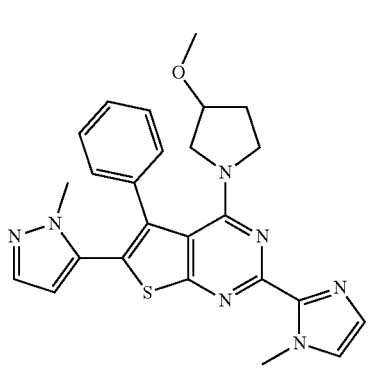 HCl | C | C | B | A | C | D |

TABLE 8-continued

% Inhibition at 20 μM of KRas G12D mutant, Rac-1 and Rho-A protein

| Structure | KRas G12D mutant: % inh. | KRas G12D mutant + SOS: % inh. | Rac-1: % inh. | Rac-1 + SOS: % inh. | Rho-A: % inh. | Rho-A + SOS: % inh. |
|---|---|---|---|---|---|---|
| (structure with methoxy phenyl, fluoro-methoxyphenyl, thienopyrimidine, methylimidazole, pyrrolidine-methoxy; HCl) | C | C | A | 0 | A | C |
| (structure with hydroxy thienopyrimidine, pyridine, imidazole-methoxybenzyl) | A | 0 | A | A | 0 | 0 |
| (structure with methoxy-isothiazole, phenyl, thienopyrimidine, methylimidazole, methoxy-pyrrolidine; HCl) | B | C | B | B | A | A |
| (structure with methoxyethyl-pyrazole, thienopyrimidine, methylimidazole, phenyl, methoxy-pyrrolidine; HCl) | C | C | C | C | B | B |

TABLE 8-continued
% Inhibition at 20 μM of KRas G12D mutant, Rac-1 and Rho-A protein
| Structure | KRas G12D mutant: % inh. | KRas G12D mutant + SOS: % inh. | Rac-1: % inh. | Rac-1 + SOS: % inh. | Rho-A: % inh. | Rho-A + SOS: % inh. |
|---|---|---|---|---|---|---|
| 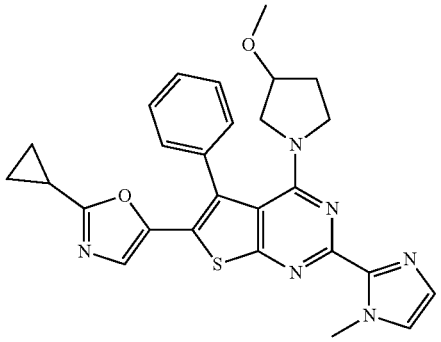 HCl | C | C | A | A | B | C |
| 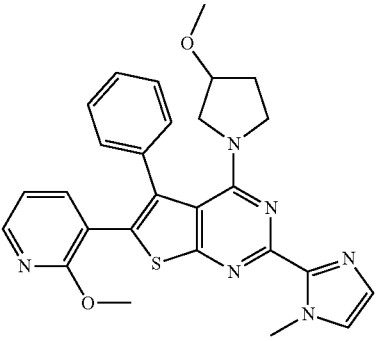 HCl | C | C | B | C | C | C |
| 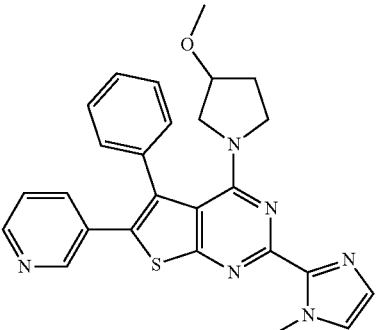 HCl | C | C | D | C | C | C |

TABLE 8-continued
% Inhibition at 20 μM of KRas G12D mutant, Rac-1 and Rho-A protein
| Structure | KRas G12D mutant: % inh. | KRas G12D mutant + SOS: % inh. | Rac-1: % inh. | Rac-1 + SOS: % inh. | Rho-A: % inh. | Rho-A + SOS: % inh. |
|---|---|---|---|---|---|---|
| 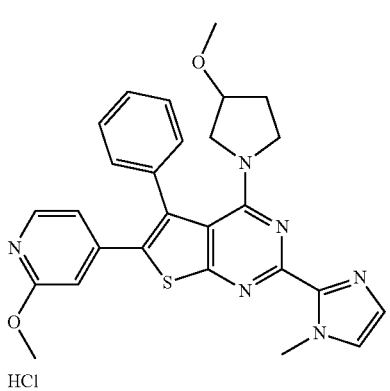 [SMILES: COc1cc(-c2sc3nc(-c4nccn4C)nc(N4CCC(OC)C4)c3c2-c2ccccc2)ccn1 ; Cl] | C | C | B | A | A | B |
| 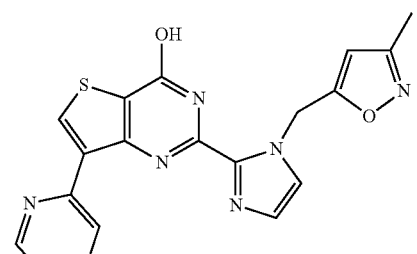 | C | B | C | C | A | B |
| 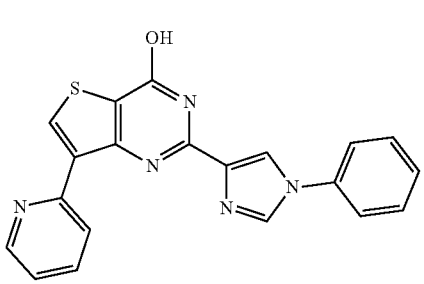 [SMILES: Oc1nc(-c2cn(-c3ccccc3)cn2)nc2c(-c3ccccn3)csc12] | A | A | B | A | 0 | B |
| 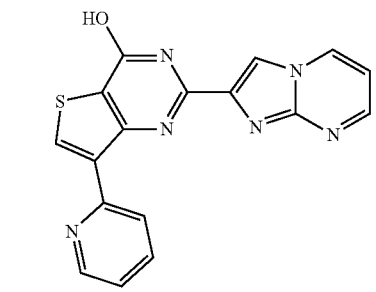 [SMILES: Oc1nc(-c2cn3cccnc3n2)nc2c(-c3ccccn3)csc12] | A | A | 0 | 0 | B | A |

TABLE 8-continued

% Inhibition at 20 μM of KRas G12D mutant, Rac-1 and Rho-A protein

| Structure | KRas G12D mutant: % inh. | KRas G12D mutant + SOS: % inh. | Rac-1: % inh. | Rac-1 + SOS: % inh. | Rho-A: % inh. | Rho-A + SOS: % inh. |
| --- | --- | --- | --- | --- | --- | --- |
| *structure* | C | C | C | D | 0 | C |
| *structure* | D | C | D | D | B | C |
| *structure* | D | C | D | C | C | C |
| *structure* | D | C | D | D | C | C |
| *structure* | D | C | C | D | C | D |

TABLE 8-continued

% Inhibition at 20 μM of KRas G12D mutant, Rac-1 and Rho-A protein

| Structure | KRas G12D mutant: % inh. | KRas G12D mutant + SOS: % inh. | Rac-1: % inh. | Rac-1 + SOS: % inh. | Rho-A: % inh. | Rho-A + SOS: % inh. |
|---|---|---|---|---|---|---|
| | C | C | B | B | B | B |
| | C | C | B | A | B | B |
| | B | B | B | B | 0 | 0 |
| | B | A | B | B | 0 | D |

TABLE 8-continued

% Inhibition at 20 μM of KRas G12D mutant, Rac-1 and Rho-A protein

| Structure | KRas G12D mutant: % inh. | KRas G12D mutant + SOS: % inh. | Rac-1: % inh. | Rac-1 + SOS: % inh. | Rho-A: % inh. | Rho-A + SOS: % inh. |
|---|---|---|---|---|---|---|
| | B | B | A | B | B | 0 |
| (+/- trans) | B | B | B | B | 0 | D |
| (+/- cis) | A | C | C | C | C | D |
| | B | A | A | B | B | 0 |

TABLE 8-continued

% Inhibition at 20 μM of KRas G12D mutant, Rac-1 and Rho-A protein

| Structure | KRas G12D mutant: % inh. | KRas G12D mutant + SOS: % inh. | Rac-1: % inh. | Rac-1 + SOS: % inh. | Rho-A: % inh. | Rho-A + SOS: % inh. |
|---|---|---|---|---|---|---|
| | A | A | B | B | 0 | C |
| | A | A | B | B | 0 | A |
| | A | B | A | A | 0 | B |
| 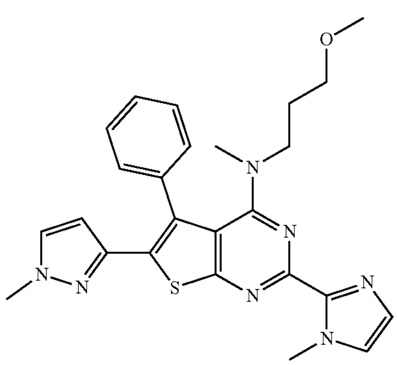 [SMILES: COCCCN(C)c1nc(-c2nccn2C)nc2sc(-c3ccn(C)n3)c(-c3ccccc3)c12] | C | B | B | B | A | 0 |

TABLE 8-continued

% Inhibition at 20 µM of KRas G12D mutant, Rac-1 and Rho-A protein

| Structure | KRas G12D mutant: % inh. | KRas G12D mutant + SOS: % inh. | Rac-1: % inh. | Rac-1 + SOS: % inh. | Rho-A: % inh. | Rho-A + SOS: % inh. |
|---|---|---|---|---|---|---|
| *(structure)* | A | B | A | B | 0 | 0 |
| *(structure)* | A | C | 0 | A | 0 | A |
| *(structure)* | 0 | A | 0 | 0 | 0 | B |
| *(structure)* | 0 | A | 0 | 0 | A | A |

TABLE 8-continued

% Inhibition at 20 μM of KRas G12D mutant, Rac-1 and Rho-A protein

| Structure | KRas G12D mutant: % inh. | KRas G12D mutant + SOS: % inh. | Rac-1: % inh. | Rac-1 + SOS: % inh. | Rho-A: % inh. | Rho-A + SOS: % inh. |
|---|---|---|---|---|---|---|
| (structure) | 0 | A | 0 | 0 | A | C |
| (structure) | B | A | A | B | A | C |
| (structure) | A | D | C | B | C | C |
| (structure) | B | D | B | B | 0 | 0 |

TABLE 8-continued

% Inhibition at 20 μM of KRas G12D mutant, Rac-1 and Rho-A protein

| Structure | KRas G12D mutant: % inh. | KRas G12D mutant + SOS: % inh. | Rac-1: % inh. | Rac-1 + SOS: % inh. | Rho-A: % inh. | Rho-A + SOS: % inh. |
| --- | --- | --- | --- | --- | --- | --- |
| (structure) | A | C | B | C | B | B |
| (structure) | C | D | A | B | 0 | 0 |
| (structure) | B | D | A | B | 0 | 0 |
| (structure) | A | B | A | A | B | A |

TABLE 8-continued

% Inhibition at 20 μM of KRas G12D mutant, Rac-1 and Rho-A protein

| Structure | KRas G12D mutant: % inh. | KRas G12D mutant + SOS: % inh. | Rac-1: % inh. | Rac-1 + SOS: % inh. | Rho-A: % inh. | Rho-A + SOS: % inh. |
|---|---|---|---|---|---|---|
| 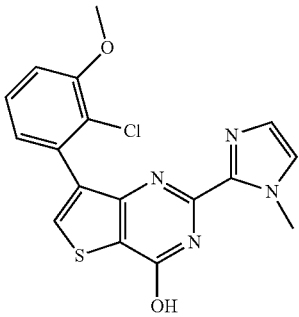 [SMILES: COc1cccc(-c2csc3c(O)nc(-c4nccn4C)nc23)c1Cl] | A | A | A | B | A | A |

0 = 0% inhibition, A = 1-25% inhibition, B = 26-50% inhibition, C = 51-75% inhibition, D = 76-100% inhibition.

TABLE 8A

% Inhibition at 20 μM of KRas G12D mutant, Rac-1, Rho-A, and HRas wild type protein,

| Compound | KRas G12D mutant: % inh. | KRas G12D mutant + SOS: % inh. | Rac-1: % inh. | Rac-1 + SOS: % inh. | Rho-A: % inh. | Rho-A + SOS: % inh. | HRas wild type: % inh. | HRas wild type + SOS: % inh. |
|---|---|---|---|---|---|---|---|---|
| 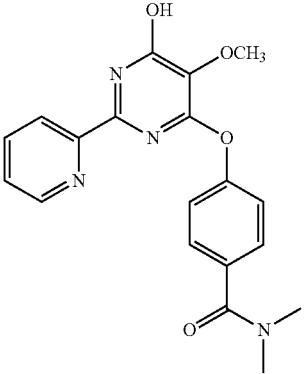 | C | B | C | C | C | C | | |
| 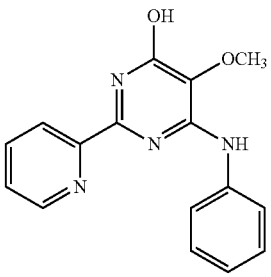 [SMILES: COc1c(O)nc(-c2ccccn2)nc1Nc1ccccc1] | B | B | C | C | C | C | | |

TABLE 8A-continued
% Inhibition at 20 μM of KRas G12D mutant, Rac-1, Rho-A, and HRas wild type protein.
| Compound | KRas G12D mutant: % inh. | KRas G12D mutant + SOS: % inh. | Rac-1: % inh. | Rac-1 + SOS: % inh. | Rho-A: % inh. | Rho-A + SOS: % inh. | HRas wild type % inh. | HRAs wild type + SOS: % inh. |
|---|---|---|---|---|---|---|---|---|
| 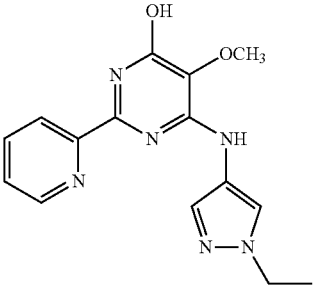 [SMILES: CCn1cc(Nc2nc(-c3ccccn3)nc(O)c2OC)cn1] | B | B | C | D | C | C | | |
| 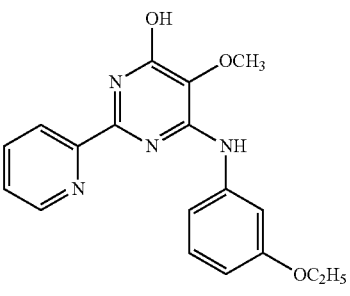 [SMILES: CCOc1cccc(Nc2nc(-c3ccccn3)nc(O)c2OC)c1] | C | B | D | D | C | C | | |
| 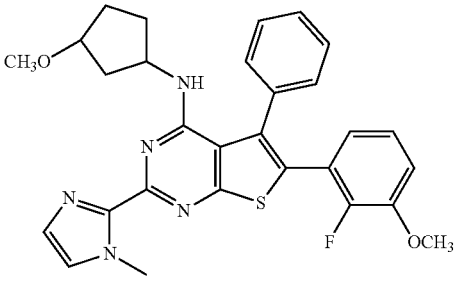 | B | C | C | C | C | C | D | D |
| 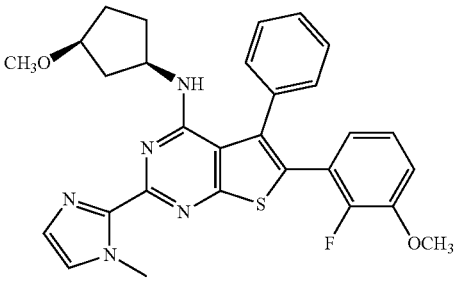 (+/−) | C | C | | | | | | |
| 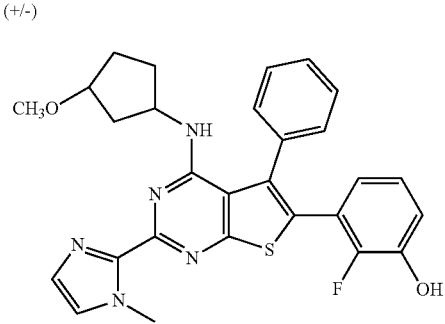 | B | C | C | B | A | A | B | D |

TABLE 8A-continued

% Inhibition at 20 μM of KRas G12D mutant, Rac-1, Rho-A, and HRas wild type protein,

| Compound | KRas G12D mutant: % inh. | KRas G12D mutant + SOS: % inh. | Rac-1: % inh. | Rac-1 + SOS: % inh. | Rho-A: % inh. | Rho-A + SOS: % inh. | HRas wild type % inh. | HRas wild type + SOS: % inh. |
|---|---|---|---|---|---|---|---|---|
| [structure] | A | A | B | C | B | B | | |
| [structure] (+/-) | D | D | | | | | | |
| [structure] | B | B | C | C | B | A | B | D |
| [structure] (+/-) | C | C | | | | | | |

TABLE 8A-continued

% Inhibition at 20 μM of KRas G12D mutant, Rac-1, Rho-A, and HRas wild type protein,

| Compound | KRas G12D mutant: % inh. | KRas G12D mutant + SOS: % inh. | Rac-1: % inh. | Rac-1 + SOS: % inh. | Rho-A: % inh. | Rho-A + SOS: % inh. | HRas wild type: % inh. | HRas wild type + SOS: % inh. |
|---|---|---|---|---|---|---|---|---|
| (structure) | A | C | B | B | B | B | | |
| (structure) | B | C | C | C | C | C | | |
| (structure) | C | D | D | D | D | D | | |
| (structure) | D | C | C | C | D | D | | |

TABLE 8A-continued

% Inhibition at 20 μM of KRas G12D mutant, Rac-1, Rho-A, and HRas wild type protein,

| Compound | KRas G12D mutant: % inh. | KRas G12D mutant + SOS: % inh. | Rac-1: % inh. | Rac-1 + SOS: % inh. | Rho-A: % inh. | Rho-A + SOS: % inh. | HRas wild type % inh. | HRas wild type + SOS: % inh. |
|---|---|---|---|---|---|---|---|---|
| (structure; +/-) | C | C | | | | | | |
| (structure; +/-) | B | C | C | C | C | B | | |
| (structure; +/-) | A | B | | | | | | |
| (structure; +/-) | B | B | | | | | | |

TABLE 8A-continued
% Inhibition at 20 μM of KRas G12D mutant, Rac-1, Rho-A, and HRas wild type protein.
| Compound | KRas G12D mutant: % inh. | KRas G12D mutant + SOS: % inh. | Rac-1: % inh. | Rac-1 + SOS: % inh. | Rho-A: % inh. | Rho-A + SOS: % inh. | HRas wild type % inh. | HRas wild type + SOS: % inh. |
|---|---|---|---|---|---|---|---|---|
| 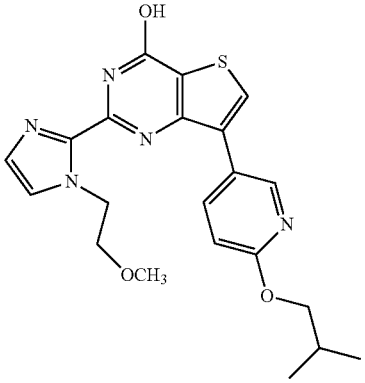 [SMILES: COCCn1ccnc1-c1nc(O)c2scc(-c3ccc(OCC(C)C)nc3)c2n1] | C | C | D | D | D | D | | |
| 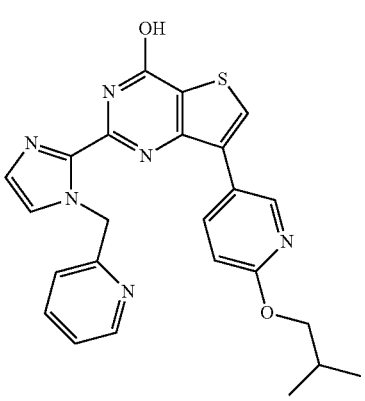 [SMILES: CC(C)COc1ccc(-c2csc3c(O)nc(-c4nccn4Cc4ccccn4)nc23)cn1] | D | C | D | D | D | D | | |
| 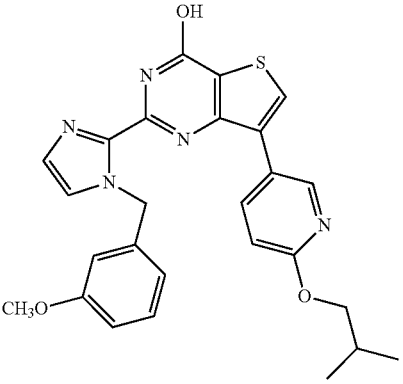 | C | C | D | D | D | C | | |
| 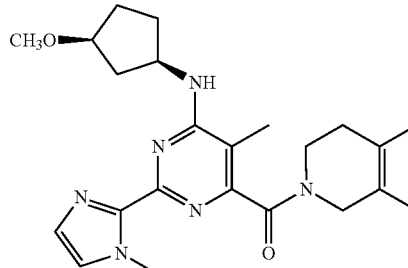 | B | B | C | C | C | D | | |

TABLE 8A-continued
% Inhibition at 20 μM of KRas G12D mutant, Rac-1, Rho-A, and HRas wild type protein,
| Compound | KRas G12D mutant: % inh. | KRas G12D mutant + SOS: % inh. | Rac-1: % inh. | Rac-1 + SOS: % inh. | Rho-A: % inh. | Rho-A + SOS: % inh. | HRas wild type % inh. | HRas wild type + SOS: % inh. |
|---|---|---|---|---|---|---|---|---|
| 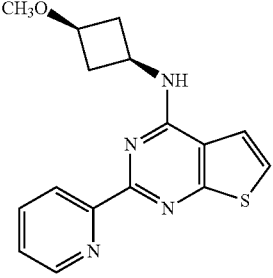 | C | C | D | D | D | C | C | D |
| 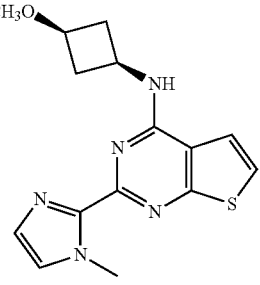 | D | D | D | D | D | B | C | D |
| 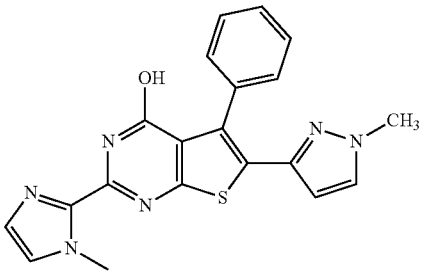 [SMILES: Cn1ccc(-c2sc3nc(-c4nccn4C)nc(O)c3c2-c2ccccc2)n1] | B | B | B | B | B | B | | |
| 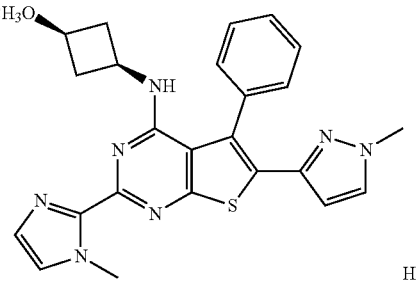 | B | C | C | D | C | C | B | D |
| 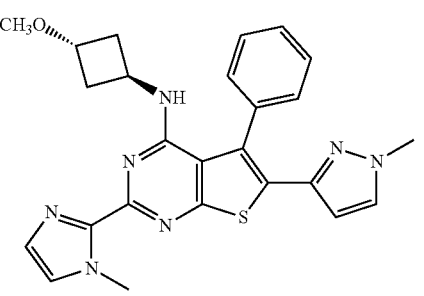 | B | C | C | C | C | C | B | D |

TABLE 8A-continued

% Inhibition at 20 μM of KRas G12D mutant, Rac-1, Rho-A, and HRas wild type protein.

| Compound | KRas G12D mutant: % inh. | KRas G12D mutant + SOS: % inh. | Rac-1: % inh. | Rac-1 + SOS: % inh. | Rho-A: % inh. | Rho-A + SOS: % inh. | HRas wild type % inh. | HRAs wild type + SOS: % inh. |
|---|---|---|---|---|---|---|---|---|
| [structure with (CH₃)₂N-CH₂CH₂-O-CH₂CH₂-NH- substituent] | B | C | C | C | C | C | B | D |
| [structure with HO-cyclobutyl-NH- substituent] | 0 | 0 | A | A | B | B | C | A |
| [structure with HO-cyclopentyl-NH- substituent, (+/-)] | 0 | 0 | A | A | B | A | C | A |
| [structure with CH₃O-cyclobutyl-NH- substituent, NH-imidazole] | B | B | B | B | B | B | | |
| [structure with CH₃O-cyclopentyl-NH- substituent, (+/-), NH-imidazole] | B | C | C | C | C | B | | |

TABLE 8A-continued

% Inhibition at 20 μM of KRas G12D mutant, Rac-1, Rho-A, and HRas wild type protein.

| Compound | KRas G12D mutant: % inh. | KRas G12D mutant + SOS: % inh. | Rac-1: % inh. | Rac-1 + SOS: % inh. | Rho-A: % inh. | Rho-A + SOS: % inh. | HRas wild type % inh. | HRAs wild type + SOS: % inh. |
|---|---|---|---|---|---|---|---|---|
| (structure) (+/−) | C | C | C | C | D | D | | |
| (structure) | B | A | B | B | B | B | | |
| (structure) | C | C | C | C | D | D | | |
| (structure) (+/−) | B | C | D | D | D | D | | |
| (structure) | D | D | D | C | C | C | | |

TABLE 8A-continued

% Inhibition at 20 μM of KRas G12D mutant, Rac-1, Rho-A, and HRas wild type protein,

| Compound | KRas G12D mutant: % inh. | KRas G12D mutant + SOS: % inh. | Rac-1: % inh. | Rac-1 + SOS: % inh. | Rho-A: % inh. | Rho-A + SOS: % inh. | HRas wild type % inh. | HRas wild type + SOS: % inh. |
|---|---|---|---|---|---|---|---|---|
| [structure] | C | D | D | D | D | D | | |
| [structure] | D | D | D | C | D | C | | |
| [structure] (+/-) | C | C | C | C | D | D | C | D |
| [structure] | C | C | D | D | C | C | | |
| [structure] | C | C | C | D | C | C | | |

TABLE 8A-continued
% Inhibition at 20 μM of KRas G12D mutant, Rac-1, Rho-A, and HRas wild type protein,
| Compound | KRas G12D mutant: % inh. | KRas G12D mutant + SOS: % inh. | Rac-1: % inh. | Rac-1 + SOS: % inh. | Rho-A: % inh. | Rho-A + SOS: % inh. | HRas wild type: % inh. | HRas wild type + SOS: % inh. |
|---|---|---|---|---|---|---|---|---|
| 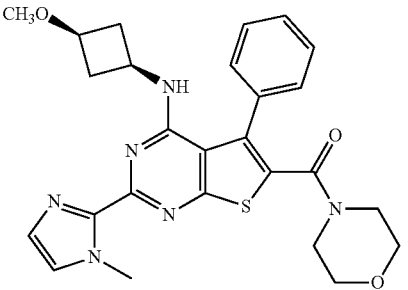 | C | C | C | D | C | C | | |
| (+/-) 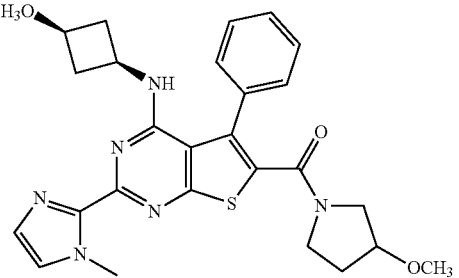 | C | C | D | C | B | D | | |
| 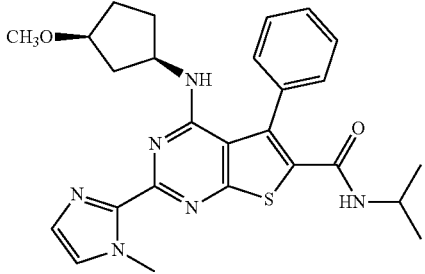 (+/-) | D | D | D | D | D | D | | |
| (+/-) 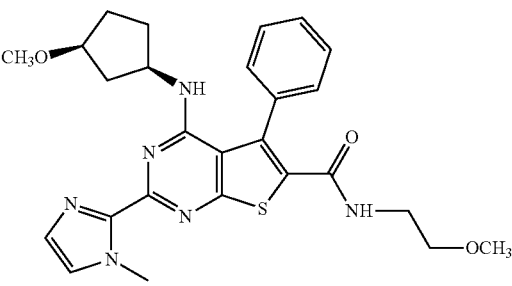 | D | D | D | D | D | D | | |

TABLE 8A-continued
% Inhibition at 20 μM of KRas G12D mutant, Rac-1, Rho-A, and HRas wild type protein.
| Compound | KRas G12D mutant: % inh. | KRas G12D mutant + SOS: % inh. | Rac-1: % inh. | Rac-1 + SOS: % inh. | Rho-A: % inh. | Rho-A + SOS: % inh. | HRas wild type % inh. | HRas wild type + SOS: % inh. |
|---|---|---|---|---|---|---|---|---|
| 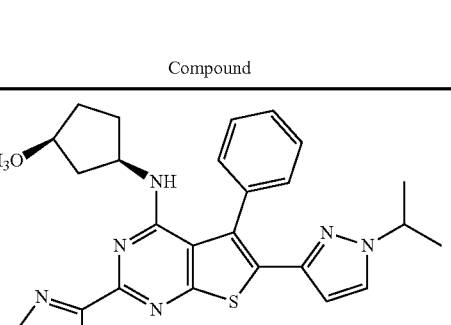 (+/−) | | C | C | D | D | D | D | |
| 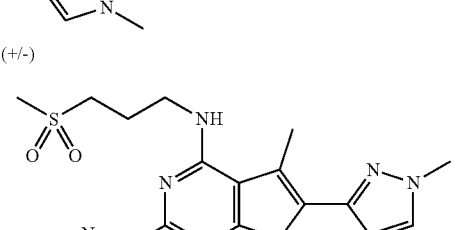 (+/−) | | D | C | D | D | D | D | |
0 = 0% inhibition, A = 1-25% inhibition, B = 26-50% inhibition, C = 51-75% inhibition, D = 76-100% inhibition.

TABLE 9-continued
KRas G12D mutant IC50 (nM) values
| Compound | KRas G12D mutant: IC50 |
|---|---|
| 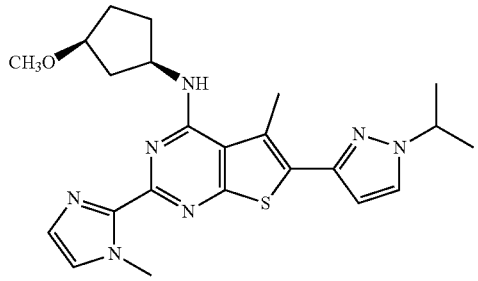<br>(+/−) | J |
| 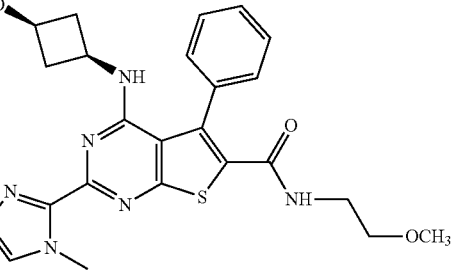 | J |
| 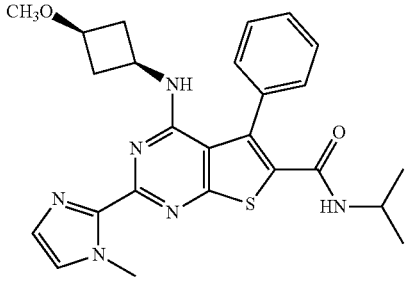 | J |
| 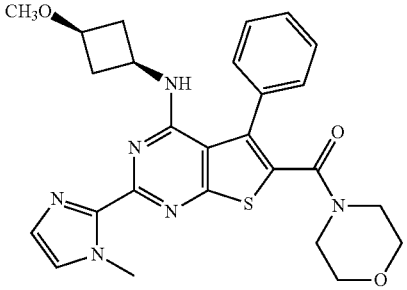 | J |
TABLE 9-continued
KRas G12D mutant IC50 (nM) values
| Compound | KRas G12D mutant: IC50 |
|---|---|
| 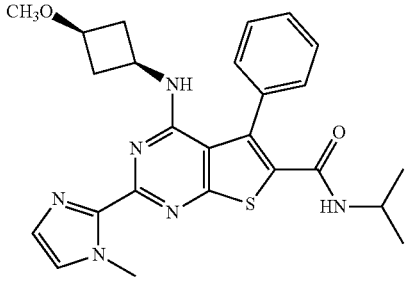<br>(+/−) | J |
| 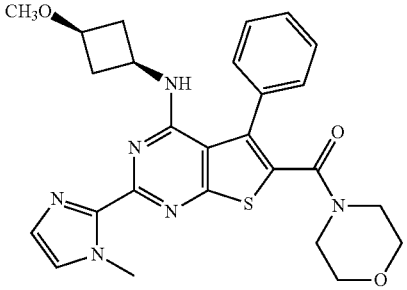<br>(+/−) | J |
| 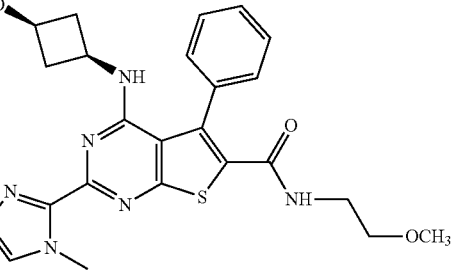<br>(+/−) | J |
| 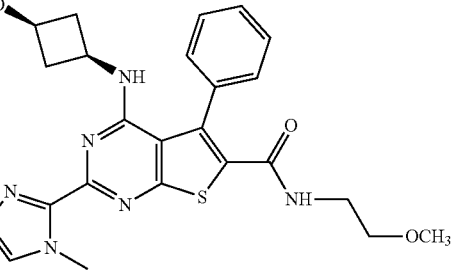<br>(+/−) | J |

TABLE 9-continued

KRas G12D mutant IC$_{50}$ (nM) values

| Compound | KRas G12D mutant: IC50 |
|---|---|
| (structure: 4-((methoxycyclopentyl)amino)-2-(1-methylimidazol-2-yl)-6-(morpholine-4-carbonyl)-5-phenylthieno[2,3-d]pyrimidine) (+/-) | J |

I = >10 uM IC$_{50}$, J = 5-10 uM IC$_{50}$, K = 1-4.99 uM IC$_{50}$, L = <1 uM IC$_{50}$

Example 140

Protocol for Cell-Based Ras-GTP Pulldown Assay

Cell lines: Human NSCLC cells NCI-H1975, and tumor-derived pancreatic cancer cell lines Panc-1, and MIA-PaCa-2, were all purchased from American Type Culture Collection and grown in complete RPMI medium (NCI-H1975) or DMEM-High Glucose (Panc1 and MIA-PaCa-2), supplemented with penicillin (100 U/mL), streptomycin (100 μg/mL), and 10% heat-inactivated FBS at 37° C. in a humidified incubator with 5% CO$_2$.

Method: Cells were plated at 2·10$^6$ cells/well density in a 6-well plate, allowed 3 hours to adhere to the plate, then starved in the appropriate medium in the presence of 0.5% FBS overnight. The small molecules to be tested were added to the cells in the final concentration of 10 μM in the presence of 0.3% DMSO for 6 hours incubation at 37° C. For IC$_{50}$ value determination, serial dilutions of compounds were added to cells under the same conditions. Next, cells were stimulated with 5 ng/mL EGF for 5 minutes, rinsed with ice-cold PBS and then lysed with 500 μL of lysis/binding/wash buffer (25 mM Tris-HCl, pH 7.2, 150 mM NaCl, 5 mM MgCl$_2$, 5% glycerol, 1% NP40) from Active Ras Detection kit (Cell signaling Technology, #8821) supplemented with Halt™ Protease & Phosphatase Inhibitor Cocktail (Thermo Scientific). To account for significant differences in cell number due to the treatment, a small sample of lysate was saved for protein quantification and the rest of the lysate was snap frozen. Protein concentration was assessed by BCA protein assay (Thermo Scientific). To ensure that equal amount of protein undergoes RBD pull-down, lysates were subsequently thawed (at RT) and adjusted to 1 mg/mL with lysis/binding/wash buffer (0.5 mL volume). Equal amounts of lysate were then added to 0.5 mL lysis buffer containing RAF-RBD (1 mL total volume). Lysates were vortexed, incubated for 10 min on ice and subsequently pre-cleared at 14,000 rpm for 5 min at 4° C. 90% of the pre-cleared lysates were subsequently added to pre-washed glutathione agarose beads from Active Ras Detection kit (Cell signaling Technology, #8821) for 1 hour at 4° C. under constant rocking. The beads were subsequently pelleted, washed 3 times with lysis/binding/wash buffer, and eluted for western blotting with 50 μL of 1×SDS-PAGE sample buffer. Level of GTP-bound RAS was determined by western blot.

Western blot protocol: Equal volumes of eluate (25 μL) were separated by 16% SDS-PAGE and transferred to nitrocellulose membranes (Invitrogen by Thermo Fisher Scientific). The membrane was stained with Ponceau S Stain (Boston BioProducts) to verify uniform protein loading. Membranes were blocked with 5% BSA in TBST and then incubated overnight at 4° C. with anti-RAS mouse monoclonal antibody from the Active Ras Detection kit (Cell signaling Technology, #8821), followed by HRP-conjugated secondary antibody (Jackson Immunoresearch, West Grove, PA). Membranes were incubated in Amersham ECL Prime Western Blotting Detection Reagent (GE Healthcare) and bands were visualized using the ChemiDoc MP imaging system (Bio-Rad).

Tables 10 and 11 show inhibition data for selected compounds tested in the cellular assays described above.

TABLE 10

% inhibition of Ras-GTP pulldown assay at 10 μM in the PANC-1, MIA PaCa-2 pancreatic cell lines, and NCI H1975 non-small-cell lung cancer cell

| Compound | PANC-1 | MIA PaCa-2 | H1975 |
|---|---|---|---|
| (structure: thieno[2,3-d]pyrimidine with CH$_3$O-ethyl-NH, phenyl, 1-methylimidazol-2-yl, and 2-chloro-3-methoxyphenyl substituents) | D | D | D |

TABLE 10-continued

% inhibition of Ras-GTP pulldown assay at 10 μM in the PANC-1, MIA PaCa-2 pancreatic cell lines, and NCI H1975 non-small-cell lung cancer cell

| Compound | PANC-1 | MIA PaCa-2 | H1975 |
|---|---|---|---|
| 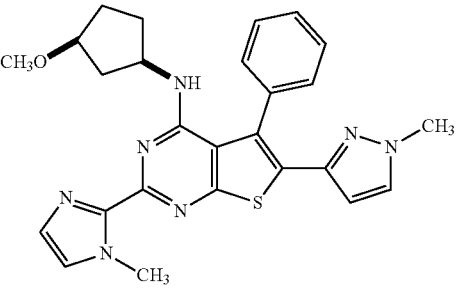 (+/-) | D | D | D |
| 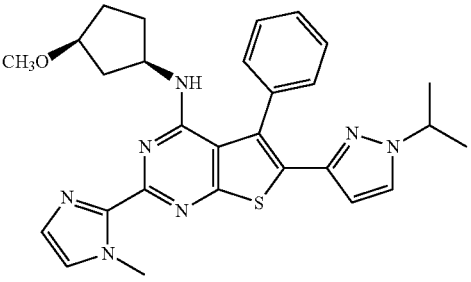 (+/-) |  | D |  |

0 = 0% inhibition, A = 1-25% inhibition, B = 26-50% inhibition, C = 51-75% inhibition, D = 76-100% inhibition.

TABLE 11

Ras-GTP pulldown IC$_{50}$ (nM) values in the PANC-1, MIA PaCa-2 pancreatic cell lines, and NCI H1975 non-small-cell lung cancer cell

| Compound | PANC-1 | MIA PaCa-2 | H1975 |
|---|---|---|---|
| 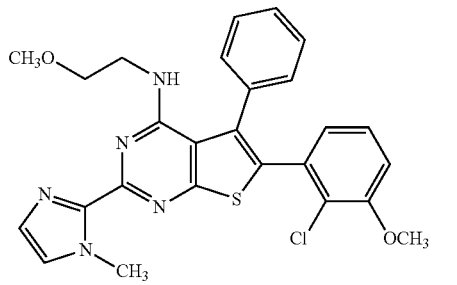 | F | F | E |

TABLE 11-continued

Ras-GTP pulldown IC$_{50}$ (nM) values in the PANC-1, MIA PaCa-2 pancreatic cell lines, and NCI H1975 non-small-cell lung cancer cell

| Compound | PANC-1 | MIA PaCa-2 | H1975 |
|---|---|---|---|
| 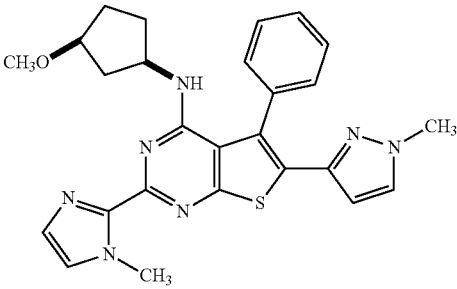 (+/-) | F | E | E |

E = >1000 nM IC$_{50}$, F = 750-1000 nM IC$_{50}$, G = 500-749 nM IC$_{50}$, H = <500 nM IC$_{50}$.

This disclosure is not to be limited in scope by the embodiments disclosed in the examples which are intended as single illustrations of individual aspects, and any methods which are functionally equivalent are within the scope of this disclosure. Indeed, various modifications in addition to those shown and described herein will become apparent to those skilled in the art from the foregoing description. Such modifications are intended to fall within the scope of the appended claims.

Various references such as patents, patent applications, and publications are cited herein, the disclosures of which are hereby incorporated by reference herein in their entireties.

What is claimed is:

1. A compound of Formula IIIA, IIIA1, IIIA2, IIIB, IIIC, IIID, IIIE or IIIF:

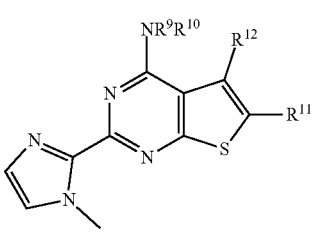

Formula IIIA wherein:

—NR$^9$R$^{10}$ is

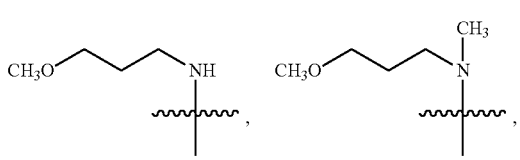

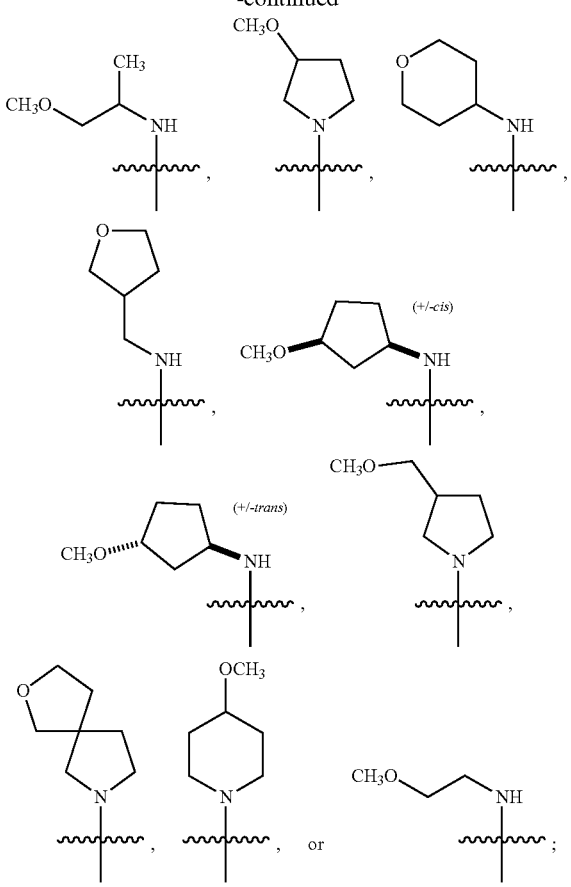

R$^{11}$ is

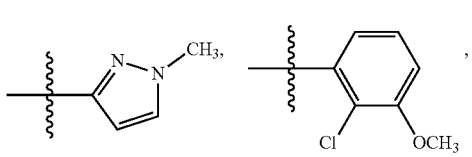

-continued
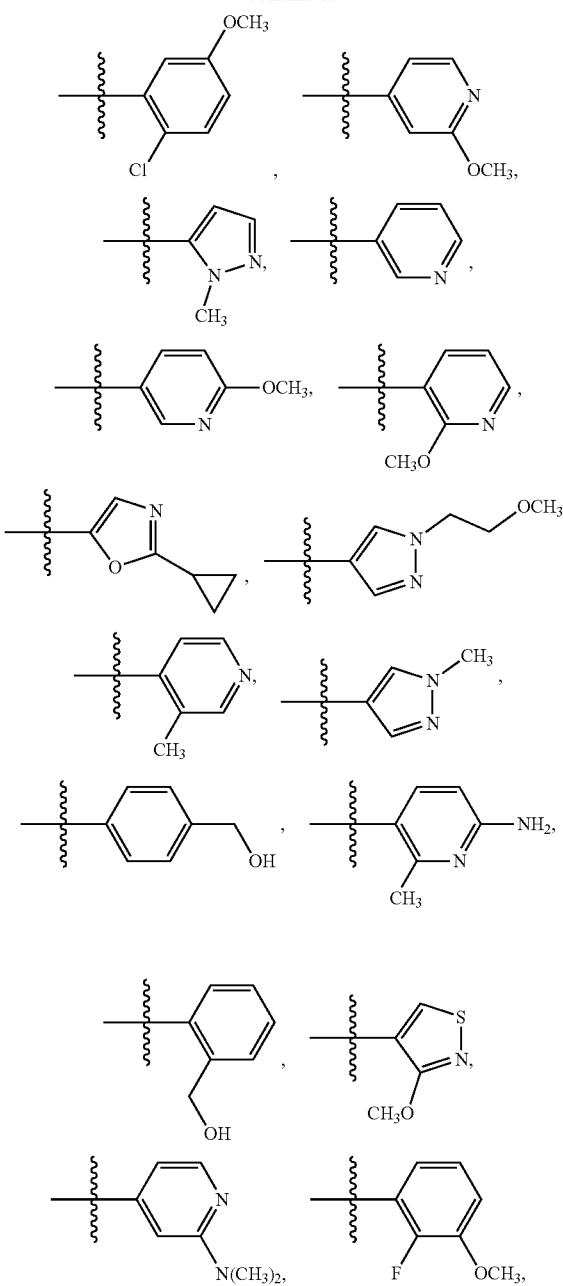
or Br; and
R$^{12}$ is phenyl;
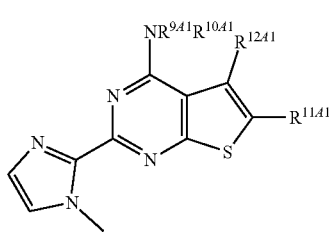
Formula IIIA1
wherein:
—NR$^{9A1}$R$^{10A1}$ is
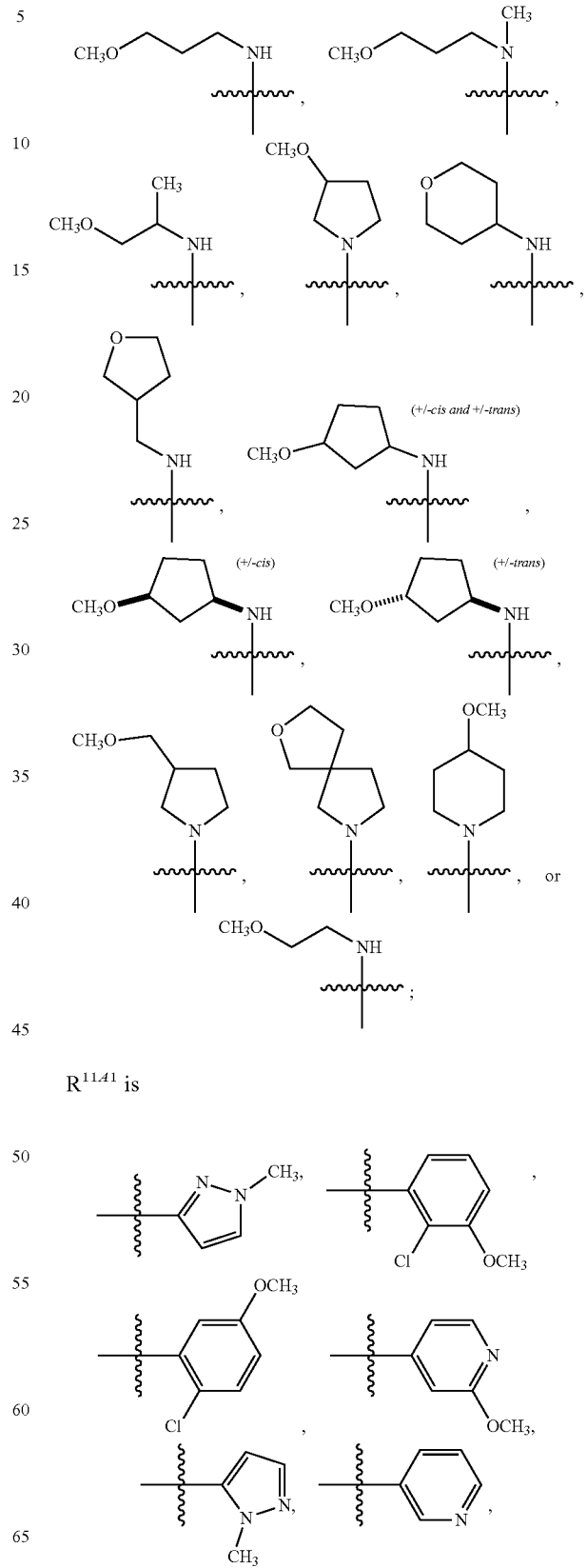
R$^{11A1}$ is -continued
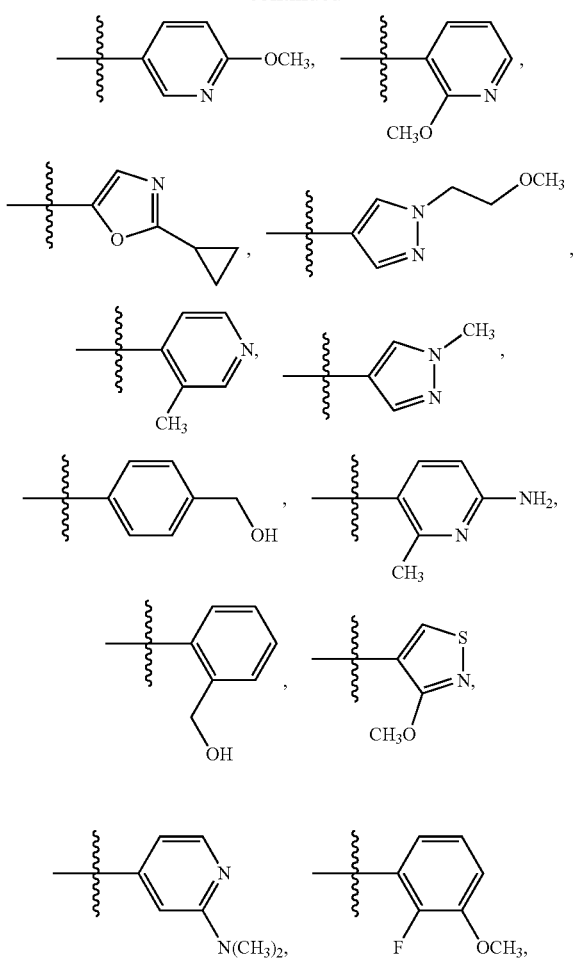
or Br; and
R$^{12A1}$ is phenyl;
Formula IIIA2
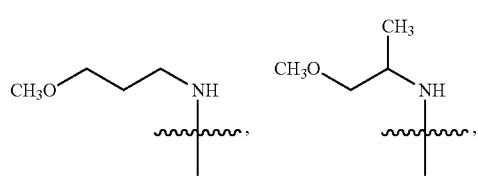
wherein:
—NR$^{9A2}$R$^{10A2}$ is
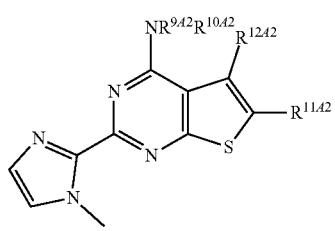
-continued
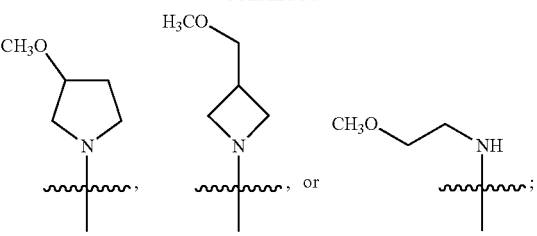
R$^{11A2}$ is
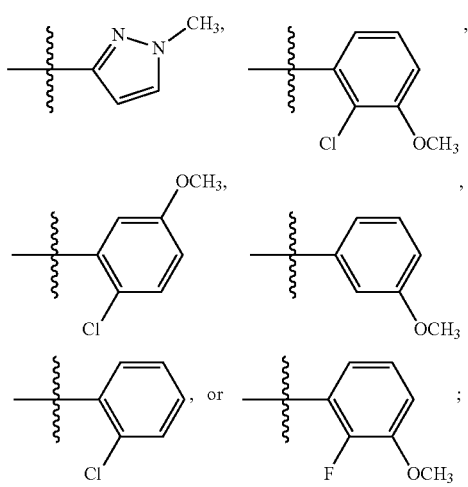
and
R$^{12A2}$ is
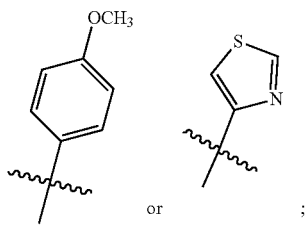 [SMILES: *c1ccc(OC)cc1 ; *c1cscn1]
Formula IIIB
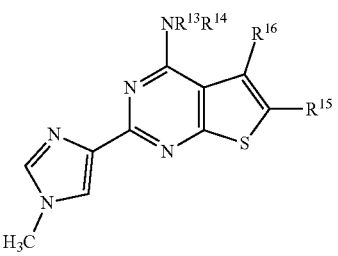

wherein:
—NR¹³R¹⁴ is
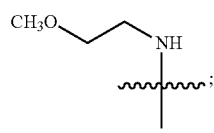
R¹⁵ is
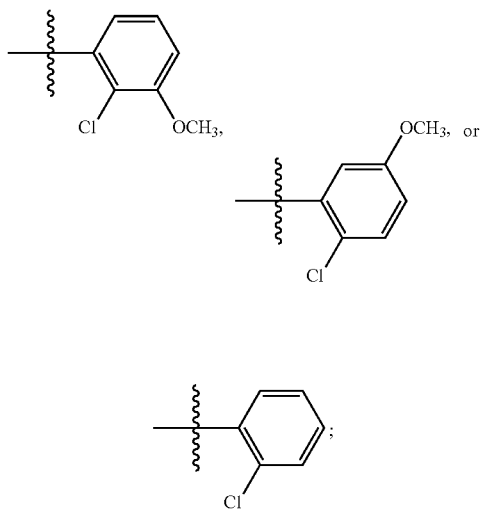
and
R¹⁶ is
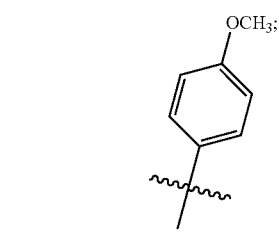 [SMILES: *c1ccc(OC)cc1]
wherein:
—NR¹⁷R¹⁸ is
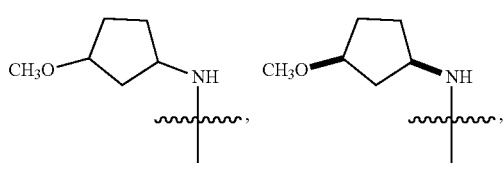
(+/- cis and +/- trans)    (+/- cis)
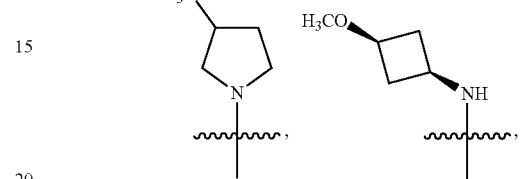
(cis)
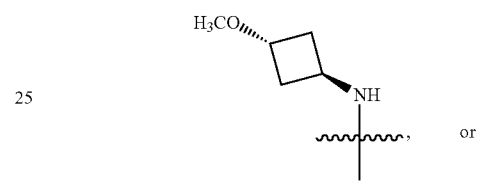
(trans)
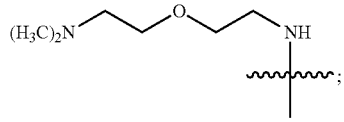
R¹⁹ is
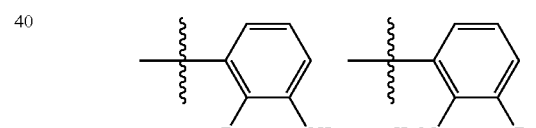
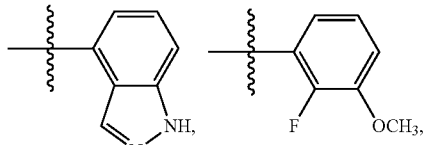
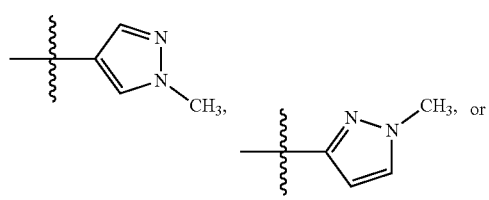
Formula IIIC
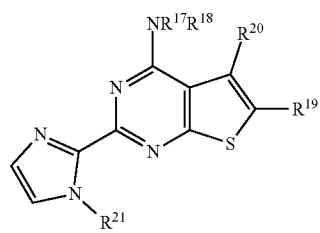

$R^{20}$ is phenyl; and
$R^{21}$ is hydrogen or methyl;
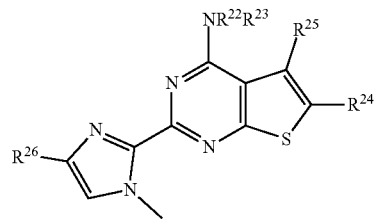
Formula IIID
wherein:
—$NR^{22}R^{23}$ is
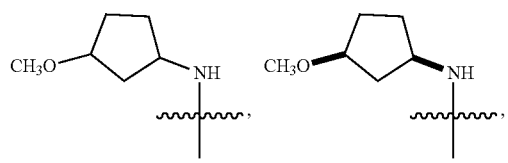
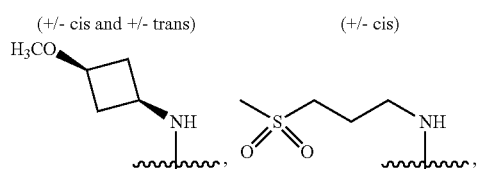
$R^{24}$ is
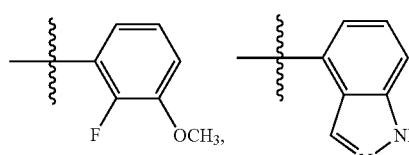
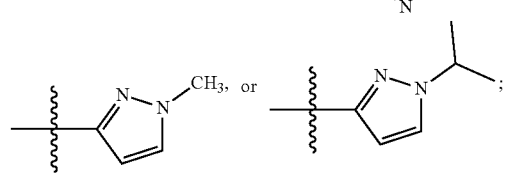
$R^{25}$ is methyl; and
$R^{26}$ is hydrogen or methyl;
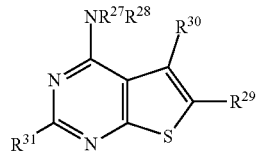
Formula IIIE
wherein:
$NR^{27}R^{28}$ is
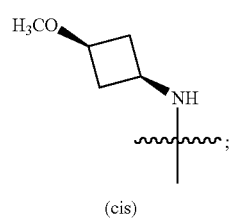
(cis)
$R^{29}$ is hydrogen;
$R^{30}$ is hydrogen; and
$R^{31}$ is
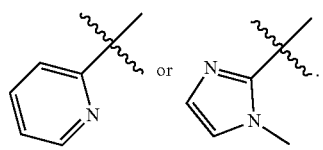
or
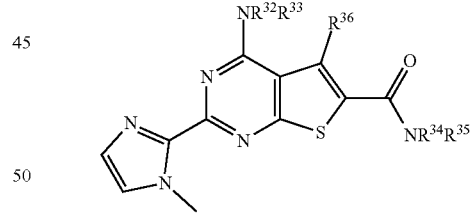
Formula IIIF
wherein:
—$NR^{32}R^{33}$ is
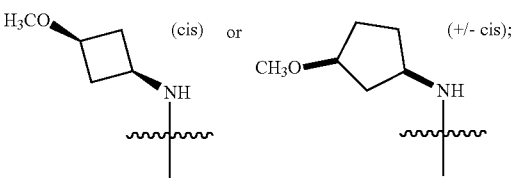

—NR$^{34}$R$^{35}$ is
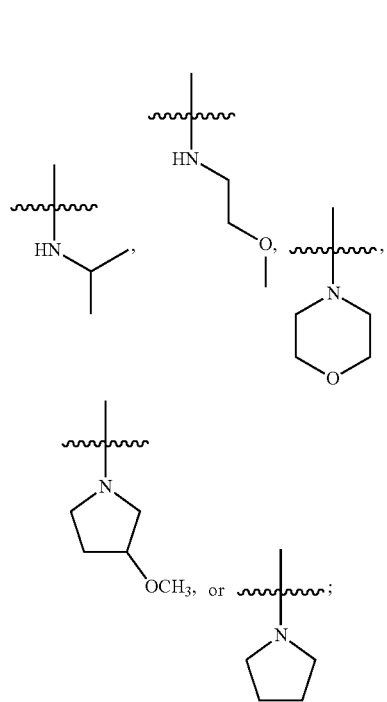
and
R$^{36}$ is phenyl;
or a pharmaceutically acceptable salt thereof.
2. The compound of claim 1, wherein the compound is selected from the group consisting of:
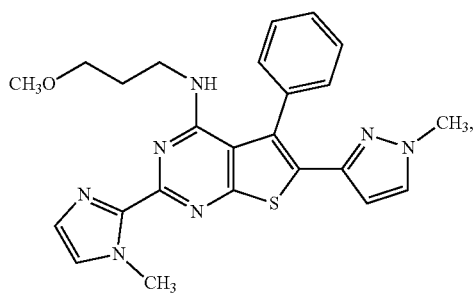
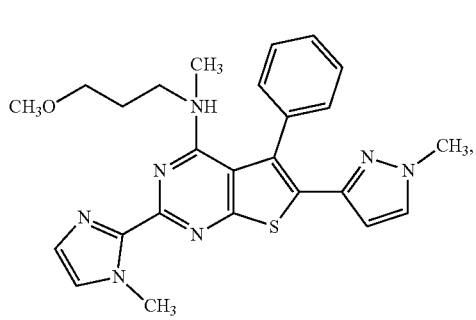
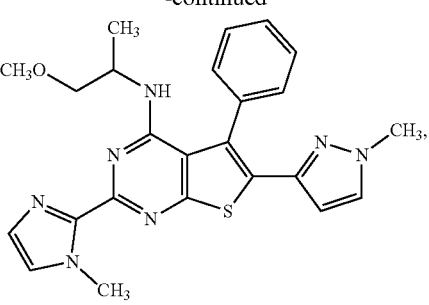
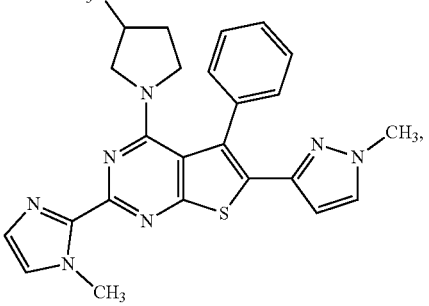
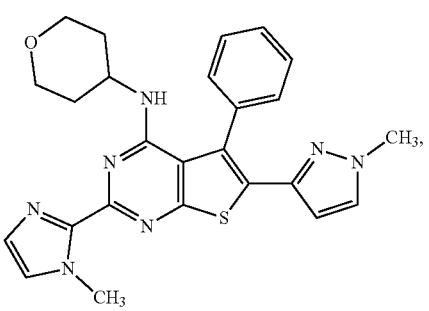
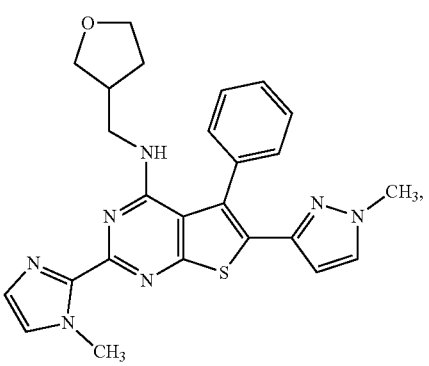
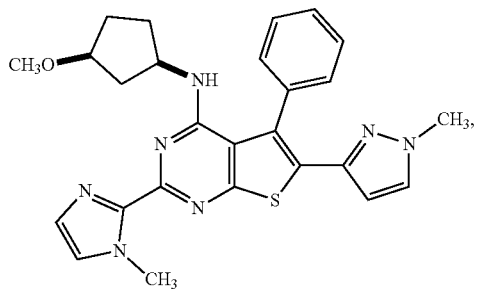
(+/- cis)

675
-continued
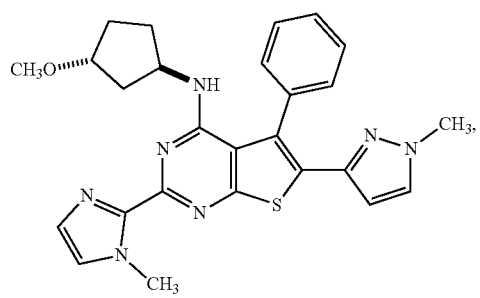
(+/- trans)
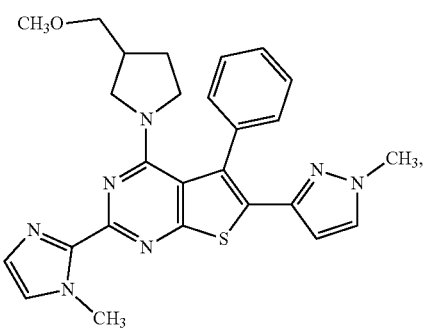
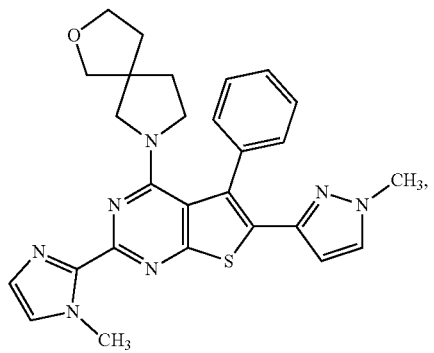
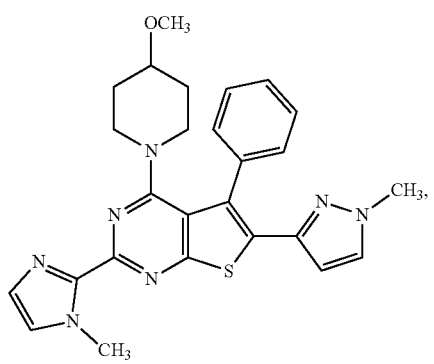
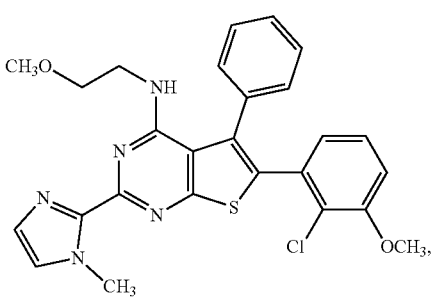
676
-continued
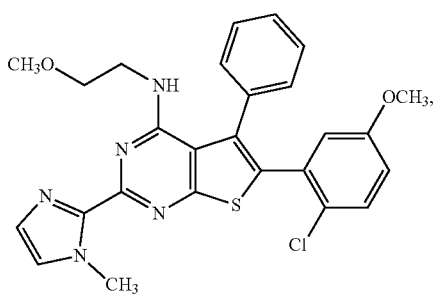
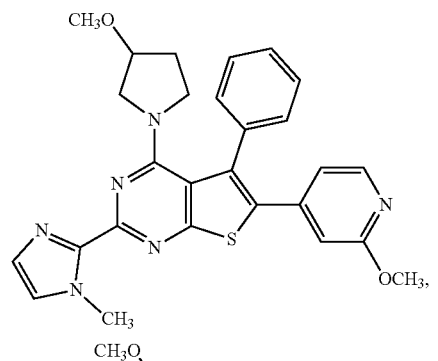
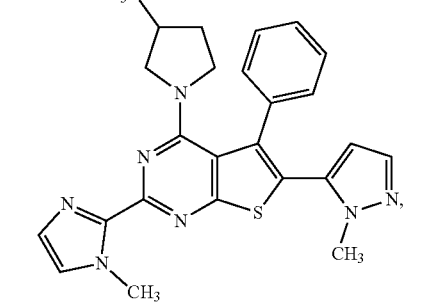
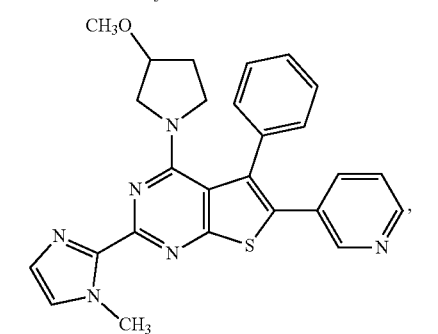
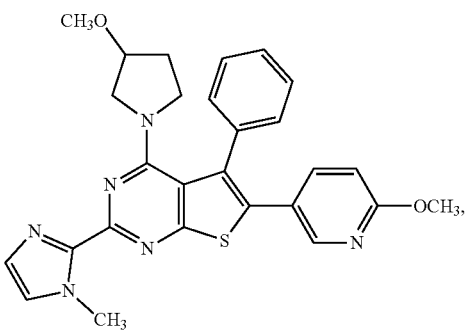

677
-continued
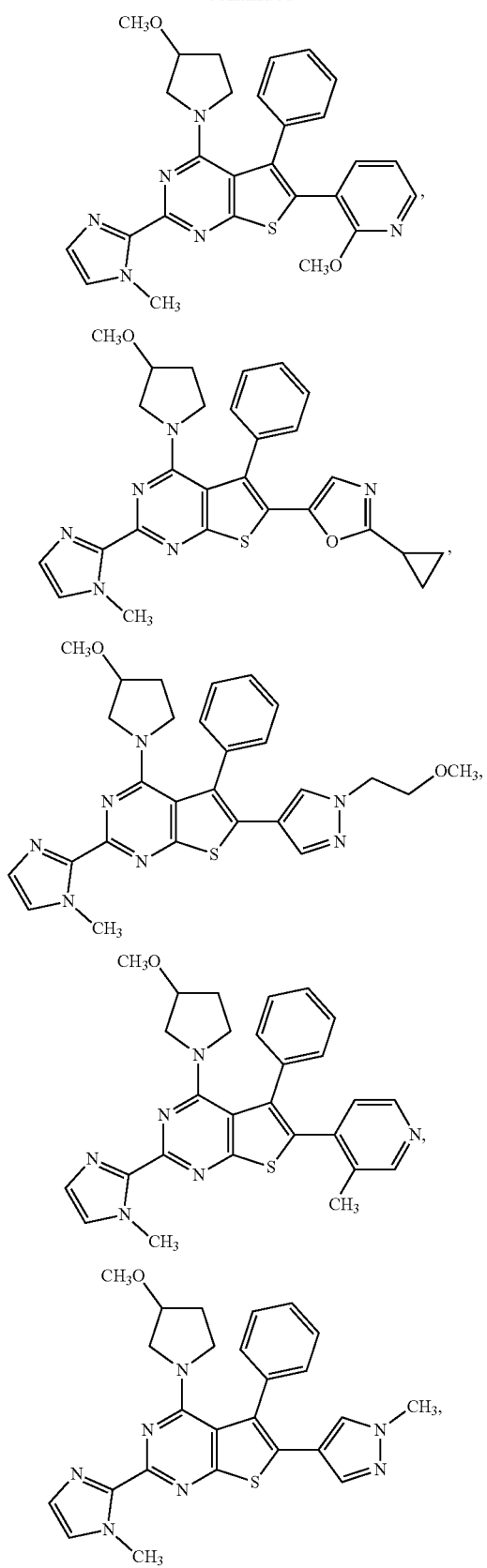
678
-continued
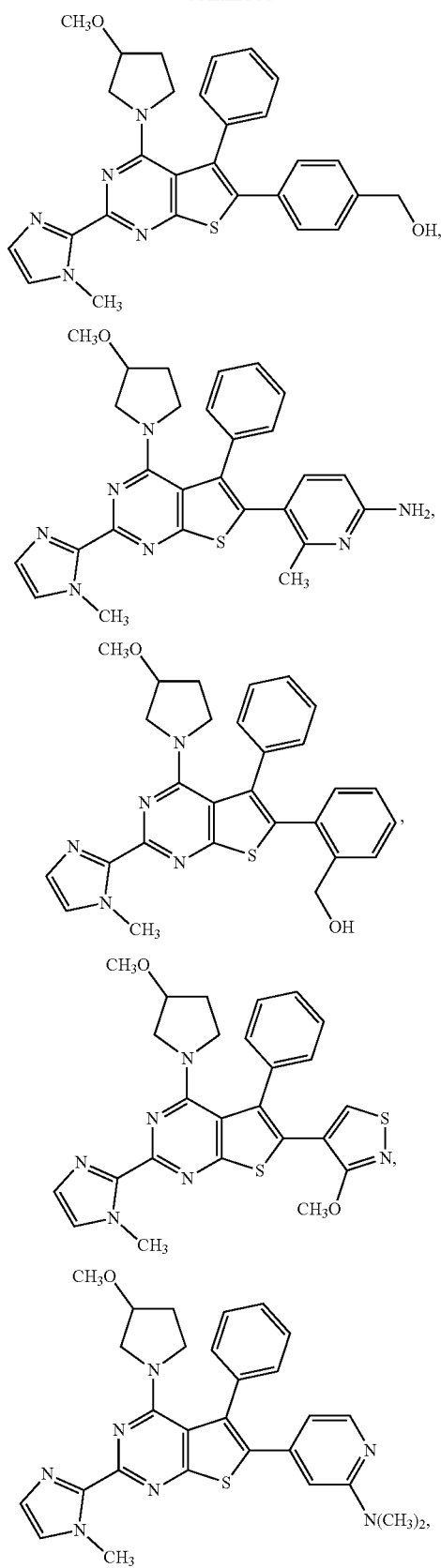

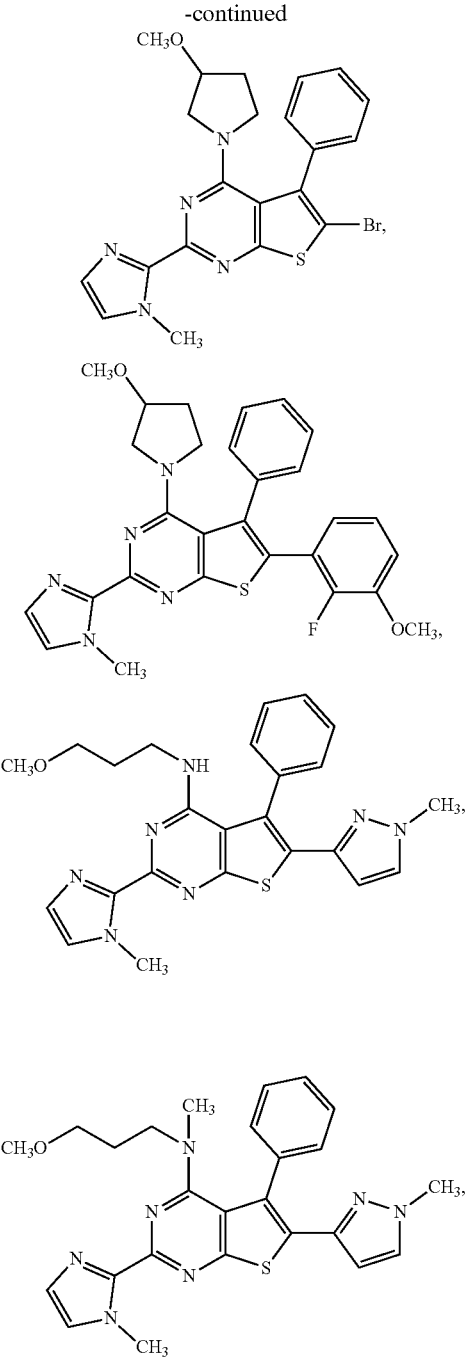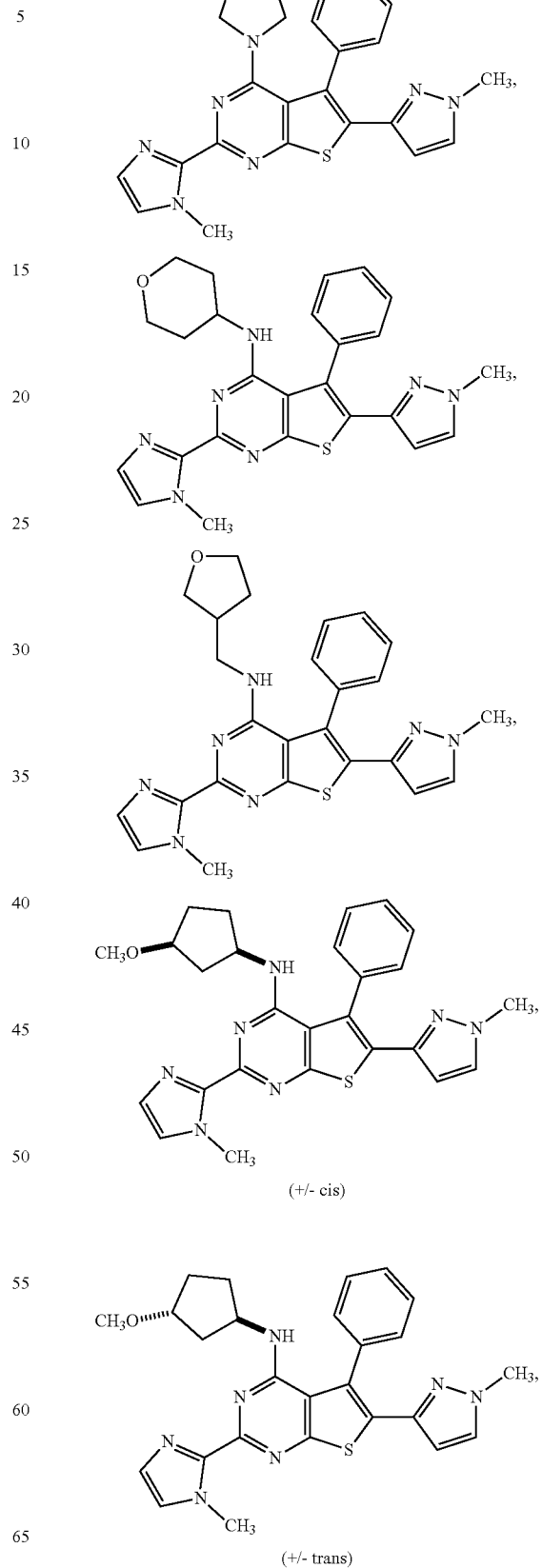

681
-continued
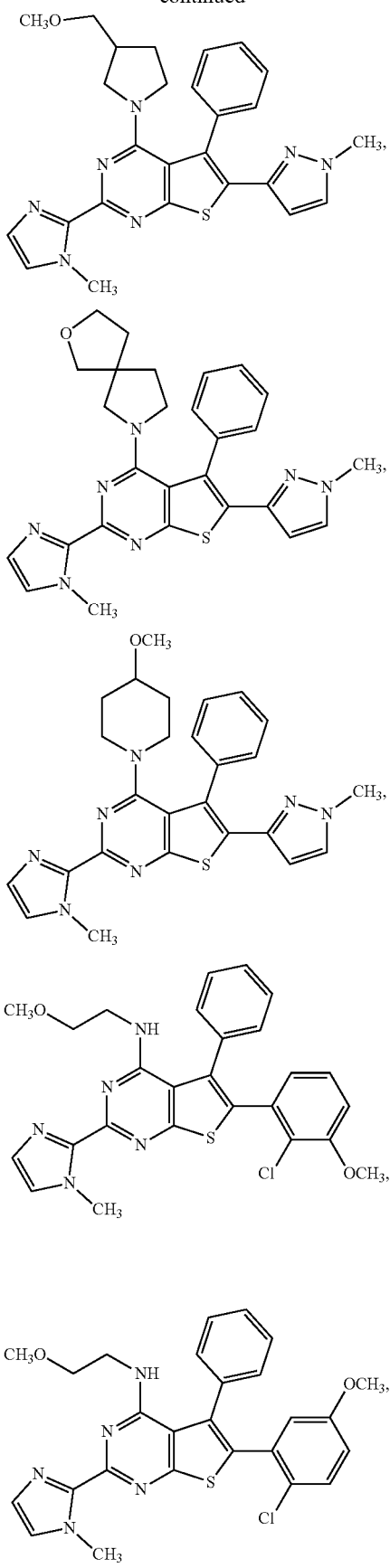
682
-continued
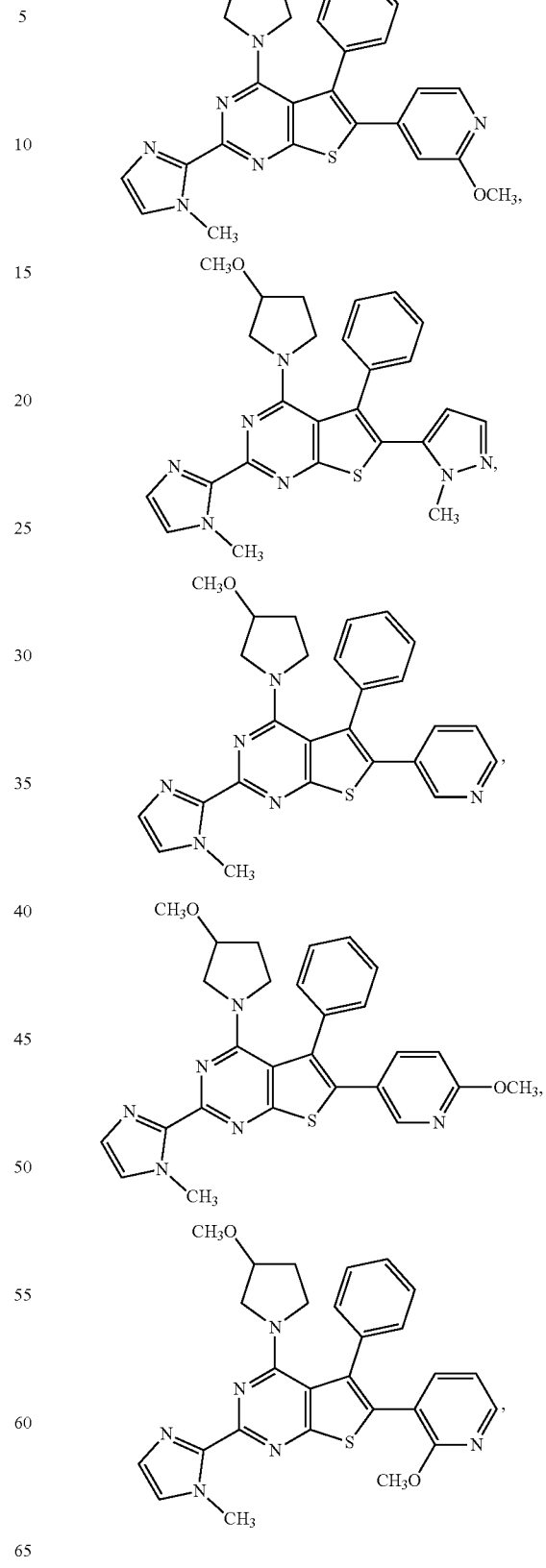

683
-continued
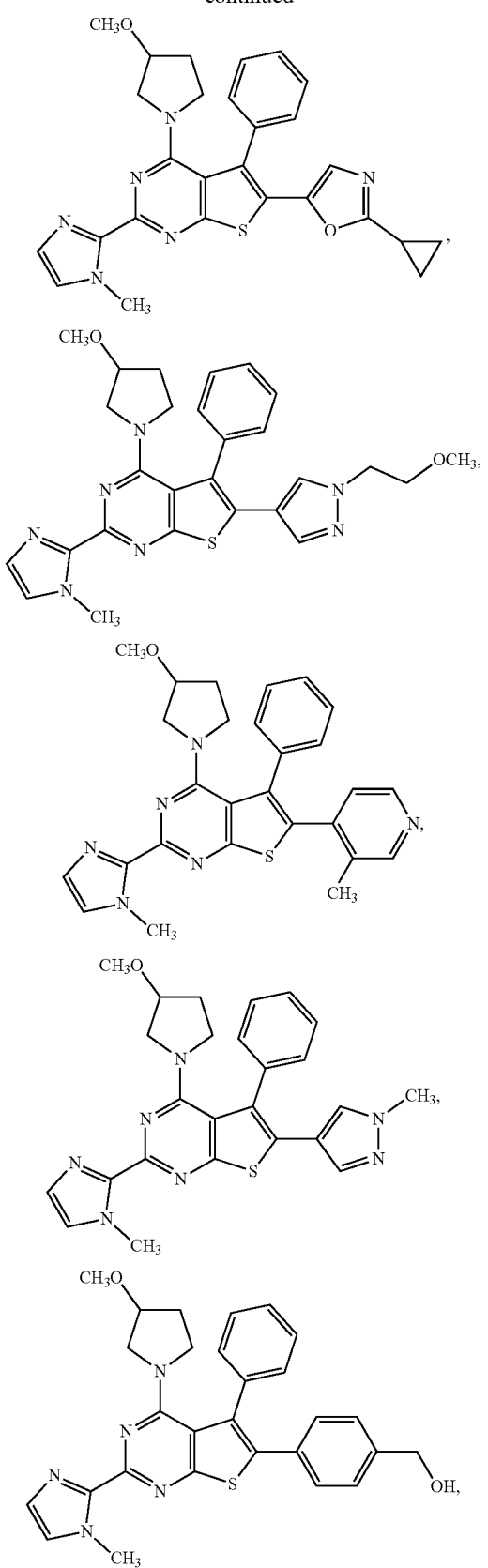
684
-continued
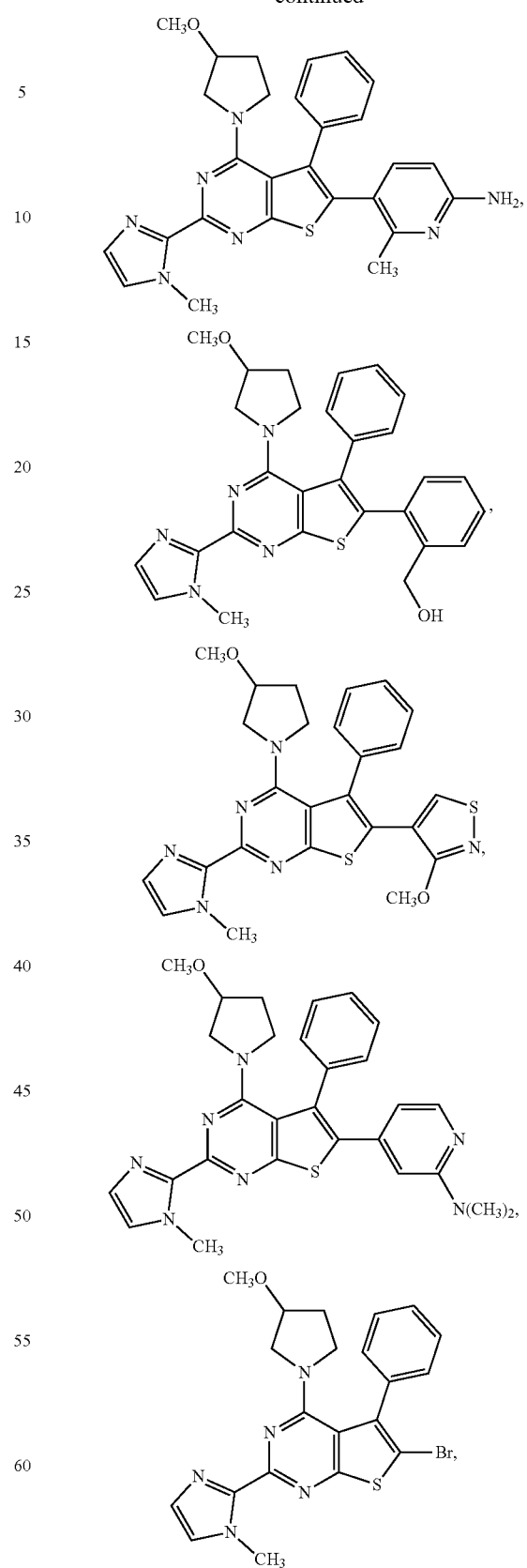

685
-continued
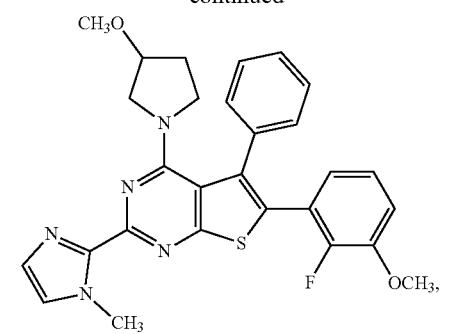
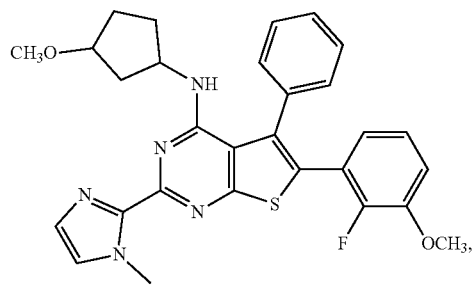
(+/- cis and +/- trans)
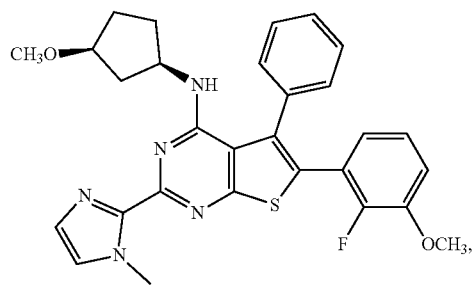
(+/- cis)
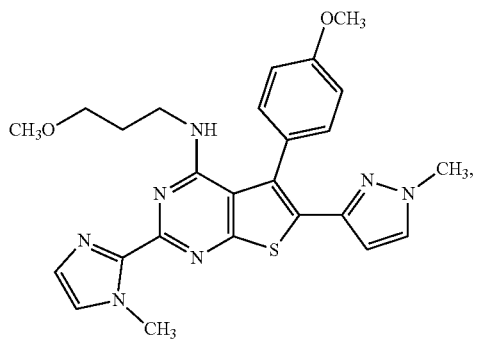
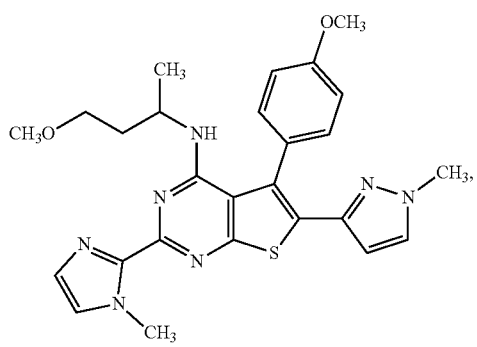
686
-continued
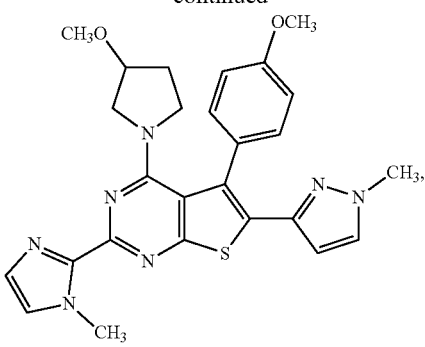
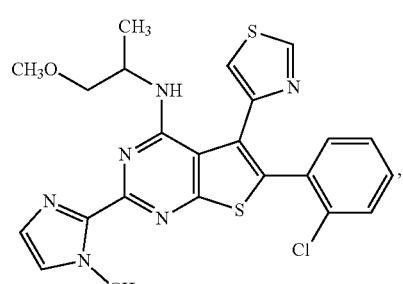
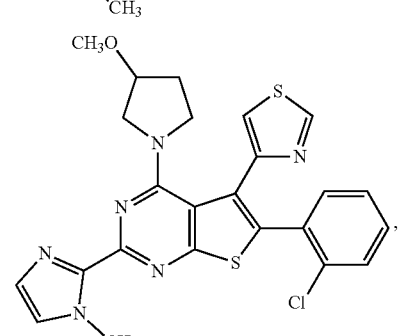
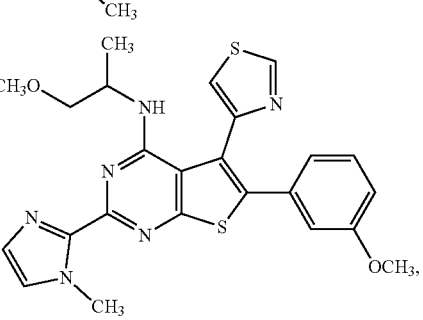
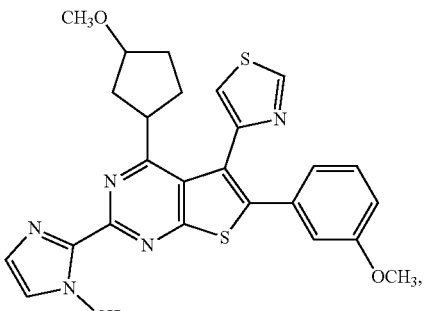

687
-continued
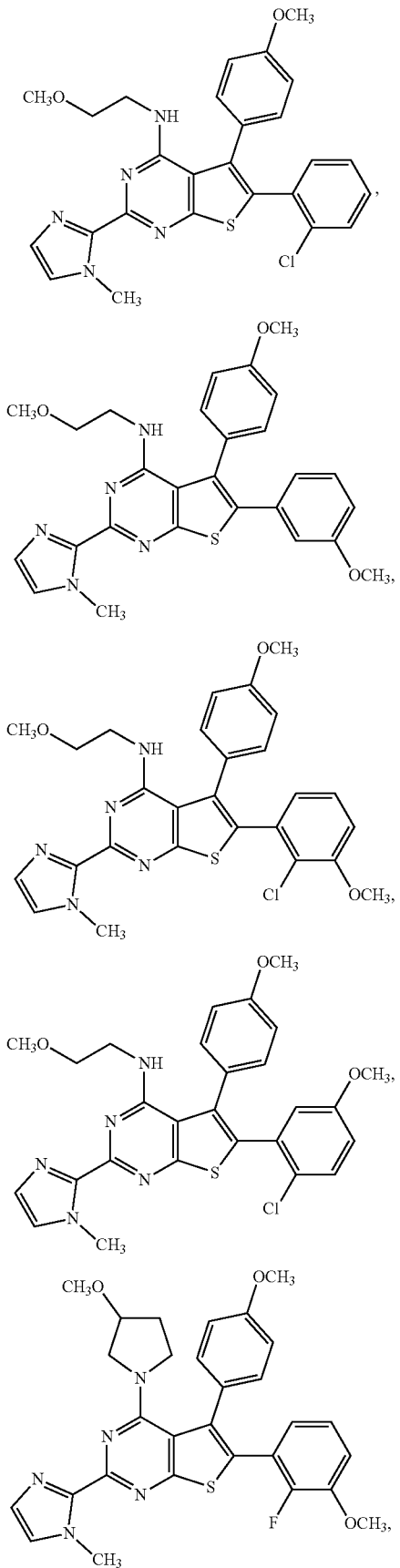
688
-continued
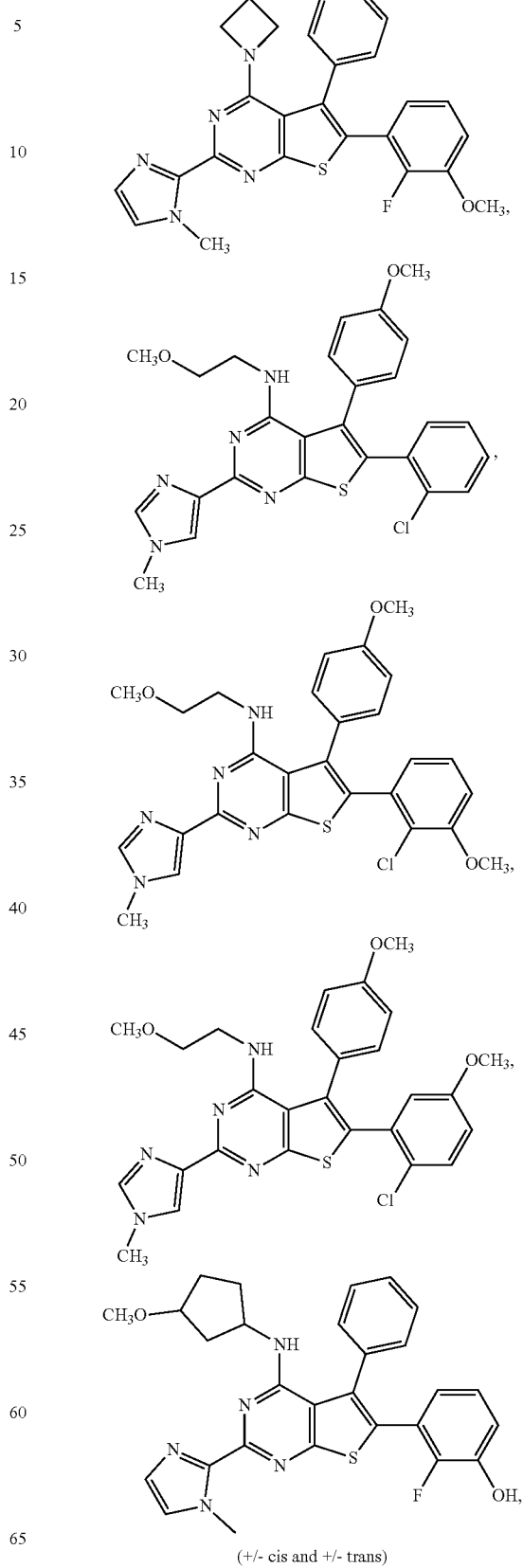
(+/- cis and +/- trans)

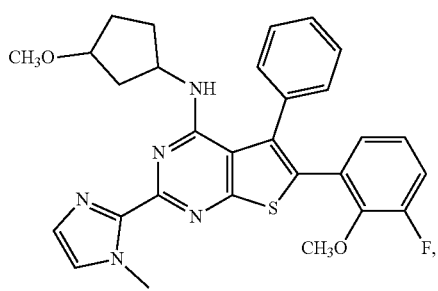
(+/- cis and +/- trans)
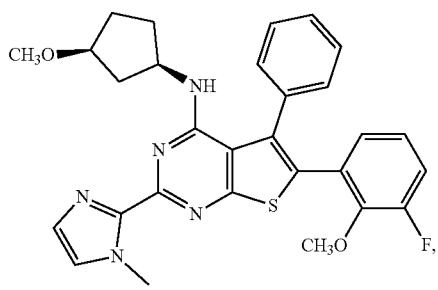
(+/- cis)
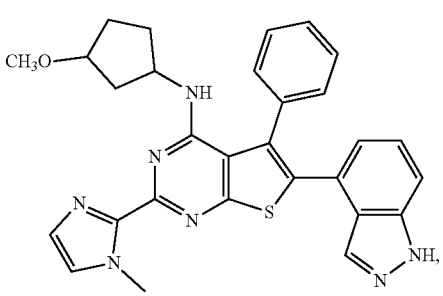
(+/- cis and +/- trans)
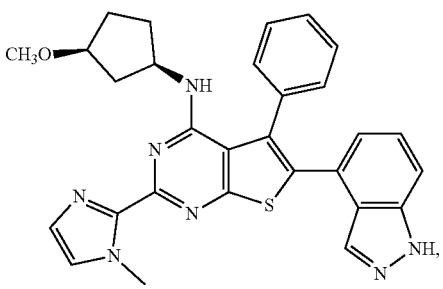
(+/- cis)
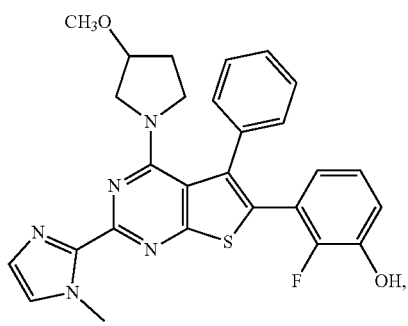
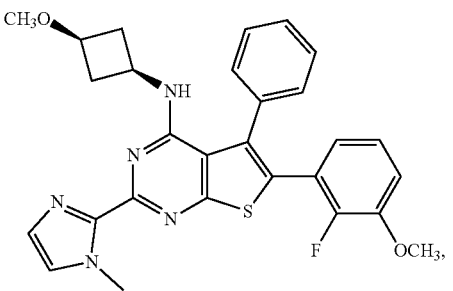
(cis)
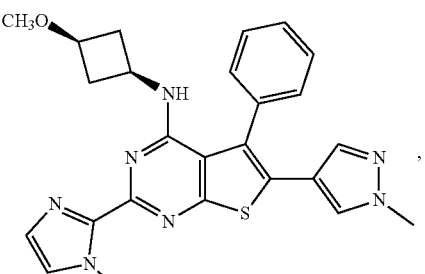
(cis)
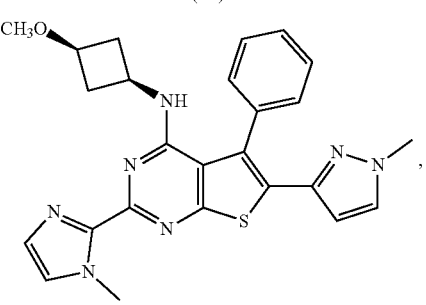
(cis)
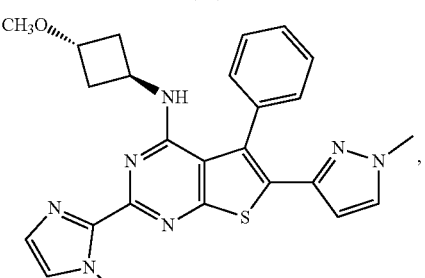
(trans)
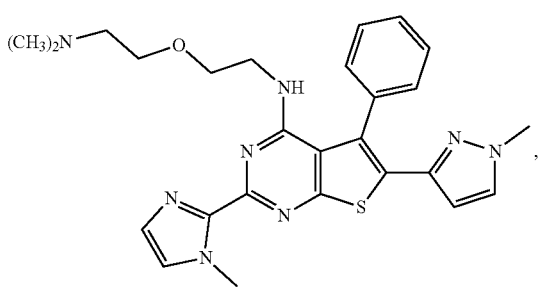

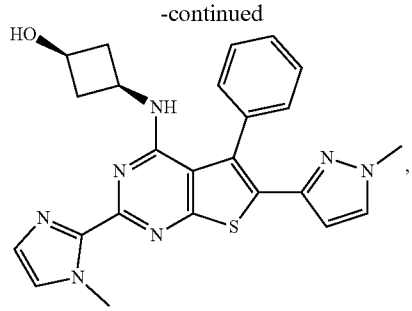
(cis)
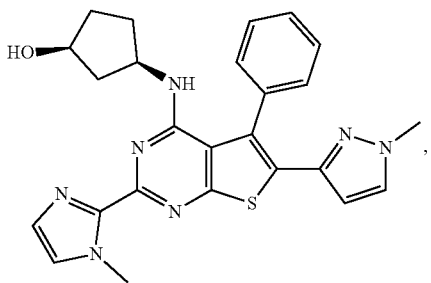
(+/- cis)
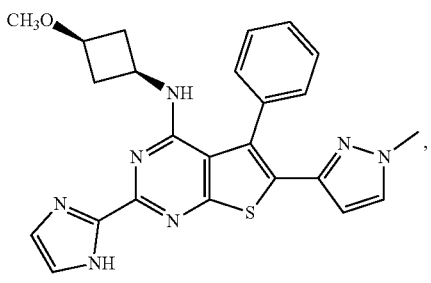
(cis)
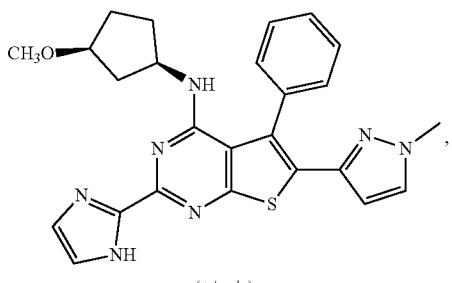
(+/- cis)
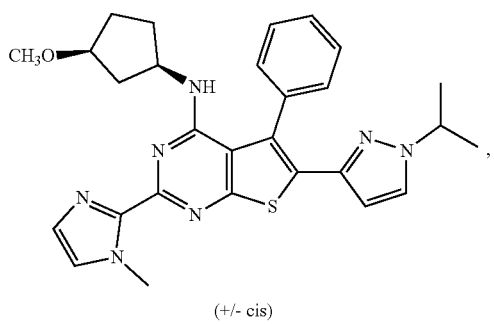
(+/- cis)
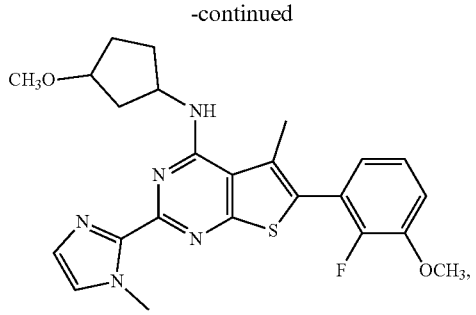
(+/- cis and +/- trans)
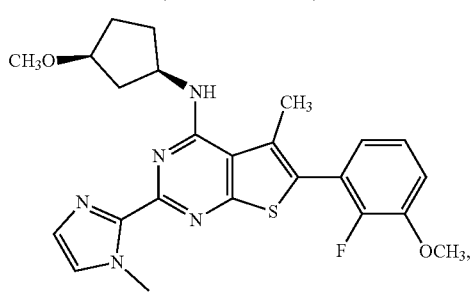
(+/- cis)
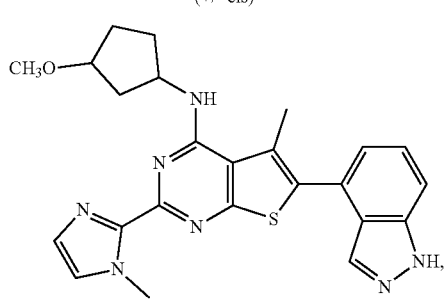
(+/- cis and +/- trans)
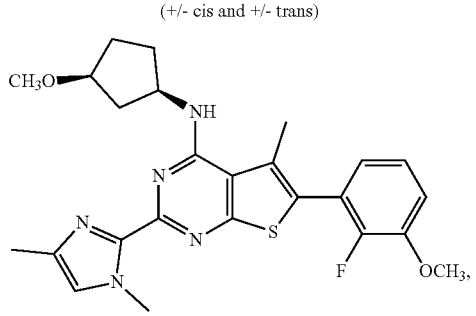
(+/- cis)
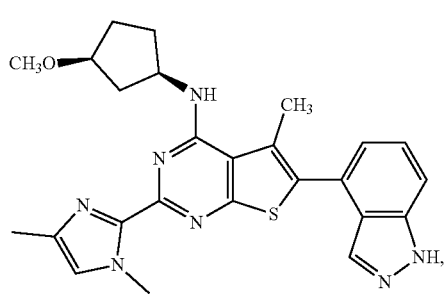
(+/- cis)

693
-continued
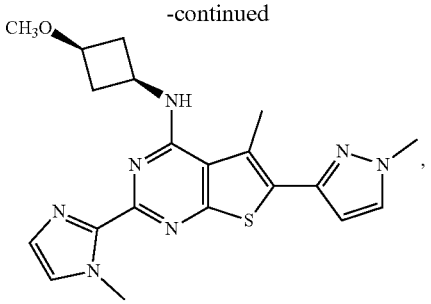
(cis)
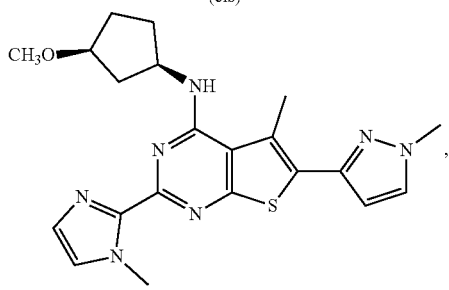
(+/- cis)
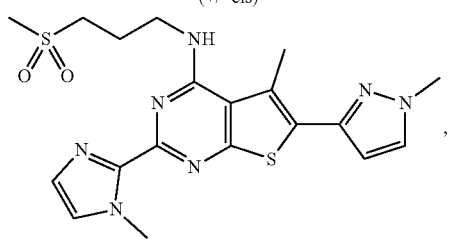
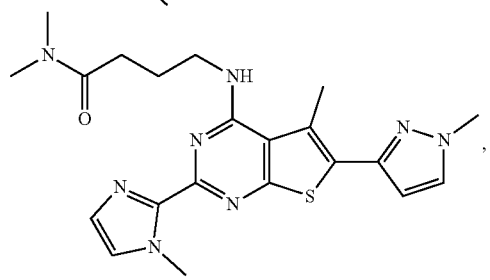
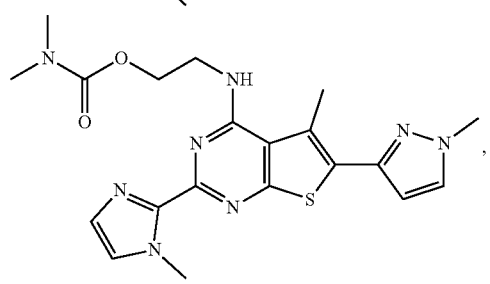
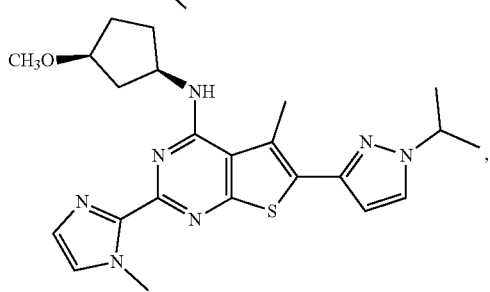
(+/- cis)
694
-continued
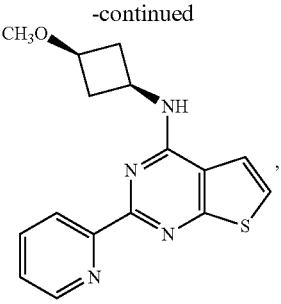
(cis)
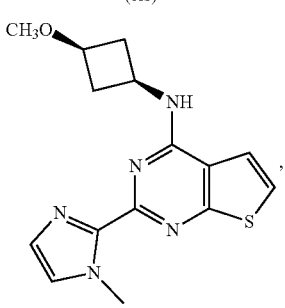
(cis)
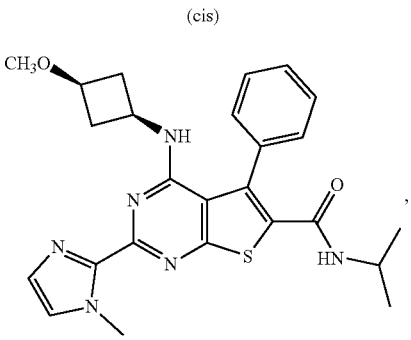
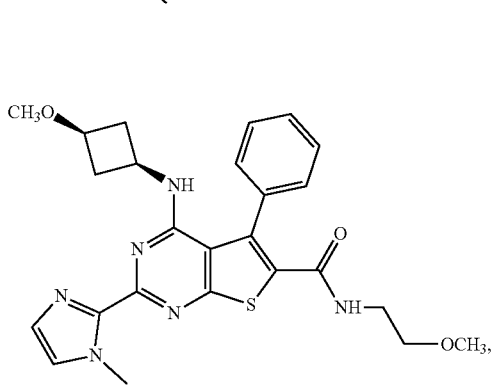
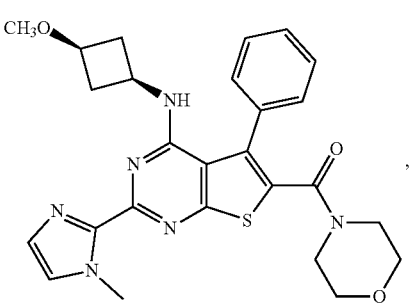

-continued

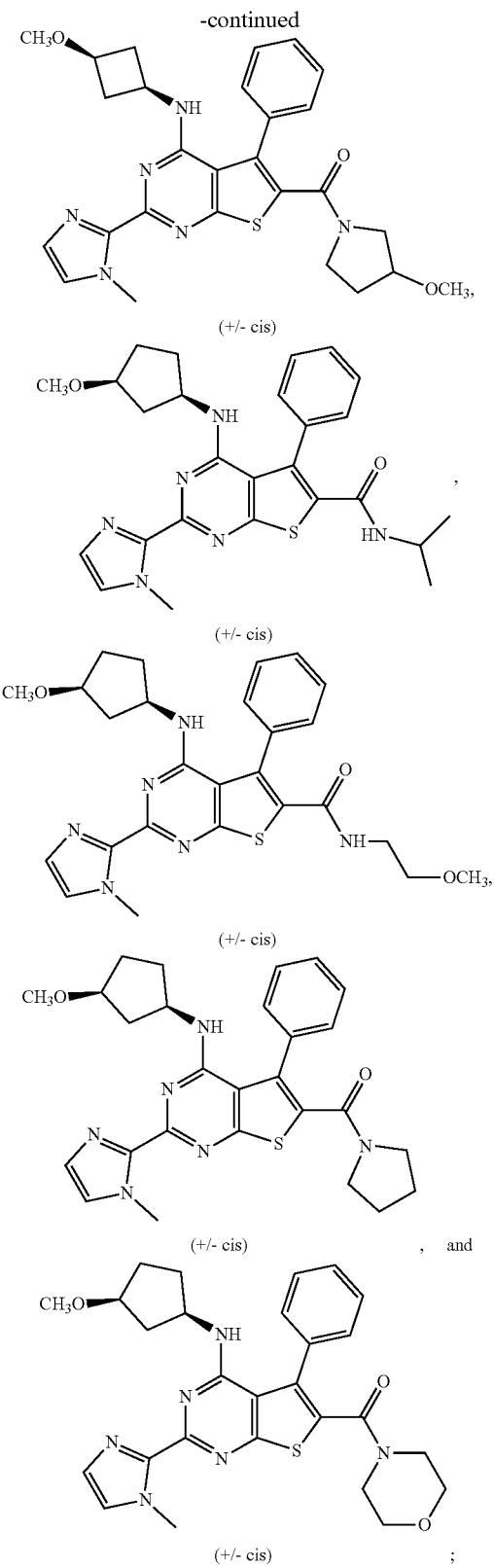

or a pharmaceutically acceptable salt thereof.

3. The compound of claim 1, wherein the compound is the compound of Formula (IIIA), (IIIA1) or (IIIA2), or pharmaceutically acceptable salt thereof.

4. The compound of claim 1, wherein the compound is the compound of Formula (IIIB), or pharmaceutically acceptable salt thereof.

5. The compound of claim 1, wherein the compound is the compound of Formula (IIIC), or pharmaceutically acceptable salt thereof.

6. The compound of claim 1, wherein the compound is the compound of Formula (IIID), or pharmaceutically acceptable salt thereof.

7. The compound of claim 1, wherein the compound is the compound of Formula (IIIE), or pharmaceutically acceptable salt thereof.

8. The compound of claim 1, wherein the compound is the compound of Formula (IIIF), or pharmaceutically acceptable salt thereof.

9. A compound selected from the group consisting of:

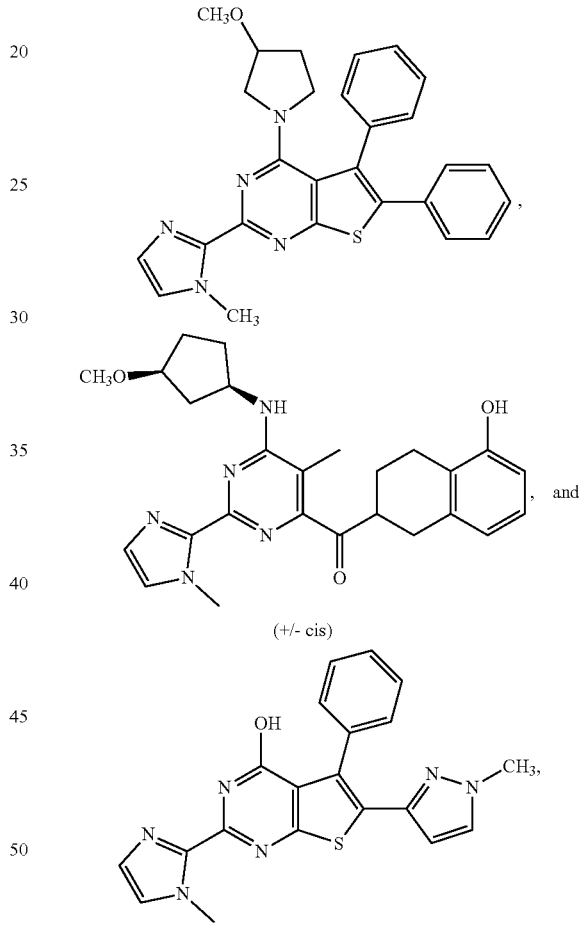

or a pharmaceutically acceptable salt thereof.

10. A pharmaceutical composition comprising the compound or pharmaceutically acceptable salt thereof of claim 1 and a pharmaceutically acceptable carrier.

11. A method of inhibiting the function of one or more members of the Ras superfamily, comprising administering to a subject the compound or pharmaceutically acceptable salt thereof of claim 1, wherein the one or more members of the Ras superfamily are selected from the group consisting of HRas, KRas, NRas, Rac-1, Rho-A, and a mutant of any of the foregoing.

12. The method of claim 11, wherein the compound or pharmaceutically acceptable salt thereof binds to the GTP binding domain of the one or more members of the Ras superfamily and inhibits the one or more members of the Ras superfamily with an $IC_{50}$ value of less than 10 micromolar.

13. A method of treating cancer, or a KRas, NRas, Rac-1, Rho-A or HRas-associated autoimmune leukoproliferative disorder in a subject comprising administering to the subject the compound or pharmaceutically acceptable salt thereof of claim 1, wherein the cancer is hepatocellular carcinoma, prostate cancer, pancreatic cancer, lung cancer, ovarian cancer, colon cancer, small intestine cancer, biliary tract cancer, endometrium cancer, skin cancer, cervix cancer, urinary tract cancer, breast cancer, breast cancer, or brain cancer, optionally wherein the lung cancer is non-small cell lung cancer, the brain cancer is glioblastoma, and the skin cancer is melanoma.

14. A pharmaceutical composition comprising the compound or pharmaceutically acceptable salt thereof of claim 9 and a pharmaceutically acceptable carrier.

15. A method of inhibiting the function of one or more members of the Ras superfamily, comprising administering to a subject the compound or pharmaceutically acceptable salt thereof of claim 9, wherein the one or more members of the Ras superfamily are selected from the group consisting of HRas, KRas, NRas, Rac-1, Rho-A, and a mutant of any of the foregoing.

16. The method of claim 9, wherein the compound or pharmaceutically acceptable salt thereof binds to the GTP binding domain of the one or more members of the Ras superfamily and inhibits the one or more members of the Ras superfamily with an $IC_{50}$ value of less than 10 micromolar.

17. A method of treating cancer, or a KRas, NRas, Rac-1, Rho-A or HRas-associated autoimmune leukoproliferative disorder in a subject comprising administering to the subject the compound or pharmaceutically acceptable salt thereof of claim 9, wherein the cancer is hepatocellular carcinoma, prostate cancer, pancreatic cancer, lung cancer, ovarian cancer, colon cancer, small intestine cancer, biliary tract cancer, endometrium cancer, skin cancer, cervix cancer, urinary tract cancer, breast cancer, breast cancer, or brain cancer, optionally wherein the lung cancer is non-small cell lung cancer, the brain cancer is glioblastoma, and the skin cancer is melanoma.

18. A method of treating cancer, or a KRas, NRas, Rac-1, Rho-A, or HRas-associated autoimmune leukoproliferative disorder in a subject comprising administering to the subject the compound or pharmaceutically acceptable salt thereof of claim 2, wherein the cancer is hepatocellular carcinoma, prostate cancer, pancreatic cancer, lung cancer, ovarian cancer, colon cancer, small intestine cancer, biliary tract cancer, endometrium cancer, skin cancer, cervix cancer, urinary tract cancer, breast cancer, breast cancer, or brain cancer, optionally wherein the lung cancer is non-small cell lung cancer, the brain cancer is glioblastoma, and the skin cancer is melanoma.

19. The method of claim 18, wherein the method is for treating pancreatic cancer.

20. The method of claim 17, wherein the method is for treating pancreatic cancer.

21. The compound of claim 1, wherein the compound is

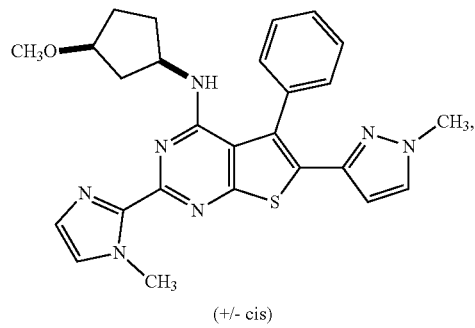

(+/- cis)

or a pharmaceutically acceptable salt thereof.

22. The compound of claim 1, wherein the compound is

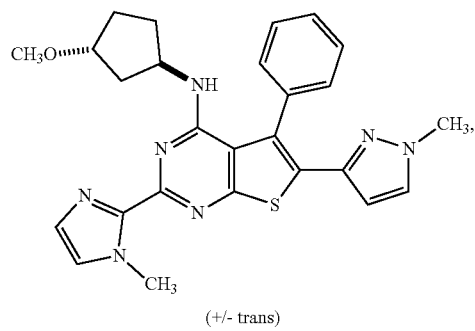

(+/- trans)

or a pharmaceutically acceptable salt thereof.

23. The compound of claim 1, wherein the compound is

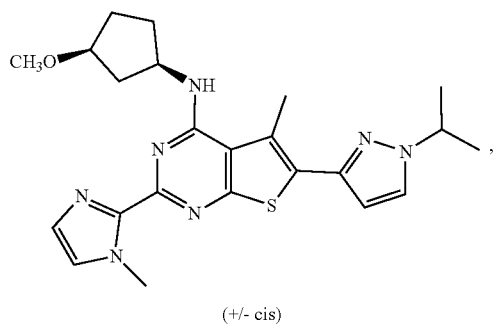

(+/- cis)

or a pharmaceutically acceptable salt thereof.

24. The compound of claim 1, wherein the compound is

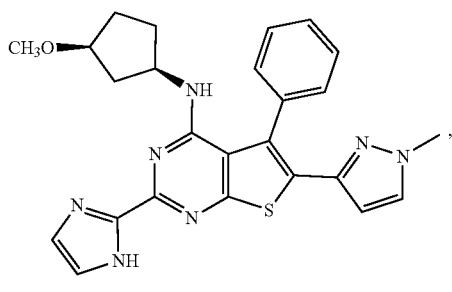

(+/- cis)

or a pharmaceutically acceptable salt thereof.

25. The compound of claim 1, wherein the compound is

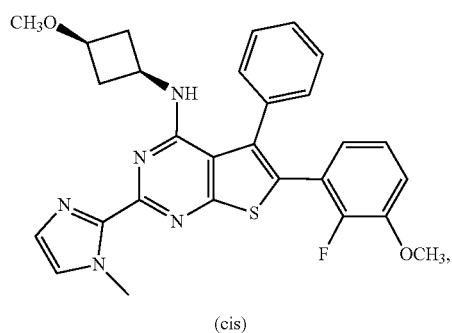

(cis)

or a pharmaceutically acceptable salt thereof.

26. The compound of claim 1, wherein the compound is

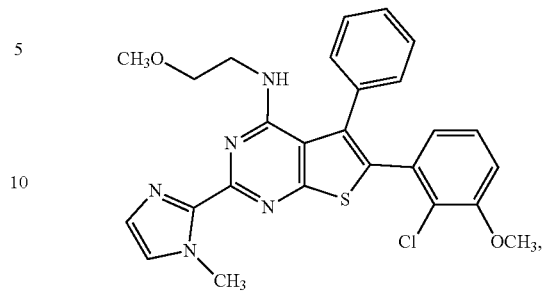

or a pharmaceutically acceptable salt thereof.

27. The compound of claim 1, wherein the compound is

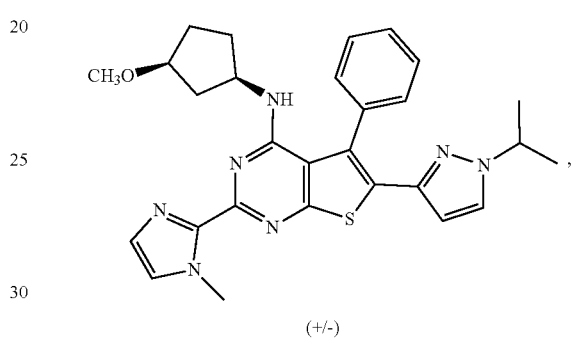

(+/-)

or a pharmaceutically acceptable salt thereof.

* * * * *

UNITED STATES PATENT AND TRADEMARK OFFICE
CERTIFICATE OF CORRECTION

PATENT NO. : 12,391,705 B2
APPLICATION NO. : 17/414565
DATED : August 19, 2025
INVENTOR(S) : Hadari et al.

Page 1 of 2

It is certified that error appears in the above-identified patent and that said Letters Patent is hereby corrected as shown below:

In the Claims

In Column 672, Line 11, Claim 1, replace "$NR^{27}R^{28}$" with -- $-NR^{27}R^{28}$--;

In Column 685, Lines 52-65, Claim 2, replace " 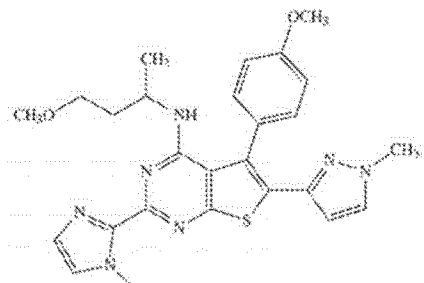 " with -- 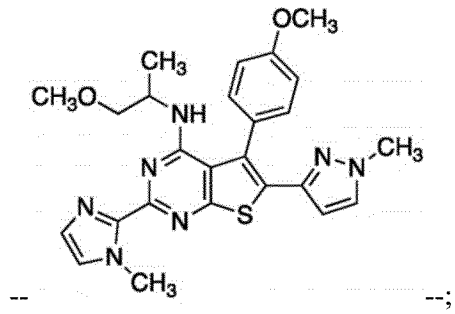 --;

Signed and Sealed this
Eleventh Day of November, 2025

John A. Squires
*Director of the United States Patent and Trademark Office*

CERTIFICATE OF CORRECTION (continued)
U.S. Pat. No. 12,391,705 B2

In Column 686, Lines 52-65, Claim 2, replace " 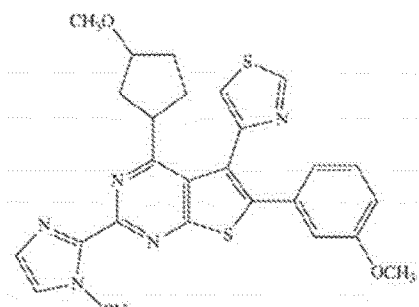 " with 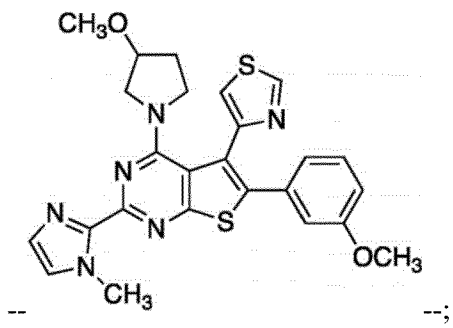 --;

In Column 686, Lines 52-65, Claim 9, replace " 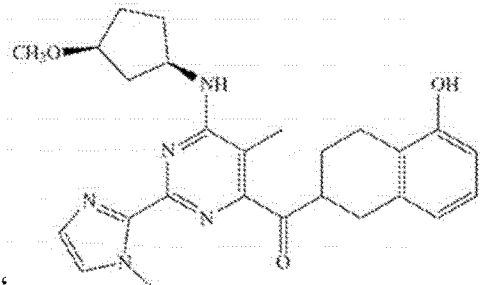 " with 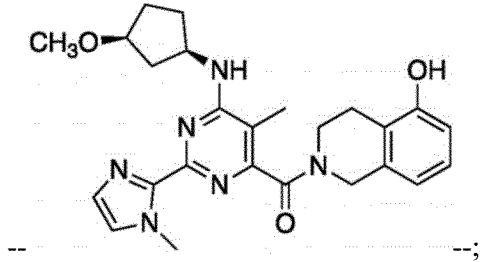 --;

In Column 697, Line 13, Claim 13, replace "breast cancer, breast cancer" with --breast cancer--;

In Column 697, Line 45, Claim 17, replace "breast cancer, breast cancer" with --breast cancer--; and In Column 697, Line 59, Claim 18, replace "breast cancer, breast cancer" with --breast cancer--.